(12) United States Patent
Carstensen et al.

(10) Patent No.: US 10,927,359 B2
(45) Date of Patent: Feb. 23, 2021

(54) COMPOSITIONS COMPRISING POLYPEPTIDES HAVING GALACTANASE ACTIVITY AND POLYPEPTIDES HAVING BETA-GALACTOSIDASE ACTIVITY

(71) Applicant: Novozymes A/S, Bagsvaerd (DK)

(72) Inventors: Lone Carstensen, Allerod (DK); Nikolaj Spodsberg, Holte (DK); Morten Gjermansen, Greve (DK); Jesper Salomon, Holte (DK); Kristian B. R. M. Krogh, Bagsvaerd (DK); Wei Peng, Beijing (CN); Cui Liu, Beijing (CN); Eduardo Antonio Della Pia, Bagsvaerd (DK)

(73) Assignee: Novozymes A/S, Bagsvaerd (DK)

( * ) Notice: Subject to any disclaimer, the term of this patent is extended or adjusted under 35 U.S.C. 154(b) by 82 days.

(21) Appl. No.: 16/300,978

(22) PCT Filed: May 24, 2017

(86) PCT No.: PCT/EP2017/062680
§ 371 (c)(1),
(2) Date: Nov. 13, 2018

(87) PCT Pub. No.: WO2017/202997
PCT Pub. Date: Nov. 30, 2017

(65) Prior Publication Data
US 2019/0161744 A1    May 30, 2019

(30) Foreign Application Priority Data
May 24, 2016   (EP) .................................... 16170963

(51) Int. Cl.
| | | |
|---|---|---|
| *C12N 9/12* | (2006.01) | |
| *C12N 9/38* | (2006.01) | |
| *C12N 9/24* | (2006.01) | |
| *A23K 20/142* | (2016.01) | |
| *A23K 20/174* | (2016.01) | |
| *A23K 20/189* | (2016.01) | |
| *A23K 20/20* | (2016.01) | |
| *A23K 10/14* | (2016.01) | |
| *A23K 10/30* | (2016.01) | |
| *C12N 9/20* | (2006.01) | |
| *C12N 15/52* | (2006.01) | |
| *C12N 15/72* | (2006.01) | |
| *C12N 15/75* | (2006.01) | |

(52) U.S. Cl.
CPC ............ *C12N 9/2471* (2013.01); *A23K 10/14* (2016.05); *A23K 10/30* (2016.05); *A23K 20/142* (2016.05); *A23K 20/174* (2016.05); *A23K 20/189* (2016.05); *A23K 20/20* (2016.05); *C12N 9/20* (2013.01); *C12N 9/2402* (2013.01); *C12N 15/52* (2013.01); *C12N 15/72* (2013.01); *C12N 15/75* (2013.01); *C12Y 302/01023* (2013.01)

(58) Field of Classification Search
CPC .................. C12N 9/2471; C12N 15/76; C12Y 302/01023
USPC ........................................................ 435/207
See application file for complete search history.

(56) References Cited

U.S. PATENT DOCUMENTS

2019/0194635 A1*  6/2019  Nymand-Grarup .... A23K 50/30

FOREIGN PATENT DOCUMENTS

| WO | 97/16982 A1 | 5/1997 |
|---|---|---|
| WO | 01/59083 A1 | 8/2001 |
| WO | 2008/102743 A1 | 8/2008 |
| WO | 2009/132008 A2 | 10/2009 |
| WO | 2017/202946 A1 | 11/2017 |
| WO | 2017/202997 A1 | 11/2017 |

OTHER PUBLICATIONS

Anonymous, NCBI Reference Sequence WP_019006306.1 (2013).
Anonymous, NCBI Reference Sequence WP_075154426.1 (2016).
Anonymous, UniParc Accession No. UPI000AE4DCAA (2017).
Vahjen et al., Animal Feed Science and Technology, vol. 120, Nos. 3-4, pp. 259-276 (2005).
Andrew, UniProt accession No. A0A0Q4QZW5 (2016).
Andrew, UniProt accession No. A0A0Q9KNZ9 (2016).
Andrew, UniProt accession No. A0A0Q9MEL5 (2016).
Condon et al., UniProt accession No. W7F3E0 (2014).
Dodson et al., UniProt accession No. B4AK09 (2008).
Dragosits et al., UniProt accession No. T1SCI0 (2013).
Ehrlich et al., UniProt accession No. A0A0F0IMF7 (2015).
Jeong et al., UniProt accession No. A0A0K2FAB3 (2015).
Kocher et al., British Poultry Science, vol. 43, No. 1, pp. 54-63 (2002).
Lian et al., EMBLCDS Accession No. AFK65333 (2014).
Meng et al., Poultry Science, vol. 84, No. 8, pp. 1242-1251 (2005).
Moreno et al., UniProt accession No. W4AK00 (2014).

(Continued)

*Primary Examiner* — Tekchand Saidha
(74) *Attorney, Agent, or Firm* — Elias Lambiris

(57) ABSTRACT

The present invention relates to compositions comprising polypeptides having galactanase activity and polypeptides having beta-galactosidase activity for use in e.g. animal feed. The present invention further relates to polypeptides having beta-galactosidase activity, polypeptides having galactanase activity and polynucleotides encoding the polypeptides. The invention also relates to nucleic acid constructs, vectors, and host cells comprising the polynucleotides as well as methods of producing and using the polypeptides.

18 Claims, No Drawings
Specification includes a Sequence Listing.

(56) References Cited

OTHER PUBLICATIONS

Orly et al., FEBS Journal, vol. 280, No. 3, pp. 950-964 (2013).
Sakamoto et al., Appl. Microbiol. Biotechnol., vol. 97, No. 7, pp. 2895-2906 (2013).
Sakamoto et al., Appl. Microbiol. Biotechnol., vol. 97, No. 12, pp. 5201-5213 (2013).
Shipkowshi et al., Applied and Environmental Microbiology, vol. 72, No. 12, pp. 7730-7738 (2006).
Uroz et al., UniProt accession No. A0A0J1CW07 (2015).
Vries et al., Carbohydrate Research, vol. 327, No. 4, pp. 401-410 (2000).
Ward et al., UniProt accession No. C6J3F7 (2009).

\* cited by examiner

COMPOSITIONS COMPRISING POLYPEPTIDES HAVING GALACTANASE ACTIVITY AND POLYPEPTIDES HAVING BETA-GALACTOSIDASE ACTIVITY

CROSS-REFERENCE TO RELATED APPLICATIONS

This application is a 35 U.S.C. 371 national application of international application no. PCT/EP2017/062680 filed May 24, 2017, which claims priority or the benefit under 35 U.S.C. 119 of European application no. 16170963.9 filed May 24, 2016. The content of each application is fully incorporated herein by reference.

REFERENCE TO A SEQUENCE LISTING

This application contains a Sequence Listing in computer readable form, which is incorporated herein by reference.

BACKGROUND OF THE INVENTION

Field of the Invention

The present invention relates to compositions comprising polypeptides having galactanase activity and polypeptides having beta-galactosidase activity for use in e.g. animal feed. The present invention further relates to polypeptides having beta-galactosidase activity, polypeptides having galactanase activity and polynucleotides encoding the polypeptides. The invention also relates to nucleic acid constructs, vectors, and host cells comprising the polynucleotides as well as methods of producing and using the polypeptides.

Description of the Related Art

Soybean is a species of legume native to East Asia and is the second biggest feed crop globally and the biggest protein source applied in animal feed. Soybean can be manufactured (defatted) to produce soybean meal (SBM), and SBM is a significant and cheap source of high quality protein for animal feeds. Other common types of legume are chickpea, lupin, lentil, peanut, beans or peas which can also be processed and used as animal feed. Legumes, such as soybean, contain significant amounts of galactan polysaccharides which need to be degraded by enzymes to release the sugars, and thus energy, therein.

However, there are few solutions which efficiently degrade galactan polysaccharides and thus energy which is in the legume cannot be properly utilised by an animal. Up to 70% of a farmers expenses is from the cost of animal feed.

Sakamoto et al, in *Appl Microbiol Biotechnol.* 2013 9:2895-2906, disclose the combination of a GH35 beta-galactosidase and a GH53 galactanase from *Penicillium chrysogenum*. De Vries et al, in *Carbohydrate Research* 327 (2000) disclose the combination of the GH35 beta-galactosidase LacA and the GH53 galactanase GalA from *Aspergillus niger*. However, as disclosed herein these prior art solutions are not very effective at releasing galactose from legumes, such as soybean. Thus the object of this invention is to provide a solution which efficiently releases sugars from galactan polysaccharides and thereby improves the nutritional value of the legumes to reduce the feed costs by reformulation of the diet or to provide more energy to the animal resulting in improved animal growth.

SUMMARY OF THE INVENTION

The present invention relates to compositions comprising one or more GH53 polypeptides having galactanase activity and one or more GH35 polypeptides having beta-galactosidase activity.

The present application further relates to granules comprising the polypeptide(s) of the invention; animal feed additives comprising the composition(s) of the invention; liquid formulations comprising the polypeptide(s) of the invention; animal feed and pelleted animal feed comprising the polypeptide(s) of the invention; methods of releasing galactose from plant based material; methods of improving one or more performance parameters of an animal and use of the composition of the invention in animal feed, in animal feed additives, in the preparation of a composition for use in animal feed, for improving the nutritional value of an animal feed, for increasing digestibility of the animal feed, for improving one or more performance parameters in an animal and/or for releasing galactose from plant based material.

The invention also relates to isolated polypeptide having beta-galactosidase or galactanase activity, polynucleotides encoding the polypeptides of the present invention; nucleic acid constructs; expression vectors; recombinant host cells comprising the polynucleotides and methods of producing the polypeptides.

Overview of Sequence Listing

SEQ ID NO: 1 is the gene sequence of the GH53 galactanase as isolated from *Cohnella* sp-60555.

SEQ ID NO: 2 is the amino acid sequence as deduced from SEQ ID NO: 1.

SEQ ID NO: 3 is the amino acid sequence of the mature GH53 galactanase from *Cohnella* sp-60555.

SEQ ID NO: 4 is the amino acid sequence of SEQ ID NO: 3 with His-tag.

SEQ ID NO: 5 is the gene sequence of the GH53 galactanase as isolated from *Cohnella xylanilytica*.

SEQ ID NO: 6 is the amino acid sequence as deduced from SEQ ID NO: 5.

SEQ ID NO: 7 is the amino acid sequence of the mature GH53 galactanase from *Cohnella xylanilytica*.

SEQ ID NO: 8 is the amino acid sequence of SEQ ID NO: 7 with His-tag.

SEQ ID NO: 9 is the gene sequence of the GH53 galactanase as isolated from *Paenibacillus tundrae*.

SEQ ID NO: 10 is the amino acid sequence as deduced from SEQ ID NO: 9.

SEQ ID NO: 11 is the amino acid sequence of the mature GH53 galactanase from *Paenibacillus tundrae*.

SEQ ID NO: 12 is the amino acid sequence of SEQ ID NO: 11 with His-tag.

SEQ ID NO: 13 is the gene sequence of the GH53 galactanase as isolated from *Paenibacillus barcinonensis*.

SEQ ID NO: 14 is the amino acid sequence as deduced from SEQ ID NO: 13.

SEQ ID NO: 15 is the amino acid sequence of the mature GH53 galactanase from *Paenibacillus barcinonensis*.

SEQ ID NO: 16 is the amino acid sequence of SEQ ID NO: 15 with His-tag.

SEQ ID NO: 17 is the gene sequence of the GH53 galactanase as isolated from *Paenibacillus* sp-62603.

SEQ ID NO: 18 is the amino acid sequence as deduced from SEQ ID NO: 17.

SEQ ID NO: 19 is the amino acid sequence of the mature GH53 galactanase from *Paenibacillus* sp-62603.

SEQ ID NO: 20 is the amino acid sequence of SEQ ID NO: 19 with His-tag.

SEQ ID NO: 21 is the gene sequence of the GH53 galactanase as isolated from *Paenibacillus xylanilyticus*.

SEQ ID NO: 22 is the amino acid sequence as deduced from SEQ ID NO: 21.

SEQ ID NO: 23 is the amino acid sequence of the mature GH53 galactanase from *Paenibacillus xylanilyticus*.

SEQ ID NO: 24 is the amino acid sequence of SEQ ID NO: 23 with His-tag.

SEQ ID NO: 25 is the gene sequence of the GH53 galactanase as isolated from *Paenibacillus* sp-18179.

SEQ ID NO: 26 is the amino acid sequence as deduced from SEQ ID NO: 25.

SEQ ID NO: 27 is the amino acid sequence of the mature GH53 galactanase from *Paenibacillus* sp-18179.

SEQ ID NO: 28 is the amino acid sequence of SEQ ID NO: 27 with His-tag.

SEQ ID NO: 29 is the gene sequence of the GH53 galactanase as isolated from *Paenibacillus peoriae*. (D448RG)

SEQ ID NO: 30 is the amino acid sequence as deduced from SEQ ID NO: 29.

SEQ ID NO: 31 is the amino acid sequence of the mature GH53 galactanase from *Paenibacillus peoriae*.

SEQ ID NO: 32 is the amino acid sequence of SEQ ID NO: 31 with His-tag.

SEQ ID NO: 33 is the gene sequence of the GH53 galactanase as isolated from *Paenibacillus xylanexedens*.

SEQ ID NO: 34 is the amino acid sequence as deduced from SEQ ID NO: 33.

SEQ ID NO: 35 is the amino acid sequence of the mature GH53 galactanase from *Paenibacillus xylanexedens*.

SEQ ID NO: 36 is the amino acid sequence of SEQ ID NO: 35 with His-tag.

SEQ ID NO: 37 is the gene sequence of the GH53 galactanase as isolated from *Cohnella laeviribosi*.

SEQ ID NO: 38 is the amino acid sequence as deduced from SEQ ID NO: 37.

SEQ ID NO: 39 is the amino acid sequence of the mature GH53 galactanase from *Cohnella laeviribosi*.

SEQ ID NO: 40 is the amino acid sequence of SEQ ID NO: 39 with His-tag.

SEQ ID NO: 41 is the gene sequence of the GH35 beta-galactosidase as isolated from *Hamigera paravellanea*.

SEQ ID NO: 42 is the amino acid sequence as deduced from SEQ ID NO: 41.

SEQ ID NO: 43 is the amino acid sequence of the mature GH35 beta-galactosidase from *Hamigera paravellanea*.

SEQ ID NO: 44 is the gene sequence of the GH35 beta-galactosidase as isolated from *Aspergillus unguis*.

SEQ ID NO: 45 is the amino acid sequence as deduced from SEQ ID NO: 44.

SEQ ID NO: 46 is the amino acid sequence of the mature GH35 beta-galactosidase from *Aspergillus unguis*.

SEQ ID NO: 47 is the gene sequence of the GH35 beta-galactosidase as isolated from *Aspergillus tamarii*.

SEQ ID NO: 48 is the amino acid sequence as deduced from SEQ ID NO: 47.

SEQ ID NO: 49 is the amino acid sequence of the mature GH35 beta-galactosidase from *Aspergillus tamarii*.

SEQ ID NO: 50 is the gene sequence of the GH35 beta-galactosidase as isolated from *Curvularia spicifera*.

SEQ ID NO: 51 is the amino acid sequence as deduced from SEQ ID NO: 51.

SEQ ID NO: 52 is the amino acid sequence of the mature GH35 beta-galactosidase from *Curvularia spicifera*.

SEQ ID NO: 53 is the gene sequence of the GH35 beta-galactosidase as isolated from *Aspergillus oryzae*.

SEQ ID NO: 54 is the amino acid sequence as deduced from SEQ ID NO: 53.

SEQ ID NO: 55 is the amino acid sequence of the mature GH35 beta-galactosidase from *Aspergillus oryzae*.

SEQ ID NO: 56 is the gene sequence of the GH35 beta-galactosidase as isolated from *Aspergillus carneus*.

SEQ ID NO: 57 is the amino acid sequence as deduced from SEQ ID NO: 56.

SEQ ID NO: 58 is the amino acid sequence of the mature GH35 beta-galactosidase from *Aspergillus carneus*.

SEQ ID NO: 59 is the gene sequence of the GH35 beta-galactosidase as isolated from *Penicillium quercetorum*.

SEQ ID NO: 60 is the amino acid sequence as deduced from SEQ ID NO: 59.

SEQ ID NO: 61 is the amino acid sequence of the mature GH35 beta-galactosidase from *Penicillium quercetorum*.

SEQ ID NO: 62 is the amino acid sequence of the mature GH53 galactanase from *Humicola insolens* as disclosed in WO1997/032014.

SEQ ID NO: 63 is the amino acid sequence of the mature GH53 galactanase from *Myceliophthora thermophile* as disclosed in WO1997/032014.

SEQ ID NO: 64 is the amino acid sequence of the mature GH53 galactanase from *Meripilus giganteus* as disclosed in WO1997/032013.

SEQ ID NO: 65 is the conserved motif GV[T/M]PD[W/M]VQ[I/V]GNE.

SEQ ID NO: 66 is the conserved motif WADP[A/G]xQxKPxAW.

SEQ ID NO: 67 is the *Bacillus clausii* secretion signal.

SEQ ID NO: 68 is the cDNA sequence of the GH35 beta-galactosidase as isolated from *Penicillium simplicissimum*.

SEQ ID NO: 69 is the amino acid sequence as deduced from SEQ ID NO: 68.

SEQ ID NO: 70 is the amino acid sequence of the mature GH35 beta-galactosidase from *Penicillium simplicissimum*.

SEQ ID NO: 71 is the cDNA sequence of the GH35 beta-galactosidase as isolated from *Aspergillus westerdijkiae*.

SEQ ID NO: 72 is the amino acid sequence as deduced from SEQ ID NO: 71.

SEQ ID NO: 73 is the amino acid sequence of the mature GH35 beta-galactosidase from *Aspergillus westerdijkiae*.

SEQ ID NO: 74 is the cDNA sequence of the GH35 beta-galactosidase as isolated from *Aspergillus wentii*.

SEQ ID NO: 75 is the amino acid sequence as deduced from SEQ ID NO: 75.

SEQ ID NO: 76 is the amino acid sequence of the mature GH35 beta-galactosidase from *Aspergillus wentii*.

SEQ ID NO: 77 is the cDNA sequence of the GH35 beta-galactosidase as isolated from *Aspergillus lentulus*.

SEQ ID NO: 78 is the amino acid sequence as deduced from SEQ ID NO: 77.

SEQ ID NO: 79 is the amino acid sequence of the mature GH35 beta-galactosidase from *Aspergillus lentulus*.

SEQ ID NO: 80 is the conserved motif Y[Y/F][D/Q][Y/H/W]F.

SEQ ID NO: 81 is the conserved motif K[Y/F][Y/S]ETK.

SEQ ID NO: 82 is the amino acid sequence of the GH35 beta-galactosidase from *Penicillium chrysogenum* as disclosed by Sakamoto et al, in *Appl Microbiol Biotechnol*. 2013 9:2895-2906 (Swissprot: I0IV51).

SEQ ID NO: 83 is the amino acid sequence of the GH53 galactanase from *Penicillium chrysogenum* as disclosed by Sakamoto et al, in *Appl Microbiol Biotechnol.* 2013 9:2895-2906 (Swissprot: B5MGR3).

SEQ ID NO: 84 is the amino acid sequence of the GH35 beta-galactosidase LacA from *Aspergillus niger* as disclosed by De Vries et al, in *Carbohydrate Research* 327 (2000) 401-410 (Swissprot: G3XR77).

SEQ ID NO: 85 is the amino acid sequence of the GH53 galactanase GalA from *Aspergillus niger* as disclosed by De Vries et al, in *Carbohydrate Research* 327 (2000) 401-410.

Definitions

Allelic variant: The term "allelic variant" means any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Alpha-galactosidase: The term "alpha-galactosidase", also called α-D-galactoside galactohydrolase (E.C. 3.2.1.22), means an enzyme that catalyses the hydrolysis of terminal, non-reducing α-D-galactose residues in α-D-galactosides, such as galactose oligosaccharides, galactomannans and galactolipids. Alpha-galactosidase activity can be determined using 4-nitrophenyl α-D-galactopyranoside (available from Megazyme International, Bray, Co. Wicklow, Ireland) as substrate in 100 mM MES (Sigma) buffer pH 7.0±0.05 at room temperature. The enzyme is diluted in 2-fold dilutions and then the 4-nitrophenyl α-D-galactopyranoside substrate is dissolved in the solution containing the enzyme. The alpha-galactosidase activity is followed directly in the buffer by measuring the absorbance of released pNP at 405 nm as function of time. A detailed assay can be found in the alpha-galactosidase assay as described herein. An example of an alpha-galactosidase is that disclosed in WO1994/23022 (AAR60801). In one aspect, the alpha-galactosidase has at least 50%, such as at least 70%, at least 75%, at least 80%, at least 85%, at least 90%, at least 95% or at least 100% of the alpha-galactosidase activity of AAR60801.

Animal: The term "animal" refers to all animals except humans. Examples of animals are non-ruminants, and ruminants. Ruminant animals include, for example, animals such as sheep, goats, cattle, e.g. beef cattle, cows, and young calves, deer, yank, camel, llama and kangaroo. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; fish (including but not limited to amberjack, arapaima, barb, bass, bluefish, bocachico, bream, bullhead, cachama, carp, catfish, catla, chanos, char, cichlid, cobia, cod, crappie, dorada, drum, eel, goby, goldfish, gourami, grouper, guapote, halibut, java, labeo, lai, loach, mackerel, milkfish, mojarra, mudfish, mullet, paco, pearlspot, pejerrey, perch, pike, pompano, roach, salmon, sampa, sauger, sea bass, seabream, shiner, sleeper, snakehead, snapper, snook, sole, spinefoot, sturgeon, sunfish, sweetfish, tench, terror, tilapia, trout, tuna, turbot, vendace, walleye and whitefish); and crustaceans (including but not limited to shrimps and prawns).

Animal feed: The term "animal feed" refers to any compound, preparation, or mixture suitable for, or intended for intake by an animal. Animal feed for a mono-gastric animal typically comprises concentrates as well as vitamins, minerals, enzymes, direct fed microbial, amino acids and/or other feed ingredients (such as in a premix) whereas animal feed for ruminants generally comprises forage (including roughage and silage) and may further comprise concentrates as well as vitamins, minerals, enzymes direct fed microbial, amino acid and/or other feed ingredients (such as in a premix).

Beta-galactosidase: The term "beta-galactosidase" means an β-D-galactoside galactohydrolase (EC 3.2.1.23) that catalyzes the hydrolysis of terminal non-reducing β-D-galactose residues in β-D-galactosides, such as lactose (1,4-O-β-D-galactopyranosyl-D-glucose), oligosaccharides, glycolipids, and glycoproteins. Beta-galactosidase activity can be determined using 4-nitrophenyl beta-D-galactopyranoside (available from Megazyme International, Bray, Co. Wicklow, Ireland) as substrate in 100 mM MES (Sigma) buffer pH 7.0±0.05 at room temperature. The enzyme is diluted in 2-fold dilutions and then the 4-nitrophenyl beta-D-galactopyranoside substrate is dissolved in the solution containing the enzyme. The beta-galactosidase activity is followed directly in the buffer by measuring the absorbance of released pNP at 405 nm as function of time. A detailed assay can be found in the beta-galactosidase assay as described herein. In one aspect, the polypeptides of the present invention have at least 60%, such as at least 70%, at least 75%, at least 80%, at least 85%, at least 90%, at least 95% or at least 100% of the beta-galactosidase activity of the polypeptide of SEQ ID NO: 43.

Body Weight Gain: The term "body weight gain" means an increase in live weight of an animal during a given period of time e.g. the increase in weight from day 1 to day 21.

cDNA: The term "cDNA" means a DNA molecule that can be prepared by reverse transcription from a mature, spliced, mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

Coding sequence: The term "coding sequence" means a polynucleotide, which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

Control sequences: The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

Expression: The term "expression" includes any step involved in the production of a polypeptide including, but not limited to, transcription, post-transcriptional modification, translation, post-translational modification, and secretion.

Expression vector: The term "expression vector" means a linear or circular DNA molecule that comprises a polynucleotide encoding a polypeptide and is operably linked to control sequences that provide for its expression.

Feed Conversion Ratio: The term "feed conversion ratio" the amount of feed fed to an animal to increase the weight of the animal by a specified amount. An improved feed conversion ratio means a lower feed conversion ratio. By "lower feed conversion ratio" or "improved feed conversion ratio" it is meant that the use of a feed additive composition in feed results in a lower amount of feed being required to be fed to an animal to increase the weight of the animal by a specified amount compared to the amount of feed required to increase the weight of the animal by the same amount when the feed does not comprise said feed additive composition.

Feed efficiency: The term "feed efficiency" means the amount of weight gain per unit of feed when the animal is fed ad-libitum or a specified amount of food during a period of time. By "increased feed efficiency" it is meant that the use of a feed additive composition according the present invention in feed results in an increased weight gain per unit of feed intake compared with an animal fed without said feed additive composition being present.

Fragment: The term "fragment" means a polypeptide having one or more (e.g., several) amino acids absent from the amino and/or carboxyl terminus of a mature polypeptide or domain; wherein the fragment has beta-galactosidase activity or galactanase activity.

In one aspect, the fragment has galactanase activity and comprises at least 90% of the length of the mature polypeptide, such as at least 284 amino acids of SEQ ID NO: 3, at least 286 amino acids of SEQ ID NO: 7, at least 284 amino acids of SEQ ID NO: 11, at least 284 amino acids of SEQ ID NO: 15, at least 284 amino acids of SEQ ID NO: 19, at least 284 amino acids of SEQ ID NO: 23, at least 464 amino acids of SEQ ID NO: 27, at least 285 amino acids of SEQ ID NO: 31, at least 284 amino acids of SEQ ID NO: 35 or at least 284 amino acids of SEQ ID NO: 39.

In one aspect, the fragment has galactanase activity and comprises at least 92% of the length of the mature polypeptide, such as at least 290 amino acids of SEQ ID NO: 3, at least 292 amino acids of SEQ ID NO: 7, at least 290 amino acids of SEQ ID NO: 11, at least 290 amino acids of SEQ ID NO: 15, at least 290 amino acids of SEQ ID NO: 19, at least 290 amino acids of SEQ ID NO: 23, at least 474 amino acids of SEQ ID NO: 27, at least 291 amino acids of SEQ ID NO: 31, at least 290 amino acids of SEQ ID NO: 35 or at least 290 amino acids of SEQ ID NO: 39.

In one aspect, the fragment has galactanase activity and comprises at least 94% of the length of the mature polypeptide, such as at least 297 amino acids of SEQ ID NO: 3, at least 298 amino acids of SEQ ID NO: 7, at least 297 amino acids of SEQ ID NO: 11, at least 297 amino acids of SEQ ID NO: 15, at least 297 amino acids of SEQ ID NO: 19, at least 297 amino acids of SEQ ID NO: 23, at least 485 amino acids of SEQ ID NO: 27, at least 297 amino acids of SEQ ID NO: 31, at least 297 amino acids of SEQ ID NO: 35 or at least 297 amino acids of SEQ ID NO: 39.

In one aspect, the fragment has galactanase activity and comprises at least 96% of the length of the mature polypeptide, such as at least 303 amino acids of SEQ ID NO: 3, at least 305 amino acids of SEQ ID NO: 7, at least 303 amino acids of SEQ ID NO: 11, at least 303 amino acids of SEQ ID NO: 15, at least 303 amino acids of SEQ ID NO: 19, at least 303 amino acids of SEQ ID NO: 23, at least 495 amino acids of SEQ ID NO: 27, at least 304 amino acids of SEQ ID NO: 31, at least 303 amino acids of SEQ ID NO: 35 or at least 303 amino acids of SEQ ID NO: 39.

In one aspect, the fragment has galactanase activity and comprises at least 98% of the length of the mature polypeptide, such as at least 309 amino acids of SEQ ID NO: 3, at least 311 amino acids of SEQ ID NO: 7, at least 309 amino acids of SEQ ID NO: 11, at least 309 amino acids of SEQ ID NO: 15, at least 309 amino acids of SEQ ID NO: 19, at least 309 amino acids of SEQ ID NO: 23, at least 505 amino acids of SEQ ID NO: 27, at least 310 amino acids of SEQ ID NO: 31, at least 309 amino acids of SEQ ID NO: 35 or at least 309 amino acids of SEQ ID NO: 39.

In one aspect, the fragment has galactanase activity and comprises at least 99% of the length of the mature polypeptide, such as at least 312 amino acids of SEQ ID NO: 3, at least 314 amino acids of SEQ ID NO: 7, at least 312 amino acids of SEQ ID NO: 11, at least 312 amino acids of SEQ ID NO: 15, at least 312 amino acids of SEQ ID NO: 19, at least 312 amino acids of SEQ ID NO: 23, at least 510 amino acids of SEQ ID NO: 27, at least 313 amino acids of SEQ ID NO: 31, at least 312 amino acids of SEQ ID NO: 35 or at least 312 amino acids of SEQ ID NO: 39.

In one aspect, the fragment has beta-galactosidase activity and comprises at least 90% of the length of the mature polypeptide, such as at least 886 amino acids of SEQ ID NO: 43, at least 913 amino acids of SEQ ID NO: 46, at least 898 amino acids of SEQ ID NO: 49, at least 884 amino acids of SEQ ID NO: 52, at least 898 amino acids of SEQ ID NO: 55, at least 906 amino acids of SEQ ID NO: 58, at least 889 amino acids of SEQ ID NO: 61, at least 865 amino acids of SEQ ID NO: 70, at least 900 amino acids of SEQ ID NO: 73, at least 900 amino acids of SEQ ID NO: 76 or at least 894 amino acids of SEQ ID NO: 79.

In one aspect, the fragment has beta-galactosidase activity and comprises at least 92% of the length of the mature polypeptide, such as at least 906 amino acids of SEQ ID NO: 43, at least 933 amino acids of SEQ ID NO: 46, at least 918 amino acids of SEQ ID NO: 49, at least 904 amino acids of SEQ ID NO: 52, at least 918 amino acids of SEQ ID NO: 55, at least 926 amino acids of SEQ ID NO: 58, at least 908 amino acids of SEQ ID NO: 61, at least 885 amino acids of SEQ ID NO: 70, at least 920 amino acids of SEQ ID NO: 73, at least 920 amino acids of SEQ ID NO: 76 or at least 914 amino acids of SEQ ID NO: 79.

In one aspect, the fragment has beta-galactosidase activity and comprises at least 94% of the length of the mature polypeptide, such as at least 925 amino acids of SEQ ID NO: 43, at least 954 amino acids of SEQ ID NO: 46, at least 938 amino acids of SEQ ID NO: 49, at least 924 amino acids of SEQ ID NO: 52, at least 938 amino acids of SEQ ID NO: 55, at least 946 amino acids of SEQ ID NO: 58, at least 928 amino acids of SEQ ID NO: 61, at least 904 amino acids of SEQ ID NO: 70, at least 940 amino acids of SEQ ID NO: 73, at least 940 amino acids of SEQ ID NO: 76 or at least 934 amino acids of SEQ ID NO: 79.

In one aspect, the fragment has beta-galactosidase activity and comprises at least 96% of the length of the mature polypeptide, such as at least 945 amino acids of SEQ ID NO: 43, at least 974 amino acids of SEQ ID NO: 46, at least 958 amino acids of SEQ ID NO: 49, at least 943 amino acids of SEQ ID NO: 52, at least 958 amino acids of SEQ ID NO:

55, at least 966 amino acids of SEQ ID NO: 58, at least 948 amino acids of SEQ ID NO: 61, at least 923 amino acids of SEQ ID NO: 70, at least 960 amino acids of SEQ ID NO: 73, at least 960 amino acids of SEQ ID NO: 76 or at least 954 amino acids of SEQ ID NO: 79.

In one aspect, the fragment has beta-galactosidase activity and comprises at least 98% of the length of the mature polypeptide, such as at least 965 amino acids of SEQ ID NO: 43, at least 994 amino acids of SEQ ID NO: 46, at least 978 amino acids of SEQ ID NO: 49, at least 963 amino acids of SEQ ID NO: 52, at least 978 amino acids of SEQ ID NO: 55, at least 986 amino acids of SEQ ID NO: 58, at least 968 amino acids of SEQ ID NO: 61, at least 942 amino acids of SEQ ID NO: 70, at least 980 amino acids of SEQ ID NO: 73, at least 980 amino acids of SEQ ID NO: 76 or at least 974 amino acids of SEQ ID NO: 79.

In one aspect, the fragment has beta-galactosidase activity and comprises at least 99% of the length of the mature polypeptide, such as at least 975 amino acids of SEQ ID NO: 43, at least 1004 amino acids of SEQ ID NO: 46, at least 988 amino acids of SEQ ID NO: 49, at least 973 amino acids of SEQ ID NO: 52, at least 988 amino acids of SEQ ID NO: 55, at least 996 amino acids of SEQ ID NO: 58, at least 978 amino acids of SEQ ID NO: 61, at least 952 amino acids of SEQ ID NO: 70, at least 990 amino acids of SEQ ID NO: 73, at least 990 amino acids of SEQ ID NO: 76 or at least 984 amino acids of SEQ ID NO: 79.

Galactanase: The term "galactanase", also called endo-1,4-β-galactanase, means an arabinogalactan endo-β-1,4-galactanase (E.C. 3.2.1.89) that catalyses the hydrolysis of (1-4)-β-D-galactosidic linkages in type I arabinogalactans. Galactanase activity can be determined by reducing ends using the colorimetric assay developed by Lever (Analytical Biochemistry 47, 273-279, 1972). The galactanase produces reducing end sugars which react with PAH BAH generating an increase of colour which is proportional to the enzyme activity under the conditions used in the assay. A detailed assay can be found in the galactanase assay as described herein.

The galactanases of the present invention have at least 60%, such as at least 70%, at least 75%, at least 80%, at least 85%, at least 90%, at least 95% or at least 100% of the galactanase activity of the polypeptide of SEQ ID NO: 3.

Host cell: The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

Isolated: The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance).

Mature polypeptide: The term "mature polypeptide" means a polypeptide in its final form following translation and any post-translational modifications, such as N-terminal processing, C-terminal truncation, glycosylation, phosphorylation, etc.

In one aspect, the mature polypeptide is amino acids 1 to 316 of SEQ ID NO: 2 and amino acids −32 to −1 of SEQ ID NO: 2 are a signal peptide. In another aspect, the mature polypeptide is amino acids 1 to 316 of SEQ ID NO: 3. In an alternative aspect, the mature polypeptide is amino acids 1 to 324 of SEQ ID NO: 4.

In one aspect, the mature polypeptide is amino acids 1 to 318 of SEQ ID NO: 6 and amino acids −29 to −1 of SEQ ID NO: 6 are a signal peptide. In another aspect, the mature polypeptide is amino acids 1 to 318 of SEQ ID NO: 7. In an alternative aspect, the mature polypeptide is amino acids 1 to 326 of SEQ ID NO: 8.

In one aspect, the mature polypeptide is amino acids 1 to 316 of SEQ ID NO: 10 and amino acids −33 to −1 of SEQ ID NO: 10 are a signal peptide. In another aspect, the mature polypeptide is amino acids 1 to 316 of SEQ ID NO: 11. In an alternative aspect, the mature polypeptide is amino acids 1 to 324 of SEQ ID NO: 12.

In one aspect, the mature polypeptide is amino acids 1 to 316 of SEQ ID NO: 14 and amino acids −35 to −1 of SEQ ID NO: 14 are a signal peptide. In another aspect, the mature polypeptide is amino acids 1 to 316 of SEQ ID NO: 15. In an alternative aspect, the mature polypeptide is amino acids 1 to 324 of SEQ ID NO: 16.

In one aspect, the mature polypeptide is amino acids 1 to 316 of SEQ ID NO: 18 and amino acids −31 to −1 of SEQ ID NO: 18 are a signal peptide. In another aspect, the mature polypeptide is amino acids 1 to 316 of SEQ ID NO: 19. In an alternative aspect, the mature polypeptide is amino acids 1 to 324 of SEQ ID NO: 20.

In one aspect, the mature polypeptide is amino acids 1 to 316 of SEQ ID NO: 22 and amino acids −33 to −1 of SEQ ID NO: 22 are a signal peptide. In another aspect, the mature polypeptide is amino acids 1 to 316 of SEQ ID NO: 23. In an alternative aspect, the mature polypeptide is amino acids 1 to 324 of SEQ ID NO: 24.

In one aspect, the mature polypeptide is amino acids 1 to 516 of SEQ ID NO: 26 and amino acids −29 to −1 of SEQ ID NO: 26 are a signal peptide. In another aspect, the mature polypeptide is amino acids 1 to 516 of SEQ ID NO: 27. In an alternative aspect, the mature polypeptide is amino acids 1 to 524 of SEQ ID NO: 28.

In one aspect, the mature polypeptide is amino acids 1 to 317 of SEQ ID NO: 30 and amino acids −33 to −1 of SEQ ID NO: 30 are a signal peptide. In another aspect, the mature polypeptide is amino acids 1 to 317 of SEQ ID NO: 31. In an alternative aspect, the mature polypeptide is amino acids 1 to 325 of SEQ ID NO: 32.

In one aspect, the mature polypeptide is amino acids 1 to 316 of SEQ ID NO: 34 and amino acids −33 to −1 of SEQ ID NO: 34 are a signal peptide. In another aspect, the mature polypeptide is amino acids 1 to 316 of SEQ ID NO: 35. In an alternative aspect, the mature polypeptide is amino acids 1 to 324 of SEQ ID NO: 36.

In one aspect, the mature polypeptide is amino acids 1 to 316 of SEQ ID NO: 38 and amino acids −31 to −1 of SEQ ID NO: 38 are a signal peptide. In another aspect, the mature polypeptide is amino acids 1 to 316 of SEQ ID NO: 39. In an alternative aspect, the mature polypeptide is amino acids 1 to 324 of SEQ ID NO: 40.

In one aspect, the mature polypeptide is amino acids 1 to 985 of SEQ ID NO: 42 and amino acids −23 to −1 of SEQ ID NO: 42 are a signal peptide. In another aspect, the mature polypeptide is amino acids 1 to 985 of SEQ ID NO: 43.

In one aspect, the mature polypeptide is amino acids 1 to 1015 of SEQ ID NO: 45 and amino acids −20 to −1 of SEQ ID NO: 45 are a signal peptide. In another aspect, the mature polypeptide is amino acids 1 to 1015 of SEQ ID NO: 46.

In one aspect, the mature polypeptide is amino acids 1 to 998 of SEQ ID NO: 48 and amino acids −22 to −1 of SEQ ID NO: 48 are a signal peptide. In another aspect, the mature polypeptide is amino acids 1 to 998 of SEQ ID NO: 49.

In one aspect, the mature polypeptide is amino acids 1 to 983 of SEQ ID NO: 51 and amino acids −27 to −1 of SEQ ID NO: 51 are a signal peptide. In another aspect, the mature polypeptide is amino acids 1 to 983 of SEQ ID NO: 52.

In one aspect, the mature polypeptide is amino acids 1 to 998 of SEQ ID NO: 54 and amino acids −22 to −1 of SEQ ID NO: 54 are a signal peptide. In another aspect, the mature polypeptide is amino acids 1 to 998 of SEQ ID NO: 55.

In one aspect, the mature polypeptide is amino acids 1 to 1007 of SEQ ID NO: 57 and amino acids −20 to −1 of SEQ ID NO: 57 are a signal peptide. In another aspect, the mature polypeptide is amino acids 1 to 1007 of SEQ ID NO: 58.

In one aspect, the mature polypeptide is amino acids 1 to 988 of SEQ ID NO: 60 and amino acids −23 to −1 of SEQ ID NO: 60 are a signal peptide. In another aspect, the mature polypeptide is amino acids 1 to 988 of SEQ ID NO: 61.

In one aspect, the mature polypeptide is amino acids 1 to 962 of SEQ ID NO: 69 and amino acids −21 to −1 of SEQ ID NO: 69 are a signal peptide. In another aspect, the mature polypeptide is amino acids 1 to 962 of SEQ ID NO: 70.

In one aspect, the mature polypeptide is amino acids 1 to 1000 of SEQ ID NO: 72 and amino acids −20 to −1 of SEQ ID NO: 72 are a signal peptide. In another aspect, the mature polypeptide is amino acids 1 to 1000 of SEQ ID NO: 73.

In one aspect, the mature polypeptide is amino acids 1 to 1000 of SEQ ID NO: 75 and amino acids −20 to −1 of SEQ ID NO: 75 are a signal peptide. In another aspect, the mature polypeptide is amino acids 1 to 1000 of SEQ ID NO: 76.

In one aspect, the mature polypeptide is amino acids 1 to 994 of SEQ ID NO: 78 and amino acids −20 to −1 of SEQ ID NO: 78 are a signal peptide. In another aspect, the mature polypeptide is amino acids 1 to 994 of SEQ ID NO: 79.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

Mature polypeptide coding sequence: The term "mature polypeptide coding sequence" means a polynucleotide that encodes a mature polypeptide having beta-galactosidase or galactanase activity.

Nucleic acid construct: The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

Nutrient Digestibility: The term "nutrient digestibility" means the fraction of a nutrient that disappears from the gastro-intestinal tract or a specified segment of the gastro-intestinal tract, e.g. the small intestine. Nutrient digestibility may be measured as the difference between what is administered to the subject and what. comes out in the faeces of the subject, or between what is administered to the subject and what remains in the digesta on a specified segment of the gastro intestinal tract, e.g. the ileum.

Nutrient digestibility as used herein may be measured by the difference between the intake of a nutrient and the excreted nutrient by means of the total collection of excreta during a period of time; or with the use of an inert marker that is not absorbed by the animal, and allows the researcher calculating the amount of nutrient that disappeared in the entire gastro-intestinal tract or a segment of the gastro-intestinal tract. Such an inert marker may be titanium dioxide, chromic oxide or acid insoluble ash. Digestibility may be expressed as a percentage of the nutrient in the feed, or as mass units of digestible nutrient per mass units of nutrient in the feed. Nutrient digestibility as used herein encompasses starch digestibility, fat digestibility, protein digestibility, and amino acid digestibility.

Energy digestibility as used herein means the gross energy of the feed consumed minus the gross energy of the faeces or the gross energy of the feed consumed minus the gross energy of the remaining digesta on a specified segment of the gastro-intestinal tract of the animal, e.g. the ileum. Metabolizable energy as used herein refers to apparent metabolizable energy and means the gross energy of the feed consumed minus the gross energy contained in the faeces, urine, and gaseous products of digestion. Energy digestibility and metabolizable energy may be measured as the difference between the intake of gross energy and the gross energy excreted in the faeces or the digesta present in specified segment of the gastro-intestinal tract using the same methods to measure the digestibility of nutrients, with appropriate corrections for nitrogen excretion to calculate metabolizable energy of feed.

Operably linked: The term "operably linked" means a configuration in which a control sequence is placed at an appropriate position relative to the coding sequence of a polynucleotide such that the control sequence directs expression of the coding sequence.

Release x g galactose per kg soybean meal: The term "release x g galactose per kg soybean meal" means the amount of galactose in grams which is released into the supernatant after soybean meal has been incubation with an enzyme. For the purpose of the present invention, the release of galactose per kg soybean meal may be determined when performed under the reaction conditions 20 mg galactanase and 20 mg beta-galactosidase per kg soybean meal in 10% w/v 0.1 M citric acid-phosphate buffer pH 6.5 incubating at 40° C. for 2 hours as described in the Galactose SBM Assay herein.

In a more detailed embodiment, a 10 w/v % slurry of soybean meal is prepared from soybean meal milled to a 0.5 mm particle size and 0.1 M citric acid-phosphate buffer, pH 6.5±0.05. The incubation vessels with the 10 w/v % slurry of soybean meal are heated to a stable temperature of 40±2° C. while stirring. When a stable temperature had been achieved, the six D-(+)-galactose standards are added to the incubation vessels to in-vessel concentrations of 5, 2.5, 1.25, 0.625, 0.313 and 0.157 mg galactose per mL incubation volume. Each standard is incubated in duplicates. The diluted enzymes are then added to their respective incubation vessels in the volumes required to reach their desired concentrations (in mg EP/kg soybean meal). Each enzyme treatment is incubated in triplicates. Additionally, two times three incubation vessels are included without standards or enzyme treatments as blank treatments to obtain the baseline galactose concentration in the soybean meal slurry. The incubation vessels are incubated at 40±2° C., while stirring for 2 hours. After incubation the vessels are centrifuged at 1500 g at 5° C. for 15 minutes. The supernatants are then analyzed in an assay based on the Raffinose/Galactose kit from Megazyme (product name K-RAFGA) and the concentration of galactose is then calculated as described in the Galactose SBM Assay herein.

Plant based material: The term "plant based material" means that the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Sequence Identity: The relatedness between two amino acid sequences or between two nucleotide sequences is described by the parameter "sequence identity".

For purposes of the present invention, the degree of sequence identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends Genet.* 16: 276-277), preferably version 3.0.0 or later. Version 6.1.0 was used. The optional parameters used are gap open penalty of 10, gap extension penalty of 0.5, and the EBLOSUM62 (EMBOSS version of BLOSUM62) substitution matrix. The output of Needle labelled "longest identity" (obtained using the –nobrief option) is used as the percent identity and is calculated as follows:

(Identical Residues×100)/(Length of Alignment–
Total Number of Gaps in Alignment)

For purposes of the present invention, the degree of sequence identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. Version 6.1.0 was used. The optional parameters used are gap open penalty of 10, gap extension penalty of 0.5, and the EDNAFULL (EMBOSS version of NCBI NUC4.4) substitution matrix. The output of Needle labelled "longest identity" (obtained using the –nobrief option) is used as the percent identity and is calculated as follows:

(Identical Deoxyribonucleotides×100)/(Length of
Alignment–Total Number of Gaps in Alignment)

Subsequence: The term "subsequence" means a polynucleotide having one or more (e.g., several) nucleotides absent from the 5' and/or 3' end of a mature polypeptide coding sequence; wherein the subsequence encodes a fragment having beta-galactosidase or galactanase activity.

Substantially pure polypeptide: The term "substantially pure polypeptide" means a preparation that contains at most 10%, at most 8%, at most 6%, at most 5%, at most 4%, at most 3%, at most 2%, at most 1%, and at most 0.5% by weight of other polypeptide material with which it is natively or recombinantly associated. Preferably, the polypeptide is at least 92% pure, e.g., at least 94% pure, at least 95% pure, at least 96% pure, at least 97% pure, at least 98% pure, at least 99%, at least 99.5% pure, and 100% pure by weight of the total polypeptide material present in the preparation. The polypeptides of the present invention are preferably in a substantially pure form. This can be accomplished, for example, by preparing the polypeptide by well-known recombinant methods or by classical purification methods.

Variant: The term "variant" means a polypeptide having galactanase or beta-galactosidase activity comprising an alteration, i.e., a substitution, insertion, and/or deletion of one or more (several) amino acid residues at one or more (several) positions. A substitution means a replacement of an amino acid occupying a position with a different amino acid; a deletion means removal of an amino acid occupying a position; and an insertion means adding 1-3 amino acids adjacent to an amino acid occupying a position. In one aspect, the galactanase variants of the present invention have at least 60%, such as at least 70%, at least 75%, at least 80%, at least 85%, at least 90%, at least 95% or at least 100% of the galactanase activity of the polypeptide of SEQ ID NO: 3. In one aspect, the beta-galactosidase variants of the present invention have at least 60%, such as at least 70%, at least 75%, at least 80%, at least 85%, at least 90%, at least 95% or at least 100% of the beta-galactosidase activity of the polypeptide of SEQ ID NO: 43.

Nomenclature

For purposes of the present invention, the nomenclature [Y/F] means that the amino acid at this position may be a tyrosine (Try, Y) or a phenylalanine (Phe, F). Likewise the nomenclature [V/G/A/I] means that the amino acid at this position may be a valine (Val, V), glycine (Gly, G), alanine (Ala, A) or isoleucine (Ile, I), and so forth for other combinations as described herein. Unless otherwise limited further, the amino acid X is defined such that it may be any of the 20 natural amino acids.

DETAILED DESCRIPTION OF THE INVENTION

Beta-galactosidase is a glycoside hydrolase enzyme that hydrolyses the terminal non-reducing β-D-galactose residues in β-D-galactosides, such as lactose, oligosaccharides, glycolipids, and glycoproteins that is present in, e.g. legumes, vegetables, grains, cereals and the like. Galactanase is a glycoside hydrolase enzyme that hydrolyses the endo galactosidic linkages in type I arabinogalactans.

The inventors have found that beta-galactosidases from glycoside hydrolase family 35 (herein referred to as GH35) in combination with one or more GH53 galactanases are surprisingly good at releasing galactose by degrading galactan polymers found in the pectin of legumes, such as soybean. The use of a single enzyme class does not result in a significant release of galactose.

The degradation of galactan can be measured as the amount of galactose released into the supernatant when e.g. soybean meal is treated with a GH35 beta-galactosidases and a GH53 galactanase. Increased amounts of solubilisation will result in more galactose being released which can be detected using e.g. the Galactose SBM Assay method as described herein.

Compositions Comprising GH35 Beta-Galactosidases and GH53 Galactanases

Thus in a first aspect, the invention relates to a composition comprising one or more GH53 polypeptides having galactanase activity and one or more GH35 polypeptides having beta-galactosidase activity.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65). In one embodiment, the GH53 polypeptide comprises the motif WADP[A/G]xQxKPxAW (SEQ ID NO: 66). In a preferred embodiment, the GH53 polypeptide comprises the motifs GV[T/M]PD[W/M]VQ[I/V]GNE (SEQ ID NO: 65) and WADP[A/G]xQxKPxAW (SEQ ID NO: 66).

In a further embodiment, the GH53 polypeptide having galactanase activity is obtained or obtainable from the taxonomic family Aspergillaceae.

In one embodiment, the GH35 polypeptide comprises the motif Y[Y/F][D/Q][Y/H/W]F (SEQ ID NO: 80). In one embodiment, the GH35 polypeptide comprises the motif K[Y/F][Y/S]ETK (SEQ ID NO: 81). In a preferred embodiment, the GH35 polypeptide comprises the motifs Y[Y/F][D/Q][Y/H/W]F (SEQ ID NO: 80) and K[Y/F][Y/S]ETK (SEQ ID NO: 81).

In a further embodiment, the GH35 polypeptide having beta-galactosidase activity is obtained or obtainable from the taxonomic family Paenibacillaceae.

In another embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein:

(a) the GH53 polypeptide comprises the motif GV[T/M]PD[W/M]VQ[I/V]GNE (SEQ ID NO: 65) and/or the motif WADP[A/G]xQxKPxAW (SEQ ID NO: 66); and (b) the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In a further embodiment, the GH53 polypeptide having galactanase activity is obtained or obtainable from the taxonomic family Paenibacillaceae.

In an embodiment, the invention relates to a composition comprising one or more GH53 polypeptides having galactanase activity and one or more GH35 polypeptides having beta-galactosidase activity, wherein:

(a) the GH35 polypeptide comprises the motif Y[Y/F][D/Q][Y/H/W]F (SEQ ID NO: 80) and/or the motif K[Y/F][Y/S]ETK (SEQ ID NO: 81); and (b) the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In a further embodiment, the GH53 polypeptide having galactanase activity is obtained or obtainable from the taxonomic family Paenibacillaceae.

In an embodiment, the invention relates to a composition comprising one or more GH53 polypeptides having galactanase activity and one or more GH35 polypeptides having beta-galactosidase activity, wherein:

(a) the GH53 polypeptide comprises the motif GV[T/M]PD[W/M]VQ[I/V]GNE (SEQ ID NO: 65) and/or the motif WADP[A/G]xQxKPxAW (SEQ ID NO: 66);

(b) the GH35 polypeptide comprises the motif Y[Y/F][D/Q][Y/H/W]F (SEQ ID NO: 80) and/or the motif K[Y/F][Y/S]ETK (SEQ ID NO: 81); and (c) the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In a further embodiment, the GH53 polypeptide having galactanase activity is obtained or obtainable from the taxonomic family Paenibacillaceae.

In an embodiment, the invention relates to a composition comprising one or more GH53 polypeptides having galactanase activity and one or more GH35 polypeptides having beta-galactosidase activity, wherein the GH53 polypeptide is selected from the group consisting of:
- (a) a polypeptide having at least 80% sequence identity to the polypeptide of SEQ ID NO: 3;
- (b) a polypeptide having at least 80% sequence identity to the polypeptide of SEQ ID NO: 7;
- (c) a polypeptide having at least 80% sequence identity to the polypeptide of SEQ ID NO: 11;
- (d) a polypeptide having at least 80% sequence identity to the polypeptide of SEQ ID NO: 15;
- (e) a polypeptide having at least 80% sequence identity to the polypeptide of SEQ ID NO: 19;
- (f) a polypeptide having at least 80% sequence identity to the polypeptide of SEQ ID NO: 23;
- (g) a polypeptide having at least 80% sequence identity to the polypeptide of SEQ ID NO: 27;
- (h) a polypeptide having at least 80% sequence identity to the polypeptide of SEQ ID NO: 31;
- (i) a polypeptide having at least 80% sequence identity to the polypeptide of SEQ ID NO: 35;
- (j) a polypeptide having at least 80% sequence identity to the polypeptide of SEQ ID NO: 39;
- (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
- (l) a polypeptide comprising the polypeptide of (a), (b), (c), (d), (e), (f), (g), (h), (i), (j) or (k) and a N-terminal and/or C-terminal His-tag and/or HQ-tag;
- (m) a polypeptide comprising the polypeptide of (a), (b), (c), (d), (e), (f), (g), (h), (i), (j) or (k) and a N-terminal and/or C-terminal extension of between 1 and 10 amino acids; and
- (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH53 polypeptide is selected from the group consisting of:
- (a) a polypeptide having at least 85% sequence identity to the polypeptide of SEQ ID NO: 3;
- (b) a polypeptide having at least 85% sequence identity to the polypeptide of SEQ ID NO: 7;
- (c) a polypeptide having at least 85% sequence identity to the polypeptide of SEQ ID NO: 11;
- (d) a polypeptide having at least 85% sequence identity to the polypeptide of SEQ ID NO: 15;
- (e) a polypeptide having at least 85% sequence identity to the polypeptide of SEQ ID NO: 19;
- (f) a polypeptide having at least 85% sequence identity to the polypeptide of SEQ ID NO: 23;
- (g) a polypeptide having at least 85% sequence identity to the polypeptide of SEQ ID NO: 27;
- (h) a polypeptide having at least 85% sequence identity to the polypeptide of SEQ ID NO: 31;
- (i) a polypeptide having at least 85% sequence identity to the polypeptide of SEQ ID NO: 35;
- (j) a polypeptide having at least 85% sequence identity to the polypeptide of SEQ ID NO: 39;
- (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
- (l) a polypeptide comprising the polypeptide of (a), (b), (c), (d), (e), (f), (g), (h), (i), (j) or (k) and a N-terminal and/or C-terminal His-tag and/or HQ-tag;
- (m) a polypeptide comprising the polypeptide of (a), (b), (c), (d), (e), (f), (g), (h), (i), (j) or (k) and a N-terminal and/or C-terminal extension of between 1 and 10 amino acids; and
- (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH53 polypeptide is selected from the group consisting of:
  (a) a polypeptide having at least 90% sequence identity to the polypeptide of SEQ ID NO: 3;
  (b) a polypeptide having at least 90% sequence identity to the polypeptide of SEQ ID NO: 7;
  (c) a polypeptide having at least 90% sequence identity to the polypeptide of SEQ ID NO: 11;
  (d) a polypeptide having at least 90% sequence identity to the polypeptide of SEQ ID NO: 15;
  (e) a polypeptide having at least 90% sequence identity to the polypeptide of SEQ ID NO: 19;
  (f) a polypeptide having at least 90% sequence identity to the polypeptide of SEQ ID NO: 23;
  (g) a polypeptide having at least 90% sequence identity to the polypeptide of SEQ ID NO: 27;
  (h) a polypeptide having at least 90% sequence identity to the polypeptide of SEQ ID NO: 31;
  (i) a polypeptide having at least 90% sequence identity to the polypeptide of SEQ ID NO: 35;
  (j) a polypeptide having at least 90% sequence identity to the polypeptide of SEQ ID NO: 39;
  (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (l) a polypeptide comprising the polypeptide of (a), (b), (c), (d), (e), (f), (g), (h), (i), (j) or (k) and a N-terminal and/or C-terminal His-tag and/or HQ-tag;
  (m) a polypeptide comprising the polypeptide of (a), (b), (c), (d), (e), (f), (g), (h), (i), (j) or (k) and a N-terminal and/or C-terminal extension of between 1 and 10 amino acids; and
  (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH53 polypeptide is selected from the group consisting of:
  (a) a polypeptide having at least 95% sequence identity to the polypeptide of SEQ ID NO: 3;
  (b) a polypeptide having at least 95% sequence identity to the polypeptide of SEQ ID NO: 7;
  (c) a polypeptide having at least 95% sequence identity to the polypeptide of SEQ ID NO: 11;
  (d) a polypeptide having at least 95% sequence identity to the polypeptide of SEQ ID NO: 15;
  (e) a polypeptide having at least 95% sequence identity to the polypeptide of SEQ ID NO: 19;
  (f) a polypeptide having at least 95% sequence identity to the polypeptide of SEQ ID NO: 23;
  (g) a polypeptide having at least 95% sequence identity to the polypeptide of SEQ ID NO: 27;
  (h) a polypeptide having at least 95% sequence identity to the polypeptide of SEQ ID NO: 31;
  (i) a polypeptide having at least 95% sequence identity to the polypeptide of SEQ ID NO: 35;
  (j) a polypeptide having at least 95% sequence identity to the polypeptide of SEQ ID NO: 39;
  (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
  (l) a polypeptide comprising the polypeptide of (a), (b), (c), (d), (e), (f), (g), (h), (i), (j) or (k) and a N-terminal and/or C-terminal His-tag and/or HQ-tag;
  (m) a polypeptide comprising the polypeptide of (a), (b), (c), (d), (e), (f), (g), (h), (i), (j) or (k) and a N-terminal and/or C-terminal extension of between 1 and 10 amino acids; and (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH35 polypeptide is selected from the group consisting of:
(a) a polypeptide having at least 80% sequence identity to the polypeptide of SEQ ID NO: 43;
(b) a polypeptide having at least 80% sequence identity to the polypeptide of SEQ ID NO: 46;
(c) a polypeptide having at least 80% sequence identity to the polypeptide of SEQ ID NO: 49;
(d) a polypeptide having at least 80% sequence identity to the polypeptide of SEQ ID NO: 52;
(e) a polypeptide having at least 80% sequence identity to the polypeptide of SEQ ID NO: 55;
(f) a polypeptide having at least 80% sequence identity to the polypeptide of SEQ ID NO: 58;
(g) a polypeptide having at least 80% sequence identity to the polypeptide of SEQ ID NO: 61;
(h) a polypeptide having at least 80% sequence identity to the polypeptide of SEQ ID NO: 70;
(i) a polypeptide having at least 80% sequence identity to the polypeptide of SEQ ID NO: 73;
(j) a polypeptide having at least 80% sequence identity to the polypeptide of SEQ ID NO: 76;
(k) a polypeptide having at least 80% sequence identity to the polypeptide of SEQ ID NO: 79;
(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(m) a polypeptide comprising the polypeptide of (a), (b), (c), (d), (e), (f), (g), (h), (i), (j), (k) or (l) and a N-terminal and/or C-terminal His-tag and/or HQ-tag;
(n) a polypeptide comprising the polypeptide of (a), (b), (c), (d), (e), (f), (g), (h), (i), (j), (k) or (l) and a N-terminal and/or C-terminal extension of between 1 and 10 amino acids; and
(o) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH35 polypeptide is selected from the group consisting of:
(a) a polypeptide having at least 85% sequence identity to the polypeptide of SEQ ID NO: 43;
(b) a polypeptide having at least 85% sequence identity to the polypeptide of SEQ ID NO: 46;
(c) a polypeptide having at least 85% sequence identity to the polypeptide of SEQ ID NO: 49;
(d) a polypeptide having at least 85% sequence identity to the polypeptide of SEQ ID NO: 52;
(e) a polypeptide having at least 85% sequence identity to the polypeptide of SEQ ID NO: 55;
(f) a polypeptide having at least 85% sequence identity to the polypeptide of SEQ ID NO: 58;
(g) a polypeptide having at least 85% sequence identity to the polypeptide of SEQ ID NO: 61;
(h) a polypeptide having at least 85% sequence identity to the polypeptide of SEQ ID NO: 70;

(i) a polypeptide having at least 85% sequence identity to the polypeptide of SEQ ID NO: 73;

(j) a polypeptide having at least 85% sequence identity to the polypeptide of SEQ ID NO: 76;

(k) a polypeptide having at least 85% sequence identity to the polypeptide of SEQ ID NO: 79;

(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(m) a polypeptide comprising the polypeptide of (a), (b), (c), (d), (e), (f), (g), (h), (i), (j), (k) or (l) and a N-terminal and/or C-terminal His-tag and/or HQ-tag;

(n) a polypeptide comprising the polypeptide of (a), (b), (c), (d), (e), (f), (g), (h), (i), (j), (k) or (l) and a N-terminal and/or C-terminal extension of between 1 and 10 amino acids; and (o) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[IN]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH35 polypeptide is selected from the group consisting of:

(a) a polypeptide having at least 90% sequence identity to the polypeptide of SEQ ID NO: 43;

(b) a polypeptide having at least 90% sequence identity to the polypeptide of SEQ ID NO: 46;

(c) a polypeptide having at least 90% sequence identity to the polypeptide of SEQ ID NO: 49;

(d) a polypeptide having at least 90% sequence identity to the polypeptide of SEQ ID NO: 52;

(e) a polypeptide having at least 90% sequence identity to the polypeptide of SEQ ID NO: 55;

(f) a polypeptide having at least 90% sequence identity to the polypeptide of SEQ ID NO: 58;

(g) a polypeptide having at least 90% sequence identity to the polypeptide of SEQ ID NO: 61;

(h) a polypeptide having at least 90% sequence identity to the polypeptide of SEQ ID NO: 70;

(i) a polypeptide having at least 90% sequence identity to the polypeptide of SEQ ID NO: 73;

(j) a polypeptide having at least 90% sequence identity to the polypeptide of SEQ ID NO: 76;

(k) a polypeptide having at least 90% sequence identity to the polypeptide of SEQ ID NO: 79;

(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(m) a polypeptide comprising the polypeptide of (a), (b), (c), (d), (e), (f), (g), (h), (i), (j), (k) or (l) and a N-terminal and/or C-terminal His-tag and/or HQ-tag;

(n) a polypeptide comprising the polypeptide of (a), (b), (c), (d), (e), (f), (g), (h), (i), (j), (k) or (l) and a N-terminal and/or C-terminal extension of between 1 and 10 amino acids; and (o) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH35 polypeptide is selected from the group consisting of:
(a) a polypeptide having at least 95% sequence identity to the polypeptide of SEQ ID NO: 43;
(b) a polypeptide having at least 95% sequence identity to the polypeptide of SEQ ID NO: 46;
(c) a polypeptide having at least 95% sequence identity to the polypeptide of SEQ ID NO: 49;
(d) a polypeptide having at least 95% sequence identity to the polypeptide of SEQ ID NO: 52;
(e) a polypeptide having at least 95% sequence identity to the polypeptide of SEQ ID NO: 55;
(f) a polypeptide having at least 95% sequence identity to the polypeptide of SEQ ID NO: 58;
(g) a polypeptide having at least 95% sequence identity to the polypeptide of SEQ ID NO: 61;
(h) a polypeptide having at least 95% sequence identity to the polypeptide of SEQ ID NO: 70;
(i) a polypeptide having at least 95% sequence identity to the polypeptide of SEQ ID NO: 73;
(j) a polypeptide having at least 95% sequence identity to the polypeptide of SEQ ID NO: 76;
(k) a polypeptide having at least 95% sequence identity to the polypeptide of SEQ ID NO: 79;
(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(m) a polypeptide comprising the polypeptide of (a), (b), (c), (d), (e), (f), (g), (h), (i), (j), (k) or (l) and a N-terminal and/or C-terminal His-tag and/or HQ-tag;
(n) a polypeptide comprising the polypeptide of (a), (b), (c), (d), (e), (f), (g), (h), (i), (j), (k) or (l) and a N-terminal and/or C-terminal extension of between 1 and 10 amino acids; and
(o) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH53 polypeptide is selected from the group consisting of:
(a) a polypeptide having at least 80% sequence identity to the polypeptide of SEQ ID NO: 3;
(b) a polypeptide having at least 80% sequence identity to the polypeptide of SEQ ID NO: 7;
(c) a polypeptide having at least 80% sequence identity to the polypeptide of SEQ ID NO: 11;
(d) a polypeptide having at least 80% sequence identity to the polypeptide of SEQ ID NO: 15;
(e) a polypeptide having at least 80% sequence identity to the polypeptide of SEQ ID NO: 19;
(f) a polypeptide having at least 80% sequence identity to the polypeptide of SEQ ID NO: 23;
(g) a polypeptide having at least 80% sequence identity to the polypeptide of SEQ ID NO: 27;
(h) a polypeptide having at least 80% sequence identity to the polypeptide of SEQ ID NO: 31;
(i) a polypeptide having at least 80% sequence identity to the polypeptide of SEQ ID NO: 35;
(j) a polypeptide having at least 80% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide.
and wherein the GH35 polypeptide is selected from the group consisting of:
(a) a polypeptide having at least 80% sequence identity to the polypeptide of SEQ ID NO: 43;

(b) a polypeptide having at least 80% sequence identity to the polypeptide of SEQ ID NO: 46;
(c) a polypeptide having at least 80% sequence identity to the polypeptide of SEQ ID NO: 49;
(d) a polypeptide having at least 80% sequence identity to the polypeptide of SEQ ID NO: 52;
(e) a polypeptide having at least 80% sequence identity to the polypeptide of SEQ ID NO: 55;
(f) a polypeptide having at least 80% sequence identity to the polypeptide of SEQ ID NO: 58;
(g) a polypeptide having at least 80% sequence identity to the polypeptide of SEQ ID NO: 61;
(h) a polypeptide having at least 80% sequence identity to the polypeptide of SEQ ID NO: 70;
(i) a polypeptide having at least 80% sequence identity to the polypeptide of SEQ ID NO: 73;
(j) a polypeptide having at least 80% sequence identity to the polypeptide of SEQ ID NO: 76;
(k) a polypeptide having at least 80% sequence identity to the polypeptide of SEQ ID NO: 79;
(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(m) a polypeptide comprising the polypeptide of (a), (b), (c), (d), (e), (f), (g), (h), (i), (j), (k) or (l) and a N-terminal and/or C-terminal His-tag and/or HQ-tag;
(n) a polypeptide comprising the polypeptide of (a), (b), (c), (d), (e), (f), (g), (h), (i), (j), (k) or (l) and a N-terminal and/or C-terminal extension of between 1 and 10 amino acids; and
(o) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH53 polypeptide is selected from the group consisting of:
(a) a polypeptide having at least 85% sequence identity to the polypeptide of SEQ ID NO: 3;
(b) a polypeptide having at least 85% sequence identity to the polypeptide of SEQ ID NO: 7;
(c) a polypeptide having at least 85% sequence identity to the polypeptide of SEQ ID NO: 11;
(d) a polypeptide having at least 85% sequence identity to the polypeptide of SEQ ID NO: 15;
(e) a polypeptide having at least 85% sequence identity to the polypeptide of SEQ ID NO: 19;
(f) a polypeptide having at least 85% sequence identity to the polypeptide of SEQ ID NO: 23;
(g) a polypeptide having at least 85% sequence identity to the polypeptide of SEQ ID NO: 27;
(h) a polypeptide having at least 85% sequence identity to the polypeptide of SEQ ID NO: 31;
(i) a polypeptide having at least 85% sequence identity to the polypeptide of SEQ ID NO: 35;
(j) a polypeptide having at least 85% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide.
and wherein the GH35 polypeptide is selected from the group consisting of:
(a) a polypeptide having at least 85% sequence identity to the polypeptide of SEQ ID NO: 43;
(b) a polypeptide having at least 85% sequence identity to the polypeptide of SEQ ID NO: 46;
(c) a polypeptide having at least 85% sequence identity to the polypeptide of SEQ ID NO: 49;
(d) a polypeptide having at least 85% sequence identity to the polypeptide of SEQ ID NO: 52;
(e) a polypeptide having at least 85% sequence identity to the polypeptide of SEQ ID NO: 55;
(f) a polypeptide having at least 85% sequence identity to the polypeptide of SEQ ID NO: 58;

29

(g) a polypeptide having at least 85% sequence identity to the polypeptide of SEQ ID NO: 61;
(h) a polypeptide having at least 85% sequence identity to the polypeptide of SEQ ID NO: 70;
(i) a polypeptide having at least 85% sequence identity to the polypeptide of SEQ ID NO: 73;
(j) a polypeptide having at least 85% sequence identity to the polypeptide of SEQ ID NO: 76;
(k) a polypeptide having at least 85% sequence identity to the polypeptide of SEQ ID NO: 79;
(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(m) a polypeptide comprising the polypeptide of (a), (b), (c), (d), (e), (f), (g), (h), (i), (j), (k) or (l) and a N-terminal and/or C-terminal His-tag and/or HQ-tag;
(n) a polypeptide comprising the polypeptide of (a), (b), (c), (d), (e), (f), (g), (h), (i), (j), (k) or (l) and a N-terminal and/or C-terminal extension of between 1 and 10 amino acids; and
(o) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH53 polypeptide is selected from the group consisting of:

30

(a) a polypeptide having at least 90% sequence identity to the polypeptide of SEQ ID NO: 3;
(b) a polypeptide having at least 90% sequence identity to the polypeptide of SEQ ID NO: 7;
(c) a polypeptide having at least 90% sequence identity to the polypeptide of SEQ ID NO: 11;
(d) a polypeptide having at least 90% sequence identity to the polypeptide of SEQ ID NO: 15;
(e) a polypeptide having at least 90% sequence identity to the polypeptide of SEQ ID NO: 19;
(f) a polypeptide having at least 90% sequence identity to the polypeptide of SEQ ID NO: 23;
(g) a polypeptide having at least 90% sequence identity to the polypeptide of SEQ ID NO: 27;
(h) a polypeptide having at least 90% sequence identity to the polypeptide of SEQ ID NO: 31;
(i) a polypeptide having at least 90% sequence identity to the polypeptide of SEQ ID NO: 35;
(j) a polypeptide having at least 90% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide.

and wherein the GH35 polypeptide is selected from the group consisting of:

(a) a polypeptide having at least 90% sequence identity to the polypeptide of SEQ ID NO: 43;
(b) a polypeptide having at least 90% sequence identity to the polypeptide of SEQ ID NO: 46;
(c) a polypeptide having at least 90% sequence identity to the polypeptide of SEQ ID NO: 49;
(d) a polypeptide having at least 90% sequence identity to the polypeptide of SEQ ID NO: 52;
(e) a polypeptide having at least 90% sequence identity to the polypeptide of SEQ ID NO: 55;
(f) a polypeptide having at least 90% sequence identity to the polypeptide of SEQ ID NO: 58;
(g) a polypeptide having at least 90% sequence identity to the polypeptide of SEQ ID NO: 61;
(h) a polypeptide having at least 90% sequence identity to the polypeptide of SEQ ID NO: 70;
(i) a polypeptide having at least 90% sequence identity to the polypeptide of SEQ ID NO: 73;
(j) a polypeptide having at least 90% sequence identity to the polypeptide of SEQ ID NO: 76;
(k) a polypeptide having at least 90% sequence identity to the polypeptide of SEQ ID NO: 79;

(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(m) a polypeptide comprising the polypeptide of (a), (b), (c), (d), (e), (f), (g), (h), (i), (j), (k) or (l) and a N-terminal and/or C-terminal His-tag and/or HQ-tag;

(n) a polypeptide comprising the polypeptide of (a), (b), (c), (d), (e), (f), (g), (h), (i), (j), (k) or (l) and a N-terminal and/or C-terminal extension of between 1 and 10 amino acids; and (o) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH53 polypeptide is selected from the group consisting of:

(a) a polypeptide having at least 95% sequence identity to the polypeptide of SEQ ID NO: 3;

(b) a polypeptide having at least 95% sequence identity to the polypeptide of SEQ ID NO: 7;

(c) a polypeptide having at least 95% sequence identity to the polypeptide of SEQ ID NO: 11;

(d) a polypeptide having at least 95% sequence identity to the polypeptide of SEQ ID NO: 15;

(e) a polypeptide having at least 95% sequence identity to the polypeptide of SEQ ID NO: 19;

(f) a polypeptide having at least 95% sequence identity to the polypeptide of SEQ ID NO: 23;

(g) a polypeptide having at least 95% sequence identity to the polypeptide of SEQ ID NO: 27;

(h) a polypeptide having at least 95% sequence identity to the polypeptide of SEQ ID NO: 31;

(i) a polypeptide having at least 95% sequence identity to the polypeptide of SEQ ID NO: 35;

(j) a polypeptide having at least 95% sequence identity to the polypeptide of SEQ ID NO: 39;

(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(l) a polypeptide comprising the polypeptide of (a), (b), (c), (d), (e), (f), (g), (h), (i), (j) or (k) and a N-terminal and/or C-terminal His-tag and/or HQ-tag;

(m) a polypeptide comprising the polypeptide of (a), (b), (c), (d), (e), (f), (g), (h), (i), (j) or (k) and a N-terminal and/or C-terminal extension of between 1 and 10 amino acids; and (n) a fragment of the polypeptide of (a), (b), (c), (d), (e), (f), (g), (h), (i), (j), (k) or (l) having galactanase activity and having at least 90% of the length of the mature polypeptide.

and wherein the GH35 polypeptide is selected from the group consisting of:

(a) a polypeptide having at least 95% sequence identity to the polypeptide of SEQ ID NO: 43;

(b) a polypeptide having at least 95% sequence identity to the polypeptide of SEQ ID NO: 46;

(c) a polypeptide having at least 95% sequence identity to the polypeptide of SEQ ID NO: 49;

(d) a polypeptide having at least 95% sequence identity to the polypeptide of SEQ ID NO: 52;

(e) a polypeptide having at least 95% sequence identity to the polypeptide of SEQ ID NO: 55;

(f) a polypeptide having at least 95% sequence identity to the polypeptide of SEQ ID NO: 58;

(g) a polypeptide having at least 95% sequence identity to the polypeptide of SEQ ID NO: 61;

(h) a polypeptide having at least 95% sequence identity to the polypeptide of SEQ ID NO: 70;

(i) a polypeptide having at least 95% sequence identity to the polypeptide of SEQ ID NO: 73;

(j) a polypeptide having at least 95% sequence identity to the polypeptide of SEQ ID NO: 76;

(k) a polypeptide having at least 95% sequence identity to the polypeptide of SEQ ID NO: 79;

(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(m) a polypeptide comprising the polypeptide of (a), (b), (c), (d), (e), (f), (g), (h), (i), (j), (k) or (l) and a N-terminal and/or C-terminal His-tag and/or HQ-tag;
(n) a polypeptide comprising the polypeptide of (a), (b), (c), (d), (e), (f), (g), (h), (i), (j), (k) or (l) and a N-terminal and/or C-terminal extension of between 1 and 10 amino acids; and
(o) a fragment of the polypeptide of (a), (b), (c), (d), (e), (f), (g), (h), (i), (j), (k) or (l) having galactanase activity and having at least 90% of the length of the mature polypeptide.

In one embodiment, the composition is a granule comprising a core comprising (a) a beta-galactosidase and galactanase according to the invention, and (b) a coating consisting of one or more layer(s) surrounding the core. In one embodiment, the coating comprises a salt coating as described herein. In one embodiment, the coating comprises a wax coating as described herein. In one embodiment, the coating comprises a salt coating and a wax coating as described herein.

In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66). In one embodiment, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81).

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

In an embodiment, the invention relates to a composition comprising one or more GH53 polypeptides having galactanase activity and one or more GH35 polypeptides having beta-galactosidase activity, wherein the GH53 polypeptide is selected from the group consisting of:
(a) a polypeptide comprising or consisting of amino acids 1 to 316 of SEQ ID NO: 3;
(b) a polypeptide comprising or consisting of amino acids 1 to 318 of SEQ ID NO: 7;
(c) a polypeptide comprising or consisting of amino acids 1 to 316 of SEQ ID NO: 11;
(d) a polypeptide comprising or consisting of amino acids 1 to 316 of SEQ ID NO: 15;
(e) a polypeptide comprising or consisting of amino acids 1 to 316 of SEQ ID NO: 19;
(f) a polypeptide comprising or consisting of amino acids 1 to 316 of SEQ ID NO: 23;
(g) a polypeptide comprising or consisting of amino acids 1 to 516 of SEQ ID NO: 27;
(h) a polypeptide comprising or consisting of amino acids 1 to 317 of SEQ ID NO: 31;
(i) a polypeptide comprising or consisting of amino acids 1 to 316 of SEQ ID NO: 35;
(j) a polypeptide comprising or consisting of amino acids 1 to 316 of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid substitutions, preferably conservative substitutions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide;
and wherein the GH35 polypeptide is selected from the group consisting of:
(a) a polypeptide comprising or consisting of amino acids 1 to 985 of SEQ ID NO: 43;
(b) a polypeptide comprising or consisting of amino acids 1 to 1015 of SEQ ID NO: 46;
(c) a polypeptide comprising or consisting of amino acids 1 to 998 of SEQ ID NO: 49;
(d) a polypeptide comprising or consisting of amino acids 1 to 983 of SEQ ID NO: 52;
(e) a polypeptide comprising or consisting of amino acids 1 to 998 of SEQ ID NO: 55;
(f) a polypeptide comprising or consisting of amino acids 1 to 1007 of SEQ ID NO: 58;
(g) a polypeptide comprising or consisting of amino acids 1 to 988 of SEQ ID NO: 61;
(h) a polypeptide comprising or consisting of amino acids 1 to 962 of SEQ ID NO: 70;
(i) a polypeptide comprising or consisting of amino acids 1 to 1000 of SEQ ID NO: 73;
(j) a polypeptide comprising or consisting of amino acids 1 to 1000 of SEQ ID NO: 76;
(k) a polypeptide comprising or consisting of amino acids 1 to 994 of SEQ ID NO: 79;
(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acid substitutions, preferably conservative substitutions;
(m) a polypeptide comprising the polypeptide of (a), (b), (c), (d), (e), (f), (g), (h), (i), (j), (k) or (l) and a N-terminal and/or C-terminal His-tag and/or HQ-tag; and
(n) a polypeptide comprising the polypeptide of (a), (b), (c), (d), (e), (f), (g), (h), (i), (j), (k) or (l) and a N-terminal and/or C-terminal extension of between 1 and 10 amino acids; and (o) a fragment of the polypeptide of (a), (b), (c), (d), (e), (f), (g), (h), (i), (j), (k) or (l) having galactanase activity and having at least 90% of the length of the mature polypeptide.

In one embodiment to any part of the first aspect, the GH53 polypeptide comprises the motif GV[T/M]PD[W/M]VQ[IN]GNE (SEQ ID NO: 65) and/or the motif WADP[A/G]xQxKPxAW (SEQ ID NO: 66).

In one embodiment to any part of the first aspect, the GH53 polypeptide having galactanase activity is obtained or obtainable from the taxonomic family Aspergillaceae.

In one embodiment to any part of the first aspect, the GH35 polypeptide comprises the motif Y[Y/F][D/Q][Y/H/W]F (SEQ ID NO: 80) and/or the motif K[Y/F][Y/S]ETK (SEQ ID NO: 81).

In one embodiment to any part of the first aspect, the GH35 polypeptide having beta-galactosidase activity is obtained or obtainable from the taxonomic family Paenibacillaceae.

Combinations

Specific combinations of GH53 polypeptides having galactanase activity and GH35 polypeptides having beta-galactosidase activity of the first aspect of the invention are as follows.

In an embodiment, the composition of the invention comprises the GH53 polypeptide of SEQ ID NO: 3 and the GH35 polypeptide of SEQ ID NO: 43. In an embodiment, the composition of the invention comprises the GH53 polypeptide of SEQ ID NO: 3 and the GH35 polypeptide of SEQ ID NO: 46. In an embodiment, the composition of the invention comprises the GH53 polypeptide of SEQ ID NO: 3 and the GH35 polypeptide of SEQ ID NO: 49. In an embodiment, the composition of the invention comprises the GH53 polypeptide of SEQ ID NO: 3 and the GH35 polypeptide of SEQ ID NO: 52. In an embodiment, the composition of the invention comprises the GH53 polypeptide of SEQ ID NO: 3 and the GH35 polypeptide of SEQ ID NO: 55. In an embodiment, the composition of the invention comprises the GH53 polypeptide of SEQ ID NO: 3 and the GH35 polypeptide of SEQ ID NO: 58. In an embodiment, the composition of the invention comprises the GH53 polypeptide of SEQ ID NO: 3 and the GH35 polypeptide of SEQ ID NO: 61. In an embodiment, the composition of the invention comprises the GH53 polypeptide of SEQ ID NO: 3 and the GH35 polypeptide of SEQ ID NO: 70. In an embodiment, the composition of the invention comprises the GH53 polypeptide of SEQ ID NO: 3 and the GH35 polypeptide of SEQ ID NO: 73. In an embodiment, the composition of the invention comprises the GH53 polypeptide of SEQ ID NO: 3 and the GH35 polypeptide of SEQ ID NO: 76. In an embodiment, the composition of the invention comprises the GH53 polypeptide of SEQ ID NO: 3 and the GH35 polypeptide of SEQ ID NO: 79.

In an embodiment, the composition of the invention comprises the GH53 polypeptide of SEQ ID NO: 7 and the GH35 polypeptide of SEQ ID NO: 43. In an embodiment, the composition of the invention comprises the GH53 polypeptide of SEQ ID NO: 7 and the GH35 polypeptide of SEQ ID NO: 46. In an embodiment, the composition of the invention comprises the GH53 polypeptide of SEQ ID NO: 7 and the GH35 polypeptide of SEQ ID NO: 49. In an embodiment, the composition of the invention comprises the GH53 polypeptide of SEQ ID NO: 7 and the GH35 polypeptide of SEQ ID NO: 52. In an embodiment, the composition of the invention comprises the GH53 polypeptide of SEQ ID NO: 7 and the GH35 polypeptide of SEQ ID NO: 55. In an embodiment, the composition of the invention comprises the GH53 polypeptide of SEQ ID NO: 7 and the GH35 polypeptide of SEQ ID NO: 58. In an embodiment, the composition of the invention comprises the GH53 polypeptide of SEQ ID NO: 7 and the GH35 polypeptide of SEQ ID NO: 61. In an embodiment, the composition of the invention comprises the GH53 polypeptide of SEQ ID NO: 7 and the GH35 polypeptide of SEQ ID NO: 70. In an embodiment, the composition of the invention comprises the GH53 polypeptide of SEQ ID NO: 7 and the GH35 polypeptide of SEQ ID NO: 73. In an embodiment, the composition of the invention comprises the GH53 polypeptide of SEQ ID NO: 7 and the GH35 polypeptide of SEQ ID NO: 76. In an embodiment, the composition of the invention comprises the GH53 polypeptide of SEQ ID NO: 7 and the GH35 polypeptide of SEQ ID NO: 79.

In an embodiment, the composition of the invention comprises the GH53 polypeptide of SEQ ID NO: 11 and the GH35 polypeptide of SEQ ID NO: 43. In an embodiment, the composition of the invention comprises the GH53 polypeptide of SEQ ID NO: 11 and the GH35 polypeptide of SEQ ID NO: 46. In an embodiment, the composition of the invention comprises the GH53 polypeptide of SEQ ID NO: 11 and the GH35 polypeptide of SEQ ID NO: 49. In an embodiment, the composition of the invention comprises the GH53 polypeptide of SEQ ID NO: 11 and the GH35 polypeptide of SEQ ID NO: 52. In an embodiment, the composition of the invention comprises the GH53 polypeptide of SEQ ID NO: 11 and the GH35 polypeptide of SEQ ID NO: 55. In an embodiment, the composition of the invention comprises the GH53 polypeptide of SEQ ID NO: 11 and the GH35 polypeptide of SEQ ID NO: 58. In an embodiment, the composition of the invention comprises the GH53 polypeptide of SEQ ID NO: 11 and the GH35 polypeptide of SEQ ID NO: 61. In an embodiment, the composition of the invention comprises the GH53 polypeptide of SEQ ID NO: 11 and the GH35 polypeptide of SEQ ID NO: 70. In an embodiment, the composition of the invention comprises the GH53 polypeptide of SEQ ID NO: 11 and the GH35 polypeptide of SEQ ID NO: 73. In an embodiment, the composition of the invention comprises the GH53 polypeptide of SEQ ID NO: 11 and the GH35 polypeptide of SEQ ID NO: 76. In an embodiment, the composition of the invention comprises the GH53 polypeptide of SEQ ID NO: 11 and the GH35 polypeptide of SEQ ID NO: 79.

In an embodiment, the composition of the invention comprises the GH53 polypeptide of SEQ ID NO: 15 and the GH35 polypeptide of SEQ ID NO: 43. In an embodiment, the composition of the invention comprises the GH53 polypeptide of SEQ ID NO: 15 and the GH35 polypeptide of SEQ ID NO: 46. In an embodiment, the composition of the invention comprises the GH53 polypeptide of SEQ ID NO: 15 and the GH35 polypeptide of SEQ ID NO: 49. In an embodiment, the composition of the invention comprises the GH53 polypeptide of SEQ ID NO: 15 and the GH35 polypeptide of SEQ ID NO: 52. In an embodiment, the composition of the invention comprises the GH53 polypeptide of SEQ ID NO: 15 and the GH35 polypeptide of SEQ ID NO: 55. In an embodiment, the composition of the invention comprises the GH53 polypeptide of SEQ ID NO: 15 and the GH35 polypeptide of SEQ ID NO: 58. In an embodiment, the composition of the invention comprises the GH53 polypeptide of SEQ ID NO: 15 and the GH35 polypeptide of SEQ ID NO: 61. In an embodiment, the composition of the invention comprises the GH53 polypeptide of SEQ ID NO: 15 and the GH35 polypeptide of SEQ ID NO: 70. In an embodiment, the composition of the invention comprises the GH53 polypeptide of SEQ ID NO: 15 and the GH35 polypeptide of SEQ ID NO: 73. In an embodiment, the composition of the invention comprises the GH53 polypeptide of SEQ ID NO: 15 and the GH35 polypeptide of SEQ ID NO: 76. In an embodiment, the composition of the invention comprises the GH53 polypeptide of SEQ ID NO: 15 and the GH35 polypeptide of SEQ ID NO: 79.

In an embodiment, the composition of the invention comprises the GH53 polypeptide of SEQ ID NO: 19 and the GH35 polypeptide of SEQ ID NO: 43. In an embodiment, the composition of the invention comprises the GH53 polypeptide of SEQ ID NO: 19 and the GH35 polypeptide of SEQ ID NO: 46. In an embodiment, the composition of the invention comprises the GH53 polypeptide of SEQ ID NO: 19 and the GH35 polypeptide of SEQ ID NO: 49. In an embodiment, the composition of the invention comprises the GH53 polypeptide of SEQ ID NO: 19 and the GH35 polypeptide of SEQ ID NO: 52. In an embodiment, the composition of the invention comprises the GH53 polypeptide of SEQ ID NO: 19 and the GH35 polypeptide of SEQ ID NO: 55. In an embodiment, the composition of the invention comprises the GH53 polypeptide of SEQ ID NO: 19 and the GH35 polypeptide of SEQ ID NO: 58. In an embodiment, the composition of the invention comprises the GH53 polypeptide of SEQ ID NO: 19 and the GH35 polypeptide of SEQ ID NO: 61. In an embodiment, the composition of the invention comprises the GH53 polypeptide of SEQ ID NO: 19 and the GH35 polypeptide of SEQ ID NO: 70. In an embodiment, the composition of the invention comprises the GH53 polypeptide of SEQ ID NO: 19 and the GH35 polypeptide of SEQ ID NO: 73. In an embodiment, the composition of the invention comprises the GH53 polypeptide of SEQ ID NO: 19 and the GH35 polypeptide of SEQ ID NO: 76. In an embodiment, the composition of the invention comprises the GH53 polypeptide of SEQ ID NO: 19 and the GH35 polypeptide of SEQ ID NO: 79.

In an embodiment, the composition of the invention comprises the GH53 polypeptide of SEQ ID NO: 23 and the GH35 polypeptide of SEQ ID NO: 43. In an embodiment, the composition of the invention comprises the GH53 polypeptide of SEQ ID NO: 23 and the GH35 polypeptide of SEQ ID NO: 46. In an embodiment, the composition of the invention comprises the GH53 polypeptide of SEQ ID NO: 23 and the GH35 polypeptide of SEQ ID NO: 49. In an embodiment, the composition of the invention comprises the GH53 polypeptide of SEQ ID NO: 23 and the GH35 polypeptide of SEQ ID NO: 52. In an embodiment, the composition of the invention comprises the GH53 polypeptide of SEQ ID NO: 23 and the GH35 polypeptide of SEQ ID NO: 55. In an embodiment, the composition of the invention comprises the GH53 polypeptide of SEQ ID NO: 23 and the GH35 polypeptide of SEQ ID NO: 58. In an embodiment, the composition of the invention comprises the GH53 polypeptide of SEQ ID NO: 23 and the GH35 polypeptide of SEQ ID NO: 61. In an embodiment, the composition of the invention comprises the GH53 polypeptide of SEQ ID NO: 23 and the GH35 polypeptide of SEQ ID NO: 70. In an embodiment, the composition of the invention comprises the GH53 polypeptide of SEQ ID NO: 23 and the GH35 polypeptide of SEQ ID NO: 73. In an embodiment, the composition of the invention comprises the GH53 polypeptide of SEQ ID NO: 23 and the GH35 polypeptide of SEQ ID NO: 76. In an embodiment, the composition of the invention comprises the GH53 polypeptide of SEQ ID NO: 23 and the GH35 polypeptide of SEQ ID NO: 79.

In an embodiment, the composition of the invention comprises the GH53 polypeptide of SEQ ID NO: 27 and the GH35 polypeptide of SEQ ID NO: 43. In an embodiment, the composition of the invention comprises the GH53 polypeptide of SEQ ID NO: 27 and the GH35 polypeptide of SEQ ID NO: 46. In an embodiment, the composition of the invention comprises the GH53 polypeptide of SEQ ID NO: 27 and the GH35 polypeptide of SEQ ID NO: 49. In an embodiment, the composition of the invention comprises the GH53 polypeptide of SEQ ID NO: 27 and the GH35 polypeptide of SEQ ID NO: 52. In an embodiment, the composition of the invention comprises the GH53 polypeptide of SEQ ID NO: 27 and the GH35 polypeptide of SEQ ID NO: 55. In an embodiment, the composition of the invention comprises the GH53 polypeptide of SEQ ID NO: 27 and the GH35 polypeptide of SEQ ID NO: 58. In an embodiment, the composition of the invention comprises the GH53 polypeptide of SEQ ID NO: 27 and the GH35 polypeptide of SEQ ID NO: 61. In an embodiment, the composition of the invention comprises the GH53 polypeptide of SEQ ID NO: 27 and the GH35 polypeptide of SEQ ID NO: 70. In an embodiment, the composition of the invention comprises the GH53 polypeptide of SEQ ID NO: 27 and the GH35 polypeptide of SEQ ID NO: 73. In an embodiment, the composition of the invention comprises the GH53 polypeptide of SEQ ID NO: 27 and the GH35 polypeptide of SEQ ID NO: 76. In an embodiment, the composition of the invention comprises the GH53 polypeptide of SEQ ID NO: 27 and the GH35 polypeptide of SEQ ID NO: 79.

In an embodiment, the composition of the invention comprises the GH53 polypeptide of SEQ ID NO: 31 and the GH35 polypeptide of SEQ ID NO: 43. In an embodiment, the composition of the invention comprises the GH53 polypeptide of SEQ ID NO: 31 and the GH35 polypeptide of SEQ ID NO: 46. In an embodiment, the composition of the invention comprises the GH53 polypeptide of SEQ ID NO: 31 and the GH35 polypeptide of SEQ ID NO: 49. In an embodiment, the composition of the invention comprises the GH53 polypeptide of SEQ ID NO: 31 and the GH35 polypeptide of SEQ ID NO: 52. In an embodiment, the composition of the invention comprises the GH53 polypeptide of SEQ ID NO: 31 and the GH35 polypeptide of SEQ ID NO: 55. In an embodiment, the composition of the invention comprises the GH53 polypeptide of SEQ ID NO: 31 and the GH35 polypeptide of SEQ ID NO: 58. In an embodiment, the composition of the invention comprises the GH53 polypeptide of SEQ ID NO: 31 and the GH35 polypeptide of SEQ ID NO: 61. In an embodiment, the composition of the invention comprises the GH53 polypeptide of SEQ ID NO: 31 and the GH35 polypeptide of SEQ ID NO: 70. In an embodiment, the composition of the invention comprises the GH53 polypeptide of SEQ ID NO: 31 and the GH35 polypeptide of SEQ ID NO: 73. In an embodiment, the composition of the invention comprises the GH53 polypeptide of SEQ ID NO: 31 and the GH35 polypeptide of SEQ ID NO: 76. In an embodiment, the composition of the invention comprises the GH53 polypeptide of SEQ ID NO: 31 and the GH35 polypeptide of SEQ ID NO: 79.

In an embodiment, the composition of the invention comprises the GH53 polypeptide of SEQ ID NO: 35 and the GH35 polypeptide of SEQ ID NO: 43. In an embodiment, the composition of the invention comprises the GH53 polypeptide of SEQ ID NO: 35 and the GH35 polypeptide of SEQ ID NO: 46. In an embodiment, the composition of the invention comprises the GH53 polypeptide of SEQ ID NO: 35 and the GH35 polypeptide of SEQ ID NO: 49. In an embodiment, the composition of the invention comprises the GH53 polypeptide of SEQ ID NO: 35 and the GH35 polypeptide of SEQ ID NO: 52. In an embodiment, the composition of the invention comprises the GH53 polypeptide of SEQ ID NO: 35 and the GH35 polypeptide of SEQ ID NO: 55. In an embodiment, the composition of the invention comprises the GH53 polypeptide of SEQ ID NO: 35 and the GH35 polypeptide of SEQ ID NO: 58. In an embodiment, the composition of the invention comprises the GH53 polypeptide of SEQ ID NO: 35 and the GH35 polypeptide of SEQ ID NO: 61. In an embodiment, the composition of the invention comprises the GH53 polypeptide of SEQ ID NO: 7 and the GH35 polypeptide of SEQ ID NO: 70. In an embodiment, the composition of the invention comprises the GH53 polypeptide of SEQ ID NO: 7 and the GH35 polypeptide of SEQ ID NO: 73. In an embodiment, the composition of the invention comprises the GH53 polypeptide of SEQ ID NO: 7 and the GH35 polypeptide of SEQ ID NO: 76. In an embodiment, the composition of the invention comprises the GH53 polypeptide of SEQ ID NO: 7 and the GH35 polypeptide of SEQ ID NO: 79.

In an embodiment, the composition of the invention comprises the GH53 polypeptide of SEQ ID NO: 39 and the GH35 polypeptide of SEQ ID NO: 43. In an embodiment, the composition of the invention comprises the GH53 polypeptide of SEQ ID NO: 39 and the GH35 polypeptide of SEQ ID NO: 46. In an embodiment, the composition of the invention comprises the GH53 polypeptide of SEQ ID NO: 39 and the GH35 polypeptide of SEQ ID NO: 49. In an embodiment, the composition of the invention comprises the GH53 polypeptide of SEQ ID NO: 39 and the GH35 polypeptide of SEQ ID NO: 52. In an embodiment, the composition of the invention comprises the GH53 polypeptide of SEQ ID NO: 39 and the GH35 polypeptide of SEQ ID NO: 55. In an embodiment, the composition of the invention comprises the GH53 polypeptide of SEQ ID NO: 39 and the GH35 polypeptide of SEQ ID NO: 58. In an embodiment, the composition of the invention comprises the GH53 polypeptide of SEQ ID NO: 39 and the GH35 polypeptide of SEQ ID NO: 61. In an embodiment, the composition of the invention comprises the GH53 polypeptide of SEQ ID NO: 39 and the GH35 polypeptide of SEQ ID NO: 70. In an embodiment, the composition of the invention comprises the GH53 polypeptide of SEQ ID NO: 39 and the GH35 polypeptide of SEQ ID NO: 73. In an embodiment, the composition of the invention comprises the GH53 polypeptide of SEQ ID NO: 39 and the GH35 polypeptide of SEQ ID NO: 76. In an embodiment, the composition of the invention comprises the GH53 polypeptide of SEQ ID NO: 39 and the GH35 polypeptide of SEQ ID NO: 79.

In an embodiment, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1 M citric acid-phosphate buffer pH 6.5 incubating at 40° C. for 2 hours.

Polypeptides Having Galactanase Activity

In a second aspect, the invention relates to polypeptides having galactanase activity and having a sequence identity to the mature polypeptide of SEQ ID NO: 2 of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 2.

In one embodiment, the polypeptide preferably comprises or consists of the amino acid sequence of SEQ ID NO: 2 or an allelic variant thereof; comprises the amino acid sequence of SEQ ID NO: 2 and a N-terminal and/or C-terminal His-tag and/or HQ-tag; comprises the amino acid sequence of SEQ ID NO: 2 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 2. In another embodiment, the polypeptide comprises or consists of amino acids 1 to 316 of SEQ ID NO: 2. In an embodiment, the polypeptide has been isolated.

In a continuation of the second aspect, the invention further relates to polypeptides having galactanase activity having a sequence identity to SEQ ID NO: 3 of at least 82%. In an embodiment, the polypeptide has a sequence identity to SEQ ID NO: 3 of at least 85%. In an embodiment, the polypeptide has a sequence identity to SEQ ID NO: 3 of at least 86%. In an embodiment, the polypeptide has a sequence identity to SEQ ID NO: 3 of at least 87%. In an embodiment, the polypeptide has a sequence identity to SEQ ID NO: 3 of at least 88%. In an embodiment, the polypeptide has a sequence identity to SEQ ID NO: 3 of at least 89%. In an embodiment, the polypeptide has a sequence identity to SEQ ID NO: 3 of at least 90%. In an embodiment, the polypeptide has a sequence identity to SEQ ID NO: 3 of at least 91%. In an embodiment, the polypeptide has a sequence identity to SEQ ID NO: 3 of at least 92%. In an embodiment, the polypeptide has a sequence identity to SEQ ID NO: 3 of at least 93%. In an embodiment, the polypeptide has a sequence identity to SEQ ID NO: 3 of at least 94%. In an embodiment, the polypeptide has a sequence identity to SEQ ID NO: 3 of at least 95%. In an embodiment, the polypeptide has a sequence identity to SEQ ID NO: 3 of at least 96%. In an embodiment, the polypeptide has a sequence identity to SEQ ID NO: 3 of at least 97%. In an embodiment, the polypeptide has a sequence identity to SEQ ID NO: 3 of at least 98%. In an embodiment, the polypeptide has a sequence identity to SEQ ID NO: 3 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 3. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 4.

In one embodiment, the polypeptide preferably comprises or consists of the amino acid sequence of SEQ ID NO: 3 or an allelic variant thereof; comprises the amino acid sequence of SEQ ID NO: 3 and a N-terminal and/or C-terminal His-tag and/or HQ-tag such as SEQ ID NO: 4; comprises the amino acid sequence of SEQ ID NO: 3 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 3. In another embodiment, the polypeptide comprises or consists of amino acids 1 to 324 of SEQ ID NO: 4. In an embodiment, the polypeptide has been isolated.

In a continuation of the second aspect, the invention relates to a polypeptide having galactanase activity encoded by a polynucleotide having a sequence identity to the mature polypeptide coding sequence of SEQ ID NO: 1 or the cDNA sequence thereof of at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the second aspect, the invention relates to variants of SEQ ID NO: 3 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 3 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 3 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 3 is not more than 10, e.g., 1, 2, 3, 4, 5, 6, 7, 8, 9 or 10. In another embodiment, the number of substitutions, deletions, and/or insertions in SEQ ID NO: 3 is not more than 10, e.g., 1, 2, 3, 4, 5, 6, 7, 8, 9 or 10. In a further embodiment, the number of substitutions in SEQ ID NO: 3 is not more than 10, e.g., 1, 2, 3, 4, 5, 6, 7, 8, 9 or 10. In a further embodiment, the number of conservative substitutions in SEQ ID NO: 3 is not more than 10, e.g., 1, 2, 3, 4, 5, 6, 7, 8, 9 or 10.

The amino acid changes may be of a minor nature, that is conservative amino acid substitutions or insertions that do not significantly affect the folding and/or activity of the protein; small deletions, typically of 1-30 amino acids; small amino- or carboxyl-terminal extensions, such as an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, The Proteins, Academic Press, New York. Common substitutions are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly. Other examples of conservative substitutions are G to A; A to G, S; V to I, L, A, T, S; I to V, L, M; L to I, M, V; M to L, I, V; P to A, S, N; F to Y, W, H; Y to F, W, H; W to Y, F, H; R to K, E, D; K to R, E, D; H to Q, N, S; D to N, E, K, R, Q; E to Q, D, K, R, N; S to T, A; T to S, V, A; C to S, T, A; N to D, Q, H, S; Q to E, N, H, K, R.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in a polypeptide can be identified according to procedures known in the art, such as site-directed mutagenesis or alanine-scanning mutagenesis (Cunningham and Wells, 1989, Science 244: 1081-1085). In the latter technique, single alanine mutations are introduced at every residue in the molecule, and the resultant mutant molecules are tested for beta-galactosidase activity to identify amino acid residues that are critical to the activity of the molecule. See also, Hilton et al., 1996, J. Biol. Chem. 271: 4699-4708. The active site of the enzyme or other biological interaction can also be determined by physical analysis of structure, as determined by such techniques as nuclear magnetic resonance, crystallography, electron diffraction, or photoaffinity labelling, in conjunction with mutation of putative contact site amino acids. See, for example, de Vos et al., 1992, Science 255: 306-312; Smith et al., 1992, J. Mol. Biol. 224: 899-904; Wlodaver et al., 1992, FEBS Lett. 309: 59-64. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, Science 241: 53-57; Bowie and Sauer, 1989, Proc. Natl. Acad. Sci. USA 86: 2152-2156; WO 95/17413; or WO 95/22625. Other methods that can be used include error-prone PCR, phage display (e.g., Lowman et al., 1991, Biochemistry 30: 10832-10837; U.S. Pat. No. 5,223,409; WO 92/06204), and region-directed mutagenesis (Derbyshire et al., 1986, Gene 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, Nature Biotechnology 17: 893-896). Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art, and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally (Cooper et al., 1993, *EMBO J.* 12: 2575-2583; Dawson et al., 1994, *Science* 266: 776-779).

A fusion polypeptide can further comprise a cleavage site between the two polypeptides. Upon secretion of the fusion protein, the site is cleaved releasing the two polypeptides. Examples of cleavage sites include, but are not limited to, the sites disclosed in Martin et al., 2003, *J. Ind. Microbiol. Biotechnol.* 3: 568-576; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381; Eaton et al., 1986, *Biochemistry* 25: 505-512; Collins-Racie et al., 1995, *Biotechnology* 13: 982-987; Carter et al., 1989, Proteins: Structure, *Function, and Genetics* 6: 240-248; and Stevens, 2003, *Drug Discovery World* 4: 35-48.

Carbohydrate molecules are often attached to a polypeptide from a fungal source during post-translational modification. In order to aid mass spectrometry analysis, the polypeptide can be incubated with an endoglycosidase to deglycosylate each N-linked position. For every deglycosylated N-linked site, one N-acetyl hexosamine remains on the protein backbone.

In an embodiment, the polypeptide of the second aspect comprises the motif GV[T/M]PD[W/M]VQ[I/V]GNE (SEQ ID NO: 65) and/or the motif WADP[A/G]xQxKPxAW (SEQ ID NO: 66).

In a third aspect, the invention relates to polypeptides having galactanase activity and having a sequence identity to the mature polypeptide of SEQ ID NO: 6 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 6.

In one embodiment, the polypeptide preferably comprises or consists of the amino acid sequence of SEQ ID NO: 6 or an allelic variant thereof; comprises the amino acid sequence of SEQ ID NO: 6 and a N-terminal and/or C-terminal His-tag and/or HQ-tag; comprises the amino acid sequence of SEQ ID NO: 6 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 6. In another embodiment, the polypeptide comprises or consists of amino acids 1 to 318 of SEQ ID NO: 6. In an embodiment, the polypeptide has been isolated.

In a continuation of the third aspect, the invention further relates to polypeptides having galactanase activity having a sequence identity to SEQ ID NO: 7 of at least 83%. In an embodiment, the polypeptide has a sequence identity to SEQ ID NO: 7 of at least 85%. In an embodiment, the polypeptide has a sequence identity to SEQ ID NO: 7 of at least 86%. In an embodiment, the polypeptide has a sequence identity to SEQ ID NO: 7 of at least 87%. In an embodiment, the polypeptide has a sequence identity to SEQ ID NO: 7 of at least 88%. In an embodiment, the polypeptide has a sequence identity to SEQ ID NO: 7 of at least 89%. In an embodiment, the polypeptide has a sequence identity to SEQ ID NO: 7 of at least 90%. In an embodiment, the polypeptide has a sequence identity to SEQ ID NO: 7 of at least 91%. In an embodiment, the polypeptide has a sequence identity to SEQ ID NO: 7 of at least 92%. In an embodiment, the polypeptide has a sequence identity to SEQ ID NO: 7 of at least 93%. In an embodiment, the polypeptide has a sequence identity to SEQ ID NO: 7 of at least 94%. In an embodiment, the polypeptide has a sequence identity to SEQ ID NO: 7 of at least 95%. In an embodiment, the polypeptide has a sequence identity to SEQ ID NO: 7 of at least 96%. In an embodiment, the polypeptide has a sequence identity to SEQ ID NO: 7 of at least 97%. In an embodiment, the polypeptide has a sequence identity to SEQ ID NO: 7 of at least 98%. In an embodiment, the polypeptide has a sequence identity to SEQ ID NO: 7 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 7. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 8.

In one embodiment, the polypeptide preferably comprises or consists of the amino acid sequence of SEQ ID NO: 7 or an allelic variant thereof; comprises the amino acid sequence of SEQ ID NO: 7 and a N-terminal and/or C-terminal His-tag and/or HQ-tag such as SEQ ID NO: 8; comprises the amino acid sequence of SEQ ID NO: 7 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 318 of SEQ ID NO: 7. In another embodiment, the polypeptide comprises or consists of amino acids 1 to 326 of SEQ ID NO: 8. In an embodiment, the polypeptide has been isolated.

In a continuation of the third aspect, the invention relates to a polypeptide having galactanase activity encoded by a polynucleotide having a sequence identity to the mature polypeptide coding sequence of SEQ ID NO: 5 or the cDNA sequence thereof of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the third aspect, the invention relates to variants of SEQ ID NO: 7 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 7 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 7 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 7 is not more than 10, e.g., 1, 2, 3, 4, 5, 6, 7, 8, 9 or 10. In another embodiment, the number of substitutions, deletions, and/or insertions in SEQ ID NO: 7 is not more than 10, e.g., 1, 2, 3, 4, 5, 6, 7, 8, 9 or 10. In a further embodiment, the number of substitutions in SEQ ID NO: 7 is not more than 10, e.g., 1, 2, 3, 4, 5, 6, 7, 8, 9 or 10. In a further embodiment, the number of conservative substitutions in SEQ ID NO: 7 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the third aspect comprises the motif GV[T/M]PD[W/M]VQ[I/V]GNE (SEQ ID NO: 65) and/or the motif WADP[A/G]xQxKPxAW (SEQ ID NO: 66).

In a fourth aspect, the invention relates to polypeptides having galactanase activity and having a sequence identity to the mature polypeptide of SEQ ID NO: 10 of at least 99.0%, e.g., at least 99.3%, at least 99.6% which have galactanase activity. In one embodiment, the polypeptides differ by up to 3 amino acids, e.g., 1, 2 or 3 amino acids from the mature polypeptide of SEQ ID NO: 10.

In one embodiment, the polypeptide preferably comprises or consists of the amino acid sequence of SEQ ID NO: 10 or an allelic variant thereof; comprises the amino acid sequence of SEQ ID NO: 10 and a N-terminal and/or C-terminal His-tag and/or HQ-tag; comprises the amino acid sequence of SEQ ID NO: 10 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 10. In another embodiment, the polypeptide comprises or consists of amino acids 1 to 316 of SEQ ID NO: 10. In an embodiment, the polypeptide has been isolated.

In a continuation of the fourth aspect, the invention further relates to polypeptides having galactanase activity having a sequence identity to SEQ ID NO: 11 of at least 99.0%. In an embodiment, the polypeptide has a sequence identity to SEQ ID NO: 11 of at least 99.3%. In an embodiment, the polypeptide has a sequence identity to SEQ ID NO: 11 of at least 99.6%.

In one embodiment, the polypeptides differ by up to 3 amino acids, e.g., 1, 2 or 3 amino acids from SEQ ID NO: 11. In one embodiment, the polypeptides differ by up to 3 amino acids, e.g., 1, 2 or 3 amino acids from SEQ ID NO: 12.

In one embodiment, the polypeptide preferably comprises or consists of the amino acid sequence of SEQ ID NO: 11 or an allelic variant thereof; comprises the amino acid sequence of SEQ ID NO: 11 and a N-terminal and/or C-terminal His-tag and/or HQ-tag such as SEQ ID NO: 12; comprises the amino acid sequence of SEQ ID NO: 11 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 11. In another embodiment, the polypeptide comprises or consists of amino acids 1 to 324 of SEQ ID NO: 12. In an embodiment, the polypeptide has been isolated.

In a continuation of the fourth aspect, the invention relates to a polypeptide having galactanase activity encoded by a polynucleotide having a sequence identity to the mature polypeptide coding sequence of SEQ ID NO: 9 or the cDNA sequence thereof of at least 99.0%, e.g., at least 99.3%, at least 99.6%, or 100%. In a further embodiment, the polypeptide has been isolated.

In a continuation of the fourth aspect, the invention relates to variants of SEQ ID NO: 11 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 11 is not more than 3, e.g., 1, 2 or 3. In another embodiment, the number of substitutions, deletions, and/or insertions in SEQ ID NO: 11 is not more than 3, e.g., 1, 2 or 3. In a further embodiment, the number of substitutions in SEQ ID NO: 11 is not more than 3, e.g., 1, 2 or 3. In a further embodiment, the number of conservative substitutions in SEQ ID NO: 11 is not more than 3, e.g., 1, 2 or 3.

Examples of amino acid changes and conservative substitutions are described in the second aspect of the invention.

In an embodiment, the polypeptide of the fourth aspect comprises the motif GV[T/M]PD[W/M]VQ[I/V]GNE (SEQ ID NO: 65) and/or the motif WADP[A/G]xQxKPxAW (SEQ ID NO: 66).

In a fifth aspect, the invention relates to polypeptides having galactanase activity and having a sequence identity to the mature polypeptide of SEQ ID NO: 14 of at least 96.4%, e.g., at least 96.7%, at least 97.0%, at least 97.3%, at least 97.6%, at least 98.0%, at least 98.3%, at least 98.6%, at least 99.0%, at least 99.3% or at least 99.6%, which have galactanase activity. In one embodiment, the polypeptides differ by up to 11 amino acids, e.g., 1, 2, 3, 4, 5, 6, 7, 8, 9, 10 or 11 amino acids from the mature polypeptide of SEQ ID NO: 14.

In one embodiment, the polypeptide preferably comprises or consists of the amino acid sequence of SEQ ID NO: 14 or an allelic variant thereof; comprises the amino acid sequence of SEQ ID NO: 14 and a N-terminal and/or C-terminal His-tag and/or HQ-tag; comprises the amino acid sequence of SEQ ID NO: 14 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 14. In another embodiment, the polypeptide comprises or consists of amino acids 1 to 316 of SEQ ID NO: 14. In an embodiment, the polypeptide has been isolated.

In a continuation of the fifth aspect, the invention further relates to polypeptides having galactanase activity having a sequence identity to SEQ ID NO: 15 of at least 96.4%. In an embodiment, the polypeptide has a sequence identity to SEQ ID NO: 15 of at least 96.7%. In an embodiment, the polypeptide has a sequence identity to SEQ ID NO: 15 of at least 97.0%. In an embodiment, the polypeptide has a sequence identity to SEQ ID NO: 15 of at least 97.3%. In an embodiment, the polypeptide has a sequence identity to SEQ ID NO: 15 of at least 97.6%. In an embodiment, the polypeptide has a sequence identity to SEQ ID NO: 15 of at least 98.0%. In an embodiment, the polypeptide has a sequence identity to SEQ ID NO: 15 of at least 98.3%. In an embodiment, the polypeptide has a sequence identity to SEQ ID NO: 15 of at least 98.6%. In an embodiment, the polypeptide has a sequence identity to SEQ ID NO: 15 of at least 99.0%. In an embodiment, the polypeptide has a sequence identity to SEQ ID NO: 15 of at least 99.3%. In an embodiment, the polypeptide has a sequence identity to SEQ ID NO: 15 of at least 99.6%.

In one embodiment, the polypeptides differ by up to 11 amino acids, e.g., 1, 2, 3, 4, 5, 6, 7, 8, 9, 10 or 11 amino acids from SEQ ID NO: 15. In one embodiment, the polypeptides differ by up to 11 amino acids, e.g., 1, 2, 3, 4, 5, 6, 7, 8, 9, 10 or 11 amino acids from SEQ ID NO: 16.

In one embodiment, the polypeptide preferably comprises or consists of the amino acid sequence of SEQ ID NO: 15 or an allelic variant thereof; comprises the amino acid sequence of SEQ ID NO: 15 and a N-terminal and/or C-terminal His-tag and/or HQ-tag such as SEQ ID NO: 16; comprises the amino acid sequence of SEQ ID NO: 15 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 15. In another embodiment, the polypeptide comprises or consists of amino acids 1 to 324 of SEQ ID NO: 16. In an embodiment, the polypeptide has been isolated.

In a continuation of the fifth aspect, the invention relates to a polypeptide having galactanase activity encoded by a polynucleotide having a sequence identity to the mature polypeptide coding sequence of SEQ ID NO: 13 or the cDNA sequence thereof of at least 96.4%, e.g., at least 96.7%, at least 97.0%, at least 97.3%, at least 97.6%, at least 98.0%, at least 98.3%, at least 98.6%, at least 99.0%, at least 99.3% or at least 99.6%, or 100%. In a further embodiment, the polypeptide has been isolated.

In a continuation of the fifth aspect, the invention relates to variants of SEQ ID NO: 15 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 15 is not more than 11, e.g., 1, 2, 3, 4, 5, 6, 7, 8, 9, 10 or 11. In another embodiment, the number of substitutions, deletions, and/or insertions in SEQ ID NO: 15 is not more than 10, e.g., 1, 2, 3, 4, 5, 6, 7, 8, 9 or 10. In a further embodiment, the number of substitutions in SEQ ID NO: 15 is not more than 10, e.g., 1, 2, 3, 4, 5, 6, 7, 8, 9 or 10. In a further embodiment, the number of conservative substitutions in SEQ ID NO: 15 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the fifth aspect comprises the motif GV[T/M]PD[W/M]VQ[I/V]GNE (SEQ ID NO: 65) and/or the motif WADP[A/G]xQxKPxAW (SEQ ID NO: 66).

In a sixth aspect, the invention relates to polypeptides having galactanase activity and having a sequence identity to the mature polypeptide of SEQ ID NO: 18 of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 18.

In one embodiment, the polypeptide preferably comprises or consists of the amino acid sequence of SEQ ID NO: 18 or an allelic variant thereof; comprises the amino acid sequence of SEQ ID NO: 18 and a N-terminal and/or C-terminal His-tag and/or HQ-tag; comprises the amino acid sequence of SEQ ID NO: 18 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 18. In another embodiment, the polypeptide comprises or consists of amino acids 1 to 316 of SEQ ID NO: 18. In an embodiment, the polypeptide has been isolated.

In a continuation of the sixth aspect, the invention further relates to polypeptides having galactanase activity having a sequence identity to SEQ ID NO: 19 of at least 84%. In an embodiment, the polypeptide has a sequence identity to SEQ ID NO: 19 of at least 85%. In an embodiment, the polypeptide has a sequence identity to SEQ ID NO: 19 of at least 86%. In an embodiment, the polypeptide has a sequence identity to SEQ ID NO: 19 of at least 87%. In an embodiment, the polypeptide has a sequence identity to SEQ ID NO: 19 of at least 88%. In an embodiment, the polypeptide has a sequence identity to SEQ ID NO: 19 of at least 89%. In an embodiment, the polypeptide has a sequence identity to SEQ ID NO: 19 of at least 90%. In an embodiment, the polypeptide has a sequence identity to SEQ ID NO: 19 of at least 91%. In an embodiment, the polypeptide has a sequence identity to SEQ ID NO: 19 of at least 92%. In an embodiment, the polypeptide has a sequence identity to SEQ ID NO: 19 of at least 93%. In an embodiment, the polypeptide has a sequence identity to SEQ ID NO: 19 of at least 94%. In an embodiment, the polypeptide has a sequence identity to SEQ ID NO: 19 of at least 95%. In an embodiment, the polypeptide has a sequence identity to SEQ ID NO: 19 of at least 96%. In an embodiment, the polypeptide has a sequence identity to SEQ ID NO: 19 of at least 97%. In an embodiment, the polypeptide has a sequence identity to SEQ ID NO: 19 of at least 98%. In an embodiment, the polypeptide has a sequence identity to SEQ ID NO: 19 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 19. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 20.

In one embodiment, the polypeptide preferably comprises or consists of the amino acid sequence of SEQ ID NO: 19 or an allelic variant thereof; comprises the amino acid sequence of SEQ ID NO: 19 and a N-terminal and/or C-terminal His-tag and/or HQ-tag such as SEQ ID NO: 20; comprises the amino acid sequence of SEQ ID NO: 19 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 19. In another embodiment, the polypeptide comprises or consists of amino acids 1 to 324 of SEQ ID NO: 20. In an embodiment, the polypeptide has been isolated.

In a continuation of the sixth aspect, the invention relates to a polypeptide having galactanase activity encoded by a polynucleotide having a sequence identity to the mature polypeptide coding sequence of SEQ ID NO: 17 or the cDNA sequence thereof of at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the sixth aspect, the invention relates to variants of SEQ ID NO: 19 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 19 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 19 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 19 is not more than 10, e.g., 1, 2, 3, 4, 5, 6, 7, 8, 9 or 10. In another embodiment, the number of substitutions, deletions, and/or insertions in SEQ ID NO: 19 is not more than 10, e.g., 1, 2, 3, 4, 5, 6, 7, 8, 9 or 10. In a further embodiment, the number of substitutions in SEQ ID NO: 19 is not more than 10, e.g., 1, 2, 3, 4, 5, 6, 7, 8, 9 or 10. In a further embodiment, the number of conservative substitutions in SEQ ID NO: 19 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the sixth aspect comprises the motif GV[T/M]PD[W/M]VQ[I/V]GNE (SEQ ID NO: 65) and/or the motif WADP[A/G]xQxKPxAW (SEQ ID NO: 66).

In a seventh aspect, the invention relates to polypeptides having galactanase activity and having a sequence identity to the mature polypeptide of SEQ ID NO: 22 of at least 96.4%, e.g., at least 96.7%, at least 97.0%, at least 97.3%, at least 97.6%, at least 98.0%, at least 98.3%, at least 98.6%, at least 99.0%, at least 99.3% or at least 99.6%, which have galactanase activity. In one embodiment, the polypeptides differ by up to 11 amino acids, e.g., 1, 2, 3, 4, 5, 6, 7, 8, 9, 10 or 11 amino acids from the mature polypeptide of SEQ ID NO: 22.

In one embodiment, the polypeptide preferably comprises or consists of the amino acid sequence of SEQ ID NO: 22 or an allelic variant thereof; comprises the amino acid sequence of SEQ ID NO: 22 and a N-terminal and/or C-terminal His-tag and/or HQ-tag; comprises the amino acid sequence of SEQ ID NO: 22 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 22. In another embodiment, the polypeptide comprises or consists of amino acids 1 to 316 of SEQ ID NO: 22. In an embodiment, the polypeptide has been isolated.

In a continuation of the seventh aspect, the invention further relates to polypeptides having galactanase activity having a sequence identity to SEQ ID NO: 23 of at least 96.4%. In an embodiment, the polypeptide has a sequence identity to SEQ ID NO: 23 of at least 96.7%. In an embodiment, the polypeptide has a sequence identity to SEQ ID NO: 23 of at least 97.0%. In an embodiment, the polypeptide has a sequence identity to SEQ ID NO: 23 of at least 97.3%. In an embodiment, the polypeptide has a sequence identity to SEQ ID NO: 23 of at least 97.6%. In an embodiment, the polypeptide has a sequence identity to SEQ ID NO: 23 of at least 98.0%. In an embodiment, the polypeptide has a sequence identity to SEQ ID NO: 23 of at least 98.3%. In an embodiment, the polypeptide has a sequence identity to SEQ ID NO: 23 of at least 98.6%. In an embodiment, the polypeptide has a sequence identity to SEQ ID NO: 23 of at least 99.0%. In an embodiment, the polypeptide has a sequence identity to SEQ ID NO: 23 of at least 99.3%. In an embodiment, the polypeptide has a sequence identity to SEQ ID NO: 23 of at least 99.6%.

In one embodiment, the polypeptides differ by up to 11 amino acids, e.g., 1, 2, 3, 4, 5, 6, 7, 8, 9, 10 or 11 amino acids from SEQ ID NO: 23. In one embodiment, the polypeptides differ by up to 11 amino acids, e.g., 1, 2, 3, 4, 5, 6, 7, 8, 9, 10 or 11 amino acids from SEQ ID NO: 24.

In one embodiment, the polypeptide preferably comprises or consists of the amino acid sequence of SEQ ID NO: 23 or an allelic variant thereof; comprises the amino acid sequence of SEQ ID NO: 23 and a N-terminal and/or C-terminal His-tag and/or HQ-tag such as SEQ ID NO: 24; comprises the amino acid sequence of SEQ ID NO: 23 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 23. In another embodiment, the polypeptide comprises or consists of amino acids 1 to 324 of SEQ ID NO: 24. In an embodiment, the polypeptide has been isolated.

In a continuation of the seventh aspect, the invention relates to a polypeptide having galactanase activity encoded by a polynucleotide having a sequence identity to the mature polypeptide coding sequence of SEQ ID NO: 21 or the cDNA sequence thereof of at least 96.4%, e.g., at least 96.7%, at least 97.0%, at least 97.3%, at least 97.6%, at least 98.0%, at least 98.3%, at least 98.6%, at least 99.0%, at least 99.3% or at least 99.6%, or 100%. In a further embodiment, the polypeptide has been isolated.

In a continuation of the seventh aspect, the invention relates to variants of SEQ ID NO: 23 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 23 is not more than 11, e.g., 1, 2, 3, 4, 5, 6, 7, 8, 9, 10 or 11. In another embodiment, the number of substitutions, deletions, and/or insertions in SEQ ID NO: 23 is not more than 10, e.g., 1, 2, 3, 4, 5, 6, 7, 8, 9 or 10. In a further embodiment, the number of substitutions in SEQ ID NO: 23 is not more than 10, e.g., 1, 2, 3, 4, 5, 6, 7, 8, 9 or 10. In a further embodiment, the number of conservative substitutions in SEQ ID NO: 23 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the seventh aspect comprises the motif GV[T/M]PD[W/M]VQ[I/V]GNE (SEQ ID NO: 65) and/or the motif WADP[A/G]xQxKPxAW (SEQ ID NO: 66).

In an eighth aspect, the invention relates to polypeptides having galactanase activity and having a sequence identity to the mature polypeptide of SEQ ID NO: 26 of at least 86%, e.g., at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 26.

In one embodiment, the polypeptide preferably comprises or consists of the amino acid sequence of SEQ ID NO: 26 or an allelic variant thereof; comprises the amino acid sequence of SEQ ID NO: 26 and a N-terminal and/or C-terminal His-tag and/or HQ-tag; comprises the amino acid sequence of SEQ ID NO: 26 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 26. In another embodiment, the polypeptide comprises or consists of amino acids 1 to 516 of SEQ ID NO: 26. In an embodiment, the polypeptide has been isolated.

In a continuation of the eighth aspect, the invention further relates to polypeptides having galactanase activity having a sequence identity to SEQ ID NO: 27 of at least 86%. In an embodiment, the polypeptide has a sequence identity to SEQ ID NO: 27 of at least 87%. In an embodiment, the polypeptide has a sequence identity to SEQ ID NO: 27 of at least 88%. In an embodiment, the polypeptide has a sequence identity to SEQ ID NO: 27 of at least 89%. In an embodiment, the polypeptide has a sequence identity to SEQ ID NO: 27 of at least 90%. In an embodiment, the polypeptide has a sequence identity to SEQ ID NO: 27 of at least 91%. In an embodiment, the polypeptide has a sequence identity to SEQ ID NO: 27 of at least 92%. In an embodiment, the polypeptide has a sequence identity to SEQ ID NO: 27 of at least 93%. In an embodiment, the polypeptide has a sequence identity to SEQ ID NO: 27 of at least 94%. In an embodiment, the polypeptide has a sequence identity to SEQ ID NO: 27 of at least 95%. In an embodiment, the polypeptide has a sequence identity to SEQ ID NO: 27 of at least 96%. In an embodiment, the polypeptide has a sequence identity to SEQ ID NO: 27 of at least 97%. In an embodiment, the polypeptide has a sequence identity to SEQ ID NO: 27 of at least 98%. In an embodiment, the polypeptide has a sequence identity to SEQ ID NO: 27 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 27. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 28.

In one embodiment, the polypeptide preferably comprises or consists of the amino acid sequence of SEQ ID NO: 27 or an allelic variant thereof; comprises the amino acid sequence of SEQ ID NO: 27 and a N-terminal and/or C-terminal His-tag and/or HQ-tag such as SEQ ID NO: 28; comprises the amino acid sequence of SEQ ID NO: 27 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 516 of SEQ ID NO: 27. In another embodiment, the polypeptide comprises or consists of amino acids 1 to 524 of SEQ ID NO: 28. In an embodiment, the polypeptide has been isolated.

In a continuation of the eighth aspect, the invention relates to a polypeptide having galactanase activity encoded by a polynucleotide having a sequence identity to the mature polypeptide coding sequence of SEQ ID NO: 25 or the cDNA sequence thereof of at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eighth aspect, the invention relates to variants of SEQ ID NO: 27 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 27 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 27 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 27 is not more than 10, e.g., 1, 2, 3, 4, 5, 6, 7, 8, 9 or 10. In another embodiment, the number of substitutions, deletions, and/or insertions in SEQ ID NO: 27 is not more than 10, e.g., 1, 2, 3, 4, 5, 6, 7, 8, 9 or 10. In a further embodiment, the number of substitutions in SEQ ID NO: 27 is not more than 10, e.g., 1, 2, 3, 4, 5, 6, 7, 8, 9 or 10. In a further embodiment, the number of conservative substitutions in SEQ ID NO: 27 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the eighth aspect comprises the motif GV[T/M]PD[W/M]VQ[I/V]GNE (SEQ ID NO: 65) and/or the motif WADP[A/G]xQxKPxAW (SEQ ID NO: 66).

In a ninth aspect, the invention relates to polypeptides having galactanase activity and having a sequence identity to the mature polypeptide of SEQ ID NO: 30 of at least 99.3%, e.g., at least 99.6% which have galactanase activity. In one embodiment, the polypeptides differ by up to 2 amino acids, e.g., 1 or 2 amino acids from the mature polypeptide of SEQ ID NO: 30.

In one embodiment, the polypeptide preferably comprises or consists of the amino acid sequence of SEQ ID NO: 30 or an allelic variant thereof; comprises the amino acid sequence of SEQ ID NO: 30 and a N-terminal and/or C-terminal His-tag and/or HQ-tag; comprises the amino acid sequence of SEQ ID NO: 30 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 30. In another embodiment, the polypeptide comprises or consists of amino acids 1 to 317 of SEQ ID NO: 30. In an embodiment, the polypeptide has been isolated.

In a continuation of the ninth aspect, the invention further relates to polypeptides having galactanase activity having a sequence identity to SEQ ID NO: 31 of at least 99.3%. In an embodiment, the polypeptide has a sequence identity to SEQ ID NO: 31 of at least 99.6%.

In one embodiment, the polypeptides differ by up to 2 amino acids, e.g., 1 or 2 amino acids from SEQ ID NO: 31. In one embodiment, the polypeptides differ by up to 2 amino acids, e.g., 1 or 2 amino acids from SEQ ID NO: 32.

In one embodiment, the polypeptide preferably comprises or consists of the amino acid sequence of SEQ ID NO: 31 or an allelic variant thereof; comprises the amino acid sequence of SEQ ID NO: 31 and a N-terminal and/or C-terminal His-tag and/or HQ-tag such as SEQ ID NO: 32; comprises the amino acid sequence of SEQ ID NO: 31 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 317 of SEQ ID NO: 31. In another embodiment, the polypeptide comprises or consists of amino acids 1 to 325 of SEQ ID NO: 32. In an embodiment, the polypeptide has been isolated.

In a continuation of the ninth aspect, the invention relates to a polypeptide having galactanase activity encoded by a polynucleotide having a sequence identity to the mature polypeptide coding sequence of SEQ ID NO: 29 or the cDNA sequence thereof of at least 99.3%, e.g., at least 99.6%, or 100%. In a further embodiment, the polypeptide has been isolated.

In a continuation of the ninth aspect, the invention relates to variants of SEQ ID NO: 31 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 31 is not more than 2 amino acids, e.g., 1 or 2. In another embodiment, the number of substitutions, deletions, and/or insertions in SEQ ID NO: 31 is not more than 2 amino acids, e.g., 1 or 2. In a further embodiment, the number of substitutions in SEQ ID NO: 31 is not more than 2 amino acids, e.g., 1 or 2. In a further embodiment, the number of conservative substitutions in SEQ ID NO: 31 is not more than 2 amino acids, e.g., 1 or 2.

Examples of amino acid changes and conservative substitutions are described in the second aspect of the invention.

In an embodiment, the polypeptide of the ninth aspect comprises the motif GV[T/M]PD[W/M]VQ[I/V]GNE (SEQ ID NO: 65) and/or the motif WADP[A/G]xQxKPxAW (SEQ ID NO: 66).

In a tenth aspect, the invention relates to polypeptides having galactanase activity and having a sequence identity to the mature polypeptide of SEQ ID NO: 34 of at least 99.3%, e.g., at least 99.6% which have galactanase activity. In one embodiment, the polypeptides differ by up to 2 amino acids, e.g., 1 or 2 amino acids from the mature polypeptide of SEQ ID NO: 34.

In one embodiment, the polypeptide preferably comprises or consists of the amino acid sequence of SEQ ID NO: 34 or an allelic variant thereof; comprises the amino acid sequence of SEQ ID NO: 34 and a N-terminal and/or C-terminal His-tag and/or HQ-tag; comprises the amino acid sequence of SEQ ID NO: 34 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 34. In another embodiment, the polypeptide comprises or consists of amino acids 1 to 316 of SEQ ID NO: 34. In an embodiment, the polypeptide has been isolated.

In a continuation of the tenth aspect, the invention further relates to polypeptides having galactanase activity having a sequence identity to SEQ ID NO: 35 of at least 99.3%. In an embodiment, the polypeptide has a sequence identity to SEQ ID NO: 35 of at least 99.6%.

In one embodiment, the polypeptides differ by up to 2 amino acids, e.g., 1 or 2 amino acids from SEQ ID NO: 35. In one embodiment, the polypeptides differ by up to 2 amino acids, e.g., 1 or 2 amino acids from SEQ ID NO: 36.

In one embodiment, the polypeptide preferably comprises or consists of the amino acid sequence of SEQ ID NO: 35 or an allelic variant thereof; comprises the amino acid sequence of SEQ ID NO: 35 and a N-terminal and/or C-terminal His-tag and/or HQ-tag such as SEQ ID NO: 36; comprises the amino acid sequence of SEQ ID NO: 35 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 35. In another embodiment, the polypeptide comprises or consists of amino acids 1 to 324 of SEQ ID NO: 36. In an embodiment, the polypeptide has been isolated.

In a continuation of the tenth aspect, the invention relates to a polypeptide having galactanase activity encoded by a polynucleotide having a sequence identity to the mature polypeptide coding sequence of SEQ ID NO: 33 or the cDNA sequence thereof of at least 99.3%, e.g., at least 99.6%, or 100%. In a further embodiment, the polypeptide has been isolated.

In a continuation of the tenth aspect, the invention relates to variants of SEQ ID NO: 35 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 35 is not more than 2 amino acids, e.g., 1 or 2. In another embodiment, the number of substitutions, deletions, and/or insertions in SEQ ID NO: 35 is not more than 2 amino acids, e.g., 1 or 2. In a further embodiment, the number of substitutions in SEQ ID NO: 35 is not more than 2 amino acids, e.g., 1 or 2. In a further embodiment, the number of conservative substitutions in SEQ ID NO: 35 is not more than 2 amino acids, e.g., 1 or 2.

Examples of amino acid changes and conservative substitutions are described in the second aspect of the invention.

In an embodiment, the polypeptide of the tenth aspect comprises the motif GV[T/M]PD[W/M]VQ[I/V]GNE (SEQ ID NO: 65) and/or the motif WADP[A/G]xQxKPxAW (SEQ ID NO: 66).

In a eleventh aspect, the invention relates to polypeptides having galactanase activity and having a sequence identity to the mature polypeptide of SEQ ID NO: 38 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have galactanase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 38.

In one embodiment, the polypeptide preferably comprises or consists of the amino acid sequence of SEQ ID NO: 38 or an allelic variant thereof; comprises the amino acid sequence of SEQ ID NO: 38 and a N-terminal and/or C-terminal His-tag and/or HQ-tag; comprises the amino acid sequence of SEQ ID NO: 38 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 38. In another embodiment, the polypeptide comprises or consists of amino acids 1 to 316 of SEQ ID NO: 38. In an embodiment, the polypeptide has been isolated.

In a continuation of the eleventh aspect, the invention further relates to polypeptides having galactanase activity having a sequence identity to SEQ ID NO: 39 of at least 83%. In an embodiment, the polypeptide has a sequence identity to SEQ ID NO: 39 of at least 85%. In an embodiment, the polypeptide has a sequence identity to SEQ ID NO: 39 of at least 86%. In an embodiment, the polypeptide has a sequence identity to SEQ ID NO: 39 of at least 87%. In an embodiment, the polypeptide has a sequence identity to SEQ ID NO: 39 of at least 88%. In an embodiment, the polypeptide has a sequence identity to SEQ ID NO: 39 of at least 89%. In an embodiment, the polypeptide has a sequence identity to SEQ ID NO: 39 of at least 90%. In an embodiment, the polypeptide has a sequence identity to SEQ ID NO: 39 of at least 91%. In an embodiment, the polypeptide has a sequence identity to SEQ ID NO: 39 of at least 92%. In an embodiment, the polypeptide has a sequence identity to SEQ ID NO: 39 of at least 93%. In an embodiment, the polypeptide has a sequence identity to SEQ ID NO: 39 of at least 94%. In an embodiment, the polypeptide has a sequence identity to SEQ ID NO: 39 of at least 95%. In an embodiment, the polypeptide has a sequence identity to SEQ ID NO: 39 of at least 96%. In an embodiment, the polypeptide has a sequence identity to SEQ ID NO: 39 of at least 97%. In an embodiment, the polypeptide has a sequence identity to SEQ ID NO: 39 of at least 98%. In an embodiment, the polypeptide has a sequence identity to SEQ ID NO: 39 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 39. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 40.

In one embodiment, the polypeptide preferably comprises or consists of the amino acid sequence of SEQ ID NO: 39 or an allelic variant thereof; comprises the amino acid sequence of SEQ ID NO: 39 and a N-terminal and/or C-terminal His-tag and/or HQ-tag such as SEQ ID NO: 40; comprises the amino acid sequence of SEQ ID NO: 39 and a N-terminal and/or C-terminal extension of between 1 and 10 amino acids; or is a fragment thereof having galactanase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 316 of SEQ ID NO: 39. In another embodiment, the polypeptide comprises or consists of amino acids 1 to 324 of SEQ ID NO: 40. In an embodiment, the polypeptide has been isolated.

In a continuation of the eleventh aspect, the invention relates to a polypeptide having galactanase activity encoded by a polynucleotide having a sequence identity to the mature polypeptide coding sequence of SEQ ID NO: 37 or the cDNA sequence thereof of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eleventh aspect, the invention relates to variants of SEQ ID NO: 39 having galactanase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 39 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 39 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 39 is not more than 10, e.g., 1, 2, 3, 4, 5, 6, 7, 8, 9 or 10. In another embodiment, the number of substitutions, deletions, and/or insertions in SEQ ID NO: 39 is not more than 10, e.g., 1, 2, 3, 4, 5, 6, 7, 8, 9 or 10. In a further embodiment, the number of substitutions in SEQ ID NO: 39 is not more than 10, e.g., 1, 2, 3, 4, 5, 6, 7, 8, 9 or 10. In a further embodiment, the number of conservative substitutions in SEQ ID NO: 39 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the eleventh aspect comprises the motif GV[T/M]PD[W/M]VQ[I/V]GNE (SEQ ID NO: 65) and/or the motif WADP[A/G]xQxKPxAW (SEQ ID NO: 66).

Polypeptides Having Beta-Galactosidase Activity

In a twelfth aspect, the invention relates to polypeptides having beta-galactosidase activity and having a sequence identity to the mature polypeptide of SEQ ID NO: 42 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 42.

In one embodiment, the polypeptide preferably comprises or consists of the amino acid sequence of SEQ ID NO: 42 or an allelic variant thereof; comprises the amino acid sequence of SEQ ID NO: 42 and a N-terminal and/or C-terminal His-tag and/or HQ-tag; comprises the amino acid sequence of SEQ ID NO: 42 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 42. In another embodiment, the polypeptide comprises or consists of amino acids 1 to 985 of SEQ ID NO: 42. In an embodiment, the polypeptide has been isolated.

In a continuation of the twelfth aspect, the invention further relates to polypeptides having beta-galactosidase activity having a sequence identity to SEQ ID NO: 43 of at least 80%. In an embodiment, the polypeptide has a sequence identity to SEQ ID NO: 43 of at least 85%. In an embodiment, the polypeptide has a sequence identity to SEQ ID NO: 43 of at least 86%. In an embodiment, the polypeptide has a sequence identity to SEQ ID NO: 43 of at least 87%. In an embodiment, the polypeptide has a sequence identity to SEQ ID NO: 43 of at least 88%. In an embodiment, the polypeptide has a sequence identity to SEQ ID NO: 43 of at least 89%. In an embodiment, the polypeptide has a sequence identity to SEQ ID NO: 43 of at least 90%. In an embodiment, the polypeptide has a sequence identity to SEQ ID NO: 43 of at least 91%. In an embodiment, the polypeptide has a sequence identity to SEQ ID NO: 43 of at least 92%. In an embodiment, the polypeptide has a sequence identity to SEQ ID NO: 43 of at least 93%. In an embodiment, the polypeptide has a sequence identity to SEQ ID NO: 43 of at least 94%. In an embodiment, the polypeptide has a sequence identity to SEQ ID NO: 43 of at least 95%. In an embodiment, the polypeptide has a sequence identity to SEQ ID NO: 43 of at least 96%. In an embodiment, the polypeptide has a sequence identity to SEQ ID NO: 43 of at least 97%. In an embodiment, the polypeptide has a sequence identity to SEQ ID NO: 43 of at least 98%. In an embodiment, the polypeptide has a sequence identity to SEQ ID NO: 43 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 43.

In one embodiment, the polypeptide preferably comprises or consists of the amino acid sequence of SEQ ID NO: 43 or an allelic variant thereof; comprises the amino acid sequence of SEQ ID NO: 43 and a N-terminal and/or C-terminal His-tag and/or HQ-tag; comprises the amino acid sequence of SEQ ID NO: 43 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 985 of SEQ ID NO: 43. In an embodiment, the polypeptide has been isolated.

In a continuation of the twelfth aspect, the invention relates to a polypeptide having beta-galactosidase activity encoded by a polynucleotide having a sequence identity to the mature polypeptide coding sequence of SEQ ID NO: 41 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twelfth aspect, the invention relates to variants of SEQ ID NO: 43 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 43 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 43 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 43 is not more than 10, e.g., 1, 2, 3, 4, 5, 6, 7, 8, 9 or 10. In another embodiment, the number of substitutions, deletions, and/or insertions in SEQ ID NO: 43 is not more than 10, e.g., 1, 2, 3, 4, 5, 6, 7, 8, 9 or 10. In a further embodiment, the number of substitutions in SEQ ID NO: 43 is not more than 10, e.g., 1, 2, 3, 4, 5, 6, 7, 8, 9 or 10. In a further embodiment, the number of conservative substitutions in SEQ ID NO: 43 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twelfth aspect comprises the motif Y[Y/F][D/Q][Y/H/W]F (SEQ ID NO: 80) and/or the motif K[Y/F][Y/S]ETK (SEQ ID NO: 81).

In a thirteenth aspect, the invention relates to polypeptides having beta-galactosidase activity and having a sequence identity to the mature polypeptide of SEQ ID NO: 45 of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 45.

In one embodiment, the polypeptide preferably comprises or consists of the amino acid sequence of SEQ ID NO: 45 or an allelic variant thereof; comprises the amino acid sequence of SEQ ID NO: 45 and a N-terminal and/or C-terminal His-tag and/or HQ-tag; comprises the amino acid sequence of SEQ ID NO: 45 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 45. In another embodiment, the polypeptide comprises or consists of amino acids 1 to 1015 of SEQ ID NO: 45. In an embodiment, the polypeptide has been isolated.

In a continuation of the thirteenth aspect, the invention further relates to polypeptides having beta-galactosidase activity having a sequence identity to SEQ ID NO: 46 of at least 83%. In an embodiment, the polypeptide has a sequence identity to SEQ ID NO: 46 of at least 85%. In an embodiment, the polypeptide has a sequence identity to SEQ ID NO: 46 of at least 86%. In an embodiment, the polypeptide has a sequence identity to SEQ ID NO: 46 of at least 87%. In an embodiment, the polypeptide has a sequence identity to SEQ ID NO: 46 of at least 88%. In an embodiment, the polypeptide has a sequence identity to SEQ ID NO: 46 of at least 89%. In an embodiment, the polypeptide has a sequence identity to SEQ ID NO: 46 of at least 90%. In an embodiment, the polypeptide has a sequence identity to SEQ ID NO: 46 of at least 91%. In an embodiment, the polypeptide has a sequence identity to SEQ ID NO: 46 of at least 92%. In an embodiment, the polypeptide has a sequence identity to SEQ ID NO: 46 of at least 93%. In an embodiment, the polypeptide has a sequence identity to SEQ ID NO: 46 of at least 94%. In an embodiment, the polypeptide has a sequence identity to SEQ ID NO: 46 of at least 95%. In an embodiment, the polypeptide has a sequence identity to SEQ ID NO: 46 of at least 96%. In an embodiment, the polypeptide has a sequence identity to SEQ ID NO: 46 of at least 97%. In an embodiment, the polypeptide has a sequence identity to SEQ ID NO: 46 of at least 98%. In an embodiment, the polypeptide has a sequence identity to SEQ ID NO: 46 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 46.

In one embodiment, the polypeptide preferably comprises or consists of the amino acid sequence of SEQ ID NO: 46 or an allelic variant thereof; comprises the amino acid sequence of SEQ ID NO: 46 and a N-terminal and/or C-terminal His-tag and/or HQ-tag; comprises the amino acid sequence of SEQ ID NO: 46 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 1015 of SEQ ID NO: 46. In an embodiment, the polypeptide has been isolated.

In a continuation of the thirteenth aspect, the invention relates to a polypeptide having beta-galactosidase activity encoded by a polynucleotide having a sequence identity to the mature polypeptide coding sequence of SEQ ID NO: 44 or the cDNA sequence thereof of at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the thirteenth aspect, the invention relates to variants of SEQ ID NO: 46 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 46 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 46 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 46 is not more than 10, e.g., 1, 2, 3, 4, 5, 6, 7, 8, 9 or 10. In another embodiment, the number of substitutions, deletions, and/or insertions in SEQ ID NO: 46 is not more than 10, e.g., 1, 2, 3, 4, 5, 6, 7, 8, 9 or 10. In a further embodiment, the number of substitutions in SEQ ID NO: 46 is not more than 10, e.g., 1, 2, 3, 4, 5, 6, 7, 8, 9 or 10. In a further embodiment, the number of conservative substitutions in SEQ ID NO: 46 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the thirteenth aspect comprises the motif Y[Y/F][D/Q][Y/H/W]F (SEQ ID NO: 80) and/or the motif K[Y/F][Y/S]ETK (SEQ ID NO: 81).

In a fourteenth aspect, the invention relates to polypeptides having beta-galactosidase activity and having a sequence identity to the mature polypeptide of SEQ ID NO: 48 of at least 96.4%, e.g., at least 96.6%, at least 96.8%, at least 97.0%, at least 97.2%, at least 97.4%, at least 97.6%, at least 97.8%, at least 98.0%, at least 98.2%, at least 98.4%, at least 98.6%, at least 98.8%, at least 99.0%, at least 99.2%, at least 99.4%, at least 99.6%, at least 99.8% which have beta-galactosidase activity. In one embodiment, the polypeptides differ by up to 38 amino acids, e.g., between 1 and 38 amino acids, such as 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from the mature polypeptide of SEQ ID NO: 48.

In one embodiment, the polypeptide preferably comprises or consists of the amino acid sequence of SEQ ID NO: 48 or an allelic variant thereof; comprises the amino acid sequence of SEQ ID NO: 48 and a N-terminal and/or C-terminal His-tag and/or HQ-tag; comprises the amino acid sequence of SEQ ID NO: 48 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 48. In another embodiment, the polypeptide comprises or consists of amino acids 1 to 998 of SEQ ID NO: 48. In an embodiment, the polypeptide has been isolated.

In a continuation of the fourteenth aspect, the invention further relates to polypeptides having beta-galactosidase activity having a sequence identity to SEQ ID NO: 49 of at least 96.4%.

In an embodiment, the polypeptide has a sequence identity to SEQ ID NO: 49 of at least 96.6%. In an embodiment, the polypeptide has a sequence identity to SEQ ID NO: 49 of at least 96.8%. In an embodiment, the polypeptide has a sequence identity to SEQ ID NO: 49 of at least 97.0%. In an embodiment, the polypeptide has a sequence identity to SEQ ID NO: 49 of at least 97.2%. In an embodiment, the polypeptide has a sequence identity to SEQ ID NO: 49 of at least 97.4%. In an embodiment, the polypeptide has a sequence identity to SEQ ID NO: 49 of at least 97.6%. In an embodiment, the polypeptide has a sequence identity to SEQ ID NO: 49 of at least 97.8%. In an embodiment, the polypeptide has a sequence identity to SEQ ID NO: 49 of at least 98.0%. In an embodiment, the polypeptide has a sequence identity to SEQ ID NO: 49 of at least 98.2%. In an embodiment, the polypeptide has a sequence identity to SEQ ID NO: 49 of at least 98.4%. In an embodiment, the polypeptide has a sequence identity to SEQ ID NO: 49 of at least 98.6%. In an embodiment, the polypeptide has a sequence identity to SEQ ID NO: 49 of at least 98.8%. In an embodiment, the polypeptide has a sequence identity to SEQ ID NO: 49 of at least 99.0%. In an embodiment, the polypeptide has a sequence identity to SEQ ID NO: 49 of at least 99.2%. In an embodiment, the polypeptide has a sequence identity to SEQ ID NO: 49 of at least 99.4%. In an embodiment, the polypeptide has a sequence identity to SEQ ID NO: 49 of at least 99.6%. In an embodiment, the polypeptide has a sequence identity to SEQ ID NO: 49 of at least 99.8%.

In one embodiment, the polypeptides differ by up to 38 amino acids, e.g., between 1 and 38 amino acids, such as 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 amino acids from SEQ ID NO: 49.

In one embodiment, the polypeptide preferably comprises or consists of the amino acid sequence of SEQ ID NO: 49 or an allelic variant thereof; comprises the amino acid sequence of SEQ ID NO: 49 and a N-terminal and/or C-terminal His-tag and/or HQ-tag; comprises the amino acid sequence of SEQ ID NO: 49 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 998 of SEQ ID NO: 49. In an embodiment, the polypeptide has been isolated.

In a continuation of the fourteenth aspect, the invention relates to a polypeptide having beta-galactosidase activity encoded by a polynucleotide having a sequence identity to the mature polypeptide coding sequence of SEQ ID NO: 47 or the cDNA sequence thereof of at least 96.4%, e.g., at least 96.6%, at least 96.8%, at least 97.0%, at least 97.2%, at least 97.4%, at least 97.6%, at least 97.8%, at least 98.0%, at least 98.2%, at least 98.4%, at least 98.6%, at least 98.8%, at least 99.0%, at least 99.2%, at least 99.4%, at least 99.6%, at least 99.8%, or 100%. In a further embodiment, the polypeptide has been isolated.

In a continuation of the fourteenth aspect, the invention relates to variants of SEQ ID NO: 49 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 49 is not more than 38, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38. In another embodiment, the number of positions comprising one or more amino acid substitutions, and/or one or more amino acid deletions, and/or one or more amino acid insertions or any combination thereof in SEQ ID NO: 49 is between 1 and 38, such as 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 49 is not more than 10, e.g., 1, 2, 3, 4, 5, 6, 7, 8, 9 or 10. In another embodiment, the number of substitutions, deletions, and/or insertions in SEQ ID NO: 49 is not more than 10, e.g., 1, 2, 3, 4, 5, 6, 7, 8, 9 or 10. In a further embodiment, the number of substitutions in SEQ ID NO: 49 is not more than 10, e.g., 1, 2, 3, 4, 5, 6, 7, 8, 9 or 10. In a further embodiment, the number of conservative substitutions in SEQ ID NO: 49 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the fourteenth aspect comprises the motif Y[Y/F][D/Q][Y/H/W]F (SEQ ID NO: 80) and/or the motif K[Y/F][Y/S]ETK (SEQ ID NO: 81).

In a fifteenth aspect, the invention relates to polypeptides having beta-galactosidase activity and having a sequence identity to the mature polypeptide of SEQ ID NO: 51 of at least 92%, e.g., at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 51.

In one embodiment, the polypeptide preferably comprises or consists of the amino acid sequence of SEQ ID NO: 51 or an allelic variant thereof; comprises the amino acid sequence of SEQ ID NO: 51 and a N-terminal and/or C-terminal His-tag and/or HQ-tag; comprises the amino acid sequence of SEQ ID NO: 51 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 51. In another embodiment, the polypeptide comprises or consists of amino acids 1 to 983 of SEQ ID NO: 51. In an embodiment, the polypeptide has been isolated.

In a continuation of the fifteenth aspect, the invention further relates to polypeptides having beta-galactosidase activity having a sequence identity to SEQ ID NO: 52 of at least 92%. In an embodiment, the polypeptide has a sequence identity to SEQ ID NO: 52 of at least 93%. In an embodiment, the polypeptide has a sequence identity to SEQ ID NO: 52 of at least 94%. In an embodiment, the polypeptide has a sequence identity to SEQ ID NO: 52 of at least 95%. In an embodiment, the polypeptide has a sequence identity to SEQ ID NO: 52 of at least 96%. In an embodiment, the polypeptide has a sequence identity to SEQ ID NO: 52 of at least 97%. In an embodiment, the polypeptide has a sequence identity to SEQ ID NO: 52 of at least 98%. In an embodiment, the polypeptide has a sequence identity to SEQ ID NO: 52 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 52.

In one embodiment, the polypeptide preferably comprises or consists of the amino acid sequence of SEQ ID NO: 52 or an allelic variant thereof; comprises the amino acid sequence of SEQ ID NO: 52 and a N-terminal and/or C-terminal His-tag and/or HQ-tag; comprises the amino acid sequence of SEQ ID NO: 52 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 983 of SEQ ID NO: 52. In an embodiment, the polypeptide has been isolated.

In a continuation of the fifteenth aspect, the invention relates to a polypeptide having beta-galactosidase activity encoded by a polynucleotide having a sequence identity to the mature polypeptide coding sequence of SEQ ID NO: 50 or the cDNA sequence thereof of at least 892%, e.g., at least 93%, at least 94%, at least 95%, at least 96%, at least 97%, at least 98%, at least 99%, or 100%. In a further embodiment, the polypeptide has been isolated.

In a continuation of the fifteenth aspect, the invention relates to variants of SEQ ID NO: 52 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 52 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 52 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 52 is not more than 10, e.g., 1, 2, 3, 4, 5, 6, 7, 8, 9 or 10. In another embodiment, the number of substitutions, deletions, and/or insertions in SEQ ID NO: 52 is not more than 10, e.g., 1, 2, 3, 4, 5, 6, 7, 8, 9 or 10. In a further embodiment, the number of substitutions in SEQ ID NO: 52 is not more than 10, e.g., 1, 2, 3, 4, 5, 6, 7, 8, 9 or 10. In a further embodiment, the number of conservative substitutions in SEQ ID NO: 52 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the fifteenth aspect comprises the motif Y[Y/F][D/Q][Y/H/W]F (SEQ ID NO: 80) and/or the motif K[Y/F][Y/S]ETK (SEQ ID NO: 81).

In a sixteenth aspect, the invention relates to polypeptides having beta-galactosidase activity and having a sequence identity to the mature polypeptide of SEQ ID NO: 54 of at least 99.7%, e.g., at least 99.8%, at least 99.9%, which have beta-galactosidase activity. In one embodiment, the polypeptides differ by up to 3 amino acids, or 1, 2, or 3 amino acids from the mature polypeptide of SEQ ID NO: 54.

In one embodiment, the polypeptide preferably comprises or consists of the amino acid sequence of SEQ ID NO: 54 or an allelic variant thereof; comprises the amino acid sequence of SEQ ID NO: 54 and a N-terminal and/or C-terminal His-tag and/or HQ-tag; comprises the amino acid sequence of SEQ ID NO: 54 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 54. In another embodiment, the polypeptide comprises or consists of amino acids 1 to 998 of SEQ ID NO: 54. In an embodiment, the polypeptide has been isolated.

In a continuation of the sixteenth aspect, the invention further relates to polypeptides having beta-galactosidase activity having a sequence identity to SEQ ID NO: 55 of at least 99.7%. In an embodiment, the polypeptide has a sequence identity to SEQ ID NO: 55 of at least 99.8%. In an embodiment, the polypeptide has a sequence identity to SEQ ID NO: 55 of at least 99.9%.

In one embodiment, the polypeptides differ by up to 3 amino acids, or 1, 2, or 3 amino acids from SEQ ID NO: 55.

In one embodiment, the polypeptide preferably comprises or consists of the amino acid sequence of SEQ ID NO: 55 or an allelic variant thereof; comprises the amino acid sequence of SEQ ID NO: 55 and a N-terminal and/or C-terminal His-tag and/or HQ-tag; comprises the amino acid sequence of SEQ ID NO: 55 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 998 of SEQ ID NO: 55. In an embodiment, the polypeptide has been isolated.

In a continuation of the sixteenth aspect, the invention relates to a polypeptide having beta-galactosidase activity encoded by a polynucleotide having a sequence identity to the mature polypeptide coding sequence of SEQ ID NO: 53 or the cDNA sequence thereof of at least 99.7%, e.g., at least 99.8%, at least 99.9%, or 100%. In a further embodiment, the polypeptide has been isolated.

In a continuation of the sixteenth aspect, the invention relates to variants of SEQ ID NO: 55 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 55 is not more than 3 amino acids, or 1, 2, or 3. In another embodiment, the number of substitutions, deletions, and/or insertions in SEQ ID NO: 55 is not more than 3, e.g., 1, 2 or 3. In a further embodiment, the number of substitutions in SEQ ID NO: 55 is not more than 3, e.g., 1, 2 or 3. In a further embodiment, the number of conservative substitutions in SEQ ID NO: 55 is not more than 3, e.g., 1, 2 or 3.

Examples of amino acid changes and conservative substitutions are described in the second aspect of the invention.

In an embodiment, the polypeptide of the sixteenth aspect comprises the motif Y[Y/F][D/Q][Y/H/W]F (SEQ ID NO: 80) and/or the motif K[Y/F][Y/S]ETK (SEQ ID NO: 81).

In a seventeenth aspect, the invention relates to polypeptides having beta-galactosidase activity and having a sequence identity to the mature polypeptide of SEQ ID NO: 57 of at least 93%, e.g., at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 57.

In one embodiment, the polypeptide preferably comprises or consists of the amino acid sequence of SEQ ID NO: 57 or an allelic variant thereof; comprises the amino acid sequence of SEQ ID NO: 57 and a N-terminal and/or C-terminal His-tag and/or HQ-tag; comprises the amino acid sequence of SEQ ID NO: 57 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 57. In another embodiment, the polypeptide comprises or consists of amino acids 1 to 1007 of SEQ ID NO: 57. In an embodiment, the polypeptide has been isolated.

In a continuation of the seventeenth aspect, the invention further relates to polypeptides having beta-galactosidase activity having a sequence identity to SEQ ID NO: 58 of at least 93%. In an embodiment, the polypeptide has a sequence identity to SEQ ID NO: 58 of at least 94%. In an embodiment, the polypeptide has a sequence identity to SEQ ID NO: 58 of at least 95%. In an embodiment, the polypeptide has a sequence identity to SEQ ID NO: 58 of at least 96%. In an embodiment, the polypeptide has a sequence identity to SEQ ID NO: 58 of at least 97%. In an embodiment, the polypeptide has a sequence identity to SEQ ID NO: 58 of at least 98%. In an embodiment, the polypeptide has a sequence identity to SEQ ID NO: 58 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 58.

In one embodiment, the polypeptide preferably comprises or consists of the amino acid sequence of SEQ ID NO: 58 or an allelic variant thereof; comprises the amino acid sequence of SEQ ID NO: 58 and a N-terminal and/or C-terminal His-tag and/or HQ-tag; comprises the amino acid sequence of SEQ ID NO: 58 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 1007 of SEQ ID NO: 58. In an embodiment, the polypeptide has been isolated.

In a continuation of the seventeenth aspect, the invention relates to a polypeptide having beta-galactosidase activity encoded by a polynucleotide having a sequence identity to the mature polypeptide coding sequence of SEQ ID NO: 56 or the cDNA sequence thereof of at least 93%, e.g., at least 94%, at least 95%, at least 96%, at least 97%, at least 98%, at least 99%, or 100%. In a further embodiment, the polypeptide has been isolated.

In a continuation of the seventeenth aspect, the invention relates to variants of SEQ ID NO: 58 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 58 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 58 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 58 is not more than 10, e.g., 1, 2, 3, 4, 5, 6, 7, 8, 9 or 10. In another embodiment, the number of substitutions, deletions, and/or insertions in SEQ ID NO: 58 is not more than 10, e.g., 1, 2, 3, 4, 5, 6, 7, 8, 9 or 10. In a further embodiment, the number of substitutions in SEQ ID NO: 58 is not more than 10, e.g., 1, 2, 3, 4, 5, 6, 7, 8, 9 or 10. In a further embodiment, the number of conservative substitutions in SEQ ID NO: 58 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the seventeenth aspect comprises the motif Y[Y/F][D/Q][Y/H/W]F (SEQ ID NO: 80) and/or the motif K[Y/F][Y/S]ETK (SEQ ID NO: 81).

In an eighteenth aspect, the invention relates to polypeptides having beta-galactosidase activity and having a sequence identity to the mature polypeptide of SEQ ID NO: 60 of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 60.

In one embodiment, the polypeptide preferably comprises or consists of the amino acid sequence of SEQ ID NO: 60 or an allelic variant thereof; comprises the amino acid sequence of SEQ ID NO: 60 and a N-terminal and/or C-terminal His-tag and/or HQ-tag; comprises the amino acid sequence of SEQ ID NO: 60 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 60. In another embodiment, the polypeptide comprises or consists of amino acids 1 to 988 of SEQ ID NO: 60. In an embodiment, the polypeptide has been isolated.

In a continuation of the eighteenth aspect, the invention further relates to polypeptides having beta-galactosidase activity having a sequence identity to SEQ ID NO: 61 of at least 85%. In an embodiment, the polypeptide has a sequence identity to SEQ ID NO: 61 of at least 86%. In an embodiment, the polypeptide has a sequence identity to SEQ ID NO: 61 of at least 87%. In an embodiment, the polypeptide has a sequence identity to SEQ ID NO: 61 of at least 88%. In an embodiment, the polypeptide has a sequence identity to SEQ ID NO: 61 of at least 89%. In an embodiment, the polypeptide has a sequence identity to SEQ ID NO: 61 of at least 90%. In an embodiment, the polypeptide has a sequence identity to SEQ ID NO: 61 of at least 91%. In an embodiment, the polypeptide has a sequence identity to SEQ ID NO: 61 of at least 92%. In an embodiment, the polypeptide has a sequence identity to SEQ ID NO: 61 of at least 93%. In an embodiment, the polypeptide has a sequence identity to SEQ ID NO: 61 of at least 94%. In an embodiment, the polypeptide has a sequence identity to SEQ ID NO: 61 of at least 95%. In an embodiment, the polypeptide has a sequence identity to SEQ ID NO: 61 of at least 96%. In an embodiment, the polypeptide has a sequence identity to SEQ ID NO: 61 of at least 97%. In an embodiment, the polypeptide has a sequence identity to SEQ ID NO: 61 of at least 98%. In an embodiment, the polypeptide has a sequence identity to SEQ ID NO: 61 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 61.

In one embodiment, the polypeptide preferably comprises or consists of the amino acid sequence of SEQ ID NO: 61 or an allelic variant thereof; comprises the amino acid sequence of SEQ ID NO: 61 and a N-terminal and/or C-terminal His-tag and/or HQ-tag; comprises the amino acid sequence of SEQ ID NO: 61 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 988 of SEQ ID NO: 61. In an embodiment, the polypeptide has been isolated.

In a continuation of the eighteenth aspect, the invention relates to a polypeptide having beta-galactosidase activity encoded by a polynucleotide having a sequence identity to the mature polypeptide coding sequence of SEQ ID NO: 59 or the cDNA sequence thereof of at least 85%, e.g., at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the eighteenth aspect, the invention relates to variants of SEQ ID NO: 61 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 61 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 61 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 61 is not more than 10, e.g., 1, 2, 3, 4, 5, 6, 7, 8, 9 or 10. In another embodiment, the number of substitutions, deletions, and/or insertions in SEQ ID NO: 61 is not more than 10, e.g., 1, 2, 3, 4, 5, 6, 7, 8, 9 or 10. In a further embodiment, the number of substitutions in SEQ ID NO: 61 is not more than 10, e.g., 1, 2, 3, 4, 5, 6, 7, 8, 9 or 10. In a further embodiment, the number of conservative substitutions in SEQ ID NO: 61 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the eighteenth aspect comprises the motif Y[Y/F][D/Q][Y/H/W]F (SEQ ID NO: 80) and/or the motif K[Y/F][Y/S]ETK (SEQ ID NO: 81).

In a nineteenth aspect, the invention relates to polypeptides having beta-galactosidase activity and having a sequence identity to the mature polypeptide of SEQ ID NO: 69 of at least 95.5%, e.g., at least 96.0%, at least 96.5%, at least 97.0%, at least 97.2%, at least 97.4%, at least 97.6%, at least 97.8%, at least 98.0%, at least 98.2%, at least 98.4%, at least 98.6%, at least 98.8%, at least 99.0%, at least 99.2%, at least 99.4%, at least 99.6%, at least 99.8% which have beta-galactosidase activity. In one embodiment, the polypeptides differ by up to 43 amino acids, e.g., between 1 and 43 amino acids, such as 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or 43 amino acids from the mature polypeptide of SEQ ID NO: 69.

In one embodiment, the polypeptide preferably comprises or consists of the amino acid sequence of SEQ ID NO: 69 or an allelic variant thereof; comprises the amino acid sequence of SEQ ID NO: 69 and a N-terminal and/or C-terminal His-tag and/or HQ-tag; comprises the amino acid sequence of SEQ ID NO: 69 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 69. In another embodiment, the polypeptide comprises or consists of amino acids 1 to 962 of SEQ ID NO: 69. In an embodiment, the polypeptide has been isolated.

In a continuation of the nineteenth aspect, the invention further relates to polypeptides having beta-galactosidase activity having a sequence identity to SEQ ID NO: 70 of at least 95.5%. In an embodiment, the polypeptide has a sequence identity to SEQ ID NO: 70 of at least 96.0%. In an embodiment, the polypeptide has a sequence identity to SEQ ID NO: 70 of at least 96.5%. In an embodiment, the polypeptide has a sequence identity to SEQ ID NO: 70 of at least 97.0%. In an embodiment, the polypeptide has a sequence identity to SEQ ID NO: 70 of at least 97.2%. In an embodiment, the polypeptide has a sequence identity to SEQ ID NO: 70 of at least 97.4%. In an embodiment, the polypeptide has a sequence identity to SEQ ID NO: 70 of at least 97.6%. In an embodiment, the polypeptide has a sequence identity to SEQ ID NO: 70 of at least 97.8%. In an embodiment, the polypeptide has a sequence identity to SEQ ID NO: 70 of at least 98.0%. In an embodiment, the polypeptide has a sequence identity to SEQ ID NO: 70 of at least 98.2%. In an embodiment, the polypeptide has a sequence identity to SEQ ID NO: 70 of at least 98.4%. In an embodiment, the polypeptide has a sequence identity to SEQ ID NO: 70 of at least 98.6%. In an embodiment, the polypeptide has a sequence identity to SEQ ID NO: 70 of at least 98.8%. In an embodiment, the polypeptide has a sequence identity to SEQ ID NO: 70 of at least 99.0%. In an embodiment, the polypeptide has a sequence identity to SEQ ID NO: 70 of at least 99.2%. In an embodiment, the polypeptide has a sequence identity to SEQ ID NO: 70 of at least 99.4%. In an embodiment, the polypeptide has a sequence identity to SEQ ID NO: 70 of at least 99.6%. In an embodiment, the polypeptide has a sequence identity to SEQ ID NO: 70 of at least 99.8%.

In one embodiment, the polypeptides differ by up to 43 amino acids, e.g., between 1 and 43 amino acids, such as 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or 43 amino acids from SEQ ID NO: 70.

In one embodiment, the polypeptide preferably comprises or consists of the amino acid sequence of SEQ ID NO: 70 or an allelic variant thereof; comprises the amino acid sequence of SEQ ID NO: 70 and a N-terminal and/or C-terminal His-tag and/or HQ-tag; comprises the amino acid sequence of SEQ ID NO: 70 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 962 of SEQ ID NO: 70. In an embodiment, the polypeptide has been isolated.

In a continuation of the nineteenth aspect, the invention relates to a polypeptide having beta-galactosidase activity encoded by a polynucleotide having a sequence identity to the mature polypeptide coding sequence of SEQ ID NO: 68 or the cDNA sequence thereof of at least 95.5%, e.g., at least 96.0%, at least 96.5%, at least 97.0%, at least 97.2%, at least 97.4%, at least 97.6%, at least 97.8%, at least 98.0%, at least 98.2%, at least 98.4%, at least 98.6%, at least 98.8%, at least 99.0%, at least 99.2%, at least 99.4%, at least 99.6%, at least 99.8%, or 100%. In a further embodiment, the polypeptide has been isolated.

In a continuation of the nineteenth aspect, the invention relates to variants of SEQ ID NO: 70 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 70 is not more than 43, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or 43. In another embodiment, the number of positions comprising one or more amino acid substitutions, and/or one or more amino acid deletions, and/or one or more amino acid insertions or any combination thereof in SEQ ID NO: 70 is between 1 and 43, such as 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 70 is not more than 10, e.g., 1, 2, 3, 4, 5, 6, 7, 8, 9 or 10. In another embodiment, the number of substitutions, deletions, and/or insertions in SEQ ID NO: 70 is not more than 10, e.g., 1, 2, 3, 4, 5, 6, 7, 8, 9 or 10. In a further embodiment, the number of substitutions in SEQ ID NO: 70 is not more than 10, e.g., 1, 2, 3, 4, 5, 6, 7, 8, 9 or 10. In a further embodiment, the number of conservative substitutions in SEQ ID NO: 70 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the nineteenth aspect comprises the motif Y[Y/F][D/Q][Y/H/W]F (SEQ ID NO: 80).

In a twentieth aspect, the invention relates to polypeptides having beta-galactosidase activity and having a sequence identity to the mature polypeptide of SEQ ID NO: 72 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 72.

In one embodiment, the polypeptide preferably comprises or consists of the amino acid sequence of SEQ ID NO: 72 or an allelic variant thereof; comprises the amino acid sequence of SEQ ID NO: 72 and a N-terminal and/or C-terminal His-tag and/or HQ-tag; comprises the amino acid sequence of SEQ ID NO: 72 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 72. In another embodiment, the polypeptide comprises or consists of amino acids 1 to 1000 of SEQ ID NO: 72. In an embodiment, the polypeptide has been isolated.

In a continuation of the twentieth aspect, the invention further relates to polypeptides having beta-galactosidase activity having a sequence identity to SEQ ID NO: 73 of at least 80%. In an embodiment, the polypeptide has a sequence identity to SEQ ID NO: 73 of at least 85%. In an embodiment, the polypeptide has a sequence identity to SEQ ID NO: 73 of at least 86%. In an embodiment, the polypeptide has a sequence identity to SEQ ID NO: 73 of at least 87%. In an embodiment, the polypeptide has a sequence identity to SEQ ID NO: 73 of at least 88%. In an embodiment, the polypeptide has a sequence identity to SEQ ID NO: 73 of at least 89%. In an embodiment, the polypeptide has a sequence identity to SEQ ID NO: 73 of at least 90%. In an embodiment, the polypeptide has a sequence identity to SEQ ID NO: 73 of at least 91%. In an embodiment, the polypeptide has a sequence identity to SEQ ID NO: 73 of at least 92%. In an embodiment, the polypeptide has a sequence identity to SEQ ID NO: 73 of at least 93%. In an embodiment, the polypeptide has a sequence identity to SEQ ID NO: 73 of at least 94%. In an embodiment, the polypeptide has a sequence identity to SEQ ID NO: 73 of at least 95%. In an embodiment, the polypeptide has a sequence identity to SEQ ID NO: 73 of at least 96%. In an embodiment, the polypeptide has a sequence identity to SEQ ID NO: 73 of at least 97%. In an embodiment, the polypeptide has a sequence identity to SEQ ID NO: 73 of at least 98%. In an embodiment, the polypeptide has a sequence identity to SEQ ID NO: 73 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 73.

In one embodiment, the polypeptide preferably comprises or consists of the amino acid sequence of SEQ ID NO: 73 or an allelic variant thereof; comprises the amino acid sequence of SEQ ID NO: 73 and a N-terminal and/or C-terminal His-tag and/or HQ-tag; comprises the amino acid sequence of SEQ ID NO: 73 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 1000 of SEQ ID NO: 73. In an embodiment, the polypeptide has been isolated.

In a continuation of the twentieth aspect, the invention relates to a polypeptide having beta-galactosidase activity encoded by a polynucleotide having a sequence identity to the mature polypeptide coding sequence of SEQ ID NO: 71 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twentieth aspect, the invention relates to variants of SEQ ID NO: 73 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 73 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 73 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 73 is not more than 10, e.g., 1, 2, 3, 4, 5, 6, 7, 8, 9 or 10. In another embodiment, the number of substitutions, deletions, and/or insertions in SEQ ID NO: 73 is not more than 10, e.g., 1, 2, 3, 4, 5, 6, 7, 8, 9 or 10. In a further embodiment, the number of substitutions in SEQ ID NO: 73 is not more than 10, e.g., 1, 2, 3, 4, 5, 6, 7, 8, 9 or 10. In a further embodiment, the number of conservative substitutions in SEQ ID NO: 73 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twentieth aspect comprises the motif Y[Y/F][D/Q][Y/H/W]F (SEQ ID NO: 80) and/or the motif K[Y/F][Y/S]ETK (SEQ ID NO: 81).

In a twenty-first aspect, the invention relates to polypeptides having beta-galactosidase activity and having a sequence identity to the mature polypeptide of SEQ ID NO: 75 of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, which have beta-galactosidase activity. In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from the mature polypeptide of SEQ ID NO: 75.

In one embodiment, the polypeptide preferably comprises or consists of the amino acid sequence of SEQ ID NO: 75 or an allelic variant thereof; comprises the amino acid sequence of SEQ ID NO: 75 and a N-terminal and/or C-terminal His-tag and/or HQ-tag; comprises the amino acid sequence of SEQ ID NO: 75 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of the mature polypeptide of SEQ ID NO: 75. In another embodiment, the polypeptide comprises or consists of amino acids 1 to 1000 of SEQ ID NO: 75. In an embodiment, the polypeptide has been isolated.

In a continuation of the twenty-first aspect, the invention further relates to polypeptides having beta-galactosidase activity having a sequence identity to SEQ ID NO: 76 of at least 80%. In an embodiment, the polypeptide has a sequence identity to SEQ ID NO: 76 of at least 85%. In an embodiment, the polypeptide has a sequence identity to SEQ ID NO: 76 of at least 86%. In an embodiment, the polypeptide has a sequence identity to SEQ ID NO: 76 of at least 87%. In an embodiment, the polypeptide has a sequence identity to SEQ ID NO: 76 of at least 88%. In an embodiment, the polypeptide has a sequence identity to SEQ ID NO: 76 of at least 89%. In an embodiment, the polypeptide has a sequence identity to SEQ ID NO: 76 of at least 90%. In an embodiment, the polypeptide has a sequence identity to SEQ ID NO: 76 of at least 91%. In an embodiment, the polypeptide has a sequence identity to SEQ ID NO: 76 of at least 92%. In an embodiment, the polypeptide has a sequence identity to SEQ ID NO: 76 of at least 93%. In an embodiment, the polypeptide has a sequence identity to SEQ ID NO: 76 of at least 94%. In an embodiment, the polypeptide has a sequence identity to SEQ ID NO: 76 of at least 95%. In an embodiment, the polypeptide has a sequence identity to SEQ ID NO: 76 of at least 96%. In an embodiment, the polypeptide has a sequence identity to SEQ ID NO: 76 of at least 97%. In an embodiment, the polypeptide has a sequence identity to SEQ ID NO: 76 of at least 98%. In an embodiment, the polypeptide has a sequence identity to SEQ ID NO: 76 of at least 99%.

In one embodiment, the polypeptides differ by up to 50 amino acids, e.g., between 1 and 50 amino acids, such as 1-45, 1-40, 1-35, 1-30, 1-25, 1-20, 1-15, 1-10 or 1-5 amino acids, or 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 amino acids from SEQ ID NO: 76.

In one embodiment, the polypeptide preferably comprises or consists of the amino acid sequence of SEQ ID NO: 76 or an allelic variant thereof; comprises the amino acid sequence of SEQ ID NO: 76 and a N-terminal and/or C-terminal His-tag and/or HQ-tag; comprises the amino acid sequence of SEQ ID NO: 76 and a N-terminal and/or C-terminal extension of between 1 and 10 amino acids; or is a fragment thereof having beta-galactosidase activity and having at least 90% such as at least 91%, at least 92%, at least 93%, at least 94%, at least 95%, at least 96%, at least 97%, at least 98% or at least 99% of the length of the mature polypeptide. In another embodiment, the polypeptide comprises or consists of amino acids 1 to 1000 of SEQ ID NO: 76. In an embodiment, the polypeptide has been isolated.

In a continuation of the twenty-first aspect, the invention relates to a polypeptide having beta-galactosidase activity encoded by a polynucleotide having a sequence identity to the mature polypeptide coding sequence of SEQ ID NO: 74 or the cDNA sequence thereof of at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%. In a further embodiment, the polypeptide has been isolated.

In a continuation of the twenty-first aspect, the invention relates to variants of SEQ ID NO: 76 having beta-galactosidase activity comprising one or more amino acid substitutions, and/or one or more amino acid deletions, and/or one or more amino acid insertions or any combination thereof at one or more (e.g., several) positions. In an embodiment, the number of positions comprising one or more amino acid substitutions, and/or one or more amino acid deletions, and/or one or more amino acid insertions or any combination thereof in SEQ ID NO: 76 is not more than 50, e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50. In another embodiment, the number of positions comprising one or more amino acid substitutions, and/or one or more amino acid deletions, and/or one or more amino acid insertions or any combination thereof in SEQ ID NO: 76 is between 1 and 50, such as 1-45, 1-40, 1-35, 1-30, 1-25, 1-20, 1-15, 1-10 or 1-5 positions. In an embodiment, the number of positions comprising one or more amino acid substitutions, and/or one or more amino acid deletions, and/or one or more amino acid insertions or any combination thereof in SEQ ID NO: 76 is not more than 10, e.g., 1, 2, 3, 4, 5, 6, 7, 8, 9 or 10. In another embodiment, the number of substitutions, deletions, and/or insertions in SEQ ID NO: 76 is not more than 10, e.g., 1, 2, 3, 4, 5, 6, 7, 8, 9 or 10. In a further embodiment, the number of substitutions in SEQ ID NO: 76 is not more than 10, e.g., 1, 2, 3, 4, 5, 6, 7, 8, 9 or 10. In a further embodiment, the number of conservative substitutions in SEQ ID NO: 76 is not more than 10, e.g., 1, 2, 3, 4, 5, 6, 7, 8, 9 or 10.

Examples of amino acid changes and conservative substitutions are described in the second aspect of the invention.

In an embodiment, the polypeptide of the twenty-first aspect comprises the motif Y[Y/F][D/Q][Y/H/W]F (SEQ ID NO: 80) and/or the motif K[Y/F][Y/S]ETK (SEQ ID NO: 81).

Sources of Polypeptides Having Beta-Galactosidase or Galactanase Activity

A polypeptide having beta-galactosidase or galactanase activity of the present invention may be obtained from microorganisms of any genus. For purposes of the present invention, the term "obtained from" as used herein in connection with a given source shall mean that the polypeptide encoded by a polynucleotide is produced by the source or by a strain in which the polynucleotide from the source has been inserted. In one aspect, the polypeptide obtained from a given source is secreted extracellularly.

The polypeptide having galactanase activity is a bacterial polypeptide, preferably from the phylum Firmicutes or more preferably from the class Bacilli. In one embodiment, the polypeptide having galactanase activity is from a bacterium of the order Bacillales, or from the family Paenibacillaceae, or from the genus *Cohnella* or from the species *Cohnella* sp-60555, *Cohnella xylanilytica* or *Cohnella laeviribosi*. In another embodiment, the polypeptide having galactanase activity is from a bacterium of the order Bacillales, or from the family Paenibacillaceae, or from the genus *Paenibacillus* or from the species *Paenibacillus* tundra, *Paenibacillus barcinonensis*, *Paenibacillus* sp-62603, *Paenibacillus xylanilyticus*, *Paenibacillus* sp-18179, *Paenibacillus peoriae* or *Paenibacillus xylanexedens*.

The polypeptide having beta-galactosidase activity is a fungal polypeptide, preferably from the phylum Ascomycota or more preferably from the class Eurotiomycetes or the class Dothideomycetes. In one embodiment, the polypeptide having beta-galactosidase activity is from a fungus of the order Eurotiales, or from the family Aspergillaceae, or from the genus *Hamigera* or from the species *Hamigera paravellanea*. In one embodiment, the polypeptide is from a fungus of the order Eurotiales, or from the family Aspergillaceae, or from the genus *Aspergillus* or from the species *Aspergillus unguis*, *Aspergillus tamari Aspergillus oryzae*, *Aspergillus carneus*, *Aspergillus westerdijkiae*, *Aspergillus wentii* or *Aspergillus lentulus*. In one embodiment, the polypeptide is from a fungus of the order Pleosporales, or from the family Pleosporaceae, or from the genus *Curvularia* or from the species *Curvularia spicifera*. In one embodiment, the polypeptide is from a fungus of the order Eurotiales, or from the family Aspergillaceae, or from the genus *Penicillium* or from the species *Penicillium quercetorum* or *Penicillium simplicissimum*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art (see, e.g., Sambrook et al., 1989, supra).

Liquid Formulations Comprising GH35 Beta-Galactosidases and GH53 Galactanases

In a nineteenth aspect, the invention relates to a liquid formulation comprising one or more GH53 polypeptides having galactanase activity and one or more GH35 polypeptides having beta-galactosidase activity, wherein the liquid formulation comprises:
(A) 0.001% to 25% w/w of polypeptide having galactanase activity;
(B) 0.001% to 25% w/w of polypeptide having beta-galactosidase activity; and
(C) water.

In one embodiment of the nineteenth aspect, the invention relates to a liquid formulation comprising one or more GH53 polypeptides having galactanase activity and one or more GH35 polypeptides having beta-galactosidase activity, wherein the liquid formulation comprises:
(A) 0.001% to 25% w/w of polypeptide having galactanase activity;
(B) 0.001% to 25% w/w of polypeptide having beta-galactosidase activity;
(C) 20% to 80% w/w of polyol; and
(D) water.

In one embodiment of the nineteenth aspect, the invention relates to a liquid formulation comprising one or more GH53 polypeptides having galactanase activity and one or more GH35 polypeptides having beta-galactosidase activity, wherein the liquid formulation comprises:
(A) 0.001% to 25% w/w of polypeptide having galactanase activity;
(B) 0.001% to 25% w/w of polypeptide having beta-galactosidase activity;
(C) 0.001% to 2.0% w/w preservative; and
(D) water.

In one embodiment of the nineteenth aspect, the invention relates to a liquid formulation comprising one or more GH53 polypeptides having galactanase activity and one or more GH35 polypeptides having beta-galactosidase activity, wherein the liquid formulation comprises:
(A) 0.001% to 25% w/w of polypeptide having galactanase activity;
(B) 0.001% to 25% w/w of polypeptide having beta-galactosidase activity;
(C) 20% to 80% w/w of polyol;
(D) 0.001% to 2.0% w/w preservative; and
(E) water.

In one embodiment to any part of the nineteenth aspect, the GH53 polypeptide comprises the motif GV[T/M]PD[W/M]VQ[IN]GNE (SEQ ID NO: 65) and/or the motif WADP[A/G]xQxKPxAW (SEQ ID NO: 66). In one embodiment to any part of the nineteenth aspect, the GH53 polypeptide is selected from the group consisting of:
(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 7;
(c) a polypeptide having at least 80%, e.g., at least 85%, at least 90% or at least 95% sequence identity to the polypeptide of SEQ ID NO: 11;
(d) a polypeptide having at least 80%, e.g., at least 85%, at least 90% or at least 95% sequence identity to the polypeptide of SEQ ID NO: 15;
(e) a polypeptide having at least 80%, e.g., at least 85%, at least 90% or at least 95% sequence identity to the polypeptide of SEQ ID NO: 19;
(f) a polypeptide having at least 80%, e.g., at least 85%, at least 90% or at least 95% sequence identity to the polypeptide of SEQ ID NO: 23;
(g) a polypeptide having at least 80%, e.g., at least 85%, at least 90% or at least 95% sequence identity to the polypeptide of SEQ ID NO: 27;
(h) a polypeptide having at least 80%, e.g., at least 85%, at least 90% or at least 95% sequence identity to the polypeptide of SEQ ID NO: 31;
(i) a polypeptide having at least 80%, e.g., at least 85%, at least 90% or at least 95% sequence identity to the polypeptide of SEQ ID NO: 35;
(j) a polypeptide having at least 80%, e.g., at least 85%, at least 90% or at least 95% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide.

In one embodiment to any part of the nineteenth aspect, the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment to any part of the nineteenth aspect, the GH35 polypeptide is selected from the group consisting of:
(a) a polypeptide having at least 80%, e.g., at least 85%, at least 90% or at least 95% sequence identity to the polypeptide of SEQ ID NO: 43;
(b) a polypeptide having at least 80%, e.g., at least 85%, at least 90% or at least 95% sequence identity to the polypeptide of SEQ ID NO: 46;
(c) a polypeptide having at least 80%, e.g., at least 85%, at least 90% or at least 95% sequence identity to the polypeptide of SEQ ID NO: 49;
(d) a polypeptide having at least 80%, e.g., at least 85%, at least 90% or at least 95% sequence identity to the polypeptide of SEQ ID NO: 52;
(e) a polypeptide having at least 80%, e.g., at least 85%, at least 90% or at least 95% sequence identity to the polypeptide of SEQ ID NO: 55;
(f) a polypeptide having at least 80%, e.g., at least 85%, at least 90% or at least 95% sequence identity to the polypeptide of SEQ ID NO: 58;
(g) a polypeptide having at least 80%, e.g., at least 85%, at least 90% or at least 95% sequence identity to the polypeptide of SEQ ID NO: 61;
(h) a polypeptide having at least 80%, e.g., at least 85%, at least 90% or at least 95% sequence identity to the polypeptide of SEQ ID NO: 70;

(i) a polypeptide having at least 80%, e.g., at least 85%, at least 90% or at least 95% sequence identity to the polypeptide of SEQ ID NO: 73;

(j) a polypeptide having at least 80%, e.g., at least 85%, at least 90% or at least 95% sequence identity to the polypeptide of SEQ ID NO: 76;

(k) a polypeptide having at least 80%, e.g., at least 85%, at least 90% or at least 95% sequence identity to the polypeptide of SEQ ID NO: 79;

(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(m) a polypeptide comprising the polypeptide of (a), (b), (c), (d), (e), (f), (g), (h), (i), (j), (k) or (l) and a N-terminal and/or C-terminal His-tag and/or HQ-tag;

(n) a polypeptide comprising the polypeptide of (a), (b), (c), (d), (e), (f), (g), (h), (i), (j), (k) or (l) and a N-terminal and/or C-terminal extension of between 1 and 10 amino acids; and (o) a fragment of the polypeptide of (a), (b), (c), (d), (e), (f), (g), (h), (i), (j), (k) or (l) having galactanase activity and having at least 90% of the length of the mature polypeptide.

In one embodiment to any part of the nineteenth aspect, the GH53 polypeptide comprises the motif GV[T/M]PD[W/M]VQ[I/V]GNE (SEQ ID NO: 65) and/or the motif WADP[A/G]xQxKPxAW (SEQ ID NO: 66) and the GH35 polypeptide comprises the motif Y[Y/F][D/Q][Y/H/W]F (SEQ ID NO: 80) and/or the motif K[Y/F][Y/S]ETK (SEQ ID NO: 81). In one embodiment to any part of the nineteenth aspect, the GH53 polypeptide is selected from the group consisting of:

(a) a polypeptide having at least 80%, e.g., at least 85%, at least 90% or at least 95% sequence identity to the polypeptide of SEQ ID NO: 3;

(b) a polypeptide having at least 80%, e.g., at least 85%, at least 90% or at least 95% sequence identity to the polypeptide of SEQ ID NO: 7;

(c) a polypeptide having at least 80%, e.g., at least 85%, at least 90% or at least 95% sequence identity to the polypeptide of SEQ ID NO: 11;

(d) a polypeptide having at least 80%, e.g., at least 85%, at least 90% or at least 95% sequence identity to the polypeptide of SEQ ID NO: 15;

(e) a polypeptide having at least 80%, e.g., at least 85%, at least 90% or at least 95% sequence identity to the polypeptide of SEQ ID NO: 19;

(f) a polypeptide having at least 80%, e.g., at least 85%, at least 90% or at least 95% sequence identity to the polypeptide of SEQ ID NO: 23;

(g) a polypeptide having at least 80%, e.g., at least 85%, at least 90% or at least 95% sequence identity to the polypeptide of SEQ ID NO: 27;

(h) a polypeptide having at least 80%, e.g., at least 85%, at least 90% or at least 95% sequence identity to the polypeptide of SEQ ID NO: 31;

(i) a polypeptide having at least 80%, e.g., at least 85%, at least 90% or at least 95% sequence identity to the polypeptide of SEQ ID NO: 35;

(j) a polypeptide having at least 80%, e.g., at least 85%, at least 90% or at least 95% sequence identity to the polypeptide of SEQ ID NO: 39;

(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(l) a polypeptide comprising the polypeptide of (a), (b), (c), (d), (e), (f), (g), (h), (i), (j) or (k) and a N-terminal and/or C-terminal His-tag and/or HQ-tag;

(m) a polypeptide comprising the polypeptide of (a), (b), (c), (d), (e), (f), (g), (h), (i), (j) or (k) and a N-terminal and/or C-terminal extension of between 1 and 10 amino acids; and (n) a fragment of the polypeptide of (a), (b), (c), (d), (e), (f), (g), (h), (i), (j), (k) or (l) having galactanase activity and having at least 90% of the length of the mature polypeptide;

and the GH35 polypeptide is selected from the group consisting of:

(a) a polypeptide having at least 80%, e.g., at least 85%, at least 90% or at least 95% sequence identity to the polypeptide of SEQ ID NO: 43;

(b) a polypeptide having at least 80%, e.g., at least 85%, at least 90% or at least 95% sequence identity to the polypeptide of SEQ ID NO: 46;

(c) a polypeptide having at least 80%, e.g., at least 85%, at least 90% or at least 95% sequence identity to the polypeptide of SEQ ID NO: 49;

(d) a polypeptide having at least 80%, e.g., at least 85%, at least 90% or at least 95% sequence identity to the polypeptide of SEQ ID NO: 52;

(e) a polypeptide having at least 80%, e.g., at least 85%, at least 90% or at least 95% sequence identity to the polypeptide of SEQ ID NO: 55;

(f) a polypeptide having at least 80%, e.g., at least 85%, at least 90% or at least 95% sequence identity to the polypeptide of SEQ ID NO: 58;

(g) a polypeptide having at least 80%, e.g., at least 85%, at least 90% or at least 95% sequence identity to the polypeptide of SEQ ID NO: 61;

(h) a polypeptide having at least 80%, e.g., at least 85%, at least 90% or at least 95% sequence identity to the polypeptide of SEQ ID NO: 70;

(i) a polypeptide having at least 80%, e.g., at least 85%, at least 90% or at least 95% sequence identity to the polypeptide of SEQ ID NO: 73;

(j) a polypeptide having at least 80%, e.g., at least 85%, at least 90% or at least 95% sequence identity to the polypeptide of SEQ ID NO: 76;

(k) a polypeptide having at least 80%, e.g., at least 85%, at least 90% or at least 95% sequence identity to the polypeptide of SEQ ID NO: 79;

(l) a variant of SEQ ID NO: 43, SEQ ID NO: 46, SEQ ID NO: 49, SEQ ID NO: 52, SEQ ID NO: 55, SEQ ID NO: 58, SEQ ID NO: 61, SEQ ID NO: 70, SEQ ID NO: 73, SEQ ID NO: 76 or SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(m) a polypeptide comprising the polypeptide of (a), (b), (c), (d), (e), (f), (g), (h), (i), (j), (k) or (l) and a N-terminal and/or C-terminal His-tag and/or HQ-tag;
(n) a polypeptide comprising the polypeptide of (a), (b), (c), (d), (e), (f), (g), (h), (i), (j), (k) or (l) and a N-terminal and/or C-terminal extension of between 1 and 10 amino acids; and
(o) a fragment of the polypeptide of (a), (b), (c), (d), (e), (f), (g), (h), (i), (j), (k) or (l) having galactanase activity and having at least 90% of the length of the mature polypeptide.

In one embodiment to any part of the nineteenth aspect, the GH53 polypeptide having galactanase activity is obtained or obtainable from the taxonomic family Paenibacillaceae.

In one embodiment to any part of the nineteenth aspect, the GH53 polypeptide having galactanase activity is obtained or obtainable from the taxonomic family Aspergillaceae.

In one embodiment to any part of the nineteenth aspect, the composition releases at least 12 g, such as at least 13 g, such as at least 14 g, at least 15 g, at least 16 g, at least 17 g, at least 18 g, at least 19 g, at least 20 g or at least 22 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

In one embodiment to any part of the nineteenth aspect, the liquid formulation comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1, 2-propylene glycol, 1, 3-propylene glycol, sodium sulfate, dextrin, cellulose, sodium thiosulfate, kaolin and calcium carbonate.

In one embodiment to any part of the nineteenth aspect, the liquid formulation comprises one or more polyols, preferably a polyol selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment to any part of the nineteenth aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol. In one embodiment to any part of the nineteenth aspect, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600. In one embodiment to any part of the nineteenth aspect, the liquid formulation comprises 20%-80% polyol (i.e. total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment to any part of the nineteenth aspect, the preservative is selected from the group consisting of sodium sorbate, potassium sorbate, sodium benzoate and potassion benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.01% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassion benzoate or any combination thereof.

In one embodiment to any part of the ninth aspect, the liquid formulation comprises 0.01% to 25% w/w polypeptide having beta-galactosidase activity, preferably 0.05% to 20% w/w polypeptide having beta-galactosidase activity, more preferably 0.2% to 15% w/w polypeptide having beta-galactosidase activity, more preferably 0.5% to 15% w/w polypeptide having beta-galactosidase activity or most preferably 1.0% to 10% w/w polypeptide having beta-galactosidase activity.

In one embodiment to any part of the ninth aspect, the liquid formulation comprises 0.01% to 25% w/w polypeptide having galactanase activity, preferably 0.05% to 20% w/w polypeptide having galactanase activity, more preferably 0.2% to 15% w/w polypeptide having galactanase activity, more preferably 0.5% to 15% w/w polypeptide having galactanase activity or most preferably 1.0% to 10% w/w polypeptide having galactanase activity.

In one embodiment to any part of the nineteenth aspect, the liquid formulation comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment to any part of the nineteenth aspect, the liquid formulation comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum,*

*Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

Methods of Improving Animal Performance

In a twentieth aspect, the invention relates to a method of improving one or more performance parameters of an animal comprising administering to one or more animals the composition of the first aspect of the invention or any embodiment of the first aspect of the invention herein defined, such as in the section related to 'Compositions comprising GH35 beta-galactosidases and GH53 galactanases' or the section on 'Combinations'. In one preferred embodiment, the composition is a granule that optionally comprises a salt and/or wax and/or a flour coating. In one preferred embodiment, the composition is a liquid formulation as described in the twentieth aspect.

The twentieth aspect of the invention also relates to a method of improving one or more performance parameters of an animal comprising administering to one or more animals an animal feed additive comprising the composition of the first aspect of the invention or any embodiment of the first aspect of the invention herein defined, such as in the section related to 'Compositions comprising GH35 beta-galactosidases and GH53 galactanases' or the section on 'Combinations'. In one embodiment, animal feed additive comprises of one or more additional enzymes, one or more microbes, one or more vitamins, one or more minerals, one or more amino acids or any combination thereof. In a preferred embodiment, the animal feed additive is a granule that optionally comprises a salt and/or wax and/or a flour coating.

The twentieth aspect of the invention also relates to a method of improving one or more performance parameters of an animal comprising administering to one or more animals an animal feed comprising the composition of the first aspect of the invention or any embodiment of the first aspect of the invention herein defined, such as in the section related to 'Compositions comprising GH35 beta-galactosidases and GH53 galactanases' or the section on 'Combinations' and plant based material. In one embodiment, the plant based material is from the taxonomic subclass rosids. In one embodiment, the animal feed comprises one or more formulating agents as defined herein. In one embodiment, the animal feed comprises one or more additional enzymes as defined herein. In one embodiment, the animal feed comprises one or more microbes as defined herein. In a preferred embodiment, the animal feed has been pelleted.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In an embodiment, the performance parameter is selected from the list consisting of body weight gain (BWG), European Production Efficiency Factor (EPEF) and feed conversion ratio (FCR).

Methods of Releasing Galactose

In a twenty-first aspect, the invention relates to method of releasing galactose from plant based material, comprising treating plant based material with the composition of the first aspect of the invention or any embodiment of the first aspect of the invention herein defined, such as in the section related to 'Compositions comprising GH35 beta-galactosidases and GH53 galactanases' or the section on 'Combinations'. In an embodiment, the plant based material is from the taxonomic subclass rosids. In one preferred embodiment, the composition is a granule that optionally comprises a salt and/or wax and/or a flour coating. In one preferred embodiment, the composition is a liquid formulation as described in the twentieth aspect.

The twenty-first aspect of the invention also relates to a method of releasing galactose from plant based material, comprising treating plant based material with and animal feed additive comprising the composition of the first aspect of the invention or any embodiment of the first aspect of the invention herein defined, such as in the section related to 'Compositions comprising GH35 beta-galactosidases and GH53 galactanases' or the section on 'Combinations'. In one embodiment, the animal feed additive comprises one or more additional enzymes, one or more microbes, one or more vitamins, one or more minerals, one or more amino acids or any combination thereof. In an embodiment, the plant based material is from the taxonomic subclass rosids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Methods for Improving the Nutritional Value of an Animal Feed

The term improving the nutritional value of an animal feed means improving the availability of nutrients in the feed. The nutritional values refers in particular to improving the solubilisation and degradation of the non starch polysaccharide (NSP) fraction, such as the galactan polysaccharide in the cell wall pectic network, thereby increasing the amount of galactose released which can be utilised by the animal. Consequently, an improved galactose release will result in an improvement of the nutritional value of the feed, thus resulting in increased growth rate and/or weight gain and/or feed conversion (i.e. the weight of ingested feed relative to weight gain).

In a twenty-second aspect, the invention relates to a method for improving the nutritional value of an animal feed comprising treating the animal feed with the composition of the first aspect of the invention or any embodiment of the first aspect of the invention herein defined, such as in the section related to 'Compositions comprising GH35 beta-galactosidases and GH53 galactanases' or the section on 'Combinations'. In an embodiment, the animal feed comprises plant based material from the taxonomic subclass rosids. In one preferred embodiment, the composition is a granule that optionally comprises a salt and/or wax and/or a flour coating. In one preferred embodiment, the composition is a liquid formulation as described in the twentieth aspect.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

The twenty-second aspect of the invention also relates to a method for improving the nutritional value of an animal feed comprising treating the animal feed with an animal feed additive comprising the composition of the first aspect of the invention or any embodiment of the first aspect of the invention herein defined, such as in the section related to 'Compositions comprising GH35 beta-galactosidases and GH53 galactanases' or the section on 'Combinations'. In an embodiment, the animal feed comprises plant based material from the taxonomic subclass rosids. In a preferred embodiment, the animal feed additive is a granule that optionally comprises a salt and/or wax and/or a flour coating. In an embodiment, the animal feed will have improved nutrient digestibility.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Method for Reducing the Antinutritional Effects of an Animal Feed

An excessive amount of oligosaccharides in the hindgut can result in antinutritional effects due to flatulence production. By reducing the amount of oligosaccharide fermentation, the antinutritional effects of some animal feeds can be reduced resulting in improved gut and animal health.

In a twenty-third aspect, the invention relates to a method for improving the nutritional value of an animal feed comprising treating the animal feed with the composition of the first aspect of the invention or any embodiment of the first aspect of the invention herein defined, such as in the section related to 'Compositions comprising GH35 beta-galactosidases and GH53 galactanases' or the section on 'Combinations'. In an embodiment, the animal feed comprises plant based material from the taxonomic subclass rosids. In one preferred embodiment, the composition is a granule that optionally comprises a salt and/or wax and/or a flour coating. In one preferred embodiment, the composition is a liquid formulation as described in the twentieth aspect.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

The twenty-third aspect of the invention also relates to a method for improving the nutritional value of an animal feed comprising treating the animal feed with an animal feed additive comprising the composition of the first aspect of the invention or any embodiment of the first aspect of the invention herein defined, such as in the section related to 'Compositions comprising GH35 beta-galactosidases and GH53 galactanases' or the section on 'Combinations'. In an embodiment, the animal feed comprises plant based material from the taxonomic subclass rosids. In a preferred embodiment, the animal feed additive is a granule that optionally comprises a salt and/or wax and/or a flour coating. In an embodiment, the animal feed will have improved nutrient digestibility.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Methods of Preparing an Animal Feed

In a twenty-fourth aspect, the invention relates to a method of preparing an animal feed, comprising mixing the composition of the first aspect of the invention or any embodiment of the first aspect of the invention herein defined, such as in the section related to 'Compositions comprising GH35 beta-galactosidases and GH53 galactanases' or the section on 'Combinations' with plant based material.

In one embodiment, the composition comprises one or more formulating agents as defined herein. In one embodiment, the composition comprises one or more additional enzymes as defined herein. In one embodiment, the composition comprises one or more microbes as defined herein. In a preferred embodiment, the composition is a granule that optionally comprises a salt and/or wax and/or a flour coating.

The twenty-fourth aspect of the invention also relates to a method of preparing an animal feed, comprising mixing the composition of the first aspect of the invention or any embodiment of the first aspect of the invention herein defined, such as in the section related to 'Compositions comprising GH35 beta-galactosidases and GH53 galactanases' or the section on 'Combinations' with plant based material. In an embodiment, the animal feed comprises plant based material from the taxonomic subclass rosids. In one preferred embodiment, the composition is a granule that optionally comprises a salt and/or wax and/or a flour coating. In one preferred embodiment, the composition is a liquid formulation as described in the twentieth aspect. In an embodiment, the animal feed will have improved nutrient digestibility.

In one embodiment, the animal feed additive comprises one or more formulating agents as defined herein. In one embodiment, the animal feed additive comprises one or more additional enzymes as defined herein. In one embodiment, the animal feed additive comprises one or more microbes as defined herein. In one embodiment, the animal feed additive comprises one or more vitamins, one or more minerals and/or one or more amino acids. In a preferred embodiment, the animal feed additive is a granule that optionally comprises a salt and/or wax and/or a flour coating.

In an embodiment, the plant based material is from the taxonomic subclass rosids. In one aspect, the plant based material is from the taxonomic order Fabales, such as the family Fabaceae, preferably the subfamilies Caesalpinioideae or Mimosoideae or Papilionoideae, or more preferably from the tribes Phaseoleae, Cicereae, Genisteae, Fabeae, Dalbergieae or Phaseoleae. In one aspect, the plant based material is from the taxonomic order Brassicales, such as the family Brassicaceae, preferably the tribe Brassiceae, more preferably the family *Brassica*.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

In a preferred embodiment, the animal feed has been pelleted. The animal feed may be treated with the enzyme of the invention before the pelleting step or sprayed on after the pelleting step.

Polynucleotides

The present invention also relates to isolated polynucleotides encoding a polypeptide of the present invention.

The techniques used to isolate or clone a polynucleotide are known in the art and include isolation from genomic DNA or cDNA, or a combination thereof. The cloning of the polynucleotides from genomic DNA can be effected, e.g., by using the well-known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligation activated transcription (LAT) and polynucleotide-based amplification (NASBA) may be used. The polynucleotides may be cloned from a strain of *Bacillus*, or a related organism and thus, for example, may be an allelic or species variant of the polypeptide encoding region of the polynucleotide.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including mutant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus*

*licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* ctyIIIA gene (Agaisse and Lereclus, 1994, *Molecular Microbiology* 13: 97-107), *E. coli* lac operon, *E. coli* trc promoter (Egon et al., 1988, *Gene* 69: 301-315), *Streptomyces coelicolor* agarase gene (dagA), and prokaryotic beta-lactamase gene (Villa-Kamaroff et al., 1978, *Proc. Natl. Acad. Sci. USA* 75: 3727-3731), as well as the tac promoter (DeBoer et al., 1983, *Proc. Natl. Acad. Sci. USA* 80: 21-25). Further promoters are described in "Useful proteins from recombinant bacteria" in Gilbert et al., 1980, *Scientific American* 242: 74-94; and in Sambrook et al., 1989, supra. Examples of tandem promoters are disclosed in WO 99/43835.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease (WO 96/00787), *Fusarium venenatum* amyloglucosidase (WO 00/56900), *Fusarium venenatum* Daria (WO 00/56900), *Fusarium venenatum* Quinn (WO 00/56900), *Rhizomucor miehei* lipase, *Rhizomucor miehei* aspartic proteinase, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* galactanase I, *Trichoderma reesei* galactanase II, *Trichoderma reesei* galactanase III, *Trichoderma reesei* beta-xylosidase, and *Trichoderma reesei* translation elongation factor, as well as the NA2-tpi promoter (a modified promoter from an *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and mutant, truncated, and hybrid promoters thereof. Other promoters are described in U.S. Pat. No. 6,011,147.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase V, *Trichoderma reesei* galactanase I, *Trichoderma reesei* galactanase II, *Trichoderma reesei* galactanase III, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* ctyIIIA gene (WO 94/25612) and a *Bacillus subtilis* SP82 gene (Hue et al., 1995, *Journal of Bacteriology* 177: 3465-3471).

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for *Aspergillus nidulans* anthranilate synthase, *Aspergillus niger* glucoamylase, *Aspergillus niger* alpha-glucosidase *Aspergillus oryzae* TAKA amylase, and *Fusarium oxysporum* trypsin-like protease.

Useful polyadenylation sequences for yeast host cells are described by Guo and Sherman, 1995, *Mol. Cellular Biol.* 15: 5983-5990.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for *Bacillus* NCIB 11837 maltogenic amylase, *Bacillus licheniformis* subtilisin, *Bacillus licheniformis* beta-lactamase, *Bacillus stearothermophilus* alpha-amylase, *Bacillus stearothermophilus* neutral proteases (nprT, nprS, nprM), and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus niger* neutral amylase, *Aspergillus niger* glucoamylase, *Aspergillus oryzae* TAKA amylase, *Humicola insolens* cellulase, *Humicola insolens* endoglucanase V, *Humicola lanuginosa* lipase, and *Rhizomucor miehei* aspartic proteinase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Myceliophthora thermophila* laccase (WO 95/33836), *Rhizomucor miehei* aspartic proteinase, and *Saccharomyces cerevisiae* alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the *Aspergillus niger* glucoamylase promoter, *Aspergillus oryzae* TAKA alpha-amylase promoter, and *Aspergillus oryzae* glucoamylase promoter, *Trichoderma reesei* cellobiohydrolase I promoter, and *Trichoderma reesei* cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosylaminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bar gene. Preferred for use in a *Trichoderma* cell are adeA, adeB, amdS, hph, and pyrG genes.

The selectable marker may be a dual selectable marker system as described in WO 2010/039889. In one aspect, the dual selectable marker is an hph-tk dual selectable marker system.

The vector preferably contains an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANSI (Gems et al., 1991, *Gene* 98: 61-67; Cullen et al., 1987, *Nucleic Acids Res.* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells.

The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

The introduction of DNA into a *Bacillus* cell may be effected by protoplast transformation (see, e.g., Chang and Cohen, 1979, *Mol. Gen. Genet.* 168: 111-115), competent cell transformation (see, e.g., Young and Spizizen, 1961, *J. Bacteriol.* 81: 823-829, or Dubnau and Davidoff-Abelson, 1971, *J. Mol. Biol.* 56: 209-221), electroporation (see, e.g., Shigekawa and Dower, 1988, *Biotechniques* 6: 742-751), or conjugation (see, e.g., Koehler and Thorne, 1987, *J. Bacteriol.* 169: 5271-5278). The introduction of DNA into an *E. coli* cell may be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may be effected by protoplast transformation, electroporation (see, e.g., Gong et al., 2004, *Folia Microbiol. (Praha)* 49: 399-405), conjugation (see, e.g., Mazodier et al., 1989, *J. Bacteriol.* 171: 3583-3585), or transduction (see, e.g., Burke et al., 2001, *Proc. Natl. Acad. Sci. USA* 98: 6289-6294). The introduction of DNA into a *Pseudomonas* cell may be effected by electroporation (see, e.g., Choi et al., 2006, *J. Microbiol. Methods* 64: 391-397) or conjugation (see, e.g., Pinedo and Smets, 2005, *Appl. Environ. Microbiol.* 71: 51-57). The introduction of DNA into a *Streptococcus* cell may be effected by natural competence (see, e.g., Perry and Kuramitsu, 1981, *Infect. Immun.* 32: 1295-1297), protoplast transformation (see, e.g., Catt and Jollick, 1991, *Microbios* 68: 189-207), electroporation (see, e.g., Buckley et al., 1999, *Appl. Environ. Microbiol.* 65: 3800-3804), or conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell. The host cell may be a fungal cell. "Fungi" as used herein includes the phyla Ascomycota, Basidiomycota, Chytridiomycota, and Zygomycota as well as the Oomycota and all mitosporic fungi (as defined by Hawksworth et al., *In, Ainsworth and Bisby's Dictionary of The Fungi*, 8th edition, 1995, CAB International, University Press, Cambridge, UK).

The fungal host cell may be a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in Biology and Activities of Yeast (Skinner, Passmore, and Davenport, editors, *Soc. App. Bacteriol. Symposium Series No. 9*, 1980).

The yeast host cell may be a *Candida, Hansenula, Kluyveromyces, Pichia, Saccharomyces, Schizosaccharomyces,* or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis,* or *Yarrowia lipolytica* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes,* or *Trichoderma* cell.

For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei,* or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238023, Yelton et al., 1984, *Proc. Natl. Acad. Sci. USA* 81: 1470-1474, and Christensen et al., 1988, *Bio/Technology* 6: 1419-1422. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *J. Bacteriol.* 153: 163; and Hinnen et al., 1978, *Proc. Natl. Acad. Sci. USA* 75: 1920.

Methods of Production

The present invention also relates to methods of producing a polypeptide of the present invention, comprising (a) cultivating a cell, which in its wild-type form produces the polypeptide, under conditions conducive for production of the polypeptide; and optionally, (b) recovering the polypeptide. In one aspect, the cell is a *Cohnella* cell. In another aspect, the cell is a *Cohnella* sp-60555 cell. In a further aspect, the cell is a *Cohnella xylanilytica* cell. In a further aspect, the cell is a *Cohnella laeviribosi* cell. In one aspect, the cell is a *Paenibacillus* cell. In another aspect, the cell is a *Paenibacillus* tundra cell. In a further aspect, the cell is a *Paenibacillus barcinonensis* cell. In another aspect, the cell is a *Paenibacillus* sp-62603 cell. In a further aspect, the cell is a *Paenibacillus xylanilyticus* cell. In another aspect, the cell is a *Paenibacillus* sp-18179 cell. In a further aspect, the cell is a *Paenibacillus peoriae* cell. In another aspect, the cell is a *Paenibacillus xylanexedens* cell.

In one aspect, the cell is a *Hamigera* cell. In another aspect, the cell is a *Hamigera paravellanea* cell. In one aspect, the cell is an *Aspergillus* cell. In another aspect, the cell is an *Aspergillus unguis* cell. In a further aspect, the cell is an *Aspergillus tamari* cell. In another aspect, the cell is an *Aspergillus oryzae* cell. In a further aspect, the cell is an *Aspergillus carneus* cell. In one aspect, the cell is a *Curvularia* cell. In another aspect, the cell is a *Curvularia spicifera* cell. In one aspect, the cell is a *Penicillium* cell. In another aspect, the cell is a *Penicillium quercetorum* cell.

The present invention also relates to methods of producing a polypeptide of the present invention, comprising (a) cultivating a recombinant host cell of the present invention under conditions conducive for production of the polypeptide; and optionally, (b) recovering the polypeptide.

The host cells are cultivated in a nutrient medium suitable for production of the polypeptide using methods known in the art. For example, the cells may be cultivated by shake flask cultivation, or small-scale or large-scale fermentation (including continuous, batch, fed-batch, or solid state fermentations) in laboratory or industrial fermentors in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted, it can be recovered from cell lysates.

The polypeptide may be detected using methods known in the art that are specific for the polypeptides. These detection methods include, but are not limited to, use of specific antibodies, formation of an enzyme product, or disappearance of an enzyme substrate. For example, an enzyme assay may be used to determine the activity of the polypeptide.

The polypeptide may be recovered using methods known in the art. For example, the polypeptide may be recovered from the nutrient medium by conventional procedures including, but not limited to, collection, centrifugation, filtration, extraction, spray-drying, evaporation, or precipitation. In one aspect, a fermentation broth comprising the polypeptide is recovered.

The polypeptide may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, Janson and Ryden, editors, VCH Publishers, New York, 1989) to obtain substantially pure polypeptides.

In an alternative aspect, the polypeptide is not recovered, but rather a host cell of the present invention expressing the polypeptide is used as a source of the polypeptide.

Production in Plants

The present invention also relates to isolated plants, e.g., a transgenic plant, plant part, or plant cell, comprising a polynucleotide of the present invention so as to express and produce a polypeptide or domain in recoverable quantities. The polypeptide or domain may be recovered from the plant or plant part. Alternatively, the plant or plant part containing the polypeptide or domain may be used as such for improving the quality of a food or feed, e.g., improving nutritional value, palatability, and rheological properties, or to destroy an antinutritive factor.

The transgenic plant can be dicotyledonous (a dicot) or monocotyledonous (a monocot). Examples of monocot plants are grasses, such as meadow grass (blue grass, Poa), forage grass such as *Festuca, Lolium*, temperate grass, such as *Agrostis*, and cereals, e.g., wheat, oats, rye, barley, rice, sorghum, and maize (corn).

Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*.

Examples of plant parts are stem, callus, leaves, root, fruits, seeds, and tubers as well as the individual tissues comprising these parts, e.g., epidermis, mesophyll, parenchyme, vascular tissues, meristems.

Plant cells and specific plant cell compartments, such as chloroplasts, apoplasts, mitochondria, vacuoles, peroxisomes and cytoplasm are also considered to be a plant part.

Also included within the scope of the present invention are the progeny of such plants, plant parts, and plant cells.

The transgenic plant or plant cell expressing the polypeptide or domain may be constructed in accordance with methods known in the art.

The present invention also relates to methods of producing a polypeptide or domain of the present invention comprising (a) cultivating a transgenic plant or a plant cell comprising a polynucleotide encoding the polypeptide or domain under conditions conducive for production of the polypeptide or domain; and (b) recovering the polypeptide or domain.

Fermentation Broth Formulations or Cell Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In an embodiment, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

The whole broth formulations and cell compositions of the present invention may be produced by a method described in WO 90/15861 or WO 2010/096673.

Enzyme Compositions

Preferably, the compositions are enriched in the polypeptides of the first aspect of the invention. The term "enriched" indicates that the beta-galactosidase activity and the galactanase activity of the composition has been increased, e.g., with an enrichment factor of at least 1.1, such as at least 1.2, at least 1.3, at least 1.4, at least 1.5, at least 2.0, at least 3.0, at least 4.0, at least 5.0, at least 10. In an embodiment, the composition comprises the polypeptides of the first aspect of the invention and one or more formulating agents, as described in the 'formulating agent' section below.

The present invention also relates to compositions comprising the polypeptide of the second aspect of the invention (SEQ ID NO: 3) having galactanase activity. In an embodiment, the composition further comprises one or more formulating agents.

The present invention also relates to compositions comprising the polypeptide of the third aspect of the invention (SEQ ID NO: 7) having galactanase activity. In an embodiment, the composition further comprises one or more formulating agents.

The present invention also relates to compositions comprising the polypeptide of the fourth aspect of the invention (SEQ ID NO: 11) having galactanase activity. In an embodiment, the composition further comprises one or more formulating agents.

The present invention also relates to compositions comprising the polypeptide of the fifth aspect of the invention (SEQ ID NO: 15) having galactanase activity. In an embodiment, the composition further comprises one or more formulating agents.

The present invention also relates to compositions comprising the polypeptide of the sixth aspect of the invention (SEQ ID NO: 19) having galactanase activity. In an embodiment, the composition further comprises one or more formulating agents.

The present invention also relates to compositions comprising the polypeptide of the seventh aspect of the invention (SEQ ID NO: 23) having galactanase activity. In an embodiment, the composition further comprises one or more formulating agents.

The present invention also relates to compositions comprising the polypeptide of the eighth aspect of the invention (SEQ ID NO: 27) having galactanase activity. In an embodiment, the composition further comprises one or more formulating agents.

The present invention also relates to compositions comprising the polypeptide of the ninth aspect of the invention (SEQ ID NO: 31) having galactanase activity. In an embodiment, the composition further comprises one or more formulating agents.

The present invention also relates to compositions comprising the polypeptide of the tenth aspect of the invention (SEQ ID NO: 35) having galactanase activity. In an embodiment, the composition further comprises one or more formulating agents.

The present invention also relates to compositions comprising the polypeptide of the eleventh aspect of the invention (SEQ ID NO: 39) having galactanase activity. In an embodiment, the composition further comprises one or more formulating agents.

The present invention also relates to compositions comprising the polypeptide of the twelfth aspect of the invention (SEQ ID NO: 43) having beta-galactosidase activity. In an embodiment, the composition further comprises one or more formulating agents.

The present invention also relates to compositions comprising the polypeptide of the thirteenth aspect of the invention (SEQ ID NO: 46) having beta-galactosidase activity. In an embodiment, the composition further comprises one or more formulating agents.

The present invention also relates to compositions comprising the polypeptide of the fourteenth aspect of the invention (SEQ ID NO: 49) having beta-galactosidase activity. In an embodiment, the composition further comprises one or more formulating agents.

The present invention also relates to compositions comprising the polypeptide of the fifteenth aspect of the invention (SEQ ID NO: 52) having beta-galactosidase activity. In an embodiment, the composition further comprises one or more formulating agents.

The present invention also relates to compositions comprising the polypeptide of the sixteenth aspect of the invention (SEQ ID NO: 55) having beta-galactosidase activity. In an embodiment, the composition further comprises one or more formulating agents.

The present invention also relates to compositions comprising the polypeptide of the seventeenth aspect of the invention (SEQ ID NO: 58) having beta-galactosidase activity. In an embodiment, the composition further comprises one or more formulating agents.

The present invention also relates to compositions comprising the polypeptide of the eighteenth aspect of the invention (SEQ ID NO: 61) having beta-galactosidase activity. In an embodiment, the composition further comprises one or more formulating agents.

The present invention also relates to compositions comprising the polypeptide of the eighteenth aspect of the invention (SEQ ID NO: 70) having beta-galactosidase activity. In an embodiment, the composition further comprises one or more formulating agents.

The present invention also relates to compositions comprising the polypeptide of the eighteenth aspect of the invention (SEQ ID NO: 73) having beta-galactosidase activity. In an embodiment, the composition further comprises one or more formulating agents.

The present invention also relates to compositions comprising the polypeptide of the eighteenth aspect of the invention (SEQ ID NO: 76) having beta-galactosidase activity. In an embodiment, the composition further comprises one or more formulating agents.

The present invention also relates to compositions comprising the polypeptide of the eighteenth aspect of the invention (SEQ ID NO: 79) having beta-galactosidase activity. In an embodiment, the composition further comprises one or more formulating agents.

The compositions may comprise a polypeptide of the present invention as the major enzymatic component, e.g., a mono-component composition. Such a composition may further comprise a formulating agent, as described in the 'formulating agent' section below. Alternatively, the compositions may comprise multiple enzymatic activities, such as one or more (e.g., several) enzymes selected from the group consisting of phytase, galactanase, galactanase, protease, phospholipase, glucoronidase, lysophospholipase, amylase, beta-glucanase, beta-galactosidase, beta-xylosidase, endo-1,4-beta-galactanase acetyl xylan esterase, feruloyl esterase, cellulase, cellobiohydrolase, beta-glycosidase, pullulanase, or any mixture thereof.

It is at present contemplated that the galactanase is used (e.g. in feed) in one or more of the following amounts (dosage ranges): 0.01-200; 0.05-100; 0.1-50; 0.2-20; 0.1-1; 0.2-2; 0.5-5; or 1-10 wherein all these ranges are mg galactanase protein per kg substrate (ppm). It is at present contemplated that the beta-galactosidase is administered (e.g. in feed) in one or more of the following amounts (dosage ranges): 0.01-200; 0.05-100; 0.1-50; 0.2-20; 0.1-1; 0.2-2; 0.5-5; or 1-10 wherein all these ranges are mg beta-galactosidase protein per kg substrate (ppm). It is further contemplated that the ratio of galactanase to beta-galactosidase is in the range of 100:1 to 1:100 galactanase: beta-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: beta-galactosidase.

In one aspect, the invention relates to a composition comprising one or more GH53 polypeptides having galactanase activity, wherein the GH53 polypeptide is dosed at between 0.01 mg and 100 g of polypeptide (enzyme protein) per kilogram of composition and is selected from the group consisting of:
 (a) a polypeptide having at least 80%, e.g., at least 85%, at least 90% or at least 95% sequence identity to the polypeptide of SEQ ID NO: 3;
 (b) a polypeptide having at least 80%, e.g., at least 85%, at least 90% or at least 95% sequence identity to the polypeptide of SEQ ID NO: 7;
 (c) a polypeptide having at least 80%, e.g., at least 85%, at least 90% or at least 95% sequence identity to the polypeptide of SEQ ID NO: 11;
 (d) a polypeptide having at least 80%, e.g., at least 85%, at least 90% or at least 95% sequence identity to the polypeptide of SEQ ID NO: 15;
 (e) a polypeptide having at least 80%, e.g., at least 85%, at least 90% or at least 95% sequence identity to the polypeptide of SEQ ID NO: 19;
 (f) a polypeptide having at least 80%, e.g., at least 85%, at least 90% or at least 95% sequence identity to the polypeptide of SEQ ID NO: 23;
 (g) a polypeptide having at least 80%, e.g., at least 85%, at least 90% or at least 95% sequence identity to the polypeptide of SEQ ID NO: 27;
 (h) a polypeptide having at least 80%, e.g., at least 85%, at least 90% or at least 95% sequence identity to the polypeptide of SEQ ID NO: 31;
 (i) a polypeptide having at least 80%, e.g., at least 85%, at least 90% or at least 95% sequence identity to the polypeptide of SEQ ID NO: 35;
 (j) a polypeptide having at least 80%, e.g., at least 85%, at least 90% or at least 95% sequence identity to the polypeptide of SEQ ID NO: 39;
 (k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
 (l) a polypeptide comprising the polypeptide of (a), (b), (c), (d), (e), (f), (g), (h), (i), (j) or (k) and a N-terminal and/or C-terminal His-tag and/or HQ-tag;
 (m) a polypeptide comprising the polypeptide of (a), (b), (c), (d), (e), (f), (g), (h), (i), (j) or (k) and a N-terminal and/or C-terminal extension of between 1 and 10 amino acids; and
 (n) a fragment of the polypeptide of (a), (b), (c), (d), (e), (f), (g), (h), (i), (j), (k) or (l) having galactanase activity and having at least 90% of the length of the mature polypeptide.

In one embodiment, the composition comprises at least 0.02 mg of polypeptide (enzyme protein) per kilogram of composition, such as at least 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g or 75 g per kilogram of composition. In one embodiment, the composition comprises at most 75 g of polypeptide per kilogram of composition, such as at most 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 75 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g or 50 g per kilogram of composition and 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment, the composition comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment, the composition comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment, the composition comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri,*

Lactobacillus salivarius, Lactococcus lactis, Lactococcus sp., Leuconostoc sp., Megasphaera elsdenii, Megasphaera sp., Pediococcus acidilactici, Pediococcus sp., Propionibacterium thoenii, Propionibacterium sp. and Streptococcus sp. or any combination thereof.

In one embodiment, the composition may be used:
in animal feed;
in animal feed additives;
in the preparation of a composition for use in animal feed;
for improving the nutritional value of an animal feed;
for increasing digestibility of the animal feed;
for improving one or more performance parameters in an animal; and/or
for releasing galactose from plant based material of the taxonomic subclass rosids.

In one embodiment, the composition is an animal feed additive and further comprises one or more components selected from the list consisting of:
one or more vitamins;
one or more minerals;
one or more amino acids;
one or more phytogenics;
one or more prebiotics;
one or more organic acids; and
one or more other feed ingredients.

In one embodiment, the composition is an animal feed comprising plant based material and optionally one or more components selected from the list consisting of:
one or more vitamins;
one or more minerals;
one or more amino acids;
one or more phytogenics;
one or more prebiotics;
one or more organic acids; and
one or more other feed ingredients.

In one aspect, the invention relates to a composition comprising one or more GH53 polypeptides having galactanase activity and one or more polypeptides having alpha-galactosidase activity (EC 3.2.1.22), wherein the total amount of enzyme is dosed at between 0.01 mg and 100 g of polypeptide (enzyme protein) per kilogram of composition and the GH53 polypeptide is selected from the group consisting of:

(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 7;
(c) a polypeptide having at least 80%, e.g., at least 85%, at least 90% or at least 95% sequence identity to the polypeptide of SEQ ID NO: 11;
(d) a polypeptide having at least 80%, e.g., at least 85%, at least 90% or at least 95% sequence identity to the polypeptide of SEQ ID NO: 15;
(e) a polypeptide having at least 80%, e.g., at least 85%, at least 90% or at least 95% sequence identity to the polypeptide of SEQ ID NO: 19;
(f) a polypeptide having at least 80%, e.g., at least 85%, at least 90% or at least 95% sequence identity to the polypeptide of SEQ ID NO: 23;
(g) a polypeptide having at least 80%, e.g., at least 85%, at least 90% or at least 95% sequence identity to the polypeptide of SEQ ID NO: 27;
(h) a polypeptide having at least 80%, e.g., at least 85%, at least 90% or at least 95% sequence identity to the polypeptide of SEQ ID NO: 31;
(i) a polypeptide having at least 80%, e.g., at least 85%, at least 90% or at least 95% sequence identity to the polypeptide of SEQ ID NO: 35;
(j) a polypeptide having at least 80%, e.g., at least 85%, at least 90% or at least 95% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide.

In one embodiment, the composition comprises at least 0.02 mg of polypeptide (enzyme protein) per kilogram of composition, such as at least 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g or 75 g per kilogram of composition. In one embodiment, the composition comprises at most 75 g of polypeptide per kilogram of composition, such as at most 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 75 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g or 50 g per kilogram of composition and 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment, the ratio of the galactanase to the alpha-galactosidase is in the range of 100:1 to 1:100 galactanase: alpha-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: alpha-galactosidase.

In one embodiment, the composition comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment, the composition comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment, the composition comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

In one embodiment, the composition may be used:
in animal feed;
in animal feed additives;
in the preparation of a composition for use in animal feed;
for improving the nutritional value of an animal feed;
for increasing digestibility of the animal feed;
for improving one or more performance parameters in an animal; and/or
for releasing galactose from plant based material of the taxonomic subclass rosids.

In one embodiment, the composition is an animal feed additive and further comprises one or more components selected from the list consisting of:
one or more vitamins;
one or more minerals;
one or more amino acids;
one or more phytogenics;
one or more prebiotics;
one or more organic acids; and
one or more other feed ingredients.

In one embodiment, the composition is an animal feed comprising plant based material and optionally one or more components selected from the list consisting of:
one or more vitamins;
one or more minerals;
one or more amino acids;
one or more phytogenics;
one or more prebiotics;
one or more organic acids; and
one or more other feed ingredients.

In one aspect, the invention relates to a granule comprising one or more GH53 polypeptides having galactanase activity, wherein the GH53 polypeptide is dosed at between 0.01 mg and 100 g of polypeptide (enzyme protein) per kilogram of composition and is selected from the group consisting of:
(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 7;
(c) a polypeptide having at least 80%, e.g., at least 85%, at least 90% or at least 95% sequence identity to the polypeptide of SEQ ID NO: 11;
(d) a polypeptide having at least 80%, e.g., at least 85%, at least 90% or at least 95% sequence identity to the polypeptide of SEQ ID NO: 15;
(e) a polypeptide having at least 80%, e.g., at least 85%, at least 90% or at least 95% sequence identity to the polypeptide of SEQ ID NO: 19;
(f) a polypeptide having at least 80%, e.g., at least 85%, at least 90% or at least 95% sequence identity to the polypeptide of SEQ ID NO: 23;
(g) a polypeptide having at least 80%, e.g., at least 85%, at least 90% or at least 95% sequence identity to the polypeptide of SEQ ID NO: 27;
(h) a polypeptide having at least 80%, e.g., at least 85%, at least 90% or at least 95% sequence identity to the polypeptide of SEQ ID NO: 31;
(i) a polypeptide having at least 80%, e.g., at least 85%, at least 90% or at least 95% sequence identity to the polypeptide of SEQ ID NO: 35;
(j) a polypeptide having at least 80%, e.g., at least 85%, at least 90% or at least 95% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment, the granule comprises at least 0.02 mg of polypeptide (enzyme protein) per kilogram of composition, such as at least 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g or 75 g per kilogram of composition. In one embodiment, the composition comprises at most 75 g of polypeptide per kilogram of composition, such as at most 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 75 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g or 50 g per kilogram of composition and 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment, the granule comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment, the granule comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment, the granule comprises one or more probiotics. The one or more probiotics is preferably selected from the group consisting of Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium sp., Carnobacterium sp., Clostridium butyricum, Clostridium sp., Enterococcus faecium, Enterococcus sp., Lactobacillus sp., Lactobacillus acidophilus, Lactobacillus farciminus, Lactobacillus rhamnosus, Lactobacillus reuteri, Lactobacillus salivarius, Lactococcus lactis, Lactococcus sp., Leuconostoc sp., Megasphaera elsdenii, Megasphaera sp., Pediococcus acidilactici, Pediococcus sp., Propionibacterium thoenii, Propionibacterium sp. and Streptococcus sp. or any combination thereof.

In one embodiment, the granule may be used:
in animal feed;
in animal feed additives;
in the preparation of a composition for use in animal feed;
for improving the nutritional value of an animal feed;
for increasing digestibility of the animal feed;
for improving one or more performance parameters in an animal; and/or
for releasing galactose from plant based material of the taxonomic subclass rosids.

In one aspect, the invention relates to a granule comprising one or more GH53 polypeptides having galactanase activity and one or more polypeptides having alpha-galactosidase activity (EC 3.2.1.22), wherein the total amount of enzyme is dosed at between 0.01 mg and 100 g of polypeptide (enzyme protein) per kilogram of composition and the GH53 polypeptide is selected from the group consisting of:
(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 7;
(c) a polypeptide having at least 80%, e.g., at least 85%, at least 90% or at least 95% sequence identity to the polypeptide of SEQ ID NO: 11;
(d) a polypeptide having at least 80%, e.g., at least 85%, at least 90% or at least 95% sequence identity to the polypeptide of SEQ ID NO: 15;
(e) a polypeptide having at least 80%, e.g., at least 85%, at least 90% or at least 95% sequence identity to the polypeptide of SEQ ID NO: 19;
(f) a polypeptide having at least 80%, e.g., at least 85%, at least 90% or at least 95% sequence identity to the polypeptide of SEQ ID NO: 23;
(g) a polypeptide having at least 80%, e.g., at least 85%, at least 90% or at least 95% sequence identity to the polypeptide of SEQ ID NO: 27;
(h) a polypeptide having at least 80%, e.g., at least 85%, at least 90% or at least 95% sequence identity to the polypeptide of SEQ ID NO: 31;
(i) a polypeptide having at least 80%, e.g., at least 85%, at least 90% or at least 95% sequence identity to the polypeptide of SEQ ID NO: 35;
(j) a polypeptide having at least 80%, e.g., at least 85%, at least 90% or at least 95% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide.

In one embodiment, the granule comprises a core particle and one or more coatings. In a preferred embodiment, the coating comprises salt and/or wax and/or flour. Preferred formulations are disclosed in the formulation section below.

In one embodiment, the granule comprises at least 0.02 mg of polypeptide (enzyme protein) per kilogram of composition, such as at least 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g, 50 g or 75 g per kilogram of composition. In one embodiment, the composition comprises at most 75 g of polypeptide per kilogram of composition, such as at most 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition. In one embodiment, the composition comprises between 0.01 mg and 75 g of polypeptide (enzyme protein) per kilogram of composition, such as between 0.02 mg, 0.05 mg, 0.10 mg, 0.2 mg, 0.5 mg, 1.0 mg, 2 mg, 5 mg, 10 mg, 20 mg, 50 mg, 100 mg, 200 mg, 500 mg, 1.0 g, 2.5 g, 5 g, 7.5 g, 10 g, 25 g or 50 g per kilogram of composition and 50 g, 40 g, 30 g, 20 g, 10 g, 7.5 g, 5 g, 2.5 g, 1.0 g, 750 mg, 500 mg, 250 mg, 100 mg, 50 mg, 25 mg, 10 mg, 5 mg, 2.5 mg or 1 mg per kilogram of composition, or any combination thereof.

In one embodiment, the ratio of the galactanase to the alpha-galactosidase is in the range of 100:1 to 1:100 galactanase: alpha-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: alpha-galactosidase.

In one embodiment, the granule comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin, maltodextrin, cyclodextrin, wheat, PVA, acetate, phosphate and cellulose, preferably selected from the list consisting of 1, 2-propylene glycol, 1, 3-propylene glycol, sodium sulfate, dextrin, cellulose, sodium thiosulfate, kaolin and calcium carbonate.

In one embodiment, the granule comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment, the granule comprises one or more probiotics. The one or more probiotics is preferably selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

In one embodiment, the granule may be used:
in animal feed;
in animal feed additives;
in the preparation of a composition for use in animal feed;
for improving the nutritional value of an animal feed;
for increasing digestibility of the animal feed;
for improving one or more performance parameters in an animal; and/or
for releasing galactose from plant based material of the taxonomic subclass rosids.

In one aspect, the invention relates to a liquid formulation comprising one or more GH53 polypeptides having galactanase activity, wherein the liquid formulation comprises:

(A) 0.001% to 25% w/w of polypeptide having galactanase activity wherein the polypeptide having galactanase activity is selected from the group consisting of:
(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 7;
(c) a polypeptide having at least 80%, e.g., at least 85%, at least 90% or at least 95% sequence identity to the polypeptide of SEQ ID NO: 11;
(d) a polypeptide having at least 80%, e.g., at least 85%, at least 90% or at least 95% sequence identity to the polypeptide of SEQ ID NO: 15;
(e) a polypeptide having at least 80%, e.g., at least 85%, at least 90% or at least 95% sequence identity to the polypeptide of SEQ ID NO: 19;
(f) a polypeptide having at least 80%, e.g., at least 85%, at least 90% or at least 95% sequence identity to the polypeptide of SEQ ID NO: 23;
(g) a polypeptide having at least 80%, e.g., at least 85%, at least 90% or at least 95% sequence identity to the polypeptide of SEQ ID NO: 27;
(h) a polypeptide having at least 80%, e.g., at least 85%, at least 90% or at least 95% sequence identity to the polypeptide of SEQ ID NO: 31;
(i) a polypeptide having at least 80%, e.g., at least 85%, at least 90% or at least 95% sequence identity to the polypeptide of SEQ ID NO: 35;
(j) a polypeptide having at least 80%, e.g., at least 85%, at least 90% or at least 95% sequence identity to the polypeptide of SEQ ID NO: 39;
(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
(l) a polypeptide comprising the polypeptide of (a), (b), (c), (d), (e), (f), (g), (h), (i), (j) or (k) and a N-terminal and/or C-terminal His-tag and/or HQ-tag;
(m) a polypeptide comprising the polypeptide of (a), (b), (c), (d), (e), (f), (g), (h), (i), (j) or (k) and a N-terminal and/or C-terminal extension of between 1 and 10 amino acids; and
(n) a fragment of the polypeptide of (a), (b), (c), (d), (e), (f), (g), (h), (i), (j), (k) or (l) having galactanase activity and having at least 90% of the length of the mature polypeptide; and
(B) water.

In one embodiment, the liquid formulation comprises one or more formulating agents (such as those described herein), preferably a formulating agent selected from the list consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, PVA, acetate and phosphate, preferably selected from the list consisting of 1, 2-propylene glycol, 1, 3-propylene glycol, sodium sulfate, dextrin, cellulose, sodium thiosulfate, kaolin and calcium carbonate.

In one embodiment, the liquid formulation comprises one or more polyols, preferably a polyol selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600, more preferably selected from the group consisting of glycerol, sorbitol and propylene glycol (MPG) or any combination thereof.

In one embodiment, the liquid formulation comprises 20%-80% polyol (i.e. total amount of polyol), preferably 25%-75% polyol, more preferably 30%-70% polyol, more preferably 35%-65% polyol or most preferably 40%-60% polyol. In one embodiment, the liquid formulation comprises 20%-80% polyol, preferably 25%-75% polyol, more preferably 30%-70% polyol, more preferably 35%-65% polyol or most preferably 40%-60% polyol wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600. In one embodiment, the liquid formulation comprises 20%-80% polyol (i.e. total amount of polyol), preferably 25%-75% polyol, more preferably 30%-70% polyol, more preferably 35%-65% polyol or most preferably 40%-60% polyol wherein the polyol is selected from the group consisting of glycerol, sorbitol and propylene glycol (MPG).

In one embodiment, the preservative is selected from the group consisting of sodium sorbate, potassium sorbate, sodium benzoate and potassion benzoate or any combination thereof. In one embodiment, the liquid formulation comprises 0.02% to 1.5% w/w preservative, more preferably 0.05% to 1.0% w/w preservative or most preferably 0.1% to 0.5% w/w preservative. In one embodiment, the liquid formulation comprises 0.001% to 2.0% w/w preservative (i.e. total amount of preservative), preferably 0.02% to 1.5% w/w preservative, more preferably 0.05% to 1.0% w/w preservative or most preferably 0.1% to 0.5% w/w preservative wherein the preservative is selected from the group consisting of sodium sorbate, potassium sorbate, sodium benzoate and potassion benzoate or any combination thereof.

In one embodiment, the liquid formulation comprises 0.01% to 25% w/w polypeptide having galactanase activity, preferably 0.05% to 20% w/w polypeptide having galactanase activity, more preferably 0.2% to 15% w/w polypeptide having galactanase activity, more preferably 0.5% to 15% w/w polypeptide having galactanase activity or most preferably 1.0% to 10% w/w polypeptide having galactanase activity.

In one embodiment, the liquid formulation comprises one or more additional enzymes. The one or more additional enzymes is preferably selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

In one embodiment, the liquid formulation comprises an alpha-galactosidase. In one embodiment, the liquid formulation comprises an alpha-galactosidase wherein the ratio of galactanase to alpha-galactosidase is in the range of 100:1 to 1:100 galactanase: alpha-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: alpha-galactosidase.

In one embodiment, the liquid formulation comprises one or more probiotics. The one or more probiotics is preferably selected from the group consisting of *Bacillus subtilis*, *Bacillus licheniformis*, *Bacillus amyloliquefaciens*, *Bacillus cereus*, *Bacillus pumilus*, *Bacillus polymyxa*, *Bacillus megaterium*, *Bacillus coagulans*, *Bacillus circulans*, *Bifidobacterium bifidum*, *Bifidobacterium animalis*, *Bifidobacterium* sp., *Carnobacterium* sp., *Clostridium butyricum*, *Clostridium* sp., *Enterococcus faecium*, *Enterococcus* sp., *Lactobacillus* sp., *Lactobacillus acidophilus*, *Lactobacillus farciminus*, *Lactobacillus rhamnosus*, *Lactobacillus reuteri*, *Lactobacillus salivarius*, *Lactococcus lactis*, *Lactococcus* sp., *Leuconostoc* sp., *Megasphaera elsdenii*, *Megasphaera* sp., *Pediococcus acidilactici*, *Pediococcus* sp., *Propionibacterium thoenii*, *Propionibacterium* sp. and *Streptococcus* sp. or any combination thereof.

In one embodiment, the liquid formulation may be used:
in animal feed;
in animal feed additives;
in the preparation of a composition for use in animal feed;
for improving the nutritional value of an animal feed;
for increasing digestibility of the animal feed;
for improving one or more performance parameters in an animal; and/or
for releasing galactose from plant based material of the taxonomic subclass rosids.

Thus in one embodiment, the invention relates to a liquid formulation comprising one or more GH53 polypeptides having galactanase activity, wherein the liquid formulation comprises:

(A) 0.001% to 25% w/w of polypeptide having galactanase activity (such as 0.05% to 20% w/w, preferably 0.2% to 15% w/w, more preferably 0.5% to 15% w/w or most preferably 1.0% to 10% w/w polypeptide having galactanase activity), wherein the polypeptide having galactanase activity is selected from the group consisting of:
(a) a polypeptide having at least 80%, e.g., at least 85%, at least 90% or at least 95% sequence identity to the polypeptide of SEQ ID NO: 3;
(b) a polypeptide having at least 80%, e.g., at least 85%, at least 90% or at least 95% sequence identity to the polypeptide of SEQ ID NO: 7;
(c) a polypeptide having at least 80%, e.g., at least 85%, at least 90% or at least 95% sequence identity to the polypeptide of SEQ ID NO: 11;
(d) a polypeptide having at least 80%, e.g., at least 85%, at least 90% or at least 95% sequence identity to the polypeptide of SEQ ID NO: 15;
(e) a polypeptide having at least 80%, e.g., at least 85%, at least 90% or at least 95% sequence identity to the polypeptide of SEQ ID NO: 19;
(f) a polypeptide having at least 80%, e.g., at least 85%, at least 90% or at least 95% sequence identity to the polypeptide of SEQ ID NO: 23;

(g) a polypeptide having at least 80%, e.g., at least 85%, at least 90% or at least 95% sequence identity to the polypeptide of SEQ ID NO: 27;

(h) a polypeptide having at least 80%, e.g., at least 85%, at least 90% or at least 95% sequence identity to the polypeptide of SEQ ID NO: 31;

(i) a polypeptide having at least 80%, e.g., at least 85%, at least 90% or at least 95% sequence identity to the polypeptide of SEQ ID NO: 35;

(j) a polypeptide having at least 80%, e.g., at least 85%, at least 90% or at least 95% sequence identity to the polypeptide of SEQ ID NO: 39;

(k) a variant of SEQ ID NO: 3, SEQ ID NO: 7, SEQ ID NO: 11, SEQ ID NO: 15, SEQ ID NO: 19, SEQ ID NO: 23, SEQ ID NO: 27, SEQ ID NO: 31, SEQ ID NO: 35 or SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(l) a polypeptide comprising the polypeptide of (a), (b), (c), (d), (e), (f), (g), (h), (i), (j) or (k) and a N-terminal and/or C-terminal His-tag and/or HQ-tag;

(m) a polypeptide comprising the polypeptide of (a), (b), (c), (d), (e), (f), (g), (h), (i), (j) or (k) and a N-terminal and/or C-terminal extension of between 1 and 10 amino acids; and (n) a fragment of the polypeptide of (a), (b), (c), (d), (e), (f), (g), (h), (i), (j), (k) or (l) having galactanase activity and having at least 90% of the length of the mature polypeptide; and (B) 20% to 80% w/w of polyol;

(C) 0.001% to 2.0% w/w preservative;

(D) optionally 0.001% to 25% w/w of polypeptide having alpha-galactosidase activity (such as 0.05% to 20% w/w, preferably 0.2% to 15% w/w, more preferably 0.5% to 15% w/w or most preferably 1.0% to 10% w/w polypeptide having alpha-galactosidase activity); and (E) water.

The types and amounts of polyol and preservative may be selected as described above. In one embodiment, the liquid formulation comprises one or more additional enzymes, such as those described above. In one embodiment, the liquid formulation comprises one or more probiotics, such as those described above. In one embodiment, the ratio of the galactanase to the alpha-galactosidase is in the range of 100:1 to 1:100 galactanase: alpha-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: alpha-galactosidase.

In one embodiment, the liquid formulation may be used:
in animal feed;
in animal feed additives;
in the preparation of a composition for use in animal feed;
for improving the nutritional value of an animal feed;
for increasing digestibility of the animal feed;
for improving one or more performance parameters in an animal; and/or
for releasing galactose from plant based material of the taxonomic subclass rosids.

Formulation

The enzyme of the invention may be formulated as a liquid or a solid. For a liquid formulation, the formulating agent may comprise a polyol (such as e.g. glycerol, ethylene glycol or propylene glycol), a salt (such as e.g. sodium chloride, sodium benzoate, potassium sorbate) or a sugar or sugar derivative (such as e.g. dextrin, glucose, sucrose, and sorbitol). Thus in one embodiment, the composition is a liquid composition comprising the polypeptide of the invention and one or more formulating agents selected from the list consisting of glycerol, ethylene glycol, 1,2-propylene glycol, 1,3-propylene glycol, sodium chloride, sodium benzoate, potassium sorbate, dextrin, glucose, sucrose, and sorbitol. The liquid formulation may be sprayed onto the feed after it has been pelleted or may be added to drinking water given to the animals.

For a solid formulation, the formulation may be for example as a granule, spray dried powder or agglomerate (e.g. as disclosed in WO2000/70034). The formulating agent may comprise a salt (organic or inorganic zinc, sodium, potassium or calcium salts such as e.g. such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol).

In one embodiment, the composition is a solid composition, such as a spray dried composition, comprising the beta-galactosidase and/or galactanase of the invention and one or more formulating agents selected from the list consisting of sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose. In a preferred embodiment, the formulating agent is selected from one or more of the following compounds: sodium sulfate, dextrin, cellulose, sodium thiosulfate, magnesium sulfate and calcium carbonate.

The present invention also relates to enzyme granules/particles comprising the beta-galactosidase and/or galactanase of the invention optionally combined with one or more additional enzymes. The granule is composed of a core, and optionally one or more coatings (outer layers) surrounding the core.

Typically the granule/particle size, measured as equivalent spherical diameter (volume based average particle size), of the granule is 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation.

Methods for preparing the core can be found in Handbook of Powder Technology; Particle size enlargement by C. E. Capes; Volume 1; 1980; Elsevier. Preparation methods include known feed and granule formulation technologies, e.g.:

a) spray dried products, wherein a liquid enzyme-containing solution is atomized in a spray drying tower to form small droplets which during their way down the drying tower dry to form an enzyme-containing particulate material;

b) layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found. This type of product is described in, e.g., WO 97/23606;

c) absorbed core particles, wherein rather than coating the enzyme as a layer around the core, the enzyme is absorbed onto and/or into the surface of the core. Such a process is described in WO 97/39116.

d) extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) prilled products, wherein an enzyme-containing powder is suspended in molten wax and the suspension is sprayed, e.g., through a rotating disk atomiser, into a cooling chamber where the droplets quickly solidify (Michael S. Showell (editor); Powdered detergents; Surfactant Science Series; 1998; vol. 71; page 140-142; Marcel Dekker). The product obtained is one wherein the enzyme is uniformly distributed throughout an inert material instead of being concentrated on its surface. Also U.S. Pat. Nos. 4,016,040 and 4,713,245 are documents relating to this technique;

f) mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. Such a process is described in U.S. Pat. No. 4,106,991 and related documents EP 170360, EP 304332, EP 304331, WO 90/09440 and WO 90/09428. In a particular product of this process wherein various high-shear mixers can be used as granulators, granulates consisting of enzyme as enzyme, fillers and binders etc. are mixed with cellulose fibres to reinforce the particles to give the so-called T-granulate. Reinforced particles, being more robust, release less enzymatic dust.

g) size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled. Size reduction is described in (Martin Rhodes (editor); Principles of Powder Technology; 1990; Chapter 10; John Wiley & Sons);

h) fluid bed granulation, which involves suspending particulates in an air stream and spraying a liquid onto the fluidized particles via nozzles. Particles hit by spray droplets get wetted and become tacky. The tacky particles collide with other particles and adhere to them and form a granule;

i) the cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores preferably contain 0.1-10% w/w water.

The core may include additional materials such as fillers, fibre materials (cellulose or synthetic fibres), stabilizing agents, solubilizing agents, suspension agents, viscosity regulating agents, light spheres, plasticizers, salts, lubricants and fragrances.

The core may include a binder, such as synthetic polymer, wax, fat, or carbohydrate.

The core may include a salt of a multivalent cation, a reducing agent, an antioxidant, a peroxide decomposing catalyst and/or an acidic buffer component, typically as a homogenous blend.

In one embodiment, the core comprises a material selected from the group consisting of salts (such as calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, potassium sulfate, sodium acetate, sodium benzoate, sodium carbonate, sodium chloride, sodium citrate, sodium sulfate, zinc acetate, zinc benzoate, zinc carbonate, zinc chloride, zinc citrate, zinc sorbate, zinc sulfate), starch or a sugar or sugar derivative (such as e.g. sucrose, dextrin, glucose, lactose, sorbitol), sugar or sugar derivative (such as e.g. sucrose, dextrin, glucose, lactose, sorbitol), small organic molecules, starch, flour, cellulose and minerals and clay minerals (also known as hydrous aluminium phyllosilicates). In one embodiment, the core comprises a clay mineral such as kaolinite or kaolin.

The core may include an inert particle with the enzyme absorbed into it, or applied onto the surface, e.g., by fluid bed coating.

The core may have a diameter of 20-2000 µm, particularly 50-1500 µm, 100-1500 µm or 250-1200 µm.

The core may be surrounded by at least one coating, e.g., to improve the storage stability, to reduce dust formation during handling, or for coloring the granule. The optional coating(s) may include a salt and/or wax and/or flour coating, or other suitable coating materials.

The coating may be applied in an amount of at least 0.1% by weight of the core, e.g., at least 0.5%, 1% or 5%. The amount may be at most 100%, 70%, 50%, 40% or 30%.

The coating is preferably at least 0.1 µm thick, particularly at least 0.5 µm, at least 1 µm or at least 5 µm. In some embodiments the thickness of the coating is below 100 µm, such as below 60 µm, or below 40 µm.

The coating should encapsulate the core unit by forming a substantially continuous layer. A substantially continuous layer is to be understood as a coating having few or no holes, so that the core unit is encapsulated or enclosed with few or no uncoated areas. The layer or coating should in particular be homogeneous in thickness.

The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight of a salt, e.g., at least 65%, at least 70%, at least 75%, at least 80%, at least 85%, at least 90%, at least 95% or at least 99% by weight.

The salt may be added from a salt solution where the salt is completely dissolved or from a salt suspension wherein the fine particles are less than 50 µm, such as less than 10 µm or less than 5 µm.

The salt coating may comprise a single salt or a mixture of two or more salts. The salt may be water soluble, in particular having a solubility at least 0.1 g in 100 g of water at 20° C., preferably at least 0.5 g per 100 g water, e.g., at least 1 g per 100 g water, e.g., at least 5 g per 100 g water.

The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, sorbate, lactate, formate, acetate, butyrate, propionate, benzoate, tartrate, ascorbate or gluconate. In particular alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). The salt coating may be as described in WO1997/05245, WO1998/54980, WO1998/55599, WO2000/70034, WO2006/034710, WO2008/017661, WO2008/017659, WO2000/020569, WO2001/004279, WO1997/05245, WO2000/01793, WO2003/059086, WO2003/059087, WO2007/031483, WO2007/031485, WO2007/044968, WO2013/192043, WO2014/014647 and WO2015/197719 or polymer coating such as described in WO 2001/00042.

Specific examples of suitable salts are NaCl (CH20° C.=76%), Na2CO3 (CH20° C.=92%), NaNO3 (CH20° C.=73%), Na2HPO4 (CH20° C.=95%), Na3PO4 (CH25° C.=92%), NH4Cl (CH20° C.=79.5%), (NH4)2HPO4 (CH20° C.=93.0%), NH4H2PO4 (CH20° C.=93.1%), (NH4)2SO4 (CH20° C.=81.1%), KCl (CH20° C.=85%), K2HPO4 (CH20° C.=92%), KH2PO4 (CH20° C.=96.5%), KNO3 (CH20° C.=93.5%), Na2SO4 (CH20° C.=93%), K2SO4 (CH20° C.=98%), KHSO4 (CH20° C.=86%), MgSO4 (CH20° C.=90%), ZnSO4 (CH20° C.=90%) and sodium citrate (CH25° C.=86%). Other examples include NaH2PO4, (NH4)H2PO4, CuSO4, Mg(NO3)2, magnesium acetate, calcium acetate, calcium benzoate, calcium carbonate, calcium chloride, calcium citrate, calcium sorbate, calcium sulfate, potassium acetate, potassium benzoate, potassium carbonate, potassium chloride, potassium citrate, potassium sorbate, sodium acetate, sodium benzoate, sodium citrate, sodium sulfate, zinc acetate, zinc benzoate, zinc carbonate, zinc chloride, zinc citrate and zinc sorbate.

The salt may be in anhydrous form, or it may be a hydrated salt, i.e. a crystalline salt hydrate with bound water(s) of crystallization, such as described in WO 99/32595. Specific examples include anhydrous sodium sulfate (Na2SO4), anhydrous magnesium sulfate (MgSO4), magnesium sulfate heptahydrate (MgSO4.7H2O), zinc sulfate heptahydrate (ZnSO4.7H2O), sodium phosphate dibasic heptahydrate (Na2HPO4.7H2O), magnesium nitrate hexahydrate (Mg(NO3)2(6H2O)), sodium citrate dihydrate and magnesium acetate tetrahydrate.

Preferably the salt is applied as a solution of the salt, e.g., using a fluid bed.

A wax coating may comprise at least 60% by weight of a wax, e.g., at least 65%, at least 70%, at least 75%, at least 80%, at least 85%, at least 90%, at least 95% or at least 99% by weight.

Specific examples of waxes are polyethylene glycols; polypropylenes; Carnauba wax; Candelilla wax; bees wax; hydrogenated plant oil or animal tallow such as polyethylene glycol (PEG), methyl hydroxy-propyl cellulose (MHPC), polyvinyl alcohol (PVA), hydrogenated ox tallow, hydrogenated palm oil, hydrogenated cotton seeds and/or hydrogenated soy bean oil; fatty acid alcohols; mono-glycerides and/or di-glycerides, such as glyceryl stearate, wherein stearate is a mixture of stearic and palmitic acid; microcrystalline wax; paraffin's; and fatty acids, such as hydrogenated linear long chained fatty acids and derivatives thereof. A preferred wax is palm oil or hydrogenated palm oil.

The granule may comprise a core comprising the beta-galactosidase and/or galactanase of the invention, one or more salt coatings and one or more wax coatings. Examples of enzyme granules with multiple coatings are shown in WO1993/07263, WO1997/23606 and WO2016/149636.

Non-dusting granulates may be produced, e.g., as disclosed in U.S. Pat. Nos. 4,106,991 and 4,661,452 and may optionally be coated by methods known in the art. The coating materials can be waxy coating materials and film-forming coating materials. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591.

The granulate may further comprise one or more additional enzymes. Each enzyme will then be present in more granules securing a more uniform distribution of the enzymes, and also reduces the physical segregation of different enzymes due to different particle sizes. Methods for producing multi-enzyme co-granulates is disclosed in the ip.com disclosure IPCOM000200739D.

Another example of formulation of enzymes by the use of co-granulates is disclosed in WO 2013/188331.

The present invention also relates to protected enzymes prepared according to the method disclosed in EP 238,216.

Thus, in a further aspect, the present invention provides a granule, which comprises:

(a) a core comprising a beta-galactosidase according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating and a wax coating as described herein.

Thus, in a further aspect, the present invention provides a granule, which comprises:

(a) a core comprising a galactanase according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating and a wax coating as described herein.

Thus, in a further aspect, the present invention provides a granule, which comprises:

(a) a core comprising a beta-galactosidase and galactanase according to the invention, and (b) a coating consisting of one or more layer(s) surrounding the core.

In one embodiment, the coating comprises a salt coating as described herein. In one embodiment, the coating comprises a wax coating as described herein. In one embodiment, the coating comprises a salt coating and a wax coating as described herein.

Plant Based Material

In an embodiment, the plant based material is from the taxonomic subclass rosids such as the taxonomic order Fabales or the taxonomic order Brassicales.

In one embodiment, the plant based material from is from the family Fabaceae, such as the subfamilies Caesalpinioideae or Mimosoideae or Papilionoideae. In an embodiment, the plant based material from is from the sub-family Papilionoideae, such as the tribe Abreae or Amorpheae or Bossiaeeae or Brongniartieae or Cicereae or Crotalarieae or Dalbergieae or Desmodieae or Dipterygeae or Euchresteae or Fabeae or Galegeae or Genisteae or Hedysareae or Hypocalypteae or Indigofereae or Loteae or Millettieae or Mirbelieae or Phaseoleae or Podalyrieae or Psoraleeae or Robinieae or Sesbanieae or Sophoreae or Swartzieae or Thermopsideae or Trifolieae.

In one embodiment, the plant based material from the sub-family Papilionoideae is from the tribe Phaseoleae, such as the genus *Adenodolichos* or *Alistilus* or *Amphicarpaea* or *Ancistrotropis* or *Apios* or *Atylosia* or *Bionia* or *Bolusafra* or *Butea* or *Cajanus* or *Calopogonium* or *Camptosema* or *Canavalia* or *Centrosema* or *Cleobulia* or *Clitoria* or *Cochlianthus* or *Cochliasanthus* or *Collaea* or *Cologania* or *Condylostylis* or *Cratylia* or *Cymbosema* or *Decorsea* or *Dioclea* or *Dipogon* or *Dolichopsis* or *Dolichos* or *Dumasia* or *Dunbaria* or *Eriosema* or *Erythrina* or *Flemingia* or *Galactia* or *Glycine* or *Hardenbergia* or *Helicotropis* or *Kennedia* or *Lablab* or *Leptospron* or *Macroptilium* or *Macrotyloma* or *Mastersia* or *Mucuna* or *Mysanthus* or *Neonotonia* or *Neorautanenia* or *Nesphostylis* or *Nogra* or *Ophrestia* or *Otoptera* or *Oxyrhynchus* or *Pachyrhizus* or *Paracalyx* or *Phaseolus* or *Phylacium* or *Physostigma* or *Pseudeminia* or *Pseudovigna* or *Psophocarpus* or *Pueraria* or *Ramirezella* or *Rhodopis* or *Rhynchosia* or *Shuteria* or *Sigmoidotropis* or *Sinodolichos* or *Spathionema* or *Spatholobus* or *Sphenostylis* or *Strongylodon* or *Strophostyles* or *Teramnus* or *Teyleria* or *Vandasina* or *Vatovaea* or *Vigna* or *Wajira*.

In one embodiment, the plant based material from the sub-family Papilionoideae is from the genus *Glycine*, such as the species *Glycine* aff. *tabacina* or *Glycine albicans* or *Glycine aphyonota* or *Glycine arenaria* or *Glycine argyrea* or *Glycine canescens* or *Glycine clandestina* or *Glycine curvata* or *Glycine cyrtoloba* or *Glycine dolichocarpa* or *Glycine falcata* or *Glycine gracei* or *Glycine hirticaulis* or *Glycine lactovirens* or *Glycine latifolia* or *Glycine latrobeana* or *Glycine microphylla* or *Glycine peratosa* or *Glycine pindanica* or *Glycine pullenii* or *Glycine rubiginosa* or *Glycine stenophita* or *Glycine syndetika* or *Glycine tabacina* or *Glycine tomentella* or *Glycine* sp. T1 or *Glycine* sp. T5 or *Glycine gracilis* or *Glycine max* (soy bean) or *Glycine max×Glycine soja* or *Glycine soja* (wild soybean).

In one embodiment, the plant based material from the sub-family Papilionoideae is from the genus *Cajanus* such as the species *Cajanus cajan* (pigeon pea), *Cajanus cajanifolius* and *Cajanus scarabaeoide*.

In one embodiment, the plant based material from the sub-family Papilionoideae is from the genus *Phaseolus*, such as the species *Phaseolus acutifolius* (tepary bean) or *Phaseolus acutifolius* var. *latifolius* or *Phaseolus albescens* or *Phaseolus albiflorus* or *Phaseolus albinervus* or *Phaseolus altimontanus* or *Phaseolus amblyosepalus* or *Phaseolus angustissimus* or *Phaseolus augusti* or *Phaseolus bolivianus* or *Phaseolus campanulatus* or *Phaseolus carteri* or *Phaseolus chiapasanus* or *Phaseolus coccineus* (scarlet runner bean) or *Phaseolus coccineus* subsp. *coccineus* or *Phaseolus coccineus* subsp. *polyanthus* or *Phaseolus costaricensis* or *Phaseolus dasycarpus* or *Phaseolus dumosus* or *Phaseolus esperanzae* or *Phaseolus esquincensis* or *Phaseolus filiformis* (slimjim bean) or *Phaseolus glabellus* or *Phaseolus gladiolatus* or *Phaseolus grayanus* or *Phaseolus hintonii* or *Phaseolus jaliscanus* or *Phaseolus juquilensis* or *Phaseolus laxiflorus* or *Phaseolus leptostachyus* or *Phaseolus lignosus* or *Phaseolus lunatus* (lima bean) or *Phaseolus macrolepis* or *Phaseolus maculatifolius* or *Phaseolus maculatus* (cocolmeca bean) or *Phaseolus maculatus* subsp. *ritensis* or *Phaseolus macvaughii* or *Phaseolus magnilobatus* or *Phaseolus marechalii* or *Phaseolus micranthus* or *Phaseolus microcarpus* or *Phaseolus mollis* or *Phaseolus neglectus* or *Phaseolus nelsonii* or *Phaseolus nodosus* or *Phaseolus novoleonensis* or *Phaseolus oaxacanus* or *Phaseolus oligospermus* or *Phaseolus pachyrrhizoides* or *Phaseolus parvifolius* or *Phaseolus parvulus* or *Phaseolus pauciflorus* or *Phaseolus pedicellatus* or *Phaseolus perplexus* or *Phaseolus persistentus* or *Phaseolus plagiocylix* or *Phaseolus pluriflorus* or *Phaseolus polymorphus* or *Phaseolus polystachios* or *Phaseolus polystachios* subsp. *sinuatus* or *Phaseolus polystachios* subsp. *smilacifolius* or *Phaseolus reticulatus* or *Phaseolus rotundatus* or *Phaseolus salicifolius* or *Phaseolus sonorensis* or *Phaseolus talamancensis* or *Phaseolus tenellus* or *Phaseolus texensis* or *Phaseolus tuerckheimii* or *Phaseolus vulgaris* (French bean) or *Phaseolus vulgaris* var. *aborigineus* or *Phaseolus vulgaris* var. *nanus* or *Phaseolus xanthotrichus* or *Phaseolus xolocotzii* or *Phaseolus zimapanensis*.

In one embodiment, the plant based material from the sub-family Papilionoideae is from the tribe Cicereae, such as the genus *Cicer*, such as the species *Cicer anatolicum* or *Cicer arietinum* (chickpea) or *Cicer bijugum* or *Cicer canariense* or *Cicer chorassanicum* or *Cicer cuneatum* or *Cicer echinospermum* or *Cicer flexuosum* or *Cicer floribundum* or *Cicer graecum* or *Cicer incisum* or *Cicer isauricum* or *Cicer judaicum* or *Cicer kermanense* or *Cicer macracanthum* or *Cicer microphyllum* or *Cicer montbretii* or *Cicer multijugum* or *Cicer nuristanicum* or *Cicer oxyodon* or *Cicer pinnatifidum* or *Cicer pungens* or *Cicer rechingeri* or *Cicer reticulaturn* or *Cicer songaricum* or *Cicer spiroceras* or *Cicer stapfianum* or *Cicer subaphyllum* or *Cicer tragacanthoides* or *Cicer yamashitae*

In one embodiment, the plant based material from the sub-family Papilionoideae is from the tribe Genisteae, such as the genus *Adenocarpus* or *Anarthrophyllum* or *Argyrocytisus* or *Argyrolobium* or *Calicotome* or *Chamaecytisus* or *Cytisophyllum* or *Cytisus* or *Dichilus* or *Echinospartum* or *Erinacea* or *Genista* or *Gonocytisus* or *Hesperolaburnum* or *Laburnum* or *Lembotropis* or *Lupinus* or *Melolobium* or

*Petteria* or *Podocytisus* or *Polhillia* or *Retama* or *Sellocharis* or *Spartium* or *Stauracanthus* or *Teline* or *Ulex*

In one embodiment, the plant based material from the sub-family Papilionoideae is from the tribe Fabeae, such as the genus *Lathyrus* or *Lens* or *Pisum* or *Vavilovia* or *Vicia*. In one embodiment, the plant based material from the sub-family Papilionoideae is from the genus *Lens*, such as the species *Lens culinaris* (lentil) or *Lens culinaris* subsp. *culinaris* or *Lens culinaris* subsp. *odemensis* or *Lens culinaris* subsp. *tomentosus* or *Lens cyanea* or *Lens ervoides* or *Lens lamottei* or *Lens nigricans* or *Lens orientalis* (ye bing dou).

In one embodiment, the plant based material from the sub-family Papilionoideae is from the genus *Vicia*, such as the species *Vicia garinensis* or *Vicia sojakii* or *Vicia rechingeri* or *Vicia kurdica* or *Vicia multijuga* or *Vicia akhmaganica* or *Vicia variabilis* or *Vicia variegata* or *Vicia persica* or *Vicia kotschyana* or *Vicia hirta* or *Vicia gregaria* or *Vicia ciceroidea* or *Vicia cappadocica* or *Vicia balansae* or *Vicia aucheri* or *Vicia* sp. 'telaponensis' or *Vicia venulosa* or *Vicia subvillosa* or *Vicia stenophylla* or *Vicia sicula* or *Vicia sibthorpii* or *Vicia semiglabra* or *Vicia scandens* or *Vicia pinetorum* or *Vicia picta* or *Vicia pectinata* or *Vicia paucifolia* or *Vicia palaestina* or *Vicia onobrychioides* or *Vicia ochroleuca* or *Vicia nataliae* or *Vicia montevidensis* or *Vicia monardii* or *Vicia minutiflora* or *Vicia menziesii* or *Vicia megalotropis* or *Vicia malosana* or *Vicia lunata* or *Vicia leucantha* or *Vicia leavenworthii* or *Vicia larissae* or *Vicia iranica* or *Vicia incana* or *Vicia hololasia* or *Vicia glauca* or *Vicia freyniana* or *Vicia floridana* or *Vicia filicaulis* or *Vicia ferreirensis* or *Vicia exigua* or *Vicia dennesiana* or *Vicia cypria* or *Vicia cretica* or *Vicia costata* or *Vicia claessensii* or *Vicia chaetocalyx* or *Vicia cassia* or *Vicia capreolata* or *Vicia caesarea* or *Vicia biennis* or *Vicia baicalensis* or *Vicia altissima* or *Vicia alpestris* or *Vicia acutifolia* or *Vicia pubescens* or *Vicia cirrhosa* or *Vicia koeieana* or *Vicia ramuliflora* or *Vicia multicaulis* or *Vicia parviflora* or *Vicia vicioides* or *Vicia tenuifolia* or *Vicia orobus* or *Vicia nigra* or *Vicia incisa* or *Vicia epetiolaris* or *Vicia crocea* or *Vicia sparsiflora* or *Vicia nummularia* or *Vicia dichroantha* or *Vicia cassubica* or *Vicia monantha* (bard vetch) or *Vicia cinerea* or *Vicia oroboides* or *Vicia tibetica* or *Vicia caroliniana* (Carolina or wood vetch) or *Vicia disperma* or *Vicia esdraelonensis* or *Vicia pulchella* or *Vicia mexicana* or *Vicia leucophaea* or *Vicia humilis* or *Vicia barbazitae* or *Vicia pyrenaica* or *Vicia qatmensis* or *Vicia lathyroides* or *Vicia cuspidata* or *Vicia dionysiensis* or *Vicia abbreviata* or *Vicia sepium* or *Vicia sericocarpa* or *Vicia noeana* or *Vicia hyrcanica* or *Vicia hybrida* or *Vicia galeata* or *Vicia ciliatula* or *Vicia assyriaca* or *Vicia tigridis* or *Vicia anatolica* or *Vicia sylvatica* or *Vicia dumetorum* or *Vicia mollis* or *Vicia aintabensis* or *Vicia peregrina* or *Vicia lutea* (yellow vetch) or *Vicia grandiflora* or *Vicia articulata* or *Vicia americana* or *Vicia michauxii* or *Vicia vicina* or *Vicia venosa* or *Vicia tetrasperma* or *Vicia ervilia* or *Vicia benghalensis* (purple or winter vetch) or *Vicia angustipinnata* or *Vicia amurensis* or *Vicia unijuga* or *Vicia pseudo-orobus* or *Vicia pisiformis* or *Vicia nipponica* or *Vicia nigricans* or *Vicia linearifolia* or *Vicia japonica* or *Vicia hirticalycina* or *Vicia fauriae* or *Vicia chosenensis* or *Vicia bungei* or *Vicia bifolia* or *Vicia amoena* or *Vicia montbretii* or *Vicia serratifolia* or *Vicia paucijuga* or *Vicia kalakhensis* or *Vicia johannis* or *Vicia hyaeniscyamus* or *Vicia galilaea* or *Vicia eristalioides* or *Vicia bithynica* or *Vicia melanops* or *Vicia ludoviciana* or *Vicia pannonica* or *Vicia narbonensis* or *Vicia villosa* or *Vicia hirsuta* or *Vicia sativa* (spring vetch) or *Vicia faba* (broad bean or fava bean) or *Vicia cracca* (bird vetech).

In one embodiment, the plant based material from the sub-family Papilionoideae is from the genus *Pisum*, such as the species *Pisum abyssinicum* (Abyssinian pea) or *Pisum fulvum* or *Pisum sativum* (pea) or *Pisum sativum* subsp. *asiaticum* or *Pisum sativum* subsp. *elatius* (wild pea) or *Pisum sativum* var. *pumilio* (Syrian fodder pea) or *Pisum sativum* subsp. *jomardii* or *Pisum sativum* subsp. *Sativum* or *Pisum sativum* var. *arvense* or *Pisum sativum* var. *choresmicum* or *Pisum sativum* var. *macrocarpon* (snow pea) or *Pisum sativum* var. *ponderosum* or *Pisum sativum* var. *tibetanicum* or *Pisum sativum* subsp. *transcaucasicum*

In one embodiment, the plant based material from the sub-family Papilionoideae is from the tribe Dalbergieae, such as the genus *Adesmia* or *Aeschynomene* or *Amicia* or *Andira* or *Arachis* or *Brya* or *Bryaspis* or *Cascaronia* or *Centrolobium* or *Chaetocalyx* or *Chapmannia* or *Cranocarpus* or *Cyclocarpa* or *Dalbergia* or *Diphysa* or *Discolobium* or *Etaballia* or *Fiebrigiella* or *Fissicalyx* or *Geissaspis* or *Geoffroea* or *Grazielodendron* or *Humularia* or *Hymenolobium* or *Inocarpus* or *Kotschya* or *Machaerium* or *Maraniona* or *Nissolia* or *Ormocarpopsis* or *Ormocarpum* or *Paramachaerium* or *Peltiera* or *Pictetia* or *Platymiscium* or *Platypodium* or *Poiretia* or *Pterocarpus* or *Ramorinoa* or *Riedeliella* or *Smithia* or *Soemmeringia* or *Steinbachiella* or *Stylosanthes* or *Tipuana* or *Weberbauerella* or *Zornia*.

In one embodiment, the plant based material from the sub-family Papilionoideae is from the genus *Arachis*, such as the species *Appressipila* (amendoim bravo) or *Arachis batizocoi* or *Arachis brevipetiolata* or *Arachis burcheffii* or *Arachis burkartii* or *Arachis cardenasii* or *Arachis chiquitana* or *Arachis correntina* or *Arachis cruziana* or *Arachis decora* or *Arachis diogoi* or *Arachis duranensis* or *Arachis duranensis*×*Arachis stenosperma* or *Arachis glabrata* (amendoim-bravo) or *Arachis glabrata* var. *glabrata* or *Arachis glabrata* var. *hagenbeckii* or *Arachis glabrata*× *Arachis hypogaea* or *Arachis glandulifera* or *Arachis guaranitica* or *Arachis helodes* or *Arachis hermannii* or *Arachis hoehnei* or *Arachis hypogaea* (peanut) or *Arachis hypogaea* subsp. *Fastigiata* or *Arachis hypogaea* var. *vulgaris* (Spanish peanut) or *Arachis hypogaea* subsp. *Hypogaea* or *Arachis hypogaea* var. *hirsuta* or *Arachis ipaensis* or *Arachis ipaensis*×*Arachis magna* or *Arachis kempff-mercadoi* or *Arachis kretschmeri* or *Arachis kuhlmannii* or *Arachis linearifolia* or *Arachis lutescens* or *Arachis magna* or *Arachis major* or *Arachis matiensis* or *Arachis microsperma* or *Arachis monticola* or *Arachis palustris* or *Arachis paraguariensis* or *Arachis paraguariensis* subsp. *capibarensis* or *Arachis paraguariensis* subsp. *paraguariensis* or *Arachis pflugeae* or *Arachis pintoi* or *Arachis praecox* or *Arachis pusilla* (amendoim de caracar) or *Arachis repens* or *Arachis rigonii* or *Arachis schinini* or *Arachis simpsonii* or *Arachis stenophylla* or *Arachis stenosperma* or *Arachis stenosperma*×*Arachis cardenasii* or *Arachis sylvestris* (amendoim do porco) or *Arachis trinitensis* or *Arachis triseminata* or *Arachis tuberosa* or *Arachis valida* or *Arachis villosa* or *Arachis villosulicarpa* or *Arachis wiffiamsii*.

In one aspect, the plant based material is from the taxonomic order Brassicales, such as the family Brassicaceae, preferably the tribe Brassiceae, more preferably the family *Brassica*.

In one embodiment, the plant based material from the tribe Brassiceae is from the family *Brassica*, such as *Brassica aucheri, Brassica balearica, Brassica barrelieri, Brassica carinata* (Abyssinian mustard), *Brassica carinata*× *Brassica napus, Brassica carinata*×*Brassica rapa, Brassica cretica, Brassica deflexa, Brassica desnottesii, Brassica drepanensis, Brassica elongata, Brassica fruticulosa, Bras-* sica fruticulosa subsp. cossoniana, Brassica fruticulosa subsp. mauritanica, Brassica fruticulosa subsp. rifana, Brassica gravinae, Brassica hilarionis, Brassica hybrid cultivar, Brassica incana, Brassica insularis, Brassica insularis subsp. insularis, Brassica juncea (Indian mustard), Brassica juncea var. crassicaulis, Brassica juncea var. gemmifera, Brassica juncea var. gracilis, Brassica juncea var. juncea, Brassica juncea var. multiceps, Brassica juncea var. multisecta, Brassica juncea var. napiformis (jie cai ge da), Brassica juncea var. rugosa, Brassica juncea var. strumata, Brassica juncea var. subintegrifolia, Brassica juncea var. tumida (zha cai), Brassica juncea var. utilis, Brassica macrocarpa, Brassica maurorum, Brassica montana, Brassica napus (rape), Brassica napus subsp. rapifera (Swedish turnip), Brassica napus var. napus (annual rape), Brassica napus×Brassica rapa, Brassica nigra (black mustard), Brassica nigra var. abyssinica, Brassica oleracea, Brassica oleracea var. albiflora, Brassica oleracea var. alboglabra (Chinese kale), Brassica oleracea var. botrytis (cauliflower), Brassica oleracea var. capitata (cabbage), Brassica oleracea var. costata (Bedford cabbage), Brassica oleracea var. gemmifera (Brussels sprouts), Brassica oleracea var. gongylodes (kohlrabi), Brassica oleracea var. italica (asparagus broccoli), Brassica oleracea var. medullosa (marrow-stem kale), Brassica oleracea var. oleracea, Brassica oleracea var. ramosa (branching bush kale), Brassica oleracea var. sabauda, Brassica oleracea var. viridis (kale), Brassica oleracea×Brassica rapa subsp. pekinensis, Brassica oxyrrhina, Brassica procumbens, Brassica rapa (field mustard), Brassica rapa subsp. chinensis (bok-choy), Brassica rapa var. parachinensis (cai xin), Brassica rapa var. purpuraria (purple stem mustard), Brassica rapa subsp. narinosa, Brassica rapa subsp. nipposinica (mizuna), Brassica rapa var. perviridis (kabuna), Brassica rapa subsp. oleifera (biennial turnip rape), Brassica rapa (Nippo-oleifera Group), Brassica rapa subsp. pekinensis (Chinese cabbage), Brassica rapa subsp. rapa (turnip), Brassica rapa var. oleifera, Brassica rapa×Brassica nigra, Brassica repanda, Brassica repanda subsp. baldensis, Brassica repanda subsp. blancoana, Brassica repanda subsp. cadevallii, Brassica repanda subsp. confusa, Brassica repanda subsp. glabrescens, Brassica repanda subsp. gypsicola, Brassica repanda subsp. latisiliqua, Brassica repanda subsp. maritima, Brassica repanda subsp. repanda, Brassica repanda subsp. saxatilis, Brassica rupestris, Brassica ruvo (broccoletto), Brassica souliei, Brassica souliei subsp. amplexicaulis, Brassica spinescens, Brassica toumefortii, Brassica villosa or Brassica villosa subsp. Bivoniana.

In particular embodiments, the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof. In a preferred embodiment, the plant based material is soybean or soybean meal.

Animal Feed and Animal Feed Additives

The present invention also relates to animal feed compositions and animal feed additives comprising one or more beta-galactosidases of the invention and one or more galactanases of the invention. In an embodiment, the animal feed or animal feed additive comprises a formulating agent, one or more beta-galactosidases of the invention and one or more galactanases of the invention. In a further embodiment, the formulating agent comprises one or more of the following compounds: glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch, kaolin and cellulose.

Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg.

An animal feed composition according to the invention has a crude protein content of 50-800 g/kg, and furthermore comprises at least one beta-galactosidase of the invention and at least one galactanase of the invention as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.5-50 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e. Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & looijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein as defined above.

The animal feed composition of the invention may also contain animal protein, such as Meat and Bone Meal, Feather meal, and/or Fish Meal, typically in an amount of 0-25%. The animal feed composition of the invention may also comprise Dried Distillers Grains with Solubles (DDGS), typically in amounts of 0-30%.

The animal feed composition of the invention may also contain insect protein, such as protein from mealworm, housefly or black soldier fly larvae, typically in meal form. Insect meal may replace fishmeal entirely or in part, and thus may constitute 0-10% of the total feed.

In still further particular embodiments, the animal feed composition of the invention contains 0-80% maize; and/or 0-80% sorghum; and/or 0-70% wheat; and/or 0-70% Barley;

and/or 0-30% oats; and/or 0-40% soybean meal; and/or 0-25% fish meal; and/or 0-25% meat and bone meal; and/or 0-20% whey.

The animal feed may comprise vegetable proteins. In particular embodiments, the protein content of the vegetable proteins is at least 10, 20, 30, 40, 50, 60, 70, 80, or 90% (w/w). Vegetable proteins may be derived from vegetable protein sources, such as legumes and cereals, for example, materials from plants of the families Fabaceae (Leguminosae), Brassicaceae, Amaranthaceae, and Poaceae, such as soybean meal, lupin meal, rapeseed meal, and combinations thereof.

In a particular embodiment, the vegetable protein source is material from one or more plants of the family Fabaceae, e.g., soybean, lupine, pea, or bean. In another particular embodiment, the vegetable protein source is material from one or more plants of the family Amaranthaceae, e.g. beet, sugar beet, spinach or quinoa. Other examples of vegetable protein sources are rapeseed, crambe and cabbage. In another particular embodiment, soybean is a preferred vegetable protein source. Other examples of vegetable protein sources are cereals such as barley, wheat, rye, oat, maize (corn), rice, and sorghum.

Animal diets can e.g. be manufactured as mash feed (non-pelleted) or pelleted feed. Typically, the milled feedstuffs are mixed and sufficient amounts of essential vitamins and minerals are added according to the specifications for the species in question. Enzymes can be added as solid or liquid enzyme formulations. For example, for mash feed a solid or liquid enzyme formulation may be added before or during the ingredient mixing step. For pelleted feed the (liquid or solid) beta-galactosidase/galactanase enzyme preparation may also be added before or during the feed ingredient step. Typically a liquid beta-galactosidase/galactanase enzyme preparation comprises a beta-galactosidase of the invention and a galactanase of the invention optionally with a polyol, such as glycerol, ethylene glycol or propylene glycol, and is added after the pelleting step, such as by spraying the liquid formulation onto the pellets. The enzyme may also be incorporated in a feed additive or premix.

Alternatively, the beta-galactosidase/galactanase can be prepared by freezing a mixture of liquid enzyme solution with a bulking agent such as ground soybean meal, and then lyophilizing the mixture.

In an embodiment, the animal feed or animal feed additive comprises one or more additional enzymes. In an embodiment, the animal feed comprises one or more microbes. In an embodiment, the animal feed comprises one or more vitamins. In an embodiment, the animal feed comprises one or more minerals. In an embodiment, the animal feed comprises one or more amino acids. In an embodiment, the animal feed comprises one or more other feed ingredients.

In another embodiment, the animal feed or animal feed additive comprises the polypeptide of the invention, one or more formulating agents and one or more additional enzymes. In an embodiment, the animal feed or animal feed additive comprises the polypeptide of the invention, one or more formulating agents and one or more microbes. In an embodiment, the animal feed comprises the polypeptide of the invention, one or more formulating agents and one or more vitamins. In an embodiment, the animal feed or animal feed additive comprises one or more minerals. In an embodiment, the animal feed or animal feed additive comprises the polypeptide of the invention, one or more formulating agents and one or more amino acids. In an embodiment, the animal feed or animal feed additive comprises the polypeptide of the invention, one or more formulating agents and one or more other feed ingredients.

In a further embodiment, the animal feed or animal feed additive comprises the polypeptide of the invention, one or more formulating agents and one or more components selected from the list consisting of: one or more additional enzymes; one or more microbes; one or more vitamins; one or more minerals; one or more amino acids; and one or more other feed ingredients.

In an embodiment, the animal feed additive comprises one or more formulating agents, preferably as described herein below.

In an embodiment, the animal feed additive comprises one or more additional enzymes, preferably as described herein below.

In an embodiment, the animal feed additive comprises one or more probiotics, preferably as described herein below.

In an embodiment, the animal feed additive comprises one or more vitamins, preferably as described herein below.

In an embodiment, the animal feed additive comprises one or more minerals, preferably as described herein below.

In an embodiment, the animal feed additive comprises one or more amino acids, preferably as described herein below.

In an embodiment, the animal feed additive comprises one or more prebiotics, preferably as described herein below.

In an embodiment, the animal feed additive comprises one or more organic acids, preferably as described herein below.

In an embodiment, the animal feed additive comprises one or more phytogenics, preferably as described herein below.

The final enzyme concentration in the diet is within the range of 0.01-200 mg enzyme protein per kg diet, preferably between 0.05-100 mg/kg diet, more preferably 0.1-50 mg, even more preferably 0.2-20 mg enzyme protein per kg animal diet, for each enzyme.

It is at present contemplated that the galactanase is administered in one or more of the following amounts (dosage ranges): 0.01-200; 0.05-100; 0.1-50; 0.2-20; 0.1-1; 0.2-2; 0.5-5; or 1-10 wherein all these ranges are mg galactanase protein per kg feed (ppm). It is at present contemplated that the beta-galactosidase is administered in one or more of the following amounts (dosage ranges): 0.01-200; 0.05-100; 0.1-50; 0.2-20; 0.1-1; 0.2-2; 0.5-5; or 1-10 wherein all these ranges are mg beta-galactosidase protein per kg feed (ppm). It is further contemplated that the ratio of the galactanase to beta-galactosidase is in the range of 100:1 to 1:100 galactanase: beta-galactosidase such as the ranges 50:1 to 1:50, 50:1 to 1:10, 25:1 to 1:5, 10:1 to 1:2 or such as 10:1 to 1:50, 5:1 to 1:25, 2:1 to 1:10 galactanase: beta-galactosidase.

For determining mg galactanase and/or mg beta-galactosidase protein per kg feed, the galactanase and/or beta-galactosidase is purified from the feed composition, and the specific activity of the purified galactanase and/or beta-galactosidase is determined using a relevant assay (see under galactanase or beta-galactosidase activity). The galactanase and/or beta-galactosidase activity of the feed composition as such is also determined using the same assay, and on the basis of these two determinations, the dosage in mg galactanase and/or mg beta-galactosidase protein per kg feed is calculated.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (')/0 meaning g additive per 100 g feed). This is so in particular for premixes.

The same principles apply for determining mg galactanase or mg beta-galactosidase protein in feed additives. Of course, if a sample is available of the galactanase or beta-galactosidase used for preparing the feed additive or the feed, the specific activity is determined from this sample (no need to purify the galactanase or beta-galactosidase from the feed composition or the additive).

Additional Enzymes

In another embodiment, the compositions described herein optionally include one or more enzymes. Enzymes can be classified on the basis of the handbook Enzyme Nomenclature from NC-IUBMB, 1992), see also the ENZYME site at the internet: http://www.expasy.ch/enzyme/. ENZYME is a repository of information relative to the nomenclature of enzymes. It is primarily based on the recommendations of the Nomenclature Committee of the International Union of Biochemistry and Molecular Biology (IUB-MB), Academic Press, Inc., 1992, and it describes each type of characterized enzyme for which an EC (Enzyme Commission) number has been provided (Bairoch A. The ENZYME database, 2000, Nucleic Acids Res 28:304-305). This IUB-MB Enzyme nomenclature is based on their substrate specificity and occasionally on their molecular mechanism; such a classification does not reflect the structural features of these enzymes.

Another classification of certain glycoside hydrolase enzymes, such as endoglucanase, galactanase, mannanase, dextranase, lysozyme and galactosidase is described in Henrissat et al, "The carbohydrate-active enzymes database (CAZy) in 2013", Nucl. Acids Res. (1 Jan. 2014) 42 (D1): D490-D495; see also www.cazy.org.

Thus the composition of the invention may also comprise at least one other enzyme selected from the group comprising of acetylxylan esterase (EC 3.1.1.23), acylglycerol lipase (EC 3.1.1.72), alpha-amylase (EC 3.2.1.1), beta-amylase (EC 3.2.1.2), arabinofuranosidase (EC 3.2.1.55), cellobiohydrolases (EC 3.2.1.91), cellulase (EC 3.2.1.4), feruloyl esterase (EC 3.1.1.73), galactanase (EC 3.2.1.89), alpha-galactosidase (EC 3.2.1.22), beta-galactosidase (EC 3.2.1.23), beta-glucanase (EC 3.2.1.6), beta-glucosidase (EC 3.2.1.21), triacylglycerol lipase (EC 3.1.1.3), lysophospholipase (EC 3.1.1.5), lysozyme (EC 3.2.1.17), alpha-mannosidase (EC 3.2.1.24), beta-mannosidase (mannanase) (EC 3.2.1.25), phytase (EC 3.1.3.8, EC 3.1.3.26, EC 3.1.3.72), phospholipase A1 (EC 3.1.1.32), phospholipase A2 (EC 3.1.1.4), phospholipase D (EC 3.1.4.4), protease (EC 3.4), pullulanase (EC 3.2.1.41), pectinesterase (EC 3.1.1.11), xylanase (EC 3.2.1.8, EC 3.2.1.136), beta-xylosidase (EC 3.2.1.37), or any combination thereof.

In a particular embodiment, the composition of the invention comprises a phytase (EC 3.1.3.8 or 3.1.3.26). Examples of commercially available phytases include Bio-Feed™ Phytase (Novozymes), Ronozyme® P, Ronozyme® NP and Ronozyme® HiPhos (DSM Nutritional Products), Natuphos™ (BASF), Natuphos™ E (BASF), Finase® and Quantum® Blue (AB Enzymes), OptiPhos® (Huvepharma), AveMix® Phytase (Aveve Biochem), Phyzyme® XP (Verenium/DuPont) and Axtra® PHY (DuPont). Other preferred phytases include those described in e.g. WO 98/28408, WO 00/43503, and WO 03/066847.

In a particular embodiment, the composition of the invention comprises a xylanase (EC 3.2.1.8). Examples of commercially available xylanases include Ronozyme® WX (DSM Nutritional Products), Econase® XT and Barley (AB Vista), Xylathin® (Verenium), Hostazym® X (Huvepharma), Axtra® XB (Xylanase/beta-glucanase, DuPont) and Axtra® XAP (Xylanase/amylase/protease, DuPont), AveMix® XG 10 (xylanase/glucanase) and AveMix® 02 CS (xylanase/glucanase/pectinase, Aveve Biochem), and Naturgrain (BASF).

In a particular embodiment, the composition of the invention comprises a protease (EC 3.4). Examples of commercially available proteases include Ronozyme® ProAct (DSM Nutritional Products).

In a particular embodiment, the composition of the invention comprises an alpha-amylase (EC 3.2.1.1). Examples of commercially available alpha-amylases include Ronozyme® A and RONOZYME® RumiStar™ (DSM Nutritional Products).

In one embodiment, the composition of the invention comprises a multicomponent enzyme product, such as FRA® Octazyme (Framelco), Ronozyme® G2, Ronozyme® VP and Ronozyme® MultiGrain (DSM Nutritional Products), Rovabio® Excel or Rovabio® Advance (Adisseo).

Eubiotics

Eubiotics are compounds which are designed to give a healthy balance of the micro-flora in the gastrointestinal tract. Eubiotics cover a number of different feed additives, such as probiotics, prebiotics, phytogenics (essential oils) and organic acids which are described in more detail below.

Probiotics

In an embodiment, the animal feed composition further comprises one or more additional probiotic. In a particular embodiment, the animal feed composition further comprises a bacterium from one or more of the following genera: *Lactobacillus, Lactococcus, Streptococcus, Bacillus, Pediococcus, Enterococcus, Leuconostoc, Carnobacterium, Propionibacterium, Bifidobacterium, Clostridium* and *Megasphaera* or any combination thereof.

In a preferred embodiment, animal feed composition further comprises a bacterium from one or more of the following strains: *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Enterococcus faecium, Enterococcus* spp, and *Pediococcus* spp, *Lactobacillus* spp, *Bifidobacterium* spp, *Lactobacillus acidophilus, Pediococsus acidilactici, Lactococcus lactis, Bifidobacterium bifidum, Propionibacterium thoenii, Lactobacillus farciminus, Lactobacillus rhamnosus, Clostridium butyricum, Bifidobacterium animalis* ssp. *animalis, Lactobacillus reuteri, Lactobacillus salivarius* ssp. *salivarius, Megasphaera elsdenii, Propionibacteria* sp.

In a more preferred embodiment, composition, animal feed additive or animal feed further comprises a bacterium from one or more of the following strains of *Bacillus subtilis:* 3A-P4 (PTA-6506), 15A-P4 (PTA-6507), 22C-P1 (PTA-6508), 2084 (NRRL B-500130), LSSA01 (NRRL-B-50104), BS27 (NRRL B-501 05), BS 18 (NRRL B-50633), BS 278 (NRRL B-50634), DSM 29870, DSM 29871, DSM 32315, NRRL B-50136, NRRL B-50605, NRRL B-50606, NRRL B-50622 and PTA-7547.

In a more preferred embodiment, composition, animal feed additive or animal feed further comprises a bacterium from one or more of the following strains of *Bacillus pumilus*: NRRL B-50016, ATCC 700385, NRRL B-50885 or NRRL B-50886.

In a more preferred embodiment, composition, animal feed additive or animal feed further comprises a bacterium from one or more of the following strains of *Bacillus lichenformis*: NRRL B 50015, NRRL B-50621 or NRRL B-50623.

In a more preferred embodiment, composition, animal feed additive or animal feed further comprises a bacterium from one or more of the following strains of *Bacillus amyloliquefaciens*: DSM 29869, DSM 29869, NRRL B 50607, PTA-7543, PTA-7549, NRRL B-50349, NRRL B-50606, NRRL B-50013, NRRL B-50151, NRRL B-50141, NRRL B-50147 or NRRL B-50888.

The bacterial count of each of the bacterial strains in the animal feed composition is between $1 \times 10^4$ and $1 \times 10^{14}$ CFU/kg of dry matter, preferably between $1 \times 10^6$ and $1 \times 10^{12}$ CFU/kg of dry matter, and more preferably between $1 \times 10^7$ and $1 \times 10^{11}$ CFU/kg of dry matter. In a more preferred embodiment the bacterial count of each of the bacterial strains in the animal feed composition is between $1 \times 10^8$ and $1 \times 10^{10}$ CFU/kg of dry matter.

The bacterial count of each of the bacterial strains in the animal feed composition is between $1 \times 10^5$ and $1 \times 10^{15}$ CFU/animal/day, preferably between $1 \times 10^7$ and $1 \times 10^{13}$ CFU/animal/day, and more preferably between $1 \times 10^8$ and $1 \times 10^{12}$ CFU/animal/day. In a more preferred embodiment the bacterial count of each of the bacterial strains in the animal feed composition is between $1 \times 10^9$ and $1 \times 10^{11}$ CFU/animal/day.

In another embodiment, the one or more bacterial strains are present in the form of a stable spore.

Examples of commercial products are Cylactin® (DSM Nutritional Products), Alterion (Adisseo), Enviva PRO (DuPont Animal Nutrition), Gallipro®, Gallipro® Max, Probios® Guard, Lactiferm® and Bioplus® (Chr Hansen), PoultryStar®, PoultryStar® sol, PoultryStar® me, AquaStar® (Biomin), Syncra® (mix enzyme+probiotic, DuPont Animal Nutrition), Ecobiol® and Fecinor® (Norel/Evonik) and GutCare® PY1 (Evonik).

Prebiotics

Prebiotics are substances that induce the growth or activity of microorganisms (e.g., bacteria and fungi) that contribute to the well-being of their host. Prebiotics are typically non-digestible fiber compounds that pass undigested through the upper part of the gastrointestinal tract and stimulate the growth or activity of advantageous bacteria that colonize the large bowel by acting as substrate for them. Normally, prebiotics increase the number or activity of bifidobacteria and lactic acid bacteria in the GI tract.

Yeast derivatives (inactivated whole yeasts or yeast cell walls) can also be considered as prebiotics. They often comprise mannan-oligosaccharids, yeast beta-glucans or protein contents and are normally derived from the cell wall of the yeast, *Saccharomyces cerevisiae*.

Examples of yeast products are Yang® and Agrimos (Lallemand Animal Nutrition).

Phytogenics

Phytogenics are a group of natural growth promoters or non-antibiotic growth promoters used as feed additives, derived from herbs, spices or other plants. Phytogenics can be single substances prepared from essential oils/extracts, essential oils/extracts, single plants and mixture of plants (herbal products) or mixture of essential oils/extracts/plants (specialized products).

Examples of phytogenics are rosemary, sage, oregano, thyme, clove, and lemongrass. Examples of essential oils are thymol, eugenol, meta-cresol, vaniline, salicylate, resorcine, guajacol, gingerol, lavender oil, ionones, irone, eucalyptol, menthol, peppermint oil, alpha-pinene; limonene, anethol, linalool, methyl dihydrojasmonate, carvacrol, propionic acid/propionate, acetic acid/acetate, butyric acid/butyrate, rosemary oil, clove oil, geraniol, terpineol, citronellol, amyl and/or benzyl salicylate, cinnamaldehyde, plant polyphenol (tannin), turmeric and curcuma extract.

Examples of commercial products are Crina® (DSM Nutritional Products); Cinergy™, Cinergy™ FIT, Biacid™, (Cargill), Digestarom® and Digestarom® DC (Biomin) and Envivo EO (DuPont Animal Nutrition).

Organic Acids

Organic acids (C1-C7) are widely distributed in nature as normal constituents of plants or animal tissues. They are also formed through microbial fermentation of carbohydrates mainly in the large intestine. They are often used in swine and poultry production as a replacement of antibiotic growth promoters since they have a preventive effect on the intestinal problems like necrotic enteritis in chickens and *Escherichia coli* infection in young pigs. Organic acids can be sold as mono component or mixtures of typically 2 or 3 different organic acids. Examples of organic acids are propionic acid, formic acid, citric acid, lactic acid, sorbic acid, malic acid, acetic acid, fumaric acid, benzoic acid, butyric acid and tartaric acid or their salt (typically sodium or potassium salt such as potassium diformate or sodium butyrate).

Examples of commercial products are VevoVitall® (DSM Nutritional Products), Amasil®, Luprisil®, Lupro-Grain®, Lupro-Cid®, Lupro-Mix®, Lupro-Mix® NA (BASF), n-Butyric Acid AF (OXEA), Biacid™, Prohacid™ Classic and Prohacid™ Advance™ (Cargill), Biotronic® (Biomin) and Adimix Precision (Nutriad).

Premix

The incorporation of the composition of feed additives as exemplified herein above to animal feeds, for example poultry feeds, is in practice carried out using a concentrate or a premix. A premix designates a preferably uniform mixture of one or more microingredients with diluent and/or carrier. Premixes are used to facilitate uniform dispersion of micro-ingredients in a larger mix. A premix according to the invention can be added to feed ingredients or to the drinking water as solids (for example as water soluble powder) or liquids.

Amino Acids

The composition of the invention may further comprise one or more amino acids. Examples of amino acids which are used in animal feed are lysine, alanine, beta-alanine, threonine, methionine and tryptophan.

Vitamins and Minerals

In another embodiment, the animal feed may include one or more vitamins, such as one or more fat-soluble vitamins and/or one or more water-soluble vitamins. In another embodiment, the animal feed may optionally include one or more minerals, such as one or more trace minerals and/or one or more macro minerals.

Usually fat- and water-soluble vitamins, as well as trace minerals form part of a so-called premix intended for addition to the feed, whereas macro minerals are usually separately added to the feed.

Non-limiting examples of fat-soluble vitamins include vitamin A, vitamin D3, vitamin E, and vitamin K, e.g., vitamin K3.

Non-limiting examples of water-soluble vitamins include vitamin B12, biotin and choline, vitamin B1, vitamin B2, vitamin B6, niacin, folic acid and panthothenate, e.g., Ca-D-panthothenate.

Non-limiting examples of trace minerals include boron, cobalt, chloride, chromium, copper, fluoride, iodine, iron, manganese, molybdenum, selenium and zinc.

Non-limiting examples of macro minerals include calcium, magnesium, potassium and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

In a still further embodiment, the animal feed additive of the invention comprises at least one of the below vitamins, preferably to provide an in-feed-concentration within the ranges specified in the below Table 1 (for piglet diets, and broiler diets, respectively).

TABLE 1

Typical vitamin recommendations

| Vitamin | Piglet diet | Broiler diet |
| --- | --- | --- |
| Vitamin A | 10,000-15,000 IU/kg feed | 8-12,500 IU/kg feed |
| Vitamin D3 | 1800-2000 IU/kg feed | 3000-5000 IU/kg feed |
| Vitamin E | 60-100 mg/kg feed | 150-240 mg/kg feed |
| Vitamin K3 | 2-4 mg/kg feed | 2-4 mg/kg feed |
| Vitamin B1 | 2-4 mg/kg feed | 2-3 mg/kg feed |
| Vitamin B2 | 6-10 mg/kg feed | 7-9 mg/kg feed |
| Vitamin B6 | 4-8 mg/kg feed | 3-6 mg/kg feed |
| Vitamin B12 | 0.03-0.05 mg/kg feed | 0.015-0.04 mg/kg feed |
| Niacin (Vitamin B3) | 30-50 mg/kg feed | 50-80 mg/kg feed |
| Pantothenic acid | 20-40 mg/kg feed | 10-18 mg/kg feed |
| Folic acid | 1-2 mg/kg feed | 1-2 mg/kg feed |
| Biotin | 0.15-0.4 mg/kg feed | 0.15-0.3 mg/kg feed |
| Choline chloride | 200-400 mg/kg feed | 300-600 mg/kg feed |

Other Feed Ingredients

The composition of the invention may further comprise colouring agents, stabilisers, growth improving additives and aroma compounds/flavourings, polyunsaturated fatty acids (PUFAs); reactive oxygen generating species, antioxidants, anti-microbial peptides, anti-fungal polypeptides and mycotoxin management compounds.

Examples of colouring agents are carotenoids such as beta-carotene, astaxanthin, and lutein.

Examples of aroma compounds/flavourings are creosol, anethol, deca-, undeca- and/or dodeca-lactones, ionones, irone, gingerol, piperidine, propylidene phatalide, butylidene phatalide, capsaicin and tannin.

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in WO 03/044049 and WO 03/048148, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Examples of polyunsaturated fatty acids are 018, C20 and C22 polyunsaturated fatty acids, such as arachidonic acid, docosohexaenoic acid, eicosapentaenoic acid and gamma-linoleic acid.

Examples of reactive oxygen generating species are chemicals such as perborate, persulphate, or percarbonate; and enzymes such as an oxidase, an oxygenase or a synthetase.

Antioxidants can be used to limit the number of reactive oxygen species which can be generated such that the level of reactive oxygen species is in balance with antioxidants.

Mycotoxins, such as deoxynivalenol, aflatoxin, zearalenone and fumonisin can be found in animal feed and can result in nmegative animal performance or illness. Compounds which can manage the levels of mycotoxin, such as via deactivation of the mycotoxin or via binding of the mycotoxin, can be added to the feed to ameliorate these negative effects. Examples of mycotoxin management compounds are Vitafix®, Vitafix Ultra (Nuscience), Mycofix®, Mycofix® Secure, FUMzyme®, Biomin® BBSH, Biomin® MTV (Biomin), Mold-Nil®, Toxy-Nil® and Unike® Plus (Nutriad).

Uses

The present invention is also directed to methods for using the polypeptides having galactanase and/or beta-galactosidase activity, or compositions thereof, for e.g. animal feed. The present invention is also directed to processes for using the polypeptides having galactanase and/or beta-galactosidase activity, or compositions thereof, such as e.g. those described below.

Use in Animal Feed

The present invention is also directed to methods for using the galactanases and beta-galactosidase of the invention in animal feed.

The term animal includes all animals. Examples of animals are non-ruminants, and ruminants. Ruminant animals include, for example, animals such as sheep, goats, and cattle, e.g. beef cattle, cows, and young calves. In a particular embodiment, the animal is a non-ruminant animal. Non-ruminant animals include mono-gastric animals, e.g. pigs or swine (including, but not limited to, piglets, growing pigs, and sows); poultry such as turkeys, ducks and chicken (including but not limited to broiler chicks, layers); horses (including but not limited to hotbloods, coldbloods and warm bloods), young calves; and fish (including but not limited to salmon, trout, tilapia, catfish and carps; and crustaceans (including but not limited to shrimps and prawns).

In the use according to the invention the galactanases and beta-galactosidases can be fed to the animal before, after, or simultaneously with the diet. The latter is preferred.

In a particular embodiment, the form in which the galactanase and beta-galactosidase is added to the feed, or animal feed additive, is well-defined. Well-defined means that the galactanase and beta-galactosidase preparation is at least 50% pure as determined by Size-exclusion chromatography (see Example 12 of WO 01/58275). In other particular embodiments the galactanase and beta-galactosidase preparation is at least 60, 70, 80, 85, 88, 90, 92, 94, or at least 95% pure as determined by this method.

A well-defined galactanase and beta-galactosidase preparation is advantageous. For instance, it is much easier to dose correctly to the feed a galactanase and beta-galactosidase that is essentially free from interfering or contaminating other galactanases and beta-galactosidases. The term dose correctly refers in particular to the objective of obtaining consistent and constant results, and the capability of optimizing dosage based upon the desired effect.

For the use in animal feed, however, the galactanase and beta-galactosidase need not be that pure; it may e.g. include other enzymes, in which case it could be termed a galactanase and beta-galactosidase preparation.

The galactanase and beta-galactosidase preparation can be (a) added directly to the feed, or (b) it can be used in the production of one or more intermediate compositions such as feed additives or premixes that is subsequently added to the feed (or used in a treatment process). The degree of purity described above refers to the purity of the original galactanase and beta-galactosidase preparation, whether used according to (a) or (b) above.

Preferred Embodiments of the Invention

Preferred embodiments of the invention are described in the set of items below.

1. A composition comprising one or more GH53 polypeptides having galactanase activity and one or more GH35 polypeptides having beta-galactosidase activity.
2. The composition of item 1, wherein the GH53 polypeptide comprises the motif GV[T/M]PD[W/M]VQ[I/V]GNE (SEQ ID NO: 65) and/or the motif WADP[A/G]xQxKPxAW (SEQ ID NO: 66).
3. The composition of any of items 1 to 2, wherein the GH53 polypeptide is obtained or obtainable from the taxonomic family Paenibacillaceae.
4. The composition of any of items 1 to 3 wherein the GH53 polypeptide is selected from the group consisting of:
   (a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;
   (b) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 7;
   (c) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 11;
   (d) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 15;
   (e) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 19;
   (f) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 23;
   (g) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 27;
   (h) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 31;
   (i) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 35;
   (j) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 39;
   (k) a variant of SEQ ID NO: 3 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (l) a variant of SEQ ID NO: 7 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (m) a variant of SEQ ID NO: 11 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (n) a variant of SEQ ID NO: 15 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (o) a variant of SEQ ID NO: 19 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
   (p) a variant of SEQ ID NO: 23 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(q) a variant of SEQ ID NO: 27 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(r) a variant of SEQ ID NO: 31 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(s) a variant of SEQ ID NO: 35 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(t) a variant of SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(u) a polypeptide comprising the polypeptide of (a), (b), (c), (d), (e), (f), (g), (h), (i), (j), (k), (l), (m), (n), (o), (p), (q), (r), (s) or (t) and a N-terminal and/or C-terminal His-tag and/or HQ-tag;

(v) a polypeptide comprising the polypeptide of (a), (b), (c), (d), (e), (f), (g), (h), (i), (j), (k), (l), (m), (n), (o), (p), (q), (r), (s) or (t) and a N-terminal and/or C-terminal extension of between 1 and 10 amino acids; and (w) a fragment of the polypeptide of (a), (b), (c), (d), (e), (f), (g), (h), (i), (j), (k), (l), (m), (n), (o), (p), (q), (r), (s), (t) or (u) having galactanase activity and having at least 90% of the length of the mature polypeptide.

5. The composition of item 4, wherein the GH53 polypeptide comprises or consists of amino acids 1 to 316 of SEQ ID NO: 2, amino acids 1 to 316 of SEQ ID NO: 3, amino acids 1 to 324 of SEQ ID NO: 4, amino acids 1 to 318 of SEQ ID NO: 6, amino acids 1 to 318 of SEQ ID NO: 7, amino acids 1 to 326 of SEQ ID NO: 8, amino acids 1 to 316 of SEQ ID NO: 10, amino acids 1 to 316 of SEQ ID NO: 11, amino acids 1 to 324 of SEQ ID NO: 12, amino acids 1 to 316 of SEQ ID NO: 14, amino acids 1 to 316 of SEQ ID NO: 15, amino acids 1 to 324 of SEQ ID NO: 16, amino acids 1 to 316 of SEQ ID NO: 18, amino acids 1 to 316 of SEQ ID NO: 19, amino acids 1 to 324 of SEQ ID NO: 20, amino acids 1 to 316 of SEQ ID NO: 22, amino acids 1 to 316 of SEQ ID NO: 23, amino acids 1 to 324 of SEQ ID NO: 24, amino acids 1 to 516 of SEQ ID NO: 26, amino acids 1 to 516 of SEQ ID NO: 27, amino acids 1 to 524 of SEQ ID NO: 28, amino acids 1 to 317 of SEQ ID NO: 30, amino acids 1 to 317 of SEQ ID NO: 31, amino acids 1 to 325 of SEQ ID NO: 32, amino acids 1 to 316 of SEQ ID NO: 34, amino acids 1 to 316 of SEQ ID NO: 35, amino acids 1 to 324 of SEQ ID NO: 36, amino acids 1 to 316 of SEQ ID NO: 38, amino acids 1 to 316 of SEQ ID NO: 39 or amino acids 1 to 324 of SEQ ID NO: 40.

6. The composition of any of items 1 to 5, wherein the GH35 polypeptide is selected from the group consisting of:

(a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 43;

(b) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 46;

(c) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 49;

(d) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 52;

(e) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 55;

(f) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 58;

(g) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 61;

(h) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 70;

(i) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 73;

(j) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 76;

(k) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 79;

(l) a variant of SEQ ID NO: 43 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(m) a variant of SEQ ID NO: 46 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(n) a variant of SEQ ID NO: 49 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(o) a variant of SEQ ID NO: 52 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(p) a variant of SEQ ID NO: 55 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(q) a variant of SEQ ID NO: 58 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(r) a variant of SEQ ID NO: 61 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(s) a variant of SEQ ID NO: 70 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(t) a variant of SEQ ID NO: 73 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(u) a variant of SEQ ID NO: 76 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(v) a variant of SEQ ID NO: 79 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(w) a polypeptide comprising the polypeptide of (a), (b), (c), (d), (e), (f), (g), (h), (i), (j), (k), (l), (m), (n), (o), (p), (q), (r), (s), (t), (u) or (v) and a N-terminal and/or C-terminal His-tag and/or HQ-tag;

(x) a polypeptide comprising the polypeptide of (a), (b), (c), (d), (e), (f), (g), (h), (i), (j), (k), (l), (m), (n), (o), (p), (q), (r), (s), (t), (u) or (v) and a N-terminal and/or C-terminal extension of up to 10 amino acids, e.g. 1, 2, 3, 4, 5, 6, 7, 8, 9 or 10 amino acids; and (y) a fragment of the polypeptide of (a), (b), (c), (d), (e), (f), (g), (h), (i), (j), (k), (l), (m), (n), (o), (p), (q), (r), (s), (t), (u) or (v) having beta-galactosidase activity and having at least 90% of the length of the mature polypeptide.

7. The composition of item 6, wherein the GH35 polypeptide comprises or consists of amino acids 1 to 985 of SEQ ID NO: 42, amino acids 1 to 985 of SEQ ID NO: 43, amino acids 1 to 1015 of SEQ ID NO: 45, amino acids 1 to 1015 of SEQ ID NO: 46, amino acids 1 to 998 of SEQ ID NO: 48, amino acids 1 to 998 of SEQ ID NO: 49, amino acids 1 to 983 of SEQ ID NO: 51, amino acids 1 to 983 of SEQ ID NO: 52, amino acids 1 to 998 of SEQ ID NO: 54, amino acids 1 to 998 of SEQ ID NO: 55, amino acids 1 to 1007 of SEQ ID NO: 57, amino acids 1 to 1007 of SEQ ID NO: 58, amino acids 1 to 988 of SEQ ID NO: 60, amino acids 1 to 988 of SEQ ID NO: 61, amino acids 1 to 962 of SEQ ID NO: 69, amino acids 1 to 962 of SEQ ID NO: 70, amino acids 1 to 1000 of SEQ ID NO: 72, amino acids 1 to 1000 of SEQ ID NO: 73, amino acids 1 to 1000 of SEQ ID NO: 75, amino acids 1 to 1000 of SEQ ID NO: 76, amino acids 1 to 994 of SEQ ID NO: 78 and amino acids 1 to 994 of SEQ ID NO: 79.

8. The composition of any of items 1 to 7 further comprising one or more formulating agents.

9. The composition of item 8, wherein the one or more formulating agent is selected from the group consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

10. The composition of any of items 1 to 9 further comprising one or more additional enzymes.

11. The composition of item 10 wherein the one or more additional enzymes is selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

12. The composition of any of items 1 to 11 further comprising one or more microbes.

13. The composition of item 12, wherein the one or more microbes is selected from the group consisting of *Bacillus subtilis, Bacillus licheniformis, Bacillus amyloliquefaciens, Bacillus cereus, Bacillus pumilus, Bacillus polymyxa, Bacillus megaterium, Bacillus coagulans, Bacillus circulans, Bifidobacterium bifidum, Bifidobacterium animalis, Bifidobacterium* sp., *Carnobacterium* sp., *Clostridium butyricum, Clostridium* sp., *Enterococcus faecium, Enterococcus* sp., *Lactobacillus* sp., *Lactobacillus acidophilus, Lactobacillus farciminus, Lactobacillus rhamnosus, Lactobacillus reuteri, Lactobacillus salivarius, Lactococcus lactis, Lactococcus* sp., *Leuconostoc* sp., *Megasphaera elsdenii, Megasphaera* sp., *Pediococcus acidilactici, Pediococcus* sp., *Propionibacterium thoenii, Propionibacterium* sp. and *Streptococcus* sp. or any combination thereof.

14. The composition of any of items 1 to 13, wherein the composition releases at least 12 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

15. The composition of item 14, wherein the composition releases at least 13 g, such as at least 14 g, at least 15 g, at least 16 g, at least 17 g, at least 18 g, at least 19 g, at least 20 g or at least 22 g galactose per kg soybean meal.

16. The composition of any of items 1 to 15 further comprising plant based material.

17. The composition of item 16, wherein the plant based material is from the taxonomic subclass rosids.

18. The composition of item 16, wherein the plant based material is from the family Fabaceae, preferably the sub-family Papilionoideae.

19. The composition of item 16, wherein the plant based material is from the tribe Phaseoleae, Cicereae, Genisteae, Fabeae, Dalbergieae or Phaseoleae or any combination thereof.

20. The composition of item 16, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

21. A granule comprising the composition of any of items 1 to 15.

22. The granule of item 21 wherein the granule is coated.

23. The granule of item 22 wherein the coating comprises a salt and/or wax and/or a flour.

24. An animal feed additive comprising the composition of any of items 1 to 15 or the granule of any of items 21 to 23.

25. The animal feed additive of item 24 further comprising one or more components selected from the list consisting of:
one or more vitamins;
one or more minerals;
one or more amino acids;
one or more phytogenics;
one or more prebiotics;
one or more organic acids; and
one or more other feed ingredients.

26. An animal feed comprising plant based material and the composition of any of items 1 to 15, the granule of any of items 21 to 23 or the animal feed additive of any of items 24 to 25.

27. The animal feed of item 26, wherein the plant based material is from the taxonomic subclass rosids, preferably from the family Fabaceae, more preferably the sub-family Papilionoideae or even more preferably is from the tribe Phaseoleae, Cicereae, Genisteae, Fabeae, Dalbergieae or Phaseoleae or any combination thereof.

28. The animal feed of item 26, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

29. A pelleted animal feed comprising plant based material and the composition of any of items 1 to 15, the granule of any of items 21 to 23 or the animal feed additive of any of items 24 to 25.

30. The pelleted animal feed of item 29, wherein the plant based material is from the taxonomic subclass rosids, preferably from the family Fabaceae, more preferably the sub-family Papilionoideae or even more preferably is from the tribe Phaseoleae, Cicereae, Genisteae, Fabeae, Dalbergieae or Phaseoleae or any combination thereof.

31. The pelleted animal feed of item 29, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.

32. The pelleted animal feed of any of items 29 to 31, wherein the composition of any of items 1 to 15, the granule of any of items 21 to 23 or the animal feed additive of any of items 24 to 25 is sprayed onto the pellet.
33. A liquid formulation comprising the composition of any of items 1 to 15.
34. The liquid formulation of item 33, wherein the polypeptide having beta-galactosidase activity is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.
35. The liquid formulation of any of items 33 to 34, wherein the polypeptide having galactanase activity is dosed between 0.001% to 25% w/w of liquid formulation, preferably 0.01% to 25% w/w, more preferably 0.05% to 20% w/w, more preferably 0.2% to 15% w/w, even more preferably 0.5% to 15% w/w or most preferably 1.0% to 10% w/w polypeptide.
36. The liquid formulation of any of items 33 to 35, wherein the formulation further comprises 20% to 80% w/w of polyol.
37. The liquid formulation of item 36, wherein the polyol is selected from the group consisting of glycerol, sorbitol, propylene glycol (MPG), ethylene glycol, diethylene glycol, triethylene glycol, 1, 2-propylene glycol or 1, 3-propylene glycol, dipropylene glycol, polyethylene glycol (PEG) having an average molecular weight below about 600 and polypropylene glycol (PPG) having an average molecular weight below about 600 or any combination thereof.
38. The liquid formulation of any of items 33 to 37, wherein the formulation further comprises 0.01% to 2.0% w/w preservative.
39. The liquid formulation of item 38, wherein the preservative is selected from the group consisting of sodium sorbate, potassium sorbate, sodium benzoate and potassion benzoate or any combination thereof.
40. The liquid formulation of any of items 33 to 39 further comprising one or more components selected from the list consisting of:
    one or more enzymes;
    one or more microbes;
    one or more vitamins;
    one or more minerals;
    one or more amino acids;
    one or more phytogenics;
    one or more prebiotics;
    one or more organic acids; and
    one or more other feed ingredients.
41. A method of preparing an animal feed comprising applying the liquid formulation of any of items 33 to 40 onto plant based material.
42. The method of item 41, wherein the liquid formulation is applied via a spray.
43. The method of any of items 41 to 42, wherein the plant based material is selected from the group consisting of soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
44. The method of any of items 41 to 43, wherein the plant based material is in pelleted form.
45. A pelleted animal feed prepared using the method of any of items 41 to 44.
46. A method of releasing galactose from plant based material, comprising treating the plant based material with the composition of any of items 1 to 15, the granule of any of items 21 to 23, the animal feed additive of any of items 24 to 25 or the liquid formulation of any of items 33 to 40.
47. A method of improving one or more performance parameters of an animal comprising administering to one or more animals the composition of any of items 1 to 15, the granule of any of items 21 to 23, the animal feed additive of any of items 24 to 25, the animal feed of any of items 26 to 28, the pelleted animal feed of any of items 29 to 32 or 45 or the liquid formulation of any of items 33 to 40.
48. The method of item 47, wherein the performance parameter is selected from the list consisting of body weight gain (BWG), European Production Efficiency Factor (EPEF) and Feed Conversion Ratio (FCR) or any combination thereof.
49. A method for improving the nutritional value of an animal feed, comprising adding to the feed the composition of any of items 1 to 15, the granule of any of items 21 to 23, the animal feed additive of any of items 24 to 25 or the liquid formulation of any of items 33 to 40.
50. A method of preparing an animal feed, comprising mixing the composition of any of items 1 to 15, the granule of any of items 21 to 23, the animal feed additive of any of items 24 to 25 or the liquid formulation of any of items 33 to 40.
51. A method for reducing the antinutritional effects of an animal feed, comprising adding to the feed the composition of any of items 1 to 15, the granule of any of items 21 to 23, the animal feed additive of any of items 24 to 25 or the liquid formulation of any of items 33 to 40.
52. The method of any of items 46 to 51, wherein the plant based material is from the taxonomic subclass rosids.
53. The method of any of items 46 to 51, wherein the plant based material is from the family Fabaceae, preferably the sub-family Papilionoideae.
54. The method of any of items 46 to 51, wherein the plant based material is from the tribe Phaseoleae, Cicereae, Genisteae, Fabeae, Dalbergieae or Phaseoleae or any combination thereof.
55. The method of any of items 46 to 51, wherein the plant based material is soybean, wild soybean, beans, lupin, tepary bean, scarlet runner bean, slimjim bean, lima bean, French bean, Broad bean (fava bean), chickpea, lentil, peanut, Spanish peanut, canola, rapeseed (oilseed rape) or pea or in a processed form such as soybean meal, full fat soy bean meal, soy protein concentrate (SPC), fermented soybean meal (FSBM) or any combination thereof.
56. Use of the composition of any of items 1 to 15, the granule of any of items 21 to 23, the animal feed additive of any of items 24 to 25, the animal feed of any of items 26 to 28, the pelleted animal feed of any of items 29 to 32 or 45 or the liquid formulation of any of items 33 to 40:
    in animal feed;
    in animal feed additives;
    in the preparation of a composition for use in animal feed;
    for improving the nutritional value of an animal feed;
    for increasing digestibility of the animal feed;
    for improving one or more performance parameters in an animal; and/or
    for releasing galactose from plant based material of the taxonomic subclass rosids.

57. An isolated polypeptide having galactanase activity, selected from the group consisting of:
- (a) a polypeptide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 3;
- (b) a polypeptide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 7;
- (c) a polypeptide having at least 99.0%, e.g., at least 99.3%, at least 99.6% or 100% sequence identity to the polypeptide of SEQ ID NO: 11;
- (d) a polypeptide having at least 96.4%, e.g., at least 96.7%, at least 97.0%, at least 97.3%, at least 97.6%, at least 98.0%, at least 98.3%, at least 98.6%, at least 99.0%, at least 99.3% at least 99.6% or 100% sequence identity to the polypeptide of SEQ ID NO: 15;
- (e) a polypeptide having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 19;
- (f) a polypeptide having at least 96.4%, e.g., at least 96.7%, at least 97.0%, at least 97.3%, at least 97.6%, at least 98.0%, at least 98.3%, at least 98.6%, at least 99.0%, at least 99.3% at least 99.6% or 100% sequence identity to the polypeptide of SEQ ID NO: 23;
- (g) a polypeptide having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 27;
- (h) a polypeptide having at least 99.3%, e.g., at least 99.6% or 100% sequence identity to the polypeptide of SEQ ID NO: 31;
- (i) a polypeptide having at least 99.3%, e.g., at least 99.6% or 100% sequence identity to the polypeptide of SEQ ID NO: 35;
- (j) a polypeptide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 39;
- (k) a polypeptide encoded by a polynucleotide having at least 82%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 1;
- (l) a polypeptide encoded by a polynucleotide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 5;
- (m) a polypeptide encoded by a polynucleotide having at least 99.0%, e.g., at least 99.3%, at least 99.6% or 100% sequence identity to the mature polypeptide coding sequence of SEQ ID NO: 9;
- (n) a polypeptide encoded by a polynucleotide having at least 96.4%, e.g., at least 96.7%, at least 97.0%, at least 97.3%, at least 97.6%, at least 98.0%, at least 98.3%, at least 98.6%, at least 99.0%, at least 99.3% at least 99.6% or 100% sequence identity to the mature polypeptide coding sequence of SEQ ID NO: 13;
- (o) a polypeptide encoded by a polynucleotide having at least 84%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 17;
- (p) a polypeptide encoded by a polynucleotide having at least 96.4%, e.g., at least 96.7%, at least 97.0%, at least 97.3%, at least 97.6%, at least 98.0%, at least 98.3%, at least 98.6%, at least 99.0%, at least 99.3% at least 99.6% or 100% sequence identity to the mature polypeptide coding sequence of SEQ ID NO: 21;
- (q) a polypeptide encoded by a polynucleotide having at least 86%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 25;
- (r) a polypeptide encoded by a polynucleotide having at least 99.3%, e.g., at least 99.6% or 100% sequence identity to the mature polypeptide coding sequence of SEQ ID NO: 29;
- (s) a polypeptide encoded by a polynucleotide having at least 99.3%, e.g., at least 99.6% or 100% sequence identity to the mature polypeptide coding sequence of SEQ ID NO: 33;
- (t) a polypeptide encoded by a polynucleotide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 37;
- (u) a variant of SEQ ID NO: 3 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
- (v) a variant of SEQ ID NO: 7 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;
- (w) a variant of SEQ ID NO: 11 wherein the variant has galactanase activity and comprises one or more amino acid substitutions, and/or one or more amino acid deletions, and/or one or more amino acid insertions or any combination thereof in 1, 2 or 3 positions;
- (x) a variant of SEQ ID NO: 15 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10 or 11 positions;

(y) a variant of SEQ ID NO: 19 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(z) a variant of SEQ ID NO: 23 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10 or 11 positions;

(aa) a variant of SEQ ID NO: 27 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(ab) a variant of SEQ ID NO: 31 wherein the variant has galactanase activity and comprises one or more amino acid substitutions, and/or one or more amino acid deletions, and/or one or more amino acid insertions or any combination thereof in 1 or 2 positions;

(ac) a variant of SEQ ID NO: 35 wherein the variant has galactanase activity and comprises one or more amino acid substitutions, and/or one or more amino acid deletions, and/or one or more amino acid insertions or any combination thereof in 1 or 2 positions;

(ad) a variant of SEQ ID NO: 39 wherein the variant has galactanase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(ae) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac) or (ad) and a N-terminal and/or C-terminal His-tag and/or HQ-tag; and (af) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac) or (ad) and a N-terminal and/or C-terminal extension of up to 10 amino acids, e.g. 1, 2, 3, 4, 5, 6, 7, 8, 9 or 10 amino acids; and (ag) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac), (ad) or (ae) having galactanase activity and having at least 90% of the length of the mature polypeptide.

58. The polypeptide according to item 57, wherein the polypeptide comprises or consists of amino acids 1 to 316 of SEQ ID NO: 2, amino acids 1 to 316 of SEQ ID NO: 3, amino acids 1 to 324 of SEQ ID NO: 4, amino acids 1 to 318 of SEQ ID NO: 6, amino acids 1 to 318 of SEQ ID NO: 7, amino acids 1 to 326 of SEQ ID NO: 8, amino acids 1 to 316 of SEQ ID NO: 10, amino acids 1 to 316 of SEQ ID NO: 11, amino acids 1 to 324 of SEQ ID NO: 12, amino acids 1 to 316 of SEQ ID NO: 14, amino acids 1 to 316 of SEQ ID NO: 15, amino acids 1 to 324 of SEQ ID NO: 16, amino acids 1 to 316 of SEQ ID NO: 18, amino acids 1 to 316 of SEQ ID NO: 19, amino acids 1 to 324 of SEQ ID NO: 20, amino acids 1 to 316 of SEQ ID NO: 22, amino acids 1 to 316 of SEQ ID NO: 23, amino acids 1 to 324 of SEQ ID NO: 24, amino acids 1 to 516 of SEQ ID NO: 26, amino acids 1 to 516 of SEQ ID NO: 27, amino acids 1 to 524 of SEQ ID NO: 28, amino acids 1 to 317 of SEQ ID NO: 30, amino acids 1 to 317 of SEQ ID NO: 31, amino acids 1 to 325 of SEQ ID NO: 32, amino acids 1 to 316 of SEQ ID NO: 34, amino acids 1 to 316 of SEQ ID NO: 35, amino acids 1 to 324 of SEQ ID NO: 36, amino acids 1 to 316 of SEQ ID NO: 38, amino acids 1 to 316 of SEQ ID NO: 39 or amino acids 1 to 324 of SEQ ID NO: 40.

59. An isolated polypeptide having beta-galactosidase activity, selected from the group consisting of:

(a) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 43;

(b) a polypeptide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 46;

(c) a polypeptide having at least 96.4%, e.g., at least 96.6%, at least 96.8%, at least 97.0%, at least 97.2%, at least 97.4%, at least 97.6%, at least 97.8%, at least 98.0%, at least 98.2%, at least 98.4%, at least 98.6%, at least 98.8%, at least 99.0%, at least 99.2%, at least 99.4%, at least 99.6%, at least 99.8% or 100% sequence identity to the polypeptide of SEQ ID NO: 49;

(d) a polypeptide having at least 92%, e.g., at least 93%, at least 94%, at least 95%, at least 96%, at least 97%, at least 98%, at least 99%, or 100% sequence identity to the polypeptide of SEQ ID NO: 52;

(e) a polypeptide having at least 99.7%, e.g., at least 99.8%, at least 99.9%, or 100% sequence identity to the polypeptide of SEQ ID NO: 55;

(f) a polypeptide having at least 93%, e.g., at least 94%, at least 95%, at least 96%, at least 97%, at least 98%, at least 99%, or 100%, sequence identity to the polypeptide of SEQ ID NO: 58;

(g) a polypeptide having at least 85%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 61;

(h) a polypeptide having at least 95.5%, e.g., at least 96.0%, at least 96.5%, at least 97.0%, at least 97.2%, at least 97.4%, at least 97.6%, at least 97.8%, at least 98.0%, at least 98.2%, at least 98.4%, at least 98.6%, at least 98.8%, at least 99.0%, at least 99.2%, at least 99.4%, at least 99.6%, at least 99.8% or 100% sequence identity to the polypeptide of SEQ ID NO: 70;

(i) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 73;

(j) a polypeptide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the polypeptide of SEQ ID NO: 76;

(k) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 41;

(l) a polypeptide encoded by a polynucleotide having at least 83%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 44;

(m) a polypeptide encoded by a polynucleotide having at least 96.4%, e.g., at least 96.6%, at least 96.8%, at least 97.0%, at least 97.2%, at least 97.4%, at least 97.6%, at least 97.8%, at least 98.0%, at least 98.2%, at least 98.4%, at least 98.6%, at least 98.8%, at least 99.0%, at least 99.2%, at least 99.4%, at least 99.6%, at least 99.8% or 100% sequence identity to the mature polypeptide coding sequence of SEQ ID NO: 47;

(n) a polypeptide encoded by a polynucleotide having at least 92%, e.g., at least 93%, at least 94%, at least 95%, at least 96%, at least 97%, at least 98%, at least 99%, or 100% sequence identity to the mature polypeptide coding sequence of SEQ ID NO: 50;

(o) a polypeptide encoded by a polynucleotide having at least 99.7%, e.g., at least 99.8%, at least 99.9%, or 100% sequence identity to the mature polypeptide coding sequence of SEQ ID NO: 53;

(p) a polypeptide encoded by a polynucleotide having at least 93%, e.g., at least 94%, at least 95%, at least 96%, at least 97%, at least 98%, at least 99%, or 100% sequence identity to the mature polypeptide coding sequence of SEQ ID NO: 56;

(q) a polypeptide encoded by a polynucleotide having at least 85%, e.g., at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 59;

(r) a polypeptide encoded by a polynucleotide having at least 95.5%, e.g., at least 96.0%, at least 96.5%, at least 97.0%, at least 97.2%, at least 97.4%, at least 97.6%, at least 97.8%, at least 98.0%, at least 98.2%, at least 98.4%, at least 98.6%, at least 98.8%, at least 99.0%, at least 99.2%, at least 99.4%, at least 99.6%, at least 99.8% or 100% sequence identity to the mature polypeptide coding sequence of SEQ ID NO: 70;

(s) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 73;

(t) a polypeptide encoded by a polynucleotide having at least 80%, e.g., at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100% sequence identity to the mature polypeptide coding sequence of SEQ ID NO: 76;

(u) a variant of SEQ ID NO: 43 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(v) a variant of SEQ ID NO: 46 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(w) a variant of SEQ ID NO: 49 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37 or 38 positions;

(x) a variant of SEQ ID NO: 52 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(y) a variant of SEQ ID NO: 55 wherein the variant has beta-galactosidase activity and comprises one or more amino acid substitutions, and/or one or more amino acid deletions, and/or one or more amino acid insertions or any combination thereof in 1, 2 or 3 positions;

(z) a variant of SEQ ID NO: 58 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(aa) a variant of SEQ ID NO: 61 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(ab) a variant of SEQ ID NO: 70 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42 or 43 positions;

(ac) a variant of SEQ ID NO: 73 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(ad) a variant of SEQ ID NO: 76 wherein the variant has beta-galactosidase activity and comprises one or more amino acid substitutions, and/or one or more amino acid deletions, and/or one or more amino acid insertions or any combination thereof in 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 positions;

(ae) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac) or (ad) and a N-terminal and/or C-terminal His-tag and/or HQ-tag; and (af) a polypeptide comprising the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac) or (ad) and a N-terminal and/or C-terminal extension of up to 10 amino acids, e.g. 1, 2, 3, 4, 5, 6, 7, 8, 9 or 10 amino acids; and (ag) a fragment of the polypeptide of (a), (b), (c), (d), (e), (f), (g), (h), (i), (j), (k), (l), (m), (n), (o), (p), (q), (r), (s), (t), (u), (v), (w), (x), (y), (z), (aa), (ab), (ac) or (ad) having beta-galactosidase activity and having at least 90% of the length of the mature polypeptide.

60. The polypeptide according to item 59, wherein the polypeptide comprises or consists of amino acids 1 to 985 of SEQ ID NO: 42, amino acids 1 to 985 of SEQ ID NO: 43, amino acids 1 to 1015 of SEQ ID NO: 45, amino acids 1 to 1015 of SEQ ID NO: 46, amino acids 1 to 998 of SEQ ID NO: 48, amino acids 1 to 998 of SEQ ID NO: 49, amino acids 1 to 983 of SEQ ID NO: 51, amino acids 1 to 983 of SEQ ID NO: 52, amino acids 1 to 998 of SEQ ID NO: 54, amino acids 1 to 998 of SEQ ID NO: 55, amino acids 1 to 1007 of SEQ ID NO: 57, amino acids 1 to 1007 of SEQ ID NO: 58, amino acids 1 to 988 of SEQ ID NO: 60, amino acids 1 to 988 of SEQ ID NO: 61, amino acids 1 to 962 of SEQ ID NO: 69, amino acids 1 to 962 of SEQ ID NO: 70, amino acids 1 to 1000 of SEQ ID NO: 72, amino acids 1 to 1000 of SEQ ID NO: 73, amino acids 1 to 1000 of SEQ ID NO: 75 or amino acids 1 to 1000 of SEQ ID NO: 76.

61. A polynucleotide encoding the polypeptide of any of items 57 to 60.

62. A nucleic acid construct or expression vector comprising the polynucleotide of item 61 operably linked to one or more control sequences that direct the production of the polypeptide in an expression host.

63. A recombinant host cell comprising the polynucleotide of item 61 operably linked to one or more control sequences that direct the production of the polypeptide.

64. A method of producing the polypeptide of any of items 57 to 60, comprising:

(a) cultivating a cell, which in its wild-type form produces the polypeptide, under conditions conductive for production of the polypeptide; and (b) recovering the polypeptide.

65. A method of producing the polypeptide of any of items 57 to 60, comprising:

(a) cultivating the recombinant host cell of item 63 under conditions conducive for production of the polypeptide; and (b) recovering the polypeptide.

66. A transgenic plant, plant part or plant cell transformed with a polynucleotide encoding the polypeptide of any of items 57 to 60.

67. A whole broth formulation or cell culture composition comprising a polypeptide of any of items 57 to 60.

68. A composition comprising the polypeptide of any of items 57 to 60.

69. The composition of item 68 further comprising one or more formulating agents.

70. The composition of item 69, wherein the one or more formulating agents is selected from the group consisting of glycerol, ethylene glycol, 1, 2-propylene glycol or 1, 3-propylene glycol, sodium chloride, sodium benzoate, potassium sorbate, sodium sulfate, potassium sulfate, magnesium sulfate, sodium thiosulfate, calcium carbonate, sodium citrate, dextrin, glucose, sucrose, sorbitol, lactose, starch and cellulose or any combination thereof.

71. The composition of any of items 68 to 70 which is in granulate form.

72. The composition of item 71 wherein the granule is coated.

73. The composition of item 72 wherein the coating comprises a salt and/or wax and/or a flour coating.

74. The composition of any of items 68 to 73 further comprising one or more additional enzymes.

75. The composition of item 74 wherein the one or more additional enzymes is selected from the group consisting of acetylxylan esterase, acylglycerol lipase, amylase, alpha-amylase, beta-amylase, arabinofuranosidase, cellobiohydrolases, cellulase, feruloyl esterase, galactanase, alpha-galactosidase, beta-galactosidase, beta-glucanase, beta-glucosidase, lysophospholipase, lysozyme, alpha-mannosidase, beta-mannosidase (mannanase), phytase, phospholipase A1, phospholipase A2, phospholipase D, protease, pullulanase, pectinesterase, triacylglycerol lipase, xylanase, beta-xylosidase or any combination thereof.

The present invention is further described by the following examples that should not be construed as limiting the scope of the invention.

EXAMPLES

Strains

The galactanases were derived from bacterial strains isolated from environmental samples by standard microbiological isolation techniques. Strains were identified and taxonomy was assigned based on DNA sequencing of the 16S ribosomal genes (Tables 2a and 2b).

TABLE 2a

Isolation of bacterial strains

| Strain | Source | Country | Year | SEQ ID NO of gene | SEQ ID NO of polypeptide |
|---|---|---|---|---|---|
| *Cohnella* sp-60555 | Humus | Denmark | 2007 | 1 | 2 |
| *Cohnella xylanilytica* | Humus | Denmark | 2002 | 5 | 6 |
| *Paenibacillus tundrae* | Humus | Denmark | 2004 | 9 | 10 |
| *Paenibacillus barcinonensis* (DSM15478) | Soil from a rice field in Ebro River Delta | Tarragona, Spain | 1993 | 13 | 14 |
| *Paenibacillus* sp-62603 | Soil | China | 2009 | 17 | 18 |
| *Paenibacillus xylanilyticus* | Sand | United States | 1999 | 21 | 22 |
| *Paenibacillus* sp-18179 | Soil | Sweden | 2000 | 25 | 26 |
| *Paenibacillus peoriae* | Soil | Denmark | 2011 | 29 | 30 |
| *Paenibacillus xylanexedens* | Soil | Egypt | 1991 | 33 | 34 |
| *Cohnella laeviribosi* | Sand | Thailand | 1990 | 37 | 38 |

TABLE 2b

Isolation of fungal strains

| Strain | Source | Country | Year | SEQ ID NO of gene | SEQ ID NO of polypeptide |
|---|---|---|---|---|---|
| *Hamigera paravellanea*[1] (CBS 501.94) | Sea foam | Japan | On or before 1988 | 41 | 42 |
| *Aspergillus unguis* | Environmental sample | Egypt | 1992 | 44 | 45 |
| *Aspergillus tamari* | Salt mine soil | Egypt | 1984 | 47 | 48 |
| *Curvularia spicifera* | Soil | United States | 1993 | 50 | 51 |
| *Aspergillus oryzae* | CBS 205.89 | Japan | 1942 | 53 | 54 |
| *Aspergillus carneus* | Salt mine soil | Egypt | 1984 | 56 | 57 |
| *Penicillium quercetorum* | Soil | Japan | 2013 | 59 | 60 |
| *Penicillium simplicissimum* | Soil | China | June 1998 | 68 | 69 |
| *Aspergillus westerdijkiae* (CBS 112804) | Saltern | Secovlje, Slovenia | 2002 | 71 | 72 |
| *Aspergillus wentii* (CBS 104.07) | Soybean | Java, Indonesia | 1907 | 74 | 75 |
| *Aspergillus lentulus* | Soil | Yunnan, China | 2008 | 77 | 78 |

[1]Originally classified as *Hamigera avellanea*.

Chromosomal DNA isolated from pure cultures of the individual strains with the DNeasy Blood & Tissue Kit from Qiagen (Hilden, Germany) was subjected to full genome sequencing using Illumina technology. Genome sequencing, the subsequent assembly of reads and the gene discovery (i.e. annotation of gene functions) is known to the person skilled in the art and the service can be purchased commercially.

The bacterial genome sequences were analyzed for galactanases from the CAZY database family GH53 (Lombard et al. The Carbohydrate-active enzymes database CAZy. Nucleic Acids Res 2013, 42:D490-D495.) This analysis identified ten gene encoding putative galactanases with the nucleotide sequences given in SEQ ID NO: 1, 5, 9, 13, 17, 21, 25, 29, 33 and 37.

The fungal genome sequences were analyzed for beta-galactosdases from the CAZY database family GH35 (Lombard et al. The Carbohydrate-active enzymes database CAZy. Nucleic Acids Res 2013, 42:D490-D495.). This analysis identified seven gene encoding putative beta-galactosdases with the nucleotide sequences given in SEQ ID NO: 41, 44, 47, 50, 53, 56, 59, 68, 71, 74 and 77.

Alpha-Galactosidase Assay

Alpha-galactosidase activity can be determined using 4-nitrophenyl α-D-galactopyranoside (product code O-PNPBGAL, available from Megazyme International, Bray, Co. Wicklow, Ireland) as follows.

The enzyme was diluted using 100 mM MES (Sigma) buffer pH 7.0±0.05 in 2-fold dilutions and then the 4-nitrophenyl α-D-galactopyranoside (1 mg/ml in 100 mM MES buffer pH 7.0±0.05, prepared immediately before use) was added in the solution containing the enzyme. The respective galactosidase activity was followed directly in the buffer by measuring the absorbance of released pNP (para-nitro-phenol) at 405 nm for 5 minutes as function of time at room temperature (typically 23° C.). A concentration of 1 mg/mL of enzyme is a good starting point; it will however depend from enzyme to enzyme and their specific activity.

The activity is calculated as the slope of a plot of absorbance versus time (units: mOD/min) using the 1-5 minute time window and the 0-2 absorbance window. The activity can then be converted to specific activity by dividing the activity for the concentration of the enzyme (units: (mOD/min)/(mg/ml)).

Beta-Galactosidase Assay

Beta-galactosidase activity can be determined using 4-nitrophenyl β-D-galactopyranoside (available from Megazyme International, Bray, Co. Wicklow, Ireland) as follows.

The enzyme was diluted using 100 mM MES (Sigma) buffer pH 7.0±0.05 in 2-fold dilutions and then the 4-nitrophenyl β-D-galactopyranoside (1 mg/ml in 100 mM MES buffer pH 7.0±0.05) was added in the solution containing the enzyme. The respective galactosidase activity was followed directly in the buffer by measuring the absorbance of released pNP (para-nitro-phenol) at 405 nm for 5 minutes as function of time at room temperature (typically 23° C.). A concentration of 1 mg/mL of enzyme is a good starting point; it will however depend from enzyme to enzyme and their specific activity.

The activity is calculated as the slope of a plot of absorbance versus time (units: mOD/min) using the 1-5 minute time window and the 0-2 absorbance window. The activity can then be converted to specific activity by dividing the activity for the concentration of the enzyme (units: (mOD/min)/(mg/ml)).

Galactanase Assay

Galactanase activity can be determined using the reducing ends colorimetric assay. 10 soybean meal substrate (prepared from soybean meal milled to a 0.5 mm particle size) was filled with a solid dispenser into 96 well format plates. The weight was measured before and after addition of soybean meal and the substrate amount per well was estimated assuming equal distribution along the plate.

The enzymes were diluted to 0.6 ppm (final enzyme concentration in solution) in 100 mM activity buffer (100 mM acetate, 100 mM MES, 100 mM *Glycine* in 0.01% Triton X100, 1 mM $CaCl_2$), pH 6.5) and the samples were shaken for 2 hours at 40° C. The samples were centrifuged at 3000×g for 5 minutes and 75 µl of each sample (supernatant) was transferred to a new PCR-plate. 75 µl activity buffer was added to each sample, the samples were mixed then 75 µl of stop solution (15 mg/ml PAHBAH (Sigma H-9882) in Ka-Na-tartrate/NaOH solution, pH>10) was added. The solution was mixed for 10 min at 95° C., then 1 min. 10° C. and the samples were transferred to a new 96 MTP and absorbance was measured at 405 nm.

Galactose SBM Assay

Introduction

The concentration of galactose monosaccharides in a solution was measured spectrophotometrically after enzymatic hydrolysis of a galactose-rich substrate; soybean meal.

Summarizing, the enzyme(s) were incubated in a 10 w/v % slurry of soybean meal at pH 6.5±0.05 for 2 hours at 40±2° C. The supernatant was then analyzed in an assay based on the Raffinose/Galactose kit from Megazyme (product name K-RAFGA). First α-D-galactose in the supernatant was converted to β-D-galactose with the enzyme galactose mutarotase. Then β-D-galactose was oxidised by NAD+ to D-galactonic acid in the presence of β-galactose dehydrogenase. The amount of NADH formed in this reaction was stoichiometric with the amount of D-Galactose in the supernatant. NADH concentration was then measured by the increase in absorbance at 340 nm.

Soybean Meal Slurry

A 10 w/v % slurry of soybean meal was prepared from soybean meal milled to a 0.5 mm particle size and 0.1 M citric acid-phosphate buffer, pH 6.5±0.05.

0.1 M citric acid-phosphate buffer, pH 6.5±0.05 was heated to a temperature of approximately 40° C. while stirring. The preheated buffer was then transferred to the soybean meal. The resulting slurry was stirred while being heated (temperature was not monitored at this point—heating was only applied to ensure that temperature would not decrease too much while the slurry stirred). The slurry was then transferred with a pre-wetted wide-bore pipette to the vessel in which it should be incubated. The slurry was pipetted from an approximately central point in the mix. The time elapsed from the mixing of the slurry until transfer to the last incubation vessel was, at most, 15 minutes. Stirring speed was adjusted in such a way that particles were evenly distributed in the slurry.

Dilution of Enzymes

The enzymes were diluted to their desired concentrations in ultrapure water. The concentration to which the enzymes were diluted to was based on the prior concentration of the enzyme in mg enzyme protein per mL (mg EP/mL) and the mass (kg) of dry matter (soybean meal) in each incubation vessel.

$$V_{enzyme}(\text{mL}) = \frac{c_{enzyme}\left(\text{mg}\frac{EP}{\text{mL}}\right)}{m_{SBM}(\text{kg})}$$

D-(+)-Galactose Standards

A standard curve was prepared from D-(+)-galactose and ultrapure water. A D-(+)-galactose stock was prepared by dissolving D-(+)-galactose in ultrapure water to a final concentration of 250 mg galactose per mL. The stock solution was diluted in a two-fold dilution row to obtain six standards with concentrations of 250, 125, 62.5, 31.25, 15.625 and 7.813 mg galactose per mL.

Incubation of α-Galactosidases on Soybean Meal

The incubation vessels with the 10 w/v % slurry of soybean meal were heated to a stable temperature of 40±2° C. while stirring. When a stable temperature had been achieved, the six D-(+)-galactose standards were added to the incubation vessels to in-vessel concentrations of 5, 2.5, 1.25, 0.625, 0.313 and 0.157 mg galactose per mL incubation volume. Each standard was incubated in duplicates.

The diluted enzymes were then added to their respective incubation vessels in the volumes required to reach their desired concentrations (in mg EP/kg soybean meal). Each enzyme treatment was incubated in triplicates.

Additionally, two times three incubation vessels were included without standards or enzyme treatments as blank treatments to obtain the baseline galactose concentration in the soybean meal slurry.

The incubation vessels were incubated at 40±2° C., while stirring for 2 hours. After incubation the vessels were centrifuged at 1500 g at 5° C. for 15 minutes.

Incubation of Galactanases and Beta-Galactosidases on Soybean Meal

The incubation vessels with the 10 w/v % slurry of soybean meal were heated to a stable temperature of 40±2° C. while stirring. When a stable temperature had been achieved, the six D-(+)-galactose standards were added to the incubation vessels to in-vessel concentrations of 5, 2.5, 1.25, 0.625, 0.313 and 0.157 mg galactose per mL incubation volume. Each standard was incubated in duplicates.

The diluted enzymes were then added to their respective incubation vessels in the volumes required to reach their desired concentrations (in mg EP/kg soybean meal). Each enzyme treatment was incubated in triplicates.

Additionally, two times three incubation vessels were included without standards or enzyme treatments as blank treatments to obtain the baseline galactose concentration in the soybean meal slurry.

The incubation vessels were incubated at 40±2° C., while stirring for 2 hours. After incubation the vessels were centrifuged at 1500 g at 5° C. for 15 minutes.

Determination of Galactose Concentration

The supernatants in the now centrifuged incubation vessels were then analyzed in an assay based on the Raffinose/Galactose kit from Megazyme (product name K-RAFGA). Three reagents from the K-RAFGA kit was used in the assay: Assay Buffer (supplied and ready in Bottle 1 in the kit), β-NAD reagent (supplied in Bottle 2 in the kit, prepared as described in the kit prior to use) and GalDH+GalM solution (supplied in Bottle 3 in the kit, diluted 1:1 in ultrapure water prior to use). All steps described in the following were carried out using an Eppendorf 5075 automated pipetting system.

First the supernatants from the centrifuged incubation vessels were diluted 10 times in 0.1 M citric acid-phosphate buffer, pH 6.5±0.05 (1 part supernatant plus 9 parts 0.1 M citric acid-phosphate buffer, pH 6.5±0.05).

69 µL of each diluted supernatant was then transferred to a new vessel and 34 µL of ultrapure water was added to the diluted supernatants (which will be referred to as assay samples from here on out). Then 69 µL Assay Buffer was added to the assay samples followed by dilution in 687 µL ultrapure water. 34 µL β-NAD reagent was added to the assay samples, followed by addition of 14 µL GalDH+GalM solution and vigorous mixing.

262 µL of each assay sample was then transferred to a 96 well micro titer plate. Absorbance in each well of the 96 well micro titer plate was measured at 340 nm at 40±2° C. for a duration of 20 minutes or until absorbance in each well had reached a stable level. When a stable absorbance had been reached this stable absorbance was used in later calculations.

Calculation of Galactose Concentration

Absorbance of the assay samples from the galactose standards in the incubation vessels were used as a standard curve (6 standards, 5, 2.5, 1.25, 0.625, 0.313 and 0.157 mg galactose per mL incubation volume, n=2 per standard). An equation for the galactose standard curve was calculated in excel, where y is OD340 and x is galactose concentration in mg galactose per mL incubation volume:

$$OD_{340} = a * c_{gal}\left(\frac{mg}{mL}\right) + b$$

Galactose concentration in mg galactose per mL incubation volume for each sample was then given by:

$$c_{gal}\left(\frac{mg}{mL}\right) = \frac{OD_{340} - b}{a}$$

Galactose concentrations were then calculated on a dry-matter basis (g galactose per kg soybean meal) and are reported in the examples below:

$$c_{gal}\left(\frac{g}{kg}SBM\right) = \frac{c_{gal}\left(\frac{mg}{mL}\right) * V_{sample}(mL)}{m_{SBM}(g)}$$

Example 1: Cloning of GH53 Galactanases from *Cohnella* sp-60555, *Cohnella xylanilytica*, *Paenibacillus tundra*, *Paenibacillus barcinonensis*, *Paenibacillus* sp-62603, *Paenibacillus xylanilyticus*, *Paenibacillus* sp-18179, *Paenibacillus peoriae*, *Paenibacillus Xylanexedens* and *Cohnella laeviribosi* (SEQ ID NO: 4, 8, 12, 16, 20, 24, 28, 32, 36 and 40)

The genes encoding the galactanases were amplified by PCR and fused with regulatory elements, affinity purification tag and homology regions for recombination into the *B. subtilis* genome. The linear integration construct was a SOE-PCR fusion product (Horton, R. M., Hunt, H. D., Ho, S. N., Pullen, J. K. and Pease, L. R. (1989) Engineering hybrid genes without the use of restriction enzymes, gene splicing by overlap extension Gene 77: 61-68) made by fusion of the gene between two *Bacillus subtilis* chromosomal regions along with strong promoters and a chloramphenicol resistance marker. The SOE PCR method is also described in patent application WO 2003095658.

The gene was expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence.

The gene was expressed with a *Bacillus clausii* secretion signal (encoding the following amino acid sequence: MKKPLGKIVASTALLISVAFSSSIASA, SEQ ID NO: 67) replacing the native secretion signal. Furthermore the expression construct results in the addition of an amino terminal poly histidine purification tag on the natural mature protein allowing for enzyme purification through immobilized metal ion affinity chromatography.

The SOE-PCR product was transformed into *Bacillus subtilis* and integrated in the chromosome by homologous recombination into the pectate lyase locus. Subsequently one recombinant *Bacillus subtilis* clone containing the respective galactanase expression construct was selected and was cultivated on a rotary shaking table in 500 ml baffled Erlenmeyer flasks each containing 100 ml rich starch based media. After 3-5 days cultivation time at 30° C. to 37° C., enzyme containing supernatants were harvested by centrifugation and the enzymes were purified by immobilized metal affinity chromatography.

Example 2: Purification of GH53 Galactanases from *Cohnella* sp-60555, *Cohnella Xylanilytica*, *Paenibacillus Tundra*, *Paenibacillus barcinonensis*, *Paenibacillus* sp-62603, *Paenibacillus xylanilyticus*, *Paenibacillus* sp-18179, *Paenibacillus peoriae*, *Paenibacillus Xylanexedens* and *Cohnella laeviribosi* (SEQ ID NO: 4, 8, 12, 16, 20, 24, 28, 32, 36 and 40)

The pH of the supernatant from example 1 was adjusted to pH 8, filtrated through a 0.2 µM filter, and then applied to a 5 ml HisTrap™ excel column (GE Healthcare Life Sciences, Pittsburgh, USA). Prior to loading, the column had been equilibrated in 5 column volumes (CV) of 50 mM Tris/HCl pH 8. In order to remove unbound material, the column was washed with 8 CV of 50 mM Tris/HCl pH 8, and elution of the target was obtained with 50 mM HEPES pH 7+10 mM imidazole. The eluted protein was desalted on a HiPrep™ 26/10 desalting column (GE Healthcare Life Sciences, Pittsburgh, USA)., equilibrated using 3 CV of 50 mM HEPES pH 7+100 mM NaCl. This buffer was also used for elution of the target, and the flow rate was 10 ml/min. Relevant fractions were selected and pooled based on the chromatogram and SDS-PAGE analysis.

Example 3: Cloning of GH35 Beta-Galactosidases from *Hamigera paravellanea*, *Aspergillus unguis*, *Aspergillus tamari*, *Curvularia spicifera*, *Aspergillus Carneus* and *Penicillium Quercetorum* (SEQ ID NO: 43, 46, 49, 52, 58 and 61)

The beta-galactosidases with nucleotide sequence SEQ ID NO: 41, 44, 47, 50, 56, and 59 and the peptide translation of the protein shown in SEQ ID NO: 42, 45, 48, 51, 57, and 60 were PCR amplified from genomic DNA and cloned into the expression vector pDAu222 as described in WO 2013024021 using BamHI and XhoI restriction sites.

The sequences of the beta-galactosidase encoding genes cloned in the expression vector were confirmed and the expression constructs were transformed into the *Aspergillus oryzae* strain MT3568 (WO 11/057140) to produce the secreted mature peptide with protein sequence SEQ ID NO: 43, 46, 49, 52, 58, and 61 respectively. Transformants were selected on acetamide during regeneration from protoplasts and subsequently re-isolated under selection (Christensen et al., 1988, Biotechnology 6, 1419-1422 and WO 04/032648).

For production of the recombinant beta-galactosidases, a single *Aspergillus* transformant for each plasmid construct was cultured in two 500 ml baffled flasks each containing 150 ml of DAP-4C-1 medium (WO 12/103350). The cultures were shaken on a rotary table at 100 RPM at 30° C. for 4 days. The culture broth subsequently was separated from cellular material by passage through a 0.22 um filter.

Example 4: Cloning of GH35 Beta-Galactosidases from *Aspergillus oryzae* (SEQ ID NO: 55)

The beta-galactosidase with nucleotide sequence SEQ ID NO: 53 and the peptide translation of the protein shown in SEQ ID NO: 54 was PCR amplified from genomic DNA isolated from *Aspergillus oryzae* and cloned into the expression vector pDAu222 as described in WO 2013024021 using BamHI and HindIII restriction sites.

The sequence of the beta-galactosidase encoding gene cloned in the expression vector was confirmed and the expression constructs were transformed into the *Aspergillus oryzae* strain MT3568 (WO 11/057140) to produce the secreted mature peptide with protein sequence SEQ ID NO: 55. Transformants were selected on acetamide during regeneration from protoplasts and subsequently re-isolated under selection (Christensen et al., 1988, *Biotechnology* 6, 1419-1422 and WO 04/032648).

For production of the recombinant beta-galactosidase, a single *Aspergillus* transformant was cultured in two 500 ml baffled flasks each containing 150 ml of DAP-4C-1 medium (WO 12/103350). The cultures were shaken on a rotary table at 100 RPM at 30° C. for 4 days. The culture broth subsequently was separated from cellular material by passage through a 0.22 um filter.

Example 5: Purification of GH35 Beta-Galactosidases from *Hamigera paravellanea*, *Aspergillus unguis*, *Aspergillus Tamari*, *Curvularia spicifera*, *Aspergillus Oryzae*, *Aspergillus Carneus* and *Penicillium quercetorum* (SEQ ID NO: 43, 46, 49, 52, 55, 58 and 61)

Filtrated broth was adjusted to pH7.0 and filtrated on 0.22 μm PES filter (Nalge Nunc International, Nalgene labware cat #595-4520). Following, the filtrate was added 1.8M ammonium sulphate. The filtrate was loaded onto a Phenyl Sepharose™ 6 Fast Flow column (high sub) (GE Healthcare, Piscataway, N.J., USA) equilibrated with 1.2M ammonium sulphate, 25 mM HEPES pH7.0. After wash with 1.0M ammonium sulphate, the bound proteins were batch eluted with 25 mM HEPES pH 7.0. Fractions were collected and analyzed by SDS-PAGE. The fractions were pooled and applied to a Sephadex™ G-25 (medium) (GE Healthcare, Piscataway, N.J., USA) column equilibrated in 25 mM HEPES pH 7.5. The fractions were applied to a SOURCE™ 15Q (GE Healthcare, Piscataway, N.J., USA) column equilibrated in 25 mM HEPES pH 7 and bound proteins were eluted with 25 mM HEPES pH 7, 1 M sodium chloride over ca. 20CV. Fractions were collected and analyzed by SDS-PAGE.

Example 6: Hydrolysis of Soybean Meal (SBM) Using GH53 Galactanases

The release of galactose from soybean meal using two known galactanases (SEQ ID NO: 62 and 63) were determined using the Galactose SBM Assay. The results are presented in table 3 below.

TABLE 3

Release of galactose from soybean meal using known galactanases

| GH53 galactanase | Conc. GH53 [mg EP/kg] | Mean Galactose Release (g gal/kg SBM) |
|---|---|---|
| SEQ ID NO: 62 | 20 | 2.8 |
| SEQ ID NO: 62 | 20 | 3.4 |
| SEQ ID NO: 63 | 20 | 1.9 |
| SEQ ID NO: 63 | 20 | 2.6 |
| Blank | — | 0.1 |

The results show that these GH53 galactanases do not release significant amounts of galactose on their own from soybean meal.

Example 7: Hydrolysis of Soybean Meal (SBM) Using Known GH53 Galactanases in Combination with Known GH35 Beta-Galactosidases The release of galactose from soybean meal using 3 prior art galactanases (SEQ ID NO: 62, 63 or 64) or a galactanase of the invention (SEQ ID NO: 4) with a beta-galactosidase of the invention (SEQ ID NO: 43) was determined using the Galactose SBM Assay. The results are presented in tables 4 and 5 below.

TABLE 4

Release of galactose from soybean meal using known polypeptides compared to polypeptides of the invention

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 100 | 20 | 25.6 | A |
| SEQ ID NO: 43 | SEQ ID NO: 64 | 100 | 20 | 9.6 | B |
| SEQ ID NO: 43 | SEQ ID NO: 62 | 100 | 20 | 9.5 | B |
| Blank | Blank | — | — | −0.1 | C |

ABC: Values within a column not sharing a capital letter are significantly different (p < 0.05).
Means were compared by Tukey HSD procedure in SAS JMP 11

TABLE 5

Release of galactose from soybean meal using known polypeptides compared to polypeptides of the invention

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 100 | 20 | 26.4 | A |
| SEQ ID NO: 43 | SEQ ID NO: 63 | 100 | 20 | 8.9 | B |
| Blank | Blank | — | — | 0.2 | C |

ABC: Values within a column not sharing a capital letter are significantly different ($p < 0.05$).
Means were compared by Tukey HSD procedure in SAS JMP 11

The results demonstrate that the GH35 beta-galactosidase of the invention (SEQ ID NO: 43) in combination with any of the GH53 galactanases releases significantly higher amounts of galactose from soybean meal than using the galactanase on its own (from table 3).

Example 8: Hydrolysis of Soybean Meal (SBM) Using GH53 Galactanases in Combination with GH35 Beta-Galactosidases The release of galactose from soybean meal using four beta-galactosidases (SEQ ID NO: 43, 46, 49 and 52) in combination with a GH53 galactanase (SEQ ID NO: 4) were determined using the Galactose SBM Assay. The results are presented in tables 6, 7 and 8 below.

TABLE 6

Release of galactose from soybean meal using a GH53 galactanase (SEQ ID NO: 4) in combination with three GH35 beta-galactosidases (SEQ ID NO: 43 and 46)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 20.1 | A |
| SEQ ID NO: 46 | SEQ ID NO: 4 | 20 | 20 | 17.1 | A |
| Blank | Blank | — | — | 0.0 | B |

AB: Values within a column not sharing a capital letter are significantly different ($p < 0.05$).
Means were compared by Tukey HSD procedure in SAS JMP 1207

TABLE 7

Release of galactose from soybean meal using a GH53 galactanase (SEQ ID NO: 4) in combination with two GH35 beta-galactosidases (SEQ ID NO: 43 and 49)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 17.6 | B |
| SEQ ID NO: 49 | SEQ ID NO: 4 | 20 | 20 | 26.6 | A |
| Blank | Blank | — | — | −0.2 | C |

ABC: Values within a column not sharing a capital letter are significantly different ($p < 0.05$).
Means were compared by Tukey HSD procedure in SAS JMP 11

TABLE 8

Release of galactose from soybean meal using a GH53 galactanase (SEQ ID NO: 4) in combination with two GH35 beta-galactosidases (SEQ ID NO: 43 and 52)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 19.5 | A |
| SEQ ID NO: 52 | SEQ ID NO: 4 | 20 | 20 | 20.7 | A |
| Blank | Blank | — | — | −0.1 | B |

AB: Values within a column not sharing a capital letter are significantly different ($p < 0.05$).
Means were compared by Tukey HSD procedure in SAS JMP 11

The results demonstrate that the GH35 beta-galactosidase of the invention (SEQ ID NO: 43, 46, 49 and 52) in combination with a GH53 galactanase of the invention (SEQ ID NO: 4) all release significantly higher amounts of galactose from soybean meal than the prior art galactanases as demonstrated in example 5.

Example 9: Hydrolysis of Soybean Meal (SBM) Using GH53 Galactanases in Combination with GH35 Beta-Galactosidases The release of galactose from soybean meal using a beta-galactosidase of the invention (SEQ ID NO: 43) in combination with nine GH53 galactanases of the invention (SEQ ID NO: 4, 8, 12, 16, 20, 24, 28, 32, and 40) were determined using the Galactose SBM Assay. The results are presented in tables 9, 10 and 11 below.

The results demonstrate that the GH53 galactanases of the invention (SEQ ID NO: 4, 8, 12, 16, 20, 24, 28, 32, 36 and 40) together with a GH35 beta-galactosidase of the invention (SEQ ID NO: 43) all release significantly higher amounts of galactose from soybean meal than the prior art galactanases as demonstrated in example 5.

Example 10: Hydrolysis of Soybean Meal (SBM) Using GH53 Galactanases in Combination with GH35 Beta-Galactosidases The release of galactose from soybean meal using three GH35 beta-galactosidases of the invention (SEQ ID NO: 43, 58 and 61) in combination with two GH53 galactanases of the invention (SEQ ID NO: 4 and 40) were determined using the Galactose SBM Assay. The results are presented in table 12 below.

TABLE 9

Release of galactose from soybean meal using a GH53 galactanase (SEQ ID NO: 4) in combination with four GH35 beta-galactosidases (SEQ ID NO: 4, 8, 12 and 16)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 16.83 | A |
| SEQ ID NO: 43 | SEQ ID NO: 8 | 20 | 20 | 16.60 | A |
| SEQ ID NO: 43 | SEQ ID NO: 12 | 20 | 20 | 15.87 | AB |
| SEQ ID NO: 43 | SEQ ID NO: 16 | 20 | 20 | 15.37 | B |
| Blank | Blank | — | — | 0.40 | C |

ABC: Values within a column not sharing a capital letter are significantly different ($p < 0.05$).
Means were compared by Tukey HSD procedure in SAS JMP 11

TABLE 10

Release of galactose from soybean meal using a GH53 galactanase (SEQ ID NO: 4) in combination with four GH35 beta-galactosidases (SEQ ID NO: 4, 20, 24 and 28)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 18.10 | A |
| SEQ ID NO: 43 | SEQ ID NO: 20 | 20 | 20 | 12.57 | B |
| SEQ ID NO: 43 | SEQ ID NO: 24 | 20 | 20 | 14.07 | B |
| SEQ ID NO: 43 | SEQ ID NO: 28 | 20 | 20 | 16.90 | A |
| Blank | Blank | — | — | 0.03 | C |

ABC: Values within a column not sharing a capital letter are significantly different ($p < 0.05$).
Means were compared by Tukey HSD procedure in SAS JMP 11

TABLE 11

Release of galactose from soybean meal using a GH53 galactanase (SEQ ID NO: 4) in combination with four GH35 beta-galactosidases (SEQ ID NO: 4, 32, 36 and 40)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 18.70 | AB |
| SEQ ID NO: 43 | SEQ ID NO: 32 | 20 | 20 | 19.77 | A |
| SEQ ID NO: 43 | SEQ ID NO: 36 | 20 | 20 | 16.17 | C |
| SEQ ID NO: 43 | SEQ ID NO: 40 | 20 | 20 | 18.43 | B |
| Blank | Blank | — | — | 0.07 | D |

ABCD: Values within a column not sharing a capital letter are significantly different ($p < 0.05$).
Means were compared by Tukey HSD procedure in SAS JMP 11

TABLE 12

Release of galactose from soybean meal using two GH53 galactanase (SEQ ID NO: 4 and 40) in combination with three GH35 beta-galactosidases (SEQ ID NO: 43, 58 and 61)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 58 | SEQ ID NO: 40 | 20 | 20 | 19.5 | AB |
| SEQ ID NO: 58 | SEQ ID NO: 4 | 20 | 20 | 17.9 | AB |
| SEQ ID NO: 43 | SEQ ID NO: 40 | 20 | 20 | 16.4 | B |
| SEQ ID NO: 43 | SEQ ID NO: 4 | 20 | 20 | 16.0 | B |
| SEQ ID NO: 61 | SEQ ID NO: 40 | 20 | 20 | 15.7 | B |
| SEQ ID NO: 61 | SEQ ID NO: 4 | 20 | 20 | 15.6 | B |
| Blank | Blank | — | — | −0.3 | C |

ABC: Values within a column not sharing a capital letter are significantly different ($p < 0.05$).
Means were compared by Tukey HSD procedure in SAS JMP 11

The results demonstrate that the GH53 galactanases of the invention (SEQ ID NO: 4 and 40) together with the GH35 beta-galactosidases of the invention (SEQ ID NO: 43, 58 and 61) all release significantly higher amounts of galactose from soybean meal than the prior art galactanases as demonstrated in example 5.

Example 11: Hydrolysis of Soybean Meal (SBM) Using GH53 Galactanases in Combination with GH35 Beta-Galactosidases The release of galactose from soybean meal using two GH35 beta-galactosidases of the invention (SEQ ID NO: 43 and 55) in combination with three GH53 galactanases of the invention (SEQ ID NO: 4, 8 and 40) were determined using the Galactose SBM Assay. The results are presented in table 13 below.

TABLE 13

Release of galactose from soybean meal using two GH53 galactanase (SEQ ID NO: 4, 8 and 40) in combination with three GH35 beta-galactosidases (SEQ ID NO: 43 and 55)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 55 | SEQ ID NO: 8 | 20 | 20 | 23.0 | AB |
| SEQ ID NO: 55 | SEQ ID NO: 4 | 20 | 20 | 22.6 | AB |
| SEQ ID NO: 55 | SEQ ID NO: 40 | 20 | 20 | 20.1 | BC |
| SEQ ID NO: 43 | SEQ ID NO: 4 | 20 | 20 | 16.1 | C |
| Blank | Blank | — | — | −0.3 | D |

ABCD: Values within a column not sharing a capital letter are significantly different ($p < 0.05$).
Means were compared by Tukey HSD procedure in SAS JMP 11

The results demonstrate that the GH53 galactanases of the invention (SEQ ID NO: 4, 8 and 40) together with the GH35 beta-galactosidases of the invention (SEQ ID NO: 43 and 55) all release significantly higher amounts of galactose from soybean meal than the prior art galactanases as demonstrated in example 5.

Example 12: Hydrolysis of Soybean Meal (SBM) Using a GH53 Galactanase Alone, a GH35 Beta-Galactosidase Alone or a Combination of a GH53 Galactanase with a GH35 Beta-Galactosidase The release of galactose from soybean meal using three different GH35 beta-galactosidases (SEQ ID NO: 43, 58 and 61) alone or using three different GH53 galactanases (SEQ ID NO: 4, 8 and 32) alone was determined using the Galactose SBM Assay. Three different combinations using one of the GH35 beta-galactosidases together with one of the GH53 galactanases was also tested to demonstrate the synergistic effect of the combination of enzymes. The results are presented in table 14 below.

TABLE 14

Release of galactose from soybean meal using a GH53 galactanase alone, a GH35 beta-galactosidase alone or a combination of a GH53 galactanase with a GH35 beta-galactosidase

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 58 | SEQ ID NO: 32 | 20 | 20 | 19.0 | A |
| SEQ ID NO: 43 | SEQ ID NO: 4 | 20 | 20 | 15.2 | B |
| SEQ ID NO: 61 | SEQ ID NO: 8 | 20 | 20 | 14.6 | B |
| SEQ ID NO: 43 | — | — | 20 | 0.7 | C |
| SEQ ID NO: 58 | — | — | 20 | 0.6 | CD |

TABLE 14-continued

Release of galactose from soybean meal using a GH53 galactanase alone, a GH35 beta-galactosidase alone or a combination of a GH53 galactanase with a GH35 beta-galactosidase

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 61 | — | 20 | — | 0.4 | CD |
| — | SEQ ID NO: 8 | — | 20 | 0.1 | CD |
| — | SEQ ID NO: 32 | — | 20 | −0.1 | CD |
| Blank | — | — | — | −0.2 | D |
| — | SEQ ID NO: 4 | — | 20 | −0.3 | D |

ABCD: Values within a column not sharing a capital letter are significantly different (p < 0.05).
Means were compared by Tukey HSD procedure in SAS JMP 11

The results demonstrate that neither the GH53 galactanase alone nor the GH35 beta-galactosidase alone released a significant amount of galactose under the conditions tested. However, the three tested combinations of a GH53 galactanase together with a GH35 beta-galactosidase all released a significant amount of galactose from soybean meal, demonstrating the synergistic effects of the combination of enzymes.

Example 13: Animal Feed and Animal Feed Additives Comprising Galactanases and Beta-Galactosidases Animal Feed Additive A formulation of a galactanase and a beta-galactosidase (e.g. one or more of SEQ ID NO: 3, 4, 7, 8, 11, 12, 15, 16, 19, 20, 23, 24, 27, 28, 31, 32, 35, 36, 39 or 40 and one or more of SEQ ID NO: 43, 46, 49, 52, 55, 58 or 61) containing 0.01 g to 10 g enzyme protein is added to the following premix (per kilo of premix):

| | | |
|---|---|---|
| 5000000 | IE | Vitamin A |
| 1000000 | IE | Vitamin D3 |
| 13333 | mg | Vitamin E |
| 1000 | mg | Vitamin K3 |
| 750 | mg | Vitamin B1 |
| 2500 | mg | Vitamin B2 |
| 1500 | mg | Vitamin B6 |
| 7666 | mcg | Vitamin B12 |
| 12333 | mg | Niacin |
| 33333 | mcg | Biotin |
| 300 | mg | Folic Acid |
| 3000 | mg | Ca-D-Panthothenate |
| 1666 | mg | Cu |
| 16666 | mg | Fe |
| 16666 | mg | Zn |
| 23333 | mg | Mn |
| 133 | mg | Co |
| 66 | mg | I |
| 66 | mg | Se |
| 5.8 | % | Calcium |
| 25 | % | Sodium |

Animal Feed

This is an example of an animal feed (broiler feed) comprising the animal feed additive as described above:
62.55% Maize
33.8% Soybean meal (50% crude protein)
1.0% Soybean oil
0.2% DL-Methionine
0.22% DCP (dicalcium phosphate)
0.76% CaCO$_3$ (calcium carbonate)
0.32% Sand
0.15% NaCl (sodium chloride)
1% of the above Premix The ingredients are mixed, and the feed is pelleted at the desired temperature, e.g. 60, 65, 75, 80, 85, 90 or even 95° C.

Liquid Formulation

A liquid formulation of a galactanase and a beta-galactosidase (e.g. one or more of SEQ ID NO: 3, 4, 7, 8, 11, 12, 15, 16, 19, 20, 23, 24, 27, 28, 31, 32, 35, 36, 39 or 40 and one or more of SEQ ID NO: 43, 46, 49, 52, 55, 58 or 61) comprises 0.1% to 10 w/w enzyme protein (combined), 40-60% glycerol, 0.1 to 0.5% sodium benzoate and water. The liquid formulation is sprayed onto the pelleted animal feed described above (in this case the animal feed additive would not include the beta-galactosidase or galactanase of the invention present).

Example 14: Cloning of GH35 Beta-Galactosidases from *Penicillium simplicissimum*, *Aspergillus Westerdijkiae* and *Aspergillus wentii* (SEQ ID NO: 70, 73 and 76)

The beta-galactosidases with nucleotide sequence SEQ ID NO: 41, 44, 47, 50, 56, and 59 and the peptide translation of the protein shown in SEQ ID NO: 42, 45, 48, 51, 57, and 60 were PCR amplified from genomic DNA and cloned into the expression vector pDAu222 as described in WO 2013024021 using BamHI and XhoI restriction sites.

The sequences of the beta-galactosidase encoding genes cloned in the expression vector were confirmed and the expression constructs were transformed into the *Aspergillus oryzae* strain MT3568 (WO 11/057140) to produce the secreted mature peptide with protein sequence SEQ ID NO: 43, 46, 49, 52, 58, and 61 respectively. Transformants were selected on acetamide during regeneration from protoplasts and subsequently re-isolated under selection (Christensen et al., 1988, *Biotechnology* 6, 1419-1422 and WO 04/032648).

For production of the recombinant beta-galactosidases, a single *Aspergillus* transformant for each plasmid construct was cultured in two 500 ml baffled flasks each containing 150 ml of DAP-4C-1 medium (WO 12/103350). The cultures were shaken on a rotary table at 100 RPM at 30° C. for 4 days. The culture broth subsequently was separated from cellular material by passage through a 0.22 um filter.

Example 15: Purification of GH35 Beta-Galactosidases from *Penicillium simplicissimum*, *Aspergillus Westerdijkiae* and *Aspergillus wentii* (SEQ ID NO: 70, 73 and 76)

The broth was diluted 50:50 with 3.6M ammonium sulphate, stirred for 30 minutes and then filtered through a 0.2 μm filter. The sample was applied to a 5 ml HiTrap™ Phenyl (FF) column (GE Healthcare, Piscataway, N.J., USA) on an Akta purifier. Prior to loading, the column had been equilibrated in 5 column volumes (CV) of 50 mM HEPES+1.8M ammonium sulphate pH 7. In order to remove unbound material, the column was washed with 5 CV of 50 mM HEPES+1.8M ammonium sulphate pH 7. The target protein was eluted from the column into a 10 ml loop using 50 mM HEPES+20% isopropanol pH 7. From the loop, the sample was loaded onto a desalting column (HiPrep™ 26/10 Desalting), which had been equilibrated with 3CV of 50 mM HEPES+100 mM NaCl pH 7.0. The target protein was eluted with 50 mM HEPES+100 mM NaCl pH 7.0 and relevant fractions were selected and pooled based on the chromatogram. The flow rate was 5 ml/min.

Example 16: Cloning of GH35 Beta-Galactosidases from *Aspergillus lentulus* (SEQ ID NO: 79)

The beta-galactosidase with nucleotide sequence SEQ ID NO: 77 was PCR amplified from genomic DNA isolated from *Aspergillus lentulus* and cloned into the expression vector pSUN515, which is a derivative of pCaHj505 (WO2013/029496).

The final expression plasmid was transformed into the *Aspergillus oryzae* MT3568 expression host. *A. oryzae* MT3568 is a derivative of *A. oryzae* JaL355 (WO02/40694) in which pyrG auxotrophy was restored by disrupting the *A. oryzae* acetamidase (amdS) gene with the pyrG gene. The beta-galactosidase gene was integrated by homologous recombination into the *A. oryzae* MT3568 host cell genome upon transformation.

The gene coding for amdS was used as marker. Transformants were selected on pyrG media agar supplemented with 10 mM acetamide. One recombinant *Aspergillus oryzae* clone containing the beta-galactosidase expression construct was selected and was cultivated on a rotary shaking table in 4 2-liter baffled Erlenmeyer flasks each containing 400 ml YPM (1% Yeast extract, 2% Peptone and 2% Maltose). After 3 days cultivation time at 30° C., enzyme containing supernatants were harvested by filtration using a 0.2 μm 1-liter bottle top vacuum filter (Thermo Fisher Scientific Inc., Waltham, Mass., USA).

Example 17: Purification of GH35 Beta-Galactosidases from *Aspergillus lentulus* (SEQ ID NO: 79)

The culture broth harvested was precipitated with ammonium sulfate (80% saturated). Precipitates were re-dissolved in 50 ml of 20 mM PBS pH 7.0, and then filtered through a 0.45 μm filter. The filtered crude protein solution was applied to a 20 ml self-packed Ni sepharose excel affinity column (GE Healthcare, Buckinghamshire, UK) equilibrated with 20 mM PBS pH 7.0 and 300 mM sodium chloride. Proteins were eluted by a linear 0-0.5 M imidazole gradient for 0.5 CV, followed by 0.5 M imidazole for another 4 CV (CV is short for colume volume, CV=20 ml). Fractions were analyzed by SDS-PAGE using a Mini-PROTEAN TGX Stain-Free 4-15% Precast Gel (Bio-Rad Laboratories, CA, United States). Beta-galactosidase activities of fractions were assessed on ortho-nitrophenyl-D-galactopyranoside (ONPG) by observing absorbance at wavelength of 400 nm, at pH 6.5, 40° C. Fractions were pooled containing recombinant protein bands and showing positive activities. Then the pooled solution was concentrated by ultrafiltration.

Example 18: Hydrolysis of Soybean Meal (SBM) Using a GH53 Galactanase Alone, a GH35 Beta-Galactosidase Alone or a Combination of a GH53 Galactanase with a GH35 Beta-Galactosidase The release of galactose from soybean meal using six GH35 beta-galactosidases of the invention (SEQ ID NO: 43, 55, 70, 73, 76 or 79) in combination with a GH53 galactanase of the invention (SEQ ID NO: 4) were determined using the Galactose SBM Assay. The results are presented in tables 15 to 18 below.

TABLE 15

Release of galactose from soybean meal using a GH53 galactanase (SEQ ID NO: 4) in combination with a GH35 beta-galactosidase (SEQ ID NO: 43 or 70)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 15.6 | A |
| SEQ ID NO: 70 | SEQ ID NO: 4 | 20 | 20 | 15.4 | A |
| Blank | Blank | — | — | −0.2 | B |

ABCD: Values within a column not sharing a capital letter are significantly different (p < 0.05).
Means were compared by Tukey HSD procedure in SAS JMP 11

TABLE 16

Release of galactose from soybean meal using a GH53 galactanase (SEQ ID NO: 4) in combination with a GH35 beta-galactosidase (SEQ ID NO: 43 or 73)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 15.2 | A |
| SEQ ID NO: 73 | SEQ ID NO: 4 | 20 | 20 | 16.3 | A |
| Blank | Blank | — | — | −0.3 | B |

ABCD: Values within a column not sharing a capital letter are significantly different (p < 0.05).
Means were compared by Tukey HSD procedure in SAS JMP 11

TABLE 17

Release of galactose from soybean meal using a GH53 galactanase (SEQ ID NO: 4) in combination with a GH35 beta-galactosidase (SEQ ID NO: 43, 55 or 76)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 18.7 | A |
| SEQ ID NO: 55 | SEQ ID NO: 4 | 20 | 20 | 22.6 | B |
| SEQ ID NO: 76 | SEQ ID NO: 4 | 20 | 20 | 18.3 | B |
| Blank | Blank | — | — | 1.5 | C |

ABCD: Values within a column not sharing a capital letter are significantly different ($p < 0.05$).
Means were compared by Tukey HSD procedure in SAS JMP 11

TABLE 18

Release of galactose from soybean meal using a GH53 galactanas (SEQ ID NO: 4) in combination with a GH35 beta-galactosidase (SEQ ID NO: 43 or 79)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 15.8 | A |
| SEQ ID NO: 79 | SEQ ID NO: 4 | 20 | 20 | 15.2 | A |
| Blank | Blank | — | — | 0.8 | B |

ABCD: Values within a column not sharing a capital letter are significantly different ($p < 0.05$).
Means were compared by Tukey HSD procedure in SAS JMP 11

The results demonstrate that the GH53 galactanase of the invention (SEQ ID NO: 4) together with the GH35 beta-galactosidases of the invention (SEQ ID NO: 43, 55, 70, 73, 76 or 79) all release significantly higher amounts of galactose from soybean meal than the prior art galactanases as demonstrated in example 5.

Example 19: Hydrolysis of Soybean Meal (SBM) Using the Prior Art Combinations of GH53 Galactanases and GH35 Beta-Galactosidases Sakamoto et al, in *Appl Microbiol Biotechnol.* 2013 9:2895-2906, describe a GH53 galactanase (Swissprot: B5MGR3, SEQ ID NO: 83) and a GH35 beta-galactosidase from *Penicillium chrysogenum* (Swissprot: I0IV51, SEQ ID NO: 82).

De Vries et al, in *Carbohydrate Research* 327 (2000) 401-410, describe a GH53 galactanase GalA (Swissprot: G3XR77, SEQ ID NO: 84) and a GH35 beta-galactosidase LacA (Swissprot: Q8X168 with 1 AA correction, SEQ ID NO: 85) from *Aspergillus niger*.

The release of galactose from soybean meal using the prior art combination B5MGR3+I0IV51 and the prior art combination G3XR77+Q8X168 were determined using the Galactose SBM. As negative control, a blank sample was run. As positive control, the GH35 beta-galactosidase having SEQ ID NO: 43 and the GH53 galactanase having SEQ ID NO: 4 were used. The results are presented in table 19 below.

TABLE 19

Release of galactose from soybean meal using a GH53 galactanas (SEQ ID NO: 4) in combination with a GH35 beta-galactosidase (SEQ ID NO: 43 or 79)

| GH35 beta-galactosidase | GH53 galactanase | Conc. GH35 [mg EP/kg] | Conc. GH53 [mg EP/kg] | Mean Galactose Release (g gal/kg SBM) | Signifcance |
|---|---|---|---|---|---|
| SEQ ID NO: 43 | SEQ ID NO: 4 | 20 | 20 | 19.2 | A |
| I0IV51 SEQ ID NO: 82 | B5MGR3 SEQ ID NO: 83 | 20 | 20 | 6.9 | B |
| LacA (Q8X168*) SEQ ID NO: 85 | GalA (G3XR77) SEQ ID NO: 84 | 20 | 20 | 3.8 | C |
| Blank | Blank | — | — | 4.0 | C |

ABCD: Values within a column not sharing a capital letter are significantly different ($p < 0.05$).
Means were compared by Tukey HSD procedure in SAS JMP 11.
*with 1 AA correction.

The results demonstrate that the prior art combinations release significantly less galactose from soybean meal compared to a GH53 galactanase of the invention (SEQ ID NO: 4) together with a GH35 beta-galactosidases of the invention (SEQ ID NO: 43).

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

What is claimed is:

1. A method of improving one or more performance parameters of an animal, comprising feeding the animal with plant-based material and a composition comprising one or more GH53 polypeptides having galactanase activity and one or more GH35 polypeptides having beta-galactosidase activity, wherein the plant-based material comprises soybean or soybean meal and the one or more performance parameters are selected from the group consisting of body weight gain (BWG), European Production Efficiency Factor (EPEF) and feed conversion ratio (FCR).

2. The method of claim 1, wherein the composition is a granule.

3. The method of claim 1, wherein the plant-based material and the composition are a pelleted animal feed.

4. The method of claim 1, wherein the composition further comprises one or more components selected from the group consisting of:
one or more vitamins;
one or more minerals;
one or more amino acids;
one or more prebiotics;
one or more phytogenics;
one or more organic acids; and
one or more other feed ingredients.

5. The method of claim 1, wherein the composition is a liquid composition.

6. The method of claim 1, wherein the GH53 polypeptide comprises the motif GV[T/M]PD[W/M]VQ[I/V]GNE (SEQ ID NO: 65) and/or the motif WADP[A/G]xQxKPxAW (SEQ ID NO: 66).

7. The method of claim 1, wherein the GH53 polypeptide is selected from the group consisting of:
(a) a polypeptide having at least 80% sequence identity to the polypeptide of SEQ ID NO: 3;
(b) a polypeptide having at least 80% sequence identity to the polypeptide of SEQ ID NO: 7;
(c) a polypeptide having at least 80% sequence identity to the polypeptide of SEQ ID NO: 11;
(d) a polypeptide having at least 80% sequence identity to the polypeptide of SEQ ID NO: 15;
(e) a polypeptide having at least 80% sequence identity to the polypeptide of SEQ ID NO: 19;
(f) a polypeptide having at least 80% sequence identity to the polypeptide of SEQ ID NO: 23;
(g) a polypeptide having at least 80% sequence identity to the polypeptide of SEQ ID NO: 27;
(h) a polypeptide having at least 80% sequence identity to the polypeptide of SEQ ID NO: 31;
(i) a polypeptide having at least 80% sequence identity to the polypeptide of SEQ ID NO: 35; and
(j) a polypeptide having at least 80% sequence identity to the polypeptide of SEQ ID NO: 39.

8. The method of claim 1, wherein the GH35 polypeptide is selected from the group consisting of:
(a) a polypeptide having at least 80% sequence identity to the polypeptide of SEQ ID NO: 43;
(b) a polypeptide having at least 80% sequence identity to the polypeptide of SEQ ID NO: 46;
(c) a polypeptide having at least 80% sequence identity to the polypeptide of SEQ ID NO: 49;
(d) a polypeptide having at least 80% sequence identity to the polypeptide of SEQ ID NO: 52;
(e) a polypeptide having at least 80% sequence identity to the polypeptide of SEQ ID NO: 55;
(f) a polypeptide having at least 80% sequence identity to the polypeptide of SEQ ID NO: 58;
(g) a polypeptide having at least 80% sequence identity to the polypeptide of SEQ ID NO: 61;
(h) a polypeptide having at least 80% sequence identity to the polypeptide of SEQ ID NO: 70;
(i) a polypeptide having at least 80% sequence identity to the polypeptide of SEQ ID NO: 73;
(j) a polypeptide having at least 80% sequence identity to the polypeptide of SEQ ID NO: 76; and
(k) a polypeptide having at least 80% sequence identity to the polypeptide of SEQ ID NO: 79.

9. The method of claim 1, wherein the GH53 polypeptide has at least 80% sequence identity to the polypeptide of SEQ ID NO: 3 and the GH35 polypeptide has at least 80% sequence identity to the polypeptide of SEQ ID NO: 58.

10. The method of claim 1, wherein the GH53 polypeptide has at least 85% sequence identity to the polypeptide of SEQ ID NO: 3 and the GH35 polypeptide has at least 85% sequence identity to the polypeptide of SEQ ID NO: 58.

11. The method of claim 1, wherein the GH53 polypeptide has at least 90% sequence identity to the polypeptide of SEQ ID NO: 3 and the GH35 polypeptide has at least 90% sequence identity to the polypeptide of SEQ ID NO: 58.

12. The method of claim 1, wherein the GH53 polypeptide has at least 95% sequence identity to the polypeptide of SEQ ID NO: 3 and the GH35 polypeptide has at least 95% sequence identity to the polypeptide of SEQ ID NO: 58.

13. The method of claim 1, wherein the GH53 is the polypeptide of SEQ ID NO: 3 or 4 and the GH35 polypeptide is the polypeptide of SEQ ID NO: 58.

14. The method of claim 9, wherein the GH53 polypeptide:
comprises an N-terminal and/or C-terminal His-tag and/or HQ-tag;
comprises an N-terminal and/or C-terminal extension of up to 10 amino acids; or
is a fragment having galactanase activity and having at least 90% of the length of the mature polypeptide.

15. The method of claim 9, wherein the GH35 polypeptide:
comprises an N-terminal and/or C-terminal His-tag and/or HQ-tag;
comprises an N-terminal and/or C-terminal extension of up to 10 amino acids; or
is a fragment having beta-galactosidase activity and having at least 90% of the length of the mature polypeptide.

16. The method of claim 9, wherein the GH53 polypeptide is a variant of SEQ ID NO: 3, wherein the variant has galactanase activity and comprises one or more amino acid substitutions, one or more amino acid deletions, and/or one or more amino acid insertions.

17. The method of claim 9, wherein the GH35 polypeptide is a variant of SEQ ID NO: 58, wherein the variant has beta-galactosidase activity and comprises one or more amino acid substitutions, one or more amino acid deletions, and/or one or more amino acid insertions.

18. The method of claim 1, wherein the composition releases at least 12 g galactose per kg soybean meal when performed under the reaction conditions 20 mg galactanase and 20 mg beta-galactosidase per kg soybean meal in 10% w/v 0.1M citric acid-phosphate buffer pH 6.5 incubating at 40° C. for 2 hours.

* * * * *

SEQUENCE LISTING

```
<160> NUMBER OF SEQ ID NOS: 85

<210> SEQ ID NO 1
<211> LENGTH: 1047
<212> TYPE: DNA
<213> ORGANISM: Cohnella sp-60555
<220> FEATURE:
<221> NAME/KEY: CDS
<222> LOCATION: (1)..(1044)
<220> FEATURE:
<221> NAME/KEY: sig_peptide
<222> LOCATION: (1)..(96)
<220> FEATURE:
<221> NAME/KEY: mat_peptide
<222> LOCATION: (97)..(1044)

<400> SEQUENCE: 1 atg atg ttc aag aga acg gta acg ggc atg atg gcc ttg ctg ctg gtg      48
Met Met Phe Lys Arg Thr Val Thr Gly Met Met Ala Leu Leu Leu Val
        -30                 -25                 -20 ctg gct ctg ttc gtc gcg caa ggt tcg cag ccg cac caa gcc gcc gcg      96
Leu Ala Leu Phe Val Ala Gln Gly Ser Gln Pro His Gln Ala Ala Ala
    -15                 -10                  -5                 -1 gcg ccg tcg ttc gcc aaa ggg gcg gac atc agc tgg gtg ccg gga atg     144
Ala Pro Ser Phe Ala Lys Gly Ala Asp Ile Ser Trp Val Pro Gly Met
1                   5                  10                  15 gaa gcc cag ggg tac aag tgg aag gac aag aac ggc gtg cag cgg gac     192
Glu Ala Gln Gly Tyr Lys Trp Lys Asp Lys Asn Gly Val Gln Arg Asp
                20                  25                  30 att ttg gac att ttg aaa aac gat tat cag atc aac tcc gtg cgc atc     240
Ile Leu Asp Ile Leu Lys Asn Asp Tyr Gln Ile Asn Ser Val Arg Ile
            35                  40                  45 cgc gtg tgg gtc aac cct tcg agc agc tac acg aac ggg tac ctg aac     288
Arg Val Trp Val Asn Pro Ser Ser Ser Tyr Thr Asn Gly Tyr Leu Asn
        50                  55                  60 aag gac cgt gcg gcc gcg ctg gcg aag cgg gcc aag gcg gcg ggg atg     336
Lys Asp Arg Ala Ala Ala Leu Ala Lys Arg Ala Lys Ala Ala Gly Met
65                  70                  75                  80 agc gtc atg ctg acg ctc cat tac agc gac agc tgg gcg gac ccc ggc     384
Ser Val Met Leu Thr Leu His Tyr Ser Asp Ser Trp Ala Asp Pro Gly
                85                  90                  95 caa cag acg aag ccg gcg gca tgg aag agc tac acg ttc cag caa ctg     432
Gln Gln Thr Lys Pro Ala Ala Trp Lys Ser Tyr Thr Phe Gln Gln Leu
            100                 105                 110 atg gac gcc gtg tgg aac tgg aca cgc gac gtc atg acg acg atg cag     480
Met Asp Ala Val Trp Asn Trp Thr Arg Asp Val Met Thr Thr Met Gln
        115                 120                 125 gcg aac ggc gtg acg ccg gac tgg gtg cag atc ggc aac gag acg aac     528
Ala Asn Gly Val Thr Pro Asp Trp Val Gln Ile Gly Asn Glu Thr Asn
    130                 135                 140 aac ggc atg ctg tgg gac gac ggc aag gct tcg ctc agc atg aag aat     576
Asn Gly Met Leu Trp Asp Asp Gly Lys Ala Ser Leu Ser Met Lys Asn
145                 150                 155                 160 tat gcg tgg ctc gtg aac acg ggc aac aac gcg gtg aag tcg atc agc     624
```

```
Tyr Ala Trp Leu Val Asn Thr Gly Asn Asn Ala Val Lys Ser Ile Ser
                165                 170                 175 agc tcg acc aag acg atc gtg cac ctg gcc aac ggc tac gac aat tcg    672
Ser Ser Thr Lys Thr Ile Val His Leu Ala Asn Gly Tyr Asp Asn Ser
            180                 185                 190 ctg ttc gtc tgg aac atc gga ggc ttg atc gcc aac gga gcg acg ttc    720
Leu Phe Val Trp Asn Ile Gly Gly Leu Ile Ala Asn Gly Ala Thr Phe
        195                 200                 205 gac atc atc ggc atg tcg ctc tat ccg agc gcg tcg gat tgg tcg gcc    768
Asp Ile Ile Gly Met Ser Leu Tyr Pro Ser Ala Ser Asp Trp Ser Ala
    210                 215                 220 aag gtg acg cag acg atc gcg aac gcg aac gac atg atc tcg cgt tac    816
Lys Val Thr Gln Thr Ile Ala Asn Ala Asn Asp Met Ile Ser Arg Tyr
225                 230                 235                 240 ggc aag ccg atc atg gtg acg gag atc ggc atg gac tac agc cag ccg    864
Gly Lys Pro Ile Met Val Thr Glu Ile Gly Met Asp Tyr Ser Gln Pro
                245                 250                 255 agc gcg gcc aag agc ttc gtg tcg gac atc aag acg aag atc cgc aac    912
Ser Ala Ala Lys Ser Phe Val Ser Asp Ile Lys Thr Lys Ile Arg Asn
            260                 265                 270 ctg tcc ggc ggc aag ggg caa ggc gtg ttc tac tgg gag ccc gaa gcg    960
Leu Ser Gly Gly Lys Gly Gln Gly Val Phe Tyr Trp Glu Pro Glu Ala
        275                 280                 285 acg ccc ggc tac aac ggc ggc tac agc atg ggc gcc tgg caa gcg gac   1008
Thr Pro Gly Tyr Asn Gly Gly Tyr Ser Met Gly Ala Trp Gln Ala Asp
    290                 295                 300 atg aag ccg acg atc gcg ctc gag ggc ttc tgg aac taa                1047
Met Lys Pro Thr Ile Ala Leu Glu Gly Phe Trp Asn
305                 310                 315

<210> SEQ ID NO 2
<211> LENGTH: 348
<212> TYPE: PRT
<213> ORGANISM: Cohnella sp-60555

<400> SEQUENCE: 2

Met Met Phe Lys Arg Thr Val Thr Gly Met Met Ala Leu Leu Leu Val
        -30                 -25                 -20

Leu Ala Leu Phe Val Ala Gln Gly Ser Gln Pro His Gln Ala Ala Ala
    -15                 -10                  -5                  -1

Ala Pro Ser Phe Ala Lys Gly Ala Asp Ile Ser Trp Val Pro Gly Met
1                5                  10                  15

Glu Ala Gln Gly Tyr Lys Trp Lys Asp Lys Asn Gly Val Gln Arg Asp
            20                  25                  30

Ile Leu Asp Ile Leu Lys Asn Asp Tyr Gln Ile Asn Ser Val Arg Ile
        35                  40                  45

Arg Val Trp Val Asn Pro Ser Ser Tyr Thr Asn Gly Tyr Leu Asn
    50                  55                  60

Lys Asp Arg Ala Ala Ala Leu Ala Lys Arg Ala Lys Ala Ala Gly Met
65                  70                  75                  80

Ser Val Met Leu Thr Leu His Tyr Ser Asp Ser Trp Ala Asp Pro Gly
                85                  90                  95

Gln Gln Thr Lys Pro Ala Ala Trp Lys Ser Tyr Thr Phe Gln Gln Leu
            100                 105                 110

Met Asp Ala Val Trp Asn Trp Thr Arg Asp Val Met Thr Thr Met Gln
        115                 120                 125

Ala Asn Gly Val Thr Pro Asp Trp Val Gln Ile Gly Asn Glu Thr Asn
    130                 135                 140
```

Asn Gly Met Leu Trp Asp Asp Gly Lys Ala Ser Leu Ser Met Lys Asn
145                 150                 155                 160

Tyr Ala Trp Leu Val Asn Thr Gly Asn Asn Ala Val Lys Ser Ile Ser
                165                 170                 175

Ser Ser Thr Lys Thr Ile Val His Leu Ala Asn Gly Tyr Asp Asn Ser
            180                 185                 190

Leu Phe Val Trp Asn Ile Gly Gly Leu Ile Ala Asn Gly Ala Thr Phe
        195                 200                 205

Asp Ile Ile Gly Met Ser Leu Tyr Pro Ser Ala Ser Asp Trp Ser Ala
    210                 215                 220

Lys Val Thr Gln Thr Ile Ala Asn Ala Asn Asp Met Ile Ser Arg Tyr
225                 230                 235                 240

Gly Lys Pro Ile Met Val Thr Glu Ile Gly Met Asp Tyr Ser Gln Pro
                245                 250                 255

Ser Ala Ala Lys Ser Phe Val Ser Asp Ile Lys Thr Lys Ile Arg Asn
            260                 265                 270

Leu Ser Gly Gly Lys Gly Gln Gly Val Phe Tyr Trp Glu Pro Glu Ala
        275                 280                 285

Thr Pro Gly Tyr Asn Gly Gly Tyr Ser Met Gly Ala Trp Gln Ala Asp
    290                 295                 300

Met Lys Pro Thr Ile Ala Leu Glu Gly Phe Trp Asn
305                 310                 315

<210> SEQ ID NO 3
<211> LENGTH: 316
<212> TYPE: PRT
<213> ORGANISM: Cohnella sp-60555
<220> FEATURE:
<221> NAME/KEY: mat_peptide
<222> LOCATION: (1)..(316)

<400> SEQUENCE: 3

Ala Pro Ser Phe Ala Lys Gly Ala Asp Ile Ser Trp Val Pro Gly Met
1               5                   10                  15

Glu Ala Gln Gly Tyr Lys Trp Lys Asp Lys Asn Gly Val Gln Arg Asp
                20                  25                  30

Ile Leu Asp Ile Leu Lys Asn Asp Tyr Gln Ile Asn Ser Val Arg Ile
            35                  40                  45

Arg Val Trp Val Asn Pro Ser Ser Tyr Thr Asn Gly Tyr Leu Asn
        50                  55                  60

Lys Asp Arg Ala Ala Leu Ala Lys Arg Ala Lys Ala Ala Gly Met
65                  70                  75                  80

Ser Val Met Leu Thr Leu His Tyr Ser Asp Ser Trp Ala Asp Pro Gly
                85                  90                  95

Gln Gln Thr Lys Pro Ala Ala Trp Lys Ser Tyr Thr Phe Gln Gln Leu
            100                 105                 110

Met Asp Ala Val Trp Asn Trp Thr Arg Asp Val Met Thr Thr Met Gln
        115                 120                 125

Ala Asn Gly Val Thr Pro Asp Trp Val Gln Ile Gly Asn Glu Thr Asn
    130                 135                 140

Asn Gly Met Leu Trp Asp Asp Gly Lys Ala Ser Leu Ser Met Lys Asn
145                 150                 155                 160

Tyr Ala Trp Leu Val Asn Thr Gly Asn Asn Ala Val Lys Ser Ile Ser
                165                 170                 175

Ser Ser Thr Lys Thr Ile Val His Leu Ala Asn Gly Tyr Asp Asn Ser

```
                      180                 185                 190
Leu Phe Val Trp Asn Ile Gly Gly Leu Ile Ala Asn Gly Ala Thr Phe
            195                 200                 205
Asp Ile Ile Gly Met Ser Leu Tyr Pro Ser Ala Ser Asp Trp Ser Ala
        210                 215                 220
Lys Val Thr Gln Thr Ile Ala Asn Ala Asn Asp Met Ile Ser Arg Tyr
225                 230                 235                 240
Gly Lys Pro Ile Met Val Thr Glu Ile Gly Met Asp Tyr Ser Gln Pro
                245                 250                 255
Ser Ala Ala Lys Ser Phe Val Ser Asp Ile Lys Thr Lys Ile Arg Asn
            260                 265                 270
Leu Ser Gly Gly Lys Gly Gln Gly Val Phe Tyr Trp Glu Pro Glu Ala
        275                 280                 285
Thr Pro Gly Tyr Asn Gly Gly Tyr Ser Met Gly Ala Trp Gln Ala Asp
        290                 295                 300
Met Lys Pro Thr Ile Ala Leu Glu Gly Phe Trp Asn
305                 310                 315

<210> SEQ ID NO 4
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 4

His His His His His His Pro Arg Ala Pro Ser Phe Ala Lys Gly Ala
1               5                   10                  15
Asp Ile Ser Trp Val Pro Gly Met Glu Ala Gln Gly Tyr Lys Trp Lys
                20                  25                  30
Asp Lys Asn Gly Val Gln Arg Asp Ile Leu Asp Ile Leu Lys Asn Asp
            35                  40                  45
Tyr Gln Ile Asn Ser Val Arg Ile Arg Val Trp Val Asn Pro Ser Ser
50                  55                  60
Ser Tyr Thr Asn Gly Tyr Leu Asn Lys Asp Arg Ala Ala Leu Ala
65                  70                  75                  80
Lys Arg Ala Lys Ala Ala Gly Met Ser Val Met Leu Thr Leu His Tyr
                85                  90                  95
Ser Asp Ser Trp Ala Asp Pro Gly Gln Gln Thr Lys Pro Ala Ala Trp
                100                 105                 110
Lys Ser Tyr Thr Phe Gln Gln Leu Met Asp Ala Val Trp Asn Trp Thr
            115                 120                 125
Arg Asp Val Met Thr Thr Met Gln Ala Asn Gly Val Thr Pro Asp Trp
        130                 135                 140
Val Gln Ile Gly Asn Glu Thr Asn Asn Gly Met Leu Trp Asp Asp Gly
145                 150                 155                 160
Lys Ala Ser Leu Ser Met Lys Asn Tyr Ala Trp Leu Val Asn Thr Gly
                165                 170                 175
Asn Asn Ala Val Lys Ser Ile Ser Ser Thr Lys Thr Ile Val His
            180                 185                 190
Leu Ala Asn Gly Tyr Asp Asn Ser Leu Phe Val Trp Asn Ile Gly Gly
        195                 200                 205
Leu Ile Ala Asn Gly Ala Thr Phe Asp Ile Ile Gly Met Ser Leu Tyr
```

```
            210                 215                 220
Pro Ser Ala Ser Asp Trp Ser Ala Lys Val Thr Gln Thr Ile Ala Asn
225                 230                 235                 240

Ala Asn Asp Met Ile Ser Arg Tyr Gly Lys Pro Ile Met Val Thr Glu
                245                 250                 255

Ile Gly Met Asp Tyr Ser Gln Pro Ser Ala Ala Lys Ser Phe Val Ser
                    260                 265                 270

Asp Ile Lys Thr Lys Ile Arg Asn Leu Ser Gly Gly Lys Gly Gln Gly
                275                 280                 285

Val Phe Tyr Trp Glu Pro Glu Ala Thr Pro Gly Tyr Asn Gly Gly Tyr
            290                 295                 300

Ser Met Gly Ala Trp Gln Ala Asp Met Lys Pro Thr Ile Ala Leu Glu
305                 310                 315                 320

Gly Phe Trp Asn

<210> SEQ ID NO 5
<211> LENGTH: 1044
<212> TYPE: DNA
<213> ORGANISM: Cohnella xylanilytica
<220> FEATURE:
<221> NAME/KEY: CDS
<222> LOCATION: (1)..(1041)
<220> FEATURE:
<221> NAME/KEY: sig_peptide
<222> LOCATION: (1)..(87)
<220> FEATURE:
<221> NAME/KEY: mat_peptide
<222> LOCATION: (88)..(1041)

<400> SEQUENCE: 5 atg ttg cgc aaa gcg gtt gcg gtg ttc atc acc ttg gtg ttg gga ctg     48
Met Leu Arg Lys Ala Val Ala Val Phe Ile Thr Leu Val Leu Gly Leu
            -25                 -20                 -15 act cta cta tcg gcg cag gga gga cga ccg cag gaa gcg gcg gcg gct     96
Thr Leu Leu Ser Ala Gln Gly Gly Arg Pro Gln Glu Ala Ala Ala Ala
        -10                 -5                  -1   1 ccg tcg ttc gct aag gga gcg gac atc agc tgg gtg ccg gga atg gaa    144
Pro Ser Phe Ala Lys Gly Ala Asp Ile Ser Trp Val Pro Gly Met Glu
        5                   10                  15 gcg caa ggg tac agg tgg aag gac aag aac ggc gtg cag cgg gac atc    192
Ala Gln Gly Tyr Arg Trp Lys Asp Lys Asn Gly Val Gln Arg Asp Ile
 20                  25                  30                  35 ctg gac att ctc aag aac gat tac cag atc aac tcc gtc cgc att cgg    240
Leu Asp Ile Leu Lys Asn Asp Tyr Gln Ile Asn Ser Val Arg Ile Arg
                40                  45                  50 gta tgg gtc aat cct tcg agc agc tat acg aac ggc tac ctg aac aag    288
Val Trp Val Asn Pro Ser Ser Ser Tyr Thr Asn Gly Tyr Leu Asn Lys
            55                  60                  65 gac cgg gcg gcc gcg ctc gcg aag cgg gcg aag gcg gcg ggg ctc agc    336
Asp Arg Ala Ala Ala Leu Ala Lys Arg Ala Lys Ala Ala Gly Leu Ser
        70                  75                  80 gtc atg ctg acg ctg cat tac agc gac agc tgg gcc gac ccc ggg aag    384
Val Met Leu Thr Leu His Tyr Ser Asp Ser Trp Ala Asp Pro Gly Lys
        85                  90                  95 cag acg aag ccg gcg gcg tgg gcc ggg tac aac ttc cag cag ctg atg    432
Gln Thr Lys Pro Ala Ala Trp Ala Gly Tyr Asn Phe Gln Gln Leu Met
100                 105                 110                 115 gac gcg gtg tgg aac tgg acg cgc gag gtc atg acg acg atg cag gcc    480
Asp Ala Val Trp Asn Trp Thr Arg Glu Val Met Thr Thr Met Gln Ala
                120                 125                 130
```

```
agc ggg gtg acg ccg gac tgg gtg cag atc ggc aac gag acg aac aac      528
Ser Gly Val Thr Pro Asp Trp Val Gln Ile Gly Asn Glu Thr Asn Asn
            135                 140                 145 ggc atg ctg tgg gac gac ggg aag gcc tcg ctg agc atg aag aat tac      576
Gly Met Leu Trp Asp Asp Gly Lys Ala Ser Leu Ser Met Lys Asn Tyr
        150                 155                 160 gcc tgg ctc gtc aac acg ggc aac aac gcg gtc aag tcg atc agc agc      624
Ala Trp Leu Val Asn Thr Gly Asn Asn Ala Val Lys Ser Ile Ser Ser
    165                 170                 175 ggg acg aaa acg atc gtg cat ctc gcc aac ggg tac gac aat tcg ttg      672
Gly Thr Lys Thr Ile Val His Leu Ala Asn Gly Tyr Asp Asn Ser Leu
180                 185                 190                 195 ttc gtc tgg aac atc ggc ggc ctg atc gcg aac ggc gcc acg ttc gac      720
Phe Val Trp Asn Ile Gly Gly Leu Ile Ala Asn Gly Ala Thr Phe Asp
                200                 205                 210 att atc ggc atg tcg ctg tat ccg agc gcg tcc gac tgg tcc tcg aag      768
Ile Ile Gly Met Ser Leu Tyr Pro Ser Ala Ser Asp Trp Ser Ser Lys
            215                 220                 225 gtg acg cag acg atc tcc aac gcg aac gat atg atc tcc cgg tac ggc      816
Val Thr Gln Thr Ile Ser Asn Ala Asn Asp Met Ile Ser Arg Tyr Gly
        230                 235                 240 aag ccg atc atg atc acg gag atc ggc atg gac tac aac cag ccg tcg      864
Lys Pro Ile Met Ile Thr Glu Ile Gly Met Asp Tyr Asn Gln Pro Ser
    245                 250                 255 gcg gcc aag agc ttc gtc gcg gat atc aag acg aag atc cgc agc ctg      912
Ala Ala Lys Ser Phe Val Ala Asp Ile Lys Thr Lys Ile Arg Ser Leu
260                 265                 270                 275 tcc ggc ggc cga ggg ctc ggc gtc ttc tac tgg gag ccg gag gcg acc      960
Ser Gly Gly Arg Gly Leu Gly Val Phe Tyr Trp Glu Pro Glu Ala Thr
                280                 285                 290 ccg ggt tat aac gga ggc tat aac aag gga gcc tgg cag gca gac atg     1008
Pro Gly Tyr Asn Gly Gly Tyr Asn Lys Gly Ala Trp Gln Ala Asp Met
            295                 300                 305 aag ccg acg atc gct ctc gaa ggt ttt ctg aac taa                      1044
Lys Pro Thr Ile Ala Leu Glu Gly Phe Leu Asn
        310                 315

<210> SEQ ID NO 6
<211> LENGTH: 347
<212> TYPE: PRT
<213> ORGANISM: Cohnella xylanilytica

<400> SEQUENCE: 6

Met Leu Arg Lys Ala Val Ala Val Phe Ile Thr Leu Val Leu Gly Leu
                -25                 -20                 -15

Thr Leu Leu Ser Ala Gln Gly Gly Arg Pro Gln Glu Ala Ala Ala Ala
            -10                  -5                  -1   1

Pro Ser Phe Ala Lys Gly Ala Asp Ile Ser Trp Val Pro Gly Met Glu
  5                  10                  15

Ala Gln Gly Tyr Arg Trp Lys Asp Lys Asn Gly Val Gln Arg Asp Ile
 20                  25                  30                  35

Leu Asp Ile Leu Lys Asn Asp Tyr Gln Ile Asn Ser Val Arg Ile Arg
                 40                  45                  50

Val Trp Val Asn Pro Ser Ser Tyr Thr Asn Gly Tyr Leu Asn Lys
             55                  60                  65

Asp Arg Ala Ala Ala Leu Ala Lys Arg Ala Lys Ala Ala Gly Leu Ser
         70                  75                  80

Val Met Leu Thr Leu His Tyr Ser Asp Ser Trp Ala Asp Pro Gly Lys
     85                  90                  95
```

```
Gln Thr Lys Pro Ala Ala Trp Ala Gly Tyr Asn Phe Gln Gln Leu Met
100                 105                 110                 115

Asp Ala Val Trp Asn Trp Thr Arg Glu Val Met Thr Thr Met Gln Ala
            120                 125                 130

Ser Gly Val Thr Pro Asp Trp Val Gln Ile Gly Asn Glu Thr Asn Asn
            135                 140                 145

Gly Met Leu Trp Asp Asp Gly Lys Ala Ser Leu Ser Met Lys Asn Tyr
            150                 155                 160

Ala Trp Leu Val Asn Thr Gly Asn Asn Ala Val Lys Ser Ile Ser Ser
165                 170                 175

Gly Thr Lys Thr Ile Val His Leu Ala Asn Gly Tyr Asp Asn Ser Leu
180                 185                 190                 195

Phe Val Trp Asn Ile Gly Gly Leu Ile Ala Asn Gly Ala Thr Phe Asp
            200                 205                 210

Ile Ile Gly Met Ser Leu Tyr Pro Ser Ala Ser Asp Trp Ser Ser Lys
            215                 220                 225

Val Thr Gln Thr Ile Ser Asn Ala Asn Asp Met Ile Ser Arg Tyr Gly
            230                 235                 240

Lys Pro Ile Met Ile Thr Glu Ile Gly Met Asp Tyr Asn Gln Pro Ser
245                 250                 255

Ala Ala Lys Ser Phe Val Ala Asp Ile Lys Thr Lys Ile Arg Ser Leu
260                 265                 270                 275

Ser Gly Gly Arg Gly Leu Gly Val Phe Tyr Trp Glu Pro Glu Ala Thr
            280                 285                 290

Pro Gly Tyr Asn Gly Gly Tyr Asn Lys Gly Ala Trp Gln Ala Asp Met
            295                 300                 305

Lys Pro Thr Ile Ala Leu Glu Gly Phe Leu Asn
            310                 315

<210> SEQ ID NO 7
<211> LENGTH: 318
<212> TYPE: PRT
<213> ORGANISM: Cohnella xylanilytica
<220> FEATURE:
<221> NAME/KEY: mat_peptide
<222> LOCATION: (1)..(318)

<400> SEQUENCE: 7

Ala Ala Ala Pro Ser Phe Ala Lys Gly Ala Asp Ile Ser Trp Val Pro
1               5                   10                  15

Gly Met Glu Ala Gln Gly Tyr Arg Trp Lys Asp Lys Asn Gly Val Gln
            20                  25                  30

Arg Asp Ile Leu Asp Ile Leu Lys Asn Asp Tyr Gln Ile Asn Ser Val
            35                  40                  45

Arg Ile Arg Val Trp Val Asn Pro Ser Ser Ser Tyr Thr Asn Gly Tyr
50                  55                  60

Leu Asn Lys Asp Arg Ala Ala Ala Leu Ala Lys Arg Ala Lys Ala Ala
65                  70                  75                  80

Gly Leu Ser Val Met Leu Thr Leu His Tyr Ser Asp Ser Trp Ala Asp
            85                  90                  95

Pro Gly Lys Gln Thr Lys Pro Ala Ala Trp Ala Gly Tyr Asn Phe Gln
            100                 105                 110

Gln Leu Met Asp Ala Val Trp Asn Trp Thr Arg Glu Val Met Thr Thr
            115                 120                 125

Met Gln Ala Ser Gly Val Thr Pro Asp Trp Val Gln Ile Gly Asn Glu
```

```
                130                 135                 140
Thr Asn Asn Gly Met Leu Trp Asp Asp Gly Lys Ala Ser Leu Ser Met
145                 150                 155                 160

Lys Asn Tyr Ala Trp Leu Val Asn Thr Gly Asn Asn Ala Val Lys Ser
                165                 170                 175

Ile Ser Ser Gly Thr Lys Thr Ile Val His Leu Ala Asn Gly Tyr Asp
                180                 185                 190

Asn Ser Leu Phe Val Trp Asn Ile Gly Gly Leu Ile Ala Asn Gly Ala
                195                 200                 205

Thr Phe Asp Ile Ile Gly Met Ser Leu Tyr Pro Ser Ala Ser Asp Trp
                210                 215                 220

Ser Ser Lys Val Thr Gln Thr Ile Ser Asn Ala Asn Asp Met Ile Ser
225                 230                 235                 240

Arg Tyr Gly Lys Pro Ile Met Ile Thr Glu Ile Gly Met Asp Tyr Asn
                245                 250                 255

Gln Pro Ser Ala Ala Lys Ser Phe Val Ala Asp Ile Lys Thr Lys Ile
                260                 265                 270

Arg Ser Leu Ser Gly Gly Arg Gly Leu Gly Val Phe Tyr Trp Glu Pro
                275                 280                 285

Glu Ala Thr Pro Gly Tyr Asn Gly Gly Tyr Asn Lys Gly Ala Trp Gln
                290                 295                 300

Ala Asp Met Lys Pro Thr Ile Ala Leu Glu Gly Phe Leu Asn
305                 310                 315

<210> SEQ ID NO 8
<211> LENGTH: 326
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(326)

<400> SEQUENCE: 8

His His His His His His Pro Arg Ala Ala Ala Pro Ser Phe Ala Lys
1               5                   10                  15

Gly Ala Asp Ile Ser Trp Val Pro Gly Met Glu Ala Gln Gly Tyr Arg
                20                  25                  30

Trp Lys Asp Lys Asn Gly Val Gln Arg Asp Ile Leu Asp Ile Leu Lys
                35                  40                  45

Asn Asp Tyr Gln Ile Asn Ser Val Arg Ile Arg Val Trp Val Asn Pro
                50                  55                  60

Ser Ser Ser Tyr Thr Asn Gly Tyr Leu Asn Lys Asp Arg Ala Ala Ala
65                  70                  75                  80

Leu Ala Lys Arg Ala Lys Ala Ala Gly Leu Ser Val Met Leu Thr Leu
                85                  90                  95

His Tyr Ser Asp Ser Trp Ala Asp Pro Gly Lys Gln Thr Lys Pro Ala
                100                 105                 110

Ala Trp Ala Gly Tyr Asn Phe Gln Gln Leu Met Asp Ala Val Trp Asn
                115                 120                 125

Trp Thr Arg Glu Val Met Thr Thr Met Gln Ala Ser Gly Val Thr Pro
                130                 135                 140

Asp Trp Val Gln Ile Gly Asn Glu Thr Asn Asn Gly Met Leu Trp Asp
145                 150                 155                 160

Asp Gly Lys Ala Ser Leu Ser Met Lys Asn Tyr Ala Trp Leu Val Asn
```

```
                    165                 170                 175
Thr Gly Asn Asn Ala Val Lys Ser Ile Ser Gly Thr Lys Thr Ile
                180                 185                 190

Val His Leu Ala Asn Gly Tyr Asp Asn Ser Leu Phe Val Trp Asn Ile
            195                 200                 205

Gly Gly Leu Ile Ala Asn Gly Ala Thr Phe Asp Ile Ile Gly Met Ser
        210                 215                 220

Leu Tyr Pro Ser Ala Ser Asp Trp Ser Ser Lys Val Thr Gln Thr Ile
225                 230                 235                 240

Ser Asn Ala Asn Asp Met Ile Ser Arg Tyr Gly Lys Pro Ile Met Ile
                245                 250                 255

Thr Glu Ile Gly Met Asp Tyr Asn Gln Pro Ser Ala Ala Lys Ser Phe
            260                 265                 270

Val Ala Asp Ile Lys Thr Lys Ile Arg Ser Leu Ser Gly Gly Arg Gly
        275                 280                 285

Leu Gly Val Phe Tyr Trp Glu Pro Glu Ala Thr Pro Gly Tyr Asn Gly
    290                 295                 300

Gly Tyr Asn Lys Gly Ala Trp Gln Ala Asp Met Lys Pro Thr Ile Ala
305                 310                 315                 320

Leu Glu Gly Phe Leu Asn
                325

<210> SEQ ID NO 9
<211> LENGTH: 1050
<212> TYPE: DNA
<213> ORGANISM: Paenibacillus tundrae
<220> FEATURE:
<221> NAME/KEY: CDS
<222> LOCATION: (1)..(1047)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1047)

<400> SEQUENCE: 9 atg ttc aaa aat gta agg ggt ttc aag aca tcc atc atg ttg gct ttt      48
Met Phe Lys Asn Val Arg Gly Phe Lys Thr Ser Ile Met Leu Ala Phe
            -30                 -25                 -20 gtt ttg tta ttc acc tcc atc atg ttg ccc gca ggt cag cat gcc agc      96
Val Leu Leu Phe Thr Ser Ile Met Leu Pro Ala Gly Gln His Ala Ser
        -15                 -10                  -5 gca gca cca agt ttc gcc aaa gga gcc gac atc agc tgg gtt ccc gga     144
Ala Ala Pro Ser Phe Ala Lys Gly Ala Asp Ile Ser Trp Val Pro Gly
 -1   1               5                  10                  15 atg gaa gcc caa ggt tac aaa tgg aaa gat aaa aac ggg gta cag cgt     192
Met Glu Ala Gln Gly Tyr Lys Trp Lys Asp Lys Asn Gly Val Gln Arg
                 20                  25                  30 gac atc att gat att ttg aaa aag gac tat caa att aac tcc gtt cgc     240
Asp Ile Ile Asp Ile Leu Lys Lys Asp Tyr Gln Ile Asn Ser Val Arg
             35                  40                  45 att cgg gtc ttt gtt aat cct tcg aat gat tat ggg aac ggt tac atg     288
Ile Arg Val Phe Val Asn Pro Ser Asn Asp Tyr Gly Asn Gly Tyr Met
         50                  55                  60 aat aag gaa cgt gcg gct aca ctc gca caa cgt gct aaa aat gcc ggc     336
Asn Lys Glu Arg Ala Ala Thr Leu Ala Gln Arg Ala Lys Asn Ala Gly
     65                  70                  75 atg agc gta atg ctt acc ctg cat tac agc gac tct tgg gca gac cct     384
Met Ser Val Met Leu Thr Leu His Tyr Ser Asp Ser Trp Ala Asp Pro
```

```
                80                  85                  90                  95
ggt caa cag acc aaa cca gct gcc tgg aaa aac tat acc ttc caa cag       432
Gly Gln Gln Thr Lys Pro Ala Ala Trp Lys Asn Tyr Thr Phe Gln Gln
                100                 105                 110 ctc atg gac gca gtg tgg aat cac aca cgt gat gtc atg act gcg atg       480
Leu Met Asp Ala Val Trp Asn His Thr Arg Asp Val Met Thr Ala Met
            115                 120                 125 caa agc aaa ggc gtt acc ccg gac tgg gta cag atc ggg aat gaa aca       528
Gln Ser Lys Gly Val Thr Pro Asp Trp Val Gln Ile Gly Asn Glu Thr
        130                 135                 140 agt aac ggc atg tta tgg gaa gat ggt aaa gca tcc acc aac atg aaa       576
Ser Asn Gly Met Leu Trp Glu Asp Gly Lys Ala Ser Thr Asn Met Lys
    145                 150                 155 aac tat gcg tgg ctg gtg aac aca ggc cat aat gca gtg aaa tcc ctg       624
Asn Tyr Ala Trp Leu Val Asn Thr Gly His Asn Ala Val Lys Ser Leu
160                 165                 170                 175 agc agt ggc acc aaa acc att gtg cac ctg gca ggt ggg gat gat aac       672
Ser Ser Gly Thr Lys Thr Ile Val His Leu Ala Gly Gly Asp Asp Asn
                180                 185                 190 gcc ctc tat gta tgg aat att ggt ggt ttg atc aat aat gga gct aac       720
Ala Leu Tyr Val Trp Asn Ile Gly Gly Leu Ile Asn Asn Gly Ala Asn
            195                 200                 205 ttt gac atg att gcc atg tcc ctc tac cct tcg gct tcc ggc tgg aac       768
Phe Asp Met Ile Ala Met Ser Leu Tyr Pro Ser Ala Ser Gly Trp Asn
        210                 215                 220 aca gct gtg acg aat acg gta aac aat gcc aag gat atg atc aac cgt       816
Thr Ala Val Thr Asn Thr Val Asn Asn Ala Lys Asp Met Ile Asn Arg
    225                 230                 235 tat ggc aaa gag atc atc atc tcc gaa att ggc atg gat aat aac cag       864
Tyr Gly Lys Glu Ile Ile Ile Ser Glu Ile Gly Met Asp Asn Asn Gln
240                 245                 250                 255 gct gca gca ggt aaa agt ttt gtt gcg gcg atg aaa aac caa atc cgc       912
Ala Ala Ala Gly Lys Ser Phe Val Ala Ala Met Lys Asn Gln Ile Arg
                260                 265                 270 aat ctg ccg aat ggc aaa gga aaa ggc gta ttc tac tgg gag cct cag       960
Asn Leu Pro Asn Gly Lys Gly Lys Gly Val Phe Tyr Trp Glu Pro Gln
            275                 280                 285 gct aca cca ggt tat aac agt ggc tac ggc aaa ggc gct tgg caa tcg      1008
Ala Thr Pro Gly Tyr Asn Ser Gly Tyr Gly Lys Gly Ala Trp Gln Ser
        290                 295                 300 aat atg atg ccg aca gtt gtc atg gaa gga ttt att gac tag              1050
Asn Met Met Pro Thr Val Val Met Glu Gly Phe Ile Asp
    305                 310                 315

<210> SEQ ID NO 10
<211> LENGTH: 349
<212> TYPE: PRT
<213> ORGANISM: Paenibacillus tundrae

<400> SEQUENCE: 10

Met Phe Lys Asn Val Arg Gly Phe Lys Thr Ser Ile Met Leu Ala Phe
            -30                 -25                 -20

Val Leu Leu Phe Thr Ser Ile Met Leu Pro Ala Gly Gln His Ala Ser
        -15                 -10                 -5

Ala Ala Pro Ser Phe Ala Lys Gly Ala Asp Ile Ser Trp Val Pro Gly
-1   1               5                   10                  15

Met Glu Ala Gln Gly Tyr Lys Trp Lys Asp Lys Asn Gly Val Gln Arg
                20                  25                  30

Asp Ile Ile Asp Ile Leu Lys Lys Asp Tyr Gln Ile Asn Ser Val Arg
```

```
                 35                  40                  45
Ile Arg Val Phe Val Asn Pro Ser Asn Asp Tyr Gly Asn Gly Tyr Met
                50                  55                  60

Asn Lys Glu Arg Ala Ala Thr Leu Ala Gln Arg Ala Lys Asn Ala Gly
 65                  70                  75

Met Ser Val Met Leu Thr Leu His Tyr Ser Asp Ser Trp Ala Asp Pro
 80                  85                  90                  95

Gly Gln Gln Thr Lys Pro Ala Ala Trp Lys Asn Tyr Thr Phe Gln Gln
                100                 105                 110

Leu Met Asp Ala Val Trp Asn His Thr Arg Asp Val Met Thr Ala Met
                115                 120                 125

Gln Ser Lys Gly Val Thr Pro Asp Trp Val Gln Ile Gly Asn Glu Thr
                130                 135                 140

Ser Asn Gly Met Leu Trp Glu Asp Gly Lys Ala Ser Thr Asn Met Lys
                145                 150                 155

Asn Tyr Ala Trp Leu Val Asn Thr Gly His Asn Ala Val Lys Ser Leu
160                 165                 170                 175

Ser Ser Gly Thr Lys Thr Ile Val His Leu Ala Gly Gly Asp Asp Asn
                180                 185                 190

Ala Leu Tyr Val Trp Asn Ile Gly Gly Leu Ile Asn Asn Gly Ala Asn
                195                 200                 205

Phe Asp Met Ile Ala Met Ser Leu Tyr Pro Ser Ala Ser Gly Trp Asn
                210                 215                 220

Thr Ala Val Thr Asn Thr Val Asn Asn Ala Lys Asp Met Ile Asn Arg
                225                 230                 235

Tyr Gly Lys Glu Ile Ile Ile Ser Glu Ile Gly Met Asp Asn Asn Gln
240                 245                 250                 255

Ala Ala Ala Gly Lys Ser Phe Val Ala Ala Met Lys Asn Gln Ile Arg
                260                 265                 270

Asn Leu Pro Asn Gly Lys Gly Lys Gly Val Phe Tyr Trp Glu Pro Gln
                275                 280                 285

Ala Thr Pro Gly Tyr Asn Ser Gly Tyr Gly Lys Gly Ala Trp Gln Ser
                290                 295                 300

Asn Met Met Pro Thr Val Val Met Glu Gly Phe Ile Asp
                305                 310                 315

<210> SEQ ID NO 11
<211> LENGTH: 316
<212> TYPE: PRT
<213> ORGANISM: Paenibacillus tundrae
<220> FEATURE:
<221> NAME/KEY: mat_peptide
<222> LOCATION: (1)..(316)

<400> SEQUENCE: 11

Ala Pro Ser Phe Ala Lys Gly Ala Asp Ile Ser Trp Val Pro Gly Met
 1               5                  10                  15

Glu Ala Gln Gly Tyr Lys Trp Lys Asp Lys Asn Gly Val Gln Arg Asp
                20                  25                  30

Ile Ile Asp Ile Leu Lys Lys Asp Tyr Gln Ile Asn Ser Val Arg Ile
                35                  40                  45

Arg Val Phe Val Asn Pro Ser Asn Asp Tyr Gly Asn Gly Tyr Met Asn
                50                  55                  60

Lys Glu Arg Ala Ala Thr Leu Ala Gln Arg Ala Lys Asn Ala Gly Met
 65                  70                  75                  80
```

Ser Val Met Leu Thr Leu His Tyr Ser Asp Ser Trp Ala Asp Pro Gly
            85                  90                  95

Gln Gln Thr Lys Pro Ala Ala Trp Lys Asn Tyr Thr Phe Gln Gln Leu
        100                 105                 110

Met Asp Ala Val Trp Asn His Thr Arg Asp Val Met Thr Ala Met Gln
        115                 120                 125

Ser Lys Gly Val Thr Pro Asp Trp Val Gln Ile Gly Asn Glu Thr Ser
        130                 135                 140

Asn Gly Met Leu Trp Glu Asp Gly Lys Ala Ser Thr Asn Met Lys Asn
145                 150                 155                 160

Tyr Ala Trp Leu Val Asn Thr Gly His Asn Ala Val Lys Ser Leu Ser
                165                 170                 175

Ser Gly Thr Lys Thr Ile Val His Leu Ala Gly Gly Asp Asp Asn Ala
        180                 185                 190

Leu Tyr Val Trp Asn Ile Gly Gly Leu Ile Asn Asn Gly Ala Asn Phe
        195                 200                 205

Asp Met Ile Ala Met Ser Leu Tyr Pro Ser Ala Ser Gly Trp Asn Thr
        210                 215                 220

Ala Val Thr Asn Thr Val Asn Asn Ala Lys Asp Met Ile Asn Arg Tyr
225                 230                 235                 240

Gly Lys Glu Ile Ile Ile Ser Glu Ile Gly Met Asp Asn Asn Gln Ala
                245                 250                 255

Ala Ala Gly Lys Ser Phe Val Ala Ala Met Lys Asn Gln Ile Arg Asn
        260                 265                 270

Leu Pro Asn Gly Lys Gly Lys Gly Val Phe Tyr Trp Glu Pro Gln Ala
        275                 280                 285

Thr Pro Gly Tyr Asn Ser Gly Tyr Gly Lys Gly Ala Trp Gln Ser Asn
        290                 295                 300

Met Met Pro Thr Val Val Met Glu Gly Phe Ile Asp
305                 310                 315

<210> SEQ ID NO 12
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 12

His His His His His Pro Arg Ala Pro Ser Phe Ala Lys Gly Ala
1               5                   10                  15

Asp Ile Ser Trp Val Pro Gly Met Glu Ala Gln Gly Tyr Lys Trp Lys
                20                  25                  30

Asp Lys Asn Gly Val Gln Arg Asp Ile Ile Asp Ile Leu Lys Lys Asp
        35                  40                  45

Tyr Gln Ile Asn Ser Val Arg Ile Arg Val Phe Val Asn Pro Ser Asn
        50                  55                  60

Asp Tyr Gly Asn Gly Tyr Met Asn Lys Glu Arg Ala Ala Thr Leu Ala
65                  70                  75                  80

Gln Arg Ala Lys Asn Ala Gly Met Ser Val Met Leu Thr Leu His Tyr
                85                  90                  95

Ser Asp Ser Trp Ala Asp Pro Gly Gln Gln Thr Lys Pro Ala Ala Trp
            100                 105                 110

```
Lys Asn Tyr Thr Phe Gln Gln Leu Met Asp Ala Val Trp Asn His Thr
            115                 120                 125

Arg Asp Val Met Thr Ala Met Gln Ser Lys Gly Val Thr Pro Asp Trp
130                 135                 140

Val Gln Ile Gly Asn Glu Thr Ser Asn Gly Met Leu Trp Glu Asp Gly
145                 150                 155                 160

Lys Ala Ser Thr Asn Met Lys Asn Tyr Ala Trp Leu Val Asn Thr Gly
                165                 170                 175

His Asn Ala Val Lys Ser Leu Ser Ser Gly Thr Lys Thr Ile Val His
            180                 185                 190

Leu Ala Gly Gly Asp Asp Asn Ala Leu Tyr Val Trp Asn Ile Gly Gly
        195                 200                 205

Leu Ile Asn Asn Gly Ala Asn Phe Asp Met Ile Ala Met Ser Leu Tyr
    210                 215                 220

Pro Ser Ala Ser Gly Trp Asn Thr Ala Val Thr Asn Thr Val Asn Asn
225                 230                 235                 240

Ala Lys Asp Met Ile Asn Arg Tyr Gly Lys Glu Ile Ile Ile Ser Glu
                245                 250                 255

Ile Gly Met Asp Asn Asn Gln Ala Ala Ala Gly Lys Ser Phe Val Ala
            260                 265                 270

Ala Met Lys Asn Gln Ile Arg Asn Leu Pro Asn Gly Lys Gly Lys Gly
        275                 280                 285

Val Phe Tyr Trp Glu Pro Gln Ala Thr Pro Gly Tyr Asn Ser Gly Tyr
    290                 295                 300

Gly Lys Gly Ala Trp Gln Ser Asn Met Met Pro Thr Val Val Met Glu
305                 310                 315                 320

Gly Phe Ile Asp

<210> SEQ ID NO 13
<211> LENGTH: 1056
<212> TYPE: DNA
<213> ORGANISM: Paenibacillus barcinonensis
<220> FEATURE:
<221> NAME/KEY: CDS
<222> LOCATION: (1)..(1053)
<220> FEATURE:
<221> NAME/KEY: sig_peptide
<222> LOCATION: (1)..(105)
<220> FEATURE:
<221> NAME/KEY: mat_peptide
<222> LOCATION: (106)..(1053)

<400> SEQUENCE: 13 atg ttt aaa aat gta agg ggt ttc aag gtt aag aca agc gtt ctg ctg      48
Met Phe Lys Asn Val Arg Gly Phe Lys Val Lys Thr Ser Val Leu Leu
-35                 -30                 -25                 -20 gca ttg gtt ttg tta ttt act tct att ctg ctg cct gca ggc cag cac      96
Ala Leu Val Leu Leu Phe Thr Ser Ile Leu Leu Pro Ala Gly Gln His
            -15                 -10                  -5 gcc agc gcc gca ccg agc ttt gcc aag gga gct gac atc agc tgg gtt     144
Ala Ser Ala Ala Pro Ser Phe Ala Lys Gly Ala Asp Ile Ser Trp Val
        -1   1               5                  10 ccc ggc atg gag gct caa ggg tac aaa tgg aag gat aaa aac ggg gta     192
Pro Gly Met Glu Ala Gln Gly Tyr Lys Trp Lys Asp Lys Asn Gly Val
    15                  20                  25 caa cgt gat att att gat att ttg aaa aag gat tac caa att aac tcc     240
Gln Arg Asp Ile Ile Asp Ile Leu Lys Lys Asp Tyr Gln Ile Asn Ser
30                  35                  40                  45 gtt cgt att cgg gta ttc gtt aat cca tcg aac gat tat ggt aac ggt     288
```

| | | | | | | | | | | | | |
|---|---|---|---|---|---|---|---|---|---|---|---|---|
| Val | Arg | Ile | Arg | Val | Phe | Val | Asn | Pro | Ser | Asn | Asp | Tyr | Gly | Asn | Gly |
| | | | | 50 | | | | 55 | | | | 60 | | | |

```
tac atg aat aag gat cgc gcg gct gct ctt gca cag cgt gcc aaa aat     336
Tyr Met Asn Lys Asp Arg Ala Ala Ala Leu Ala Gln Arg Ala Lys Asn
             65                  70                  75 gca ggc atg agt gtc atg ctc aca ctt cac tac agc gat tcc tgg gca     384
Ala Gly Met Ser Val Met Leu Thr Leu His Tyr Ser Asp Ser Trp Ala
         80                  85                  90 gac cca ggc aaa caa agc aaa cca gcg gca tgg aaa aat tac tcc ttc     432
Asp Pro Gly Lys Gln Ser Lys Pro Ala Ala Trp Lys Asn Tyr Ser Phe
     95                 100                 105 caa cag ctc atg gac gct gtc tgg aat tat aca cgt gaa gtg atg aca     480
Gln Gln Leu Met Asp Ala Val Trp Asn Tyr Thr Arg Glu Val Met Thr
110                 115                 120                 125 gct atg caa aac aaa ggg gtt acg ccg gac tgg gta cag atc ggt aac     528
Ala Met Gln Asn Lys Gly Val Thr Pro Asp Trp Val Gln Ile Gly Asn
                130                 135                 140 gaa aca agc aac ggc atg tta tgg gat gac ggg aaa gcc tct gtt aac     576
Glu Thr Ser Asn Gly Met Leu Trp Asp Asp Gly Lys Ala Ser Val Asn
            145                 150                 155 atg aaa aac tat gca tgg ctc gtg aac aca gga cat aat gcg gta aaa     624
Met Lys Asn Tyr Ala Trp Leu Val Asn Thr Gly His Asn Ala Val Lys
        160                 165                 170 tcc att agc agc ggc acc aaa acg atc gtt cat ctg gcc ggt ggc gac     672
Ser Ile Ser Ser Gly Thr Lys Thr Ile Val His Leu Ala Gly Gly Asp
    175                 180                 185 gac aat gcg ctg tat gtc tgg aat att ggc ggc ctg atc aac aac ggc     720
Asp Asn Ala Leu Tyr Val Trp Asn Ile Gly Gly Leu Ile Asn Asn Gly
190                 195                 200                 205 gct aac ttt gac atg atc gct atg tcg ctt tac cct tcc gct tcc ggc     768
Ala Asn Phe Asp Met Ile Ala Met Ser Leu Tyr Pro Ser Ala Ser Gly
                210                 215                 220 tgg aat act gcg gtg acc aac acg gtc aac aat gca aag gat atg atc     816
Trp Asn Thr Ala Val Thr Asn Thr Val Asn Asn Ala Lys Asp Met Ile
            225                 230                 235 aat cgg tac ggc aaa gag atc atg atc tcc gaa att ggc atg gac aac     864
Asn Arg Tyr Gly Lys Glu Ile Met Ile Ser Glu Ile Gly Met Asp Asn
        240                 245                 250 aat cag gcg gcg gca ggc aaa agc ttc gta gct gcg atg aaa aat caa     912
Asn Gln Ala Ala Ala Gly Lys Ser Phe Val Ala Ala Met Lys Asn Gln
    255                 260                 265 att cgc aat ctg cca aat ggc aaa gga aaa ggc gta ttc tac tgg gag     960
Ile Arg Asn Leu Pro Asn Gly Lys Gly Lys Gly Val Phe Tyr Trp Glu
270                 275                 280                 285 ccg cag gct aca cct ggc tat aac ggt gga tac ggt aaa ggc gct tgg    1008
Pro Gln Ala Thr Pro Gly Tyr Asn Gly Gly Tyr Gly Lys Gly Ala Trp
                290                 295                 300 cag tcc aac atg atg cca aca gcc gtc atg gaa ggg ttt att gac taa    1056
Gln Ser Asn Met Met Pro Thr Ala Val Met Glu Gly Phe Ile Asp
            305                 310                 315
```

<210> SEQ ID NO 14
<211> LENGTH: 351
<212> TYPE: PRT
<213> ORGANISM: Paenibacillus barcinonensis

<400> SEQUENCE: 14

```
Met Phe Lys Asn Val Arg Gly Phe Lys Val Lys Thr Ser Val Leu Leu
-35                 -30                 -25                 -20

Ala Leu Val Leu Leu Phe Thr Ser Ile Leu Leu Pro Ala Gly Gln His
```

```
                      -15              -10                -5
Ala Ser Ala Ala Pro Ser Phe Ala Lys Gly Ala Asp Ile Ser Trp Val
        -1  1           5                   10

Pro Gly Met Glu Ala Gln Gly Tyr Lys Trp Lys Asp Lys Asn Gly Val
        15              20              25

Gln Arg Asp Ile Ile Asp Ile Leu Lys Lys Asp Tyr Gln Ile Asn Ser
30                      35              40                  45

Val Arg Ile Arg Val Phe Val Asn Pro Ser Asn Asp Tyr Gly Asn Gly
                50                  55                  60

Tyr Met Asn Lys Asp Arg Ala Ala Leu Ala Gln Arg Ala Lys Asn
            65              70              75

Ala Gly Met Ser Val Met Leu Thr Leu His Tyr Ser Asp Ser Trp Ala
        80              85                  90

Asp Pro Gly Lys Gln Ser Lys Pro Ala Ala Trp Lys Asn Tyr Ser Phe
    95                  100                 105

Gln Gln Leu Met Asp Ala Val Trp Asn Tyr Thr Arg Glu Val Met Thr
110             115                 120                 125

Ala Met Gln Asn Lys Gly Val Thr Pro Asp Trp Val Gln Ile Gly Asn
            130                 135                 140

Glu Thr Ser Asn Gly Met Leu Trp Asp Asp Gly Lys Ala Ser Val Asn
                145                 150                 155

Met Lys Asn Tyr Ala Trp Leu Val Asn Thr Gly His Asn Ala Val Lys
            160                 165                 170

Ser Ile Ser Ser Gly Thr Lys Thr Ile Val His Leu Ala Gly Gly Asp
    175                 180                 185

Asp Asn Ala Leu Tyr Val Trp Asn Ile Gly Gly Leu Ile Asn Asn Gly
190                 195                 200                 205

Ala Asn Phe Asp Met Ile Ala Met Ser Leu Tyr Pro Ser Ala Ser Gly
                210                 215                 220

Trp Asn Thr Ala Val Thr Asn Thr Val Asn Asn Ala Lys Asp Met Ile
                225                 230                 235

Asn Arg Tyr Gly Lys Glu Ile Met Ile Ser Glu Ile Gly Met Asp Asn
            240                 245                 250

Asn Gln Ala Ala Ala Gly Lys Ser Phe Val Ala Ala Met Lys Asn Gln
    255                 260                 265

Ile Arg Asn Leu Pro Asn Gly Lys Gly Lys Gly Val Phe Tyr Trp Glu
270                 275                 280                 285

Pro Gln Ala Thr Pro Gly Tyr Asn Gly Gly Tyr Gly Lys Gly Ala Trp
                290                 295                 300

Gln Ser Asn Met Met Pro Thr Ala Val Met Glu Gly Phe Ile Asp
            305                 310                 315
```

<210> SEQ ID NO 15
<211> LENGTH: 316
<212> TYPE: PRT
<213> ORGANISM: Paenibacillus barcinonensis

<400> SEQUENCE: 15

```
Ala Pro Ser Phe Ala Lys Gly Ala Asp Ile Ser Trp Val Pro Gly Met
1               5                   10                  15

Glu Ala Gln Gly Tyr Lys Trp Lys Asp Lys Asn Gly Val Gln Arg Asp
            20                  25                  30

Ile Ile Asp Ile Leu Lys Lys Asp Tyr Gln Ile Asn Ser Val Arg Ile
        35                  40                  45
```

Arg Val Phe Val Asn Pro Ser Asn Asp Tyr Gly Asn Gly Tyr Met Asn
                50                  55                  60

Lys Asp Arg Ala Ala Leu Ala Gln Arg Ala Lys Asn Ala Gly Met
 65              70                  75                  80

Ser Val Met Leu Thr Leu His Tyr Ser Asp Ser Trp Ala Asp Pro Gly
                85                  90                  95

Lys Gln Ser Lys Pro Ala Ala Trp Lys Asn Tyr Ser Phe Gln Gln Leu
                100                 105                 110

Met Asp Ala Val Trp Asn Tyr Thr Arg Glu Val Met Thr Ala Met Gln
                115                 120                 125

Asn Lys Gly Val Thr Pro Asp Trp Val Gln Ile Gly Asn Glu Thr Ser
130                 135                 140

Asn Gly Met Leu Trp Asp Asp Gly Lys Ala Ser Val Asn Met Lys Asn
145                 150                 155                 160

Tyr Ala Trp Leu Val Asn Thr Gly His Asn Ala Val Lys Ser Ile Ser
                165                 170                 175

Ser Gly Thr Lys Thr Ile Val His Leu Ala Gly Gly Asp Asp Asn Ala
                180                 185                 190

Leu Tyr Val Trp Asn Ile Gly Gly Leu Ile Asn Asn Gly Ala Asn Phe
                195                 200                 205

Asp Met Ile Ala Met Ser Leu Tyr Pro Ser Ala Ser Gly Trp Asn Thr
210                 215                 220

Ala Val Thr Asn Thr Val Asn Asn Ala Lys Asp Met Ile Asn Arg Tyr
225                 230                 235                 240

Gly Lys Glu Ile Met Ile Ser Glu Ile Gly Met Asp Asn Asn Gln Ala
                245                 250                 255

Ala Ala Gly Lys Ser Phe Val Ala Ala Met Lys Asn Gln Ile Arg Asn
                260                 265                 270

Leu Pro Asn Gly Lys Gly Lys Gly Val Phe Tyr Trp Glu Pro Gln Ala
                275                 280                 285

Thr Pro Gly Tyr Asn Gly Gly Tyr Gly Lys Gly Ala Trp Gln Ser Asn
                290                 295                 300

Met Met Pro Thr Ala Val Met Glu Gly Phe Ile Asp
305                 310                 315

<210> SEQ ID NO 16
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 16

His His His His His His Pro Arg Ala Pro Ser Phe Ala Lys Gly Ala
 1               5                  10                  15

Asp Ile Ser Trp Val Pro Gly Met Glu Ala Gln Gly Tyr Lys Trp Lys
                20                  25                  30

Asp Lys Asn Gly Val Gln Arg Asp Ile Ile Asp Ile Leu Lys Lys Asp
                35                  40                  45

Tyr Gln Ile Asn Ser Val Arg Ile Arg Val Phe Val Asn Pro Ser Asn
                50                  55                  60

Asp Tyr Gly Asn Gly Tyr Met Asn Lys Asp Arg Ala Ala Leu Ala
 65                 70                  75                  80

```
Gln Arg Ala Lys Asn Ala Gly Met Ser Val Met Leu Thr Leu His Tyr
                85                  90                  95

Ser Asp Ser Trp Ala Asp Pro Gly Lys Gln Ser Lys Pro Ala Ala Trp
            100                 105                 110

Lys Asn Tyr Ser Phe Gln Gln Leu Met Asp Ala Val Trp Asn Tyr Thr
        115                 120                 125

Arg Glu Val Met Thr Ala Met Gln Asn Lys Gly Val Thr Pro Asp Trp
    130                 135                 140

Val Gln Ile Gly Asn Glu Thr Ser Asn Gly Met Leu Trp Asp Asp Gly
145                 150                 155                 160

Lys Ala Ser Val Asn Met Lys Asn Tyr Ala Trp Leu Val Asn Thr Gly
                165                 170                 175

His Asn Ala Val Lys Ser Ile Ser Ser Gly Thr Lys Thr Ile Val His
            180                 185                 190

Leu Ala Gly Gly Asp Asp Asn Ala Leu Tyr Val Trp Asn Ile Gly Gly
        195                 200                 205

Leu Ile Asn Asn Gly Ala Asn Phe Asp Met Ile Ala Met Ser Leu Tyr
    210                 215                 220

Pro Ser Ala Ser Gly Trp Asn Thr Ala Val Thr Asn Thr Val Asn Asn
225                 230                 235                 240

Ala Lys Asp Met Ile Asn Arg Tyr Gly Lys Glu Ile Met Ile Ser Glu
                245                 250                 255

Ile Gly Met Asp Asn Asn Gln Ala Ala Ala Gly Lys Ser Phe Val Ala
            260                 265                 270

Ala Met Lys Asn Gln Ile Arg Asn Leu Pro Asn Gly Lys Gly Lys Gly
        275                 280                 285

Val Phe Tyr Trp Glu Pro Gln Ala Thr Pro Gly Tyr Asn Gly Gly Tyr
    290                 295                 300

Gly Lys Gly Ala Trp Gln Ser Asn Met Met Pro Thr Ala Val Met Glu
305                 310                 315                 320

Gly Phe Ile Asp

<210> SEQ ID NO 17
<211> LENGTH: 1044
<212> TYPE: DNA
<213> ORGANISM: Paenibacillus sp-62603
<220> FEATURE:
<221> NAME/KEY: CDS
<222> LOCATION: (1)..(1041)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1041)

<400> SEQUENCE: 17 atg aaa cga agg ttt tac agt ttg acg ctt gtt gtc gcc ttg tta atg     48
Met Lys Arg Arg Phe Tyr Ser Leu Thr Leu Val Val Ala Leu Leu Met
    -30                 -25                 -20 act att ttt gga gtg aat ggg gga tct gtg ccg cag gtc agc gca gct     96
Thr Ile Phe Gly Val Asn Gly Gly Ser Val Pro Gln Val Ser Ala Ala
-15                 -10                  -5                 -1  1 cct gca ttc gcg aaa ggt gcg gac att agc tgg gta gtc ggc atg gag    144
Pro Ala Phe Ala Lys Gly Ala Asp Ile Ser Trp Val Val Gly Met Glu
            5                  10                  15 gcg caa ggg tat acg tgg aag gac aaa aac ggc gta act agg gac att    192
Ala Gln Gly Tyr Thr Trp Lys Asp Lys Asn Gly Val Thr Arg Asp Ile
        20                  25                  30
```

-continued

| | | |
|---|---|---|
| att caa att ttg aag cag gat tac caa atc aac tcc gta cgt att cga<br>Ile Gln Ile Leu Lys Gln Asp Tyr Gln Ile Asn Ser Val Arg Ile Arg<br>35                  40                  45 | 240 |
| gta ttc gtc aat cct tct tcg aac tat ggc aac ggg tat atg aat aaa<br>Val Phe Val Asn Pro Ser Ser Asn Tyr Gly Asn Gly Tyr Met Asn Lys<br>50                  55                  60                  65 | 288 |
| gat cgc gct gca acc ttg gcg aag cgg gcg aag gat gct ggg atg agc<br>Asp Arg Ala Ala Thr Leu Ala Lys Arg Ala Lys Asp Ala Gly Met Ser<br>          70                  75                  80 | 336 |
| gtc atg ctt aca ttg cat tac agc gat tcg tgg gcg gac ccc gga aaa<br>Val Met Leu Thr Leu His Tyr Ser Asp Ser Trp Ala Asp Pro Gly Lys<br>          85                  90                  95 | 384 |
| cag aca aag cca gcg gct tgg gca agc tat tcg ttc cag cag ctg atg<br>Gln Thr Lys Pro Ala Ala Trp Ala Ser Tyr Ser Phe Gln Gln Leu Met<br>          100                 105                 110 | 432 |
| gat gca gtt tat aat cat acg cgt gag gta atg aca gct atg caa agc<br>Asp Ala Val Tyr Asn His Thr Arg Glu Val Met Thr Ala Met Gln Ser<br>          115                 120                 125 | 480 |
| aaa ggt gtc aca ccg gat tgg gtg caa atc ggc aac gaa acg aac gat<br>Lys Gly Val Thr Pro Asp Trp Val Gln Ile Gly Asn Glu Thr Asn Asp<br>130                 135                 140                 145 | 528 |
| ggc atg ctc tgg aat gac ggg aaa gct tcc tta aac atg caa aac tac<br>Gly Met Leu Trp Asn Asp Gly Lys Ala Ser Leu Asn Met Gln Asn Tyr<br>          150                 155                 160 | 576 |
| gct tgg ctg atc aac act ggc aac aat gcg gtc aag tcc att agt tca<br>Ala Trp Leu Ile Asn Thr Gly Asn Asn Ala Val Lys Ser Ile Ser Ser<br>          165                 170                 175 | 624 |
| gct aca aaa acg att gtc cac ttg tcc aac ggt tat gac aac agt tta<br>Ala Thr Lys Thr Ile Val His Leu Ser Asn Gly Tyr Asp Asn Ser Leu<br>          180                 185                 190 | 672 |
| ttt gtc tgg aat atc ggc gga ctg atc gct aac gga gcg acc ttc gat<br>Phe Val Trp Asn Ile Gly Gly Leu Ile Ala Asn Gly Ala Thr Phe Asp<br>          195                 200                 205 | 720 |
| att atc ggg atg tca ctt tat cct acc agt gct gat tgg tcg act aag<br>Ile Ile Gly Met Ser Leu Tyr Pro Thr Ser Ala Asp Trp Ser Thr Lys<br>210                 215                 220                 225 | 768 |
| gtt acg caa acg gtc agc aac tcc aac aat atg ata tcg cgt tat ggc<br>Val Thr Gln Thr Val Ser Asn Ser Asn Asn Met Ile Ser Arg Tyr Gly<br>          230                 235                 240 | 816 |
| aag ccg gtt atg att acc gaa att ggt atg gat tat aac cag cct gcc<br>Lys Pro Val Met Ile Thr Glu Ile Gly Met Asp Tyr Asn Gln Pro Ala<br>          245                 250                 255 | 864 |
| gct gcc aaa agc ttt gtc gct gat ata aag aca aaa ata cgt aat att<br>Ala Ala Lys Ser Phe Val Ala Asp Ile Lys Thr Lys Ile Arg Asn Ile<br>          260                 265                 270 | 912 |
| gca ggt gga aaa ggg ctt ggc gtg ttt tat tgg gaa ccg gaa gcg acc<br>Ala Gly Gly Lys Gly Leu Gly Val Phe Tyr Trp Glu Pro Glu Ala Thr<br>275                 280                 285 | 960 |
| cct ggt tat aac gga ggt tat aat aag gga gct tgg cag gcg gac ggc<br>Pro Gly Tyr Asn Gly Gly Tyr Asn Lys Gly Ala Trp Gln Ala Asp Gly<br>290                 295                 300                 305 | 1008 |
| aaa cca aca att gcg ctt gac ggc ttc ttg aat taa<br>Lys Pro Thr Ile Ala Leu Asp Gly Phe Leu Asn<br>          310                 315 | 1044 |

<210> SEQ ID NO 18
<211> LENGTH: 347
<212> TYPE: PRT
<213> ORGANISM: Paenibacillus sp-62603

<400> SEQUENCE: 18

Met Lys Arg Arg Phe Tyr Ser Leu Thr Leu Val Val Ala Leu Leu Met
    -30                 -25                 -20

Thr Ile Phe Gly Val Asn Gly Ser Val Pro Gln Val Ser Ala Ala
    -15             -10              -5              -1   1

Pro Ala Phe Ala Lys Gly Ala Asp Ile Ser Trp Val Val Gly Met Glu
             5                  10                  15

Ala Gln Gly Tyr Thr Trp Lys Asp Lys Asn Gly Val Thr Arg Asp Ile
         20                  25                  30

Ile Gln Ile Leu Lys Gln Asp Tyr Gln Ile Asn Ser Val Arg Ile Arg
         35                  40                  45

Val Phe Val Asn Pro Ser Ser Asn Tyr Gly Asn Gly Tyr Met Asn Lys
50                  55                  60                  65

Asp Arg Ala Ala Thr Leu Ala Lys Arg Ala Lys Asp Ala Gly Met Ser
                 70                  75                  80

Val Met Leu Thr Leu His Tyr Ser Asp Ser Trp Ala Asp Pro Gly Lys
             85                  90                  95

Gln Thr Lys Pro Ala Ala Trp Ala Ser Tyr Ser Phe Gln Gln Leu Met
        100                 105                 110

Asp Ala Val Tyr Asn His Thr Arg Glu Val Met Thr Ala Met Gln Ser
        115                 120                 125

Lys Gly Val Thr Pro Asp Trp Val Gln Ile Gly Asn Glu Thr Asn Asp
130                 135                 140                 145

Gly Met Leu Trp Asn Asp Gly Lys Ala Ser Leu Asn Met Gln Asn Tyr
                150                 155                 160

Ala Trp Leu Ile Asn Thr Gly Asn Asn Ala Val Lys Ser Ile Ser Ser
            165                 170                 175

Ala Thr Lys Thr Ile Val His Leu Ser Asn Gly Tyr Asp Asn Ser Leu
        180                 185                 190

Phe Val Trp Asn Ile Gly Gly Leu Ile Ala Asn Gly Ala Thr Phe Asp
        195                 200                 205

Ile Ile Gly Met Ser Leu Tyr Pro Thr Ser Ala Asp Trp Ser Thr Lys
210                 215                 220                 225

Val Thr Gln Thr Val Ser Asn Ser Asn Met Ile Ser Arg Tyr Gly
                230                 235                 240

Lys Pro Val Met Ile Thr Glu Ile Gly Met Asp Tyr Asn Gln Pro Ala
            245                 250                 255

Ala Ala Lys Ser Phe Val Ala Asp Ile Lys Thr Lys Ile Arg Asn Ile
        260                 265                 270

Ala Gly Gly Lys Gly Leu Gly Val Phe Tyr Trp Glu Pro Glu Ala Thr
    275                 280                 285

Pro Gly Tyr Asn Gly Gly Tyr Asn Lys Gly Ala Trp Gln Ala Asp Gly
290                 295                 300                 305

Lys Pro Thr Ile Ala Leu Asp Gly Phe Leu Asn
            310                 315

<210> SEQ ID NO 19
<211> LENGTH: 316
<212> TYPE: PRT
<213> ORGANISM: Paenibacillus sp-62603
<220> FEATURE:
<221> NAME/KEY: mat_peptide
<222> LOCATION: (1)..(316)

<400> SEQUENCE: 19

Ala Pro Ala Phe Ala Lys Gly Ala Asp Ile Ser Trp Val Val Gly Met
1               5                   10                  15

Glu Ala Gln Gly Tyr Thr Trp Lys Asp Lys Asn Gly Val Thr Arg Asp
            20                  25                  30

Ile Ile Gln Ile Leu Lys Gln Asp Tyr Gln Ile Asn Ser Val Arg Ile
                35                  40                  45

Arg Val Phe Val Asn Pro Ser Ser Asn Tyr Gly Asn Gly Tyr Met Asn
    50                  55                  60

Lys Asp Arg Ala Ala Thr Leu Ala Lys Arg Ala Lys Asp Ala Gly Met
65                  70                  75                  80

Ser Val Met Leu Thr Leu His Tyr Ser Asp Ser Trp Ala Asp Pro Gly
                85                  90                  95

Lys Gln Thr Lys Pro Ala Ala Trp Ala Ser Tyr Ser Phe Gln Gln Leu
            100                 105                 110

Met Asp Ala Val Tyr Asn His Thr Arg Glu Val Met Thr Ala Met Gln
                115                 120                 125

Ser Lys Gly Val Thr Pro Asp Trp Val Gln Ile Gly Asn Glu Thr Asn
            130                 135                 140

Asp Gly Met Leu Trp Asn Asp Gly Lys Ala Ser Leu Asn Met Gln Asn
145                 150                 155                 160

Tyr Ala Trp Leu Ile Asn Thr Gly Asn Asn Ala Val Lys Ser Ile Ser
                165                 170                 175

Ser Ala Thr Lys Thr Ile Val His Leu Ser Asn Gly Tyr Asp Asn Ser
            180                 185                 190

Leu Phe Val Trp Asn Ile Gly Gly Leu Ile Ala Asn Gly Ala Thr Phe
            195                 200                 205

Asp Ile Ile Gly Met Ser Leu Tyr Pro Thr Ser Ala Asp Trp Ser Thr
210                 215                 220

Lys Val Thr Gln Thr Val Ser Asn Ser Asn Asn Met Ile Ser Arg Tyr
225                 230                 235                 240

Gly Lys Pro Val Met Ile Thr Glu Ile Gly Met Asp Tyr Asn Gln Pro
                245                 250                 255

Ala Ala Ala Lys Ser Phe Val Asp Ile Lys Thr Lys Ile Arg Asn
            260                 265                 270

Ile Ala Gly Gly Lys Gly Leu Gly Val Phe Tyr Trp Glu Pro Glu Ala
            275                 280                 285

Thr Pro Gly Tyr Asn Gly Gly Tyr Asn Lys Gly Ala Trp Gln Ala Asp
            290                 295                 300

Gly Lys Pro Thr Ile Ala Leu Asp Gly Phe Leu Asn
305                 310                 315

<210> SEQ ID NO 20
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 20

His His His His His His Pro Arg Ala Pro Ala Phe Ala Lys Gly Ala
1               5                   10                  15

Asp Ile Ser Trp Val Val Gly Met Glu Ala Gln Gly Tyr Thr Trp Lys
            20                  25                  30

```
Asp Lys Asn Gly Val Thr Arg Asp Ile Ile Gln Ile Leu Lys Gln Asp
             35                  40                  45

Tyr Gln Ile Asn Ser Val Arg Ile Arg Val Phe Val Asn Pro Ser Ser
 50                  55                  60

Asn Tyr Gly Asn Gly Tyr Met Asn Lys Asp Arg Ala Ala Thr Leu Ala
 65                  70                  75                  80

Lys Arg Ala Lys Asp Ala Gly Met Ser Val Met Leu Thr Leu His Tyr
                 85                  90                  95

Ser Asp Ser Trp Ala Asp Pro Gly Lys Gln Thr Lys Pro Ala Ala Trp
                100                 105                 110

Ala Ser Tyr Ser Phe Gln Gln Leu Met Asp Ala Val Tyr Asn His Thr
                115                 120                 125

Arg Glu Val Met Thr Ala Met Gln Ser Lys Gly Val Thr Pro Asp Trp
            130                 135                 140

Val Gln Ile Gly Asn Glu Thr Asn Asp Gly Met Leu Trp Asn Asp Gly
145                 150                 155                 160

Lys Ala Ser Leu Asn Met Gln Asn Tyr Ala Trp Leu Ile Asn Thr Gly
                165                 170                 175

Asn Asn Ala Val Lys Ser Ile Ser Ser Ala Thr Lys Thr Ile Val His
                180                 185                 190

Leu Ser Asn Gly Tyr Asp Asn Ser Leu Phe Val Trp Asn Ile Gly Gly
            195                 200                 205

Leu Ile Ala Asn Gly Ala Thr Phe Asp Ile Ile Gly Met Ser Leu Tyr
210                 215                 220

Pro Thr Ser Ala Asp Trp Ser Thr Lys Val Thr Gln Thr Val Ser Asn
225                 230                 235                 240

Ser Asn Asn Met Ile Ser Arg Tyr Gly Lys Pro Val Met Ile Thr Glu
                245                 250                 255

Ile Gly Met Asp Tyr Asn Gln Pro Ala Ala Ala Lys Ser Phe Val Ala
            260                 265                 270

Asp Ile Lys Thr Lys Ile Arg Asn Ile Ala Gly Gly Lys Gly Leu Gly
            275                 280                 285

Val Phe Tyr Trp Glu Pro Glu Ala Thr Pro Gly Tyr Asn Gly Gly Tyr
290                 295                 300

Asn Lys Gly Ala Trp Gln Ala Asp Gly Lys Pro Thr Ile Ala Leu Asp
305                 310                 315                 320

Gly Phe Leu Asn

<210> SEQ ID NO 21
<211> LENGTH: 1050
<212> TYPE: DNA
<213> ORGANISM: Paenibacillus xylanilyticus
<220> FEATURE:
<221> NAME/KEY: CDS
<222> LOCATION: (1)..(1047)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1047)

<400> SEQUENCE: 21 atg ctt aaa ttt gta agg ggt tac aaa aca tcg att gct ctt gtt ctt    48
Met Leu Lys Phe Val Arg Gly Tyr Lys Thr Ser Ile Ala Leu Val Leu
        -30                 -25                 -20 gtg ttg ttg ttc acc tcc att atg ctg cct gtg ggt cag cat gtc agc    96
Val Leu Leu Phe Thr Ser Ile Met Leu Pro Val Gly Gln His Val Ser
```

```
              -15                 -10                  -5
gca gca ccc agc ttc gcc aag ggg gct gat ata agc tgg gta cca ggc      144
Ala Ala Pro Ser Phe Ala Lys Gly Ala Asp Ile Ser Trp Val Pro Gly
-1  1           5                   10                  15 atg gaa gcg caa ggg tac aaa tgg aaa gac aaa aat ggt gta cag cgt      192
Met Glu Ala Gln Gly Tyr Lys Trp Lys Asp Lys Asn Gly Val Gln Arg
                20                  25                  30 gac att att gat att ttg aaa aac gat tat cag atc aac tcg gtt cgt      240
Asp Ile Ile Asp Ile Leu Lys Asn Asp Tyr Gln Ile Asn Ser Val Arg
                35                  40                  45 atc cgg gtg ttt gtt aat cct tct aat gat tac ggc aac ggg tac atg      288
Ile Arg Val Phe Val Asn Pro Ser Asn Asp Tyr Gly Asn Gly Tyr Met
        50                  55                  60 aat aag gat cgt gtc gct gct ttg gca cag cgg gcc aaa aac gcg ggc      336
Asn Lys Asp Arg Val Ala Ala Leu Ala Gln Arg Ala Lys Asn Ala Gly
    65                  70                  75 atg agc gtc atg ttg act ctg cac tac agt gat tcc tgg gca gac cct      384
Met Ser Val Met Leu Thr Leu His Tyr Ser Asp Ser Trp Ala Asp Pro
80                  85                  90                  95 ggc caa cag acc aaa ccg gca gcc tgg aaa aac tac acc ttc cag cag      432
Gly Gln Gln Thr Lys Pro Ala Ala Trp Lys Asn Tyr Thr Phe Gln Gln
                100                 105                 110 ctg atg gat gcc gtt tgg aat cat aca cgc gat gtg atg acg gcc atg      480
Leu Met Asp Ala Val Trp Asn His Thr Arg Asp Val Met Thr Ala Met
                115                 120                 125 cag agt aaa ggg gtt acg cct gac tgg gta caa atc ggg aac gaa aca      528
Gln Ser Lys Gly Val Thr Pro Asp Trp Val Gln Ile Gly Asn Glu Thr
        130                 135                 140 agc aac ggc atg tta tgg gag gac ggt aaa gcg tcc acg aac atg aaa      576
Ser Asn Gly Met Leu Trp Glu Asp Gly Lys Ala Ser Thr Asn Met Lys
    145                 150                 155 aat tac gca tgg ctg gtg aac acg ggc cat aat gcc gtc aag tcc atg      624
Asn Tyr Ala Trp Leu Val Asn Thr Gly His Asn Ala Val Lys Ser Met
160                 165                 170                 175 agt aca ggg acc aaa acg att gtc cat ctt gca ggc ggt gac gac aat      672
Ser Thr Gly Thr Lys Thr Ile Val His Leu Ala Gly Gly Asp Asp Asn
                180                 185                 190 gcc ctt tat gta tgg aat atc ggc gga ctg atc aac aac ggt gcc aac      720
Ala Leu Tyr Val Trp Asn Ile Gly Gly Leu Ile Asn Asn Gly Ala Asn
                195                 200                 205 ttc gat atg att gcc atg tcc ctc tat cct tcg gct tcc ggc tgg aat      768
Phe Asp Met Ile Ala Met Ser Leu Tyr Pro Ser Ala Ser Gly Trp Asn
            210                 215                 220 aca gct gtc acc aat acg gtg aat aat gcc aag gac ttg atc aac cgc      816
Thr Ala Val Thr Asn Thr Val Asn Asn Ala Lys Asp Leu Ile Asn Arg
    225                 230                 235 tac ggc aaa gag att atc gtc tca gaa atc ggc atg gac aac aat cag      864
Tyr Gly Lys Glu Ile Ile Val Ser Glu Ile Gly Met Asp Asn Asn Gln
240                 245                 250                 255 ccc gca gct ggc aaa agt ttc gtt gct gcg atg aaa aat caa ttc cgc      912
Pro Ala Ala Gly Lys Ser Phe Val Ala Ala Met Lys Asn Gln Phe Arg
                260                 265                 270 aac ctg cca aat ggg aaa gga aaa ggc gta ttc tac tgg gag ccg cag      960
Asn Leu Pro Asn Gly Lys Gly Lys Gly Val Phe Tyr Trp Glu Pro Gln
            275                 280                 285 gct aca cca ggt tat aac ggt ggt tac ggc aaa ggc gct tgg cag tcg     1008
Ala Thr Pro Gly Tyr Asn Gly Gly Tyr Gly Lys Gly Ala Trp Gln Ser
        290                 295                 300 aat atg atg cca aca gcg gtc atg gaa gga ttt ata gac tag              1050
```

```
Asn Met Met Pro Thr Ala Val Met Glu Gly Phe Ile Asp
    305                 310                 315
```

<210> SEQ ID NO 22
<211> LENGTH: 349
<212> TYPE: PRT
<213> ORGANISM: Paenibacillus xylanilyticus
<400> SEQUENCE: 22

```
Met Leu Lys Phe Val Arg Gly Tyr Lys Thr Ser Ile Ala Leu Val Leu
            -30                 -25                 -20

Val Leu Leu Phe Thr Ser Ile Met Leu Pro Val Gly Gln His Val Ser
        -15                 -10                  -5

Ala Ala Pro Ser Phe Ala Lys Gly Ala Asp Ile Ser Trp Val Pro Gly
 -1   1               5                  10                  15

Met Glu Ala Gln Gly Tyr Lys Trp Lys Asp Lys Asn Gly Val Gln Arg
                 20                  25                  30

Asp Ile Ile Asp Ile Leu Lys Asn Asp Tyr Gln Ile Asn Ser Val Arg
                 35                  40                  45

Ile Arg Val Phe Val Asn Pro Ser Asn Asp Tyr Gly Asn Gly Tyr Met
             50                  55                  60

Asn Lys Asp Arg Val Ala Ala Leu Ala Gln Arg Ala Lys Asn Ala Gly
 65                  70                  75

Met Ser Val Met Leu Thr Leu His Tyr Ser Asp Ser Trp Ala Asp Pro
 80                  85                  90                  95

Gly Gln Gln Thr Lys Pro Ala Ala Trp Lys Asn Tyr Thr Phe Gln Gln
                100                 105                 110

Leu Met Asp Ala Val Trp Asn His Thr Arg Asp Val Met Thr Ala Met
                115                 120                 125

Gln Ser Lys Gly Val Thr Pro Asp Trp Val Gln Ile Gly Asn Glu Thr
                130                 135                 140

Ser Asn Gly Met Leu Trp Glu Asp Gly Lys Ala Ser Thr Asn Met Lys
145                 150                 155

Asn Tyr Ala Trp Leu Val Asn Thr Gly His Asn Ala Val Lys Ser Met
160                 165                 170                 175

Ser Thr Gly Thr Lys Thr Ile Val His Leu Ala Gly Gly Asp Asp Asn
                180                 185                 190

Ala Leu Tyr Val Trp Asn Ile Gly Gly Leu Ile Asn Asn Gly Ala Asn
                195                 200                 205

Phe Asp Met Ile Ala Met Ser Leu Tyr Pro Ser Ala Ser Gly Trp Asn
                210                 215                 220

Thr Ala Val Thr Asn Thr Val Asn Asn Ala Lys Asp Leu Ile Asn Arg
225                 230                 235

Tyr Gly Lys Glu Ile Ile Val Ser Glu Ile Gly Met Asp Asn Asn Gln
240                 245                 250                 255

Pro Ala Ala Gly Lys Ser Phe Val Ala Ala Met Lys Asn Gln Phe Arg
                260                 265                 270

Asn Leu Pro Asn Gly Lys Gly Lys Gly Val Phe Tyr Trp Glu Pro Gln
                275                 280                 285

Ala Thr Pro Gly Tyr Asn Gly Gly Tyr Gly Lys Gly Ala Trp Gln Ser
                290                 295                 300

Asn Met Met Pro Thr Ala Val Met Glu Gly Phe Ile Asp
    305                 310                 315
```

<210> SEQ ID NO 23

```
<211> LENGTH: 316
<212> TYPE: PRT
<213> ORGANISM: Paenibacillus xylanilyticus
<220> FEATURE:
<221> NAME/KEY: mat_peptide
<222> LOCATION: (1)..(316)

<400> SEQUENCE: 23
```

| | | | | | | | | | | | | | | |
|---|---|---|---|---|---|---|---|---|---|---|---|---|---|---|
|Ala|Pro|Ser|Phe|Ala|Lys|Gly|Ala|Asp|Ile|Ser|Trp|Val|Pro|Gly|Met|
|1| | | |5| | | |10| | | |15| | |

Glu Ala Gln Gly Tyr Lys Trp Lys Asp Lys Asn Gly Val Gln Arg Asp
            20                  25                  30

Ile Ile Asp Ile Leu Lys Asn Asp Tyr Gln Ile Asn Ser Val Arg Ile
        35                  40                  45

Arg Val Phe Val Asn Pro Ser Asn Asp Tyr Gly Asn Gly Tyr Met Asn
    50                  55                  60

Lys Asp Arg Val Ala Ala Leu Ala Gln Arg Ala Lys Asn Ala Gly Met
65                  70                  75                  80

Ser Val Met Leu Thr Leu His Tyr Ser Asp Ser Trp Ala Asp Pro Gly
                85                  90                  95

Gln Gln Thr Lys Pro Ala Ala Trp Lys Asn Tyr Thr Phe Gln Gln Leu
            100                 105                 110

Met Asp Ala Val Trp Asn His Thr Arg Asp Val Met Thr Ala Met Gln
        115                 120                 125

Ser Lys Gly Val Thr Pro Asp Trp Val Gln Ile Gly Asn Glu Thr Ser
    130                 135                 140

Asn Gly Met Leu Trp Glu Asp Gly Lys Ala Ser Thr Asn Met Lys Asn
145                 150                 155                 160

Tyr Ala Trp Leu Val Asn Thr Gly His Asn Ala Val Lys Ser Met Ser
                165                 170                 175

Thr Gly Thr Lys Thr Ile Val His Leu Ala Gly Gly Asp Asp Asn Ala
            180                 185                 190

Leu Tyr Val Trp Asn Ile Gly Gly Leu Ile Asn Asn Gly Ala Asn Phe
        195                 200                 205

Asp Met Ile Ala Met Ser Leu Tyr Pro Ser Ala Ser Gly Trp Asn Thr
    210                 215                 220

Ala Val Thr Asn Thr Val Asn Asn Ala Lys Asp Leu Ile Asn Arg Tyr
225                 230                 235                 240

Gly Lys Glu Ile Ile Val Ser Glu Ile Gly Met Asp Asn Asn Gln Pro
                245                 250                 255

Ala Ala Gly Lys Ser Phe Val Ala Met Lys Asn Gln Phe Arg Asn
            260                 265                 270

Leu Pro Asn Gly Lys Gly Lys Gly Val Phe Tyr Trp Glu Pro Gln Ala
        275                 280                 285

Thr Pro Gly Tyr Asn Gly Gly Tyr Gly Lys Gly Ala Trp Gln Ser Asn
    290                 295                 300

Met Met Pro Thr Ala Val Met Glu Gly Phe Ile Asp
305                 310                 315

```
<210> SEQ ID NO 24
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)
```

<400> SEQUENCE: 24

```
His His His His His His Pro Arg Ala Pro Ser Phe Ala Lys Gly Ala
1               5                   10                  15

Asp Ile Ser Trp Val Pro Gly Met Glu Ala Gln Gly Tyr Lys Trp Lys
            20                  25                  30

Asp Lys Asn Gly Val Gln Arg Asp Ile Ile Asp Ile Leu Lys Asn Asp
        35                  40                  45

Tyr Gln Ile Asn Ser Val Arg Ile Arg Val Phe Val Asn Pro Ser Asn
    50                  55                  60

Asp Tyr Gly Asn Gly Tyr Met Asn Lys Asp Arg Val Ala Ala Leu Ala
65                  70                  75                  80

Gln Arg Ala Lys Asn Ala Gly Met Ser Val Met Leu Thr Leu His Tyr
                85                  90                  95

Ser Asp Ser Trp Ala Asp Pro Gly Gln Gln Thr Lys Pro Ala Ala Trp
            100                 105                 110

Lys Asn Tyr Thr Phe Gln Gln Leu Met Asp Ala Val Trp Asn His Thr
        115                 120                 125

Arg Asp Val Met Thr Ala Met Gln Ser Lys Gly Val Thr Pro Asp Trp
130                 135                 140

Val Gln Ile Gly Asn Glu Thr Ser Asn Gly Met Leu Trp Glu Asp Gly
145                 150                 155                 160

Lys Ala Ser Thr Asn Met Lys Asn Tyr Ala Trp Leu Val Asn Thr Gly
                165                 170                 175

His Asn Ala Val Lys Ser Met Ser Thr Gly Thr Lys Thr Ile Val His
            180                 185                 190

Leu Ala Gly Gly Asp Asp Asn Ala Leu Tyr Val Trp Asn Ile Gly Gly
        195                 200                 205

Leu Ile Asn Asn Gly Ala Asn Phe Asp Met Ile Ala Met Ser Leu Tyr
    210                 215                 220

Pro Ser Ala Ser Gly Trp Asn Thr Ala Val Thr Asn Thr Val Asn Asn
225                 230                 235                 240

Ala Lys Asp Leu Ile Asn Arg Tyr Gly Lys Glu Ile Ile Val Ser Glu
                245                 250                 255

Ile Gly Met Asp Asn Asn Gln Pro Ala Ala Gly Lys Ser Phe Val Ala
            260                 265                 270

Ala Met Lys Asn Gln Phe Arg Asn Leu Pro Asn Gly Lys Gly Lys Gly
        275                 280                 285

Val Phe Tyr Trp Glu Pro Gln Ala Thr Pro Gly Tyr Asn Gly Gly Tyr
    290                 295                 300

Gly Lys Gly Ala Trp Gln Ser Asn Met Met Pro Thr Ala Val Met Glu
305                 310                 315                 320

Gly Phe Ile Asp
```

<210> SEQ ID NO 25
<211> LENGTH: 1638
<212> TYPE: DNA
<213> ORGANISM: Paenibacillus sp-18179
<220> FEATURE:
<221> NAME/KEY: CDS
<222> LOCATION: (1)..(1635)
<220> FEATURE:
<221> NAME/KEY: misc_feature
<222> LOCATION: (1)..(3)
<223> OTHER INFORMATION: The gene has an alternative start codon gtg
      which would normally code for Val but is translated to Met when it
      is the first codon.

```
<220> FEATURE:
<221> NAME/KEY: sig_peptide
<222> LOCATION: (1)..(87)
<220> FEATURE:
<221> NAME/KEY: mat_peptide
<222> LOCATION: (88)..(1635)

<400> SEQUENCE: 25
```

| | | | | | | | | | | | | | | | | |
|---|---|---|---|---|---|---|---|---|---|---|---|---|---|---|---|---|
| gtg | ggt | aaa | tgg | gtt | aga | gct | att | gct | tta | gca | ggt | gta | gtt | gca | ctt | 48 |
| Val | Gly | Lys | Trp | Val | Arg | Ala | Ile | Ala | Leu | Ala | Gly | Val | Val | Ala | Leu | |
| | | | -25 | | | | -20 | | | | | -15 | | | | |
| ttt | aca | tct | atg | atc | act | cct | ctt | caa | gaa | aca | aag | gct | gct | gga | ggc | 96 |
| Phe | Thr | Ser | Met | Ile | Thr | Pro | Leu | Gln | Glu | Thr | Lys | Ala | Ala | Gly | Gly | |
| | | | -10 | | | | | -5 | | | | -1 | 1 | | | |
| ttc | gtt | atg | ggg | gga | gac | gtt | tca | atg | ctc | cat | gaa | gtt | gag | cag | tta | 144 |
| Phe | Val | Met | Gly | Gly | Asp | Val | Ser | Met | Leu | His | Glu | Val | Glu | Gln | Leu | |
| | 5 | | | | | 10 | | | | | 15 | | | | | |
| ggc | ggg | aag | ttt | tac | gat | cag | ggc | act | cca | aag | gat | gct | ttg | caa | att | 192 |
| Gly | Gly | Lys | Phe | Tyr | Asp | Gln | Gly | Thr | Pro | Lys | Asp | Ala | Leu | Gln | Ile | |
| 20 | | | | | 25 | | | | | 30 | | | | | 35 | |
| tta | agc | gca | cat | ggc | atg | aat | gct | gtc | cga | ttg | cgt | cta | tgg | gtt | gac | 240 |
| Leu | Ser | Ala | His | Gly | Met | Asn | Ala | Val | Arg | Leu | Arg | Leu | Trp | Val | Asp | |
| | | | | 40 | | | | | 45 | | | | | 50 | | |
| ccg | tat | gac | agt | ttc | gga | aat | cct | tat | ggc | ggt | gga | aca | aac | gat | ctg | 288 |
| Pro | Tyr | Asp | Ser | Phe | Gly | Asn | Pro | Tyr | Gly | Gly | Gly | Thr | Asn | Asp | Leu | |
| | | | 55 | | | | | 60 | | | | | 65 | | | |
| gct | acg | act | ata | tct | ctt | gca | cag | cga | gcg | aag | gca | caa | ggt | atg | gag | 336 |
| Ala | Thr | Thr | Ile | Ser | Leu | Ala | Gln | Arg | Ala | Lys | Ala | Gln | Gly | Met | Glu | |
| | | | 70 | | | | | 75 | | | | | 80 | | | |
| gtg | ctg | ctg | gat | ttt | cac | ttc | agt | gat | ttc | tgg | gca | gac | cca | ggg | aag | 384 |
| Val | Leu | Leu | Asp | Phe | His | Phe | Ser | Asp | Phe | Trp | Ala | Asp | Pro | Gly | Lys | |
| | 85 | | | | | 90 | | | | | 95 | | | | | |
| cag | aac | aag | cct | aaa | gct | tgg | cag | agc | tta | acg | tac | aac | cag | ctg | ctt | 432 |
| Gln | Asn | Lys | Pro | Lys | Ala | Trp | Gln | Ser | Leu | Thr | Tyr | Asn | Gln | Leu | Leu | |
| 100 | | | | | 105 | | | | | 110 | | | | | 115 | |
| act | acg | gta | tat | gat | tat | acg | cat | agt | gta | att | acg | caa | atg | aaa | gcg | 480 |
| Thr | Thr | Val | Tyr | Asp | Tyr | Thr | His | Ser | Val | Ile | Thr | Gln | Met | Lys | Ala | |
| | | | | 120 | | | | | 125 | | | | | 130 | | |
| gct | ggc | gtg | atg | cct | gat | atg | gtt | cag | gta | gga | aac | gag | gca | agc | agc | 528 |
| Ala | Gly | Val | Met | Pro | Asp | Met | Val | Gln | Val | Gly | Asn | Glu | Ala | Ser | Ser | |
| | | | 135 | | | | | 140 | | | | | 145 | | | |
| ggc | atc | ctc | tgg | aat | gat | ggc | aag | gtg | ggg | gga | ggc | att | gat | gat | ttt | 576 |
| Gly | Ile | Leu | Trp | Asn | Asp | Gly | Lys | Val | Gly | Gly | Gly | Ile | Asp | Asp | Phe | |
| | | 150 | | | | | 155 | | | | | 160 | | | | |
| acg | aaa | ctc | gga | gaa | ctg | ttt | acc | tct | gct | att | aat | ggg | att | aat | gcg | 624 |
| Thr | Lys | Leu | Gly | Glu | Leu | Phe | Thr | Ser | Ala | Ile | Asn | Gly | Ile | Asn | Ala | |
| | 165 | | | | | 170 | | | | | 175 | | | | | |
| gcc | ctc | agc | tct | agt | gag | aac | att | gag | att | gtt | ctg | cat | ttg | gat | cat | 672 |
| Ala | Leu | Ser | Ser | Ser | Glu | Asn | Ile | Glu | Ile | Val | Leu | His | Leu | Asp | His | |
| 180 | | | | | 185 | | | | | 190 | | | | | 195 | |
| ggc | ggc | gac | aac | aat | tta | tac | act | tgg | tgg | ttc | gat | aaa | att | gaa | gcg | 720 |
| Gly | Gly | Asp | Asn | Asn | Leu | Tyr | Thr | Trp | Trp | Phe | Asp | Lys | Ile | Glu | Ala | |
| | | | | 200 | | | | | 205 | | | | | 210 | | |
| gag | aac | gtg | gat | tac | gat | att | atc | ggc | ttg | acc | tac | tat | ccg | ttt | tgg | 768 |
| Glu | Asn | Val | Asp | Tyr | Asp | Ile | Ile | Gly | Leu | Thr | Tyr | Tyr | Pro | Phe | Trp | |
| | | | 215 | | | | | 220 | | | | | 225 | | | |
| cat | gga | acg | atg | gga | gaa | ttg | gcg | tat | aat | ctt | aat | gcg | atc | agc | agt | 816 |
| His | Gly | Thr | Met | Gly | Glu | Leu | Ala | Tyr | Asn | Leu | Asn | Ala | Ile | Ser | Ser | |
| | | | 230 | | | | | 235 | | | | | 240 | | | |
| cgt | tac | aat | aag | gac | gta | atg | att | gtg | gaa | acg | tcg | tat | ggc | ttt | acg | 864 |
| Arg | Tyr | Asn | Lys | Asp | Val | Met | Ile | Val | Glu | Thr | Ser | Tyr | Gly | Phe | Thr | |

```
ctg gat gat ggt gat ggt tta ggc aac tct ttt tac acg gcg gaa gaa       912
Leu Asp Asp Gly Asp Gly Leu Gly Asn Ser Phe Tyr Thr Ala Glu Glu
260                 265                 270                 275 agc att ggg ggt tac ccg gct aca gta gaa ggc cag acg gcg tat ttg       960
Ser Ile Gly Gly Tyr Pro Ala Thr Val Glu Gly Gln Thr Ala Tyr Leu
                280                 285                 290 cgg gat ttg aag gaa att gtt agg gat gtc cca aac aac cgc ggc cgc      1008
Arg Asp Leu Lys Glu Ile Val Arg Asp Val Pro Asn Asn Arg Gly Arg
            295                 300                 305 ggc att ttc tgg tgg gag ccg aca tgg ctg cct gtt gca ggg gct aac      1056
Gly Ile Phe Trp Trp Glu Pro Thr Trp Leu Pro Val Ala Gly Ala Asn
        310                 315                 320 tgg ggg acg gat gca ggc aag ctg tac aac aat gat act gga cta cta      1104
Trp Gly Thr Asp Ala Gly Lys Leu Tyr Asn Asn Asp Thr Gly Leu Leu
325                 330                 335 tct aat cct tgg gac aat cag acc ttg ttt gat ttt aat gga aat gtg      1152
Ser Asn Pro Trp Asp Asn Gln Thr Leu Phe Asp Phe Asn Gly Asn Val
340                 345                 350                 355 ttg tct aca gtt tca gta ttt aca caa agt gct cca acc aac ctt gtt      1200
Leu Ser Thr Val Ser Val Phe Thr Gln Ser Ala Pro Thr Asn Leu Val
                360                 365                 370 gct aat cat agc ttt gag gcc gat ggt tgg aca aca aca cca tct agc      1248
Ala Asn His Ser Phe Glu Ala Asp Gly Trp Thr Thr Thr Pro Ser Ser
            375                 380                 385 tgg aat cgc tgg gca gcc gat acg gca tcc tat aat gct att aag gtt      1296
Trp Asn Arg Trp Ala Ala Asp Thr Ala Ser Tyr Asn Ala Ile Lys Val
        390                 395                 400 gaa gaa aac ggt att acg ggc agc tat aag ctg acg cat tgg agt gat      1344
Glu Glu Asn Gly Ile Thr Gly Ser Tyr Lys Leu Thr His Trp Ser Asp
405                 410                 415 tct gct tat gag gcc tct acg tac cag act gtt tca gga tta agc aat      1392
Ser Ala Tyr Glu Ala Ser Thr Tyr Gln Thr Val Ser Gly Leu Ser Asn
420                 425                 430                 435 ggt acc tat act tta tcc gct tgg gtg ctt aac agt ggc gga caa aat      1440
Gly Thr Tyr Thr Leu Ser Ala Trp Val Leu Asn Ser Gly Gly Gln Asn
                440                 445                 450 acg ctg cag ctt tac gct aaa aat tac ggg ggt tca gaa cgg aac gtc      1488
Thr Leu Gln Leu Tyr Ala Lys Asn Tyr Gly Gly Ser Glu Arg Asn Val
            455                 460                 465 aat ctt cct gtt agc cca aca aag tgg gta aaa gta aaa att gaa aac      1536
Asn Leu Pro Val Ser Pro Thr Lys Trp Val Lys Val Lys Ile Glu Asn
        470                 475                 480 atc agt gtt aca aat ggt caa atc gaa tta ggc att tat tca gat gcg      1584
Ile Ser Val Thr Asn Gly Gln Ile Glu Leu Gly Ile Tyr Ser Asp Ala
485                 490                 495 aat gct gat aat tgg atg aac ctc gat aac gtc aaa ctt tat aaa aca      1632
Asn Ala Asp Asn Trp Met Asn Leu Asp Asn Val Lys Leu Tyr Lys Thr
500                 505                 510                 515 aac tag                                                              1638
Asn
```

<210> SEQ ID NO 26
<211> LENGTH: 545
<212> TYPE: PRT
<213> ORGANISM: Paenibacillus sp-18179

<400> SEQUENCE: 26

```
Val Gly Lys Trp Val Arg Ala Ile Ala Leu Ala Gly Val Val Ala Leu
            -25                 -20                 -15
```

```
Phe Thr Ser Met Ile Thr Pro Leu Gln Glu Thr Lys Ala Ala Gly Gly
            -10             -5              -1  1

Phe Val Met Gly Gly Asp Val Ser Met Leu His Glu Val Glu Gln Leu
      5              10              15

Gly Gly Lys Phe Tyr Asp Gln Gly Thr Pro Lys Asp Ala Leu Gln Ile
 20              25              30                          35

Leu Ser Ala His Gly Met Asn Ala Val Arg Leu Arg Leu Trp Val Asp
              40              45                      50

Pro Tyr Asp Ser Phe Gly Asn Pro Tyr Gly Gly Thr Asn Asp Leu
              55              60              65

Ala Thr Thr Ile Ser Leu Ala Gln Arg Ala Lys Ala Gln Gly Met Glu
              70              75              80

Val Leu Leu Asp Phe His Phe Ser Asp Phe Trp Ala Asp Pro Gly Lys
 85              90              95

Gln Asn Lys Pro Lys Ala Trp Gln Ser Leu Thr Tyr Asn Gln Leu Leu
100             105             110                         115

Thr Thr Val Tyr Asp Tyr Thr His Ser Val Ile Thr Gln Met Lys Ala
              120             125             130

Ala Gly Val Met Pro Asp Met Val Gln Val Gly Asn Glu Ala Ser Ser
              135             140             145

Gly Ile Leu Trp Asn Asp Gly Lys Val Gly Gly Ile Asp Asp Phe
              150             155             160

Thr Lys Leu Gly Glu Leu Phe Thr Ser Ala Ile Asn Gly Ile Asn Ala
              165             170             175

Ala Leu Ser Ser Ser Glu Asn Ile Glu Ile Val Leu His Leu Asp His
180             185             190             195

Gly Gly Asp Asn Asn Leu Tyr Thr Trp Trp Phe Asp Lys Ile Glu Ala
              200             205             210

Glu Asn Val Asp Tyr Asp Ile Ile Gly Leu Thr Tyr Tyr Pro Phe Trp
              215             220             225

His Gly Thr Met Gly Glu Leu Ala Tyr Asn Leu Asn Ala Ile Ser Ser
              230             235             240

Arg Tyr Asn Lys Asp Val Met Ile Val Glu Thr Ser Tyr Gly Phe Thr
245             250             255

Leu Asp Asp Gly Asp Gly Leu Gly Asn Ser Phe Tyr Thr Ala Glu Glu
260             265             270             275

Ser Ile Gly Gly Tyr Pro Ala Thr Val Glu Gly Gln Thr Ala Tyr Leu
              280             285             290

Arg Asp Leu Lys Glu Ile Val Arg Asp Val Pro Asn Asn Arg Gly Arg
              295             300             305

Gly Ile Phe Trp Trp Glu Pro Thr Trp Leu Pro Val Ala Gly Ala Asn
              310             315             320

Trp Gly Thr Asp Ala Gly Lys Leu Tyr Asn Asn Asp Thr Gly Leu Leu
325             330             335

Ser Asn Pro Trp Asp Asn Gln Thr Leu Phe Asp Phe Asn Gly Asn Val
340             345             350             355

Leu Ser Thr Val Ser Val Phe Thr Gln Ser Ala Pro Thr Asn Leu Val
              360             365             370

Ala Asn His Ser Phe Glu Ala Asp Gly Trp Thr Thr Pro Ser Ser
              375             380             385

Trp Asn Arg Trp Ala Ala Asp Thr Ala Ser Tyr Asn Ala Ile Lys Val
              390             395             400
```

```
Glu Glu Asn Gly Ile Thr Gly Ser Tyr Lys Leu Thr His Trp Ser Asp
405                 410                 415
Ser Ala Tyr Glu Ala Ser Thr Tyr Gln Thr Val Ser Gly Leu Ser Asn
420                 425                 430                 435
Gly Thr Tyr Thr Leu Ser Ala Trp Val Leu Asn Ser Gly Gly Gln Asn
                440                 445                 450
Thr Leu Gln Leu Tyr Ala Lys Asn Tyr Gly Gly Ser Glu Arg Asn Val
            455                 460                 465
Asn Leu Pro Val Ser Pro Thr Lys Trp Val Lys Val Lys Ile Glu Asn
        470                 475                 480
Ile Ser Val Thr Asn Gly Gln Ile Glu Leu Gly Ile Tyr Ser Asp Ala
485                 490                 495
Asn Ala Asp Asn Trp Met Asn Leu Asp Asn Val Lys Leu Tyr Lys Thr
500                 505                 510                 515
Asn
```

<210> SEQ ID NO 27
<211> LENGTH: 516
<212> TYPE: PRT
<213> ORGANISM: Paenibacillus sp-18179
<220> FEATURE:
<221> NAME/KEY: mat_peptide
<222> LOCATION: (1)..(516)

<400> SEQUENCE: 27

```
Ala Gly Gly Phe Val Met Gly Gly Asp Val Ser Met Leu His Glu Val
1               5                   10                  15
Glu Gln Leu Gly Gly Lys Phe Tyr Asp Gln Gly Thr Pro Lys Asp Ala
                20                  25                  30
Leu Gln Ile Leu Ser Ala His Gly Met Asn Ala Val Arg Leu Arg Leu
            35                  40                  45
Trp Val Asp Pro Tyr Asp Ser Phe Gly Asn Pro Tyr Gly Gly Gly Thr
        50                  55                  60
Asn Asp Leu Ala Thr Thr Ile Ser Leu Ala Gln Arg Ala Lys Ala Gln
65                  70                  75                  80
Gly Met Glu Val Leu Leu Asp Phe His Phe Ser Asp Phe Trp Ala Asp
                85                  90                  95
Pro Gly Lys Gln Asn Lys Pro Lys Ala Trp Gln Ser Leu Thr Tyr Asn
                100                 105                 110
Gln Leu Leu Thr Thr Val Tyr Asp Tyr Thr His Ser Val Ile Thr Gln
            115                 120                 125
Met Lys Ala Ala Gly Val Met Pro Asp Met Val Gln Val Gly Asn Glu
        130                 135                 140
Ala Ser Ser Gly Ile Leu Trp Asn Asp Gly Lys Val Gly Gly Gly Ile
145                 150                 155                 160
Asp Asp Phe Thr Lys Leu Gly Glu Leu Phe Thr Ser Ala Ile Asn Gly
                165                 170                 175
Ile Asn Ala Ala Leu Ser Ser Ser Glu Asn Ile Glu Ile Val Leu His
            180                 185                 190
Leu Asp His Gly Gly Asp Asn Asn Leu Tyr Thr Trp Trp Phe Asp Lys
        195                 200                 205
Ile Glu Ala Glu Asn Val Asp Tyr Asp Ile Ile Gly Leu Thr Tyr Tyr
210                 215                 220
Pro Phe Trp His Gly Thr Met Gly Glu Leu Ala Tyr Asn Leu Asn Ala
225                 230                 235                 240
```

```
Ile Ser Ser Arg Tyr Asn Lys Asp Val Met Ile Val Glu Thr Ser Tyr
            245                 250                 255

Gly Phe Thr Leu Asp Asp Gly Asp Gly Leu Gly Asn Ser Phe Tyr Thr
        260                 265                 270

Ala Glu Glu Ser Ile Gly Gly Tyr Pro Ala Thr Val Glu Gly Gln Thr
    275                 280                 285

Ala Tyr Leu Arg Asp Leu Lys Glu Ile Val Arg Asp Val Pro Asn Asn
290                 295                 300

Arg Gly Arg Gly Ile Phe Trp Trp Glu Pro Thr Trp Leu Pro Val Ala
305                 310                 315                 320

Gly Ala Asn Trp Gly Thr Asp Ala Gly Lys Leu Tyr Asn Asn Asp Thr
                325                 330                 335

Gly Leu Leu Ser Asn Pro Trp Asp Asn Gln Thr Leu Phe Asp Phe Asn
            340                 345                 350

Gly Asn Val Leu Ser Thr Val Ser Val Phe Thr Gln Ser Ala Pro Thr
        355                 360                 365

Asn Leu Val Ala Asn His Ser Phe Glu Ala Asp Gly Trp Thr Thr Thr
    370                 375                 380

Pro Ser Ser Trp Asn Arg Trp Ala Ala Asp Thr Ala Ser Tyr Asn Ala
385                 390                 395                 400

Ile Lys Val Glu Glu Asn Gly Ile Thr Gly Ser Tyr Lys Leu Thr His
                405                 410                 415

Trp Ser Asp Ser Ala Tyr Glu Ala Ser Thr Tyr Gln Thr Val Ser Gly
            420                 425                 430

Leu Ser Asn Gly Thr Tyr Thr Leu Ser Ala Trp Val Leu Asn Ser Gly
        435                 440                 445

Gly Gln Asn Thr Leu Gln Leu Tyr Ala Lys Asn Tyr Gly Gly Ser Glu
    450                 455                 460

Arg Asn Val Asn Leu Pro Val Ser Pro Thr Lys Trp Val Lys Val Lys
465                 470                 475                 480

Ile Glu Asn Ile Ser Val Thr Asn Gly Gln Ile Glu Leu Gly Ile Tyr
                485                 490                 495

Ser Asp Ala Asn Ala Asp Asn Trp Met Asn Leu Asp Asn Val Lys Leu
            500                 505                 510

Tyr Lys Thr Asn
        515

<210> SEQ ID NO 28
<211> LENGTH: 524
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(524)

<400> SEQUENCE: 28

His His His His His His Pro Arg Ala Gly Gly Phe Val Met Gly Gly
1               5                   10                  15

Asp Val Ser Met Leu His Glu Val Glu Gln Leu Gly Gly Lys Phe Tyr
            20                  25                  30

Asp Gln Gly Thr Pro Lys Asp Ala Leu Gln Ile Leu Ser Ala His Gly
        35                  40                  45

Met Asn Ala Val Arg Leu Arg Leu Trp Val Asp Pro Tyr Asp Ser Phe
    50                  55                  60
```

-continued

Gly Asn Pro Tyr Gly Gly Gly Thr Asn Asp Leu Ala Thr Thr Ile Ser
 65                  70                  75                  80

Leu Ala Gln Arg Ala Lys Ala Gln Gly Met Glu Val Leu Leu Asp Phe
             85                  90                  95

His Phe Ser Asp Phe Trp Ala Asp Pro Gly Lys Gln Asn Lys Pro Lys
            100                 105                 110

Ala Trp Gln Ser Leu Thr Tyr Asn Gln Leu Leu Thr Thr Val Tyr Asp
            115                 120                 125

Tyr Thr His Ser Val Ile Thr Gln Met Lys Ala Ala Gly Val Met Pro
        130                 135                 140

Asp Met Val Gln Val Gly Asn Glu Ala Ser Ser Gly Ile Leu Trp Asn
145                 150                 155                 160

Asp Gly Lys Val Gly Gly Ile Asp Asp Phe Thr Lys Leu Gly Glu
            165                 170                 175

Leu Phe Thr Ser Ala Ile Asn Gly Ile Asn Ala Ala Leu Ser Ser Ser
            180                 185                 190

Glu Asn Ile Glu Ile Val Leu His Leu Asp His Gly Asp Asn Asn
            195                 200                 205

Leu Tyr Thr Trp Trp Phe Asp Lys Ile Glu Ala Glu Asn Val Asp Tyr
        210                 215                 220

Asp Ile Ile Gly Leu Thr Tyr Tyr Pro Phe Trp His Gly Thr Met Gly
225                 230                 235                 240

Glu Leu Ala Tyr Asn Leu Asn Ala Ile Ser Ser Arg Tyr Asn Lys Asp
                245                 250                 255

Val Met Ile Val Glu Thr Ser Tyr Gly Phe Thr Leu Asp Asp Gly Asp
            260                 265                 270

Gly Leu Gly Asn Ser Phe Tyr Thr Ala Glu Glu Ser Ile Gly Gly Tyr
        275                 280                 285

Pro Ala Thr Val Glu Gly Gln Thr Ala Tyr Leu Arg Asp Leu Lys Glu
        290                 295                 300

Ile Val Arg Asp Val Pro Asn Asn Arg Gly Arg Gly Ile Phe Trp Trp
305                 310                 315                 320

Glu Pro Thr Trp Leu Pro Val Ala Gly Ala Asn Trp Gly Thr Asp Ala
            325                 330                 335

Gly Lys Leu Tyr Asn Asn Asp Thr Gly Leu Leu Ser Asn Pro Trp Asp
            340                 345                 350

Asn Gln Thr Leu Phe Asp Phe Asn Gly Asn Val Leu Ser Thr Val Ser
            355                 360                 365

Val Phe Thr Gln Ser Ala Pro Thr Asn Leu Val Ala Asn His Ser Phe
        370                 375                 380

Glu Ala Asp Gly Trp Thr Thr Thr Pro Ser Ser Trp Asn Arg Trp Ala
385                 390                 395                 400

Ala Asp Thr Ala Ser Tyr Asn Ala Ile Lys Val Glu Glu Asn Gly Ile
            405                 410                 415

Thr Gly Ser Tyr Lys Leu Thr His Trp Ser Asp Ser Ala Tyr Glu Ala
            420                 425                 430

Ser Thr Tyr Gln Thr Val Ser Gly Leu Ser Asn Gly Thr Tyr Thr Leu
            435                 440                 445

Ser Ala Trp Val Leu Asn Ser Gly Gly Gln Asn Thr Leu Gln Leu Tyr
            450                 455                 460

Ala Lys Asn Tyr Gly Gly Ser Glu Arg Asn Val Asn Leu Pro Val Ser
465                 470                 475                 480

Pro Thr Lys Trp Val Lys Val Lys Ile Glu Asn Ile Ser Val Thr Asn

```
                    485                 490                 495
Gly Gln Ile Glu Leu Gly Ile Tyr Ser Asp Ala Asn Ala Asp Asn Trp
                500                 505                 510

Met Asn Leu Asp Asn Val Lys Leu Tyr Lys Thr Asn
            515                 520

<210> SEQ ID NO 29
<211> LENGTH: 1053
<212> TYPE: DNA
<213> ORGANISM: Paenibacillus peoriae
<220> FEATURE:
<221> NAME/KEY: CDS
<222> LOCATION: (1)..(1050)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1050)

<400> SEQUENCE: 29
```

| | | | | | | | | | | | | | | | | |
|---|---|---|---|---|---|---|---|---|---|---|---|---|---|---|---|---|
| atg | aaa | aca | ggt | aac | cgc | acg | atg | gta | ttt | gcg | atg | ttg | atc | ttg | ctt | 48 |
| Met | Lys | Thr | Gly | Asn | Arg | Thr | Met | Val | Phe | Ala | Met | Leu | Ile | Leu | Leu | |
| | | | -30 | | | | -25 | | | | -20 | | | | | |
| tcc | agc | tta | ttg | tat | ccg | ttc | ggc | tct | gta | ggg | ttg | ggt | gcg | gct | tcg | 96 |
| Ser | Ser | Leu | Leu | Tyr | Pro | Phe | Gly | Ser | Val | Gly | Leu | Gly | Ala | Ala | Ser | |
| | | -15 | | | | | -10 | | | | | -5 | | | | |
| gcc | gcc | cct | gct | ttc | gcc | aaa | gga | gca | gat | ata | agc | tgg | gta | gca | gga | 144 |
| Ala | Ala | Pro | Ala | Phe | Ala | Lys | Gly | Ala | Asp | Ile | Ser | Trp | Val | Ala | Gly | |
| -1 | 1 | | | | 5 | | | | | 10 | | | | | 15 | |
| atg | gaa | gcg | caa | ggt | atg | act | tgg | aag | gat | aaa | aag | ggt | gtt | cgt | cga | 192 |
| Met | Glu | Ala | Gln | Gly | Met | Thr | Trp | Lys | Asp | Lys | Lys | Gly | Val | Arg | Arg | |
| | | | | 20 | | | | | 25 | | | | | 30 | | |
| gat | ata | ctg | caa | att | ttg | cga | gat | gac | tat | cag | atc | aac | tcg | gta | cgt | 240 |
| Asp | Ile | Leu | Gln | Ile | Leu | Arg | Asp | Asp | Tyr | Gln | Ile | Asn | Ser | Val | Arg | |
| | | | | 35 | | | | | 40 | | | | | 45 | | |
| atc | cgt | gtg | tgg | gta | aac | ccc | gac | atg | aaa | gat | tat | gca | agc | gga | tac | 288 |
| Ile | Arg | Val | Trp | Val | Asn | Pro | Asp | Met | Lys | Asp | Tyr | Ala | Ser | Gly | Tyr | |
| | | | 50 | | | | | 55 | | | | | 60 | | | |
| atg | aat | gcc | gaa | aag | gca | gca | gaa | ctg | gcg | cag | cga | gct | aaa | aaa | ttg | 336 |
| Met | Asn | Ala | Glu | Lys | Ala | Ala | Glu | Leu | Ala | Gln | Arg | Ala | Lys | Lys | Leu | |
| | 65 | | | | | 70 | | | | | 75 | | | | | |
| ggt | atg | agc | gtt | atg | ctg | act | cta | cat | tat | agt | gat | tcc | tgg | gca | gat | 384 |
| Gly | Met | Ser | Val | Met | Leu | Thr | Leu | His | Tyr | Ser | Asp | Ser | Trp | Ala | Asp | |
| 80 | | | | | 85 | | | | | 90 | | | | | 95 | |
| cca | ggg | caa | cag | aac | aaa | cct | tat | gcg | tgg | cgc | aat | ttt | aca | ttt | aca | 432 |
| Pro | Gly | Gln | Gln | Asn | Lys | Pro | Tyr | Ala | Trp | Arg | Asn | Phe | Thr | Phe | Thr | |
| | | | | 100 | | | | | 105 | | | | | 110 | | |
| caa | ctc | atg | gat | gca | gtc | tgg | tct | cat | acg | gtt | tat | gtt | atg | aac | acg | 480 |
| Gln | Leu | Met | Asp | Ala | Val | Trp | Ser | His | Thr | Val | Tyr | Val | Met | Asn | Thr | |
| | | | 115 | | | | | 120 | | | | | 125 | | | |
| atg | aaa | agc | aag | ggg | gta | aca | ccg | gac | tgg | gtg | cag | atc | ggt | aat | gag | 528 |
| Met | Lys | Ser | Lys | Gly | Val | Thr | Pro | Asp | Trp | Val | Gln | Ile | Gly | Asn | Glu | |
| | | 130 | | | | | 135 | | | | | 140 | | | | |
| acg | aac | aat | gga | atg | ctc | tgg | gaa | gac | ggc | aaa | gct | tcg | gtg | aac | atg | 576 |
| Thr | Asn | Asn | Gly | Met | Leu | Trp | Glu | Asp | Gly | Lys | Ala | Ser | Val | Asn | Met | |
| | 145 | | | | | 150 | | | | | 155 | | | | | |
| aaa | aac | tat | gcc | tgg | ctc | gtc | aat | aca | ggt | aat | aat | gct | gta | aaa | tcg | 624 |
| Lys | Asn | Tyr | Ala | Trp | Leu | Val | Asn | Thr | Gly | Asn | Asn | Ala | Val | Lys | Ser | |
| 160 | | | | | 165 | | | | | 170 | | | | | 175 | |
| gta | agc | agc | agt | act | aaa | acg | ata | gta | cat | tta | gcc | aac | ggg | gat | aac | 672 |
| Val | Ser | Ser | Ser | Thr | Lys | Thr | Ile | Val | His | Leu | Ala | Asn | Gly | Asp | Asn | |

```
                    180                 185                 190
ggt tcc gtg ttg aac tgg aat atc ggc gga ctg att gat aat gga gct    720
Gly Ser Val Leu Asn Trp Asn Ile Gly Gly Leu Ile Asp Asn Gly Ala
        195                 200                 205 cag ttt gat ctc atc ggg ctg tct ctg tat ccg tct cct tct gac tgg    768
Gln Phe Asp Leu Ile Gly Leu Ser Leu Tyr Pro Ser Pro Ser Asp Trp
    210                 215                 220 cag ggc aag gtg gat cag acg att acg aat gcc aat aac ctc att gcc    816
Gln Gly Lys Val Asp Gln Thr Ile Thr Asn Ala Asn Asn Leu Ile Ala
225                 230                 235 aaa tac ggt aaa ggt att gtc atc agt gaa atc ggg atg gaa tat aac    864
Lys Tyr Gly Lys Gly Ile Val Ile Ser Glu Ile Gly Met Glu Tyr Asn
240                 245                 250                 255 gaa cct gca gct tcc aag gca ttt att tct gca atc aaa aca aag gtt    912
Glu Pro Ala Ala Ser Lys Ala Phe Ile Ser Ala Ile Lys Thr Lys Val
            260                 265                 270 cgg aac atg gga ggc ggc aaa ggc aca ggg gta ttt tat tgg gag ccg    960
Arg Asn Met Gly Gly Gly Lys Gly Thr Gly Val Phe Tyr Trp Glu Pro
        275                 280                 285 gct gca act cca ggt tac aat caa ggt tat aac aaa ggt gct tgg cag   1008
Ala Ala Thr Pro Gly Tyr Asn Gln Gly Tyr Asn Lys Gly Ala Trp Gln
    290                 295                 300 gct gac ggt aaa cca acc tca gct ttg gag gga ttt gta aat taa       1053
Ala Asp Gly Lys Pro Thr Ser Ala Leu Glu Gly Phe Val Asn
305                 310                 315

<210> SEQ ID NO 30
<211> LENGTH: 350
<212> TYPE: PRT
<213> ORGANISM: Paenibacillus peoriae

<400> SEQUENCE: 30

Met Lys Thr Gly Asn Arg Thr Met Val Phe Ala Met Leu Ile Leu Leu
            -30                 -25                 -20

Ser Ser Leu Leu Tyr Pro Phe Gly Ser Val Gly Leu Gly Ala Ala Ser
        -15                 -10                 -5

Ala Ala Pro Ala Phe Ala Lys Gly Ala Asp Ile Ser Trp Val Ala Gly
-1  1                   5                   10                  15

Met Glu Ala Gln Gly Met Thr Trp Lys Asp Lys Lys Gly Val Arg Arg
                20                  25                  30

Asp Ile Leu Gln Ile Leu Arg Asp Asp Tyr Gln Ile Asn Ser Val Arg
            35                  40                  45

Ile Arg Val Trp Val Asn Pro Asp Met Lys Asp Tyr Ala Ser Gly Tyr
        50                  55                  60

Met Asn Ala Glu Lys Ala Ala Glu Leu Ala Gln Arg Ala Lys Lys Leu
    65                  70                  75

Gly Met Ser Val Met Leu Thr Leu His Tyr Ser Asp Ser Trp Ala Asp
80                  85                  90                  95

Pro Gly Gln Gln Asn Lys Pro Tyr Ala Trp Arg Asn Phe Thr Phe Thr
                100                 105                 110

Gln Leu Met Asp Ala Val Trp Ser His Thr Val Tyr Val Met Asn Thr
            115                 120                 125

Met Lys Ser Lys Gly Val Thr Pro Asp Trp Val Gln Ile Gly Asn Glu
        130                 135                 140

Thr Asn Asn Gly Met Leu Trp Glu Asp Gly Lys Ala Ser Val Asn Met
    145                 150                 155

Lys Asn Tyr Ala Trp Leu Val Asn Thr Gly Asn Asn Ala Val Lys Ser
```

```
                160                 165                 170                 175
Val Ser Ser Thr Lys Thr Ile Val His Leu Ala Asn Gly Asp Asn
                180                 185                 190

Gly Ser Val Leu Asn Trp Asn Ile Gly Gly Leu Ile Asp Asn Gly Ala
                195                 200                 205

Gln Phe Asp Leu Ile Gly Leu Ser Leu Tyr Pro Ser Pro Ser Asp Trp
                210                 215                 220

Gln Gly Lys Val Asp Gln Thr Ile Thr Asn Ala Asn Asn Leu Ile Ala
    225                 230                 235

Lys Tyr Gly Lys Gly Ile Val Ile Ser Glu Ile Gly Met Glu Tyr Asn
240                 245                 250                 255

Glu Pro Ala Ala Ser Lys Ala Phe Ile Ser Ala Ile Lys Thr Lys Val
                260                 265                 270

Arg Asn Met Gly Gly Lys Gly Thr Gly Val Phe Tyr Trp Glu Pro
                275                 280                 285

Ala Ala Thr Pro Gly Tyr Asn Gln Gly Tyr Asn Lys Gly Ala Trp Gln
                290                 295                 300

Ala Asp Gly Lys Pro Thr Ser Ala Leu Glu Gly Phe Val Asn
    305                 310                 315

<210> SEQ ID NO 31
<211> LENGTH: 317
<212> TYPE: PRT
<213> ORGANISM: Paenibacillus peoriae
<220> FEATURE:
<221> NAME/KEY: mat_peptide
<222> LOCATION: (1)..(317)

<400> SEQUENCE: 31

Ala Pro Ala Phe Ala Lys Gly Ala Asp Ile Ser Trp Val Ala Gly Met
1               5                   10                  15

Glu Ala Gln Gly Met Thr Trp Lys Asp Lys Lys Gly Val Arg Arg Asp
                20                  25                  30

Ile Leu Gln Ile Leu Arg Asp Asp Tyr Gln Ile Asn Ser Val Arg Ile
                35                  40                  45

Arg Val Trp Val Asn Pro Asp Met Lys Asp Tyr Ala Ser Gly Tyr Met
    50                  55                  60

Asn Ala Glu Lys Ala Ala Glu Leu Ala Gln Arg Ala Lys Lys Leu Gly
65                  70                  75                  80

Met Ser Val Met Leu Thr Leu His Tyr Ser Asp Ser Trp Ala Asp Pro
                85                  90                  95

Gly Gln Gln Asn Lys Pro Tyr Ala Trp Arg Asn Phe Thr Phe Thr Gln
                100                 105                 110

Leu Met Asp Ala Val Trp Ser His Thr Val Tyr Val Met Asn Thr Met
                115                 120                 125

Lys Ser Lys Gly Val Thr Pro Asp Trp Val Gln Ile Gly Asn Glu Thr
    130                 135                 140

Asn Asn Gly Met Leu Trp Glu Asp Gly Lys Ala Ser Val Asn Met Lys
145                 150                 155                 160

Asn Tyr Ala Trp Leu Val Asn Thr Gly Asn Asn Ala Val Lys Ser Val
                165                 170                 175

Ser Ser Ser Thr Lys Thr Ile Val His Leu Ala Asn Gly Asp Asn Gly
                180                 185                 190

Ser Val Leu Asn Trp Asn Ile Gly Gly Leu Ile Asp Asn Gly Ala Gln
                195                 200                 205
```

```
Phe Asp Leu Ile Gly Leu Ser Leu Tyr Pro Ser Pro Ser Asp Trp Gln
210                 215                 220

Gly Lys Val Asp Gln Thr Ile Thr Asn Ala Asn Asn Leu Ile Ala Lys
225                 230                 235                 240

Tyr Gly Lys Gly Ile Val Ile Ser Glu Ile Gly Met Glu Tyr Asn Glu
                245                 250                 255

Pro Ala Ala Ser Lys Ala Phe Ile Ser Ala Ile Lys Thr Lys Val Arg
                260                 265                 270

Asn Met Gly Gly Lys Gly Thr Gly Val Phe Tyr Trp Glu Pro Ala
                275                 280                 285

Ala Thr Pro Gly Tyr Asn Gln Gly Tyr Asn Lys Gly Ala Trp Gln Ala
290                 295                 300

Asp Gly Lys Pro Thr Ser Ala Leu Glu Gly Phe Val Asn
305                 310                 315
```

<210> SEQ ID NO 32
<211> LENGTH: 325
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(325)

<400> SEQUENCE: 32

```
His His His His His His Pro Arg Ala Pro Ala Phe Ala Lys Gly Ala
1               5                   10                  15

Asp Ile Ser Trp Val Ala Gly Met Glu Ala Gln Gly Met Thr Trp Lys
                20                  25                  30

Asp Lys Lys Gly Val Arg Arg Asp Ile Leu Gln Ile Leu Arg Asp Asp
            35                  40                  45

Tyr Gln Ile Asn Ser Val Arg Ile Arg Val Trp Val Asn Pro Asp Met
50                  55                  60

Lys Asp Tyr Ala Ser Gly Tyr Met Asn Ala Glu Lys Ala Ala Glu Leu
65                  70                  75                  80

Ala Gln Arg Ala Lys Lys Leu Gly Met Ser Val Met Leu Thr Leu His
                85                  90                  95

Tyr Ser Asp Ser Trp Ala Asp Pro Gly Gln Gln Asn Lys Pro Tyr Ala
                100                 105                 110

Trp Arg Asn Phe Thr Phe Thr Gln Leu Met Asp Ala Val Trp Ser His
            115                 120                 125

Thr Val Tyr Val Met Asn Thr Met Lys Ser Lys Gly Val Thr Pro Asp
130                 135                 140

Trp Val Gln Ile Gly Asn Glu Thr Asn Asn Gly Met Leu Trp Glu Asp
145                 150                 155                 160

Gly Lys Ala Ser Val Asn Met Lys Asn Tyr Ala Trp Leu Val Asn Thr
                165                 170                 175

Gly Asn Asn Ala Val Lys Ser Val Ser Ser Thr Lys Thr Ile Val
                180                 185                 190

His Leu Ala Asn Gly Asp Asn Gly Ser Val Leu Asn Trp Asn Ile Gly
            195                 200                 205

Gly Leu Ile Asp Asn Gly Ala Gln Phe Asp Leu Ile Gly Leu Ser Leu
210                 215                 220

Tyr Pro Ser Pro Ser Asp Trp Gln Gly Lys Val Asp Gln Thr Ile Thr
225                 230                 235                 240
```

```
Asn Ala Asn Asn Leu Ile Ala Lys Tyr Gly Lys Gly Ile Val Ile Ser
                245                 250                 255

Glu Ile Gly Met Glu Tyr Asn Glu Pro Ala Ala Ser Lys Ala Phe Ile
            260                 265                 270

Ser Ala Ile Lys Thr Lys Val Arg Asn Met Gly Gly Lys Gly Thr
        275                 280                 285

Gly Val Phe Tyr Trp Glu Pro Ala Ala Thr Pro Gly Tyr Asn Gln Gly
    290                 295                 300

Tyr Asn Lys Gly Ala Trp Gln Ala Asp Gly Lys Pro Thr Ser Ala Leu
305                 310                 315                 320

Glu Gly Phe Val Asn
            325

<210> SEQ ID NO 33
<211> LENGTH: 1050
<212> TYPE: DNA
<213> ORGANISM: Paenibacillus xylanexedens
<220> FEATURE:
<221> NAME/KEY: CDS
<222> LOCATION: (1)..(1047)
<220> FEATURE:
<221> NAME/KEY: sig_peptide
<222> LOCATION: (1)..(99)
<220> FEATURE:
<221> NAME/KEY: mat_peptide
<222> LOCATION: (100)..(1047)

<400> SEQUENCE: 33 atg ttc aaa aat gta agg ggt ttc agg ata tcc atc atg ttg gct ttt     48
Met Phe Lys Asn Val Arg Gly Phe Arg Ile Ser Ile Met Leu Ala Phe
            -30                 -25                 -20 gtt ttg tta ttc acc tcc atc atg ttg ccc gca ggt cag cat gcc agc     96
Val Leu Leu Phe Thr Ser Ile Met Leu Pro Ala Gly Gln His Ala Ser
        -15                 -10                  -5 gca gca cca agt ttc gcc aaa gga gcc gac atc agt tgg gtt ccc gga    144
Ala Ala Pro Ser Phe Ala Lys Gly Ala Asp Ile Ser Trp Val Pro Gly
 -1   1               5                  10                  15 atg gaa gct caa ggc tac aaa tgg aaa gat aaa aac ggg gta cag cgt    192
Met Glu Ala Gln Gly Tyr Lys Trp Lys Asp Lys Asn Gly Val Gln Arg
                 20                  25                  30 gac atc att gat att ttg aaa aat gac tat caa atc aat tcc gtt cgt    240
Asp Ile Ile Asp Ile Leu Lys Asn Asp Tyr Gln Ile Asn Ser Val Arg
             35                  40                  45 att cgg gtc ttt gtt aat cct tcg aac gat tat ggg aac ggt tac atg    288
Ile Arg Val Phe Val Asn Pro Ser Asn Asp Tyr Gly Asn Gly Tyr Met
         50                  55                  60 aac aag gat cgt gcg gct gca ctc gca caa cgt gcc aag aat gcc ggc    336
Asn Lys Asp Arg Ala Ala Ala Leu Ala Gln Arg Ala Lys Asn Ala Gly
     65                  70                  75 atg agc gta atg ctc acc ctg cac tac agc gat tcc tgg gca gac cct    384
Met Ser Val Met Leu Thr Leu His Tyr Ser Asp Ser Trp Ala Asp Pro
 80                  85                  90                  95 ggt caa cag acc aaa cca gct gcc tgg aaa aac tac acg ttc cag cag    432
Gly Gln Gln Thr Lys Pro Ala Ala Trp Lys Asn Tyr Thr Phe Gln Gln
                100                 105                 110 ctc atg gat gcg gtg tgg aat cac aca cgt gat gtc atg act gca atg    480
Leu Met Asp Ala Val Trp Asn His Thr Arg Asp Val Met Thr Ala Met
            115                 120                 125 caa agc aaa ggc gtt acc ccg gac tgg gta cag atc ggg aat gaa aca    528
Gln Ser Lys Gly Val Thr Pro Asp Trp Val Gln Ile Gly Asn Glu Thr
        130                 135                 140
```

| | | | | | | | | | | | | | | | |
|---|---|---|---|---|---|---|---|---|---|---|---|---|---|---|---|
| agc | aac | ggc | atg | tta | tgg | gaa | gat | ggc | aaa | gca | tct | acc | aac | atg | aaa | 576
| Ser | Asn | Gly | Met | Leu | Trp | Glu | Asp | Gly | Lys | Ala | Ser | Thr | Asn | Met | Lys |
| | 145 | | | | 150 | | | | | 155 | | | | | |

| | | | | | | | | | | | | | | | |
|---|---|---|---|---|---|---|---|---|---|---|---|---|---|---|---|
| aac | tat | gcg | tgg | ctg | gta | aac | aca | ggc | cat | aat | gca | gtg | aaa | tcc | ctg | 624
| Asn | Tyr | Ala | Trp | Leu | Val | Asn | Thr | Gly | His | Asn | Ala | Val | Lys | Ser | Leu |
| 160 | | | | | 165 | | | | | 170 | | | | | 175 |

| | | | | | | | | | | | | | | | |
|---|---|---|---|---|---|---|---|---|---|---|---|---|---|---|---|
| agc | agc | ggc | acc | aaa | acc | att | gtg | cat | ctg | gca | ggt | gga | gat | gat | aac | 672
| Ser | Ser | Gly | Thr | Lys | Thr | Ile | Val | His | Leu | Ala | Gly | Gly | Asp | Asp | Asn |
| | | | | 180 | | | | | 185 | | | | | 190 | |

| | | | | | | | | | | | | | | | |
|---|---|---|---|---|---|---|---|---|---|---|---|---|---|---|---|
| gcc | ctc | tat | gta | tgg | aat | att | gga | ggc | ctg | atc | aat | aac | gga | gcc | aac | 720
| Ala | Leu | Tyr | Val | Trp | Asn | Ile | Gly | Gly | Leu | Ile | Asn | Asn | Gly | Ala | Asn |
| | | | 195 | | | | | 200 | | | | | 205 | | |

| | | | | | | | | | | | | | | | |
|---|---|---|---|---|---|---|---|---|---|---|---|---|---|---|---|
| ttt | gac | atg | att | gcg | atg | tcc | ctc | tac | cct | tcg | gct | tcc | ggc | tgg | aac | 768
| Phe | Asp | Met | Ile | Ala | Met | Ser | Leu | Tyr | Pro | Ser | Ala | Ser | Gly | Trp | Asn |
| | | 210 | | | | | 215 | | | | | 220 | | | |

| | | | | | | | | | | | | | | | |
|---|---|---|---|---|---|---|---|---|---|---|---|---|---|---|---|
| aca | gct | gtg | acg | aat | aca | gta | aac | aat | gcc | aag | gat | atg | atc | aac | cgt | 816
| Thr | Ala | Val | Thr | Asn | Thr | Val | Asn | Asn | Ala | Lys | Asp | Met | Ile | Asn | Arg |
| | 225 | | | | | 230 | | | | | 235 | | | | |

| | | | | | | | | | | | | | | | |
|---|---|---|---|---|---|---|---|---|---|---|---|---|---|---|---|
| tat | ggc | aaa | gag | atc | att | atc | tcc | gaa | att | ggt | atg | gac | aat | aac | cag | 864
| Tyr | Gly | Lys | Glu | Ile | Ile | Ile | Ser | Glu | Ile | Gly | Met | Asp | Asn | Asn | Gln |
| 240 | | | | | 245 | | | | | 250 | | | | | 255 |

| | | | | | | | | | | | | | | | |
|---|---|---|---|---|---|---|---|---|---|---|---|---|---|---|---|
| gct | gca | gct | ggt | aaa | agt | ttt | gtt | gcg | gcg | atg | aaa | aac | caa | atc | cgc | 912
| Ala | Ala | Ala | Gly | Lys | Ser | Phe | Val | Ala | Ala | Met | Lys | Asn | Gln | Ile | Arg |
| | | | | 260 | | | | | 265 | | | | | 270 | |

| | | | | | | | | | | | | | | | |
|---|---|---|---|---|---|---|---|---|---|---|---|---|---|---|---|
| aat | ctg | ccg | aat | ggt | aaa | ggc | aaa | ggc | gta | ttc | tac | tgg | gag | cct | cag | 960
| Asn | Leu | Pro | Asn | Gly | Lys | Gly | Lys | Gly | Val | Phe | Tyr | Trp | Glu | Pro | Gln |
| | | | 275 | | | | | 280 | | | | | 285 | | |

| | | | | | | | | | | | | | | | |
|---|---|---|---|---|---|---|---|---|---|---|---|---|---|---|---|
| gct | aca | cca | gga | tac | aac | agc | ggc | tat | ggc | aaa | ggt | gca | tgg | caa | tcg | 1008
| Ala | Thr | Pro | Gly | Tyr | Asn | Ser | Gly | Tyr | Gly | Lys | Gly | Ala | Trp | Gln | Ser |
| | | 290 | | | | | 295 | | | | | 300 | | | |

| | | | | | | | | | | |
|---|---|---|---|---|---|---|---|---|---|---|
| aat | atg | atg | ccg | acg | gta | gtc | atg | gaa | gga | ttt | att | gac | tag | | 1050
| Asn | Met | Met | Pro | Thr | Val | Val | Met | Glu | Gly | Phe | Ile | Asp | | | |
| 305 | | | | | 310 | | | | | 315 | | | | | |

<210> SEQ ID NO 34
<211> LENGTH: 349
<212> TYPE: PRT
<213> ORGANISM: Paenibacillus xylanexedens

<400> SEQUENCE: 34

Met Phe Lys Asn Val Arg Gly Phe Arg Ile Ser Ile Met Leu Ala Phe
            -30                 -25                 -20

Val Leu Leu Phe Thr Ser Ile Met Leu Pro Ala Gly Gln His Ala Ser
        -15                 -10                  -5

Ala Ala Pro Ser Phe Ala Lys Gly Ala Asp Ile Ser Trp Val Pro Gly
-1   1               5                  10                  15

Met Glu Ala Gln Gly Tyr Lys Trp Lys Asp Lys Asn Gly Val Gln Arg
                 20                  25                  30

Asp Ile Ile Asp Ile Leu Lys Asn Asp Tyr Gln Ile Asn Ser Val Arg
             35                  40                  45

Ile Arg Val Phe Val Asn Pro Ser Asn Asp Tyr Gly Asn Gly Tyr Met
         50                  55                  60

Asn Lys Asp Arg Ala Ala Leu Ala Gln Arg Ala Lys Asn Ala Gly
     65                  70                  75

Met Ser Val Met Leu Thr Leu His Tyr Ser Asp Ser Trp Ala Asp Pro
 80                  85                  90                  95

Gly Gln Gln Thr Lys Pro Ala Ala Trp Lys Asn Tyr Thr Phe Gln Gln
                100                 105                 110

```
Leu Met Asp Ala Val Trp Asn His Thr Arg Asp Val Met Thr Ala Met
            115                 120                 125
Gln Ser Lys Gly Val Thr Pro Asp Trp Val Gln Ile Gly Asn Glu Thr
        130                 135                 140
Ser Asn Gly Met Leu Trp Glu Asp Gly Lys Ala Ser Thr Asn Met Lys
145                 150                 155                 160
Asn Tyr Ala Trp Leu Val Asn Thr Gly His Asn Ala Val Lys Ser Leu
                165                 170                 175
Ser Ser Gly Thr Lys Thr Ile Val His Leu Ala Gly Asp Asp Asn
            180                 185                 190
Ala Leu Tyr Val Trp Asn Ile Gly Gly Leu Ile Asn Asn Gly Ala Asn
        195                 200                 205
Phe Asp Met Ile Ala Met Ser Leu Tyr Pro Ser Ala Ser Gly Trp Asn
    210                 215                 220
Thr Ala Val Thr Asn Thr Val Asn Asn Ala Lys Asp Met Ile Asn Arg
225                 230                 235
Tyr Gly Lys Glu Ile Ile Ile Ser Glu Ile Gly Met Asp Asn Asn Gln
240                 245                 250                 255
Ala Ala Ala Gly Lys Ser Phe Val Ala Ala Met Lys Asn Gln Ile Arg
                260                 265                 270
Asn Leu Pro Asn Gly Lys Gly Lys Gly Val Phe Tyr Trp Glu Pro Gln
            275                 280                 285
Ala Thr Pro Gly Tyr Asn Ser Gly Tyr Gly Lys Gly Ala Trp Gln Ser
        290                 295                 300
Asn Met Met Pro Thr Val Val Met Glu Gly Phe Ile Asp
305                 310                 315

<210> SEQ ID NO 35
<211> LENGTH: 316
<212> TYPE: PRT
<213> ORGANISM: Paenibacillus xylanexedens
<220> FEATURE:
<221> NAME/KEY: mat_peptide
<222> LOCATION: (1)..(316)

<400> SEQUENCE: 35

Ala Pro Ser Phe Ala Lys Gly Ala Asp Ile Ser Trp Val Pro Gly Met
1               5                   10                  15
Glu Ala Gln Gly Tyr Lys Trp Leu Asp Lys Asn Gly Val Gln Arg Asp
                20                  25                  30
Ile Ile Asp Ile Leu Lys Asn Asp Tyr Gln Ile Asn Ser Val Arg Ile
            35                  40                  45
Arg Val Phe Val Asn Pro Ser Asn Asp Tyr Gly Asn Gly Tyr Met Asn
    50                  55                  60
Lys Asp Arg Ala Ala Leu Ala Gln Arg Lys Asn Ala Gly Met
65                  70                  75                  80
Ser Val Met Leu Thr Leu His Tyr Ser Asp Ser Trp Ala Asp Pro Gly
                85                  90                  95
Gln Gln Thr Lys Pro Ala Ala Trp Lys Asn Tyr Thr Phe Gln Gln Leu
            100                 105                 110
Met Asp Ala Val Trp Asn His Thr Arg Asp Val Met Thr Ala Met Gln
        115                 120                 125
Ser Lys Gly Val Thr Pro Asp Trp Val Gln Ile Gly Asn Glu Thr Ser
    130                 135                 140
Asn Gly Met Leu Trp Glu Asp Gly Lys Ala Ser Thr Asn Met Lys Asn
145                 150                 155                 160
```

-continued

```
Tyr Ala Trp Leu Val Asn Thr Gly His Asn Ala Val Lys Ser Leu Ser
                165                 170                 175

Ser Gly Thr Lys Thr Ile Val His Leu Ala Gly Gly Asp Asp Asn Ala
            180                 185                 190

Leu Tyr Val Trp Asn Ile Gly Gly Leu Ile Asn Asn Gly Ala Asn Phe
        195                 200                 205

Asp Met Ile Ala Met Ser Leu Tyr Pro Ser Ala Ser Gly Trp Asn Thr
    210                 215                 220

Ala Val Thr Asn Thr Val Asn Asn Ala Lys Asp Met Ile Asn Arg Tyr
225                 230                 235                 240

Gly Lys Glu Ile Ile Ile Ser Glu Ile Gly Met Asp Asn Asn Gln Ala
                245                 250                 255

Ala Ala Gly Lys Ser Phe Val Ala Ala Met Lys Asn Gln Ile Arg Asn
            260                 265                 270

Leu Pro Asn Gly Lys Gly Lys Gly Val Phe Tyr Trp Glu Pro Gln Ala
        275                 280                 285

Thr Pro Gly Tyr Asn Ser Gly Tyr Gly Lys Gly Ala Trp Gln Ser Asn
    290                 295                 300

Met Met Pro Thr Val Val Met Glu Gly Phe Ile Asp
305                 310                 315
```

<210> SEQ ID NO 36
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 36

```
His His His His His His Pro Arg Ala Pro Ser Phe Ala Lys Gly Ala
1               5                   10                  15

Asp Ile Ser Trp Val Pro Gly Met Glu Ala Gln Gly Tyr Lys Trp Lys
                20                  25                  30

Asp Lys Asn Gly Val Gln Arg Asp Ile Ile Asp Ile Leu Lys Asn Asp
            35                  40                  45

Tyr Gln Ile Asn Ser Val Arg Ile Arg Val Phe Val Asn Pro Ser Asn
        50                  55                  60

Asp Tyr Gly Asn Gly Tyr Met Asn Lys Asp Arg Ala Ala Ala Leu Ala
65                  70                  75                  80

Gln Arg Ala Lys Asn Ala Gly Met Ser Val Met Leu Thr Leu His Tyr
                85                  90                  95

Ser Asp Ser Trp Ala Asp Pro Gly Gln Gln Thr Lys Pro Ala Ala Trp
            100                 105                 110

Lys Asn Tyr Thr Phe Gln Gln Leu Met Asp Ala Val Trp Asn His Thr
        115                 120                 125

Arg Asp Val Met Thr Ala Met Gln Ser Lys Gly Val Thr Pro Asp Trp
    130                 135                 140

Val Gln Ile Gly Asn Glu Thr Ser Asn Gly Met Leu Trp Glu Asp Gly
145                 150                 155                 160

Lys Ala Ser Thr Asn Met Lys Asn Tyr Ala Trp Leu Val Asn Thr Gly
                165                 170                 175

His Asn Ala Val Lys Ser Leu Ser Ser Gly Thr Lys Thr Ile Val His
            180                 185                 190
```

```
Leu Ala Gly Gly Asp Asp Asn Ala Leu Tyr Val Trp Asn Ile Gly Gly
        195                 200                 205

Leu Ile Asn Asn Gly Ala Asn Phe Asp Met Ile Ala Met Ser Leu Tyr
    210                 215                 220

Pro Ser Ala Ser Gly Trp Asn Thr Ala Val Thr Asn Thr Val Asn Asn
225                 230                 235                 240

Ala Lys Asp Met Ile Asn Arg Tyr Gly Lys Glu Ile Ile Ser Glu
                245                 250                 255

Ile Gly Met Asp Asn Asn Gln Ala Ala Ala Gly Lys Ser Phe Val Ala
            260                 265                 270

Ala Met Lys Asn Gln Ile Arg Asn Leu Pro Asn Gly Lys Gly Lys Gly
        275                 280                 285

Val Phe Tyr Trp Glu Pro Gln Ala Thr Pro Gly Tyr Asn Ser Gly Tyr
    290                 295                 300

Gly Lys Gly Ala Trp Gln Ser Asn Met Met Pro Thr Val Val Met Glu
305                 310                 315                 320

Gly Phe Ile Asp

<210> SEQ ID NO 37
<211> LENGTH: 1044
<212> TYPE: DNA
<213> ORGANISM: Cohnella laeviribosi
<220> FEATURE:
<221> NAME/KEY: CDS
<222> LOCATION: (1)..(1041)
<220> FEATURE:
<221> NAME/KEY: sig_peptide
<222> LOCATION: (1)..(93)
<220> FEATURE:
<221> NAME/KEY: mat_peptide
<222> LOCATION: (94)..(1041)

<400> SEQUENCE: 37 atg aaa aga aaa acg ttc gga tgg ctg ttg acg gcg ctg ctc ggt ttg      48
Met Lys Arg Lys Thr Phe Gly Trp Leu Leu Thr Ala Leu Leu Gly Leu
    -30                 -25                 -20 acc ctg gcg ctc ggc aac gcc gtg tct ccc ggc gac gcg aaa gcc gcc      96
Thr Leu Ala Leu Gly Asn Ala Val Ser Pro Gly Asp Ala Lys Ala Ala
-15                 -10                 -5                  -1  1 ccg gca ttt gcg aaa ggc gcg gac atc agc tgg gtt ccg ggc atg gag     144
Pro Ala Phe Ala Lys Gly Ala Asp Ile Ser Trp Val Pro Gly Met Glu
            5                   10                  15 gcg caa ggg tac aaa tgg aag gac aaa aac ggc gtg cag cgg gac atc     192
Ala Gln Gly Tyr Lys Trp Lys Asp Lys Asn Gly Val Gln Arg Asp Ile
        20                  25                  30 att gat att tta aag cag gat tac cag atc aac tcc gtc cgg atc cgc     240
Ile Asp Ile Leu Lys Gln Asp Tyr Gln Ile Asn Ser Val Arg Ile Arg
    35                  40                  45 gtg ttt gtc aat ccg tca agc gat tac ggc aac ggc tac ttg aac aag     288
Val Phe Val Asn Pro Ser Ser Asp Tyr Gly Asn Gly Tyr Leu Asn Lys
50                  55                  60                  65 gaa cgc gcg gcc gac ttg gcc cag cgg gcg aaa aac gcc ggc atg agc     336
Glu Arg Ala Ala Asp Leu Ala Gln Arg Ala Lys Asn Ala Gly Met Ser
                70                  75                  80 gtc atg ctg acg ctg cac tac agc gat tcg tgg gcg gac ccc ggc aag     384
Val Met Leu Thr Leu His Tyr Ser Asp Ser Trp Ala Asp Pro Gly Lys
            85                  90                  95 caa acc aag ccg gcc gcg tgg caa aat tat acg ttc gag caa ttg atg     432
Gln Thr Lys Pro Ala Ala Trp Gln Asn Tyr Thr Phe Glu Gln Leu Met
        100                 105                 110
```

```
gac gcc gta tgg aac tgg acg cgc gat gtg atg acg acg atg cag agc        480
Asp Ala Val Trp Asn Trp Thr Arg Asp Val Met Thr Thr Met Gln Ser
    115                 120                 125 aga ggc gtt acg ccg gac tgg gtg cag atc ggc aac gag acg aac aac        528
Arg Gly Val Thr Pro Asp Trp Val Gln Ile Gly Asn Glu Thr Asn Asn
130                 135                 140                 145 ggc atg ctg tgg gat gac ggc aag gcg tcc gtc aac atg cgt aat tac        576
Gly Met Leu Trp Asp Asp Gly Lys Ala Ser Val Asn Met Arg Asn Tyr
                150                 155                 160 gcc tgg ctc gtc aat acc ggc aac aat gcg gtc aag tcg atc agc agc        624
Ala Trp Leu Val Asn Thr Gly Asn Asn Ala Val Lys Ser Ile Ser Ser
            165                 170                 175 tcc acg aag acg atc gtc cat ctt tcc aac ggc tac gac aat tcg ctg        672
Ser Thr Lys Thr Ile Val His Leu Ser Asn Gly Tyr Asp Asn Ser Leu
        180                 185                 190 ttc gtc tgg aac atc ggt ggg ctg atc agc aac ggc gcg acg ttt gac        720
Phe Val Trp Asn Ile Gly Gly Leu Ile Ser Asn Gly Ala Thr Phe Asp
    195                 200                 205 att atc ggc atg tcg ctg tac ccg tcc gcg tcc gac tgg cag acg aag        768
Ile Ile Gly Met Ser Leu Tyr Pro Ser Ala Ser Asp Trp Gln Thr Lys
210                 215                 220                 225 gtc aat cag acg atc agc aac gcg aac gat ctg att tcg cgc tac ggc        816
Val Asn Gln Thr Ile Ser Asn Ala Asn Asp Leu Ile Ser Arg Tyr Gly
                230                 235                 240 aag agc atc atg atc tcc gaa atc ggc atg gac tac aac cag cct tcg        864
Lys Ser Ile Met Ile Ser Glu Ile Gly Met Asp Tyr Asn Gln Pro Ser
            245                 250                 255 gcc gcg aag agc ttc atc tcc gac atc aag acg aag gtc cgg aat ctt        912
Ala Ala Lys Ser Phe Ile Ser Asp Ile Lys Thr Lys Val Arg Asn Leu
        260                 265                 270 tcc gga ggc aaa ggg ctt ggc gtg ttt tat tgg gag ccc gag gct acc        960
Ser Gly Gly Lys Gly Leu Gly Val Phe Tyr Trp Glu Pro Glu Ala Thr
    275                 280                 285 ccc ggc tac aac ggc ggc tac aac aag ggc gcc tgg cag tcc gac atg       1008
Pro Gly Tyr Asn Gly Gly Tyr Asn Lys Gly Ala Trp Gln Ser Asp Met
290                 295                 300                 305 aag ccg acg atc gcg ctg gaa ggc ttc ctg aac tga                       1044
Lys Pro Thr Ile Ala Leu Glu Gly Phe Leu Asn
                310                 315
```

<210> SEQ ID NO 38
<211> LENGTH: 347
<212> TYPE: PRT
<213> ORGANISM: Cohnella laeviribosi

<400> SEQUENCE: 38

```
Met Lys Arg Lys Thr Phe Gly Trp Leu Leu Thr Ala Leu Leu Gly Leu
    -30                 -25                 -20

Thr Leu Ala Leu Gly Asn Ala Val Ser Pro Gly Asp Ala Lys Ala Ala
-15                 -10                  -5                  -1   1

Pro Ala Phe Ala Lys Gly Ala Asp Ile Ser Trp Val Pro Gly Met Glu
                 5                  10                  15

Ala Gln Gly Tyr Lys Trp Lys Asp Lys Asn Gly Val Gln Arg Asp Ile
            20                  25                  30

Ile Asp Ile Leu Lys Gln Asp Tyr Gln Ile Asn Ser Val Arg Ile Arg
        35                  40                  45

Val Phe Val Asn Pro Ser Ser Asp Tyr Gly Asn Gly Tyr Leu Asn Lys
50                  55                  60                  65
```

Glu Arg Ala Ala Asp Leu Ala Gln Arg Ala Lys Asn Ala Gly Met Ser
            70                  75                  80

Val Met Leu Thr Leu His Tyr Ser Asp Ser Trp Ala Asp Pro Gly Lys
        85                  90                  95

Gln Thr Lys Pro Ala Ala Trp Gln Asn Tyr Thr Phe Glu Gln Leu Met
    100                 105                 110

Asp Ala Val Trp Asn Trp Thr Arg Asp Val Met Thr Thr Met Gln Ser
115                 120                 125

Arg Gly Val Thr Pro Asp Trp Val Gln Ile Gly Asn Glu Thr Asn Asn
130                 135                 140                 145

Gly Met Leu Trp Asp Asp Gly Lys Ala Ser Val Asn Met Arg Asn Tyr
            150                 155                 160

Ala Trp Leu Val Asn Thr Gly Asn Asn Ala Val Lys Ser Ile Ser Ser
            165                 170                 175

Ser Thr Lys Thr Ile Val His Leu Ser Asn Gly Tyr Asp Asn Ser Leu
            180                 185                 190

Phe Val Trp Asn Ile Gly Gly Leu Ile Ser Asn Gly Ala Thr Phe Asp
    195                 200                 205

Ile Ile Gly Met Ser Leu Tyr Pro Ser Ala Ser Asp Trp Gln Thr Lys
210                 215                 220                 225

Val Asn Gln Thr Ile Ser Asn Ala Asn Asp Leu Ile Ser Arg Tyr Gly
            230                 235                 240

Lys Ser Ile Met Ile Ser Glu Ile Gly Met Asp Tyr Asn Gln Pro Ser
            245                 250                 255

Ala Ala Lys Ser Phe Ile Ser Asp Ile Lys Thr Lys Val Arg Asn Leu
            260                 265                 270

Ser Gly Gly Lys Gly Leu Gly Val Phe Tyr Trp Glu Pro Glu Ala Thr
    275                 280                 285

Pro Gly Tyr Asn Gly Gly Tyr Asn Lys Gly Ala Trp Gln Ser Asp Met
290                 295                 300                 305

Lys Pro Thr Ile Ala Leu Glu Gly Phe Leu Asn
            310                 315

<210> SEQ ID NO 39
<211> LENGTH: 316
<212> TYPE: PRT
<213> ORGANISM: Cohnella laeviribosi
<220> FEATURE:
<221> NAME/KEY: mat_peptide
<222> LOCATION: (1)..(316)

<400> SEQUENCE: 39

Ala Pro Ala Phe Ala Lys Gly Ala Asp Ile Ser Trp Val Pro Gly Met
1               5                   10                  15

Glu Ala Gln Gly Tyr Lys Trp Lys Asp Lys Asn Gly Val Gln Arg Asp
            20                  25                  30

Ile Ile Asp Ile Leu Lys Gln Asp Tyr Gln Ile Asn Ser Val Arg Ile
        35                  40                  45

Arg Val Phe Val Asn Pro Ser Ser Asp Tyr Gly Asn Gly Tyr Leu Asn
    50                  55                  60

Lys Glu Arg Ala Ala Asp Leu Ala Gln Arg Ala Lys Asn Ala Gly Met
65                  70                  75                  80

Ser Val Met Leu Thr Leu His Tyr Ser Asp Ser Trp Ala Asp Pro Gly
            85                  90                  95

Lys Gln Thr Lys Pro Ala Ala Trp Gln Asn Tyr Thr Phe Glu Gln Leu
        100                 105                 110

```
Met Asp Ala Val Trp Asn Trp Thr Arg Asp Val Met Thr Thr Met Gln
            115                 120                 125

Ser Arg Gly Val Thr Pro Asp Trp Val Gln Ile Gly Asn Glu Thr Asn
    130                 135                 140

Asn Gly Met Leu Trp Asp Asp Gly Lys Ala Ser Val Asn Met Arg Asn
145                 150                 155                 160

Tyr Ala Trp Leu Val Asn Thr Gly Asn Asn Ala Val Lys Ser Ile Ser
                165                 170                 175

Ser Ser Thr Lys Thr Ile Val His Leu Ser Asn Gly Tyr Asp Asn Ser
            180                 185                 190

Leu Phe Val Trp Asn Ile Gly Gly Leu Ile Ser Asn Gly Ala Thr Phe
        195                 200                 205

Asp Ile Ile Gly Met Ser Leu Tyr Pro Ser Ala Ser Asp Trp Gln Thr
    210                 215                 220

Lys Val Asn Gln Thr Ile Ser Asn Ala Asn Asp Leu Ile Ser Arg Tyr
225                 230                 235                 240

Gly Lys Ser Ile Met Ile Ser Glu Ile Gly Met Asp Tyr Asn Gln Pro
                245                 250                 255

Ser Ala Ala Lys Ser Phe Ile Ser Asp Ile Lys Thr Lys Val Arg Asn
            260                 265                 270

Leu Ser Gly Gly Lys Gly Leu Gly Val Phe Tyr Trp Glu Pro Glu Ala
        275                 280                 285

Thr Pro Gly Tyr Asn Gly Gly Tyr Asn Lys Gly Ala Trp Gln Ser Asp
    290                 295                 300

Met Lys Pro Thr Ile Ala Leu Glu Gly Phe Leu Asn
305                 310                 315

<210> SEQ ID NO 40
<211> LENGTH: 324
<212> TYPE: PRT
<213> ORGANISM: Artificial Sequence
<220> FEATURE:
<223> OTHER INFORMATION: Mature sequence with His-tag
<220> FEATURE:
<221> NAME/KEY: mat_peptide
<222> LOCATION: (1)..(324)

<400> SEQUENCE: 40

His His His His His His Pro Arg Ala Pro Ala Phe Ala Lys Gly Ala
1               5                   10                  15

Asp Ile Ser Trp Val Pro Gly Met Glu Ala Gln Gly Tyr Lys Trp Lys
            20                  25                  30

Asp Lys Asn Gly Val Gln Arg Asp Ile Ile Asp Ile Leu Lys Gln Asp
        35                  40                  45

Tyr Gln Ile Asn Ser Val Arg Ile Arg Val Phe Val Asn Pro Ser Ser
    50                  55                  60

Asp Tyr Gly Asn Gly Tyr Leu Asn Lys Glu Arg Ala Ala Asp Leu Ala
65                  70                  75                  80

Gln Arg Ala Lys Asn Ala Gly Met Ser Val Met Leu Thr Leu His Tyr
                85                  90                  95

Ser Asp Ser Trp Ala Asp Pro Gly Lys Gln Thr Lys Pro Ala Ala Trp
            100                 105                 110

Gln Asn Tyr Thr Phe Glu Gln Leu Met Asp Ala Val Trp Asn Trp Thr
        115                 120                 125

Arg Asp Val Met Thr Thr Met Gln Ser Arg Gly Val Thr Pro Asp Trp
    130                 135                 140
```

```
Val Gln Ile Gly Asn Glu Thr Asn Asn Gly Met Leu Trp Asp Asp Gly
145                 150                 155                 160

Lys Ala Ser Val Asn Met Arg Asn Tyr Ala Trp Leu Val Asn Thr Gly
                165                 170                 175

Asn Asn Ala Val Lys Ser Ile Ser Ser Thr Lys Thr Ile Val His
            180                 185                 190

Leu Ser Asn Gly Tyr Asp Asn Ser Leu Phe Val Trp Asn Ile Gly Gly
        195                 200                 205

Leu Ile Ser Asn Gly Ala Thr Phe Asp Ile Ile Gly Met Ser Leu Tyr
    210                 215                 220

Pro Ser Ala Ser Asp Trp Gln Thr Lys Val Asn Gln Thr Ile Ser Asn
225                 230                 235                 240

Ala Asn Asp Leu Ile Ser Arg Tyr Gly Lys Ser Ile Met Ile Ser Glu
                245                 250                 255

Ile Gly Met Asp Tyr Asn Gln Pro Ser Ala Ala Lys Ser Phe Ile Ser
            260                 265                 270

Asp Ile Lys Thr Lys Val Arg Asn Leu Ser Gly Gly Lys Gly Leu Gly
        275                 280                 285

Val Phe Tyr Trp Glu Pro Glu Ala Thr Pro Gly Tyr Asn Gly Gly Tyr
    290                 295                 300

Asn Lys Gly Ala Trp Gln Ser Asp Met Lys Pro Thr Ile Ala Leu Glu
305                 310                 315                 320

Gly Phe Leu Asn

<210> SEQ ID NO 41
<211> LENGTH: 3352
<212> TYPE: DNA
<213> ORGANISM: Hamigera paravellanea
<220> FEATURE:
<221> NAME/KEY: CDS
<222> LOCATION: (1)..(801)
<220> FEATURE:
<221> NAME/KEY: sig_peptide
<222> LOCATION: (1)..(69)
<220> FEATURE:
<221> NAME/KEY: mat_peptide
<222> LOCATION: (70)..(3349)
<220> FEATURE:
<221> NAME/KEY: CDS
<222> LOCATION: (873)..(1869)
<220> FEATURE:
<221> NAME/KEY: CDS
<222> LOCATION: (1930)..(2223)
<220> FEATURE:
<221> NAME/KEY: CDS
<222> LOCATION: (2297)..(2368)
<220> FEATURE:
<221> NAME/KEY: CDS
<222> LOCATION: (2427)..(2514)
<220> FEATURE:
<221> NAME/KEY: CDS
<222> LOCATION: (2578)..(3349)

<400> SEQUENCE: 41 atg acg cgc ctt agt gag tgg gct ttc gtc cta ctc tca act ttg ggc      48
Met Thr Arg Leu Ser Glu Trp Ala Phe Val Leu Leu Ser Thr Leu Gly
        -20                 -15                 -10 gtc ttc gcg gct gct cag gcc caa aca gtg tcg caa tgg ccc atc cac      96
Val Phe Ala Ala Ala Gln Ala Gln Thr Val Ser Gln Trp Pro Ile His
        -5              -1   1               5 gac aat gac ttg aac aca gtc gtc cag tgg gac cac tac agc ttc atc     144
Asp Asn Asp Leu Asn Thr Val Val Gln Trp Asp His Tyr Ser Phe Ile
10                  15                  20                  25
```

```
att aac gga cag cgt atc ttc gtt ttc tcg ggc gaa ttc cac tac tgg      192
Ile Asn Gly Gln Arg Ile Phe Val Phe Ser Gly Glu Phe His Tyr Trp
             30                  35                  40 cgc att ccg gtc ccc ggg tta tgg agg gat atc ctc gag aag gtc aaa      240
Arg Ile Pro Val Pro Gly Leu Trp Arg Asp Ile Leu Glu Lys Val Lys
         45                  50                  55 gcg gcc gga ttc act gcg ttt gca ttc tac tcc agc tgg gcg tac cac      288
Ala Ala Gly Phe Thr Ala Phe Ala Phe Tyr Ser Ser Trp Ala Tyr His
             60                  65                  70 gct ccg aat aac cac acc gtc gac ttc tcg aca ggt gcc cgt gat atc      336
Ala Pro Asn Asn His Thr Val Asp Phe Ser Thr Gly Ala Arg Asp Ile
         75                  80                  85 acg ccg atc ttt gac ctg gcc aag gag ctt ggt ttg tac gtc atc gtc      384
Thr Pro Ile Phe Asp Leu Ala Lys Glu Leu Gly Leu Tyr Val Ile Val
90                  95                 100                 105 cgt ccg ggg ccc tac gtc aac gcg gaa gcc aat gct ggt ggc tac cct      432
Arg Pro Gly Pro Tyr Val Asn Ala Glu Ala Asn Ala Gly Gly Tyr Pro
                110                 115                 120 ctt tgg ctc acc acc ggt gct tat gga agc ctg agg aac aat gac acg      480
Leu Trp Leu Thr Thr Gly Ala Tyr Gly Ser Leu Arg Asn Asn Asp Thr
             125                 130                 135 cgg tac atc aat gcc ttg gaa cct tac ttt tcc aag gtg tcg cag atc      528
Arg Tyr Ile Asn Ala Leu Glu Pro Tyr Phe Ser Lys Val Ser Gln Ile
         140                 145                 150 aca agc cag tat cag atc acc aac gac cac aac acc atc tgc tat caa      576
Thr Ser Gln Tyr Gln Ile Thr Asn Asp His Asn Thr Ile Cys Tyr Gln
155                 160                 165 atc gag aac gag tat ggc cag caa tgg atc ggc agt gca tac gac agg      624
Ile Glu Asn Glu Tyr Gly Gln Gln Trp Ile Gly Ser Ala Tyr Asp Arg
170                 175                 180                 185 gtt ccg aat gag acg gcc att gca tac atg gaa atc ctc aag gcg agc      672
Val Pro Asn Glu Thr Ala Ile Ala Tyr Met Glu Ile Leu Lys Ala Ser
                190                 195                 200 gct cgc aga aat ggc att gat att cct ctc acg gcg aat gac ccg aac      720
Ala Arg Arg Asn Gly Ile Asp Ile Pro Leu Thr Ala Asn Asp Pro Asn
             205                 210                 215 atg aac act cgt tcg tgg ggg aaa gac tgg tcc gac gaa ggt gga aac      768
Met Asn Thr Arg Ser Trp Gly Lys Asp Trp Ser Asp Glu Gly Gly Asn
         220                 225                 230 gtg gac atc ccc ggc gtc gac tcc tat cct tcg gtatgtggag actatgatca   821
Val Asp Ile Pro Gly Val Asp Ser Tyr Pro Ser
     235                 240 ttttggaggt gaaccttttc tgatgttttt ttcttcatct ccgtcttcca g tgc tgg    878
                                                        Cys Trp
                                                            245 tca tgc gac ctc agt gta tgc act tcg aca aac gga gta tac gtc ccg      926
Ser Cys Asp Leu Ser Val Cys Thr Ser Thr Asn Gly Val Tyr Val Pro
         250                 255                 260 ttc cag gtc ctg aac tac tac gac tat ttc gca gaa acg tca ccg acg      974
Phe Gln Val Leu Asn Tyr Tyr Asp Tyr Phe Ala Glu Thr Ser Pro Thr
     265                 270                 275 atg ccg tca ttc atg cca gaa ttt cag ggt ggc tct tac aat ccc tgg     1022
Met Pro Ser Phe Met Pro Glu Phe Gln Gly Gly Ser Tyr Asn Pro Trp
280                 285                 290 ggc ggt ccc gaa ggt ggc tgt ccg gac gac ata gga ccg gaa ttt gcg     1070
Gly Gly Pro Glu Gly Gly Cys Pro Asp Asp Ile Gly Pro Glu Phe Ala
295                 300                 305                 310 aac ctg ttc tac agg tgg aac atc ggt cag cgt gtc acg gct atg agt     1118
Asn Leu Phe Tyr Arg Trp Asn Ile Gly Gln Arg Val Thr Ala Met Ser
```

```
                    315                 320                 325
ttg tat atg ctc tat gga gga aca aac tgg ggt gca atg gct gct ccc        1166
Leu Tyr Met Leu Tyr Gly Gly Thr Asn Trp Gly Ala Met Ala Ala Pro
            330                 335                 340 gtg aca gct agc agc tat gac tat tct gct ccc atc tca gag gat cgc        1214
Val Thr Ala Ser Ser Tyr Asp Tyr Ser Ala Pro Ile Ser Glu Asp Arg
                345                 350                 355 tcc atc ggc gcg aaa tac tat gag acc aag ctc ctg ggg ctg ttc agt        1262
Ser Ile Gly Ala Lys Tyr Tyr Glu Thr Lys Leu Leu Gly Leu Phe Ser
        360                 365                 370 cgg agc gcg cga gac ctg acc gtg acg gat ctg atc ggc aat gga acc        1310
Arg Ser Ala Arg Asp Leu Thr Val Thr Asp Leu Ile Gly Asn Gly Thr
375                 380                 385                 390 cag tat acc aac aac gtg atg att cag gca cgc gaa ctc aga aac ccg        1358
Gln Tyr Thr Asn Asn Val Met Ile Gln Ala Arg Glu Leu Arg Asn Pro
                395                 400                 405 gaa acc aat gcc gct ttc tac gtc aca gtt cat acc aac acc tct gtt        1406
Glu Thr Asn Ala Ala Phe Tyr Val Thr Val His Thr Asn Thr Ser Val
        410                 415                 420 tct act aac gag gtc ttc cac ctg aga gtc aac acc tct gcc gga gct        1454
Ser Thr Asn Glu Val Phe His Leu Arg Val Asn Thr Ser Ala Gly Ala
                425                 430                 435 cta acg att cct aaa cac gcg ctt ggc att cga ctg aat ggt cac cag        1502
Leu Thr Ile Pro Lys His Ala Leu Gly Ile Arg Leu Asn Gly His Gln
    440                 445                 450 tcg aag atc ata gtg acg gac ttt acc ttc ggc ccc agg act ctg ctc        1550
Ser Lys Ile Ile Val Thr Asp Phe Thr Phe Gly Pro Arg Thr Leu Leu
455                 460                 465                 470 tac tcg acc gca gaa gtc ctc gcc tat gcc gcg ctg gac gac acc cca        1598
Tyr Ser Thr Ala Glu Val Leu Ala Tyr Ala Ala Leu Asp Asp Thr Pro
                475                 480                 485 act ctg gct ctc tgg gtt cca cct gga gag tcc gga gag ttt aac gtc        1646
Thr Leu Ala Leu Trp Val Pro Pro Gly Glu Ser Gly Glu Phe Asn Val
        490                 495                 500 aag ggc gca aaa tcg gga tcg gtc aag aaa tgc cag ggg tgt tcg aac        1694
Lys Gly Ala Lys Ser Gly Ser Val Lys Lys Cys Gln Gly Cys Ser Asn
            505                 510                 515 gtc cag ttc cac cag gaa aac ggt ggt ctt aca gtc gcc ttc act caa        1742
Val Gln Phe His Gln Glu Asn Gly Gly Leu Thr Val Ala Phe Thr Gln
        520                 525                 530 tct caa ggg atg agc gtt gtg gaa ctg aac gat ggt agt cgc gtg gtt        1790
Ser Gln Gly Met Ser Val Val Glu Leu Asn Asp Gly Ser Arg Val Val
535                 540                 545                 550 ctg ctt gac agg gaa tcc gca tac cgt ttc tgg gct cca gca ttg act        1838
Leu Leu Asp Arg Glu Ser Ala Tyr Arg Phe Trp Ala Pro Ala Leu Thr
                555                 560                 565 aac gat cca ttc gtg ccg gag gat gag act g gtgcgtgttt tccttatgcc       1889
Asn Asp Pro Phe Val Pro Glu Asp Glu Thr
        570                 575 aatcgtgaaa aaaaaaatg cttgctgacc tgccaagcag tt ctg atc caa ggc          1943
                                              Val Leu Ile Gln Gly
                                                          580 ccc tac ctc gtc cgc ggg gct aaa ctg tca ggc tct acg ctg tcg gta        1991
Pro Tyr Leu Val Arg Gly Ala Lys Leu Ser Gly Ser Thr Leu Ser Val
            585                 590                 595 aca ggt gat atc gtg aat gca acg acc gtg gag atc ttc gcg ccc aaa        2039
Thr Gly Asp Ile Val Asn Ala Thr Thr Val Glu Ile Phe Ala Pro Lys
                600                 605                 610 acc gtc aag tcc att acc tgg aac ggg aga gaa ctg aag act tcg aag        2087
Thr Val Lys Ser Ile Thr Trp Asn Gly Arg Glu Leu Lys Thr Ser Lys
```

```
Thr Val Lys Ser Ile Thr Trp Asn Gly Arg Glu Leu Lys Thr Ser Lys
    615                 620                 625 acg tct tat ggc agt ctg cag ggc tct ttg aag gct cct gca ccc gtc        2135
Thr Ser Tyr Gly Ser Leu Gln Gly Ser Leu Lys Ala Pro Ala Pro Val
630                 635                 640                 645 aaa ttg ccc gct ctt acc ggc tgg aaa tcc aag gac agc ttg ccc gag        2183
Lys Leu Pro Ala Leu Thr Gly Trp Lys Ser Lys Asp Ser Leu Pro Glu
                650                 655                 660 cgg ctt gca tca tat gac gac tct ggt gcg gcc tgg gtt g gtgagtagaa       2233
Arg Leu Ala Ser Tyr Asp Asp Ser Gly Ala Ala Trp Val
                665                 670 gaaaatcata agcagttgaa cggagcggaa tagaacagaa tcggtaaact gacatccacc      2293 aag at  gcc aac cac atg aca aca ttg aac ccg agc cct cca gca aca        2340
        Asp Ala Asn His Met Thr Thr Leu Asn Pro Ser Pro Pro Ala Thr
        675                 680                 685 ctt cca gtc cta tac gcc gac gaa tat g gtattgccgc tcctttcca            2388
Leu Pro Val Leu Tyr Ala Asp Glu Tyr
690                 695 cctgtttccg acgatccgtc atactgactt tcgtatag gc  ttc cac aac ggc gtc      2443
                                             Gly Phe His Asn Gly Val
                                                             700 cgt ctc tgg cga ggc tac ttc aac ggc acc gct acg ggg gtc ttc ttg        2491
Arg Leu Trp Arg Gly Tyr Phe Asn Gly Thr Ala Thr Gly Val Phe Leu
705                 710                 715                 720 aac atc caa gga gga agc gcc tt  gtaagctatt cacaatcgcc actcagcaaa       2544
Asn Ile Gln Gly Gly Ser Ala Phe
                725 gcccgggtcc aatactaaca tctcgacaca cag c ggc tgg tca gcc tac ctc         2596
                                     Gly Trp Ser Ala Tyr Leu
                                             730 aac ggc cac ttc ctg gga tcc cat ctc ggc gcc gcc tcc atc gcc caa        2644
Asn Gly His Phe Leu Gly Ser His Leu Gly Ala Ala Ser Ile Ala Gln
735                 740                 745                 750 gcc aac cgt acc ctc tcc ttc gcc aac gcc acc ctc aat gcc ttt ggc        2692
Ala Asn Arg Thr Leu Ser Phe Ala Asn Ala Thr Leu Asn Ala Phe Gly
                755                 760                 765 ccc aat gtc ctc ctc gtc atc cac gac gac aca ggc cac gat caa acc        2740
Pro Asn Val Leu Leu Val Ile His Asp Asp Thr Gly His Asp Gln Thr
                770                 775                 780 acc ggt gcc ctg aac ccg cgc ggc att ctg aac gcg acc ctc ctc tcc        2788
Thr Gly Ala Leu Asn Pro Arg Gly Ile Leu Asn Ala Thr Leu Leu Ser
        785                 790                 795 ggc gac gac tcg gcc caa ttc act cac tgg cgc ctc gcc ggc acc gcc        2836
Gly Asp Asp Ser Ala Gln Phe Thr His Trp Arg Leu Ala Gly Thr Ala
800                 805                 810 ggc ggc gaa tcc aac ctc gac ccc gtc cgc ggc gtg tac aac gaa gac        2884
Gly Gly Glu Ser Asn Leu Asp Pro Val Arg Gly Val Tyr Asn Glu Asp
815                 820                 825                 830 ggc ctc ttc gcc gag cgc gtc ggc tgg cac ctc ccc ggg ttc gac gac        2932
Gly Leu Phe Ala Glu Arg Val Gly Trp His Leu Pro Gly Phe Asp Asp
                835                 840                 845 tcg gct tgg ccc gac gcc tcg tct ccg cgc gag ggc ttc gcg ggc gcg        2980
Ser Ala Trp Pro Asp Ala Ser Ser Pro Arg Glu Gly Phe Ala Gly Ala
                850                 855                 860 acc gtc cgg ttc tac cgg acc acc gtg gcc tta gac ctg ccg cgg gac        3028
Thr Val Arg Phe Tyr Arg Thr Thr Val Ala Leu Asp Leu Pro Arg Asp
                865                 870                 875 gtg gac gcg tcg ata tcg ttc gtg ttc tcg act cct ccg tcg tcg tcc        3076
Val Asp Ala Ser Ile Ser Phe Val Phe Ser Thr Pro Pro Ser Ser Ser
```

-continued

```
                880                 885                 890
gcc gcg tac cgg gcc cag ttg ttc gtg aac gga tac cag tac ggt cgg      3124
Ala Ala Tyr Arg Ala Gln Leu Phe Val Asn Gly Tyr Gln Tyr Gly Arg
895                 900                 905                 910 tat cat ccg cac atc ggc aac cag gtc gtg tac ccg gtt cca ccg ggc      3172
Tyr His Pro His Ile Gly Asn Gln Val Val Tyr Pro Val Pro Pro Gly
                915                 920                 925 atc ttg gat tac cag ggc gac aac acc atc ggg gtc gca gtg tgg gcg      3220
Ile Leu Asp Tyr Gln Gly Asp Asn Thr Ile Gly Val Ala Val Trp Ala
            930                 935                 940 cag acg gag gaa ggg gca cgg gtg ggg ttg gac tgg cgc gtg aac tat      3268
Gln Thr Glu Glu Gly Ala Arg Val Gly Leu Asp Trp Arg Val Asn Tyr
        945                 950                 955 gtg gcg gat agt tcc ttg gat gtt tct ttc gac ggg gct gcg ttg aga      3316
Val Ala Asp Ser Ser Leu Asp Val Ser Phe Asp Gly Ala Ala Leu Arg
    960                 965                 970 ccg ggg tgg gac gag ggg cgg ttg cag tat gca tag                       3352
Pro Gly Trp Asp Glu Gly Arg Leu Gln Tyr Ala
975                 980                 985
```

<210> SEQ ID NO 42
<211> LENGTH: 1008
<212> TYPE: PRT
<213> ORGANISM: Hamigera paravellanea

<400> SEQUENCE: 42

```
Met Thr Arg Leu Ser Glu Trp Ala Phe Val Leu Leu Ser Thr Leu Gly
            -20                 -15                 -10

Val Phe Ala Ala Ala Gln Ala Gln Thr Val Ser Gln Trp Pro Ile His
        -5                  -1   1               5

Asp Asn Asp Leu Asn Thr Val Val Gln Trp Asp His Tyr Ser Phe Ile
 10                  15                  20                  25

Ile Asn Gly Gln Arg Ile Phe Val Phe Ser Gly Glu Phe His Tyr Trp
                 30                  35                  40

Arg Ile Pro Val Pro Gly Leu Trp Arg Asp Ile Leu Glu Lys Val Lys
             45                  50                  55

Ala Ala Gly Phe Thr Ala Phe Ala Phe Tyr Ser Ser Trp Ala Tyr His
         60                  65                  70

Ala Pro Asn Asn His Thr Val Asp Phe Ser Thr Gly Ala Arg Asp Ile
 75                  80                  85

Thr Pro Ile Phe Asp Leu Ala Lys Glu Leu Gly Leu Tyr Val Ile Val
 90                  95                 100                 105

Arg Pro Gly Pro Tyr Val Asn Ala Glu Ala Asn Ala Gly Gly Tyr Pro
                110                 115                 120

Leu Trp Leu Thr Thr Gly Ala Tyr Gly Ser Leu Arg Asn Asn Asp Thr
            125                 130                 135

Arg Tyr Ile Asn Ala Leu Glu Pro Tyr Phe Ser Lys Val Ser Gln Ile
        140                 145                 150

Thr Ser Gln Tyr Gln Ile Thr Asn Asp His Asn Thr Ile Cys Tyr Gln
    155                 160                 165

Ile Glu Asn Glu Tyr Gly Gln Gln Trp Ile Gly Ser Ala Tyr Asp Arg
170                 175                 180                 185

Val Pro Asn Glu Thr Ala Ile Ala Tyr Met Glu Ile Leu Lys Ala Ser
                190                 195                 200

Ala Arg Arg Asn Gly Ile Asp Ile Pro Leu Thr Ala Asn Asp Pro Asn
            205                 210                 215
```

-continued

```
Met Asn Thr Arg Ser Trp Gly Lys Asp Trp Ser Asp Glu Gly Gly Asn
            220                 225                 230
Val Asp Ile Pro Gly Val Asp Ser Tyr Pro Ser Cys Trp Ser Cys Asp
235                 240                 245
Leu Ser Val Cys Thr Ser Thr Asn Gly Val Tyr Val Pro Phe Gln Val
250                 255                 260                 265
Leu Asn Tyr Tyr Asp Tyr Phe Ala Glu Thr Ser Pro Thr Met Pro Ser
                270                 275                 280
Phe Met Pro Glu Phe Gln Gly Gly Ser Tyr Asn Pro Trp Gly Gly Pro
            285                 290                 295
Glu Gly Gly Cys Pro Asp Asp Ile Gly Pro Glu Phe Ala Asn Leu Phe
            300                 305                 310
Tyr Arg Trp Asn Ile Gly Gln Arg Val Thr Ala Met Ser Leu Tyr Met
            315                 320                 325
Leu Tyr Gly Gly Thr Asn Trp Gly Ala Met Ala Ala Pro Val Thr Ala
330                 335                 340                 345
Ser Ser Tyr Asp Tyr Ser Ala Pro Ile Ser Glu Asp Arg Ser Ile Gly
                350                 355                 360
Ala Lys Tyr Tyr Glu Thr Lys Leu Leu Gly Leu Phe Ser Arg Ser Ala
            365                 370                 375
Arg Asp Leu Thr Val Thr Asp Leu Ile Gly Asn Gly Thr Gln Tyr Thr
            380                 385                 390
Asn Asn Val Met Ile Gln Ala Arg Glu Leu Arg Asn Pro Glu Thr Asn
            395                 400                 405
Ala Ala Phe Tyr Val Thr Val His Thr Asn Thr Ser Val Ser Thr Asn
410                 415                 420                 425
Glu Val Phe His Leu Arg Val Asn Thr Ser Ala Gly Ala Leu Thr Ile
                430                 435                 440
Pro Lys His Ala Leu Gly Ile Arg Leu Asn Gly His Gln Ser Lys Ile
            445                 450                 455
Ile Val Thr Asp Phe Thr Phe Gly Pro Arg Thr Leu Leu Tyr Ser Thr
            460                 465                 470
Ala Glu Val Leu Ala Tyr Ala Ala Leu Asp Asp Thr Pro Thr Leu Ala
475                 480                 485
Leu Trp Val Pro Pro Gly Glu Ser Gly Glu Phe Asn Val Lys Gly Ala
490                 495                 500                 505
Lys Ser Gly Ser Val Lys Lys Cys Gln Gly Cys Ser Asn Val Gln Phe
                510                 515                 520
His Gln Glu Asn Gly Gly Leu Thr Val Ala Phe Thr Gln Ser Gln Gly
            525                 530                 535
Met Ser Val Val Glu Leu Asn Asp Gly Ser Arg Val Val Leu Leu Asp
            540                 545                 550
Arg Glu Ser Ala Tyr Arg Phe Trp Ala Pro Ala Leu Thr Asn Asp Pro
            555                 560                 565
Phe Val Pro Glu Asp Glu Thr Val Leu Ile Gln Gly Pro Tyr Leu Val
570                 575                 580                 585
Arg Gly Ala Lys Leu Ser Gly Ser Thr Leu Ser Val Thr Gly Asp Ile
                590                 595                 600
Val Asn Ala Thr Thr Val Glu Ile Phe Ala Pro Lys Val Lys Ser
            605                 610                 615
Ile Thr Trp Asn Gly Arg Glu Leu Lys Thr Ser Lys Thr Ser Tyr Gly
            620                 625                 630
Ser Leu Gln Gly Ser Leu Lys Ala Pro Ala Pro Val Lys Leu Pro Ala
```

635                 640                 645

Leu Thr Gly Trp Lys Ser Lys Asp Ser Leu Pro Glu Arg Leu Ala Ser
650                 655                 660                 665

Tyr Asp Asp Ser Gly Ala Ala Trp Val Asp Ala Asn His Met Thr Thr
                670                 675                 680

Leu Asn Pro Ser Pro Pro Ala Thr Leu Pro Val Leu Tyr Ala Asp Glu
            685                 690                 695

Tyr Gly Phe His Asn Gly Val Arg Leu Trp Arg Gly Tyr Phe Asn Gly
        700                 705                 710

Thr Ala Thr Gly Val Phe Leu Asn Ile Gln Gly Gly Ser Ala Phe Gly
    715                 720                 725

Trp Ser Ala Tyr Leu Asn Gly His Phe Leu Gly Ser His Leu Gly Ala
730                 735                 740                 745

Ala Ser Ile Ala Gln Ala Asn Arg Thr Leu Ser Phe Ala Asn Ala Thr
                750                 755                 760

Leu Asn Ala Phe Gly Pro Asn Val Leu Leu Val Ile His Asp Asp Thr
            765                 770                 775

Gly His Asp Gln Thr Thr Gly Ala Leu Asn Pro Arg Gly Ile Leu Asn
        780                 785                 790

Ala Thr Leu Leu Ser Gly Asp Asp Ser Ala Gln Phe Thr His Trp Arg
    795                 800                 805

Leu Ala Gly Thr Ala Gly Gly Glu Ser Asn Leu Asp Pro Val Arg Gly
810                 815                 820                 825

Val Tyr Asn Glu Asp Gly Leu Phe Ala Glu Arg Val Gly Trp His Leu
                830                 835                 840

Pro Gly Phe Asp Asp Ser Ala Trp Pro Asp Ala Ser Ser Pro Arg Glu
            845                 850                 855

Gly Phe Ala Gly Ala Thr Val Arg Phe Tyr Arg Thr Thr Val Ala Leu
        860                 865                 870

Asp Leu Pro Arg Asp Val Asp Ala Ser Ile Ser Phe Val Phe Ser Thr
    875                 880                 885

Pro Pro Ser Ser Ser Ala Ala Tyr Arg Ala Gln Leu Phe Val Asn Gly
890                 895                 900                 905

Tyr Gln Tyr Gly Arg Tyr His Pro His Ile Gly Asn Gln Val Tyr
                910                 915                 920

Pro Val Pro Pro Gly Ile Leu Asp Tyr Gln Gly Asp Asn Thr Ile Gly
            925                 930                 935

Val Ala Val Trp Ala Gln Thr Glu Glu Gly Ala Arg Val Gly Leu Asp
        940                 945                 950

Trp Arg Val Asn Tyr Val Ala Asp Ser Ser Leu Asp Val Ser Phe Asp
    955                 960                 965

Gly Ala Ala Leu Arg Pro Gly Trp Asp Glu Gly Arg Leu Gln Tyr Ala
970                 975                 980                 985

<210> SEQ ID NO 43
<211> LENGTH: 985
<212> TYPE: PRT
<213> ORGANISM: Hamigera paravellanea
<220> FEATURE:
<221> NAME/KEY: mat_peptide
<222> LOCATION: (1)..(985)

<400> SEQUENCE: 43

Gln Thr Val Ser Gln Trp Pro Ile His Asp Asn Asp Leu Asn Thr Val
1               5                   10                  15

```
Val Gln Trp Asp His Tyr Ser Phe Ile Ile Asn Gly Gln Arg Ile Phe
             20                  25                  30

Val Phe Ser Gly Glu Phe His Tyr Trp Arg Ile Pro Val Pro Gly Leu
         35                  40                  45

Trp Arg Asp Ile Leu Glu Lys Val Lys Ala Ala Gly Phe Thr Ala Phe
 50                  55                  60

Ala Phe Tyr Ser Ser Trp Ala Tyr His Ala Pro Asn Asn His Thr Val
 65                  70                  75                  80

Asp Phe Ser Thr Gly Ala Arg Asp Ile Thr Pro Ile Phe Asp Leu Ala
                 85                  90                  95

Lys Glu Leu Gly Leu Tyr Val Ile Val Arg Pro Gly Pro Tyr Val Asn
             100                 105                 110

Ala Glu Ala Asn Ala Gly Gly Tyr Pro Leu Trp Leu Thr Thr Gly Ala
             115                 120                 125

Tyr Gly Ser Leu Arg Asn Asn Asp Thr Arg Tyr Ile Asn Ala Leu Glu
     130                 135                 140

Pro Tyr Phe Ser Lys Val Ser Gln Ile Thr Ser Gln Tyr Gln Ile Thr
145                 150                 155                 160

Asn Asp His Asn Thr Ile Cys Tyr Gln Ile Glu Asn Glu Tyr Gly Gln
                 165                 170                 175

Gln Trp Ile Gly Ser Ala Tyr Asp Arg Val Pro Asn Glu Thr Ala Ile
             180                 185                 190

Ala Tyr Met Glu Ile Leu Lys Ala Ser Ala Arg Arg Asn Gly Ile Asp
             195                 200                 205

Ile Pro Leu Thr Ala Asn Asp Pro Asn Met Asn Thr Arg Ser Trp Gly
210                 215                 220

Lys Asp Trp Ser Asp Glu Gly Gly Asn Val Asp Ile Pro Gly Val Asp
225                 230                 235                 240

Ser Tyr Pro Ser Cys Trp Ser Cys Asp Leu Ser Val Cys Thr Ser Thr
                 245                 250                 255

Asn Gly Val Tyr Val Pro Phe Gln Val Leu Asn Tyr Tyr Asp Tyr Phe
                 260                 265                 270

Ala Glu Thr Ser Pro Thr Met Pro Ser Phe Met Pro Glu Phe Gln Gly
             275                 280                 285

Gly Ser Tyr Asn Pro Trp Gly Gly Pro Glu Gly Gly Cys Pro Asp Asp
     290                 295                 300

Ile Gly Pro Glu Phe Ala Asn Leu Phe Tyr Arg Trp Asn Ile Gly Gln
305                 310                 315                 320

Arg Val Thr Ala Met Ser Leu Tyr Met Leu Tyr Gly Gly Thr Asn Trp
                 325                 330                 335

Gly Ala Met Ala Ala Pro Val Thr Ala Ser Ser Tyr Asp Tyr Ser Ala
                 340                 345                 350

Pro Ile Ser Glu Asp Arg Ser Ile Gly Ala Lys Tyr Tyr Glu Thr Lys
             355                 360                 365

Leu Leu Gly Leu Phe Ser Arg Ser Ala Arg Asp Leu Thr Val Thr Asp
     370                 375                 380

Leu Ile Gly Asn Gly Thr Gln Tyr Thr Asn Asn Val Met Ile Gln Ala
385                 390                 395                 400

Arg Glu Leu Arg Asn Pro Glu Thr Asn Ala Ala Phe Tyr Val Thr Val
                 405                 410                 415

His Thr Asn Thr Ser Val Ser Thr Asn Glu Val Phe His Leu Arg Val
             420                 425                 430

Asn Thr Ser Ala Gly Ala Leu Thr Ile Pro Lys His Ala Leu Gly Ile
```

```
                    435                 440                 445
Arg Leu Asn Gly His Gln Ser Lys Ile Ile Val Thr Asp Phe Thr Phe
450                 455                 460

Gly Pro Arg Thr Leu Leu Tyr Ser Thr Ala Glu Val Leu Ala Tyr Ala
465                 470                 475                 480

Ala Leu Asp Asp Thr Pro Thr Leu Ala Leu Trp Val Pro Pro Gly Glu
                485                 490                 495

Ser Gly Glu Phe Asn Val Lys Gly Ala Lys Ser Gly Ser Val Lys Lys
                500                 505                 510

Cys Gln Gly Cys Ser Asn Val Gln Phe His Gln Glu Asn Gly Gly Leu
                515                 520                 525

Thr Val Ala Phe Thr Gln Ser Gln Gly Met Ser Val Val Glu Leu Asn
530                 535                 540

Asp Gly Ser Arg Val Val Leu Leu Asp Arg Glu Ser Ala Tyr Arg Phe
545                 550                 555                 560

Trp Ala Pro Ala Leu Thr Asn Asp Pro Phe Val Pro Glu Asp Glu Thr
                565                 570                 575

Val Leu Ile Gln Gly Pro Tyr Leu Val Arg Gly Ala Lys Leu Ser Gly
                580                 585                 590

Ser Thr Leu Ser Val Thr Gly Asp Ile Val Asn Ala Thr Thr Val Glu
                595                 600                 605

Ile Phe Ala Pro Lys Thr Val Lys Ser Ile Thr Trp Asn Gly Arg Glu
610                 615                 620

Leu Lys Thr Ser Lys Thr Ser Tyr Gly Ser Leu Gln Gly Ser Leu Lys
625                 630                 635                 640

Ala Pro Ala Pro Val Lys Leu Pro Ala Leu Thr Gly Trp Lys Ser Lys
                645                 650                 655

Asp Ser Leu Pro Glu Arg Leu Ala Ser Tyr Asp Ser Gly Ala Ala
                660                 665                 670

Trp Val Asp Ala Asn His Met Thr Thr Leu Asn Pro Ser Pro Ala
                675                 680                 685

Thr Leu Pro Val Leu Tyr Ala Asp Glu Tyr Gly Phe His Asn Gly Val
690                 695                 700

Arg Leu Trp Arg Gly Tyr Phe Asn Gly Thr Ala Thr Gly Val Phe Leu
705                 710                 715                 720

Asn Ile Gln Gly Gly Ser Ala Phe Gly Trp Ser Ala Tyr Leu Asn Gly
                725                 730                 735

His Phe Leu Gly Ser His Leu Gly Ala Ala Ser Ile Ala Gln Ala Asn
                740                 745                 750

Arg Thr Leu Ser Phe Ala Asn Ala Thr Leu Asn Ala Phe Gly Pro Asn
                755                 760                 765

Val Leu Leu Val Ile His Asp Asp Thr Gly His Asp Gln Thr Thr Gly
                770                 775                 780

Ala Leu Asn Pro Arg Gly Ile Leu Asn Ala Thr Leu Leu Ser Gly Asp
785                 790                 795                 800

Asp Ser Ala Gln Phe Thr His Trp Arg Leu Ala Gly Thr Ala Gly Gly
                805                 810                 815

Glu Ser Asn Leu Asp Pro Val Arg Gly Val Tyr Asn Glu Asp Gly Leu
                820                 825                 830

Phe Ala Glu Arg Val Gly Trp His Leu Pro Gly Phe Asp Asp Ser Ala
                835                 840                 845

Trp Pro Asp Ala Ser Ser Pro Arg Glu Gly Phe Ala Gly Ala Thr Val
850                 855                 860
```

```
Arg Phe Tyr Arg Thr Thr Val Ala Leu Asp Leu Pro Arg Asp Val Asp
865                 870                 875                 880

Ala Ser Ile Ser Phe Val Phe Ser Thr Pro Ser Ser Ser Ala Ala
            885                 890                 895

Tyr Arg Ala Gln Leu Phe Val Asn Gly Tyr Gln Tyr Gly Arg Tyr His
        900                 905                 910

Pro His Ile Gly Asn Gln Val Val Tyr Pro Val Pro Pro Gly Ile Leu
            915                 920                 925

Asp Tyr Gln Gly Asp Asn Thr Ile Gly Val Ala Val Trp Ala Gln Thr
        930                 935                 940

Glu Glu Gly Ala Arg Val Gly Leu Asp Trp Arg Val Asn Tyr Val Ala
945                 950                 955                 960

Asp Ser Ser Leu Asp Val Ser Phe Asp Gly Ala Ala Leu Arg Pro Gly
            965                 970                 975

Trp Asp Glu Gly Arg Leu Gln Tyr Ala
            980                 985

<210> SEQ ID NO 44
<211> LENGTH: 3391
<212> TYPE: DNA
<213> ORGANISM: Aspergillus unguis
<220> FEATURE:
<221> NAME/KEY: CDS
<222> LOCATION: (1)..(801)
<220> FEATURE:
<221> NAME/KEY: sig_peptide
<222> LOCATION: (1)..(60)
<220> FEATURE:
<221> NAME/KEY: mat_peptide
<222> LOCATION: (61)..(3388)
<220> FEATURE:
<221> NAME/KEY: CDS
<222> LOCATION: (847)..(1831)
<220> FEATURE:
<221> NAME/KEY: CDS
<222> LOCATION: (1883)..(2176)
<220> FEATURE:
<221> NAME/KEY: CDS
<222> LOCATION: (2236)..(2307)
<220> FEATURE:
<221> NAME/KEY: CDS
<222> LOCATION: (2368)..(2458)
<220> FEATURE:
<221> NAME/KEY: CDS
<222> LOCATION: (2527)..(3388)

<400> SEQUENCE: 44 atg gcg cga gtc ttt caa ctg ctt ctc ttc ctc ctg gga agc ttt cag      48
Met Ala Arg Val Phe Gln Leu Leu Leu Phe Leu Leu Gly Ser Phe Gln
-20                 -15                 -10                 -5 ctt ctg aca gca gct cag aac agc tcc caa acc gaa tgg cct gta cat      96
Leu Leu Thr Ala Ala Gln Asn Ser Ser Gln Thr Glu Trp Pro Val His
        -1  1               5                   10 gac aac ggg cta agc gag gtc gtc caa tgg gac cat tac agc ttt tac     144
Asp Asn Gly Leu Ser Glu Val Val Gln Trp Asp His Tyr Ser Phe Tyr
        15                  20                  25 gtt cac ggc cag cgg ttc ttc ctg ttc tca ggg gaa ttt cac tac tgg     192
Val His Gly Gln Arg Phe Phe Leu Phe Ser Gly Glu Phe His Tyr Trp
    30                  35                  40 cga atc cca gtc ccg gcc ttg tgg cgc gac att ttg gag aag gtc aag     240
Arg Ile Pro Val Pro Ala Leu Trp Arg Asp Ile Leu Glu Lys Val Lys
45                  50                  55                  60 gcg ctt ggg ttc acc ggc ttt gcg ttc tac tca agc tgg gca tac cat     288
Ala Leu Gly Phe Thr Gly Phe Ala Phe Tyr Ser Ser Trp Ala Tyr His
```

```
                       65                  70                  75
gcg ccc aac aac cac acg gtc gac ttc tcg acc ggt gcg cgc aac atc      336
Ala Pro Asn Asn His Thr Val Asp Phe Ser Thr Gly Ala Arg Asn Ile
             80                  85                  90 aag cac atc ttt gac ctt gca gag gag ctt gga atg tac att att gtg      384
Lys His Ile Phe Asp Leu Ala Glu Glu Leu Gly Met Tyr Ile Ile Val
         95                 100                 105 cga ccc gga ccg tac gtc aac gct gaa gcc tct gct ggt ggg ttt ccg      432
Arg Pro Gly Pro Tyr Val Asn Ala Glu Ala Ser Ala Gly Gly Phe Pro
    110                 115                 120 ctc tgg ctt aca aca ggc gcg tat ggg tcg aca agg aac gac gat cct      480
Leu Trp Leu Thr Thr Gly Ala Tyr Gly Ser Thr Arg Asn Asp Asp Pro
125                 130                 135                 140 aga tat acc gcg gcg tgg aag cca tat ttt tct aag gtg tct gag atc      528
Arg Tyr Thr Ala Ala Trp Lys Pro Tyr Phe Ser Lys Val Ser Glu Ile
                    145                 150                 155 acg agc agg tat cag gtc acg gat ggt cac aat acg ttg att tac cag      576
Thr Ser Arg Tyr Gln Val Thr Asp Gly His Asn Thr Leu Ile Tyr Gln
                160                 165                 170 atc gag aat gag tat ggg cag cag tgg atc ggg gat ccg gtc gat agg      624
Ile Glu Asn Glu Tyr Gly Gln Gln Trp Ile Gly Asp Pro Val Asp Arg
            175                 180                 185 gac ctt aac gag aca gct gct gct tat atg gat ttg ttg aaa gcg aca      672
Asp Leu Asn Glu Thr Ala Ala Ala Tyr Met Asp Leu Leu Lys Ala Thr
        190                 195                 200 gct cgt gaa aac gga atc aag gtg ccc ttg act gcg aac gat cct aac      720
Ala Arg Glu Asn Gly Ile Lys Val Pro Leu Thr Ala Asn Asp Pro Asn
205                 210                 215                 220 atg gga tca aaa tct tgg ggc aac gac tgg tcg gat gct gca ggg aac      768
Met Gly Ser Lys Ser Trp Gly Asn Asp Trp Ser Asp Ala Ala Gly Asn
                    225                 230                 235 gtc gat gct gtg ggg ttg gac tct tat cct tct gtgagtgctc agtctccata    821
Val Asp Ala Val Gly Leu Asp Ser Tyr Pro Ser
                240                 245 atcaagtcct gtctaatcga tcaag tgc tgg agc tgc gac gtc agc gtc tgc      873
                              Cys Trp Ser Cys Asp Val Ser Val Cys
                                          250                 255 aca gga acg aac gga gaa tac gta cca tac caa gta ata aac tac tac      921
Thr Gly Thr Asn Gly Glu Tyr Val Pro Tyr Gln Val Ile Asn Tyr Tyr
                260                 265                 270 gac tac ttc aac gaa gtc cag cca agc atg cct ttc ttc atg ccc gaa      969
Asp Tyr Phe Asn Glu Val Gln Pro Ser Met Pro Phe Phe Met Pro Glu
        275                 280                 285 ttc caa gga gga tcg tat aat cca tgg ggt ggc cct gag ggt ggc tgt     1017
Phe Gln Gly Gly Ser Tyr Asn Pro Trp Gly Gly Pro Glu Gly Gly Cys
    290                 295                 300 ccc gag gac acc gga gcg gac ttt gcc aac ttg ttc tac agg tgg aat     1065
Pro Glu Asp Thr Gly Ala Asp Phe Ala Asn Leu Phe Tyr Arg Trp Asn
305                 310                 315                 320 atc ggg cag cgc gag aca gcc ata agt ctg tac atg att ttc ggg gga     1113
Ile Gly Gln Arg Glu Thr Ala Ile Ser Leu Tyr Met Ile Phe Gly Gly
                    325                 330                 335 aca aac tgg ggt ggt atc gcc gcg cca gtc acc gca acc agt tat gac     1161
Thr Asn Trp Gly Gly Ile Ala Ala Pro Val Thr Ala Thr Ser Tyr Asp
                340                 345                 350 tac tcc gct cct atc tca gag gat cga tcg ata ggc tca aag ttc tac     1209
Tyr Ser Ala Pro Ile Ser Glu Asp Arg Ser Ile Gly Ser Lys Phe Tyr
        355                 360                 365 gag aca aag ctg cta gcc ctg ttc aca cga gct gcg aaa gat ttg act     1257
```

```
                 Glu Thr Lys Leu Leu Ala Leu Phe Thr Arg Ala Ala Lys Asp Leu Thr
                     370             375                 380 gtg act gat cgt gtc ggc aac gga acg cag tat acg agc aat aaa gcc       1305
Val Thr Asp Arg Val Gly Asn Gly Thr Gln Tyr Thr Ser Asn Lys Ala
385                 390                 395                 400 gtc agc gca att gag ctg cgc aac cct gag acc aat acg ggt ttt tac       1353
Val Ser Ala Ile Glu Leu Arg Asn Pro Glu Thr Asn Thr Gly Phe Tyr
                405                 410                 415 gtg acc agc cac ttg gac act aca acc ggc aca gac gag gcc ttc aag       1401
Val Thr Ser His Leu Asp Thr Thr Thr Gly Thr Asp Glu Ala Phe Lys
            420                 425                 430 ctg cac gtc aac acc tcc gaa ggg gca ttc acc atc cca agg cta aat       1449
Leu His Val Asn Thr Ser Glu Gly Ala Phe Thr Ile Pro Arg Leu Asn
        435                 440                 445 ggc acc ata agg ctt aat ggc cat caa tca aag att atc gtc acc gac       1497
Gly Thr Ile Arg Leu Asn Gly His Gln Ser Lys Ile Ile Val Thr Asp
    450                 455                 460 ttc aaa ttc ggc ttc aag acg ctt tta tac tca acc gca gag gtt ctc       1545
Phe Lys Phe Gly Phe Lys Thr Leu Leu Tyr Ser Thr Ala Glu Val Leu
465                 470                 475                 480 acc tac gca gtc ttt gac cat aaa cca act ctc gtc ctt tgg gtt ccc       1593
Thr Tyr Ala Val Phe Asp His Lys Pro Thr Leu Val Leu Trp Val Pro
                485                 490                 495 act ggt gaa tca ggc gaa ttc gca atc aaa ggc gcg aaa tca ggt tct       1641
Thr Gly Glu Ser Gly Glu Phe Ala Ile Lys Gly Ala Lys Ser Gly Ser
                500                 505                 510 gct tcg act gcg tcg gtg cag ttc cat cgg cac gga aga aca ctg act       1689
Ala Ser Thr Ala Ser Val Gln Phe His Arg His Gly Arg Thr Leu Thr
            515                 520                 525 gtt ggg ttt acc cag gct aaa ggc ctg agt gtt ctg gag ctt gat aat       1737
Val Gly Phe Thr Gln Ala Lys Gly Leu Ser Val Leu Glu Leu Asp Asn
        530                 535                 540 ggc gtc aga gta gtt ttg ctg gat agg gag gcg gcg tat acg ttc tgg       1785
Gly Val Arg Val Val Leu Leu Asp Arg Glu Ala Ala Tyr Thr Phe Trp
545                 550                 555                 560 gca cct gcc ttg acg gac aat ccg ctt gtt cct gag ggt gaa agt g         1831
Ala Pro Ala Leu Thr Asp Asn Pro Leu Val Pro Glu Gly Glu Ser
                565                 570                 575 gtgagttccc tttttctct ctcttaataa tcggtgatgc taataaagta g tc  ctt       1887
                                                          Val Leu gtc agc gga ccc tac ctc gtc cga tcc tcc aaa cta tcc gga tca acc       1935
Val Ser Gly Pro Tyr Leu Val Arg Ser Ser Lys Leu Ser Gly Ser Thr
        580                 585                 590 cta gct cta cga ggt gac tcg ctg ggc gaa aca aca cta gaa gtc ttt       1983
Leu Ala Leu Arg Gly Asp Ser Leu Gly Glu Thr Thr Leu Glu Val Phe
595                 600                 605 gct cca aac aat gta aag aag gtg aca tgg aac gga aag aag gtc aag       2031
Ala Pro Asn Asn Val Lys Lys Val Thr Trp Asn Gly Lys Lys Val Lys
610                 615                 620                 625 gtg tct agg acc aaa tac ggg agc ctg aaa gcc aac ctc gcc gaa ccg       2079
Val Ser Arg Thr Lys Tyr Gly Ser Leu Lys Ala Asn Leu Ala Glu Pro
                630                 635                 640 cgc tct gtg gaa ctg ccc gct ctc gac gga tgg aag gtc agc gac agc       2127
Arg Ser Val Glu Leu Pro Ala Leu Asp Gly Trp Lys Val Ser Asp Ser
            645                 650                 655 ctg cca gag agg ttc tca gac tat gat gac tcg ggc aag gct tgg gtt g    2176
Leu Pro Glu Arg Phe Ser Asp Tyr Asp Asp Ser Gly Lys Ala Trp Val
        660                 665                 670 gtatgttaca tactccgtat acctggatct ttgaagagat aaaatactga catgagcag      2235
```

-continued

```
cc gca aac cat ctg aca aca ccc aat ccc aat aaa cca gcg act ctc        2282
   Ala Asn His Leu Thr Thr Pro Asn Pro Asn Lys Pro Ala Thr Leu
       675                 680                 685 ccc gtt ctc tac gcc aat gaa tat g gtattccgcc tgaactctaa               2327
Pro Val Leu Tyr Ala Asn Glu Tyr
690                 695 ctcggatcaa ccagatcatg agctaacaac ttgattccag gc ttc cac aac ggc        2381
                                               Gly Phe His Asn Gly
                                                           700 gtc cgc ctc tgg cgc ggc tac ttt aac tcc tct act gcg acg ggc gtc      2429
Val Arg Leu Trp Arg Gly Tyr Phe Asn Ser Ser Thr Ala Thr Gly Val
    705                 710                 715 ttc cta aac atc caa ggc ggc gct gca tt gtacgtccaa ccaaacccct         2478
Phe Leu Asn Ile Gln Gly Gly Ala Ala Phe
    720                 725 gccttctgta aagccagtca tgaacagaca taatactaat aaacccag c ggt tgg       2533
                                                       Gly Trp
                                                           730 tcc gcc tgg ctt aac ggc cag ctc att ggc tcg cac cta ggc aac gcg     2581
Ser Ala Trp Leu Asn Gly Gln Leu Ile Gly Ser His Leu Gly Asn Ala
            735                 740                 745 acg atc gaa caa gcc aac gca aca ctc cca ttc ccg gac aac acc ctc     2629
Thr Ile Glu Gln Ala Asn Ala Thr Leu Pro Phe Pro Asp Asn Thr Leu
            750                 755                 760 tcc aag aac gga gaa cag aat gtg ctc ctc gtc gtc cac gat gac acg     2677
Ser Lys Asn Gly Glu Gln Asn Val Leu Leu Val Val His Asp Asp Thr
        765                 770                 775 gga cat gac cag aca acg ggt gtg ctc aac cca cga gga atc ctc gaa     2725
Gly His Asp Gln Thr Thr Gly Val Leu Asn Pro Arg Gly Ile Leu Glu
        780                 785                 790 gcg cgt ctc ctc tca gac agt gaa gaa gag aat gaa gac gag caa gga     2773
Ala Arg Leu Leu Ser Asp Ser Glu Glu Glu Asn Glu Asp Glu Gln Gly
795                 800                 805                 810 gga ttc acg cat tgg cgc gtc gcg gga gct gca ggc ggc gaa tcg aac     2821
Gly Phe Thr His Trp Arg Val Ala Gly Ala Ala Gly Gly Glu Ser Asn
                815                 820                 825 ctc gat ccc gtc cga ggt gtg tat aac gag gat gga ctc tac gcg gag     2869
Leu Asp Pro Val Arg Gly Val Tyr Asn Glu Asp Gly Leu Tyr Ala Glu
            830                 835                 840 cgt gtg ggt tgg cat tta cct ggg ttc gac gac agc gag tgg tct ctc     2917
Arg Val Gly Trp His Leu Pro Gly Phe Asp Asp Ser Glu Trp Ser Leu
            845                 850                 855 gca gac aat gcg aag gca cca cta gcc ttc acc ggc gca aca gtc aag     2965
Ala Asp Asn Ala Lys Ala Pro Leu Ala Phe Thr Gly Ala Thr Val Lys
        860                 865                 870 ttc ttc cgg act gtc ata ccc ccg tta tcg atc cca gag ggc ctc gac     3013
Phe Phe Arg Thr Val Ile Pro Pro Leu Ser Ile Pro Glu Gly Leu Asp
875                 880                 885                 890 gtc tcc atc tcg ttt gtg ttt tcc acg gcg aat gtg tcg tcc atc tcg     3061
Val Ser Ile Ser Phe Val Phe Ser Thr Ala Asn Val Ser Ser Ile Ser
                895                 900                 905 acc acc acc acc aca aac tca acg gtt gga gaa gaa aac aaa ggc gat     3109
Thr Thr Thr Thr Thr Asn Ser Thr Val Gly Glu Glu Asn Lys Gly Asp
            910                 915                 920 aaa tcg gcc ttc cgc gct caa ctc ttc gtc aac ggc tac cag tac gga     3157
Lys Ser Ala Phe Arg Ala Gln Leu Phe Val Asn Gly Tyr Gln Tyr Gly
            925                 930                 935 cgg tac aat cca att gtc ggg aac caa gtt gcg tat cct gtc ccg ccg     3205
Arg Tyr Asn Pro Ile Val Gly Asn Gln Val Ala Tyr Pro Val Pro Pro
```

```
                    940                945               950
ggg att ttg gac tac aat gac gag aat acg gtt ggg gtt gca gtt tgg       3253
Gly Ile Leu Asp Tyr Asn Asp Glu Asn Thr Val Gly Val Ala Val Trp
955                 960               965                970 gca cag acg gag gcc gga gcg gaa ttc ggg ctc gat tgg aaa gtc gat       3301
Ala Gln Thr Glu Ala Gly Ala Glu Phe Gly Leu Asp Trp Lys Val Asp
            975               980                985 tat gtg ctt gag agt tcg ctg gat gtt gtg aat ttg gat gtg gag ggg       3349
Tyr Val Leu Glu Ser Ser Leu Asp Val Val Asn Leu Asp Val Glu Gly
        990                995              1000 ttg agg ccg agg tgg agt gag gag agg gag aga ttt gcg tag               3391
Leu Arg Pro Arg Trp Ser Glu Glu Arg Glu Arg Phe Ala
       1005              1010              1015

<210> SEQ ID NO 45
<211> LENGTH: 1035
<212> TYPE: PRT
<213> ORGANISM: Aspergillus unguis

<400> SEQUENCE: 45

Met Ala Arg Val Phe Gln Leu Leu Phe Leu Leu Gly Ser Phe Gln
-20                 -15                 -10                  -5

Leu Leu Thr Ala Ala Gln Asn Ser Ser Gln Thr Glu Trp Pro Val His
              -1   1               5                  10

Asp Asn Gly Leu Ser Glu Val Val Gln Trp Asp His Tyr Ser Phe Tyr
         15                  20                  25

Val His Gly Gln Arg Phe Phe Leu Phe Ser Gly Glu Phe His Tyr Trp
     30                  35                  40

Arg Ile Pro Val Pro Ala Leu Trp Arg Asp Ile Leu Glu Lys Val Lys
45                  50                  55                  60

Ala Leu Gly Phe Thr Gly Phe Ala Phe Tyr Ser Ser Trp Ala Tyr His
                 65                  70                  75

Ala Pro Asn Asn His Thr Val Asp Phe Ser Thr Gly Ala Arg Asn Ile
             80                  85                  90

Lys His Ile Phe Asp Leu Ala Glu Glu Leu Gly Met Tyr Ile Ile Val
             95                 100                 105

Arg Pro Gly Pro Tyr Val Asn Ala Glu Ala Ser Ala Gly Gly Phe Pro
        110                 115                 120

Leu Trp Leu Thr Thr Gly Ala Tyr Gly Ser Thr Arg Asn Asp Asp Pro
125                 130                 135                 140

Arg Tyr Thr Ala Ala Trp Lys Pro Tyr Phe Ser Lys Val Ser Glu Ile
                145                 150                 155

Thr Ser Arg Tyr Gln Val Thr Asp Gly His Asn Thr Leu Ile Tyr Gln
            160                 165                 170

Ile Glu Asn Glu Tyr Gly Gln Gln Trp Ile Gly Asp Pro Val Asp Arg
        175                 180                 185

Asp Leu Asn Glu Thr Ala Ala Tyr Met Asp Leu Leu Lys Ala Thr
    190                 195                 200

Ala Arg Glu Asn Gly Ile Lys Val Pro Leu Thr Ala Asn Asp Pro Asn
205                 210                 215                 220

Met Gly Ser Lys Ser Trp Gly Asn Asp Trp Ser Asp Ala Ala Gly Asn
                225                 230                 235

Val Asp Ala Val Gly Leu Asp Ser Tyr Pro Ser Cys Trp Ser Cys Asp
            240                 245                 250

Val Ser Val Cys Thr Gly Thr Asn Gly Glu Tyr Val Pro Tyr Gln Val
        255                 260                 265
```

```
Ile Asn Tyr Tyr Asp Tyr Phe Asn Glu Val Gln Pro Ser Met Pro Phe
    270                 275                 280

Phe Met Pro Glu Phe Gln Gly Gly Ser Tyr Asn Pro Trp Gly Gly Pro
285                 290                 295                 300

Glu Gly Gly Cys Pro Glu Asp Thr Gly Ala Asp Phe Ala Asn Leu Phe
                305                 310                 315

Tyr Arg Trp Asn Ile Gly Gln Arg Glu Thr Ala Ile Ser Leu Tyr Met
                320                 325                 330

Ile Phe Gly Gly Thr Asn Trp Gly Ile Ala Ala Pro Val Thr Ala
            335                 340                 345

Thr Ser Tyr Asp Tyr Ser Ala Pro Ile Ser Glu Asp Arg Ser Ile Gly
    350                 355                 360

Ser Lys Phe Tyr Glu Thr Lys Leu Leu Ala Leu Phe Thr Arg Ala Ala
365                 370                 375                 380

Lys Asp Leu Thr Val Thr Asp Arg Val Gly Asn Gly Thr Gln Tyr Thr
                385                 390                 395

Ser Asn Lys Ala Val Ser Ala Ile Glu Leu Arg Asn Pro Glu Thr Asn
                400                 405                 410

Thr Gly Phe Tyr Val Thr Ser His Leu Asp Thr Thr Gly Thr Asp
            415                 420                 425

Glu Ala Phe Lys Leu His Val Asn Thr Ser Glu Gly Ala Phe Thr Ile
    430                 435                 440

Pro Arg Leu Asn Gly Thr Ile Arg Leu Asn Gly His Gln Ser Lys Ile
445                 450                 455                 460

Ile Val Thr Asp Phe Lys Phe Gly Phe Lys Thr Leu Leu Tyr Ser Thr
                465                 470                 475

Ala Glu Val Leu Thr Tyr Ala Val Phe Asp His Lys Pro Thr Leu Val
            480                 485                 490

Leu Trp Val Pro Thr Gly Glu Ser Gly Glu Phe Ala Ile Lys Gly Ala
    495                 500                 505

Lys Ser Gly Ser Ala Ser Thr Ala Ser Val Gln Phe His Arg His Gly
510                 515                 520

Arg Thr Leu Thr Val Gly Phe Thr Gln Ala Lys Gly Leu Ser Val Leu
525                 530                 535                 540

Glu Leu Asp Asn Gly Val Arg Val Val Leu Leu Asp Arg Glu Ala Ala
                545                 550                 555

Tyr Thr Phe Trp Ala Pro Ala Leu Thr Asp Asn Pro Leu Val Pro Glu
            560                 565                 570

Gly Glu Ser Val Leu Val Ser Gly Pro Tyr Leu Val Arg Ser Ser Lys
                575                 580                 585

Leu Ser Gly Ser Thr Leu Ala Leu Arg Gly Asp Ser Leu Gly Glu Thr
    590                 595                 600

Thr Leu Glu Val Phe Ala Pro Asn Asn Val Lys Lys Val Thr Trp Asn
605                 610                 615                 620

Gly Lys Lys Val Lys Val Ser Arg Thr Lys Tyr Gly Ser Leu Lys Ala
                625                 630                 635

Asn Leu Ala Glu Pro Arg Ser Val Glu Leu Pro Ala Leu Asp Gly Trp
                640                 645                 650

Lys Val Ser Asp Ser Leu Pro Glu Arg Phe Ser Asp Tyr Asp Asp Ser
                655                 660                 665

Gly Lys Ala Trp Val Ala Ala Asn His Leu Thr Thr Pro Asn Pro Asn
    670                 675                 680
```

-continued

Lys Pro Ala Thr Leu Pro Val Leu Tyr Ala Asn Glu Tyr Gly Phe His
685                 690                 695                 700

Asn Gly Val Arg Leu Trp Arg Gly Tyr Phe Asn Ser Ser Thr Ala Thr
            705                 710                 715

Gly Val Phe Leu Asn Ile Gln Gly Gly Ala Ala Phe Gly Trp Ser Ala
        720                 725                 730

Trp Leu Asn Gly Gln Leu Ile Gly Ser His Leu Gly Asn Ala Thr Ile
    735                 740                 745

Glu Gln Ala Asn Ala Thr Leu Pro Phe Pro Asp Asn Thr Leu Ser Lys
750                 755                 760

Asn Gly Glu Gln Asn Val Leu Leu Val Val His Asp Asp Thr Gly His
765                 770                 775                 780

Asp Gln Thr Thr Gly Val Leu Asn Pro Arg Gly Ile Leu Glu Ala Arg
            785                 790                 795

Leu Leu Ser Asp Ser Glu Glu Asn Glu Asp Glu Gln Gly Gly Phe
        800                 805                 810

Thr His Trp Arg Val Ala Gly Ala Gly Gly Glu Ser Asn Leu Asp
    815                 820                 825

Pro Val Arg Gly Val Tyr Asn Glu Asp Gly Leu Tyr Ala Glu Arg Val
830                 835                 840

Gly Trp His Leu Pro Gly Phe Asp Asp Ser Glu Trp Ser Leu Ala Asp
845                 850                 855                 860

Asn Ala Lys Ala Pro Leu Ala Phe Thr Gly Ala Thr Val Lys Phe Phe
            865                 870                 875

Arg Thr Val Ile Pro Pro Leu Ser Ile Pro Glu Gly Leu Asp Val Ser
        880                 885                 890

Ile Ser Phe Val Phe Ser Thr Ala Asn Val Ser Ser Ile Ser Thr Thr
    895                 900                 905

Thr Thr Thr Asn Ser Thr Val Gly Glu Glu Asn Lys Gly Asp Lys Ser
910                 915                 920

Ala Phe Arg Ala Gln Leu Phe Val Asn Gly Tyr Gln Tyr Gly Arg Tyr
925                 930                 935                 940

Asn Pro Ile Val Gly Asn Gln Val Ala Tyr Pro Val Pro Pro Gly Ile
            945                 950                 955

Leu Asp Tyr Asn Asp Glu Asn Thr Val Gly Val Ala Val Trp Ala Gln
        960                 965                 970

Thr Glu Ala Gly Ala Glu Phe Gly Leu Asp Trp Lys Val Asp Tyr Val
    975                 980                 985

Leu Glu Ser Ser Leu Asp Val Val Asn Leu Asp Val Glu Gly Leu Arg
990                 995                 1000

Pro Arg Trp Ser Glu Glu Arg Glu Arg Phe Ala
1005                1010                1015

<210> SEQ ID NO 46
<211> LENGTH: 1015
<212> TYPE: PRT
<213> ORGANISM: Aspergillus unguis
<220> FEATURE:
<221> NAME/KEY: mat_peptide
<222> LOCATION: (1)..(1015)

<400> SEQUENCE: 46

Ala Gln Asn Ser Ser Gln Thr Glu Trp Pro Val His Asp Asn Gly Leu
1               5                   10                  15

Ser Glu Val Val Gln Trp Asp His Tyr Ser Phe Tyr Val His Gly Gln
            20                  25                  30

```
Arg Phe Phe Leu Phe Ser Gly Glu Phe His Tyr Trp Arg Ile Pro Val
            35                  40                  45

Pro Ala Leu Trp Arg Asp Ile Leu Glu Lys Val Lys Ala Leu Gly Phe
            50                  55                  60

Thr Gly Phe Ala Phe Tyr Ser Ser Trp Ala Tyr His Ala Pro Asn Asn
 65                  70                  75                  80

His Thr Val Asp Phe Ser Thr Gly Ala Arg Asn Ile Lys His Ile Phe
                     85                  90                  95

Asp Leu Ala Glu Glu Leu Gly Met Tyr Ile Ile Val Arg Pro Gly Pro
                100                 105                 110

Tyr Val Asn Ala Glu Ala Ser Ala Gly Gly Phe Pro Leu Trp Leu Thr
            115                 120                 125

Thr Gly Ala Tyr Gly Ser Thr Arg Asn Asp Asp Pro Arg Tyr Thr Ala
            130                 135                 140

Ala Trp Lys Pro Tyr Phe Ser Lys Val Ser Glu Ile Thr Ser Arg Tyr
145                 150                 155                 160

Gln Val Thr Asp Gly His Asn Thr Leu Ile Tyr Gln Ile Glu Asn Glu
                    165                 170                 175

Tyr Gly Gln Gln Trp Ile Gly Asp Pro Val Ala Arg Asp Leu Asn Glu
                180                 185                 190

Thr Ala Ala Tyr Met Asp Leu Leu Lys Ala Thr Ala Arg Glu Asn
                195                 200                 205

Gly Ile Lys Val Pro Leu Thr Ala Asn Asp Pro Asn Met Gly Ser Lys
            210                 215                 220

Ser Trp Gly Asn Asp Trp Ser Asp Ala Ala Gly Asn Val Asp Ala Val
225                 230                 235                 240

Gly Leu Asp Ser Tyr Pro Ser Cys Trp Ser Cys Asp Val Ser Val Cys
                245                 250                 255

Thr Gly Thr Asn Gly Glu Tyr Val Pro Tyr Gln Val Ile Asn Tyr Tyr
                260                 265                 270

Asp Tyr Phe Asn Glu Val Gln Pro Ser Met Pro Phe Phe Met Pro Glu
            275                 280                 285

Phe Gln Gly Gly Ser Tyr Asn Pro Trp Gly Gly Pro Glu Gly Gly Cys
            290                 295                 300

Pro Glu Asp Thr Gly Ala Asp Phe Ala Asn Leu Phe Tyr Arg Trp Asn
305                 310                 315                 320

Ile Gly Gln Arg Glu Thr Ala Ile Ser Leu Tyr Met Ile Phe Gly Gly
                325                 330                 335

Thr Asn Trp Gly Gly Ile Ala Ala Pro Val Thr Ala Thr Ser Tyr Asp
            340                 345                 350

Tyr Ser Ala Pro Ile Ser Glu Asp Arg Ser Ile Gly Ser Lys Phe Tyr
            355                 360                 365

Glu Thr Lys Leu Leu Ala Leu Phe Thr Arg Ala Ala Lys Asp Leu Thr
            370                 375                 380

Val Thr Asp Arg Val Gly Asn Gly Thr Gln Tyr Thr Ser Asn Lys Ala
385                 390                 395                 400

Val Ser Ala Ile Glu Leu Arg Asn Pro Glu Thr Asn Thr Gly Phe Tyr
                405                 410                 415

Val Thr Ser His Leu Asp Thr Thr Gly Thr Asp Glu Ala Phe Lys
                420                 425                 430

Leu His Val Asn Thr Ser Glu Gly Ala Phe Thr Ile Pro Arg Leu Asn
            435                 440                 445
```

```
Gly Thr Ile Arg Leu Asn Gly His Gln Ser Lys Ile Ile Val Thr Asp
    450                 455                 460

Phe Lys Phe Gly Phe Lys Thr Leu Leu Tyr Ser Thr Ala Glu Val Leu
465                 470                 475                 480

Thr Tyr Ala Val Phe Asp His Lys Pro Thr Leu Val Leu Trp Val Pro
                485                 490                 495

Thr Gly Glu Ser Gly Glu Phe Ala Ile Lys Gly Ala Lys Ser Gly Ser
            500                 505                 510

Ala Ser Thr Ala Ser Val Gln Phe His Arg His Gly Arg Thr Leu Thr
        515                 520                 525

Val Gly Phe Thr Gln Ala Lys Gly Leu Ser Val Leu Glu Leu Asp Asn
    530                 535                 540

Gly Val Arg Val Val Leu Leu Asp Arg Glu Ala Ala Tyr Thr Phe Trp
545                 550                 555                 560

Ala Pro Ala Leu Thr Asp Asn Pro Leu Val Pro Glu Gly Glu Ser Val
                565                 570                 575

Leu Val Ser Gly Pro Tyr Leu Val Arg Ser Ser Lys Leu Ser Gly Ser
            580                 585                 590

Thr Leu Ala Leu Arg Gly Asp Ser Leu Gly Glu Thr Thr Leu Glu Val
        595                 600                 605

Phe Ala Pro Asn Asn Val Lys Lys Val Thr Trp Asn Gly Lys Lys Val
    610                 615                 620

Lys Val Ser Arg Thr Lys Tyr Gly Ser Leu Lys Ala Asn Leu Ala Glu
625                 630                 635                 640

Pro Arg Ser Val Glu Leu Pro Ala Leu Asp Gly Trp Lys Val Ser Asp
                645                 650                 655

Ser Leu Pro Glu Arg Phe Ser Asp Tyr Asp Ser Gly Lys Ala Trp
            660                 665                 670

Val Ala Ala Asn His Leu Thr Thr Pro Asn Pro Asn Lys Pro Ala Thr
        675                 680                 685

Leu Pro Val Leu Tyr Ala Asn Glu Tyr Gly Phe His Asn Gly Val Arg
    690                 695                 700

Leu Trp Arg Gly Tyr Phe Asn Ser Ser Thr Ala Thr Gly Val Phe Leu
705                 710                 715                 720

Asn Ile Gln Gly Gly Ala Ala Phe Gly Trp Ser Ala Trp Leu Asn Gly
                725                 730                 735

Gln Leu Ile Gly Ser His Leu Gly Asn Ala Thr Ile Glu Gln Ala Asn
            740                 745                 750

Ala Thr Leu Pro Phe Pro Asp Asn Thr Leu Ser Lys Asn Gly Glu Gln
        755                 760                 765

Asn Val Leu Leu Val Val His Asp Asp Thr Gly His Asp Gln Thr Thr
    770                 775                 780

Gly Val Leu Asn Pro Arg Gly Ile Leu Glu Ala Arg Leu Leu Ser Asp
785                 790                 795                 800

Ser Glu Glu Glu Asn Gly Asp Glu Gln Gly Phe Thr His Trp Arg
                805                 810                 815

Val Ala Gly Ala Ala Gly Gly Glu Ser Asn Leu Asp Pro Val Arg Gly
            820                 825                 830

Val Tyr Asn Glu Asp Gly Leu Tyr Ala Glu Arg Val Gly Trp His Leu
        835                 840                 845

Pro Gly Phe Asp Asp Ser Glu Trp Ser Leu Ala Asp Asn Ala Lys Ala
    850                 855                 860

Pro Leu Ala Phe Thr Gly Ala Thr Val Lys Phe Phe Arg Thr Val Ile
```

```
                          865                 870                 875                 880

Pro Pro Leu Ser Ile Pro Glu Gly Leu Asp Val Ser Ile Ser Phe Val
                    885                 890                 895

Phe Ser Thr Ala Asn Val Ser Ser Ile Ser Thr Thr Thr Thr Thr Asn
                900                 905                 910

Ser Thr Val Gly Glu Glu Asn Lys Gly Asp Lys Ser Ala Phe Arg Ala
            915                 920                 925

Gln Leu Phe Val Asn Gly Tyr Gln Tyr Gly Arg Tyr Asn Pro Ile Val
        930                 935                 940

Gly Asn Gln Val Ala Tyr Pro Val Pro Pro Gly Ile Leu Asp Tyr Asn
945                 950                 955                 960

Asp Glu Asn Thr Val Gly Val Ala Val Trp Ala Gln Thr Glu Ala Gly
                965                 970                 975

Ala Glu Phe Gly Leu Asp Trp Lys Val Asp Tyr Val Leu Glu Ser Ser
                980                 985                 990

Leu Asp Val Val Asn Leu Asp Val  Glu Gly Leu Arg Pro  Arg Trp Ser
                995                 1000                1005

Glu Glu  Arg Glu Arg Phe Ala
    1010                1015

<210> SEQ ID NO 47
<211> LENGTH: 3859
<212> TYPE: DNA
<213> ORGANISM: Aspergillus tamarii
<220> FEATURE:
<221> NAME/KEY: CDS
<222> LOCATION: (1)..(125)
<220> FEATURE:
<221> NAME/KEY: sig_peptide
<222> LOCATION: (1)..(66)
<220> FEATURE:
<221> NAME/KEY: mat_peptide
<222> LOCATION: (67)..(3856)
<220> FEATURE:
<221> NAME/KEY: CDS
<222> LOCATION: (189)..(243)
<220> FEATURE:
<221> NAME/KEY: CDS
<222> LOCATION: (299)..(321)
<220> FEATURE:
<221> NAME/KEY: CDS
<222> LOCATION: (371)..(415)
<220> FEATURE:
<221> NAME/KEY: CDS
<222> LOCATION: (477)..(948)
<220> FEATURE:
<221> NAME/KEY: CDS
<222> LOCATION: (1005)..(1139)
<220> FEATURE:
<221> NAME/KEY: CDS
<222> LOCATION: (1191)..(1210)
<220> FEATURE:
<221> NAME/KEY: CDS
<222> LOCATION: (1269)..(1289)
<220> FEATURE:
<221> NAME/KEY: CDS
<222> LOCATION: (1342)..(1544)
<220> FEATURE:
<221> NAME/KEY: CDS
<222> LOCATION: (1594)..(1686)
<220> FEATURE:
<221> NAME/KEY: CDS
<222> LOCATION: (1743)..(1780)
<220> FEATURE:
<221> NAME/KEY: CDS
<222> LOCATION: (1835)..(1985)
<220> FEATURE:
<221> NAME/KEY: CDS
<222> LOCATION: (2051)..(2464)
```

<220> FEATURE:
<221> NAME/KEY: CDS
<222> LOCATION: (2523)..(2816)
<220> FEATURE:
<221> NAME/KEY: CDS
<222> LOCATION: (2886)..(3856)

<400> SEQUENCE: 47

```
atg ctc atc tcc aag acc gtg ttc agc ggg ctt gcc ttg ggg gcg tcc         48
Met Leu Ile Ser Lys Thr Val Phe Ser Gly Leu Ala Leu Gly Ala Ser
        -20                 -15                 -10 ttt gtt ggc gtt tct ggt cag cag aat tca agc cgt tgg ccg ttg cac         96
Phe Val Gly Val Ser Gly Gln Gln Asn Ser Ser Arg Trp Pro Leu His
     -5              -1  1                  5                  10 gac aac ggt ttg aca gac act gta gaa tg gtgggttcag tcaaattgcg           145
Asp Asn Gly Leu Thr Asp Thr Val Glu Trp
             15                  20 aattcaaggc tgtttggttg gctctgacac catggctata cag g gat cac tat agt      201
                                                  Asp His Tyr Ser ttc ttg att aat ggt cag aga cat ttc gtt ttc tct gga gag                243
Phe Leu Ile Asn Gly Gln Arg His Phe Val Phe Ser Gly Glu
25                  30                  35 gtttgtccgc ccaatcccct atattctgta tattcaatac attaacatca tatag ttc       301
                                                              Phe cat tac tgg cgt atc cct gt gtaaggcaag agtcccacaa cggcaacgct            351
His Tyr Trp Arg Ile Pro Val
40                  45 ctagctaatg gattaccag a ccc gaa tta tgg aga gat cta ctc gag aag         401
                      Pro Glu Leu Trp Arg Asp Leu Leu Glu Lys
                                  50                  55 atc aaa gcc gct gg gtaggtagtc tcagattctt gacgcccgtt gtcaacaaca         455
Ile Lys Ala Ala Gly
                60 cgctaataac gaattggata g t ttc act gcc ttt tcc atc tac aat cac tgg      507
                        Phe Thr Ala Phe Ser Ile Tyr Asn His Trp
                                      65                  70 gga tat cat acc ccc aag ccc ggc gtt ctc gac ttc gag aac ggg gcc        555
Gly Tyr His Thr Pro Lys Pro Gly Val Leu Asp Phe Glu Asn Gly Ala
            75                  80                  85 cac aac ttc act tcg atc atg act cta gcc aaa gag ata ggt ctc tac        603
His Asn Phe Thr Ser Ile Met Thr Leu Ala Lys Glu Ile Gly Leu Tyr
        90                  95                  100 atg att atc cga ccg ggc cca tac gtc aat gcg gaa gcc aat gct ggc        651
Met Ile Ile Arg Pro Gly Pro Tyr Val Asn Ala Glu Ala Asn Ala Gly
105                 110                 115 ggt ctc cct ctg tgg gca act aca ggt gcc tac gga aaa cta cgg gat        699
Gly Leu Pro Leu Trp Ala Thr Thr Gly Ala Tyr Gly Lys Leu Arg Asp
120                 125                 130                 135 aac gac cct cgg tac ttg gag gct ttg acc cca tac tgg gct aac att        747
Asn Asp Pro Arg Tyr Leu Glu Ala Leu Thr Pro Tyr Trp Ala Asn Ile
            140                 145                 150 tct aaa atc att gct cct cat ctc atc acc aac ggc gga aat gtc atc        795
Ser Lys Ile Ile Ala Pro His Leu Ile Thr Asn Gly Gly Asn Val Ile
        155                 160                 165 ctg tat cag atc gag aat gag tac gcc gag cag tgg ctt gac gag gaa        843
Leu Tyr Gln Ile Glu Asn Glu Tyr Ala Glu Gln Trp Leu Asp Glu Glu
                170                 175                 180 acc cag gag ccc aac acg tct ggt cag gaa tac atg cag tat ttg gag        891
Thr Gln Glu Pro Asn Thr Ser Gly Gln Glu Tyr Met Gln Tyr Leu Glu
185                 190                 195
```

| | |
|---|---|
| gac gtt gct cgg gaa aac ggc att gat gct cct ctg atc cat aat ctt<br>Asp Val Ala Arg Glu Asn Gly Ile Asp Ala Pro Leu Ile His Asn Leu<br>200                205              210              215 | 939 |
| ccg aac atg gtagggcaat acgctcgctt gctgaagata cagaattttt<br>Pro Asn Met | 988 |
| ggctgataca tagcag aac ggt cac tca tgg tcc aag gac ctc tcc aac gct<br>                   Asn Gly His Ser Trp Ser Lys Asp Leu Ser Asn Ala<br>                       220              225                  230 | 1040 |
| act gga aat gtc gat gtc att ggc gtg gac agc tat ccc act tgc tgg<br>Thr Gly Asn Val Asp Val Ile Gly Val Asp Ser Tyr Pro Thr Cys Trp<br>                235              240              245 | 1088 |
| acc tgc aat gtc agt gag tgt ctc tca act aac gga gag tat atc cca<br>Thr Cys Asn Val Ser Glu Cys Leu Ser Thr Asn Gly Glu Tyr Ile Pro<br>250                255              260 | 1136 |
| tat gtaagtaacg cctgcctttc tttggtgatt tattatacta aactctctca g aaa<br>Tyr                                                                     Lys | 1193 |
| acc ttg acc tac tac ga  gtaagtgcaa tagtacacgg atttgtatga<br>Thr Leu Thr Tyr Tyr Asp<br>265                270 | 1240 |
| gtgaaacact aatttaccct caaatcag c tac ttc aag aaa cta tca cc<br>                                      Tyr Phe Lys Lys Leu Ser Pro<br>                                                              275 | 1289 |
| gtaagctttg ccctctctga gactatctac acattctaat tctctattac ag c act<br>                                                                                            Thr | 1345 |
| cag cca agc ttt atg ccc gag ttc caa ggc ggt tca tac aac cca tgg<br>Gln Pro Ser Phe Met Pro Glu Phe Gln Gly Gly Ser Tyr Asn Pro Trp<br>      280                285                    290 | 1393 |
| ggt gga ccc caa gga ggc tgc ccg gat gat ctt ggc ccg gat ttc gcg<br>Gly Gly Pro Gln Gly Gly Cys Pro Asp Asp Leu Gly Pro Asp Phe Ala<br>295                300              305              310 | 1441 |
| aac ctc ttc tac cga aac cta atc tat cag aga gtc agt gct atc tcg<br>Asn Leu Phe Tyr Arg Asn Leu Ile Tyr Gln Arg Val Ser Ala Ile Ser<br>               315              320              325 | 1489 |
| ctg tac atg tta tac ggc ggt aca aac tgg ggc tgg cac ggc tca aca<br>Leu Tyr Met Leu Tyr Gly Gly Thr Asn Trp Gly Trp His Gly Ser Thr<br>     330                 335                   340 | 1537 |
| gat gtc g gtgagttatt cccaagtcga atttatgcca caggtgctga tgagcccag<br>Asp Val | 1593 |
| cg aca agt tac gat tac tct tct cca att tcg gag aac cga aag ctt<br>Ala Thr Ser Tyr Asp Tyr Ser Ser Pro Ile Ser Glu Asn Arg Lys Leu<br>345                350              355              360 | 1640 |
| att gag aaa tac tac gag aca aaa gtg ctc act caa ttc acg aaa a<br>Ile Glu Lys Tyr Tyr Glu Thr Lys Val Leu Thr Gln Phe Thr Lys<br>           365                370              375 | 1686 |
| gtacgcctct tttagtacga tatgtggaag cttgccaagc taacctcatg atacag tc<br>                                                                                       Ile | 1744 |
| gcc cgg gat ctg tct aaa gtc gat cgt tta ggc aac gtaagtagag<br>Ala Arg Asp Leu Ser Lys Val Asp Arg Leu Gly Asn<br>              380                    385 | 1790 |
| cagaacaata tcgtctacag agaaacgcta acaggggtca acag agc acg aga tat<br>                                                                              Ser Thr Arg Tyr<br>                                                                                 390 | 1846 |
| tca agt aac cca gct gtt tca gtt tct gag ctg cga aat cct gac aat<br>Ser Ser Asn Pro Ala Val Ser Val Ser Glu Leu Arg Asn Pro Asp Asn<br>               395              400              405 | 1894 |
| ggc gcg gct ttc tac gta act cag cac gaa tac act cca tct gga acg<br>Gly Ala Ala Phe Tyr Val Thr Gln His Glu Tyr Thr Pro Ser Gly Thr<br>410                415              420 | 1942 |

```
                                                             -continued gtc gaa aag ttc aca gtc aag gtt aac aca tcc gat ggt gct c         1985
Val Glu Lys Phe Thr Val Lys Val Asn Thr Ser Asp Gly Ala
425                 430                 435 gtatgttacc tcctgcggtc tgaatttggt atatcacaat gataatctgc taattactcg  2045 acaag tc act att cct caa tac ggc tcc caa atc act ctc aat ggt cac  2094
      Leu Thr Ile Pro Gln Tyr Gly Ser Gln Ile Thr Leu Asn Gly His
             440                 445                 450 cag tcc aag att atc gtc aca gac ttc aac ttc ggc tcg aag acg ctc   2142
Gln Ser Lys Ile Ile Val Thr Asp Phe Asn Phe Gly Ser Lys Thr Leu
455                 460                 465 ctt tac tct acg gca gaa gtt ctt acc tat gct gtt att gat ggt aaa   2190
Leu Tyr Ser Thr Ala Glu Val Leu Thr Tyr Ala Val Ile Asp Gly Lys
470                 475                 480                 485 gaa gtg ctg gct ctc tgg gtc ccg act ggt gaa tct gga gag ttc acc   2238
Glu Val Leu Ala Leu Trp Val Pro Thr Gly Glu Ser Gly Glu Phe Thr
                490                 495                 500 gtg aag gga gtg aat tcg gcc aag ttc gcc gac aaa gga cgc act gcg   2286
Val Lys Gly Val Asn Ser Ala Lys Phe Ala Asp Lys Gly Arg Thr Ala
505                 510                 515 aac atc gag att cgc ccc gga gca aac aag gtg aca gta tct ttc atg   2334
Asn Ile Glu Ile Arg Pro Gly Ala Asn Lys Val Thr Val Ser Phe Met
     520                 525                 530 cag aga gcg ggt atg agc gtg gtt gag ctt ggt gat gga aca cgc att   2382
Gln Arg Ala Gly Met Ser Val Val Glu Leu Gly Asp Gly Thr Arg Ile
535                 540                 545 gtt ctt ctc gat cgg tct gct gct cat gta ttc tgg tct cct cca ctc   2430
Val Leu Leu Asp Arg Ser Ala Ala His Val Phe Trp Ser Pro Pro Leu
550                 555                 560                 565 aac aat gac cct gcc gag gcc ggc aac aac act g gtaagtccac           2474
Asn Asn Asp Pro Ala Glu Ala Gly Asn Asn Thr
                570                 575 atcgatggcg ttatacaaac agttgataga ctcgctgaca tgcttcag tc  ctc gtc  2530
                                                       Val Leu Val cat ggt ccc tac tta gtt cgc tcg gct aga ttg gaa ggc tgt gac ttg   2578
His Gly Pro Tyr Leu Val Arg Ser Ala Arg Leu Glu Gly Cys Asp Leu
580                 585                 590                 595 aag ctc act gga gat atc cag aat tct aca aag gtc agc atc ttt gcg   2626
Lys Leu Thr Gly Asp Ile Gln Asn Ser Thr Lys Val Ser Ile Phe Ala
                600                 605                 610 ccc aat tcg gta tgc tcc gtc aat tgg aat ggc aag aag aca tcc gtc   2674
Pro Asn Ser Val Cys Ser Val Asn Trp Asn Gly Lys Lys Thr Ser Val
                 615                 620                 625 aag tca gcg aag ggt ggt gtc ata acc aca acc ttg gga ggc gat gcc   2722
Lys Ser Ala Lys Gly Gly Val Ile Thr Thr Thr Leu Gly Gly Asp Ala
                630                 635                 640 aag ttc gaa ctt ccc acg atc tcc ggc tgg aag tat gcg gac agt ctc   2770
Lys Phe Glu Leu Pro Thr Ile Ser Gly Trp Lys Tyr Ala Asp Ser Leu
645                 650                 655 cct gaa atc gcg aag gac tat tcc gct aca agc aag gct tgg gtt g     2816
Pro Glu Ile Ala Lys Asp Tyr Ser Ala Thr Ser Lys Ala Trp Val
660                 665                 670 gtatgttatt tctctcctcc tcggtcgcca atagcacccg ccagtgccag ctaacaacag  2876 aaaaaccag tg  gct acg aag aca aac tcg tct aat ccg act ccc ccg gca 2926
              Val Ala Thr Lys Thr Asn Ser Ser Asn Pro Thr Pro Pro Ala
                 675                 680                 685 cca aac aac cca gtc ctc tac gtg gac gag aac gat atc cac gtc ggc   2974
Pro Asn Asn Pro Val Leu Tyr Val Asp Glu Asn Asp Ile His Val Gly
690                 695                 700
```

| | |
|---|---|
| aac cac atc tac cgc gcc act ttc ccc agc acc gac gag ccc cca acc<br>Asn His Ile Tyr Arg Ala Thr Phe Pro Ser Thr Asp Glu Pro Pro Thr<br>705          710              715            720 | 3022 |
| gac gtc tac ctc aac atc acc gga ggt cgc gca ttc ggc tac tct gtc<br>Asp Val Tyr Leu Asn Ile Thr Gly Gly Arg Ala Phe Gly Tyr Ser Val<br>          725              730            735 | 3070 |
| tgg ctg aac tca gaa ttc atc ggc tcc tgg ctc ggc acc ccg aca acc<br>Trp Leu Asn Ser Glu Phe Ile Gly Ser Trp Leu Gly Thr Pro Thr Thr<br>               740             745           750 | 3118 |
| gag cag aac gac cag aca ttc tca ttc tcc aac gca acc ctc agc aca<br>Glu Gln Asn Asp Gln Thr Phe Ser Phe Ser Asn Ala Thr Leu Ser Thr<br>          755              760            765 | 3166 |
| gac gga gac aac atc cta gtc gtc gtc atg gac aac tcg gcc cac gat<br>Asp Gly Asp Asn Ile Leu Val Val Val Met Asp Asn Ser Ala His Asp<br>770              775            780 | 3214 |
| ctg cgc gag gga gca acc gac ccc cga gga atc aca aac gcc act ctc<br>Leu Arg Glu Gly Ala Thr Asp Pro Arg Gly Ile Thr Asn Ala Thr Leu<br>785              790            795            800 | 3262 |
| gtc ggt ccc gga acc tac tcc ttc acc gag tgg aaa ctc gcc ggc aac<br>Val Gly Pro Gly Thr Tyr Ser Phe Thr Glu Trp Lys Leu Ala Gly Asn<br>              805              810           815 | 3310 |
| gca ggc ttc gaa gac cac ctt gat ccg gtc cgc gcc ccg ctc aac gag<br>Ala Gly Phe Glu Asp His Leu Asp Pro Val Arg Ala Pro Leu Asn Glu<br>          820              825           830 | 3358 |
| ggc agt ctg tac gcc gag cga gtc ggt atc cat ctc ccg gga tat cag<br>Gly Ser Leu Tyr Ala Glu Arg Val Gly Ile His Leu Pro Gly Tyr Gln<br>835              840            845 | 3406 |
| ttc gac gag gcc gaa gag gtg cct tcg aac agc acg agc cta acc gtt<br>Phe Asp Glu Ala Glu Glu Val Pro Ser Asn Ser Thr Ser Leu Thr Val<br>850              855            860 | 3454 |
| ccc ggt gct ggt att cgc gtc ttc cgc acc gtt gtt ccc ctc tcc gtg<br>Pro Gly Ala Gly Ile Arg Val Phe Arg Thr Val Val Pro Leu Ser Val<br>865              870            875            880 | 3502 |
| ccc cag gga ctg gac gtc tct atc tcg ttc cgt ttg act gct ccc tcg<br>Pro Gln Gly Leu Asp Val Ser Ile Ser Phe Arg Leu Thr Ala Pro Ser<br>              885              890           895 | 3550 |
| aat gtg acc ttt acc tct acg gag gga tac acc aac cag ctg cgc gct<br>Asn Val Thr Phe Thr Ser Thr Glu Gly Tyr Thr Asn Gln Leu Arg Ala<br>          900              905           910 | 3598 |
| ctg ctc ttc gtt aat gga tac cag tat ggt cgc ttt aac cct tac atc<br>Leu Leu Phe Val Asn Gly Tyr Gln Tyr Gly Arg Phe Asn Pro Tyr Ile<br>915              920            925 | 3646 |
| ggt cat cag att gac ttc cct gtt cct ccg ggc gtc ctt gat tat aat<br>Gly His Gln Ile Asp Phe Pro Val Pro Pro Gly Val Leu Asp Tyr Asn<br>930              935            940 | 3694 |
| ggg gat aac acg att gcg gtg acg gtg tgg agt cag agt gtg gat ggt<br>Gly Asp Asn Thr Ile Ala Val Thr Val Trp Ser Gln Ser Val Asp Gly<br>945              950            955            960 | 3742 |
| gct gag atg aaa att gat tgg aat gtg gac tat gtc cat gag acc agc<br>Ala Glu Met Lys Ile Asp Trp Asn Val Asp Tyr Val His Glu Thr Ser<br>              965              970           975 | 3790 |
| ttc gac atg aac ttt gac gga gca tac ctg aga cct gga tgg atc gag<br>Phe Asp Met Asn Phe Asp Gly Ala Tyr Leu Arg Pro Gly Trp Ile Glu<br>          980              985           990 | 3838 |
| gag aga cgt gaa tat gct taa<br>Glu Arg Arg Glu Tyr Ala<br>          995 | 3859 |

<210> SEQ ID NO 48
<211> LENGTH: 1020

<212> TYPE: PRT
<213> ORGANISM: Aspergillus tamarii

<400> SEQUENCE: 48

```
Met Leu Ile Ser Lys Thr Val Phe Ser Gly Leu Ala Leu Gly Ala Ser
        -20                 -15                 -10
Phe Val Gly Val Ser Gly Gln Gln Asn Ser Ser Arg Trp Pro Leu His
 -5                  -1   1                   5                  10
Asp Asn Gly Leu Thr Asp Thr Val Glu Trp Asp His Tyr Ser Phe Leu
                 15                  20                  25
Ile Asn Gly Gln Arg His Phe Val Phe Ser Gly Glu Phe His Tyr Trp
             30                  35                  40
Arg Ile Pro Val Pro Glu Leu Trp Arg Asp Leu Leu Glu Lys Ile Lys
         45                  50                  55
Ala Ala Gly Phe Thr Ala Phe Ser Ile Tyr Asn His Trp Gly Tyr His
     60                  65                  70
Thr Pro Lys Pro Gly Val Leu Asp Phe Glu Asn Gly Ala His Asn Phe
 75                  80                  85                  90
Thr Ser Ile Met Thr Leu Ala Lys Glu Ile Gly Leu Tyr Met Ile Ile
                 95                 100                 105
Arg Pro Gly Pro Tyr Val Asn Ala Glu Ala Asn Ala Gly Gly Leu Pro
             110                 115                 120
Leu Trp Ala Thr Thr Gly Ala Tyr Gly Lys Leu Arg Asp Asn Asp Pro
         125                 130                 135
Arg Tyr Leu Glu Ala Leu Thr Pro Tyr Trp Ala Asn Ile Ser Lys Ile
     140                 145                 150
Ile Ala Pro His Leu Ile Thr Asn Gly Gly Asn Val Ile Leu Tyr Gln
155                 160                 165                 170
Ile Glu Asn Glu Tyr Ala Glu Gln Trp Leu Asp Glu Thr Gln Glu
                 175                 180                 185
Pro Asn Thr Ser Gly Gln Glu Tyr Met Gln Tyr Leu Glu Asp Val Ala
             190                 195                 200
Arg Glu Asn Gly Ile Asp Ala Pro Leu Ile His Asn Leu Pro Asn Met
         205                 210                 215
Asn Gly His Ser Trp Ser Lys Asp Leu Ser Asn Ala Thr Gly Asn Val
     220                 225                 230
Asp Val Ile Gly Val Asp Ser Tyr Pro Thr Cys Trp Thr Cys Asn Val
235                 240                 245                 250
Ser Glu Cys Leu Ser Thr Asn Gly Glu Tyr Ile Pro Tyr Lys Thr Leu
                 255                 260                 265
Thr Tyr Tyr Asp Tyr Phe Lys Lys Leu Ser Pro Thr Gln Pro Ser Phe
             270                 275                 280
Met Pro Glu Phe Gln Gly Gly Ser Tyr Asn Pro Trp Gly Gly Pro Gln
         285                 290                 295
Gly Gly Cys Pro Asp Asp Leu Gly Pro Asp Phe Ala Asn Leu Phe Tyr
     300                 305                 310
Arg Asn Leu Ile Tyr Gln Arg Val Ser Ala Ile Ser Leu Tyr Met Leu
315                 320                 325                 330
Tyr Gly Gly Thr Asn Trp Gly Trp His Gly Ser Thr Asp Val Ala Thr
                 335                 340                 345
Ser Tyr Asp Tyr Ser Ser Pro Ile Ser Glu Asn Arg Lys Leu Ile Glu
             350                 355                 360
Lys Tyr Tyr Glu Thr Lys Val Leu Thr Gln Phe Thr Lys Ile Ala Arg
         365                 370                 375
```

```
Asp Leu Ser Lys Val Asp Arg Leu Gly Asn Ser Thr Arg Tyr Ser Ser
    380                 385                 390

Asn Pro Ala Val Ser Val Ser Glu Leu Arg Asn Pro Asp Asn Gly Ala
395                 400                 405                 410

Ala Phe Tyr Val Thr Gln His Glu Tyr Thr Pro Ser Gly Thr Val Glu
                415                 420                 425

Lys Phe Thr Val Lys Val Asn Thr Ser Asp Gly Ala Leu Thr Ile Pro
                430                 435                 440

Gln Tyr Gly Ser Gln Ile Thr Leu Asn Gly His Gln Ser Lys Ile Ile
                445                 450                 455

Val Thr Asp Phe Asn Phe Gly Ser Lys Thr Leu Leu Tyr Ser Thr Ala
460                 465                 470

Glu Val Leu Thr Tyr Ala Val Ile Asp Gly Lys Glu Val Leu Ala Leu
475                 480                 485                 490

Trp Val Pro Thr Gly Glu Ser Gly Glu Phe Thr Val Lys Gly Val Asn
                495                 500                 505

Ser Ala Lys Phe Ala Asp Lys Gly Arg Thr Ala Asn Ile Glu Ile Arg
                510                 515                 520

Pro Gly Ala Asn Lys Val Thr Val Ser Phe Met Gln Arg Ala Gly Met
                525                 530                 535

Ser Val Val Glu Leu Gly Asp Gly Thr Arg Ile Val Leu Leu Asp Arg
540                 545                 550

Ser Ala Ala His Val Phe Trp Ser Pro Pro Leu Asn Asn Asp Pro Ala
555                 560                 565                 570

Glu Ala Gly Asn Asn Thr Val Leu Val His Gly Pro Tyr Leu Val Arg
                575                 580                 585

Ser Ala Arg Leu Glu Gly Cys Asp Leu Lys Leu Thr Gly Asp Ile Gln
                590                 595                 600

Asn Ser Thr Lys Val Ser Ile Phe Ala Pro Asn Ser Val Cys Ser Val
                605                 610                 615

Asn Trp Asn Gly Lys Lys Thr Ser Val Lys Ser Ala Lys Gly Gly Val
                620                 625                 630

Ile Thr Thr Thr Leu Gly Gly Asp Ala Lys Phe Glu Leu Pro Thr Ile
635                 640                 645                 650

Ser Gly Trp Lys Tyr Ala Asp Ser Leu Pro Glu Ile Ala Lys Asp Tyr
                655                 660                 665

Ser Ala Thr Ser Lys Ala Trp Val Val Ala Thr Lys Thr Asn Ser Ser
                670                 675                 680

Asn Pro Thr Pro Pro Ala Pro Asn Asn Pro Val Leu Tyr Val Asp Glu
                685                 690                 695

Asn Asp Ile His Val Gly Asn His Ile Tyr Arg Ala Thr Phe Pro Ser
                700                 705                 710

Thr Asp Glu Pro Pro Thr Asp Val Tyr Leu Asn Ile Thr Gly Gly Arg
715                 720                 725                 730

Ala Phe Gly Tyr Ser Val Trp Leu Asn Ser Glu Phe Ile Gly Ser Trp
                735                 740                 745

Leu Gly Thr Pro Thr Thr Glu Gln Asn Asp Gln Thr Phe Ser Phe Ser
                750                 755                 760

Asn Ala Thr Leu Ser Thr Asp Gly Asp Asn Ile Leu Val Val Val Met
                765                 770                 775

Asp Asn Ser Ala His Asp Leu Arg Glu Gly Ala Thr Asp Pro Arg Gly
780                 785                 790
```

```
Ile Thr Asn Ala Thr Leu Val Gly Pro Gly Thr Tyr Ser Phe Thr Glu
795                 800                 805                 810

Trp Lys Leu Ala Gly Asn Ala Gly Phe Glu Asp His Leu Asp Pro Val
            815                 820                 825

Arg Ala Pro Leu Asn Glu Gly Ser Leu Tyr Ala Glu Arg Val Gly Ile
        830                 835                 840

His Leu Pro Gly Tyr Gln Phe Asp Glu Ala Glu Val Pro Ser Asn
    845                 850                 855

Ser Thr Ser Leu Thr Val Pro Gly Ala Gly Ile Arg Val Phe Arg Thr
860                 865                 870

Val Val Pro Leu Ser Val Pro Gln Gly Leu Asp Val Ser Ile Ser Phe
875                 880                 885                 890

Arg Leu Thr Ala Pro Ser Asn Val Thr Phe Thr Ser Thr Glu Gly Tyr
            895                 900                 905

Thr Asn Gln Leu Arg Ala Leu Leu Phe Val Asn Gly Tyr Gln Tyr Gly
        910                 915                 920

Arg Phe Asn Pro Tyr Ile Gly His Gln Ile Asp Phe Pro Val Pro Pro
    925                 930                 935

Gly Val Leu Asp Tyr Asn Gly Asp Asn Thr Ile Ala Val Thr Val Trp
940                 945                 950

Ser Gln Ser Val Asp Gly Ala Glu Met Lys Ile Asp Trp Asn Val Asp
955                 960                 965                 970

Tyr Val His Glu Thr Ser Phe Asp Met Asn Phe Asp Gly Ala Tyr Leu
            975                 980                 985

Arg Pro Gly Trp Ile Glu Glu Arg Arg Glu Tyr Ala
        990                 995

<210> SEQ ID NO 49
<211> LENGTH: 998
<212> TYPE: PRT
<213> ORGANISM: Aspergillus tamarii
<220> FEATURE:
<221> NAME/KEY: mat_peptide
<222> LOCATION: (1)..(998)

<400> SEQUENCE: 49

Gln Gln Asn Ser Ser Arg Trp Pro Leu His Asp Asn Gly Leu Thr Asp
1               5                   10                  15

Thr Val Glu Trp Asp His Tyr Ser Phe Leu Ile Asn Gly Gln Arg His
            20                  25                  30

Phe Val Phe Ser Gly Glu Phe His Tyr Trp Arg Ile Pro Val Pro Glu
        35                  40                  45

Leu Trp Arg Asp Leu Leu Glu Lys Ile Lys Ala Ala Gly Phe Thr Ala
50                  55                  60

Phe Ser Ile Tyr Asn His Trp Gly Tyr His Thr Pro Lys Pro Gly Val
65                  70                  75                  80

Leu Asp Phe Glu Asn Gly Ala His Asn Phe Thr Ser Ile Met Thr Leu
            85                  90                  95

Ala Lys Glu Ile Gly Leu Tyr Met Ile Ile Arg Pro Gly Pro Tyr Val
        100                 105                 110

Asn Ala Glu Ala Asn Ala Gly Gly Leu Pro Leu Trp Ala Thr Thr Gly
    115                 120                 125

Ala Tyr Gly Lys Leu Arg Asp Asn Asp Pro Arg Tyr Leu Glu Ala Leu
130                 135                 140

Thr Pro Tyr Trp Ala Asn Ile Ser Lys Ile Ile Ala Pro His Leu Ile
145                 150                 155                 160
```

-continued

Thr Asn Gly Gly Asn Val Ile Leu Tyr Gln Ile Glu Asn Glu Tyr Ala
            165                 170                 175

Glu Gln Trp Leu Asp Glu Thr Gln Glu Pro Asn Thr Ser Gly Gln
            180                 185                 190

Glu Tyr Met Gln Tyr Leu Glu Asp Val Ala Arg Glu Asn Gly Ile Asp
            195                 200                 205

Ala Pro Leu Ile His Asn Leu Pro Asn Met Asn Gly His Ser Trp Ser
210                 215                 220

Lys Asp Leu Ser Asn Ala Thr Gly Asn Val Asp Val Ile Gly Val Asp
225                 230                 235                 240

Ser Tyr Pro Thr Cys Trp Thr Cys Asn Val Ser Glu Cys Leu Ser Thr
                245                 250                 255

Asn Gly Glu Tyr Ile Pro Tyr Lys Thr Leu Thr Tyr Tyr Asp Tyr Phe
                260                 265                 270

Lys Lys Leu Ser Pro Thr Gln Pro Ser Phe Met Pro Glu Phe Gln Gly
            275                 280                 285

Gly Ser Tyr Asn Pro Trp Gly Gly Pro Gln Gly Gly Cys Pro Asp Asp
            290                 295                 300

Leu Gly Pro Asp Phe Ala Asn Leu Phe Tyr Arg Asn Leu Ile Tyr Gln
305                 310                 315                 320

Arg Val Ser Ala Ile Ser Leu Tyr Met Leu Tyr Gly Gly Thr Asn Trp
                325                 330                 335

Gly Trp His Gly Ser Thr Asp Val Ala Thr Ser Tyr Asp Tyr Ser Ser
                340                 345                 350

Pro Ile Ser Glu Asn Arg Lys Leu Ile Glu Lys Tyr Tyr Glu Thr Lys
                355                 360                 365

Val Leu Thr Gln Phe Thr Lys Ile Ala Arg Asp Leu Ser Lys Val Asp
            370                 375                 380

Arg Leu Gly Asn Ser Thr Arg Tyr Ser Ser Asn Pro Ala Val Ser Val
385                 390                 395                 400

Ser Glu Leu Arg Asn Pro Asp Asn Gly Ala Ala Phe Tyr Val Thr Gln
                405                 410                 415

His Glu Tyr Thr Pro Ser Gly Thr Val Glu Lys Phe Thr Val Lys Val
                420                 425                 430

Asn Thr Ser Asp Gly Ala Leu Thr Ile Pro Gln Tyr Gly Ser Gln Ile
            435                 440                 445

Thr Leu Asn Gly His Gln Ser Lys Ile Ile Val Thr Asp Phe Asn Phe
450                 455                 460

Gly Ser Lys Thr Leu Leu Tyr Ser Thr Ala Glu Val Leu Thr Tyr Ala
465                 470                 475                 480

Val Ile Asp Gly Lys Glu Val Leu Ala Leu Trp Val Pro Thr Gly Glu
                485                 490                 495

Ser Gly Glu Phe Thr Val Lys Gly Val Asn Ser Ala Lys Phe Ala Asp
            500                 505                 510

Lys Gly Arg Thr Ala Asn Ile Glu Ile Arg Pro Gly Ala Asn Lys Val
            515                 520                 525

Thr Val Ser Phe Met Gln Arg Ala Gly Met Ser Val Val Glu Leu Gly
            530                 535                 540

Asp Gly Thr Arg Ile Val Leu Leu Asp Arg Ser Ala Ala His Val Phe
545                 550                 555                 560

Trp Ser Pro Pro Leu Asn Asn Asp Pro Ala Glu Ala Gly Asn Asn Thr
                565                 570                 575

```
Val Leu Val His Gly Pro Tyr Leu Val Arg Ser Ala Arg Leu Glu Gly
            580                 585                 590

Cys Asp Leu Lys Leu Thr Gly Asp Ile Gln Asn Ser Thr Lys Val Ser
            595                 600             605

Ile Phe Ala Pro Asn Ser Val Cys Ser Val Asn Trp Asn Gly Lys Lys
            610                 615                 620

Thr Ser Val Lys Ser Ala Lys Gly Gly Val Ile Thr Thr Thr Leu Gly
625                 630                 635                 640

Gly Asp Ala Lys Phe Glu Leu Pro Thr Ile Ser Gly Trp Lys Tyr Ala
                645                 650                 655

Asp Ser Leu Pro Glu Ile Ala Lys Asp Tyr Ser Ala Thr Ser Lys Ala
            660                 665                 670

Trp Val Ala Thr Lys Thr Asn Ser Ser Asn Pro Thr Pro Pro Ala
            675                 680                 685

Pro Asn Asn Pro Val Leu Tyr Val Asp Glu Asn Asp Ile His Val Gly
            690                 695                 700

Asn His Ile Tyr Arg Ala Thr Phe Pro Ser Thr Asp Glu Pro Pro Thr
705                 710                 715                 720

Asp Val Tyr Leu Asn Ile Thr Gly Gly Arg Ala Phe Gly Tyr Ser Val
                725                 730                 735

Trp Leu Asn Ser Glu Phe Ile Gly Ser Trp Leu Gly Thr Pro Thr Thr
            740                 745                 750

Glu Gln Asn Asp Gln Thr Phe Ser Phe Ser Asn Ala Thr Leu Ser Thr
            755                 760                 765

Asp Gly Asp Asn Ile Leu Val Val Met Asp Asn Ser Ala His Asp
770                 775                 780

Leu Arg Glu Gly Ala Thr Asp Pro Arg Gly Ile Thr Asn Ala Thr Leu
785                 790                 795                 800

Val Gly Pro Gly Thr Tyr Ser Phe Thr Glu Trp Lys Leu Ala Gly Asn
                805                 810                 815

Ala Gly Phe Glu Asp His Leu Asp Pro Val Arg Ala Pro Leu Asn Glu
            820                 825                 830

Gly Ser Leu Tyr Ala Glu Arg Val Gly Ile His Leu Pro Gly Tyr Gln
            835                 840                 845

Phe Asp Glu Ala Glu Val Pro Ser Asn Ser Thr Ser Leu Thr Val
850                 855                 860

Pro Gly Ala Gly Ile Arg Val Phe Arg Thr Val Pro Leu Ser Val
865                 870                 875                 880

Pro Gln Gly Leu Asp Val Ser Ile Ser Phe Arg Leu Thr Ala Pro Ser
                885                 890                 895

Asn Val Thr Phe Thr Ser Thr Glu Gly Tyr Thr Asn Gln Leu Arg Ala
            900                 905                 910

Leu Leu Phe Val Asn Gly Tyr Gln Tyr Gly Arg Phe Asn Pro Tyr Ile
            915                 920                 925

Gly His Gln Ile Asp Phe Pro Val Pro Pro Gly Val Leu Asp Tyr Asn
930                 935                 940

Gly Asp Asn Thr Ile Ala Val Thr Val Trp Ser Gln Ser Val Asp Gly
945                 950                 955                 960

Ala Glu Met Lys Ile Asp Trp Asn Val Asp Tyr Val His Glu Thr Ser
                965                 970                 975

Phe Asp Met Asn Phe Asp Gly Ala Tyr Leu Arg Pro Gly Trp Ile Glu
            980                 985                 990

Glu Arg Arg Glu Tyr Ala
```

```
<210> SEQ ID NO 50
<211> LENGTH: 3197
<212> TYPE: DNA
<213> ORGANISM: Curvularia spicifera
<220> FEATURE:
<221> NAME/KEY: CDS
<222> LOCATION: (1)..(265)
<220> FEATURE:
<221> NAME/KEY: sig_peptide
<222> LOCATION: (1)..(81)
<220> FEATURE:
<221> NAME/KEY: mat_peptide
<222> LOCATION: (82)..(3194)
<220> FEATURE:
<221> NAME/KEY: CDS
<222> LOCATION: (320)..(917)
<220> FEATURE:
<221> NAME/KEY: CDS
<222> LOCATION: (973)..(1925)
<220> FEATURE:
<221> NAME/KEY: CDS
<222> LOCATION: (1981)..(3194)

<400> SEQUENCE: 50
```

| | | | | | | | | | | | | | | | | |
|---|---|---|---|---|---|---|---|---|---|---|---|---|---|---|---|---|
| atg | aag | act | ttc | gtt | ggg | ctc | tcg | tgg | ctg | tcg | gcc | ttg | tct | tcg | ttg | 48 |
| Met | Lys | Thr | Phe | Val | Gly | Leu | Ser | Trp | Leu | Ser | Ala | Leu | Ser | Ser | Leu | |
| | -25 | | | | -20 | | | | | -15 | | | | | | |
| gtg | acg | ctc | cca | aat | ggc | tcc | ggt | gtt | gct | gcc | cag | aac | aac | acg | cct | 96 |
| Val | Thr | Leu | Pro | Asn | Gly | Ser | Gly | Val | Ala | Ala | Gln | Asn | Asn | Thr | Pro | |
| | -10 | | | | -5 | | | | -1 | 1 | | | | 5 | | |
| agt | acg | tgg | ccg | ctc | cac | gac | aat | ggt | ctg | aat | gat | gtc | gta | caa | tgg | 144 |
| Ser | Thr | Trp | Pro | Leu | His | Asp | Asn | Gly | Leu | Asn | Asp | Val | Val | Gln | Trp | |
| | | | | 10 | | | | | 15 | | | | | 20 | | |
| gat | cat | tat | tcc | ttt | aaa | gtg | aac | gga | aag | cgc | ctt | ttc | gtt | ttc | tct | 192 |
| Asp | His | Tyr | Ser | Phe | Lys | Val | Asn | Gly | Lys | Arg | Leu | Phe | Val | Phe | Ser | |
| | | 25 | | | | | 30 | | | | | 35 | | | | |
| gga | gaa | att | cac | tac | tgg | cgt | atc | ccg | gtc | tat | gag | gtt | tgg | gag | gac | 240 |
| Gly | Glu | Ile | His | Tyr | Trp | Arg | Ile | Pro | Val | Tyr | Glu | Val | Trp | Glu | Asp | |
| | | 40 | | | | | 45 | | | | | 50 | | | | |
| ttg | tta | gaa | aaa | att | aag | gcg | gct | g | gtaagtattt | ccatttgcat | | | | | | 285 |
| Leu | Leu | Glu | Lys | Ile | Lys | Ala | Ala | | | | | | | | | |
| | 55 | | | | | 60 | | | | | | | | | | |

| | | | | | | | | | | |
|---|---|---|---|---|---|---|---|---|---|---|
| aagatgcatg | tcgattacgg | ctgacgacca | ttag | gt | ttc | acg | gct | ttc | gcc | ttc | 339 |
| | | | | | Gly | Phe | Thr | Ala | Phe | Ala | Phe |
| | | | | | | | | 65 | | | |

| | | | | | | | | | | | | | | | | |
|---|---|---|---|---|---|---|---|---|---|---|---|---|---|---|---|---|
| tac | ggc | aac | tgg | gcc | tat | cac | agc | gca | aac | aac | cag | acc | ttg | gac | ttt | 387 |
| Tyr | Gly | Asn | Trp | Ala | Tyr | His | Ser | Ala | Asn | Asn | Gln | Thr | Leu | Asp | Phe | |
| | 70 | | | | | 75 | | | | | 80 | | | | | |
| gaa | agc | ggc | gcg | cac | gac | ttt | acg | aag | ctc | ttc | gag | atc | gcg | gag | cgc | 435 |
| Glu | Ser | Gly | Ala | His | Asp | Phe | Thr | Lys | Leu | Phe | Glu | Ile | Ala | Glu | Arg | |
| 85 | | | | | 90 | | | | | 95 | | | | | 100 | |
| gtc | ggc | ctt | tac | gtc | att | acc | agg | cct | ggt | cct | tat | gtc | aat | gct | gag | 483 |
| Val | Gly | Leu | Tyr | Val | Ile | Thr | Arg | Pro | Gly | Pro | Tyr | Val | Asn | Ala | Glu | |
| | | | | 105 | | | | | 110 | | | | | 115 | | |
| gcg | aac | gct | gga | ggc | ttc | cca | tta | tgg | ctc | act | acg | gga | gct | tat | gga | 531 |
| Ala | Asn | Ala | Gly | Gly | Phe | Pro | Leu | Trp | Leu | Thr | Thr | Gly | Ala | Tyr | Gly | |
| | | | 120 | | | | | 125 | | | | | 130 | | | |
| acg | cta | cgc | aac | gac | gac | ccc | aga | tac | ctc | caa | gca | ttg | gac | cct | tac | 579 |
| Thr | Leu | Arg | Asn | Asp | Asp | Pro | Arg | Tyr | Leu | Gln | Ala | Leu | Asp | Pro | Tyr | |
| | | 135 | | | | | 140 | | | | | 145 | | | | |
| ttc | tcc | aag | ttc | tct | gag | ctc | aca | tcc | aag | cat | ctc | gtg | acc | aag | ggc | 627 |
| Phe | Ser | Lys | Phe | Ser | Glu | Leu | Thr | Ser | Lys | His | Leu | Val | Thr | Lys | Gly | |
| | | 150 | | | | | 155 | | | | | 160 | | | | |

```
gga aaa gcg ctt gtc tac cag atc gag aac gag tat ggt gag cag tgg      675
Gly Lys Ala Leu Val Tyr Gln Ile Glu Asn Glu Tyr Gly Glu Gln Trp
165                 170                 175                 180 aag aat aga gac cag aag att ccc aat gaa agt gcc gga aga tat atg      723
Lys Asn Arg Asp Gln Lys Ile Pro Asn Glu Ser Ala Gly Arg Tyr Met
                185                 190                 195 cag gcg ctt gag gat ttg gca cgg gct cat ggc att gac gtc ccc cta      771
Gln Ala Leu Glu Asp Leu Ala Arg Ala His Gly Ile Asp Val Pro Leu
            200                 205                 210 atc cac aac gac ccc aat atg aac acc aag agc tgg agc aaa gac tat      819
Ile His Asn Asp Pro Asn Met Asn Thr Lys Ser Trp Ser Lys Asp Tyr
        215                 220                 225 gcc cct ggt gct gta gga aat gtc gat gtt gct ggg ctc gac agc tac      867
Ala Pro Gly Ala Val Gly Asn Val Asp Val Ala Gly Leu Asp Ser Tyr
    230                 235                 240 cca tcc tgt tgg tcc tgc aac ctg gat gag tgc acg ggt acc aat gga      915
Pro Ser Cys Trp Ser Cys Asn Leu Asp Glu Cys Thr Gly Thr Asn Gly
245                 250                 255                 260 ga  gtaagtgttg taaatctcaa acgctccagt aacagttact aacgttatgt tctag     972
Glu a tac gta gca tac caa acc atc aac tac ttt gat cat ttc gaa gaa gta   1021
  Tyr Val Ala Tyr Gln Thr Ile Asn Tyr Phe Asp His Phe Glu Glu Val
                265                 270                 275 tct cca acc cag cca agc ttc ttc cct gaa ttc caa ggt ggt tcg tac     1069
Ser Pro Thr Gln Pro Ser Phe Phe Pro Glu Phe Gln Gly Gly Ser Tyr
            280                 285                 290 aat cct tgg ggt gga ccc gaa ggt ggc tgt ccc ggt gac att gga gct     1117
Asn Pro Trp Gly Gly Pro Glu Gly Gly Cys Pro Gly Asp Ile Gly Ala
        295                 300                 305 gat ttc gca aat ctc ttc tac cga aac ctg gtc tcc caa cgc gtt acc     1165
Asp Phe Ala Asn Leu Phe Tyr Arg Asn Leu Val Ser Gln Arg Val Thr
310                 315                 320                 325 gca atc tca ctt tat atg gtt ttt ggc ggc aca aat tgg ggc gcc att     1213
Ala Ile Ser Leu Tyr Met Val Phe Gly Gly Thr Asn Trp Gly Ala Ile
                330                 335                 340 gca gcc cca gtc aca gcc acg tcg tat gac tat agc agt cct atc agc     1261
Ala Ala Pro Val Thr Ala Thr Ser Tyr Asp Tyr Ser Ser Pro Ile Ser
            345                 350                 355 gag aac cgg gag att ggc gcc aaa ttc tac gag acg aag aac ttg gct     1309
Glu Asn Arg Glu Ile Gly Ala Lys Phe Tyr Glu Thr Lys Asn Leu Ala
        360                 365                 370 ttg ttc act cgt gtt gcg gaa gac ttg aca gtt acc gat cgc ctt gga     1357
Leu Phe Thr Arg Val Ala Glu Asp Leu Thr Val Thr Asp Arg Leu Gly
375                 380                 385 aat tct act tct tac acg acc aac tcg gca gtc gag gcg agt gaa ctc     1405
Asn Ser Thr Ser Tyr Thr Thr Asn Ser Ala Val Glu Ala Ser Glu Leu
390                 395                 400                 405 cgc aac cca cac acc aac ggc gca ttt tac gtt acc att cat gcc aca     1453
Arg Asn Pro His Thr Asn Gly Ala Phe Tyr Val Thr Ile His Ala Thr
            410                 415                 420 tcg tct tcc gcg acg aag gaa tca ttc aag ctc cat gtg agc aca tcc     1501
Ser Ser Ser Ala Thr Lys Glu Ser Phe Lys Leu His Val Ser Thr Ser
        425                 430                 435 atc ggt aat ctc act atc cct caa cat gct ggt tct att gtt ctc gat     1549
Ile Gly Asn Leu Thr Ile Pro Gln His Ala Gly Ser Ile Val Leu Asp
440                 445                 450 ggc cat caa tcc aag atc ctt gtt acc gat ttc gca atg ggc aac agt     1597
Gly His Gln Ser Lys Ile Leu Val Thr Asp Phe Ala Met Gly Asn Ser
            455                 460                 465
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acc | ttg | aca | tac | tcc | act | gca | gaa | gtt | gtc | acc | tac | gct | ctt | atc | gac | 1645 |
| Thr | Leu | Thr | Tyr | Ser | Thr | Ala | Glu | Val | Val | Thr | Tyr | Ala | Leu | Ile | Asp |      |
| 470 |     |     |     | 475 |     |     |     |     | 480 |     |     |     |     | 485 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcc | aag | cca | gtt | gtt | ttg | cta | tca | act | ggt | att | ggc | gag | tct | gct | gaa | 1693 |
| Ser | Lys | Pro | Val | Val | Leu | Leu | Ser | Thr | Gly | Ile | Gly | Glu | Ser | Ala | Glu |      |
|     |     |     |     | 490 |     |     |     |     | 495 |     |     |     |     | 500 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ttc | cat | gtc | aag | ggc | gct | aag | aag | ggt | tcc | gct | gtc | agc | agt | ggt | gct | 1741 |
| Phe | His | Val | Lys | Gly | Ala | Lys | Lys | Gly | Ser | Ala | Val | Ser | Ser | Gly | Ala |      |
|     |     |     | 505 |     |     |     |     | 510 |     |     |     |     | 515 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agc | tcg | aat | gct | acg | ttc | tac | acc | gag | gcc | ggt | ggt | gtt | acg | acc | agc | 1789 |
| Ser | Ser | Asn | Ala | Thr | Phe | Tyr | Thr | Glu | Ala | Gly | Gly | Val | Thr | Thr | Ser |      |
|     |     | 520 |     |     |     |     | 525 |     |     |     |     | 530 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ata | cag | aaa | gtt | tcg | ggt | atg | agc | gtc | tac | cag | ttc | gat | aat | ggt | gtg | 1837 |
| Ile | Gln | Lys | Val | Ser | Gly | Met | Ser | Val | Tyr | Gln | Phe | Asp | Asn | Gly | Val |      |
|     | 535 |     |     |     |     | 540 |     |     |     |     | 545 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aag | gtt | gtt | gtt | gcg | gat | aag | cct | acc | gcg | tac | ctg | ttc | tgg | gca | cct | 1885 |
| Lys | Val | Val | Val | Ala | Asp | Lys | Pro | Thr | Ala | Tyr | Leu | Phe | Trp | Ala | Pro |      |
| 550 |     |     |     | 555 |     |     |     |     | 560 |     |     |     |     | 565 |     |      |

|     |     |     |     |     |     |     |     |     |     |         |      |
| --- | --- | --- | --- | --- | --- | --- | --- | --- | --- | ------- | ---- |
| aac | ctg | tcg | aac | gac | ccc | ttt | gcg | ccc | gtt | gat caa tcc g gtaagtatac | 1935 |
| Asn | Leu | Ser | Asn | Asp | Pro | Phe | Ala | Pro | Val | Asp Gln Ser |      |
|     |     | 570 |     |     |     |     | 575 |     |     |         |      |

|                  |                                |      |
| ---------------- | ------------------------------ | ---- |
| taaattcgtg attcttctgg ttctcgaaat ctaacatgca catag tt | ttg gtc cag | 1991 |
|                  | Val Leu Val Gln |      |
|                  | 580 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gga | cca | tac | ctc | gtc | cgc | cac | gta | gct | ctc | gac | ggc | cac | gtc | ctc | gcc | 2039 |
| Gly | Pro | Tyr | Leu | Val | Arg | His | Val | Ala | Leu | Asp | Gly | His | Val | Leu | Ala |      |
|     |     | 585 |     |     |     |     | 590 |     |     |     |     | 595 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctg | aaa | gga | gat | atc | atg | aac | agc | act | gac | atc | gaa | gtc | ttt | gcc | tgt | 2087 |
| Leu | Lys | Gly | Asp | Ile | Met | Asn | Ser | Thr | Asp | Ile | Glu | Val | Phe | Ala | Cys |      |
|     | 600 |     |     |     |     | 605 |     |     |     |     | 610 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cac | aat | gcc | aaa | act | ctg | tcc | tgg | aat | gga | aag | aag | ctc | tct | acc | tcg | 2135 |
| His | Asn | Ala | Lys | Thr | Leu | Ser | Trp | Asn | Gly | Lys | Lys | Leu | Ser | Thr | Ser |      |
| 615 |     |     |     |     | 620 |     |     |     |     | 625 |     |     |     |     | 630 |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cga | acc | tcg | tac | ggt | agt | ctg | aaa | gcc | cac | atc | acc | gct | ttc | aac | ggc | 2183 |
| Arg | Thr | Ser | Tyr | Gly | Ser | Leu | Lys | Ala | His | Ile | Thr | Ala | Phe | Asn | Gly |      |
|     |     |     |     | 635 |     |     |     |     | 640 |     |     |     |     | 645 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| act | att | cag | cta | cct | tcc | ctc | gac | aac | tgg | aaa | gtc | aac | gaa | ggt | ctc | 2231 |
| Thr | Ile | Gln | Leu | Pro | Ser | Leu | Asp | Asn | Trp | Lys | Val | Asn | Glu | Gly | Leu |      |
|     |     |     | 650 |     |     |     |     | 655 |     |     |     |     | 660 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cca | gag | aag | gag | gca | gat | tac | gat | gac | agc | agc | gcc | gct | tgg | gtt | ata | 2279 |
| Pro | Glu | Lys | Glu | Ala | Asp | Tyr | Asp | Asp | Ser | Ser | Ala | Ala | Trp | Val | Ile |      |
|     |     | 665 |     |     |     |     | 670 |     |     |     |     | 675 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gcc | gac | cac | ctc | agc | acc | ccc | aac | cct | acc | aag | ccc | gac | act | ctt | ccc | 2327 |
| Ala | Asp | His | Leu | Ser | Thr | Pro | Asn | Pro | Thr | Lys | Pro | Asp | Thr | Leu | Pro |      |
|     | 680 |     |     |     |     | 685 |     |     |     |     | 690 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtt | ctg | tac | gtc | gat | gag | tat | ggc | ttc | cac | aac | agc | ttc | cac | ctt | ttc | 2375 |
| Val | Leu | Tyr | Val | Asp | Glu | Tyr | Gly | Phe | His | Asn | Ser | Phe | His | Leu | Phe |      |
| 695 |     |     |     | 700 |     |     |     |     | 705 |     |     |     |     | 710 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| cgc | ggc | tac | ttc | gat | ggc | tcc | gcc | acc | ggc | gtc | caa | ctc | tct | gtg | caa | 2423 |
| Arg | Gly | Tyr | Phe | Asp | Gly | Ser | Ala | Thr | Gly | Val | Gln | Leu | Ser | Val | Gln |      |
|     |     | 715 |     |     |     |     | 720 |     |     |     |     | 725 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggc | ggt | ctc | gca | ttt | ggc | tgg | agt | gcc | tgg | cta | aac | ggc | aaa | cat | att | 2471 |
| Gly | Gly | Leu | Ala | Phe | Gly | Trp | Ser | Ala | Trp | Leu | Asn | Gly | Lys | His | Ile |      |
|     |     |     | 730 |     |     |     |     | 735 |     |     |     |     | 740 |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggt | tct | tgg | ctg | ggc | aat | acg | acc | ctc | ggt | gta | ggc | aac | gca | acg | ctc | 2519 |
| Gly | Ser | Trp | Leu | Gly | Asn | Thr | Thr | Leu | Gly | Val | Gly | Asn | Ala | Thr | Leu |      |
|     |     | 745 |     |     |     |     | 750 |     |     |     |     | 755 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcc | ttt | gcc | aac | gcc | aca | gtt | cac | tcc | aat | gga | acc | aac | gtc | ctc | ctc | 2567 |
| Ser | Phe | Ala | Asn | Ala | Thr | Val | His | Ser | Asn | Gly | Thr | Asn | Val | Leu | Leu |      |

-continued

```
              760                 765                 770
gtc gcc caa gac aac aca ggc cac gat ctc cgc ggc gcc acc gat    2615
Val Ala Gln Asp Asn Thr Gly His Asp Leu Arg Gly Gly Ala Thr Asp
775                 780                 785                 790 ccc cgc ggt atc ctg cgc gca tcc ctt tcc ggc ccc tca aac ttc aca    2663
Pro Arg Gly Ile Leu Arg Ala Ser Leu Ser Gly Pro Ser Asn Phe Thr
            795                 800                 805 agc tgg aaa atc gca ggt gaa gcc ggc ggc gaa tcc atc cag ctc gac    2711
Ser Trp Lys Ile Ala Gly Glu Ala Gly Gly Glu Ser Ile Gln Leu Asp
        810                 815                 820 ccc gtc cgt ggt ccc ctg gct gaa ggc ggc ctc gtc gct gaa cgc ctt    2759
Pro Val Arg Gly Pro Leu Ala Glu Gly Gly Leu Val Ala Glu Arg Leu
    825                 830                 835 ggc tgg cac ctc cct ggc ttc gac gac gcg gac tgg gcc acc agc tcg    2807
Gly Trp His Leu Pro Gly Phe Asp Asp Ala Asp Trp Ala Thr Ser Ser
840                 845                 850 cct tcc gcc gga ttc tca ggc gca gat ata aag ttc tac cgt act aca    2855
Pro Ser Ala Gly Phe Ser Gly Ala Asp Ile Lys Phe Tyr Arg Thr Thr
855                 860                 865                 870 ttc ccg ctt gat gta cct gac cat gtt gat gct tcc ttc gca ttt gtg    2903
Phe Pro Leu Asp Val Pro Asp His Val Asp Ala Ser Phe Ala Phe Val
            875                 880                 885 ctg aac gcc cct gct gcg aag acg att cgc gtc cag ctt ttt gtc aat    2951
Leu Asn Ala Pro Ala Ala Lys Thr Ile Arg Val Gln Leu Phe Val Asn
        890                 895                 900 ggg tat cag tat gcg cgg ttt aat ccg tat gtg ggt aat gaa atc aag    2999
Gly Tyr Gln Tyr Ala Arg Phe Asn Pro Tyr Val Gly Asn Glu Ile Lys
    905                 910                 915 ttc cct gtt cct ccg ggc att ctc aac tac agc gga gag aat gtg gtt    3047
Phe Pro Val Pro Pro Gly Ile Leu Asn Tyr Ser Gly Glu Asn Val Val
920                 925                 930 ggg ctg agt gtg tgg gca caa gag gaa gac gga gca aag gtc gat gtg    3095
Gly Leu Ser Val Trp Ala Gln Glu Glu Asp Gly Ala Lys Val Asp Val
935                 940                 945                 950 cgt atg gtg cag gag ttt gcg gtt gaa agt agt tgg aaa tcg agg ttt    3143
Arg Met Val Gln Glu Phe Ala Val Glu Ser Ser Trp Lys Ser Arg Phe
            955                 960                 965 aat ggc gag tat ttg agg ccg aag tgg aca gag gag aga ctg gag tat    3191
Asn Gly Glu Tyr Leu Arg Pro Lys Trp Thr Glu Glu Arg Leu Glu Tyr
        970                 975                 980 gct tga                                                             3197
Ala
```

```
<210> SEQ ID NO 51
<211> LENGTH: 1010
<212> TYPE: PRT
<213> ORGANISM: Curvularia spicifera

<400> SEQUENCE: 51

Met Lys Thr Phe Val Gly Leu Ser Trp Leu Ser Ala Leu Ser Ser Leu
        -25                 -20                 -15

Val Thr Leu Pro Asn Gly Ser Gly Val Ala Ala Gln Asn Asn Thr Pro
    -10                  -5                  -1   1               5

Ser Thr Trp Pro Leu His Asp Asn Gly Leu Asn Asp Val Val Gln Trp
                 10                  15                  20

Asp His Tyr Ser Phe Lys Val Asn Gly Lys Arg Leu Phe Val Phe Ser
             25                  30                  35

Gly Glu Ile His Tyr Trp Arg Ile Pro Val Tyr Glu Val Trp Glu Asp
         40                  45                  50
```

```
Leu Leu Glu Lys Ile Lys Ala Ala Gly Phe Thr Ala Phe Ala Phe Tyr
     55              60                  65
Gly Asn Trp Ala Tyr His Ser Ala Asn Asn Gln Thr Leu Asp Phe Glu
 70              75              80                  85
Ser Gly Ala His Asp Phe Thr Lys Leu Phe Glu Ile Ala Glu Arg Val
                 90              95                 100
Gly Leu Tyr Val Ile Thr Arg Pro Gly Pro Tyr Val Asn Ala Glu Ala
             105             110             115
Asn Ala Gly Gly Phe Pro Leu Trp Leu Thr Thr Gly Ala Tyr Gly Thr
         120             125             130
Leu Arg Asn Asp Asp Pro Arg Tyr Leu Gln Ala Leu Asp Pro Tyr Phe
     135             140             145
Ser Lys Phe Ser Glu Leu Thr Ser Lys His Leu Val Thr Lys Gly Gly
 150             155             160             165
Lys Ala Leu Val Tyr Gln Ile Glu Asn Glu Tyr Gly Glu Gln Trp Lys
                 170             175             180
Asn Arg Asp Gln Lys Ile Pro Asn Glu Ser Ala Gly Arg Tyr Met Gln
             185             190             195
Ala Leu Glu Asp Leu Ala Arg Ala His Gly Ile Asp Val Pro Leu Ile
         200             205             210
His Asn Asp Pro Asn Met Asn Thr Lys Ser Trp Ser Lys Asp Tyr Ala
     215             220             225
Pro Gly Ala Val Gly Asn Val Asp Val Ala Gly Leu Asp Ser Tyr Pro
 230             235             240             245
Ser Cys Trp Ser Cys Asn Leu Asp Glu Cys Thr Gly Thr Asn Gly Glu
                 250             255             260
Tyr Val Ala Tyr Gln Thr Ile Asn Tyr Phe Asp His Phe Glu Glu Val
             265             270             275
Ser Pro Thr Gln Pro Ser Phe Phe Pro Glu Phe Gln Gly Gly Ser Tyr
         280             285             290
Asn Pro Trp Gly Gly Pro Glu Gly Gly Cys Pro Gly Asp Ile Gly Ala
     295             300             305
Asp Phe Ala Asn Leu Phe Tyr Arg Asn Leu Val Ser Gln Arg Val Thr
 310             315             320             325
Ala Ile Ser Leu Tyr Met Val Phe Gly Gly Thr Asn Trp Gly Ala Ile
                 330             335             340
Ala Ala Pro Val Thr Ala Thr Ser Tyr Asp Tyr Ser Ser Pro Ile Ser
             345             350             355
Glu Asn Arg Glu Ile Gly Ala Lys Phe Tyr Glu Thr Lys Asn Leu Ala
         360             365             370
Leu Phe Thr Arg Val Ala Glu Asp Leu Thr Val Thr Asp Arg Leu Gly
     375             380             385
Asn Ser Thr Ser Tyr Thr Thr Asn Ser Ala Val Glu Ala Ser Glu Leu
 390             395             400             405
Arg Asn Pro His Thr Asn Gly Ala Phe Tyr Val Thr Ile His Ala Thr
                 410             415             420
Ser Ser Ser Ala Thr Lys Glu Ser Phe Lys Leu His Val Ser Thr Ser
             425             430             435
Ile Gly Asn Leu Thr Ile Pro Gln His Ala Gly Ser Ile Val Leu Asp
         440             445             450
Gly His Gln Ser Lys Ile Leu Val Thr Asp Phe Ala Met Gly Asn Ser
     455             460             465
```

-continued

```
Thr Leu Thr Tyr Ser Thr Ala Glu Val Val Thr Tyr Ala Leu Ile Asp
470                 475                 480                 485

Ser Lys Pro Val Val Leu Leu Ser Thr Gly Ile Gly Glu Ser Ala Glu
            490                 495                 500

Phe His Val Lys Gly Ala Lys Lys Gly Ser Ala Val Ser Ser Gly Ala
                505                 510                 515

Ser Ser Asn Ala Thr Phe Tyr Thr Glu Ala Gly Val Thr Thr Ser
        520                 525                 530

Ile Gln Lys Val Ser Gly Met Ser Val Tyr Gln Phe Asp Asn Gly Val
535                 540                 545

Lys Val Val Ala Asp Lys Pro Thr Ala Tyr Leu Phe Trp Ala Pro
550                 555                 560                 565

Asn Leu Ser Asn Asp Pro Phe Ala Pro Val Asp Gln Ser Val Leu Val
            570                 575                 580

Gln Gly Pro Tyr Leu Val Arg His Val Ala Leu Asp Gly His Val Leu
                585                 590                 595

Ala Leu Lys Gly Asp Ile Met Asn Ser Thr Asp Ile Glu Val Phe Ala
            600                 605                 610

Cys His Asn Ala Lys Thr Leu Ser Trp Asn Gly Lys Lys Leu Ser Thr
            615                 620                 625

Ser Arg Thr Ser Tyr Gly Ser Leu Lys Ala His Ile Thr Ala Phe Asn
630                 635                 640                 645

Gly Thr Ile Gln Leu Pro Ser Leu Asp Asn Trp Lys Val Asn Glu Gly
                650                 655                 660

Leu Pro Glu Lys Glu Ala Asp Tyr Asp Asp Ser Ser Ala Ala Trp Val
                665                 670                 675

Ile Ala Asp His Leu Ser Thr Pro Asn Pro Thr Lys Pro Asp Thr Leu
            680                 685                 690

Pro Val Leu Tyr Val Asp Glu Tyr Gly Phe His Asn Ser Phe His Leu
            695                 700                 705

Phe Arg Gly Tyr Phe Asp Gly Ser Ala Thr Gly Val Gln Leu Ser Val
710                 715                 720                 725

Gln Gly Gly Leu Ala Phe Gly Trp Ser Ala Trp Leu Asn Gly Lys His
                730                 735                 740

Ile Gly Ser Trp Leu Gly Asn Thr Thr Leu Gly Val Gly Asn Ala Thr
            745                 750                 755

Leu Ser Phe Ala Asn Ala Thr Val His Ser Asn Gly Thr Asn Val Leu
            760                 765                 770

Leu Val Ala Gln Asp Asn Thr Gly His Asp Leu Arg Gly Gly Ala Thr
775                 780                 785

Asp Pro Arg Gly Ile Leu Arg Ala Ser Leu Ser Gly Pro Ser Asn Phe
790                 795                 800                 805

Thr Ser Trp Lys Ile Ala Gly Glu Ala Gly Gly Ser Ile Gln Leu
                810                 815                 820

Asp Pro Val Arg Gly Pro Leu Ala Glu Gly Leu Val Ala Glu Arg
            825                 830                 835

Leu Gly Trp His Leu Pro Gly Phe Asp Asp Ala Asp Trp Ala Thr Ser
                840                 845                 850

Ser Pro Ser Ala Gly Phe Gly Ala Asp Ile Lys Phe Tyr Arg Thr
            855                 860                 865

Thr Phe Pro Leu Asp Val Pro Asp His Val Asp Ala Ser Phe Ala Phe
870                 875                 880                 885

Val Leu Asn Ala Pro Ala Ala Lys Thr Ile Arg Val Gln Leu Phe Val
```

```
                    890                 895                 900
Asn Gly Tyr Gln Tyr Ala Arg Phe Asn Pro Tyr Val Gly Asn Glu Ile
                905                 910                 915

Lys Phe Pro Val Pro Pro Gly Ile Leu Asn Tyr Ser Gly Glu Asn Val
            920                 925                 930

Val Gly Leu Ser Val Trp Ala Gln Glu Glu Asp Gly Ala Lys Val Asp
        935                 940                 945

Val Arg Met Val Gln Glu Phe Ala Val Glu Ser Ser Trp Lys Ser Arg
950                 955                 960                 965

Phe Asn Gly Glu Tyr Leu Arg Pro Lys Trp Thr Glu Arg Leu Glu
                970                 975                 980

Tyr Ala

<210> SEQ ID NO 52
<211> LENGTH: 983
<212> TYPE: PRT
<213> ORGANISM: Curvularia spicifera
<220> FEATURE:
<221> NAME/KEY: mat_peptide
<222> LOCATION: (1)..(983)

<400> SEQUENCE: 52

Gln Asn Asn Thr Pro Ser Thr Trp Pro Leu His Asp Asn Gly Leu Asn
1               5                   10                  15

Asp Val Val Gln Trp Asp His Tyr Ser Phe Lys Val Asn Gly Lys Arg
            20                  25                  30

Leu Phe Val Phe Ser Gly Glu Ile His Tyr Trp Arg Ile Pro Val Tyr
        35                  40                  45

Glu Val Trp Glu Asp Leu Leu Glu Lys Ile Lys Ala Ala Gly Phe Thr
    50                  55                  60

Ala Phe Ala Phe Tyr Gly Asn Trp Ala Tyr His Ser Ala Asn Asn Gln
65                  70                  75                  80

Thr Leu Asp Phe Glu Ser Gly Ala His Asp Phe Thr Lys Leu Phe Glu
                85                  90                  95

Ile Ala Glu Arg Val Gly Leu Tyr Val Ile Thr Arg Pro Gly Pro Tyr
            100                 105                 110

Val Asn Ala Glu Ala Asn Ala Gly Gly Phe Pro Leu Trp Leu Thr Thr
        115                 120                 125

Gly Ala Tyr Gly Thr Leu Arg Asn Asp Asp Pro Arg Tyr Leu Gln Ala
    130                 135                 140

Leu Asp Pro Tyr Phe Ser Lys Phe Ser Glu Leu Thr Ser Lys His Leu
145                 150                 155                 160

Val Thr Lys Gly Gly Lys Ala Leu Val Tyr Gln Ile Glu Asn Glu Tyr
                165                 170                 175

Gly Glu Gln Trp Lys Asn Arg Asp Gln Lys Ile Pro Asn Glu Ser Ala
            180                 185                 190

Gly Arg Tyr Met Gln Ala Leu Glu Asp Leu Ala Arg Ala His Gly Ile
        195                 200                 205

Asp Val Pro Leu Ile His Asn Asp Pro Asn Met Asn Thr Lys Ser Trp
    210                 215                 220

Ser Lys Asp Tyr Ala Pro Gly Ala Val Gly Asn Val Asp Val Ala Gly
225                 230                 235                 240

Leu Asp Ser Tyr Pro Ser Cys Trp Ser Cys Asn Leu Asp Glu Cys Thr
                245                 250                 255

Gly Thr Asn Gly Glu Tyr Val Ala Tyr Gln Thr Ile Asn Tyr Phe Asp
```

His Phe Glu Glu Val Ser Pro Thr Gln Pro Ser Phe Phe Pro Glu Phe
            260                 265                 270

Gln Gly Gly Ser Tyr Asn Pro Trp Gly Gly Pro Glu Gly Gly Cys Pro
    275                 280                 285

Gly Asp Ile Gly Ala Asp Phe Ala Asn Leu Phe Tyr Arg Asn Leu Val
290                 295                 300

Ser Gln Arg Val Thr Ala Ile Ser Leu Tyr Met Val Phe Gly Gly Thr
305                 310                 315                 320

Asn Trp Gly Ala Ile Ala Pro Val Thr Ala Thr Ser Tyr Asp Tyr
    325                 330                 335

Ser Ser Pro Ile Ser Glu Asn Arg Glu Ile Gly Ala Lys Phe Tyr Glu
340                 345                 350

Thr Lys Asn Leu Ala Leu Phe Thr Arg Val Ala Glu Asp Leu Thr Val
    355                 360                 365

Thr Asp Arg Leu Gly Asn Ser Thr Ser Tyr Thr Thr Asn Ser Ala Val
370                 375                 380

Glu Ala Ser Glu Leu Arg Asn Pro His Thr Asn Gly Ala Phe Tyr Val
385                 390                 395                 400

Thr Ile His Ala Thr Ser Ser Ala Thr Lys Glu Ser Phe Lys Leu
    405                 410                 415

His Val Ser Thr Ser Ile Gly Asn Leu Thr Ile Pro Gln His Ala Gly
420                 425                 430

Ser Ile Val Leu Asp Gly His Gln Ser Lys Ile Leu Val Thr Asp Phe
    435                 440                 445

Ala Met Gly Asn Ser Thr Leu Thr Tyr Ser Thr Ala Glu Val Val Thr
450                 455                 460

Tyr Ala Leu Ile Asp Ser Lys Pro Val Val Leu Leu Ser Thr Gly Ile
465                 470                 475                 480

Gly Glu Ser Ala Glu Phe His Val Lys Gly Ala Lys Lys Gly Ser Ala
    485                 490                 495

Val Ser Ser Gly Ala Ser Ser Asn Ala Thr Phe Tyr Thr Glu Ala Gly
500                 505                 510

Gly Val Thr Thr Ser Ile Gln Lys Val Ser Gly Met Ser Val Tyr Gln
    515                 520                 525

Phe Asp Asn Gly Val Lys Val Val Ala Asp Lys Pro Thr Ala Tyr
530                 535                 540

Leu Phe Trp Ala Pro Asn Leu Ser Asn Asp Pro Phe Ala Pro Val Asp
545                 550                 555                 560

Gln Ser Val Leu Val Gln Gly Pro Tyr Leu Val Arg His Val Ala Leu
    565                 570                 575

Asp Gly His Val Leu Ala Leu Lys Gly Asp Ile Met Asn Ser Thr Asp
580                 585                 590

Ile Glu Val Phe Ala Cys His Asn Ala Lys Thr Leu Ser Trp Asn Gly
    595                 600                 605

Lys Lys Leu Ser Thr Ser Arg Thr Ser Tyr Gly Ser Leu Lys Ala His
610                 615                 620

Ile Thr Ala Phe Asn Gly Thr Ile Gln Leu Pro Ser Leu Asp Asn Trp
625                 630                 635                 640

Lys Val Asn Glu Gly Leu Pro Glu Lys Glu Ala Asp Tyr Asp Asp Ser
    645                 650                 655

Ser Ala Ala Trp Val Ile Ala Asp His Leu Ser Thr Pro Asn Pro Thr
660                 665                 670

675                 680                 685

-continued

```
Lys Pro Asp Thr Leu Pro Val Leu Tyr Val Asp Glu Tyr Gly Phe His
690                 695                 700

Asn Ser Phe His Leu Phe Arg Gly Tyr Phe Asp Gly Ser Ala Thr Gly
705                 710                 715                 720

Val Gln Leu Ser Val Gln Gly Leu Ala Phe Gly Trp Ser Ala Trp
            725                 730                 735

Leu Asn Gly Lys His Ile Gly Ser Trp Leu Gly Asn Thr Thr Leu Gly
                740                 745                 750

Val Gly Asn Ala Thr Leu Ser Phe Ala Asn Ala Thr Val His Ser Asn
            755                 760                 765

Gly Thr Asn Val Leu Leu Val Ala Gln Asp Asn Thr Gly His Asp Leu
            770                 775                 780

Arg Gly Gly Ala Thr Asp Pro Arg Gly Ile Leu Arg Ala Ser Leu Ser
785                 790                 795                 800

Gly Pro Ser Asn Phe Thr Ser Trp Lys Ile Ala Gly Glu Ala Gly Gly
                805                 810                 815

Glu Ser Ile Gln Leu Asp Pro Val Arg Gly Pro Leu Ala Glu Gly Gly
                820                 825                 830

Leu Val Ala Glu Arg Leu Gly Trp His Leu Pro Gly Phe Asp Asp Ala
            835                 840                 845

Asp Trp Ala Thr Ser Ser Pro Ser Ala Gly Phe Ser Gly Ala Asp Ile
850                 855                 860

Lys Phe Tyr Arg Thr Thr Phe Pro Leu Asp Val Pro Asp His Val Asp
865                 870                 875                 880

Ala Ser Phe Ala Phe Val Leu Asn Ala Pro Ala Lys Thr Ile Arg
            885                 890                 895

Val Gln Leu Phe Val Asn Gly Tyr Gln Tyr Ala Arg Phe Asn Pro Tyr
            900                 905                 910

Val Gly Asn Glu Ile Lys Phe Pro Val Pro Pro Gly Ile Leu Asn Tyr
            915                 920                 925

Ser Gly Glu Asn Val Val Gly Leu Ser Val Trp Ala Gln Glu Glu Asp
            930                 935                 940

Gly Ala Lys Val Asp Val Arg Met Val Gln Glu Phe Ala Val Glu Ser
945                 950                 955                 960

Ser Trp Lys Ser Arg Phe Asn Gly Glu Tyr Leu Arg Pro Lys Trp Thr
                965                 970                 975

Glu Glu Arg Leu Glu Tyr Ala
            980

<210> SEQ ID NO 53
<211> LENGTH: 3829
<212> TYPE: DNA
<213> ORGANISM: Aspergillus oryzae
<220> FEATURE:
<221> NAME/KEY: CDS
<222> LOCATION: (1)..(125)
<220> FEATURE:
<221> NAME/KEY: sig_peptide
<222> LOCATION: (1)..(66)
<220> FEATURE:
<221> NAME/KEY: mat_peptide
<222> LOCATION: (67)..(3826)
<220> FEATURE:
<221> NAME/KEY: CDS
<222> LOCATION: (195)..(249)
<220> FEATURE:
<221> NAME/KEY: CDS
<222> LOCATION: (306)..(328)
<220> FEATURE:
```

```
<221> NAME/KEY: CDS
<222> LOCATION: (378)..(422)
<220> FEATURE:
<221> NAME/KEY: CDS
<222> LOCATION: (481)..(952)
<220> FEATURE:
<221> NAME/KEY: CDS
<222> LOCATION: (1009)..(1143)
<220> FEATURE:
<221> NAME/KEY: CDS
<222> LOCATION: (1193)..(1212)
<220> FEATURE:
<221> NAME/KEY: CDS
<222> LOCATION: (1266)..(1286)
<220> FEATURE:
<221> NAME/KEY: CDS
<222> LOCATION: (1337)..(1539)
<220> FEATURE:
<221> NAME/KEY: CDS
<222> LOCATION: (1588)..(1680)
<220> FEATURE:
<221> NAME/KEY: CDS
<222> LOCATION: (1735)..(1772)
<220> FEATURE:
<221> NAME/KEY: CDS
<222> LOCATION: (1826)..(1976)
<220> FEATURE:
<221> NAME/KEY: CDS
<222> LOCATION: (2035)..(2448)
<220> FEATURE:
<221> NAME/KEY: CDS
<222> LOCATION: (2507)..(2800)
<220> FEATURE:
<221> NAME/KEY: CDS
<222> LOCATION: (2856)..(3826)

<400> SEQUENCE: 53
```

| | | | | | | | | | | | | | | | | |
|---|---|---|---|---|---|---|---|---|---|---|---|---|---|---|---|---|
| atg | ctc | atc | tcc | aag | acc | gtg | ctc | agc | gga | ctt | gcc | ttg | ggg | gcg | tcc | 48 |
| Met | Leu | Ile | Ser | Lys | Thr | Val | Leu | Ser | Gly | Leu | Ala | Leu | Gly | Ala | Ser | |
| | | | -20 | | | | -15 | | | | -10 | | | | | |

| | | | | | | | | | | | | | | | | |
|---|---|---|---|---|---|---|---|---|---|---|---|---|---|---|---|---|
| ttc | gtt | ggc | gtt | tct | gct | cag | cag | aac | tca | acc | cgt | tgg | ccg | ttg | cat | 96 |
| Phe | Val | Gly | Val | Ser | Ala | Gln | Gln | Asn | Ser | Thr | Arg | Trp | Pro | Leu | His | |
| | -5 | | | | -1 | 1 | | | 5 | | | | | | 10 | |

| | | | | | | | | | | | | | |
|---|---|---|---|---|---|---|---|---|---|---|---|---|---|
| gac | aac | ggc | ttg | aca | gac | act | gta | gaa | tg | gtaggtttag | ccaatttgtg | | 145 |
| Asp | Asn | Gly | Leu | Thr | Asp | Thr | Val | Glu | Trp | | | | |
| | | 15 | | | | | 20 | | | | | | |

| | | | | | |
|---|---|---|---|---|---|
| gattcatttg | tggatcaata | ctgttagctc | tgacaccatg | gctatacag | g gat cac | 201 |
| | | | | | Asp His |

| | | | | | | | | | | | | | | | |
|---|---|---|---|---|---|---|---|---|---|---|---|---|---|---|---|
| tat | agt | ttc | ttg | att | aat | ggt | cag | aga | cat | ttt | gtt | ttc | tct | gga | gag | 249 |
| Tyr | Ser | Phe | Leu | Ile | Asn | Gly | Gln | Arg | His | Phe | Val | Phe | Ser | Gly | Glu | |
| | | 25 | | | | | 30 | | | | | 35 | | | | |

| | | | | |
|---|---|---|---|---|
| gttggtccac | ccaatcgttt | atgttctaca | tggttcaatg | cattaacatc gtatag ttc | 308 |
| | | | | Phe |

| | | | | | |
|---|---|---|---|---|---|
| cat | tac | tgg | cgt | att | cct gt gtaaggcaag agtcctacaa cggcagcgct | 358 |
| His | Tyr | Trp | Arg | Ile | Pro Val |
| 40 | | | | 45 | |

| | | | | | | | | |
|---|---|---|---|---|---|---|---|---|
| ctcgctaata | tataaccag | g ccc | gaa | tta | tgg | aga | gat cta ctg gag aag | 408 |
| | | Pro | Glu | Leu | Trp | Arg | Asp Leu Leu Glu Lys | |
| | | | 50 | | | | 55 | |

| | | | | | |
|---|---|---|---|---|---|
| atc | aag | gcc | gct | gg | gtaggtagtt ccagatttg aaagtcgttt ctcggcacgc | 462 |
| Ile | Lys | Ala | Ala | Gly | |
| | | 60 | | | |

| | | | | | | | | | | |
|---|---|---|---|---|---|---|---|---|---|---|
| taatggcaaa | ttcgacag | t ttc | act | gcc | ttt | tcc | atc | tac | aat cac tgg gga | 514 |
| | | Phe | Thr | Ala | Phe | Ser | Ile | Tyr | Asn His Trp Gly | |
| | | | | 65 | | | | 70 | | |

| | | | | | | | | | | | | | | | |
|---|---|---|---|---|---|---|---|---|---|---|---|---|---|---|---|
| tac | cac | agc | cct | aaa | ccc | ggt | gtt | ctc | gac | ttt | gag | aac | gga | gcc | cac | 562 |
| Tyr | His | Ser | Pro | Lys | Pro | Gly | Val | Leu | Asp | Phe | Glu | Asn | Gly | Ala | His | |
| | 75 | | | | | 80 | | | | | 85 | | | | | |

```
                                                               -continued aat ttc acc tcg atc atg act cta gcc aaa gag ata ggt ctc tac atg    610
Asn Phe Thr Ser Ile Met Thr Leu Ala Lys Glu Ile Gly Leu Tyr Met
 90              95                 100 atc atc cgg ccg ggc cca tac gtc aat gca gaa gcc aat gct ggc ggt    658
Ile Ile Arg Pro Gly Pro Tyr Val Asn Ala Glu Ala Asn Ala Gly Gly
105             110                 115                 120 ctc cct ctg tgg acg act aca ggt gcc tac ggg aaa ctg cgg gat aac    706
Leu Pro Leu Trp Thr Thr Thr Gly Ala Tyr Gly Lys Leu Arg Asp Asn
                125                 130                 135 gac cct cgg tat ctg gag gct ttg acc ccg tac tgg gct aac att tct    754
Asp Pro Arg Tyr Leu Glu Ala Leu Thr Pro Tyr Trp Ala Asn Ile Ser
            140                 145                 150 aaa att att gcc cct cat ctc atc act aat gac gga aat gta atc ctg    802
Lys Ile Ile Ala Pro His Leu Ile Thr Asn Asp Gly Asn Val Ile Leu
            155                 160                 165 tat cag atc gaa aat gag tac gcc gag cag tgg ctt gat gag gaa acc    850
Tyr Gln Ile Glu Asn Glu Tyr Ala Glu Gln Trp Leu Asp Glu Glu Thr
170             175                 180 cac gag ccc aac acg tct ggt cag gaa tac atg cag tat ttg gag gat    898
His Glu Pro Asn Thr Ser Gly Gln Glu Tyr Met Gln Tyr Leu Glu Asp
185             190                 195                 200 gtt gct cgg gaa aat ggc att gat gct cct ctg atc cat aat ctt ccc    946
Val Ala Arg Glu Asn Gly Ile Asp Ala Pro Leu Ile His Asn Leu Pro
                205                 210                 215 aac atg gtagggcaat atgctcactt actgaagata cagaatattt ggctgatgta    1002
Asn Met taacag aac ggt cac tca tgg tcc aag gac ctc tcc aac gcc acc gga    1050
       Asn Gly His Ser Trp Ser Lys Asp Leu Ser Asn Ala Thr Gly
           220                 225                 230 aat gtc gat gtc att ggc gtg gac agc tat ccc act tgc tgg acc tgc    1098
Asn Val Asp Val Ile Gly Val Asp Ser Tyr Pro Thr Cys Trp Thr Cys
        235                 240                 245 aat gtc agt gag tgt gct tca act aac gga gag tat atc cca tat        1143
Asn Val Ser Glu Cys Ala Ser Thr Asn Gly Glu Tyr Ile Pro Tyr
    250                 255                 260 gtaagtagga ctttgtcttt gtctggaggt tcatgctaat ttacctcag aaa acc ttg  1201
                                                    Lys Thr Leu
                                                        265 atc tac tac ga  gtaagtgtga tgcacagact gtacgagtta aaactgactt        1252
Ile Tyr Tyr Asp
        270 accctcaaat tag c tac ttt aag gaa tta tca cc  gtgagtttgc            1296
                 Tyr Phe Lys Glu Leu Ser Pro
                     275 tctacttgag actacccaca cattctaacg cctatcatag c act caa cca agc ttc  1352
                                             Thr Gln Pro Ser Phe
                                                     280 atg ccc gag ttc caa ggc ggc tcg tac aac cca tgg ggt gga cct caa    1400
Met Pro Glu Phe Gln Gly Gly Ser Tyr Asn Pro Trp Gly Gly Pro Gln
        285                 290                 295 ggc ggc tgc ccg gat gac ctt ggc ccg gat ttt gcg aat ctc ttc tac    1448
Gly Gly Cys Pro Asp Asp Leu Gly Pro Asp Phe Ala Asn Leu Phe Tyr
300             305                 310 cga aac ttg atc tcc cag aga gtc agc gct atc tcg ttg tac atg ttg    1496
Arg Asn Leu Ile Ser Gln Arg Val Ser Ala Ile Ser Leu Tyr Met Leu
315             320                 325                 330 tac ggc ggt acc aac tgg ggc tgg cac gcc tca acg gat gtc g          1539
Tyr Gly Gly Thr Asn Trp Gly Trp His Ala Ser Thr Asp Val
                335                 340
```

```
gtaagttatc cccaatccaa cttatgctat aggtgttgat gagcccag cg  acg agc   1595
                                                        Ala Thr Ser
                                                            345 tac gac tac tcc tcc cca att tcg gag aac cga aag ctc att gag aaa   1643
Tyr Asp Tyr Ser Ser Pro Ile Ser Glu Asn Arg Lys Leu Ile Glu Lys
        350                 355                 360 tac tat gag acg aaa gta ctc act caa ttc acg aaa a gtacgcctct      1690
Tyr Tyr Glu Thr Lys Val Leu Thr Gln Phe Thr Lys
    365                 370                 375 ttatccgata ggtggaagct cgccaagcta atctcaggat acag tc  gcc cag gat  1745
                                                    Ile Ala Gln Asp ctg tct aag gtc gac cgg tta ggc aac gtaagtagat gataacaata         1792
Leu Ser Lys Val Asp Arg Leu Gly Asn
380             385 tcgtgtaccg agaaacatta accaagttaa tag agc acg aaa tac tcg agc aat  1846
                                    Ser Thr Lys Tyr Ser Ser Asn
                                            390             395 cca gca gtg tcg gtt gct gag ctg cgg aac cct gac act ggc gcg gct   1894
Pro Ala Val Ser Val Ala Glu Leu Arg Asn Pro Asp Thr Gly Ala Ala
                    400                 405                 410 ttc tac gta act cag cac gag tac act cca tct gga acg gtt gaa aag   1942
Phe Tyr Val Thr Gln His Glu Tyr Thr Pro Ser Gly Thr Val Glu Lys
                415                 420                 425 ttc acg gtc aag gtt aac act tcc gag ggt gct c gtatgttatc          1986
Phe Thr Val Lys Val Asn Thr Ser Glu Gly Ala
            430                 435 tcctctagta cccatatcgc aatgatcaac tgctgacttc ttgacaag tt  act att  2042
                                                        Leu Thr Ile
                                                                440 cct cag tat ggc tcc caa atc act ctc aac ggt cac caa tcc aag atc   2090
Pro Gln Tyr Gly Ser Gln Ile Thr Leu Asn Gly His Gln Ser Lys Ile
            445                 450                 455 att gtc acg gac ttc aag ttc ggc tcg aag aca ctc ctt tac tct acg   2138
Ile Val Thr Asp Phe Lys Phe Gly Ser Lys Thr Leu Leu Tyr Ser Thr
        460                 465                 470 gcg gag gtt ctt acc tac gct gtt att gat ggc aaa gaa gtg ctg gct   2186
Ala Glu Val Leu Thr Tyr Ala Val Ile Asp Gly Lys Glu Val Leu Ala
    475                 480                 485 ctc tgg gtc cct act gga gaa tcg gga gaa ttc acc gtg aag gga gtg   2234
Leu Trp Val Pro Thr Gly Glu Ser Gly Glu Phe Thr Val Lys Gly Val
490                 495                 500                 505 aat tcg gct aag ttc gcc gac aaa ggg cgt act gcg aac atc gag att   2282
Asn Ser Ala Lys Phe Ala Asp Lys Gly Arg Thr Ala Asn Ile Glu Ile
                510                 515                 520 cac cct ggg aca aac aat gta aca gtc tct ttc atg cag aga tcg ggt   2330
His Pro Gly Thr Asn Asn Val Thr Val Ser Phe Met Gln Arg Ser Gly
            525                 530                 535 atg agc ctg gtt gag ctt ggt gat gga aca cgc att gtt ctt ctc gat   2378
Met Ser Leu Val Glu Leu Gly Asp Gly Thr Arg Ile Val Leu Leu Asp
        540                 545                 550 cgg tct gct gct cat gta ttc tgg tct act cca ctc aac aat gac cct   2426
Arg Ser Ala Ala His Val Phe Trp Ser Thr Pro Leu Asn Asn Asp Pro
    555                 560                 565 gcc gag gct ggc aac aac act g gtgagtcccc atcgatggcg gtatacaaac    2478
Ala Glu Ala Gly Asn Asn Thr
570             575 agttgatagg ctcgctgaca ctcctcag tc  ctt gtc cat ggc ccc tac tta    2529
                                  Val Leu Val His Gly Pro Tyr Leu
                                          580
```

```
gtt cgc tcg gct aaa ctg gaa ggc tgt gac ttg aaa ctc act gga gat        2577
Val Arg Ser Ala Lys Leu Glu Gly Cys Asp Leu Lys Leu Thr Gly Asp
585                 590                 595                 600 atc cag aac tct aca gag gtc agc atc ttt gca ccc aag tct gta tgc        2625
Ile Gln Asn Ser Thr Glu Val Ser Ile Phe Ala Pro Lys Ser Val Cys
            605                 610                 615 tct gtc aat tgg aat ggc aag aag aca tcc gtc aag tcg gcg aag ggt        2673
Ser Val Asn Trp Asn Gly Lys Lys Thr Ser Val Lys Ser Ala Lys Gly
        620                 625                 630 ggt gtt ata acc aca acc ctg gga ggc gat gcc aag ttc gag ctt ccc        2721
Gly Val Ile Thr Thr Thr Leu Gly Gly Asp Ala Lys Phe Glu Leu Pro
    635                 640                 645 acg atc tct ggc tgg aag tct gcg gac agt ctc cct gaa atc gca aag        2769
Thr Ile Ser Gly Trp Lys Ser Ala Asp Ser Leu Pro Glu Ile Ala Lys
650                 655                 660 gac tac tcc gct aca agc aag gct tgg gtt g gtatgttacc ctctcctcca        2820
Asp Tyr Ser Ala Thr Ser Lys Ala Trp Val
665                 670 cggccaatag tacccaccag ctaacaaaag accag tg  gct aca aag aca aac        2872
                                          Val Ala Thr Lys Thr Asn
                                                  675             680 tcg tct aac cct act ccc ccg gca ccg aac aac cca gtc ctc tac gta        2920
Ser Ser Asn Pro Thr Pro Pro Ala Pro Asn Asn Pro Val Leu Tyr Val
                685                 690                 695 gac gag aac gat atc cac gtc ggc aac cac atc tac cgc gcc aca ttc        2968
Asp Glu Asn Asp Ile His Val Gly Asn His Ile Tyr Arg Ala Thr Phe
            700                 705                 710 ccc agc acc gac gag cct cca acc gac gtc tac ctc aac atc acc gga        3016
Pro Ser Thr Asp Glu Pro Pro Thr Asp Val Tyr Leu Asn Ile Thr Gly
        715                 720                 725 ggt cgc gca ttc ggc tac tca gtc tgg ctg aac tcc gac ttc atc ggc        3064
Gly Arg Ala Phe Gly Tyr Ser Val Trp Leu Asn Ser Asp Phe Ile Gly
    730                 735                 740 tcc tgg ctc ggc act gcg aca act gag caa aac gac cag aca ttc tcc        3112
Ser Trp Leu Gly Thr Ala Thr Thr Glu Gln Asn Asp Gln Thr Phe Ser
745                 750                 755                 760 ttc tcc aac gca acc ctc agc aca gac gaa gac aac atc cta gtc gtc        3160
Phe Ser Asn Ala Thr Leu Ser Thr Asp Glu Asp Asn Ile Leu Val Val
                765                 770                 775 gtc atg gac aac tca gcc cac gac ttg cgc gac gga gca ctc aac ccc        3208
Val Met Asp Asn Ser Ala His Asp Leu Arg Asp Gly Ala Leu Asn Pro
            780                 785                 790 cga ggc atc aca aac gcc acc ctc atc ggt ccc gga agc tac tcc ttc        3256
Arg Gly Ile Thr Asn Ala Thr Leu Ile Gly Pro Gly Ser Tyr Ser Phe
        795                 800                 805 acc gag tgg aaa ctg gcc ggc aac gca ggc ttc gaa gac cac ctt gac        3304
Thr Glu Trp Lys Leu Ala Gly Asn Ala Gly Phe Glu Asp His Leu Asp
    810                 815                 820 ccg gtc cgc gcc ccg ctc aac gag ggc agt ctg tac gcc gag cgc gtc        3352
Pro Val Arg Ala Pro Leu Asn Glu Gly Ser Leu Tyr Ala Glu Arg Val
825                 830                 835                 840 ggt atc cat ctc ccg ggc tat gag ttc gac gaa gcc gag gag gtg tct        3400
Gly Ile His Leu Pro Gly Tyr Glu Phe Asp Glu Ala Glu Glu Val Ser
                845                 850                 855 tca aac agc acg agc cta acc gtt ccc ggc gct ggt att cgc gtc ttc        3448
Ser Asn Ser Thr Ser Leu Thr Val Pro Gly Ala Gly Ile Arg Val Phe
            860                 865                 870 cgc act gtt gtt ccc ctc tcc gtg ccc cag gga ctg gac gtc tct atc        3496
Arg Thr Val Val Pro Leu Ser Val Pro Gln Gly Leu Asp Val Ser Ile
```

```
                875                 880                 885
tcg ttc cgt ctg acg gcg ccc tcg aac gta acc ttt acc tct gcg gag     3544
Ser Phe Arg Leu Thr Ala Pro Ser Asn Val Thr Phe Thr Ser Ala Glu
    890                 895                 900 ggg tat act aac cag ctg cgg gct ctg ctt ttc gtc aat ggg tac cag     3592
Gly Tyr Thr Asn Gln Leu Arg Ala Leu Leu Phe Val Asn Gly Tyr Gln
905                 910                 915                 920 tat ggt cgc ttt aac ccc tat atc ggt cat cag atc gac ttc cct gtt     3640
Tyr Gly Arg Phe Asn Pro Tyr Ile Gly His Gln Ile Asp Phe Pro Val
                925                 930                 935 cct ccg ggt gtc ctt gat tac aac ggg gat aac acg att gcc gtg acg     3688
Pro Pro Gly Val Leu Asp Tyr Asn Gly Asp Asn Thr Ile Ala Val Thr
            940                 945                 950 gtg tgg agt cag agt gtg gat ggt gct gag atc aag gtc gat tgg aat     3736
Val Trp Ser Gln Ser Val Asp Gly Ala Glu Ile Lys Val Asp Trp Asn
        955                 960                 965 gtg gac tat gtc cat gag acc agc ttc gat atg aac ttt gat gga gcg     3784
Val Asp Tyr Val His Glu Thr Ser Phe Asp Met Asn Phe Asp Gly Ala
    970                 975                 980 tac ctg aga cct gga tgg atc gag gag aga cgt gaa tat gct taa         3829
Tyr Leu Arg Pro Gly Trp Ile Glu Glu Arg Arg Glu Tyr Ala
985                 990                 995

<210> SEQ ID NO 54
<211> LENGTH: 1020
<212> TYPE: PRT
<213> ORGANISM: Aspergillus oryzae

<400> SEQUENCE: 54

Met Leu Ile Ser Lys Thr Val Leu Ser Gly Leu Ala Leu Gly Ala Ser
        -20                 -15                 -10

Phe Val Gly Val Ser Ala Gln Gln Asn Ser Thr Arg Trp Pro Leu His
    -5                  -1  1               5                   10

Asp Asn Gly Leu Thr Asp Thr Val Glu Trp Asp His Tyr Ser Phe Leu
                15                  20                  25

Ile Asn Gly Gln Arg His Phe Val Phe Ser Gly Glu Phe His Tyr Trp
            30                  35                  40

Arg Ile Pro Val Pro Glu Leu Trp Arg Asp Leu Leu Glu Lys Ile Lys
        45                  50                  55

Ala Ala Gly Phe Thr Ala Phe Ser Ile Tyr Asn His Trp Gly Tyr His
    60                  65                  70

Ser Pro Lys Pro Gly Val Leu Asp Phe Glu Asn Gly Ala His Asn Phe
75                  80                  85                  90

Thr Ser Ile Met Thr Leu Ala Lys Glu Ile Gly Leu Tyr Met Ile Ile
                95                  100                 105

Arg Pro Gly Pro Tyr Val Asn Ala Glu Ala Asn Ala Gly Gly Leu Pro
            110                 115                 120

Leu Trp Thr Thr Thr Gly Ala Tyr Gly Lys Leu Arg Asp Asn Asp Pro
        125                 130                 135

Arg Tyr Leu Glu Ala Leu Thr Pro Tyr Trp Ala Asn Ile Ser Lys Ile
    140                 145                 150

Ile Ala Pro His Leu Ile Thr Asn Asp Gly Asn Val Ile Leu Tyr Gln
155                 160                 165                 170

Ile Glu Asn Glu Tyr Ala Glu Gln Trp Leu Asp Glu Glu Thr His Glu
                175                 180                 185

Pro Asn Thr Ser Gly Gln Glu Tyr Met Gln Tyr Leu Glu Asp Val Ala
            190                 195                 200
```

```
Arg Glu Asn Gly Ile Asp Ala Pro Leu Ile His Asn Leu Pro Asn Met
    205                 210                 215
Asn Gly His Ser Trp Ser Lys Asp Leu Ser Asn Ala Thr Gly Asn Val
    220                 225                 230
Asp Val Ile Gly Val Asp Ser Tyr Pro Thr Cys Trp Thr Cys Asn Val
235                 240                 245                 250
Ser Glu Cys Ala Ser Thr Asn Gly Glu Tyr Ile Pro Tyr Lys Thr Leu
                    255                 260                 265
Ile Tyr Tyr Asp Tyr Phe Lys Glu Leu Ser Pro Thr Gln Pro Ser Phe
                270                 275                 280
Met Pro Glu Phe Gln Gly Gly Ser Tyr Asn Pro Trp Gly Gly Pro Gln
    285                 290                 295
Gly Gly Cys Pro Asp Asp Leu Gly Pro Asp Phe Ala Asn Leu Phe Tyr
    300                 305                 310
Arg Asn Leu Ile Ser Gln Arg Val Ser Ala Ile Ser Leu Tyr Met Leu
315                 320                 325                 330
Tyr Gly Gly Thr Asn Trp Gly Trp His Ala Ser Thr Asp Val Ala Thr
                    335                 340                 345
Ser Tyr Asp Tyr Ser Ser Pro Ile Ser Glu Asn Arg Lys Leu Ile Glu
                350                 355                 360
Lys Tyr Tyr Glu Thr Lys Val Leu Thr Gln Phe Thr Lys Ile Ala Gln
                365                 370                 375
Asp Leu Ser Lys Val Asp Arg Leu Gly Asn Ser Thr Lys Tyr Ser Ser
                380                 385                 390
Asn Pro Ala Val Ser Val Ala Glu Leu Arg Asn Pro Asp Thr Gly Ala
395                 400                 405                 410
Ala Phe Tyr Val Thr Gln His Glu Tyr Thr Pro Ser Gly Thr Val Glu
                415                 420                 425
Lys Phe Thr Val Lys Val Asn Thr Ser Glu Gly Ala Leu Thr Ile Pro
                430                 435                 440
Gln Tyr Gly Ser Gln Ile Thr Leu Asn Gly His Gln Ser Lys Ile Ile
                445                 450                 455
Val Thr Asp Phe Lys Phe Gly Ser Lys Thr Leu Leu Tyr Ser Thr Ala
    460                 465                 470
Glu Val Leu Thr Tyr Ala Val Ile Asp Gly Lys Glu Val Leu Ala Leu
475                 480                 485                 490
Trp Val Pro Thr Gly Glu Ser Gly Glu Phe Thr Val Lys Gly Val Asn
                495                 500                 505
Ser Ala Lys Phe Ala Asp Lys Gly Arg Thr Ala Asn Ile Glu Ile His
                510                 515                 520
Pro Gly Thr Asn Asn Val Thr Val Ser Phe Met Gln Arg Ser Gly Met
                525                 530                 535
Ser Leu Val Glu Leu Gly Asp Gly Thr Arg Ile Val Leu Leu Asp Arg
    540                 545                 550
Ser Ala Ala His Val Phe Trp Ser Thr Pro Leu Asn Asn Asp Pro Ala
555                 560                 565                 570
Glu Ala Gly Asn Asn Thr Val Leu Val His Gly Pro Tyr Leu Val Arg
                575                 580                 585
Ser Ala Lys Leu Glu Gly Cys Asp Leu Lys Leu Thr Gly Asp Ile Gln
                590                 595                 600
Asn Ser Thr Glu Val Ser Ile Phe Ala Pro Lys Ser Val Cys Ser Val
                605                 610                 615
```

```
Asn Trp Asn Gly Lys Lys Thr Ser Val Lys Ser Ala Lys Gly Gly Val
    620             625                 630

Ile Thr Thr Thr Leu Gly Gly Asp Ala Lys Phe Glu Leu Pro Thr Ile
635             640                 645                 650

Ser Gly Trp Lys Ser Ala Asp Ser Leu Pro Glu Ile Ala Lys Asp Tyr
                655                 660                 665

Ser Ala Thr Ser Lys Ala Trp Val Val Ala Thr Lys Thr Asn Ser Ser
                670                 675                 680

Asn Pro Thr Pro Pro Ala Pro Asn Asn Pro Val Leu Tyr Val Asp Glu
            685                 690                 695

Asn Asp Ile His Val Gly Asn His Ile Tyr Arg Ala Thr Phe Pro Ser
    700                 705                 710

Thr Asp Glu Pro Pro Thr Asp Val Tyr Leu Asn Ile Thr Gly Gly Arg
715                 720                 725                 730

Ala Phe Gly Tyr Ser Val Trp Leu Asn Ser Asp Phe Ile Gly Ser Trp
                735                 740                 745

Leu Gly Thr Ala Thr Thr Glu Gln Asn Asp Gln Thr Phe Ser Phe Ser
                750                 755                 760

Asn Ala Thr Leu Ser Thr Asp Glu Asp Asn Ile Leu Val Val Met
                765                 770                 775

Asp Asn Ser Ala His Asp Leu Arg Asp Gly Ala Leu Asn Pro Arg Gly
    780                 785                 790

Ile Thr Asn Ala Thr Leu Ile Gly Pro Gly Ser Tyr Ser Phe Thr Glu
795                 800                 805                 810

Trp Lys Leu Ala Gly Asn Ala Gly Phe Glu Asp His Leu Asp Pro Val
                815                 820                 825

Arg Ala Pro Leu Asn Glu Gly Ser Leu Tyr Ala Glu Arg Val Gly Ile
            830                 835                 840

His Leu Pro Gly Tyr Glu Phe Asp Glu Ala Glu Val Ser Ser Asn
    845                 850                 855

Ser Thr Ser Leu Thr Val Pro Gly Ala Gly Ile Arg Val Phe Arg Thr
    860                 865                 870

Val Val Pro Leu Ser Val Pro Gln Gly Leu Asp Val Ser Ile Ser Phe
875                 880                 885                 890

Arg Leu Thr Ala Pro Ser Asn Val Thr Phe Thr Ser Ala Glu Gly Tyr
                895                 900                 905

Thr Asn Gln Leu Arg Ala Leu Leu Phe Val Asn Gly Tyr Gln Tyr Gly
            910                 915                 920

Arg Phe Asn Pro Tyr Ile Gly His Gln Ile Asp Phe Pro Val Pro Pro
            925                 930                 935

Gly Val Leu Asp Tyr Asn Gly Asp Asn Thr Ile Ala Val Thr Val Trp
940                 945                 950

Ser Gln Ser Val Asp Gly Ala Glu Ile Lys Val Asp Trp Asn Val Asp
955                 960                 965                 970

Tyr Val His Glu Thr Ser Phe Asp Met Asn Phe Asp Gly Ala Tyr Leu
                975                 980                 985

Arg Pro Gly Trp Ile Glu Glu Arg Arg Glu Tyr Ala
            990                 995
```

<210> SEQ ID NO 55
<211> LENGTH: 998
<212> TYPE: PRT
<213> ORGANISM: Aspergillus oryzae
<220> FEATURE:
<221> NAME/KEY: mat_peptide

<222> LOCATION: (1)..(998)

<400> SEQUENCE: 55

```
Gln Gln Asn Ser Thr Arg Trp Pro Leu His Asp Asn Gly Leu Thr Asp
1               5                   10                  15

Thr Val Glu Trp Asp His Tyr Ser Phe Leu Ile Asn Gly Gln Arg His
            20                  25                  30

Phe Val Phe Ser Gly Glu Phe His Tyr Trp Arg Ile Pro Val Pro Glu
        35                  40                  45

Leu Trp Arg Asp Leu Leu Glu Lys Ile Lys Ala Ala Gly Phe Thr Ala
50                  55                  60

Phe Ser Ile Tyr Asn His Trp Gly Tyr His Ser Pro Lys Pro Gly Val
65                  70                  75                  80

Leu Asp Phe Glu Asn Gly Ala His Asn Phe Thr Ser Ile Met Thr Leu
                85                  90                  95

Ala Lys Glu Ile Gly Leu Tyr Met Ile Ile Arg Pro Gly Pro Tyr Val
            100                 105                 110

Asn Ala Glu Ala Asn Ala Gly Gly Leu Pro Leu Trp Thr Thr Thr Gly
        115                 120                 125

Ala Tyr Gly Lys Leu Arg Asp Asn Asp Pro Arg Tyr Leu Glu Ala Leu
130                 135                 140

Thr Pro Tyr Trp Ala Asn Ile Ser Lys Ile Ile Ala Pro His Leu Ile
145                 150                 155                 160

Thr Asn Asp Gly Asn Val Ile Leu Tyr Gln Ile Glu Asn Glu Tyr Ala
                165                 170                 175

Glu Gln Trp Leu Asp Glu Thr His Glu Pro Asn Thr Ser Gly Gln
            180                 185                 190

Glu Tyr Met Gln Tyr Leu Glu Asp Val Ala Arg Glu Asn Gly Ile Asp
        195                 200                 205

Ala Pro Leu Ile His Asn Leu Pro Asn Met Asn Gly His Ser Trp Ser
210                 215                 220

Lys Asp Leu Ser Asn Ala Thr Gly Asn Val Asp Val Ile Gly Val Asp
225                 230                 235                 240

Ser Tyr Pro Thr Cys Trp Thr Cys Asn Val Ser Glu Cys Ala Ser Thr
                245                 250                 255

Asn Gly Glu Tyr Ile Pro Tyr Lys Thr Leu Ile Tyr Tyr Asp Tyr Phe
            260                 265                 270

Lys Glu Leu Ser Pro Thr Gln Pro Ser Phe Met Pro Glu Phe Gln Gly
        275                 280                 285

Gly Ser Tyr Asn Pro Trp Gly Gly Pro Gln Gly Gly Cys Pro Asp Asp
290                 295                 300

Leu Gly Pro Asp Phe Ala Asn Leu Phe Tyr Arg Asn Leu Ile Ser Gln
305                 310                 315                 320

Arg Val Ser Ala Ile Ser Leu Tyr Met Leu Tyr Gly Gly Thr Asn Trp
                325                 330                 335

Gly Trp His Ala Ser Thr Asp Val Ala Thr Ser Tyr Asp Tyr Ser Ser
            340                 345                 350

Pro Ile Ser Glu Asn Arg Lys Leu Ile Glu Lys Tyr Tyr Glu Thr Lys
        355                 360                 365

Val Leu Thr Gln Phe Thr Lys Ile Ala Gln Asp Leu Ser Lys Val Asp
370                 375                 380

Arg Leu Gly Asn Ser Thr Lys Tyr Ser Ser Asn Pro Ala Val Ser Val
385                 390                 395                 400
```

```
Ala Glu Leu Arg Asn Pro Asp Thr Gly Ala Ala Phe Tyr Val Thr Gln
                405                 410                 415

His Glu Tyr Thr Pro Ser Gly Thr Val Glu Lys Phe Thr Val Lys Val
            420                 425                 430

Asn Thr Ser Glu Gly Ala Leu Thr Ile Pro Gln Tyr Gly Ser Gln Ile
        435                 440                 445

Thr Leu Asn Gly His Gln Ser Lys Ile Ile Val Thr Asp Phe Lys Phe
450                 455                 460

Gly Ser Lys Thr Leu Leu Tyr Ser Thr Ala Glu Val Leu Thr Tyr Ala
465                 470                 475                 480

Val Ile Asp Gly Lys Glu Val Leu Ala Leu Trp Val Pro Thr Gly Glu
                485                 490                 495

Ser Gly Glu Phe Thr Val Lys Gly Val Asn Ser Ala Lys Phe Ala Asp
            500                 505                 510

Lys Gly Arg Thr Ala Asn Ile Glu Ile His Pro Gly Thr Asn Asn Val
        515                 520                 525

Thr Val Ser Phe Met Gln Arg Ser Gly Met Ser Leu Val Glu Leu Gly
530                 535                 540

Asp Gly Thr Arg Ile Val Leu Leu Asp Arg Ser Ala Ala His Val Phe
545                 550                 555                 560

Trp Ser Thr Pro Leu Asn Asn Asp Pro Ala Glu Ala Gly Asn Asn Thr
                565                 570                 575

Val Leu Val His Gly Pro Tyr Leu Val Arg Ser Ala Lys Leu Glu Gly
            580                 585                 590

Cys Asp Leu Lys Leu Thr Gly Asp Ile Gln Asn Ser Thr Glu Val Ser
        595                 600                 605

Ile Phe Ala Pro Lys Ser Val Cys Ser Val Asn Trp Asn Gly Lys Lys
610                 615                 620

Thr Ser Val Lys Ser Ala Lys Gly Gly Val Ile Thr Thr Leu Gly
625                 630                 635                 640

Gly Asp Ala Lys Phe Glu Leu Pro Thr Ile Ser Gly Trp Lys Ser Ala
                645                 650                 655

Asp Ser Leu Pro Glu Ile Ala Lys Asp Tyr Ser Ala Thr Ser Lys Ala
            660                 665                 670

Trp Val Val Ala Thr Lys Thr Asn Ser Ser Asn Pro Thr Pro Pro Ala
        675                 680                 685

Pro Asn Asn Pro Val Leu Tyr Val Asp Glu Asn Asp Ile His Val Gly
690                 695                 700

Asn His Ile Tyr Arg Ala Thr Phe Pro Ser Thr Asp Glu Pro Pro Thr
705                 710                 715                 720

Asp Val Tyr Leu Asn Ile Thr Gly Gly Arg Ala Phe Gly Tyr Ser Val
                725                 730                 735

Trp Leu Asn Ser Asp Phe Ile Gly Ser Trp Leu Gly Thr Ala Thr Thr
            740                 745                 750

Glu Gln Asn Asp Gln Thr Phe Ser Phe Ser Asn Ala Thr Leu Ser Thr
        755                 760                 765

Asp Glu Asp Asn Ile Leu Val Val Val Met Asp Asn Ser Ala His Asp
770                 775                 780

Leu Arg Asp Gly Ala Leu Asn Pro Arg Gly Ile Thr Asn Ala Thr Leu
785                 790                 795                 800

Ile Gly Pro Gly Ser Tyr Ser Phe Thr Glu Trp Lys Leu Ala Gly Asn
                805                 810                 815

Ala Gly Phe Glu Asp His Leu Asp Pro Val Arg Ala Pro Leu Asn Glu
```

```
                820             825             830
Gly Ser Leu Tyr Ala Glu Arg Val Gly Ile His Leu Pro Gly Tyr Glu
        835             840             845

Phe Asp Glu Ala Glu Glu Val Ser Ser Asn Ser Thr Ser Leu Thr Val
        850             855             860

Pro Gly Ala Gly Ile Arg Val Phe Arg Thr Val Pro Leu Ser Val
865             870             875             880

Pro Gln Gly Leu Asp Val Ser Ile Ser Phe Arg Leu Thr Ala Pro Ser
                885             890             895

Asn Val Thr Phe Thr Ser Ala Glu Gly Tyr Thr Asn Gln Leu Arg Ala
        900             905             910

Leu Leu Phe Val Asn Gly Tyr Gln Tyr Gly Arg Phe Asn Pro Tyr Ile
        915             920             925

Gly His Gln Ile Asp Phe Pro Val Pro Pro Gly Val Leu Asp Tyr Asn
        930             935             940

Gly Asp Asn Thr Ile Ala Val Thr Val Trp Ser Gln Ser Val Asp Gly
945             950             955             960

Ala Glu Ile Lys Val Asp Trp Asn Val Asp Tyr Val His Glu Thr Ser
        965             970             975

Phe Asp Met Asn Phe Asp Gly Ala Tyr Leu Arg Pro Gly Trp Ile Glu
        980             985             990

Glu Arg Arg Glu Tyr Ala
        995

<210> SEQ ID NO 56
<211> LENGTH: 3355
<212> TYPE: DNA
<213> ORGANISM: Aspergillus carneus
<220> FEATURE:
<221> NAME/KEY: CDS
<222> LOCATION: (1)..(801)
<220> FEATURE:
<221> NAME/KEY: sig_peptide
<222> LOCATION: (1)..(60)
<220> FEATURE:
<221> NAME/KEY: mat_peptide
<222> LOCATION: (61)..(3352)
<220> FEATURE:
<221> NAME/KEY: CDS
<222> LOCATION: (870)..(1866)
<220> FEATURE:
<221> NAME/KEY: CDS
<222> LOCATION: (1916)..(2215)
<220> FEATURE:
<221> NAME/KEY: CDS
<222> LOCATION: (2267)..(2338)
<220> FEATURE:
<221> NAME/KEY: CDS
<222> LOCATION: (2389)..(2476)
<220> FEATURE:
<221> NAME/KEY: CDS
<222> LOCATION: (2530)..(3352)

<400> SEQUENCE: 56 atg gcg cgt ctc cca cag ctc ctc ttc cta ctc ctc gcg agt gtc ggg    48
Met Ala Arg Leu Pro Gln Leu Leu Phe Leu Leu Leu Ala Ser Val Gly
-20             -15             -10             -5 ctc ctc agc gca gcc cag aac cac acc gac tcc gaa tgg cca ctc cac    96
Leu Leu Ser Ala Ala Gln Asn His Thr Asp Ser Glu Trp Pro Leu His
            -1  1               5               10 gat aac ggc cta aac acc gtc gtt caa tgg gat cac tac agc ttc cag   144
Asp Asn Gly Leu Asn Thr Val Val Gln Trp Asp His Tyr Ser Phe Gln
        15              20              25
```

| | | |
|---|---|---|
| gtc cac ggc cag cgc atc ttc gtc ttc tcc ggc gaa ttt cac tac tgg<br>Val His Gly Gln Arg Ile Phe Val Phe Ser Gly Glu Phe His Tyr Trp<br>30                       35                   40 | | 192 |
| cgc atc ccc gtc ccg gga ctc tgg cgc gac atc ctg gag aag atc aag<br>Arg Ile Pro Val Pro Gly Leu Trp Arg Asp Ile Leu Glu Lys Ile Lys<br>45                       50                   55                   60 | | 240 |
| gct gcc gga ttc act gca ttc gct ttc tac tcc agc tgg gcc tac cat<br>Ala Ala Gly Phe Thr Ala Phe Ala Phe Tyr Ser Ser Trp Ala Tyr His<br>               65                   70                   75 | | 288 |
| gca ccc aac aat cac act gtg gac ttc tcg acc ggc gcc cgc gac atc<br>Ala Pro Asn Asn His Thr Val Asp Phe Ser Thr Gly Ala Arg Asp Ile<br>                   80                   85                   90 | | 336 |
| acc ccc atc tac gag ctc gcg aaa gag ctg ggc atg tat atc atc gtc<br>Thr Pro Ile Tyr Glu Leu Ala Lys Glu Leu Gly Met Tyr Ile Ile Val<br>           95                   100                 105 | | 384 |
| cga ccg ggc ccc tac gtc aat gcg gag gcc agc gcc ggc ggc tat ccc<br>Arg Pro Gly Pro Tyr Val Asn Ala Glu Ala Ser Ala Gly Gly Tyr Pro<br>110                   115                 120 | | 432 |
| ctg tgg gtg acc acc ggt gca tac ggc agt ctg cgg aac gac gac gca<br>Leu Trp Val Thr Thr Gly Ala Tyr Gly Ser Leu Arg Asn Asp Asp Ala<br>125                   130                 135                 140 | | 480 |
| cgg tac acc gag gcc tgg aag ccg tac ttt gcc aaa atg tcg gaa atc<br>Arg Tyr Thr Glu Ala Trp Lys Pro Tyr Phe Ala Lys Met Ser Glu Ile<br>                   145                 150                 155 | | 528 |
| acg agc cag tac cag gtc acc gat ggc cac aat acg ttc tgc tat cag<br>Thr Ser Gln Tyr Gln Val Thr Asp Gly His Asn Thr Phe Cys Tyr Gln<br>                   160                 165                 170 | | 576 |
| att gag aac gag tac ggc cag caa tgg att gga gat ccc gtc gat cga<br>Ile Glu Asn Glu Tyr Gly Gln Gln Trp Ile Gly Asp Pro Val Asp Arg<br>175                   180                 185 | | 624 |
| aac ccc aac cag acg gcc gtt gcg tac atg gaa ctc ctc gaa gag agt<br>Asn Pro Asn Gln Thr Ala Val Ala Tyr Met Glu Leu Leu Glu Glu Ser<br>190                   195                 200 | | 672 |
| gcc cgc gaa aat ggc atc gtc gtg cca ttg act gcg aat gac ccc aac<br>Ala Arg Glu Asn Gly Ile Val Val Pro Leu Thr Ala Asn Asp Pro Asn<br>205                   210                 215                 220 | | 720 |
| atg aac acc aag tcc tgg ggg aat gat tgg tct aat gca ggg ggc aat<br>Met Asn Thr Lys Ser Trp Gly Asn Asp Trp Ser Asn Ala Gly Gly Asn<br>                   225                 230                 235 | | 768 |
| gtc gat gtt gtc ggg ctg gat tct tac cct tct gtaagctatt ctccctccta<br>Val Asp Val Val Gly Leu Asp Ser Tyr Pro Ser<br>240                   245 | | 821 |
| tacaacaccc ctatacaaga tctcctgacc aacaaactaa tgatacag tgc tgg act<br>                                                                                        Cys Trp Thr<br>                                                                                               250 | | 878 |
| tgc gac gtc acc caa tgc acc tcc acc aac gga gaa tac gtg ccc tac<br>Cys Asp Val Thr Gln Cys Thr Ser Thr Asn Gly Glu Tyr Val Pro Tyr<br>                   255                 260                 265 | | 926 |
| aag gtg atg ggg tac tac gac tac ttc cag gag gtg cag ccc acc atg<br>Lys Val Met Gly Tyr Tyr Asp Tyr Phe Gln Glu Val Gln Pro Thr Met<br>270                   275                 280 | | 974 |
| ccg ggc ttc atg cct gag ttc cag ggt ggg agt tac aac ccc tgg gcc<br>Pro Gly Phe Met Pro Glu Phe Gln Gly Gly Ser Tyr Asn Pro Trp Ala<br>               285                 290                 295 | | 1022 |
| ggc ccg gag ggt gga tgt ccc gga gac acg gga gtc gac ttt gcg aat<br>Gly Pro Glu Gly Gly Cys Pro Gly Asp Thr Gly Val Asp Phe Ala Asn<br>300                   305                 310 | | 1070 |
| ctc ttc tac cgg tgg aac atc gcg cag cgg gtg acg gct atg agt ctg<br>Leu Phe Tyr Arg Trp Asn Ile Ala Gln Arg Val Thr Ala Met Ser Leu<br>315                   320                 325                 330 | | 1118 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tac | atg | ctg | tac | ggg | ggc | acg | aac | tgg | ggc | gcc | atc | gcc | gcg | ccg | gtc | 1166 |
| Tyr | Met | Leu | Tyr | Gly | Gly | Thr | Asn | Trp | Gly | Ala | Ile | Ala | Ala | Pro | Val |      |
|     |     |     |     | 335 |     |     |     | 340 |     |     |     | 345 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acg | gct | acc | agc | tac | gac | tac | tcc | tcg | ccc | atc | tcg | gaa | gac | cgc | tcc | 1214 |
| Thr | Ala | Thr | Ser | Tyr | Asp | Tyr | Ser | Ser | Pro | Ile | Ser | Glu | Asp | Arg | Ser |      |
|     |     |     | 350 |     |     |     | 355 |     |     |     | 360 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | ggc | agc | aaa | tac | tac | gag | acc | aag | ctc | ctg | gcg | ctc | ttc | acc | cgc | 1262 |
| Ile | Gly | Ser | Lys | Tyr | Tyr | Glu | Thr | Lys | Leu | Leu | Ala | Leu | Phe | Thr | Arg |      |
|     |     | 365 |     |     |     | 370 |     |     |     | 375 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| agt | gcc | acg | gac | ctg | acc | atg | acc | gac | cgc | atc | gga | aac | ggc | acg | cag | 1310 |
| Ser | Ala | Thr | Asp | Leu | Thr | Met | Thr | Asp | Arg | Ile | Gly | Asn | Gly | Thr | Gln |      |
|     | 380 |     |     |     | 385 |     |     |     | 390 |     |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tac | acg | aac | aac | ccg | gct | gtc | gcc | gcc | tac | gaa | ctg | cgt | aac | ccc | gtc | 1358 |
| Tyr | Thr | Asn | Asn | Pro | Ala | Val | Ala | Ala | Tyr | Glu | Leu | Arg | Asn | Pro | Val |      |
| 395 |     |     |     | 400 |     |     |     | 405 |     |     |     | 410 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acc | aac | ggg | gcg | ttt | tac | gtg | acc | atc | cat | gca | gac | agc | acc | gtc | ggc | 1406 |
| Thr | Asn | Gly | Ala | Phe | Tyr | Val | Thr | Ile | His | Ala | Asp | Ser | Thr | Val | Gly |      |
|     |     |     | 415 |     |     |     | 420 |     |     |     | 425 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcg | gat | gag | tcg | ttc | cgg | ttg | aac | gtc | aac | acc | tcc | gca | ggt | gcg | ttc | 1454 |
| Ser | Asp | Glu | Ser | Phe | Arg | Leu | Asn | Val | Asn | Thr | Ser | Ala | Gly | Ala | Phe |      |
|     |     | 430 |     |     |     | 435 |     |     |     | 440 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acg | gtc | ccc | agc | aag | ggc | gca | atc | cgt | ctc | aac | gga | cac | caa | tcg | aag | 1502 |
| Thr | Val | Pro | Ser | Lys | Gly | Ala | Ile | Arg | Leu | Asn | Gly | His | Gln | Ser | Lys |      |
|     |     | 445 |     |     |     | 450 |     |     |     | 455 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| att | gtc | gtc | acg | gac | ttc | cgc | ttc | ggg | ccc | tct | cac | tcg | ttg | ctg | tat | 1550 |
| Ile | Val | Val | Thr | Asp | Phe | Arg | Phe | Gly | Pro | Ser | His | Ser | Leu | Leu | Tyr |      |
|     |     |     | 460 |     |     |     | 465 |     |     |     | 470 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcc | acc | gcg | gag | gtc | ctc | acc | cat | gcg | gtg | ttc | gac | aag | cag | gcc | act | 1598 |
| Ser | Thr | Ala | Glu | Val | Leu | Thr | His | Ala | Val | Phe | Asp | Lys | Gln | Ala | Thr |      |
| 475 |     |     |     | 480 |     |     |     | 485 |     |     |     | 490 |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| atc | gtc | ctt | tgg | gtt | ccc | acc | ggg | gag | tcg | ggc | gaa | ttc | gcc | gtc | aag | 1646 |
| Ile | Val | Leu | Trp | Val | Pro | Thr | Gly | Glu | Ser | Gly | Glu | Phe | Ala | Val | Lys |      |
|     |     |     | 495 |     |     |     | 500 |     |     |     | 505 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggc | gca | aag | tcc | ggt | aag | gta | gaa | agc | tgt | cca | cgg | tgc | tcc | aac | gcg | 1694 |
| Gly | Ala | Lys | Ser | Gly | Lys | Val | Glu | Ser | Cys | Pro | Arg | Cys | Ser | Asn | Ala |      |
|     |     |     | 510 |     |     |     | 515 |     |     |     | 520 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| acc | ttc | act | cgg | aag | aaa | gat | gtg | ctc | gtt | gtc | aac | ttt | acg | cag | act | 1742 |
| Thr | Phe | Thr | Arg | Lys | Lys | Asp | Val | Leu | Val | Val | Asn | Phe | Thr | Gln | Thr |      |
|     |     | 525 |     |     |     | 530 |     |     |     | 535 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ggc | ggg | atg | agt | gtg | ctc | cag | ctg | aac | aac | ggc | gtg | cgc | gtc | gtt | ctt | 1790 |
| Gly | Gly | Met | Ser | Val | Leu | Gln | Leu | Asn | Asn | Gly | Val | Arg | Val | Val | Leu |      |
|     | 540 |     |     |     | 545 |     |     |     | 550 |     |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| ctt | gat | cgt | ccc | gct | gca | tac | aac | ttc | tgg | gct | cct | ccg | gtg | acc | gac | 1838 |
| Leu | Asp | Arg | Pro | Ala | Ala | Tyr | Asn | Phe | Trp | Ala | Pro | Pro | Val | Thr | Asp |      |
| 555 |     |     |     | 560 |     |     |     | 565 |     |     |     | 570 |     |     |     |      |

|     |     |     |     |     |     |     |     |                |      |
| --- | --- | --- | --- | --- | --- | --- | --- | -------------- | ---- |
| gat | cct | ttt | gcc | cca | gag | acc | gat | ctg g gtaagatggc ttcgcccttc | 1886 |
| Asp | Pro | Phe | Ala | Pro | Glu | Thr | Asp | Leu            |      |
|     |     |     |     | 575 |     |     |     |                |      |

|     |     |     |     |     |     |     |     |     |     |     |     |      |
| --- | --- | --- | --- | --- | --- | --- | --- | --- | --- | --- | --- | ---- |
| taaggtcaca attcgttaac agtaggcag tt | | | | | ctc | gtc | caa | ggc | cca | tac | ctc | 1938 |
|     |     |     |     |     | Val | Leu | Val | Gln | Gly | Pro | Tyr | Leu |      |
|     |     |     |     |     |     |     | 580 |     |     |     | 585 |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gtg | cgt | tcc | gcg | agt | ctg | tcc | ggg | tcg | acc | ctc | gcg | ctg | aga | ggc | gac | 1986 |
| Val | Arg | Ser | Ala | Ser | Leu | Ser | Gly | Ser | Thr | Leu | Ala | Leu | Arg | Gly | Asp |      |
|     |     |     | 590 |     |     |     | 595 |     |     |     | 600 |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tcg | atc | aaa | gag | acc | gcg | ttg | gag | atc | ttc | gca | ccc | aag | aag | gtg | aag | 2034 |
| Ser | Ile | Lys | Glu | Thr | Ala | Leu | Glu | Ile | Phe | Ala | Pro | Lys | Lys | Val | Lys |      |
|     |     | 605 |     |     |     | 610 |     |     |     | 615 |     |     |     |     |     |      |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| aca | gtc | acc | tgg | aat | ggg | aag | cga | gtc | aag | act | tcc | aag | tca | tca | tac | 2082 |
| Thr | Val | Thr | Trp | Asn | Gly | Lys | Arg | Val | Lys | Thr | Ser | Lys | Ser | Ser | Tyr |      |

```
         620                 625                 630                 635
ggg agt ctc acc gcg tcg ctc gca cct cca ccg gct gtg acg ctc ccg     2130
Gly Ser Leu Thr Ala Ser Leu Ala Pro Pro Ala Val Thr Leu Pro
                640                 645                 650 gca ttg acc tcg acc cga tgg aag tcc caa gac agt ctg ccc gaa agg     2178
Ala Leu Thr Ser Thr Arg Trp Lys Ser Gln Asp Ser Leu Pro Glu Arg
                655                 660                 665 ctt cca tcc tac gac gac tcc gga ccg gcc tgg gtt g gtacgtatct        2225
Leu Pro Ser Tyr Asp Asp Ser Gly Pro Ala Trp Val
            670                 675 cgctacattc tctctatgtc ccgtactaac aacctacgca g ac  gcc gac cac atg   2280
                                                 Asp Ala Asp His Met
                                                             680 act aca cag aac ccc agg acc ccg gag acc ctc ccc gtg ctc tac gca     2328
Thr Thr Gln Asn Pro Arg Thr Pro Glu Thr Leu Pro Val Leu Tyr Ala
685                 690                 695                 700 gat gaa tac g gtactatcac cctcactcac attccctcaa acacctcact           2378
Asp Glu Tyr aacggtacag gc  ttc cac aat ggc atc cgc ctc tgg cgc ggg tcc ttc      2426
                Gly Phe His Asn Gly Ile Arg Leu Trp Arg Gly Ser Phe
                            705                 710                 715 acc gac gct gcc tcg ggc gtc tac ctc aac gtc caa ggc ggc gcc gcc     2474
Thr Asp Ala Ala Ser Gly Val Tyr Leu Asn Val Gln Gly Gly Ala Ala
                720                 725                 730 tt  gtacgtacat tccctcctca tccctcccag caccaactaa catacattcc cag t    2530
Phe ggc tgg tcc gcc tac ctg aac ggc cac ttc ctc ggc tcc cac ctc ggc     2578
Gly Trp Ser Ala Tyr Leu Asn Gly His Phe Leu Gly Ser His Leu Gly
735                 740                 745 aca gca aca acc tcc cag gcg aac aaa acg ctc gtc ttc cca acc ggt     2626
Thr Ala Thr Thr Ser Gln Ala Asn Lys Thr Leu Val Phe Pro Thr Gly
750                 755                 760                 765 gca ctc aac caa aac gcc acc aac acc ctc ctc gtc atc cat gac gac     2674
Ala Leu Asn Gln Asn Ala Thr Asn Thr Leu Leu Val Ile His Asp Asp
                770                 775                 780 acc ggc cac gac cag acc acc ggc gcg ctg aac ccg cgc ggc atc ctc     2722
Thr Gly His Asp Gln Thr Thr Gly Ala Leu Asn Pro Arg Gly Ile Leu
                785                 790                 795 gcc gcc cgg ctg ctc ccc gcc tcc aac gcc gcg gcc gac tcg acc gcc     2770
Ala Ala Arg Leu Leu Pro Ala Ser Asn Ala Ala Ala Asp Ser Thr Ala
            800                 805                 810 ccg acc ttc aca cgg tgg cgc gtc gcc ggc aca gcg ggc ggg gaa tcc     2818
Pro Thr Phe Thr Arg Trp Arg Val Ala Gly Thr Ala Gly Gly Glu Ser
815                 820                 825 gac ctc gac ccc gta cgc ggc gtc tac aac gaa gac ggg ctc ttc gcg     2866
Asp Leu Asp Pro Val Arg Gly Val Tyr Asn Glu Asp Gly Leu Phe Ala
830                 835                 840                 845 gag cgc gtc ggc tgg cac ctc ccc ggc ttc gac gac ggc gcc tgg ccc     2914
Glu Arg Val Gly Trp His Leu Pro Gly Phe Asp Asp Gly Ala Trp Pro
                850                 855                 860 gcc gcc aac acg acc gcc gtg gcg caa gaa acc gga acc gtg tcg ctg     2962
Ala Ala Asn Thr Thr Ala Val Ala Gln Glu Thr Gly Thr Val Ser Leu
                865                 870                 875 tcc ttc acc gga gca acg gtg cgc ttc ttc cgc acc gtc atc ccg ctg     3010
Ser Phe Thr Gly Ala Thr Val Arg Phe Phe Arg Thr Val Ile Pro Leu
            880                 885                 890 cat ctg ccg cgc ggc atc gac gcg tcc atc tcg ttc gtg ctg ggc acg     3058
His Leu Pro Arg Gly Ile Asp Ala Ser Ile Ser Phe Val Leu Gly Thr
            895                 900                 905
```

```
cct gcc ggc acg tcc acc gcg tac cgc gcc cag ctg ttc gtc aac ggc    3106
Pro Ala Gly Thr Ser Thr Ala Tyr Arg Ala Gln Leu Phe Val Asn Gly
910             915                 920                 925 tac cag tac ggc cgg tac tac ccg cac atc ggg aac cag gtg gtg tac    3154
Tyr Gln Tyr Gly Arg Tyr Tyr Pro His Ile Gly Asn Gln Val Val Tyr
                930                 935                 940 ccg gtt ccg gcg gga gtg ctg gac tac gac ggt gag aac acg atc ggc    3202
Pro Val Pro Ala Gly Val Leu Asp Tyr Asp Gly Glu Asn Thr Ile Gly
            945                 950                 955 gtg gcg gtg tgg gcg cag agt gac gcc ggg gcg gcc atc aat ctg gac    3250
Val Ala Val Trp Ala Gln Ser Asp Ala Gly Ala Ala Ile Asn Leu Asp
        960                 965                 970 tgg cgg gtg aac tac gtt gcc gac agc tcg ttg gac gcg gtg cgg ctt    3298
Trp Arg Val Asn Tyr Val Ala Asp Ser Ser Leu Asp Ala Val Arg Leu
    975                 980                 985 acc ggg gag ggg tcg tta aga ccc cag tgg agt gag gca aga gag cgg    3346
Thr Gly Glu Gly Ser Leu Arg Pro Gln Trp Ser Glu Ala Arg Glu Arg
990             995                 1000                1005 tac gct tag                                                        3355
Tyr Ala

<210> SEQ ID NO 57
<211> LENGTH: 1027
<212> TYPE: PRT
<213> ORGANISM: Aspergillus carneus

<400> SEQUENCE: 57

Met Ala Arg Leu Pro Gln Leu Leu Phe Leu Leu Leu Ala Ser Val Gly
-20                 -15                 -10                 -5

Leu Leu Ser Ala Ala Gln Asn His Thr Asp Ser Glu Trp Pro Leu His
             -1  1               5                   10

Asp Asn Gly Leu Asn Thr Val Val Gln Trp Asp His Tyr Ser Phe Gln
                15                  20                  25

Val His Gly Gln Arg Ile Phe Val Phe Ser Gly Glu Phe His Tyr Trp
            30                  35                  40

Arg Ile Pro Val Pro Gly Leu Trp Arg Asp Ile Leu Glu Lys Ile Lys
45                  50                  55                  60

Ala Ala Gly Phe Thr Ala Phe Ala Phe Tyr Ser Ser Trp Ala Tyr His
                65                  70                  75

Ala Pro Asn Asn His Thr Val Asp Phe Ser Thr Gly Ala Arg Asp Ile
            80                  85                  90

Thr Pro Ile Tyr Glu Leu Ala Lys Glu Leu Gly Met Tyr Ile Ile Val
        95                  100                 105

Arg Pro Gly Pro Tyr Val Asn Ala Glu Ala Ser Ala Gly Gly Tyr Pro
    110                 115                 120

Leu Trp Val Thr Thr Gly Ala Tyr Gly Ser Leu Arg Asn Asp Asp Ala
125                 130                 135                 140

Arg Tyr Thr Glu Ala Trp Lys Pro Tyr Phe Ala Lys Met Ser Glu Ile
                145                 150                 155

Thr Ser Gln Tyr Gln Val Thr Asp Gly His Asn Thr Phe Cys Tyr Gln
            160                 165                 170

Ile Glu Asn Glu Tyr Gly Gln Gln Trp Ile Gly Asp Pro Val Asp Arg
        175                 180                 185

Asn Pro Asn Gln Thr Ala Val Ala Tyr Met Glu Leu Leu Glu Glu Ser
    190                 195                 200

Ala Arg Glu Asn Gly Ile Val Val Pro Leu Thr Ala Asn Asp Pro Asn
```

```
                    205                 210                 215                 220
Met Asn Thr Lys Ser Trp Gly Asn Asp Trp Ser Asn Ala Gly Gly Asn
                225                 230                 235

Val Asp Val Val Gly Leu Asp Ser Tyr Pro Ser Cys Trp Thr Cys Asp
                240                 245                 250

Val Thr Gln Cys Thr Ser Thr Asn Gly Glu Tyr Val Pro Tyr Lys Val
                255                 260                 265

Met Gly Tyr Tyr Asp Tyr Phe Gln Glu Val Gln Pro Thr Met Pro Gly
                270                 275                 280

Phe Met Pro Glu Phe Gln Gly Gly Ser Tyr Asn Pro Trp Ala Gly Pro
285                 290                 295                 300

Glu Gly Gly Cys Pro Gly Asp Thr Gly Val Asp Phe Ala Asn Leu Phe
                305                 310                 315

Tyr Arg Trp Asn Ile Ala Gln Arg Val Thr Ala Met Ser Leu Tyr Met
                320                 325                 330

Leu Tyr Gly Gly Thr Asn Trp Gly Ala Ile Ala Ala Pro Val Thr Ala
                335                 340                 345

Thr Ser Tyr Asp Tyr Ser Ser Pro Ile Ser Glu Asp Arg Ser Ile Gly
                350                 355                 360

Ser Lys Tyr Tyr Glu Thr Lys Leu Leu Ala Leu Phe Thr Arg Ser Ala
365                 370                 375                 380

Thr Asp Leu Thr Met Thr Asp Arg Ile Gly Asn Gly Thr Gln Tyr Thr
                385                 390                 395

Asn Asn Pro Ala Val Ala Ala Tyr Glu Leu Arg Asn Pro Val Thr Asn
                400                 405                 410

Gly Ala Phe Tyr Val Thr Ile His Ala Asp Ser Thr Val Gly Ser Asp
                415                 420                 425

Glu Ser Phe Arg Leu Asn Val Asn Thr Ser Ala Gly Ala Phe Thr Val
                430                 435                 440

Pro Ser Lys Gly Ala Ile Arg Leu Asn Gly His Gln Ser Lys Ile Val
445                 450                 455                 460

Val Thr Asp Phe Arg Phe Gly Pro Ser His Ser Leu Leu Tyr Ser Thr
                465                 470                 475

Ala Glu Val Leu Thr His Ala Val Phe Asp Lys Gln Ala Thr Ile Val
                480                 485                 490

Leu Trp Val Pro Thr Gly Glu Ser Gly Glu Phe Ala Val Lys Gly Ala
                495                 500                 505

Lys Ser Gly Lys Val Glu Ser Cys Pro Arg Cys Ser Asn Ala Thr Phe
510                 515                 520

Thr Arg Lys Lys Asp Val Leu Val Asn Phe Thr Gln Thr Gly Gly Gly
525                 530                 535                 540

Met Ser Val Leu Gln Leu Asn Asn Gly Val Arg Val Val Leu Leu Asp
                545                 550                 555

Arg Pro Ala Ala Tyr Asn Phe Trp Ala Pro Val Thr Asp Asp Pro
                560                 565                 570

Phe Ala Pro Glu Thr Asp Leu Val Leu Val Gln Gly Pro Tyr Leu Val
                575                 580                 585

Arg Ser Ala Ser Leu Ser Gly Ser Thr Leu Ala Leu Arg Gly Asp Ser
                590                 595                 600

Ile Lys Glu Thr Ala Leu Glu Ile Phe Ala Pro Lys Lys Val Lys Thr
605                 610                 615                 620

Val Thr Trp Asn Gly Lys Arg Val Lys Thr Ser Lys Ser Ser Tyr Gly
                625                 630                 635
```

Ser Leu Thr Ala Ser Leu Ala Pro Pro Ala Val Thr Leu Pro Ala
            640                 645                 650

Leu Thr Ser Thr Arg Trp Lys Ser Gln Asp Ser Leu Pro Glu Arg Leu
            655                 660                 665

Pro Ser Tyr Asp Asp Ser Gly Pro Ala Trp Val Asp Ala Asp His Met
670                 675                 680

Thr Thr Gln Asn Pro Arg Thr Pro Glu Thr Leu Pro Val Leu Tyr Ala
685                 690                 695                 700

Asp Glu Tyr Gly Phe His Asn Gly Ile Arg Leu Trp Arg Gly Ser Phe
                705                 710                 715

Thr Asp Ala Ala Ser Gly Val Tyr Leu Asn Val Gln Gly Gly Ala Ala
            720                 725                 730

Phe Gly Trp Ser Ala Tyr Leu Asn Gly His Phe Leu Gly Ser His Leu
            735                 740                 745

Gly Thr Ala Thr Thr Ser Gln Ala Asn Lys Thr Leu Val Phe Pro Thr
750                 755                 760

Gly Ala Leu Asn Gln Asn Ala Thr Asn Thr Leu Leu Val Ile His Asp
765                 770                 775                 780

Asp Thr Gly His Asp Gln Thr Thr Gly Ala Leu Asn Pro Arg Gly Ile
                785                 790                 795

Leu Ala Ala Arg Leu Leu Pro Ala Ser Asn Ala Ala Asp Ser Thr
            800                 805                 810

Ala Pro Thr Phe Thr Arg Trp Arg Val Ala Gly Thr Ala Gly Gly Glu
            815                 820                 825

Ser Asp Leu Asp Pro Val Arg Gly Val Tyr Asn Glu Asp Gly Leu Phe
            830                 835                 840

Ala Glu Arg Val Gly Trp His Leu Pro Gly Phe Asp Asp Gly Ala Trp
845                 850                 855                 860

Pro Ala Ala Asn Thr Thr Ala Val Ala Gln Glu Thr Gly Thr Val Ser
                865                 870                 875

Leu Ser Phe Thr Gly Ala Thr Val Arg Phe Phe Arg Thr Val Ile Pro
            880                 885                 890

Leu His Leu Pro Arg Gly Ile Asp Ala Ser Ile Ser Phe Val Leu Gly
            895                 900                 905

Thr Pro Ala Gly Thr Ser Thr Ala Tyr Arg Ala Gln Leu Phe Val Asn
            910                 915                 920

Gly Tyr Gln Tyr Gly Arg Tyr Tyr Pro His Ile Gly Asn Gln Val Val
925                 930                 935                 940

Tyr Pro Val Pro Ala Gly Val Leu Asp Tyr Asp Gly Glu Asn Thr Ile
                945                 950                 955

Gly Val Ala Val Trp Ala Gln Ser Asp Ala Gly Ala Ile Asn Leu
            960                 965                 970

Asp Trp Arg Val Asn Tyr Val Ala Asp Ser Ser Leu Asp Ala Val Arg
            975                 980                 985

Leu Thr Gly Glu Gly Ser Leu Arg Pro Gln Trp Ser Glu Ala Arg Glu
            990                 995                 1000

Arg Tyr Ala
1005

<210> SEQ ID NO 58
<211> LENGTH: 1007
<212> TYPE: PRT
<213> ORGANISM: Aspergillus carneus
<220> FEATURE:

```
<221> NAME/KEY: mat_peptide
<222> LOCATION: (1)..(1007)

<400> SEQUENCE: 58

Ala Gln Asn His Thr Asp Ser Glu Trp Pro Leu His Asp Asn Gly Leu
1               5                   10                  15

Asn Thr Val Val Gln Trp Asp His Tyr Ser Phe Gln Val His Gly Gln
            20                  25                  30

Arg Ile Phe Val Phe Ser Gly Glu Phe His Tyr Trp Arg Ile Pro Val
        35                  40                  45

Pro Gly Leu Trp Arg Asp Ile Leu Glu Lys Ile Lys Ala Ala Gly Phe
    50                  55                  60

Thr Ala Phe Ala Phe Tyr Ser Ser Trp Ala Tyr His Ala Pro Asn Asn
65                  70                  75                  80

His Thr Val Asp Phe Ser Thr Gly Ala Arg Asp Ile Thr Pro Ile Tyr
                85                  90                  95

Glu Leu Ala Lys Glu Leu Gly Met Tyr Ile Ile Val Arg Pro Gly Pro
            100                 105                 110

Tyr Val Asn Ala Glu Ala Ser Ala Gly Gly Tyr Pro Leu Trp Val Thr
        115                 120                 125

Thr Gly Ala Tyr Gly Ser Leu Arg Asn Asp Asp Ala Arg Tyr Thr Glu
    130                 135                 140

Ala Trp Lys Pro Tyr Phe Ala Lys Met Ser Glu Ile Thr Ser Gln Tyr
145                 150                 155                 160

Gln Val Thr Asp Gly His Asn Thr Phe Cys Tyr Gln Ile Glu Asn Glu
                165                 170                 175

Tyr Gly Gln Gln Trp Ile Gly Asp Pro Val Asp Arg Asn Pro Asn Gln
            180                 185                 190

Thr Ala Val Ala Tyr Met Glu Leu Leu Glu Ser Ala Arg Glu Asn
        195                 200                 205

Gly Ile Val Val Pro Leu Thr Ala Asn Asp Pro Asn Met Asn Thr Lys
    210                 215                 220

Ser Trp Gly Asn Asp Trp Ser Asn Ala Gly Gly Asn Val Asp Val Val
225                 230                 235                 240

Gly Leu Asp Ser Tyr Pro Ser Cys Trp Thr Cys Asp Val Thr Gln Cys
                245                 250                 255

Thr Ser Thr Asn Gly Glu Tyr Val Pro Tyr Lys Val Met Gly Tyr Tyr
            260                 265                 270

Asp Tyr Phe Gln Glu Val Gln Pro Thr Met Pro Gly Phe Met Pro Glu
        275                 280                 285

Phe Gln Gly Gly Ser Tyr Asn Pro Trp Ala Gly Pro Glu Gly Gly Cys
    290                 295                 300

Pro Gly Asp Thr Gly Val Asp Phe Ala Asn Leu Phe Tyr Arg Trp Asn
305                 310                 315                 320

Ile Ala Gln Arg Val Thr Ala Met Ser Leu Tyr Met Leu Tyr Gly Gly
                325                 330                 335

Thr Asn Trp Gly Ala Ile Ala Ala Pro Val Thr Ala Thr Ser Tyr Asp
            340                 345                 350

Tyr Ser Ser Pro Ile Ser Glu Asp Arg Ser Ile Gly Ser Lys Tyr Tyr
        355                 360                 365

Glu Thr Lys Leu Leu Ala Leu Phe Thr Arg Ser Ala Thr Asp Leu Thr
    370                 375                 380

Met Thr Asp Arg Ile Gly Asn Gly Thr Gln Tyr Thr Asn Asn Pro Ala
385                 390                 395                 400
```

-continued

```
Val Ala Ala Tyr Glu Leu Arg Asn Pro Val Thr Asn Gly Ala Phe Tyr
                405                 410                 415
Val Thr Ile His Ala Asp Ser Thr Val Gly Ser Asp Glu Ser Phe Arg
            420                 425                 430
Leu Asn Val Asn Thr Ser Ala Gly Ala Phe Thr Val Pro Ser Lys Gly
        435                 440                 445
Ala Ile Arg Leu Asn Gly His Gln Ser Lys Ile Val Thr Asp Phe
450                 455                 460
Arg Phe Gly Pro Ser His Ser Leu Leu Tyr Ser Thr Ala Glu Val Leu
465                 470                 475                 480
Thr His Ala Val Phe Asp Lys Gln Ala Thr Ile Val Leu Trp Val Pro
                485                 490                 495
Thr Gly Glu Ser Gly Glu Phe Ala Val Lys Gly Ala Lys Ser Gly Lys
            500                 505                 510
Val Glu Ser Cys Pro Arg Cys Ser Asn Ala Thr Phe Thr Arg Lys Lys
        515                 520                 525
Asp Val Leu Val Val Asn Phe Thr Gln Thr Gly Gly Met Ser Val Leu
    530                 535                 540
Gln Leu Asn Asn Gly Val Arg Val Val Leu Leu Asp Arg Pro Ala Ala
545                 550                 555                 560
Tyr Asn Phe Trp Ala Pro Pro Val Thr Asp Asp Pro Phe Ala Pro Glu
                565                 570                 575
Thr Asp Leu Val Leu Val Gln Gly Pro Tyr Leu Val Arg Ser Ala Ser
            580                 585                 590
Leu Ser Gly Ser Thr Leu Ala Leu Arg Gly Asp Ser Ile Lys Glu Thr
        595                 600                 605
Ala Leu Glu Ile Phe Ala Pro Lys Lys Val Lys Thr Val Thr Trp Asn
    610                 615                 620
Gly Lys Arg Val Lys Thr Ser Lys Ser Ser Tyr Gly Ser Leu Thr Ala
625                 630                 635                 640
Ser Leu Ala Pro Pro Pro Ala Val Thr Leu Pro Ala Leu Thr Ser Thr
                645                 650                 655
Arg Trp Lys Ser Gln Asp Ser Leu Pro Glu Arg Leu Pro Ser Tyr Asp
            660                 665                 670
Asp Ser Gly Pro Ala Trp Val Asp Ala Asp His Met Thr Thr Gln Asn
        675                 680                 685
Pro Arg Thr Pro Glu Thr Leu Pro Val Leu Tyr Ala Asp Glu Tyr Gly
    690                 695                 700
Phe His Asn Gly Ile Arg Leu Trp Arg Gly Ser Phe Thr Asp Ala Ala
705                 710                 715                 720
Ser Gly Val Tyr Leu Asn Val Gln Gly Gly Ala Ala Phe Gly Trp Ser
                725                 730                 735
Ala Tyr Leu Asn Gly His Phe Leu Gly Ser His Leu Gly Thr Ala Thr
            740                 745                 750
Thr Ser Gln Ala Asn Lys Thr Leu Val Phe Pro Thr Gly Ala Leu Asn
        755                 760                 765
Gln Asn Ala Thr Asn Thr Leu Leu Val Ile His Asp Asp Thr Gly His
    770                 775                 780
Asp Gln Thr Thr Gly Ala Leu Asn Pro Arg Gly Ile Leu Ala Ala Arg
785                 790                 795                 800
Leu Leu Pro Ala Ser Asn Ala Ala Ala Asp Ser Thr Ala Pro Thr Phe
                805                 810                 815
```

Thr Arg Trp Arg Val Ala Gly Thr Ala Gly Gly Glu Ser Asp Leu Asp
        820                 825                 830

Pro Val Arg Gly Val Tyr Asn Glu Asp Gly Leu Phe Ala Glu Arg Val
            835                 840                 845

Gly Trp His Leu Pro Gly Phe Asp Asp Gly Ala Trp Pro Ala Ala Asn
    850                 855                 860

Thr Thr Ala Val Ala Gln Glu Thr Gly Thr Val Ser Leu Ser Phe Thr
865                 870                 875                 880

Gly Ala Thr Val Arg Phe Phe Arg Thr Val Ile Pro Leu His Leu Pro
                885                 890                 895

Arg Gly Ile Asp Ala Ser Ile Ser Phe Val Leu Gly Thr Pro Ala Gly
            900                 905                 910

Thr Ser Thr Ala Tyr Arg Ala Gln Leu Phe Val Asn Gly Tyr Gln Tyr
    915                 920                 925

Gly Arg Tyr Tyr Pro His Ile Gly Asn Gln Val Val Tyr Pro Val Pro
    930                 935                 940

Ala Gly Val Leu Asp Tyr Asp Gly Glu Asn Thr Ile Gly Val Ala Val
945                 950                 955                 960

Trp Ala Gln Ser Asp Ala Gly Ala Ala Ile Asn Leu Asp Trp Arg Val
                965                 970                 975

Asn Tyr Val Ala Asp Ser Ser Leu Asp Ala Val Arg Leu Thr Gly Glu
            980                 985                 990

Gly Ser Leu Arg Pro Gln Trp Ser  Glu Ala Arg Glu Arg  Tyr Ala
        995                 1000                1005

<210> SEQ ID NO 59
<211> LENGTH: 3317
<212> TYPE: DNA
<213> ORGANISM: Penicillium quercetorum
<220> FEATURE:
<221> NAME/KEY: CDS
<222> LOCATION: (1)..(810)
<220> FEATURE:
<221> NAME/KEY: sig_peptide
<222> LOCATION: (1)..(69)
<220> FEATURE:
<221> NAME/KEY: mat_peptide
<222> LOCATION: (70)..(3314)
<220> FEATURE:
<221> NAME/KEY: CDS
<222> LOCATION: (876)..(1869)
<220> FEATURE:
<221> NAME/KEY: CDS
<222> LOCATION: (1923)..(2216)
<220> FEATURE:
<221> NAME/KEY: CDS
<222> LOCATION: (2273)..(2344)
<220> FEATURE:
<221> NAME/KEY: CDS
<222> LOCATION: (2400)..(2487)
<220> FEATURE:
<221> NAME/KEY: CDS
<222> LOCATION: (2540)..(3314)

<400> SEQUENCE: 59 atg acg cgg gca acg cgt cta ttc tac gga ttg ggc acg atc ttc tcc    48
Met Thr Arg Ala Thr Arg Leu Phe Tyr Gly Leu Gly Thr Ile Phe Ser
        -20                 -15                 -10 ctg ctc ggt gct aca att gcc gcg gag aac caa aca act acc gaa tgg    96
Leu Leu Gly Ala Thr Ile Ala Ala Glu Asn Gln Thr Thr Thr Glu Trp
    -5              -1   1               5 ccc ctg cac gat gat ggt ctg aac caa gtc gtc caa tgg gac cac tac   144
Pro Leu His Asp Asp Gly Leu Asn Gln Val Val Gln Trp Asp His Tyr
10                  15                  20                  25

```
agc ttc cag atc aac agt cag cgc atc ttc atc ttc tcg ggt gaa ttc     192
Ser Phe Gln Ile Asn Ser Gln Arg Ile Phe Ile Phe Ser Gly Glu Phe
             30                  35                  40 cac tac tgg cgc atc ccc gtt cct ggt ctg tgg cgc gat atc ctc gag     240
His Tyr Trp Arg Ile Pro Val Pro Gly Leu Trp Arg Asp Ile Leu Glu
             45                  50                  55 aag atc aag gcg gtg ggt ttc acg gcg ttt gcc ttt tac tcg agc tgg     288
Lys Ile Lys Ala Val Gly Phe Thr Ala Phe Ala Phe Tyr Ser Ser Trp
             60                  65                  70 gcc tac cat gcg ccc aac aac cag acg ctg gac ttt acc acc ggc gcg     336
Ala Tyr His Ala Pro Asn Asn Gln Thr Leu Asp Phe Thr Thr Gly Ala
         75                  80                  85 cat gac ttt act ccc ctg ttt gag ttg gcg aag gag ctt gga ctg tac     384
His Asp Phe Thr Pro Leu Phe Glu Leu Ala Lys Glu Leu Gly Leu Tyr
90                  95                 100                 105 att att gtt cgc cct gga ccg tat gtc aat gcc gaa gcc agt gcg ggt     432
Ile Ile Val Arg Pro Gly Pro Tyr Val Asn Ala Glu Ala Ser Ala Gly
                    110                 115                 120 ggc ttc ccg ctg tgg ctg act acg ggt gat tat ggt acg ctt cgc aat     480
Gly Phe Pro Leu Trp Leu Thr Thr Gly Asp Tyr Gly Thr Leu Arg Asn
            125                 130                 135 aat gat acg cgc tat acg aaa gcc tgg acg ccg tac ttc acc aag atg     528
Asn Asp Thr Arg Tyr Thr Lys Ala Trp Thr Pro Tyr Phe Thr Lys Met
            140                 145                 150 tcc cag atc acc agc aag tac cag gtc act gat ggg cag aac gcg att     576
Ser Gln Ile Thr Ser Lys Tyr Gln Val Thr Asp Gly Gln Asn Ala Ile
        155                 160                 165 gtc tat cag atc gag aac gag tac ggg gag caa tgg gtt ggc tcg gcg     624
Val Tyr Gln Ile Glu Asn Glu Tyr Gly Glu Gln Trp Val Gly Ser Ala
170                 175                 180                 185 tcg aag cgt gtg ccc aat gaa aag gct atc aac tat atg gaa ctt ctc     672
Ser Lys Arg Val Pro Asn Glu Lys Ala Ile Asn Tyr Met Glu Leu Leu
                190                 195                 200 gag gcc aat gcc cgt gcc aat ggt att act gtg cca ttg act gca aac     720
Glu Ala Asn Ala Arg Ala Asn Gly Ile Thr Val Pro Leu Thr Ala Asn
            205                 210                 215 gat ccg aac atg aac tcg cac tcg tgg gga agt gat tgg tct aag gag     768
Asp Pro Asn Met Asn Ser His Ser Trp Gly Ser Asp Trp Ser Lys Glu
            220                 225                 230 ggt ggt aat gtg gat gtt gcg gga gta gac tcg tac cct tcg                810
Gly Gly Asn Val Asp Val Ala Gly Val Asp Ser Tyr Pro Ser
        235                 240                 245 gtaagttcgc tcatgtttgc tttaaatcat gactctggaa gactgatgag cctgaatgaa     870 aatag tgc tgg acc tgc gac ctc agc caa tgt acc tcc acc aat ggc gaa     920
      Cys Trp Thr Cys Asp Leu Ser Gln Cys Thr Ser Thr Asn Gly Glu
              250                 255                 260 tac atc ccg ttc cag gtc atg gac tac tac gat tac ttc caa gag tcg     968
Tyr Ile Pro Phe Gln Val Met Asp Tyr Tyr Asp Tyr Phe Gln Glu Ser
            265                 270                 275 cag cca acc atg ccc gaa ttc atg ccc gag ttc cag ggt ggt tca tac    1016
Gln Pro Thr Met Pro Glu Phe Met Pro Glu Phe Gln Gly Gly Ser Tyr
        280                 285                 290 aac ccc tgg ggt ggt cct gaa ggc ggt tgt gcc gag aac tcg aac cag    1064
Asn Pro Trp Gly Gly Pro Glu Gly Gly Cys Ala Glu Asn Ser Asn Gln
295                 300                 305                 310 gac ttt gcg aat ctg ttc tac cgg tgg aac att ggc caa cgt gtc aca    1112
Asp Phe Ala Asn Leu Phe Tyr Arg Trp Asn Ile Gly Gln Arg Val Thr
                315                 320                 325
```

```
gcg atg agc tta tac atg ctg ttc gga ggc acg aac tgg ggt gcg att    1160
Ala Met Ser Leu Tyr Met Leu Phe Gly Gly Thr Asn Trp Gly Ala Ile
            330                 335                 340 gcg gcg ccc gtc act ggc agc agc tac gat tac tcg gct cct atc tca    1208
Ala Ala Pro Val Thr Gly Ser Ser Tyr Asp Tyr Ser Ala Pro Ile Ser
        345                 350                 355 gag gat cga tct atc ggg gac aag tac tac gag acc aag ctg cta gct    1256
Glu Asp Arg Ser Ile Gly Asp Lys Tyr Tyr Glu Thr Lys Leu Leu Ala
    360                 365                 370 ttg ttc acg cgc tgt gcg aag gac ttg acg atg acg aac ttg att ggt    1304
Leu Phe Thr Arg Cys Ala Lys Asp Leu Thr Met Thr Asn Leu Ile Gly
375                 380                 385                 390 aat ggg act cag tat act gat aat ggc aat gtc cgt gcc tat gaa ctg    1352
Asn Gly Thr Gln Tyr Thr Asp Asn Gly Asn Val Arg Ala Tyr Glu Leu
            395                 400                 405 cgg aac cca gac acg aac gcc ggt ttc tat gcg act ttc cac act aac    1400
Arg Asn Pro Asp Thr Asn Ala Gly Phe Tyr Ala Thr Phe His Thr Asn
        410                 415                 420 acg tcc gtc tct acc aat gaa gcc ttc cat ctc aag gtg aac acc tct    1448
Thr Ser Val Ser Thr Asn Glu Ala Phe His Leu Lys Val Asn Thr Ser
    425                 430                 435 gct ggt gcc ttg act gtt ccc aca cat ggc ggt gtg gtt cga ttg aac    1496
Ala Gly Ala Leu Thr Val Pro Thr His Gly Gly Val Val Arg Leu Asn
440                 445                 450 gga cac caa tcc aag att ctg gtg acg gat ttc acc ttt gga aag gag    1544
Gly His Gln Ser Lys Ile Leu Val Thr Asp Phe Thr Phe Gly Lys Glu
455                 460                 465                 470 acg ttg ctg tat tcc acc gcc gag gtt ttg aca tat gcc gtg ttt gat    1592
Thr Leu Leu Tyr Ser Thr Ala Glu Val Leu Thr Tyr Ala Val Phe Asp
            475                 480                 485 aag act ccc acg ctg gtt ctg tgg atg ccg acg ggt gaa acg ggc gag    1640
Lys Thr Pro Thr Leu Val Leu Trp Met Pro Thr Gly Glu Thr Gly Glu
        490                 495                 500 ttc aat atc aag ggc gca aag aag gga tcg gtc cag aag tgt cag gga    1688
Phe Asn Ile Lys Gly Ala Lys Lys Gly Ser Val Gln Lys Cys Gln Gly
    505                 510                 515 tgc tct agt gtg aag ttc ttc aag gag cac ggc ggt ctg act gcc gcc    1736
Cys Ser Ser Val Lys Phe Phe Lys Glu His Gly Gly Leu Thr Ala Ala
520                 525                 530 att acc cag tct tct ggc atg agt gtg ctg gcg att gac gac atc caa    1784
Ile Thr Gln Ser Ser Gly Met Ser Val Leu Ala Ile Asp Asp Ile Gln
535                 540                 545                 550 gtg att gtc ctt gac aga aca tct gcg tat aaa ttc tgg gct ccg gcg    1832
Val Ile Val Leu Asp Arg Thr Ser Ala Tyr Lys Phe Trp Ala Pro Ala
            555                 560                 565 ctt acg aat gac ccg ctt gtg ccc gag acg gag agt g gtaagttaca       1879
Leu Thr Asn Asp Pro Leu Val Pro Glu Thr Glu Ser
        570                 575 ctacttgtag cgactttca taccaaatct aaccatctgg cag tg  ctt gtt caa     1933
                                                  Val Leu Val Gln
                                                          580 gga cct tat ctc gtt cgc ggc gct tct ctc tcg ggc tcg aag ctt gct    1981
Gly Pro Tyr Leu Val Arg Gly Ala Ser Leu Ser Gly Ser Lys Leu Ala
        585                 590                 595 gtt aca ggt gat att atc aac gct acg aca ctg gag gtc ttt gcc ccg    2029
Val Thr Gly Asp Ile Ile Asn Ala Thr Thr Leu Glu Val Phe Ala Pro
    600                 605                 610 aag gct gtt aag tct att act tgg aat gga aag acc ctt aaa act caa    2077
Lys Ala Val Lys Ser Ile Thr Trp Asn Gly Lys Thr Leu Lys Thr Gln
615                 620                 625                 630
```

```
cgt acc gag tat ggt agt ctg aag ggg tcc att gcg gca ccc aag gct      2125
Arg Thr Glu Tyr Gly Ser Leu Lys Gly Ser Ile Ala Ala Pro Lys Ala
            635                 640                 645 gtt act cta ccc tct ttc aaa tcc tgg aag tcc aaa gac agt ctt cct      2173
Val Thr Leu Pro Ser Phe Lys Ser Trp Lys Ser Lys Asp Ser Leu Pro
        650                 655                 660 gag cgt ttg gct gac tat gat gat gcg gga gct gcg tgg gtt g            2216
Glu Arg Leu Ala Asp Tyr Asp Asp Ala Gly Ala Ala Trp Val
            665                 670                 675 gtaagaattg cctgttcttg acacacagcc tatcattcat ctaactgtcc ttctag at     2274
                                                              Asp gca aac cac cag tcc aca ttg aac cct cgt gcc cct act act ctg cca      2322
Ala Asn His Gln Ser Thr Leu Asn Pro Arg Ala Pro Thr Thr Leu Pro
            680                 685                 690 gtc atg tac gca gat gaa tac g gtaagcgctc ccttcaatgc acacgtctag       2374
Val Met Tyr Ala Asp Glu Tyr
        695                 700 ccaataatct gacagccata tccag gc  ttc cac aac ggc gtc cgc ctg tgg      2425
                                Gly Phe His Asn Gly Val Arg Leu Trp
                                                705 cgc gga tac ttc aac ggc tct gca aca ggg gcc tac atc aac gtc cag      2473
Arg Gly Tyr Phe Asn Gly Ser Ala Thr Gly Ala Tyr Ile Asn Val Gln
710                 715                 720                 725 ggt gga tat gcc tt  gtaagtccct ctactcgaac cccaacccat gcccagcact      2527
Gly Gly Tyr Ala Phe
            730 aacacaatcc ag c ggc tgg tcc gcc tgg ctc aac ggc caa ttc atc ggc      2576
                Gly Trp Ser Ala Trp Leu Asn Gly Gln Phe Ile Gly
                                735                 740 tcc tac ctc ggc tcc gcc gac ctc gag tcc ggc aac cta tcc cta tcc      2624
Ser Tyr Leu Gly Ser Ala Asp Leu Glu Ser Gly Asn Leu Ser Leu Ser
            745                 750                 755 ttc acc aac gca acc atc aac acc aac aaa ccc aac atc ctc ctc atc      2672
Phe Thr Asn Ala Thr Ile Asn Thr Asn Lys Pro Asn Ile Leu Leu Ile
        760                 765                 770 gtc cat gac gac aca ggc cac gac gag aca agc ggc gcc ctc aat ccc      2720
Val His Asp Asp Thr Gly His Asp Glu Thr Ser Gly Ala Leu Asn Pro
775                 780                 785                 790 cgc ggt atc ctc gac gcc cac ctc ctc ggc tca tca tcc ggc ttc acc      2768
Arg Gly Ile Leu Asp Ala His Leu Leu Gly Ser Ser Ser Gly Phe Thr
            795                 800                 805 cac tgg cgt ctc gcc ggt acc gcg ggc ggc gag tcc aac ctc gac ccc      2816
His Trp Arg Leu Ala Gly Thr Ala Gly Gly Glu Ser Asn Leu Asp Pro
        810                 815                 820 gtg cgc ggc gtc ttc aac gaa gat ggg ctc tac ggc gaa cgg gtt ggc      2864
Val Arg Gly Val Phe Asn Glu Asp Gly Leu Tyr Gly Glu Arg Val Gly
            825                 830                 835 tgg cat ctc ccg ggc tac gac gac tcg acc tgg tcc agc agc ggt ggt      2912
Trp His Leu Pro Gly Tyr Asp Asp Ser Thr Trp Ser Ser Ser Gly Gly
840                 845                 850 tca agt cta agc ttc act ggc gca aca gtc cgc ttc ttc cgc aca acc      2960
Ser Ser Leu Ser Phe Thr Gly Ala Thr Val Arg Phe Phe Arg Thr Thr
855                 860                 865                 870 atc ccg ctc aat ttc ccc tcc aac aca gac gta tca atc tcc ttc atc      3008
Ile Pro Leu Asn Phe Pro Ser Asn Thr Asp Val Ser Ile Ser Phe Ile
            875                 880                 885 ttg tcc aca ccg tct ggc agc acg acc gca tac cgg gcc cag atc ttt      3056
Leu Ser Thr Pro Ser Gly Ser Thr Thr Ala Tyr Arg Ala Gln Ile Phe
        890                 895                 900
```

```
gtg aac ggg tac cag tac ggc cgg tat aac ccg tac atc ggg aac cag    3104
Val Asn Gly Tyr Gln Tyr Gly Arg Tyr Asn Pro Tyr Ile Gly Asn Gln
        905                 910                 915 gtg gtg tat cct gtt ccg gcg ggg att ttg aac tac agc ggg gag aat    3152
Val Val Tyr Pro Val Pro Ala Gly Ile Leu Asn Tyr Ser Gly Glu Asn
    920                 925                 930 acg gtg gct gtt gct gtg tgg gcg cag acg gag gag ggg gcg agg atg    3200
Thr Val Ala Val Ala Val Trp Ala Gln Thr Glu Glu Gly Ala Arg Met
935                 940                 945                 950 gag gtg gat tgg cgg gtg aat tat gtg gcg gat agt tcg ttg gat gtt    3248
Glu Val Asp Trp Arg Val Asn Tyr Val Ala Asp Ser Ser Leu Asp Val
                955                 960                 965 gtt agt gtt agt aag aag gcg gag ggg ttg agg acg aag tgg act gag    3296
Val Ser Val Ser Lys Lys Ala Glu Gly Leu Arg Thr Lys Trp Thr Glu
            970                 975                 980 gtg cgg gag aag ttt gct tga                                        3317
Val Arg Glu Lys Phe Ala
            985
```

<210> SEQ ID NO 60
<211> LENGTH: 1011
<212> TYPE: PRT
<213> ORGANISM: Penicillium quercetorum

<400> SEQUENCE: 60

```
Met Thr Arg Ala Thr Arg Leu Phe Tyr Gly Leu Gly Thr Ile Phe Ser
            -20                 -15                 -10

Leu Leu Gly Ala Thr Ile Ala Ala Glu Asn Gln Thr Thr Thr Glu Trp
         -5              -1   1               5

Pro Leu His Asp Asp Gly Leu Asn Gln Val Val Gln Trp Asp His Tyr
 10                  15                  20                  25

Ser Phe Gln Ile Asn Ser Gln Arg Ile Phe Ile Ser Gly Glu Phe
                 30                  35                  40

His Tyr Trp Arg Ile Pro Val Pro Gly Leu Trp Arg Asp Ile Leu Glu
             45                  50                  55

Lys Ile Lys Ala Val Gly Phe Thr Ala Phe Ala Phe Tyr Ser Ser Trp
 60                  65                  70

Ala Tyr His Ala Pro Asn Asn Gln Thr Leu Asp Phe Thr Thr Gly Ala
 75                  80                  85

His Asp Phe Thr Pro Leu Phe Glu Leu Ala Lys Glu Leu Gly Leu Tyr
 90                  95                 100                 105

Ile Ile Val Arg Pro Gly Pro Tyr Val Asn Ala Glu Ala Ser Ala Gly
                110                 115                 120

Gly Phe Pro Leu Trp Leu Thr Thr Gly Asp Tyr Gly Thr Leu Arg Asn
             125                 130                 135

Asn Asp Thr Arg Tyr Thr Lys Ala Trp Thr Pro Tyr Phe Thr Lys Met
         140                 145                 150

Ser Gln Ile Thr Ser Lys Tyr Gln Val Thr Asp Gly Asn Ala Ile
     155                 160                 165

Val Tyr Gln Ile Glu Asn Glu Tyr Gly Glu Gln Trp Val Gly Ser Ala
 170                 175                 180                 185

Ser Lys Arg Val Pro Asn Glu Lys Ala Ile Asn Tyr Met Glu Leu Leu
                 190                 195                 200

Glu Ala Asn Ala Arg Ala Asn Gly Ile Thr Val Pro Leu Thr Ala Asn
             205                 210                 215

Asp Pro Asn Met Asn Ser His Ser Trp Gly Ser Asp Trp Ser Lys Glu
```

-continued

```
            220                 225                 230
Gly Gly Asn Val Asp Val Ala Gly Val Asp Ser Tyr Pro Ser Cys Trp
            235                 240                 245
Thr Cys Asp Leu Ser Gln Cys Thr Ser Thr Asn Gly Glu Tyr Ile Pro
250                 255                 260                 265
Phe Gln Val Met Asp Tyr Tyr Asp Tyr Phe Gln Glu Ser Gln Pro Thr
                    270                 275                 280
Met Pro Glu Phe Met Pro Glu Phe Gln Gly Gly Ser Tyr Asn Pro Trp
                285                 290                 295
Gly Gly Pro Glu Gly Gly Cys Ala Glu Asn Ser Asn Gln Asp Phe Ala
            300                 305                 310
Asn Leu Phe Tyr Arg Trp Asn Ile Gly Gln Arg Val Thr Ala Met Ser
315                 320                 325
Leu Tyr Met Leu Phe Gly Gly Thr Asn Trp Gly Ala Ile Ala Ala Pro
330                 335                 340                 345
Val Thr Gly Ser Ser Tyr Asp Tyr Ser Ala Pro Ile Ser Glu Asp Arg
                    350                 355                 360
Ser Ile Gly Asp Lys Tyr Tyr Glu Thr Lys Leu Leu Ala Leu Phe Thr
                365                 370                 375
Arg Cys Ala Lys Asp Leu Thr Met Thr Asn Leu Ile Gly Asn Gly Thr
            380                 385                 390
Gln Tyr Thr Asp Asn Gly Asn Val Arg Ala Tyr Glu Leu Arg Asn Pro
395                 400                 405
Asp Thr Asn Ala Gly Phe Tyr Ala Thr Phe His Thr Asn Thr Ser Val
410                 415                 420                 425
Ser Thr Asn Glu Ala Phe His Leu Lys Val Asn Thr Ser Ala Gly Ala
                    430                 435                 440
Leu Thr Val Pro Thr His Gly Gly Val Val Arg Leu Asn Gly His Gln
                445                 450                 455
Ser Lys Ile Leu Val Thr Asp Phe Thr Phe Gly Lys Glu Thr Leu Leu
            460                 465                 470
Tyr Ser Thr Ala Glu Val Leu Thr Tyr Ala Val Phe Asp Lys Thr Pro
475                 480                 485
Thr Leu Val Leu Trp Met Pro Thr Gly Glu Thr Gly Glu Phe Asn Ile
490                 495                 500                 505
Lys Gly Ala Lys Lys Gly Ser Val Gln Lys Cys Gln Gly Cys Ser Ser
                    510                 515                 520
Val Lys Phe Phe Lys Glu His Gly Gly Leu Thr Ala Ala Ile Thr Gln
                525                 530                 535
Ser Ser Gly Met Ser Val Leu Ala Ile Asp Asp Ile Gln Val Ile Val
            540                 545                 550
Leu Asp Arg Thr Ser Ala Tyr Lys Phe Trp Ala Pro Ala Leu Thr Asn
555                 560                 565
Asp Pro Leu Val Pro Glu Thr Glu Ser Val Leu Val Gln Gly Pro Tyr
570                 575                 580                 585
Leu Val Arg Gly Ala Ser Leu Ser Gly Ser Lys Leu Ala Val Thr Gly
                    590                 595                 600
Asp Ile Ile Asn Ala Thr Thr Leu Glu Val Phe Ala Pro Lys Ala Val
                605                 610                 615
Lys Ser Ile Thr Trp Asn Gly Lys Thr Leu Thr Gln Arg Thr Glu
            620                 625                 630
Tyr Gly Ser Leu Lys Gly Ser Ile Ala Ala Pro Lys Ala Val Thr Leu
635                 640                 645
```

```
Pro Ser Phe Lys Ser Trp Lys Ser Lys Asp Ser Leu Pro Glu Arg Leu
650                 655                 660                 665

Ala Asp Tyr Asp Asp Ala Gly Ala Ala Trp Val Asp Ala Asn His Gln
            670                 675                 680

Ser Thr Leu Asn Pro Arg Ala Pro Thr Thr Leu Pro Val Met Tyr Ala
        685                 690                 695

Asp Glu Tyr Gly Phe His Asn Gly Val Arg Leu Trp Arg Gly Tyr Phe
    700                 705                 710

Asn Gly Ser Ala Thr Gly Ala Tyr Ile Asn Val Gln Gly Gly Tyr Ala
715                 720                 725

Phe Gly Trp Ser Ala Trp Leu Asn Gly Gln Phe Ile Gly Ser Tyr Leu
730                 735                 740                 745

Gly Ser Ala Asp Leu Glu Ser Gly Asn Leu Ser Leu Ser Phe Thr Asn
            750                 755                 760

Ala Thr Ile Asn Thr Asn Lys Pro Asn Ile Leu Ile Val His Asp
        765                 770                 775

Asp Thr Gly His Asp Glu Thr Ser Gly Ala Leu Asn Pro Arg Gly Ile
    780                 785                 790

Leu Asp Ala His Leu Leu Gly Ser Ser Gly Phe Thr His Trp Arg
795                 800                 805

Leu Ala Gly Thr Ala Gly Gly Glu Ser Asn Leu Asp Pro Val Arg Gly
810                 815                 820                 825

Val Phe Asn Glu Asp Gly Leu Tyr Gly Glu Arg Val Gly Trp His Leu
            830                 835                 840

Pro Gly Tyr Asp Asp Ser Thr Trp Ser Ser Gly Gly Ser Ser Leu
        845                 850                 855

Ser Phe Thr Gly Ala Thr Val Arg Phe Phe Arg Thr Thr Ile Pro Leu
    860                 865                 870

Asn Phe Pro Ser Asn Thr Asp Val Ser Ile Ser Phe Ile Leu Ser Thr
875                 880                 885

Pro Ser Gly Ser Thr Thr Ala Tyr Arg Ala Gln Ile Phe Val Asn Gly
890                 895                 900                 905

Tyr Gln Tyr Gly Arg Tyr Asn Pro Tyr Ile Gly Asn Gln Val Val Tyr
            910                 915                 920

Pro Val Pro Ala Gly Ile Leu Asn Tyr Ser Gly Glu Asn Thr Val Ala
        925                 930                 935

Val Ala Val Trp Ala Gln Thr Glu Glu Gly Ala Arg Met Glu Val Asp
    940                 945                 950

Trp Arg Val Asn Tyr Val Ala Asp Ser Ser Leu Asp Val Val Ser Val
955                 960                 965

Ser Lys Lys Ala Glu Gly Leu Arg Thr Lys Trp Thr Glu Val Arg Glu
970                 975                 980                 985

Lys Phe Ala

<210> SEQ ID NO 61
<211> LENGTH: 988
<212> TYPE: PRT
<213> ORGANISM: Penicillium quercetorum
<220> FEATURE:
<221> NAME/KEY: mat_peptide
<222> LOCATION: (1)..(988)

<400> SEQUENCE: 61

Ala Glu Asn Gln Thr Thr Thr Glu Trp Pro Leu His Asp Asp Gly Leu
1               5                   10                  15
```

```
Asn Gln Val Val Gln Trp Asp His Tyr Ser Phe Gln Ile Asn Ser Gln
            20                  25                  30

Arg Ile Phe Ile Phe Ser Gly Glu Phe His Tyr Trp Arg Ile Pro Val
                35                  40                  45

Pro Gly Leu Trp Arg Asp Ile Leu Glu Lys Ile Lys Ala Val Gly Phe
 50                  55                  60

Thr Ala Phe Ala Phe Tyr Ser Ser Trp Ala Tyr His Ala Pro Asn Asn
 65                  70                  75                  80

Gln Thr Leu Asp Phe Thr Thr Gly Ala His Asp Phe Thr Pro Leu Phe
                 85                  90                  95

Glu Leu Ala Lys Glu Leu Gly Leu Tyr Ile Ile Val Arg Pro Gly Pro
                100                 105                 110

Tyr Val Asn Ala Glu Ala Ser Ala Gly Gly Phe Pro Leu Trp Leu Thr
            115                 120                 125

Thr Gly Asp Tyr Gly Thr Leu Arg Asn Asn Asp Thr Arg Tyr Thr Lys
130                 135                 140

Ala Trp Thr Pro Tyr Phe Thr Lys Met Ser Gln Ile Thr Ser Lys Tyr
145                 150                 155                 160

Gln Val Thr Asp Gly Gln Asn Ala Ile Val Tyr Gln Ile Glu Asn Glu
                165                 170                 175

Tyr Gly Glu Gln Trp Val Gly Ser Ala Ser Lys Arg Val Pro Asn Glu
            180                 185                 190

Lys Ala Ile Asn Tyr Met Glu Leu Leu Glu Ala Asn Ala Arg Ala Asn
            195                 200                 205

Gly Ile Thr Val Pro Leu Thr Ala Asn Asp Pro Asn Met Asn Ser His
        210                 215                 220

Ser Trp Gly Ser Asp Trp Ser Lys Glu Gly Gly Asn Val Asp Val Ala
225                 230                 235                 240

Gly Val Asp Ser Tyr Pro Ser Cys Trp Thr Cys Asp Leu Ser Gln Cys
                245                 250                 255

Thr Ser Thr Asn Gly Glu Tyr Ile Pro Phe Gln Val Met Asp Tyr Tyr
            260                 265                 270

Asp Tyr Phe Gln Glu Ser Gln Pro Thr Met Pro Glu Phe Met Pro Glu
            275                 280                 285

Phe Gln Gly Gly Ser Tyr Asn Pro Trp Gly Pro Glu Gly Gly Cys
            290                 295                 300

Ala Glu Asn Ser Asn Gln Asp Phe Ala Asn Leu Phe Tyr Arg Trp Asn
305                 310                 315                 320

Ile Gly Gln Arg Val Thr Ala Met Ser Leu Tyr Met Leu Phe Gly Gly
                325                 330                 335

Thr Asn Trp Gly Ala Ile Ala Pro Val Thr Gly Ser Ser Tyr Asp
            340                 345                 350

Tyr Ser Ala Pro Ile Ser Glu Asp Arg Ser Ile Gly Asp Lys Tyr Tyr
            355                 360                 365

Glu Thr Lys Leu Leu Ala Leu Phe Thr Arg Cys Ala Lys Asp Leu Thr
            370                 375                 380

Met Thr Asn Leu Ile Gly Asn Gly Thr Gln Tyr Thr Asp Asn Gly Asn
385                 390                 395                 400

Val Arg Ala Tyr Glu Leu Arg Asn Pro Asp Thr Asn Ala Gly Phe Tyr
                405                 410                 415

Ala Thr Phe His Thr Asn Thr Ser Val Ser Thr Asn Glu Ala Phe His
            420                 425                 430
```

-continued

Leu Lys Val Asn Thr Ser Ala Gly Ala Leu Thr Val Pro Thr His Gly
            435                 440                 445

Gly Val Val Arg Leu Asn Gly His Gln Ser Lys Ile Leu Val Thr Asp
450                 455                 460

Phe Thr Phe Gly Lys Glu Thr Leu Leu Tyr Ser Thr Ala Glu Val Leu
465                 470                 475                 480

Thr Tyr Ala Val Phe Asp Lys Thr Pro Thr Leu Val Leu Trp Met Pro
                485                 490                 495

Thr Gly Glu Thr Gly Glu Phe Asn Ile Lys Gly Ala Lys Lys Gly Ser
            500                 505                 510

Val Gln Lys Cys Gln Gly Cys Ser Ser Val Lys Phe Phe Lys Glu His
            515                 520                 525

Gly Gly Leu Thr Ala Ala Ile Thr Gln Ser Ser Gly Met Ser Val Leu
530                 535                 540

Ala Ile Asp Asp Ile Gln Val Ile Val Leu Asp Arg Thr Ser Ala Tyr
545                 550                 555                 560

Lys Phe Trp Ala Pro Ala Leu Thr Asn Asp Pro Leu Val Pro Glu Thr
                565                 570                 575

Glu Ser Val Leu Val Gln Gly Pro Tyr Leu Val Arg Gly Ala Ser Leu
            580                 585                 590

Ser Gly Ser Lys Leu Ala Val Thr Gly Asp Ile Ile Asn Ala Thr Thr
            595                 600                 605

Leu Glu Val Phe Ala Pro Lys Ala Val Lys Ser Ile Thr Trp Asn Gly
            610                 615                 620

Lys Thr Leu Lys Thr Gln Arg Thr Glu Tyr Gly Ser Leu Lys Gly Ser
625                 630                 635                 640

Ile Ala Ala Pro Lys Ala Val Thr Leu Pro Ser Phe Lys Ser Trp Lys
                645                 650                 655

Ser Lys Asp Ser Leu Pro Glu Arg Leu Ala Asp Tyr Asp Asp Ala Gly
            660                 665                 670

Ala Ala Trp Val Asp Ala Asn His Gln Ser Thr Leu Asn Pro Arg Ala
            675                 680                 685

Pro Thr Thr Leu Pro Val Met Tyr Ala Asp Glu Tyr Gly Phe His Asn
690                 695                 700

Gly Val Arg Leu Trp Arg Gly Tyr Phe Asn Gly Ser Ala Thr Gly Ala
705                 710                 715                 720

Tyr Ile Asn Val Gln Gly Gly Tyr Ala Phe Gly Trp Ser Ala Trp Leu
                725                 730                 735

Asn Gly Gln Phe Ile Gly Ser Tyr Leu Gly Ser Ala Asp Leu Glu Ser
            740                 745                 750

Gly Asn Leu Ser Leu Ser Phe Thr Asn Ala Thr Ile Asn Thr Asn Lys
            755                 760                 765

Pro Asn Ile Leu Leu Ile Val His Asp Asp Thr Gly His Asp Glu Thr
770                 775                 780

Ser Gly Ala Leu Asn Pro Arg Gly Ile Leu Asp Ala His Leu Leu Gly
785                 790                 795                 800

Ser Ser Ser Gly Phe Thr His Trp Arg Leu Ala Gly Thr Ala Gly Gly
                805                 810                 815

Glu Ser Asn Leu Asp Pro Val Arg Gly Val Phe Asn Glu Asp Gly Leu
            820                 825                 830

Tyr Gly Glu Arg Val Gly Trp His Leu Pro Gly Tyr Asp Asp Ser Thr
            835                 840                 845

Trp Ser Ser Ser Gly Gly Ser Ser Leu Ser Phe Thr Gly Ala Thr Val

```
                 850                 855                 860

Arg Phe Phe Arg Thr Thr Ile Pro Leu Asn Phe Pro Ser Asn Thr Asp
865                 870                 875                 880

Val Ser Ile Ser Phe Ile Leu Ser Thr Pro Ser Gly Ser Thr Thr Ala
                885                 890                 895

Tyr Arg Ala Gln Ile Phe Val Asn Gly Tyr Gln Tyr Gly Arg Tyr Asn
                900                 905                 910

Pro Tyr Ile Gly Asn Gln Val Val Tyr Pro Val Pro Ala Gly Ile Leu
                915                 920                 925

Asn Tyr Ser Gly Glu Asn Thr Val Ala Val Ala Val Trp Ala Gln Thr
                930                 935                 940

Glu Glu Gly Ala Arg Met Glu Val Asp Trp Arg Val Asn Tyr Val Ala
945                 950                 955                 960

Asp Ser Ser Leu Asp Val Val Ser Val Ser Lys Lys Ala Glu Gly Leu
                965                 970                 975

Arg Thr Lys Trp Thr Glu Val Arg Glu Lys Phe Ala
                980                 985

<210> SEQ ID NO 62
<211> LENGTH: 331
<212> TYPE: PRT
<213> ORGANISM: Humicola insolens
<220> FEATURE:
<221> NAME/KEY: mat_peptide
<222> LOCATION: (1)..(331)

<400> SEQUENCE: 62

Leu Gln Tyr Lys Gly Val Asp Trp Ser Ser Val Met Val Glu Glu Arg
1               5                   10                  15

Ala Gly Val Arg Tyr Lys Asn Val Asn Gly Gln Glu Lys Pro Leu Glu
                20                  25                  30

Tyr Ile Leu Ala Glu Asn Gly Val Asn Met Val Arg Gln Arg Val Trp
            35                  40                  45

Val Asn Pro Trp Asp Gly Asn Tyr Asn Leu Asp Tyr Asn Ile Gln Leu
        50                  55                  60

Ala Arg Arg Ala Lys Ala Ala Gly Leu Gly Leu Tyr Ile Asn Phe His
65                  70                  75                  80

Tyr Ser Asp Thr Trp Ala Asp Pro Ala His Gln Thr Thr Pro Ala Gly
                85                  90                  95

Trp Pro Ser Asp Ile Asn Asn Leu Ala Trp Lys Leu Tyr Asn Tyr Thr
                100                 105                 110

Leu Asp Ser Met Asn Arg Phe Ala Asp Ala Gly Ile Gln Val Asp Ile
            115                 120                 125

Val Ser Ile Gly Asn Glu Ile Thr Gln Gly Leu Leu Trp Pro Leu Gly
        130                 135                 140

Lys Thr Asn Asn Trp Tyr Asn Ile Ala Arg Leu Leu His Ser Ala Ala
145                 150                 155                 160

Trp Gly Val Lys Asp Ser Arg Leu Asn Pro Lys Pro Lys Ile Met Val
                165                 170                 175

His Leu Asp Asn Gly Trp Asn Trp Asp Thr Gln Asn Trp Trp Tyr Thr
            180                 185                 190

Asn Val Leu Ser Gln Gly Pro Phe Glu Met Ser Asp Phe Asp Met Met
        195                 200                 205

Gly Val Ser Phe Tyr Pro Phe Tyr Ser Ala Ser Ala Thr Leu Asp Ser
    210                 215                 220
```

```
Leu Arg Arg Ser Leu Asn Asn Met Val Ser Arg Trp Gly Lys Glu Val
225                 230                 235                 240

Ala Val Val Glu Thr Asn Trp Pro Thr Ser Cys Pro Tyr Pro Arg Tyr
            245                 250                 255

Gln Phe Pro Ala Asp Val Arg Asn Val Pro Phe Ser Ala Ala Gly Gln
        260                 265                 270

Thr Gln Tyr Ile Gln Ser Val Ala Asn Val Val Ser Ser Val Ser Lys
    275                 280                 285

Gly Val Gly Leu Phe Tyr Trp Glu Pro Ala Trp Ile His Asn Ala Asn
290                 295                 300

Leu Gly Ser Ser Cys Ala Asp Asn Thr Met Phe Thr Pro Ser Gly Gln
305                 310                 315                 320

Ala Leu Ser Ser Leu Ser Val Phe His Arg Ile
                325                 330

<210> SEQ ID NO 63
<211> LENGTH: 332
<212> TYPE: PRT
<213> ORGANISM: Myceliophthora thermophile
<220> FEATURE:
<221> NAME/KEY: mat_peptide
<222> LOCATION: (1)..(332)

<400> SEQUENCE: 63

Ala Leu Thr Tyr Arg Gly Val Asp Trp Ser Ser Val Val Glu Glu
1               5                   10                  15

Arg Ala Gly Val Ser Tyr Lys Asn Thr Asn Gly Asn Ala Gln Pro Leu
            20                  25                  30

Glu Asn Ile Leu Ala Ala Asn Gly Val Asn Thr Val Arg Gln Arg Val
        35                  40                  45

Trp Val Asn Pro Ala Asp Gly Asn Tyr Asn Leu Asp Tyr Asn Ile Ala
    50                  55                  60

Ile Ala Lys Arg Ala Lys Ala Ala Gly Leu Gly Val Tyr Ile Asp Phe
65                  70                  75                  80

His Tyr Ser Asp Thr Trp Ala Asp Pro Ala His Gln Thr Met Pro Ala
                85                  90                  95

Gly Trp Pro Ser Asp Ile Asp Asn Leu Ser Trp Lys Leu Tyr Asn Tyr
            100                 105                 110

Thr Leu Asp Ala Ala Asn Lys Leu Gln Asn Ala Gly Ile Gln Pro Thr
        115                 120                 125

Ile Val Ser Ile Gly Asn Glu Ile Arg Ala Gly Leu Leu Trp Pro Thr
    130                 135                 140

Gly Arg Thr Glu Asn Trp Ala Asn Ile Ala Arg Leu Leu His Ser Ala
145                 150                 155                 160

Ala Trp Gly Ile Lys Asp Ser Ser Leu Ser Pro Lys Pro Lys Ile Met
                165                 170                 175

Ile His Leu Asp Asn Gly Trp Asp Trp Gly Thr Gln Asn Trp Trp Tyr
            180                 185                 190

Thr Asn Val Leu Lys Gln Gly Thr Leu Glu Leu Ser Asp Phe Asp Met
        195                 200                 205

Met Gly Val Ser Phe Tyr Pro Phe Tyr Ser Ser Ala Thr Leu Ser
    210                 215                 220

Ala Leu Lys Ser Ser Leu Asp Asn Met Ala Lys Thr Trp Asn Lys Glu
225                 230                 235                 240

Ile Ala Val Val Glu Thr Asn Trp Pro Ile Ser Cys Pro Asn Pro Arg
                245                 250                 255
```

Tyr Ser Phe Pro Ser Asp Val Lys Asn Ile Pro Phe Ser Pro Glu Gly
             260                 265                 270

Gln Thr Thr Phe Ile Thr Asn Val Ala Asn Ile Val Ser Ser Val Ser
             275                 280                 285

Arg Gly Val Gly Leu Phe Tyr Trp Glu Pro Ala Trp Ile His Asn Ala
290                 295                 300

Asn Leu Gly Ser Ser Cys Ala Asp Asn Thr Met Phe Ser Gln Ser Gly
305                 310                 315                 320

Gln Ala Leu Ser Ser Leu Ser Val Phe Gln Arg Ile
             325                 330

<210> SEQ ID NO 64
<211> LENGTH: 324
<212> TYPE: PRT
<213> ORGANISM: Meripilus giganteus
<220> FEATURE:
<221> NAME/KEY: mat_peptide
<222> LOCATION: (1)..(324)

<400> SEQUENCE: 64

Leu Thr Tyr Lys Gly Ala Asp Ile Ser Ser Val Pro Leu Val Glu Gln
1               5                   10                  15

Ala Gly Ile Lys Tyr Thr Asp Gly Gly Lys Val Thr Pro Phe Glu Asn
             20                  25                  30

Ile Ile His Asn His Gly Ala Asn Thr Val Arg Ile Arg Ile Trp Thr
             35                  40                  45

Ala Gly Asp Tyr Asn Leu Gln Tyr Gly Leu Ala Leu Ala Lys Arg Val
50                  55                  60

Lys Ala Ala Gly Leu Thr Leu Val Val Asp Leu His Tyr Ser Asp Thr
65                  70                  75                  80

Trp Ala Asp Pro Gly Lys Gln Ala Ile Pro Ser Ala Trp Pro Lys Asp
             85                  90                  95

Leu Asp Gly Leu Asn Thr Gln Ile Trp Gln Tyr Thr Lys Asp Val Val
             100                 105                 110

Thr Ser Phe Ala Asn Gln Gly Thr Pro Ile Asp Ile Leu Gln Val Gly
             115                 120                 125

Asn Glu Ile Asn Asn Gly Leu Leu Trp Pro Val Gly Glu Ile Ser Ser
130                 135                 140

Asn Gly Ile Asn Pro Val Ser Gln Leu Leu His Ser Ala Ile Asn Gly
145                 150                 155                 160

Ala Lys Ala Ala Gly Asn Pro Lys Ile Leu Ile His Leu Ala Asn Gly
             165                 170                 175

Trp Asp Trp Ser Gly Leu Asn Ser Phe Phe Gly Lys Val Phe Ile Pro
             180                 185                 190

Gly Ala Leu Ser Ala Asp Glu Val Asp Ile Ile Gly Val Ser Phe Tyr
             195                 200                 205

Pro Phe Tyr Asp Ala Gly Ala Thr Leu Ser Ala Leu Lys Ser Ser Leu
             210                 215                 220

Ala Asn Leu Ala Asn Thr Phe Lys Lys Pro Ile Val Val Ala Glu Thr
225                 230                 235                 240

Asp Trp Pro Val Ala Cys Ser Gly Val Lys Leu Thr Glu Pro Ser Val
             245                 250                 255

Pro Val Ser Thr Ser Gly Gln Gln Thr Trp Ile Gly Asp Ile Lys Asn
             260                 265                 270

Val Leu Gln Ser Leu Pro Asn Gly Leu Gly Gln Gly Ile Phe Tyr Trp

```
                275                 280                 285
Glu Pro Gly Trp Ile Gly Asn Ala Asn Leu Gly Ser Gly Cys Ser Asp
    290                 295                 300
Asn Leu Leu Val Ser Ser Asn Gly Ala Thr Arg Asp Ser Ile Asn Ile
305                 310                 315                 320
Phe Asn Gln Met

<210> SEQ ID NO 65
<211> LENGTH: 12
<212> TYPE: PRT
<213> ORGANISM: Artificial Sequence
<220> FEATURE:
<223> OTHER INFORMATION: SEQ ID NO: 65 is the conserved motif
      GV[T/M]PD[W/M]VQ[I/V]GNE.
<220> FEATURE:
<221> NAME/KEY: misc_feature
<222> LOCATION: (3)..(3)
<223> OTHER INFORMATION: The amino acid in position 3 of the conserved
      motif is either threonine (T) or methionine (M).
<220> FEATURE:
<221> NAME/KEY: misc_feature
<222> LOCATION: (6)..(6)
<223> OTHER INFORMATION: The amino acid in position 6 of the conserved
      motif is either tryptophan (W) or methionine (M).
<220> FEATURE:
<221> NAME/KEY: misc_feature
<222> LOCATION: (9)..(9)
<223> OTHER INFORMATION: The amino acid in position 9 of the conserved
      motif is either isoleucine (I) or valine (V).

<400> SEQUENCE: 65

Gly Val Xaa Pro Asp Xaa Val Gln Xaa Gly Asn Glu
1               5                   10

<210> SEQ ID NO 66
<211> LENGTH: 13
<212> TYPE: PRT
<213> ORGANISM: Artificial Sequence
<220> FEATURE:
<223> OTHER INFORMATION: SEQ ID NO: 66 is the conserved motif
      WADP[A/G]xQxKPxAW.
<220> FEATURE:
<221> NAME/KEY: misc_feature
<222> LOCATION: (5)..(5)
<223> OTHER INFORMATION: The amino acid in position 5 of the conserved
      motif is either alanine (A) or glycine (G).
<220> FEATURE:
<221> NAME/KEY: misc_feature
<222> LOCATION: (6)..(6)
<223> OTHER INFORMATION: The amino acid in position 6 of the conserved
      motif is any amino acid.
<220> FEATURE:
<221> NAME/KEY: misc_feature
<222> LOCATION: (8)..(8)
<223> OTHER INFORMATION: The amino acid in position 8 of the conserved
      motif is any amino acid.
<220> FEATURE:
<221> NAME/KEY: misc_feature
<222> LOCATION: (11)..(11)
<223> OTHER INFORMATION: The amino acid in position 11 of the conserved
      motif is any amino acid.

<400> SEQUENCE: 66

Trp Ala Asp Pro Xaa Xaa Gln Xaa Lys Pro Xaa Ala Trp
1               5                   10

<210> SEQ ID NO 67
<211> LENGTH: 27
<212> TYPE: PRT
<213> ORGANISM: Bacillus clausii
```

-continued

<400> SEQUENCE: 67

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25

<210> SEQ ID NO 68
<211> LENGTH: 3138
<212> TYPE: DNA
<213> ORGANISM: Penicillium simplicissimum
<220> FEATURE:
<221> NAME/KEY: CDS
<222> LOCATION: (1)..(235)
<220> FEATURE:
<221> NAME/KEY: sig_peptide
<222> LOCATION: (1)..(63)
<220> FEATURE:
<221> NAME/KEY: mat_peptide
<222> LOCATION: (64)..(3135)
<220> FEATURE:
<221> NAME/KEY: CDS
<222> LOCATION: (306)..(1382)
<220> FEATURE:
<221> NAME/KEY: CDS
<222> LOCATION: (1439)..(1940)
<220> FEATURE:
<221> NAME/KEY: CDS
<222> LOCATION: (2001)..(3135)

<400> SEQUENCE: 68

```
atg cgg ttt ttc gca ttt ctc ccg ttg ctc ctt atc ggg gcg ctg tcg      48
Met Arg Phe Phe Ala Phe Leu Pro Leu Leu Leu Ile Gly Ala Leu Ser
    -20             -15                 -10 agc att gtc tct gcg acg gac aat ggc aag act acc gat gtt act tgg      96
Ser Ile Val Ser Ala Thr Asp Asn Gly Lys Thr Thr Asp Val Thr Trp
-5              -1  1               5                   10 gac aag tat agt ctc tcc gtg aag ggg gag aga gtc ttt gtc ttt tct     144
Asp Lys Tyr Ser Leu Ser Val Lys Gly Glu Arg Val Phe Val Phe Ser
            15                  20                  25 ggt gaa ttc cat tat atg cgt ctt cct gtt ccg gag atg tgg ctt gat     192
Gly Glu Phe His Tyr Met Arg Leu Pro Val Pro Glu Met Trp Leu Asp
        30                  35                  40 gtg ttc caa aag ttg cgc tcc aat ggc ttc aac gcg gta tcc a           235
Val Phe Gln Lys Leu Arg Ser Asn Gly Phe Asn Ala Val Ser
45                  50                  55 gtgagtaaac caatatatat cccatacacc acactcaatc aattaaaacc aattcaacta   295
accgttcaag tc tac ttc ttc tgg agc ttc cac tcc gct tcg gaa gac       343
               Ile Tyr Phe Phe Trp Ser Phe His Ser Ala Ser Glu Asp
                   60                  65                  70 aca ttt gac ttt gaa aac ggc gcc cac gat gtc cag cgc gtc ttc gac     391
Thr Phe Asp Phe Glu Asn Gly Ala His Asp Val Gln Arg Val Phe Asp
                75                  80                  85 tac gct aaa caa gcc ggt ctg tat gtg att gcc cgt gca gga ccc tac     439
Tyr Ala Lys Gln Ala Gly Leu Tyr Val Ile Ala Arg Ala Gly Pro Tyr
            90                  95                  100 atc aac gct gaa acc tcg gcc ggt gga ttc gcc ctg tgg gca gcg aac     487
Ile Asn Ala Glu Thr Ser Ala Gly Gly Phe Ala Leu Trp Ala Ala Asn
        105                 110                 115 gga caa atg ggc agt gaa cga acc agt gcc tcg tcc tac tac gac aaa     535
Gly Gln Met Gly Ser Glu Arg Thr Ser Ala Ser Ser Tyr Tyr Asp Lys
    120                 125                 130 tgg ctt ccc tgg atc ctg aag atc ggc aag atc atc gcg gat aac cag     583
Trp Leu Pro Trp Ile Leu Lys Ile Gly Lys Ile Ile Ala Asp Asn Gln
135                 140                 145                 150
```

```
atc acc aac ggc gga ccg gtg atc ctg aac cag cac gag aac gag ctc      631
Ile Thr Asn Gly Gly Pro Val Ile Leu Asn Gln His Glu Asn Glu Leu
                155                 160                 165 cag gag acc acc cac agc gcg acc aac act cta gtt ctg tac atg gag      679
Gln Glu Thr Thr His Ser Ala Thr Asn Thr Leu Val Leu Tyr Met Glu
            170                 175                 180 caa atc gca gcc gca ttc gag gag gcc ggt gtc atc gtg ccc agc tcg      727
Gln Ile Ala Ala Ala Phe Glu Glu Ala Gly Val Ile Val Pro Ser Ser
        185                 190                 195 cac aac gaa aaa ggt atg cgc tcg gaa agc tgg tcg aca gat tac gaa      775
His Asn Glu Lys Gly Met Arg Ser Glu Ser Trp Ser Thr Asp Tyr Glu
    200                 205                 210 gac gtc ggc ggt gca gta aac gtc tac ggc ctc gat tca tac ccc ggc      823
Asp Val Gly Gly Ala Val Asn Val Tyr Gly Leu Asp Ser Tyr Pro Gly
215                 220                 225                 230 ggt ctg tcc tgc aca aac ccc gac tcg gga ttc aac ctc gtc cgc act      871
Gly Leu Ser Cys Thr Asn Pro Asp Ser Gly Phe Asn Leu Val Arg Thr
                235                 240                 245 tac tac caa tgg ttc cag aac tac tcc tac aca cag ccc gaa ttc ctc      919
Tyr Tyr Gln Trp Phe Gln Asn Tyr Ser Tyr Thr Gln Pro Glu Phe Leu
            250                 255                 260 ccc gaa ttt gag ggc ggc tgg ttc cag ccc tgg ggt gga tat ttc tac      967
Pro Glu Phe Glu Gly Gly Trp Phe Gln Pro Trp Gly Gly Tyr Phe Tyr
        265                 270                 275 gac gag tgt gcc gca gag cac tcg ccc gaa ttc gcc gac gtc tat tac     1015
Asp Glu Cys Ala Ala Glu His Ser Pro Glu Phe Ala Asp Val Tyr Tyr
    280                 285                 290 aag aat aac att ggg tcc cgg gtc acc ctg cag agt ctg tat atg gcc     1063
Lys Asn Asn Ile Gly Ser Arg Val Thr Leu Gln Ser Leu Tyr Met Ala
295                 300                 305                 310 ttt ggc ggg acg aat tgg ggt cat agt gcc acg ccg gtc gtt tat act     1111
Phe Gly Gly Thr Asn Trp Gly His Ser Ala Thr Pro Val Val Tyr Thr
                315                 320                 325 tcg tat gac tat gcg gcg ccg cta agg gag acg aga gag atc cag gat     1159
Ser Tyr Asp Tyr Ala Ala Pro Leu Arg Glu Thr Arg Glu Ile Gln Asp
            330                 335                 340 aaa ctc aag cag act aag ttg att ggt ttg ttt act cgg gtt tca tcg     1207
Lys Leu Lys Gln Thr Lys Leu Ile Gly Leu Phe Thr Arg Val Ser Ser
        345                 350                 355 gga ttg ttg cag act gtc atg gag ggc aat gga acg gga tat act agt     1255
Gly Leu Leu Gln Thr Val Met Glu Gly Asn Gly Thr Gly Tyr Thr Ser
    360                 365                 370 gat act agt att tat acg tgg gct ttg cgg aat ccc gag acg gac gct     1303
Asp Thr Ser Ile Tyr Thr Trp Ala Leu Arg Asn Pro Glu Thr Asp Ala
375                 380                 385                 390 ggg ttc tat gtg ctt gcg cat agt acg agt tcg tct cgt gcg gtg acg     1351
Gly Phe Tyr Val Leu Ala His Ser Thr Ser Ser Ser Arg Ala Val Thr
                395                 400                 405 acg ttc tcg ctg aat gtt aat act tcg gct g gtatggttcc tcacgctgga     1402
Thr Phe Ser Leu Asn Val Asn Thr Ser Ala
            410                 415 gtgctttgag aatattttga ctaactcgct tcttag gt  gct ctg act atc cct     1455
                                            Gly Ala Leu Thr Ile Pro
                                                            420 gac att gaa ctg gat ggt cgc caa agc aaa atc atc gtc acg gat tac     1503
Asp Ile Glu Leu Asp Gly Arg Gln Ser Lys Ile Ile Val Thr Asp Tyr
            425                 430                 435 gaa atc ggc aag gcc tcg agc ctt ctc tac tca tcc gcc gag gtt ctg     1551
Glu Ile Gly Lys Ala Ser Ser Leu Leu Tyr Ser Ser Ala Glu Val Leu
```

```
        440                 445                 450
acc tac gct acc ctc gac gtg gac gtg ctg gtg ctc tac ctg aac att      1599
Thr Tyr Ala Thr Leu Asp Val Asp Val Leu Val Leu Tyr Leu Asn Ile
455                 460                 465                 470 gga caa aag ggc gtg ttc gca ttc aag aat gcc cca tcc cac ttg acg      1647
Gly Gln Lys Gly Val Phe Ala Phe Lys Asn Ala Pro Ser His Leu Thr
                475                 480                 485 ttc aag aca tac ggt aac tcg aac ttg act tcc acc aca tcg acc aat      1695
Phe Lys Thr Tyr Gly Asn Ser Asn Leu Thr Ser Thr Thr Ser Thr Asn
                490                 495                 500 gga acg cag tac tcg tac acc caa gga gat ggt gcg acc gct gtc aag      1743
Gly Thr Gln Tyr Ser Tyr Thr Gln Gly Asp Gly Ala Thr Ala Val Lys
                505                 510                 515 ttc tcc aac ggg gtt ctt cta tat ctg ctg gac aag gaa acc gct tgg      1791
Phe Ser Asn Gly Val Leu Leu Tyr Leu Leu Asp Lys Glu Thr Ala Trp
520                 525                 530 aac ttc ttt gct gtg act acc acg tcc aac ccg aat gtg acc ccc agc      1839
Asn Phe Phe Ala Val Thr Thr Thr Ser Asn Pro Asn Val Thr Pro Ser
535                 540                 545                 550 gaa cac att ctt gct ctt gga ccg tat ttg gtt cgt gag gcg agt atc      1887
Glu His Ile Leu Ala Leu Gly Pro Tyr Leu Val Arg Glu Ala Ser Ile
                555                 560                 565 agc cat gat acc gtt agc ctg att ggt gat aat gcg aat acc acc aca      1935
Ser His Asp Thr Val Ser Leu Ile Gly Asp Asn Ala Asn Thr Thr Thr
                570                 575                 580 ctg ga  gtaagttgat tcccatggaa gggtatttgg tggaactgca cttgctaacc      1990
Leu Glu tttctcatag a gtc tac cct ggt aac gcc cag gta acc aag atc aag tgg    2040
            Val Tyr Pro Gly Asn Ala Gln Val Thr Lys Ile Lys Trp
                    585                 590                 595 aat ggc aaa ccg att gcg act aag aag acc gca tac ggc agt ctc atc      2088
Asn Gly Lys Pro Ile Ala Thr Lys Lys Thr Ala Tyr Gly Ser Leu Ile
                600                 605                 610 ggc tca gcc caa ggc gca gaa acc gcc aag atc tcc ctg ccc tct ctg      2136
Gly Ser Ala Gln Gly Ala Glu Thr Ala Lys Ile Ser Leu Pro Ser Leu
                615                 620                 625 aca tcc tgg aag tct caa gat act ctt ccc gag atc aag caa gac tac      2184
Thr Ser Trp Lys Ser Gln Asp Thr Leu Pro Glu Ile Lys Gln Asp Tyr
630                 635                 640                 645 gac gac tcg cgc tgg acg gtc tgc aac aag agc acg acg gtc aac tct      2232
Asp Asp Ser Arg Trp Thr Val Cys Asn Lys Ser Thr Thr Val Asn Ser
                650                 655                 660 gtc gca cca ctg tcg ctg ccc gtc cta tac tcg ggc gac tac gga tac      2280
Val Ala Pro Leu Ser Leu Pro Val Leu Tyr Ser Gly Asp Tyr Gly Tyr
                665                 670                 675 cac gca ggc acc aag atc tac cgc ggt cgc ttc gac gga cgc aat gcc      2328
His Ala Gly Thr Lys Ile Tyr Arg Gly Arg Phe Asp Gly Arg Asn Ala
                680                 685                 690 acc ggc gcc aac gtg acg gtg caa aac ggc gtc gcc gct ggc tgg gca      2376
Thr Gly Ala Asn Val Thr Val Gln Asn Gly Val Ala Ala Gly Trp Ala
                695                 700                 705 gcc tgg ttg aac ggc gac tat gtt ggc ggt gcc cta ggc aat cca gct      2424
Ala Trp Leu Asn Gly Asp Tyr Val Gly Gly Ala Leu Gly Asn Pro Ala
710                 715                 720                 725 ctc gca gca acc tcc gac ttg tta acc ttc aac agc tcc tcc ctc cgg      2472
Leu Ala Ala Thr Ser Asp Leu Leu Thr Phe Asn Ser Ser Ser Leu Arg
                730                 735                 740 gat acc gat aac gtc ctc acg gtc gtg atg gac tat acc ggc cac gac      2520
Asp Thr Asp Asn Val Leu Thr Val Val Met Asp Tyr Thr Gly His Asp
```

```
                    745                 750                 755
gag aac aac gtc aag ccg gcc ggt acc cag aac ccc cgc ggt atc ttg      2568
Glu Asn Asn Val Lys Pro Ala Gly Thr Gln Asn Pro Arg Gly Ile Leu
            760                 765                 770 gga gcc acc ctc ttc ggc ggc aac ttc acc tcc tgg cgc atc caa          2616
Gly Ala Thr Leu Phe Gly Gly Asn Phe Thr Ser Trp Arg Ile Gln
775                 780                 785 ggc aac gca ggc ggc gaa gca aac atc gac ccc gtc cgc ggc ccc atg      2664
Gly Asn Ala Gly Gly Glu Ala Asn Ile Asp Pro Val Arg Gly Pro Met
790                 795                 800                 805 aac gaa ggt ggc ctc tac ggc gaa cga ctc ggc tgg cat ctc ccg gga      2712
Asn Glu Gly Gly Leu Tyr Gly Glu Arg Leu Gly Trp His Leu Pro Gly
                810                 815                 820 tac acc gca ccc aag agc gcg ggc agc tca tcc ccc ctg cag ggt gtc      2760
Tyr Thr Ala Pro Lys Ser Ala Gly Ser Ser Ser Pro Leu Gln Gly Val
                825                 830                 835 tcg aac gcc gca gga cgc ttc tac acg aca acc ttc aag ctc aat cta      2808
Ser Asn Ala Ala Gly Arg Phe Tyr Thr Thr Thr Phe Lys Leu Asn Leu
                840                 845                 850 gag gcc gat ctg gac gtc ccg att ggc ctg cag ctc ggg gca gcg gcc      2856
Glu Ala Asp Leu Asp Val Pro Ile Gly Leu Gln Leu Gly Ala Ala Ala
855                 860                 865 aat acc agt gcg gtg gtg cag gtg ttt atg aac ggg tac cag ttt ggc      2904
Asn Thr Ser Ala Val Val Gln Val Phe Met Asn Gly Tyr Gln Phe Gly
870                 875                 880                 885 cat tac ctg ccg cat att gga ccg cag acg ctg ttc ccg ttc cca ccg      2952
His Tyr Leu Pro His Ile Gly Pro Gln Thr Leu Phe Pro Phe Pro Pro
                890                 895                 900 ggt att atc aat aat cgg ggg gag aat acg ttg gcg att agt ctg tgg      3000
Gly Ile Ile Asn Asn Arg Gly Glu Asn Thr Leu Ala Ile Ser Leu Trp
                905                 910                 915 gcg ttg acg gat gag ggg gcg gcg ttg gat cag gtg gag ttg gtc gcg      3048
Ala Leu Thr Asp Glu Gly Ala Ala Leu Asp Gln Val Glu Leu Val Ala
                920                 925                 930 tac ggg gcg tat cgg acc ggg ttc gat ttt aat cag gat tgg acg tac      3096
Tyr Gly Ala Tyr Arg Thr Gly Phe Asp Phe Asn Gln Asp Trp Thr Tyr
935                 940                 945 ctg cag ccg aag tgg aag aat aat cgg ggg tcg tat gtg tag              3138
Leu Gln Pro Lys Trp Lys Asn Asn Arg Gly Ser Tyr Val
950                 955                 960

<210> SEQ ID NO 69
<211> LENGTH: 983
<212> TYPE: PRT
<213> ORGANISM: Penicillium simplicissimum

<400> SEQUENCE: 69

Met Arg Phe Phe Ala Phe Leu Pro Leu Leu Leu Ile Gly Ala Leu Ser
        -20                 -15                 -10

Ser Ile Val Ser Ala Thr Asp Asn Gly Lys Thr Thr Asp Val Thr Trp
-5                  -1  1                   5                  10

Asp Lys Tyr Ser Leu Ser Val Lys Gly Glu Arg Val Phe Val Phe Ser
                15                  20                  25

Gly Glu Phe His Tyr Met Arg Leu Pro Val Pro Glu Met Trp Leu Asp
            30                  35                  40

Val Phe Gln Lys Leu Arg Ser Asn Gly Phe Asn Ala Val Ser Ile Tyr
        45                  50                  55

Phe Phe Trp Ser Phe His Ser Ala Ser Glu Asp Thr Phe Asp Phe Glu
60                  65                  70                  75
```

```
Asn Gly Ala His Asp Val Gln Arg Val Phe Asp Tyr Ala Lys Gln Ala
            80                  85                  90
Gly Leu Tyr Val Ile Ala Arg Ala Gly Pro Tyr Ile Asn Ala Glu Thr
            95                 100                 105
Ser Ala Gly Gly Phe Ala Leu Trp Ala Ala Asn Gly Gln Met Gly Ser
           110                 115                 120
Glu Arg Thr Ser Ala Ser Ser Tyr Tyr Asp Lys Trp Leu Pro Trp Ile
125                 130                 135
Leu Lys Ile Gly Lys Ile Ile Ala Asp Asn Gln Ile Thr Asn Gly Gly
140                 145                 150                 155
Pro Val Ile Leu Asn Gln His Glu Asn Glu Leu Gln Glu Thr Thr His
                160                 165                 170
Ser Ala Thr Asn Thr Leu Val Leu Tyr Met Glu Gln Ile Ala Ala Ala
                175                 180                 185
Phe Glu Glu Ala Gly Val Ile Val Pro Ser Ser His Asn Glu Lys Gly
            190                 195                 200
Met Arg Ser Glu Ser Trp Ser Thr Asp Tyr Glu Asp Val Gly Gly Ala
            205                 210                 215
Val Asn Val Tyr Gly Leu Asp Ser Tyr Pro Gly Gly Leu Ser Cys Thr
220                 225                 230                 235
Asn Pro Asp Ser Gly Phe Asn Leu Val Arg Thr Tyr Tyr Gln Trp Phe
                240                 245                 250
Gln Asn Tyr Ser Tyr Thr Gln Pro Glu Phe Leu Pro Glu Phe Glu Gly
                255                 260                 265
Gly Trp Phe Gln Pro Trp Gly Tyr Phe Tyr Asp Glu Cys Ala Ala
            270                 275                 280
Glu His Ser Pro Glu Phe Ala Asp Val Tyr Tyr Lys Asn Asn Ile Gly
            285                 290                 295
Ser Arg Val Thr Leu Gln Ser Leu Tyr Met Ala Phe Gly Gly Thr Asn
300                 305                 310                 315
Trp Gly His Ser Ala Thr Pro Val Val Tyr Thr Ser Tyr Asp Tyr Ala
                320                 325                 330
Ala Pro Leu Arg Glu Thr Arg Glu Ile Gln Asp Lys Leu Lys Gln Thr
            335                 340                 345
Lys Leu Ile Gly Leu Phe Thr Arg Val Ser Ser Gly Leu Leu Gln Thr
            350                 355                 360
Val Met Glu Gly Asn Gly Thr Gly Tyr Thr Ser Asp Thr Ser Ile Tyr
365                 370                 375
Thr Trp Ala Leu Arg Asn Pro Glu Thr Asp Ala Gly Phe Tyr Val Leu
380                 385                 390                 395
Ala His Ser Thr Ser Ser Arg Ala Val Thr Thr Phe Ser Leu Asn
            400                 405                 410
Val Asn Thr Ser Ala Gly Ala Leu Thr Ile Pro Asp Ile Glu Leu Asp
            415                 420                 425
Gly Arg Gln Ser Lys Ile Ile Val Thr Asp Tyr Glu Ile Gly Lys Ala
            430                 435                 440
Ser Ser Leu Leu Tyr Ser Ser Ala Glu Val Leu Thr Tyr Ala Thr Leu
            445                 450                 455
Asp Val Asp Val Leu Val Leu Tyr Leu Asn Ile Gly Gln Lys Gly Val
460                 465                 470                 475
Phe Ala Phe Lys Asn Ala Pro Ser His Leu Thr Phe Lys Thr Tyr Gly
                480                 485                 490
```

-continued

```
Asn Ser Asn Leu Thr Ser Thr Thr Ser Thr Asn Gly Thr Gln Tyr Ser
            495                 500                 505
Tyr Thr Gln Gly Asp Gly Ala Thr Ala Val Lys Phe Ser Asn Gly Val
        510                 515                 520
Leu Leu Tyr Leu Leu Asp Lys Glu Thr Ala Trp Asn Phe Phe Ala Val
    525                 530                 535
Thr Thr Thr Ser Asn Pro Asn Val Thr Pro Ser Glu His Ile Leu Ala
540                 545                 550                 555
Leu Gly Pro Tyr Leu Val Arg Glu Ala Ser Ile Ser His Asp Thr Val
            560                 565                 570
Ser Leu Ile Gly Asp Asn Ala Asn Thr Thr Leu Glu Val Tyr Pro
        575                 580                 585
Gly Asn Ala Gln Val Thr Lys Ile Lys Trp Asn Gly Lys Pro Ile Ala
    590                 595                 600
Thr Lys Lys Thr Ala Tyr Gly Ser Leu Ile Gly Ser Ala Gln Gly Ala
605                 610                 615
Glu Thr Ala Lys Ile Ser Leu Pro Ser Leu Thr Ser Trp Lys Ser Gln
620                 625                 630                 635
Asp Thr Leu Pro Glu Ile Lys Gln Asp Tyr Asp Asp Ser Arg Trp Thr
            640                 645                 650
Val Cys Asn Lys Ser Thr Thr Val Asn Ser Val Ala Pro Leu Ser Leu
        655                 660                 665
Pro Val Leu Tyr Ser Gly Asp Tyr Gly Tyr His Ala Gly Thr Lys Ile
    670                 675                 680
Tyr Arg Gly Arg Phe Asp Gly Arg Asn Ala Thr Gly Ala Asn Val Thr
    685                 690                 695
Val Gln Asn Gly Val Ala Ala Gly Trp Ala Ala Trp Leu Asn Gly Asp
700                 705                 710                 715
Tyr Val Gly Gly Ala Leu Gly Asn Pro Ala Leu Ala Ala Thr Ser Asp
            720                 725                 730
Leu Leu Thr Phe Asn Ser Ser Leu Arg Asp Thr Asp Asn Val Leu
        735                 740                 745
Thr Val Val Met Asp Tyr Thr Gly His Asp Glu Asn Asn Val Lys Pro
        750                 755                 760
Ala Gly Thr Gln Asn Pro Arg Gly Ile Leu Gly Ala Thr Leu Phe Gly
765                 770                 775
Gly Gly Asn Phe Thr Ser Trp Arg Ile Gln Gly Asn Ala Gly Gly Glu
780                 785                 790                 795
Ala Asn Ile Asp Pro Val Arg Gly Pro Met Asn Glu Gly Gly Leu Tyr
            800                 805                 810
Gly Glu Arg Leu Gly Trp His Leu Pro Gly Tyr Thr Ala Pro Lys Ser
        815                 820                 825
Ala Gly Ser Ser Ser Pro Leu Gln Gly Val Ser Asn Ala Ala Gly Arg
    830                 835                 840
Phe Tyr Thr Thr Thr Phe Lys Leu Asn Leu Glu Ala Asp Leu Asp Val
    845                 850                 855
Pro Ile Gly Leu Gln Leu Gly Ala Ala Ala Asn Thr Ser Ala Val Val
860                 865                 870                 875
Gln Val Phe Met Asn Gly Tyr Gln Phe Gly His Tyr Leu Pro His Ile
            880                 885                 890
Gly Pro Gln Thr Leu Phe Pro Phe Pro Pro Gly Ile Ile Asn Asn Arg
        895                 900                 905
Gly Glu Asn Thr Leu Ala Ile Ser Leu Trp Ala Leu Thr Asp Glu Gly
```

-continued

```
            910                 915                 920
Ala Ala Leu Asp Gln Val Glu Leu Val Ala Tyr Gly Ala Tyr Arg Thr
        925                 930                 935

Gly Phe Asp Phe Asn Gln Asp Trp Thr Tyr Leu Gln Pro Lys Trp Lys
940                 945                 950                 955

Asn Asn Arg Gly Ser Tyr Val
                960

<210> SEQ ID NO 70
<211> LENGTH: 962
<212> TYPE: PRT
<213> ORGANISM: Penicillium simplicissimum
<220> FEATURE:
<221> NAME/KEY: mat_peptide
<222> LOCATION: (1)..(962)

<400> SEQUENCE: 70

Thr Asp Asn Gly Lys Thr Thr Asp Val Thr Trp Asp Lys Tyr Ser Leu
1               5                   10                  15

Ser Val Lys Gly Glu Arg Val Phe Val Phe Ser Gly Glu Phe His Tyr
            20                  25                  30

Met Arg Leu Pro Val Pro Glu Met Trp Leu Asp Val Phe Gln Lys Leu
        35                  40                  45

Arg Ser Asn Gly Phe Asn Ala Val Ser Ile Tyr Phe Phe Trp Ser Phe
    50                  55                  60

His Ser Ala Ser Glu Asp Thr Phe Asp Phe Glu Asn Gly Ala His Asp
65                  70                  75                  80

Val Gln Arg Val Phe Asp Tyr Ala Lys Gln Ala Gly Leu Tyr Val Ile
                85                  90                  95

Ala Arg Ala Gly Pro Tyr Ile Asn Ala Glu Thr Ser Ala Gly Gly Phe
            100                 105                 110

Ala Leu Trp Ala Ala Asn Gly Gln Met Gly Ser Glu Arg Thr Ser Ala
        115                 120                 125

Ser Ser Tyr Tyr Asp Lys Trp Leu Pro Trp Ile Leu Lys Ile Gly Lys
    130                 135                 140

Ile Ile Ala Asp Asn Gln Ile Thr Asn Gly Gly Pro Val Ile Leu Asn
145                 150                 155                 160

Gln His Glu Asn Glu Leu Gln Glu Thr Thr His Ser Ala Thr Asn Thr
                165                 170                 175

Leu Val Leu Tyr Met Glu Gln Ile Ala Ala Ala Phe Glu Glu Ala Gly
            180                 185                 190

Val Ile Val Pro Ser Ser His Asn Glu Lys Gly Met Arg Ser Glu Ser
        195                 200                 205

Trp Ser Thr Asp Tyr Glu Asp Val Gly Gly Ala Val Asn Val Tyr Gly
    210                 215                 220

Leu Asp Ser Tyr Pro Gly Gly Leu Ser Cys Thr Asn Pro Asp Ser Gly
225                 230                 235                 240

Phe Asn Leu Val Arg Thr Tyr Tyr Gln Trp Phe Gln Asn Tyr Ser Tyr
                245                 250                 255

Thr Gln Pro Glu Phe Leu Pro Glu Phe Glu Gly Gly Trp Phe Gln Pro
            260                 265                 270

Trp Gly Gly Tyr Phe Tyr Asp Glu Cys Ala Ala Glu His Ser Pro Glu
        275                 280                 285

Phe Ala Asp Val Tyr Tyr Lys Asn Asn Ile Gly Ser Arg Val Thr Leu
    290                 295                 300
```

-continued

```
Gln Ser Leu Tyr Met Ala Phe Gly Gly Thr Asn Trp Gly His Ser Ala
305                 310                 315                 320

Thr Pro Val Val Tyr Thr Ser Tyr Asp Tyr Ala Ala Pro Leu Arg Glu
                325                 330                 335

Thr Arg Glu Ile Gln Asp Lys Leu Lys Gln Thr Lys Leu Ile Gly Leu
            340                 345                 350

Phe Thr Arg Val Ser Ser Gly Leu Leu Gln Thr Val Met Glu Gly Asn
        355                 360                 365

Gly Thr Gly Tyr Thr Ser Asp Thr Ser Ile Tyr Thr Trp Ala Leu Arg
    370                 375                 380

Asn Pro Glu Thr Asp Ala Gly Phe Tyr Val Leu Ala His Ser Thr Ser
385                 390                 395                 400

Ser Ser Arg Ala Val Thr Thr Phe Ser Leu Asn Val Asn Thr Ser Ala
                405                 410                 415

Gly Ala Leu Thr Ile Pro Asp Ile Glu Leu Asp Gly Arg Gln Ser Lys
            420                 425                 430

Ile Ile Val Thr Asp Tyr Glu Ile Gly Lys Ala Ser Ser Leu Leu Tyr
        435                 440                 445

Ser Ser Ala Glu Val Leu Thr Tyr Ala Thr Leu Asp Val Asp Val Leu
450                 455                 460

Val Leu Tyr Leu Asn Ile Gly Gln Lys Gly Val Phe Ala Phe Lys Asn
465                 470                 475                 480

Ala Pro Ser His Leu Thr Phe Lys Thr Tyr Gly Asn Ser Asn Leu Thr
                485                 490                 495

Ser Thr Thr Ser Thr Asn Gly Thr Gln Tyr Ser Tyr Thr Gln Gly Asp
            500                 505                 510

Gly Ala Thr Ala Val Lys Phe Ser Asn Gly Val Leu Leu Tyr Leu Leu
        515                 520                 525

Asp Lys Glu Thr Ala Trp Asn Phe Phe Ala Val Thr Thr Ser Asn
530                 535                 540

Pro Asn Val Thr Pro Ser Glu His Ile Leu Ala Leu Gly Pro Tyr Leu
545                 550                 555                 560

Val Arg Glu Ala Ser Ile Ser His Asp Thr Val Ser Leu Ile Gly Asp
                565                 570                 575

Asn Ala Asn Thr Thr Thr Leu Glu Val Tyr Pro Gly Asn Ala Gln Val
            580                 585                 590

Thr Lys Ile Lys Trp Asn Gly Lys Pro Ile Ala Thr Lys Thr Ala
        595                 600                 605

Tyr Gly Ser Leu Ile Gly Ser Ala Gln Gly Ala Glu Thr Ala Lys Ile
610                 615                 620

Ser Leu Pro Ser Leu Thr Ser Trp Lys Ser Gln Asp Thr Leu Pro Glu
625                 630                 635                 640

Ile Lys Gln Asp Tyr Asp Asp Ser Arg Trp Thr Val Cys Asn Lys Ser
                645                 650                 655

Thr Thr Val Asn Ser Val Ala Pro Leu Ser Leu Pro Val Leu Tyr Ser
            660                 665                 670

Gly Asp Tyr Gly Tyr His Ala Gly Thr Lys Ile Tyr Arg Gly Arg Phe
        675                 680                 685

Asp Gly Arg Asn Ala Thr Gly Ala Asn Val Thr Val Gln Asn Gly Val
    690                 695                 700

Ala Ala Gly Trp Ala Ala Trp Leu Asn Gly Asp Tyr Val Gly Gly Ala
705                 710                 715                 720

Leu Gly Asn Pro Ala Leu Ala Ala Thr Ser Asp Leu Leu Thr Phe Asn
```

```
                725                 730                 735
Ser Ser Ser Leu Arg Asp Thr Asp Asn Val Leu Thr Val Val Met Asp
            740                 745                 750
Tyr Thr Gly His Asp Glu Asn Asn Val Lys Pro Ala Gly Thr Gln Asn
        755                 760                 765
Pro Arg Gly Ile Leu Gly Ala Thr Leu Phe Gly Gly Gly Asn Phe Thr
    770                 775                 780
Ser Trp Arg Ile Gln Gly Asn Ala Gly Gly Glu Ala Asn Ile Asp Pro
785                 790                 795                 800
Val Arg Gly Pro Met Asn Glu Gly Gly Leu Tyr Gly Glu Arg Leu Gly
                805                 810                 815
Trp His Leu Pro Gly Tyr Thr Ala Pro Lys Ser Ala Gly Ser Ser Ser
            820                 825                 830
Pro Leu Gln Gly Val Ser Asn Ala Ala Gly Arg Phe Tyr Thr Thr Thr
        835                 840                 845
Phe Lys Leu Asn Leu Glu Ala Asp Leu Asp Val Pro Ile Gly Leu Gln
    850                 855                 860
Leu Gly Ala Ala Ala Asn Thr Ser Ala Val Val Gln Val Phe Met Asn
865                 870                 875                 880
Gly Tyr Gln Phe Gly His Tyr Leu Pro His Ile Gly Pro Gln Thr Leu
                885                 890                 895
Phe Pro Phe Pro Pro Gly Ile Ile Asn Asn Arg Gly Glu Asn Thr Leu
            900                 905                 910
Ala Ile Ser Leu Trp Ala Leu Thr Asp Glu Gly Ala Ala Leu Asp Gln
        915                 920                 925
Val Glu Leu Val Ala Tyr Gly Ala Tyr Arg Thr Gly Phe Asp Phe Asn
    930                 935                 940
Gln Asp Trp Thr Tyr Leu Gln Pro Lys Trp Lys Asn Asn Arg Gly Ser
945                 950                 955                 960
Tyr Val

<210> SEQ ID NO 71
<211> LENGTH: 3309
<212> TYPE: DNA
<213> ORGANISM: Aspergillus westerdijkiae
<220> FEATURE:
<221> NAME/KEY: CDS
<222> LOCATION: (1)..(801)
<220> FEATURE:
<221> NAME/KEY: sig_peptide
<222> LOCATION: (1)..(60)
<220> FEATURE:
<221> NAME/KEY: mat_peptide
<222> LOCATION: (61)..(3306)
<220> FEATURE:
<221> NAME/KEY: CDS
<222> LOCATION: (852)..(1848)
<220> FEATURE:
<221> NAME/KEY: CDS
<222> LOCATION: (1898)..(2191)
<220> FEATURE:
<221> NAME/KEY: CDS
<222> LOCATION: (2239)..(2310)
<220> FEATURE:
<221> NAME/KEY: CDS
<222> LOCATION: (2360)..(2447)
<220> FEATURE:
<221> NAME/KEY: CDS
<222> LOCATION: (2499)..(3306)

<400> SEQUENCE: 71 atg gcg cgc atc atg cac ctt gcc gtg ctg ctt ctt tcc agc atc gga        48
```

```
                Met Ala Arg Ile Met His Leu Ala Val Leu Leu Ser Ser Ile Gly
                -20             -15                 -10                 -5 ctg ctg gct gct gcc cag aat cag tcc gac tct gac tgg cct ctg cac         96
Leu Leu Ala Ala Ala Gln Asn Gln Ser Asp Ser Asp Trp Pro Leu His
            -1  1                   5                   10 gac aac ggt ctg aac acc gcc gtg caa tgg gac cat tac agc ttc cat         144
Asp Asn Gly Leu Asn Thr Ala Val Gln Trp Asp His Tyr Ser Phe His
                15                  20                  25 gtc cac gga cag cgc atc ttc atc ttc tcc ggc gag ttt cac tac tgg         192
Val His Gly Gln Arg Ile Phe Ile Phe Ser Gly Glu Phe His Tyr Trp
            30                  35                  40 cgt att ccc gtc ccc gag ctt tgg cgc gac atc ctc gag aag gtc aaa         240
Arg Ile Pro Val Pro Glu Leu Trp Arg Asp Ile Leu Glu Lys Val Lys
45                  50                  55                  60 gcc acc ggc ttc acc gcg ttt gcc ttc tac tct agc tgg gcg tac cat         288
Ala Thr Gly Phe Thr Ala Phe Ala Phe Tyr Ser Ser Trp Ala Tyr His
                65                  70                  75 gcg ccg aac aac cac acg gtg gac ttc cac acc ggt gcg cgc gac atc         336
Ala Pro Asn Asn His Thr Val Asp Phe His Thr Gly Ala Arg Asp Ile
            80                  85                  90 acg ccc atc ttc gag ctc gcc aag gag ctg ggc atg tat atg atc gtg         384
Thr Pro Ile Phe Glu Leu Ala Lys Glu Leu Gly Met Tyr Met Ile Val
                95                  100                 105 cgg ccc ggg ccg tat gtc aat gcc gag gcc agc gct ggt ggc ttt ccg         432
Arg Pro Gly Pro Tyr Val Asn Ala Glu Ala Ser Ala Gly Gly Phe Pro
110                 115                 120 ctg tgg gcg acc acc ggt gcg tat ggg tcg atg cgc aat gac gac ccc         480
Leu Trp Ala Thr Thr Gly Ala Tyr Gly Ser Met Arg Asn Asp Asp Pro
125                 130                 135                 140 agg tat act gcg gcg tgg aag ccg tac ttt gag aag atg tcg caa atc         528
Arg Tyr Thr Ala Ala Trp Lys Pro Tyr Phe Glu Lys Met Ser Gln Ile
                145                 150                 155 acc agt cag tac cag atc acc gat ggg gaa aac act ttc tgc tat cag         576
Thr Ser Gln Tyr Gln Ile Thr Asp Gly Glu Asn Thr Phe Cys Tyr Gln
            160                 165                 170 atc gag aac gag tat ggc cag cag tgg gtt ggt gat ccc cgt gat cgg         624
Ile Glu Asn Glu Tyr Gly Gln Gln Trp Val Gly Asp Pro Arg Asp Arg
                175                 180                 185 aac ccg aat aag act gcg gtc gcc tat atg gaa ctg ctc gag gag agt         672
Asn Pro Asn Lys Thr Ala Val Ala Tyr Met Glu Leu Leu Glu Glu Ser
190                 195                 200 gcc cgt gag aat ggt att gtc gtg ccg ctg acg gcc aac gat ccg aac         720
Ala Arg Glu Asn Gly Ile Val Val Pro Leu Thr Ala Asn Asp Pro Asn
205                 210                 215                 220 ctg aac acc cgc tct tgg gga aac gac tgg tcc aac gct gga gga aac         768
Leu Asn Thr Arg Ser Trp Gly Asn Asp Trp Ser Asn Ala Gly Gly Asn
                225                 230                 235 gtt gac gtt cct gga gtg gat tcg tat ccc tca gtgagttacc taaatcacat      821
Val Asp Val Pro Gly Val Asp Ser Tyr Pro Ser
                240                 245 ctgggtaatg caaattacta atctttccag tgc tgg act tgt gat gtc tct caa      875
                                 Cys Trp Thr Cys Asp Val Ser Gln
                                                 250                 255 tgc acc tcc acc aac gga gag tac gtt cct tac aaa gtg atc ccc tat        923
Cys Thr Ser Thr Asn Gly Glu Tyr Val Pro Tyr Lys Val Ile Pro Tyr
                260                 265                 270 tac gac tac ttc cag gag gtc cag ccc tcg atg cct gcc ttc atg ccc        971
Tyr Asp Tyr Phe Gln Glu Val Gln Pro Ser Met Pro Ala Phe Met Pro
            275                 280                 285
```

```
gaa ttc cag ggt gga tct tac aac ccc tgg gcc ggc ccc gaa ggt gga   1019
Glu Phe Gln Gly Gly Ser Tyr Asn Pro Trp Ala Gly Pro Glu Gly Gly
        290                 295                 300 tgt ccc gag gat acc gga gcg gac ttt gcc aac ctg ttc tac cgg tgg   1067
Cys Pro Glu Asp Thr Gly Ala Asp Phe Ala Asn Leu Phe Tyr Arg Trp
305                 310                 315 aac atc gcc cag cga gtg acc gcc atg agc ttg tac atg gta ttt ggc   1115
Asn Ile Ala Gln Arg Val Thr Ala Met Ser Leu Tyr Met Val Phe Gly
320                 325                 330                 335 gga acc aac tgg ggc tcg ctg gct gcc ccc gtt aca gcc acc agc tac   1163
Gly Thr Asn Trp Gly Ser Leu Ala Ala Pro Val Thr Ala Thr Ser Tyr
                340                 345                 350 gac tac tcc tcc ccg att gcc gaa gac cgc tcg att ggt gac aag tac   1211
Asp Tyr Ser Ser Pro Ile Ala Glu Asp Arg Ser Ile Gly Asp Lys Tyr
            355                 360                 365 tac gag acc aag ctg ctt tcc ctg ttc act cgt agc gcc aag gat ctc   1259
Tyr Glu Thr Lys Leu Leu Ser Leu Phe Thr Arg Ser Ala Lys Asp Leu
        370                 375                 380 acc atg acc gac ctc atc ggc aac ggc acc aag tac acc gac aat gct   1307
Thr Met Thr Asp Leu Ile Gly Asn Gly Thr Lys Tyr Thr Asp Asn Ala
385                 390                 395 gcc gtc agc gcg tac gaa ctc cgg aac ccc gag acc aac ggt gcc ttc   1355
Ala Val Ser Ala Tyr Glu Leu Arg Asn Pro Glu Thr Asn Gly Ala Phe
400                 405                 410                 415 tac gtc acc atc cac aag gac acc acc gtc ggc tcg gac gag tcc ttc   1403
Tyr Val Thr Ile His Lys Asp Thr Thr Val Gly Ser Asp Glu Ser Phe
                420                 425                 430 aag ctc cac gtg aac acc tcc gct ggc gcg ctg act atc cca agc gag   1451
Lys Leu His Val Asn Thr Ser Ala Gly Ala Leu Thr Ile Pro Ser Glu
            435                 440                 445 ggg gca aag atc cgc ctg aac ggc cat cag tcc aag atc atc gtg act   1499
Gly Ala Lys Ile Arg Leu Asn Gly His Gln Ser Lys Ile Ile Val Thr
        450                 455                 460 gac ttt gcc ttc ggc tct aag acc ctc ctg tac tcc acc gcc gag gtg   1547
Asp Phe Ala Phe Gly Ser Lys Thr Leu Leu Tyr Ser Thr Ala Glu Val
465                 470                 475 ttg acc tat gcg gtc atc gat gac cag cct act ctg gtg ctt tgg gtc   1595
Leu Thr Tyr Ala Val Ile Asp Asp Gln Pro Thr Leu Val Leu Trp Val
480                 485                 490                 495 ccg aag gga gaa tct ggc gag ttc gct gtc aag ggc act aag tct ggc   1643
Pro Lys Gly Glu Ser Gly Glu Phe Ala Val Lys Gly Thr Lys Ser Gly
                500                 505                 510 aag gtg gcg agc tgc aac ggc tgc tcc agc gtc aag ttc aac gga aag   1691
Lys Val Ala Ser Cys Asn Gly Cys Ser Ser Val Lys Phe Asn Gly Lys
            515                 520                 525 aag gac cac gtg gtt gtt ggg ttc aca cag gcc aag ggc atg agc gtg   1739
Lys Asp His Val Val Val Gly Phe Thr Gln Ala Lys Gly Met Ser Val
        530                 535                 540 tat cag ctg gat gat gat gtc cgt gtc gtt gtt ctc gac cgg tcg tcc   1787
Tyr Gln Leu Asp Asp Asp Val Arg Val Val Val Leu Asp Arg Ser Ser
545                 550                 555 gct tat cac ttc tgg gcc cct act ttg act gat gat ccg att gcc ccg   1835
Ala Tyr His Phe Trp Ala Pro Thr Leu Thr Asp Asp Pro Ile Ala Pro
560                 565                 570                 575 gag gat gaa att g gtatgctccc gtgtccgaga gaaatgactg attgctaata    1888
Glu Asp Glu Ile tcatactag tc  ctg gtc gag ggc ccc tac ctc gtc cgc tcg gcc agc gtc   1938
              Val Leu Val Glu Gly Pro Tyr Leu Val Arg Ser Ala Ser Val
                  580                 585                 590
```

```
gag gga tct acc ctt gct ctc cgc ggt gac tct acc gac aag acc aac    1986
Glu Gly Ser Thr Leu Ala Leu Arg Gly Asp Ser Thr Asp Lys Thr Asn
595                 600                 605 ctg gag gtt ttc gct cct aag agc gtc aag acc atc acc tgg aat ggc    2034
Leu Glu Val Phe Ala Pro Lys Ser Val Lys Thr Ile Thr Trp Asn Gly
610                 615                 620                 625 aag aag gtc aag tcc tcc gag acc tcc tat ggc agc ctc aag gcc acg    2082
Lys Lys Val Lys Ser Ser Glu Thr Ser Tyr Gly Ser Leu Lys Ala Thr
                630                 635                 640 ctc gcc gcg cca ccc tcg att aag cta ccc tct ttc ggc tca tgg cgg    2130
Leu Ala Ala Pro Pro Ser Ile Lys Leu Pro Ser Phe Gly Ser Trp Arg
                645                 650                 655 tcg aac gac agc ttg ccg gag cgc ttg gag tcg tac gat gac tct ggc    2178
Ser Asn Asp Ser Leu Pro Glu Arg Leu Glu Ser Tyr Asp Asp Ser Gly
                660                 665                 670 ccg gcc tgg gtt g gtaagtacat ctccacggcg gtccaagatt cccgctcacc      2231
Pro Ala Trp Val
675 agaacag at  gcc aac cat gaa acc acg ctg aac ccg cat ccc cct gtc    2279
            Ala Asn His Glu Thr Thr Leu Asn Pro His Pro Pro Val
                        680                 685                 690 acg act cct gtc ttg tac gca aac gaa tac g gtatgcatct ctggccttca    2330
Thr Thr Pro Val Leu Tyr Ala Asn Glu Tyr
                695                 700 ttctttagtc tcatgctcat cacgtccag gc  ttc cac aac ggc gtc cgc ctc    2382
                                    Gly Phe His Asn Gly Val Arg Leu
                                                705 tgg cgc ggc tat ttc aac gga acc gcc tcc ggc gtc ttc ctc aac atc    2430
Trp Arg Gly Tyr Phe Asn Gly Thr Ala Ser Gly Val Phe Leu Asn Ile
710                 715                 720                 725 caa ggt ggc gct gca tt  gtaagcaccc tctccctcct aacatccacg           2477
Gln Gly Gly Ala Ala Phe
                730 accatctaac caaaagtcca g c  ggc tgg tcc gcc tat ctc aac ggc cac ttc 2529
                          Gly Trp Ser Ala Tyr Leu Asn Gly His Phe
                                      735                 740 ctt ggc tcc tac ctc ggc aac gcc acc atc gcg caa gcc aac aaa acc    2577
Leu Gly Ser Tyr Leu Gly Asn Ala Thr Ile Ala Gln Ala Asn Lys Thr
                745                 750                 755 ctc acc ttc ccg aac aac acg ctc cac acg cgc ccc ggc tcc cgg aac    2625
Leu Thr Phe Pro Asn Asn Thr Leu His Thr Arg Pro Gly Ser Arg Asn
                760                 765                 770 acc ctc ctc gtc atc cac gac gac acc ggc cac gac cag acc acc ggc    2673
Thr Leu Leu Val Ile His Asp Asp Thr Gly His Asp Gln Thr Thr Gly
775                 780                 785 gtg ctc aac ccg cgc ggc atc atc gaa gcc cgc ctc ctc ggc tcc aac    2721
Val Leu Asn Pro Arg Gly Ile Ile Glu Ala Arg Leu Leu Gly Ser Asn
790                 795                 800                 805 gcc ccg aac ttc acc cac tgg cgt ctc gcc ggt acc gcc ggc ggc gaa    2769
Ala Pro Asn Phe Thr His Trp Arg Leu Ala Gly Thr Ala Gly Gly Glu
                810                 815                 820 tca aac ctc gat ccc gtc cgc ggc gtc tac aac gaa gac ggc ctc cac    2817
Ser Asn Leu Asp Pro Val Arg Gly Val Tyr Asn Glu Asp Gly Leu His
                825                 830                 835 gcg gag cgc gtc ggc tgg cat ctc cct ggc ttc gac gac agc gac tgg    2865
Ala Glu Arg Val Gly Trp His Leu Pro Gly Phe Asp Asp Ser Asp Trp
                840                 845                 850 cct gtc acc aac cac tcc tcc tcc tcc tct agc tcc aaa tcc ctc tcc    2913
Pro Val Thr Asn His Ser Ser Ser Ser Ser Ser Lys Ser Leu Ser
855                 860                 865
```

| | | | | | | | | | | | | | | | |
|---|---|---|---|---|---|---|---|---|---|---|---|---|---|---|---|
| acc | ctc | tcc | ttc | acc | ggc | gca | acc | gtt | cgc | ttc | ttc | cgc | acc | acc | atc | 2961 |
| Thr | Leu | Ser | Phe | Thr | Gly | Ala | Thr | Val | Arg | Phe | Phe | Arg | Thr | Thr | Ile | |
| 870 | | | | | 875 | | | | | 880 | | | | | 885 | |

```
acc ctc tcc ttc acc ggc gca acc gtt cgc ttc ttc cgc acc acc atc          2961
Thr Leu Ser Phe Thr Gly Ala Thr Val Arg Phe Phe Arg Thr Thr Ile
870             875                 880                 885 ccc cta aat atc ccc tcg ggc ctc gac gtc tcg atc tcc ttc ctc ctc          3009
Pro Leu Asn Ile Pro Ser Gly Leu Asp Val Ser Ile Ser Phe Leu Leu
            890                 895                 900 ggc acg ccg aca ggc acg agt aag gcc tac cgc gcg cag ctc ttc gtt          3057
Gly Thr Pro Thr Gly Thr Ser Lys Ala Tyr Arg Ala Gln Leu Phe Val
        905                 910                 915 aac ggc tac cag tac ggg cgc tac tat ccg cac atc ggc aac cag gtc          3105
Asn Gly Tyr Gln Tyr Gly Arg Tyr Tyr Pro His Ile Gly Asn Gln Val
    920                 925                 930 gtg tat ccg gtc ccg gcg ggg att ttg gat tac cgc ggc gag aac acg          3153
Val Tyr Pro Val Pro Ala Gly Ile Leu Asp Tyr Arg Gly Glu Asn Thr
935                 940                 945 atc ggg ttg gct gtt tgg gcg cag agc gag gat ggc gcg gcg gtc agt          3201
Ile Gly Leu Ala Val Trp Ala Gln Ser Glu Asp Gly Ala Ala Val Ser
950                 955                 960                 965 gtt gat tgg agg gtg aat tat gtg gcg gat agt tcg ttg gat gtt gcg          3249
Val Asp Trp Arg Val Asn Tyr Val Ala Asp Ser Ser Leu Asp Val Ala
                970                 975                 980 ggg att ggg gag gag agg ttg agg ccg ggg tat gag aag gtg agg gag          3297
Gly Ile Gly Glu Glu Arg Leu Arg Pro Gly Tyr Glu Lys Val Arg Glu
            985                 990                 995 aag ttt gct tga                                                           3309
Lys Phe Ala
        1000

<210> SEQ ID NO 72
<211> LENGTH: 1020
<212> TYPE: PRT
<213> ORGANISM: Aspergillus westerdijkiae

<400> SEQUENCE: 72

Met Ala Arg Ile Met His Leu Ala Val Leu Leu Ser Ser Ile Gly
-20                 -15                 -10                 -5

Leu Leu Ala Ala Ala Gln Asn Gln Ser Asp Ser Asp Trp Pro Leu His
            -1  1               5                   10

Asp Asn Gly Leu Asn Thr Ala Val Gln Trp Asp His Tyr Ser Phe His
        15                  20                  25

Val His Gly Gln Arg Ile Phe Ile Phe Ser Gly Glu Phe His Tyr Trp
    30                  35                  40

Arg Ile Pro Val Pro Glu Leu Trp Arg Asp Ile Leu Glu Lys Val Lys
45                  50                  55                  60

Ala Thr Gly Phe Thr Ala Phe Ala Phe Tyr Ser Ser Trp Ala Tyr His
                65                  70                  75

Ala Pro Asn Asn His Thr Val Asp Phe His Thr Gly Ala Arg Asp Ile
            80                  85                  90

Thr Pro Ile Phe Glu Leu Ala Lys Glu Leu Gly Met Tyr Met Ile Val
        95                  100                 105

Arg Pro Gly Pro Tyr Val Asn Ala Glu Ala Ser Ala Gly Gly Phe Pro
    110                 115                 120

Leu Trp Ala Thr Thr Gly Ala Tyr Gly Ser Met Arg Asn Asp Asp Pro
125                 130                 135                 140

Arg Tyr Thr Ala Ala Trp Lys Pro Tyr Phe Glu Lys Met Ser Gln Ile
                145                 150                 155

Thr Ser Gln Tyr Gln Ile Thr Asp Gly Glu Asn Thr Phe Cys Tyr Gln
```

```
                160                 165                 170
Ile Glu Asn Glu Tyr Gly Gln Gln Trp Val Gly Asp Pro Arg Asp Arg
            175                 180                 185
Asn Pro Asn Lys Thr Ala Val Ala Tyr Met Glu Leu Leu Glu Glu Ser
        190                 195                 200
Ala Arg Glu Asn Gly Ile Val Val Pro Leu Thr Ala Asn Asp Pro Asn
205                 210                 215                 220
Leu Asn Thr Arg Ser Trp Gly Asn Asp Trp Ser Asn Ala Gly Gly Asn
                225                 230                 235
Val Asp Val Pro Gly Val Asp Ser Tyr Pro Ser Cys Trp Thr Cys Asp
            240                 245                 250
Val Ser Gln Cys Thr Ser Thr Asn Gly Glu Tyr Val Pro Tyr Lys Val
        255                 260                 265
Ile Pro Tyr Tyr Asp Tyr Phe Gln Glu Val Gln Pro Ser Met Pro Ala
    270                 275                 280
Phe Met Pro Glu Phe Gln Gly Gly Ser Tyr Asn Pro Trp Ala Gly Pro
285                 290                 295                 300
Glu Gly Gly Cys Pro Glu Asp Thr Gly Ala Asp Phe Ala Asn Leu Phe
                305                 310                 315
Tyr Arg Trp Asn Ile Ala Gln Arg Val Thr Ala Met Ser Leu Tyr Met
            320                 325                 330
Val Phe Gly Gly Thr Asn Trp Gly Ser Leu Ala Ala Pro Val Thr Ala
        335                 340                 345
Thr Ser Tyr Asp Tyr Ser Ser Pro Ile Ala Glu Asp Arg Ser Ile Gly
    350                 355                 360
Asp Lys Tyr Tyr Glu Thr Lys Leu Leu Ser Leu Phe Thr Arg Ser Ala
365                 370                 375                 380
Lys Asp Leu Thr Met Thr Asp Leu Ile Gly Asn Gly Thr Lys Tyr Thr
                385                 390                 395
Asp Asn Ala Ala Val Ser Ala Tyr Glu Leu Arg Asn Pro Glu Thr Asn
            400                 405                 410
Gly Ala Phe Tyr Val Thr Ile His Lys Asp Thr Thr Val Gly Ser Asp
        415                 420                 425
Glu Ser Phe Lys Leu His Val Asn Thr Ser Ala Gly Ala Leu Thr Ile
    430                 435                 440
Pro Ser Glu Gly Ala Lys Ile Arg Leu Asn Gly His Gln Ser Lys Ile
445                 450                 455                 460
Ile Val Thr Asp Phe Ala Phe Gly Ser Lys Thr Leu Leu Tyr Ser Thr
                465                 470                 475
Ala Glu Val Leu Thr Tyr Ala Val Ile Asp Asp Gln Pro Thr Leu Val
            480                 485                 490
Leu Trp Val Pro Lys Gly Glu Ser Gly Glu Phe Ala Val Lys Gly Thr
        495                 500                 505
Lys Ser Gly Lys Val Ala Ser Cys Asn Gly Cys Ser Ser Val Lys Phe
    510                 515                 520
Asn Gly Lys Lys Asp His Val Val Gly Phe Thr Gln Ala Lys Gly
525                 530                 535                 540
Met Ser Val Tyr Gln Leu Asp Asp Val Arg Val Val Leu Asp
                545                 550                 555
Arg Ser Ser Ala Tyr His Phe Trp Ala Pro Thr Leu Thr Asp Asp Pro
            560                 565                 570
Ile Ala Pro Glu Asp Glu Ile Val Leu Val Glu Gly Pro Tyr Leu Val
        575                 580                 585
```

```
Arg Ser Ala Ser Val Glu Gly Ser Thr Leu Ala Leu Arg Gly Asp Ser
        590                 595                 600

Thr Asp Lys Thr Asn Leu Glu Val Phe Ala Pro Lys Ser Val Lys Thr
605                 610                 615                 620

Ile Thr Trp Asn Gly Lys Lys Val Lys Ser Ser Glu Thr Ser Tyr Gly
                625                 630                 635

Ser Leu Lys Ala Thr Leu Ala Ala Pro Pro Ser Ile Lys Leu Pro Ser
                640                 645                 650

Phe Gly Ser Trp Arg Ser Asn Asp Ser Leu Pro Glu Arg Leu Glu Ser
                655                 660                 665

Tyr Asp Asp Ser Gly Pro Ala Trp Val Asp Ala Asn His Glu Thr Thr
        670                 675                 680

Leu Asn Pro His Pro Pro Val Thr Thr Pro Val Leu Tyr Ala Asn Glu
685                 690                 695                 700

Tyr Gly Phe His Asn Gly Val Arg Leu Trp Arg Gly Tyr Phe Asn Gly
                705                 710                 715

Thr Ala Ser Gly Val Phe Leu Asn Ile Gln Gly Gly Ala Ala Phe Gly
                720                 725                 730

Trp Ser Ala Tyr Leu Asn Gly His Phe Leu Gly Ser Tyr Leu Gly Asn
                735                 740                 745

Ala Thr Ile Ala Gln Ala Asn Lys Thr Leu Thr Phe Pro Asn Asn Thr
        750                 755                 760

Leu His Thr Arg Pro Gly Ser Arg Asn Thr Leu Leu Val Ile His Asp
765                 770                 775                 780

Asp Thr Gly His Asp Gln Thr Thr Gly Val Leu Asn Pro Arg Gly Ile
                785                 790                 795

Ile Glu Ala Arg Leu Leu Gly Ser Asn Ala Pro Asn Phe Thr His Trp
                800                 805                 810

Arg Leu Ala Gly Thr Ala Gly Gly Glu Ser Asn Leu Asp Pro Val Arg
                815                 820                 825

Gly Val Tyr Asn Glu Asp Gly Leu His Ala Glu Arg Val Gly Trp His
        830                 835                 840

Leu Pro Gly Phe Asp Asp Ser Asp Trp Pro Val Thr Asn His Ser Ser
845                 850                 855                 860

Ser Ser Ser Ser Ser Lys Ser Leu Ser Thr Leu Ser Phe Thr Gly Ala
                865                 870                 875

Thr Val Arg Phe Phe Arg Thr Thr Ile Pro Leu Asn Ile Pro Ser Gly
                880                 885                 890

Leu Asp Val Ser Ile Ser Phe Leu Leu Gly Thr Pro Thr Gly Thr Ser
        895                 900                 905

Lys Ala Tyr Arg Ala Gln Leu Phe Val Asn Gly Tyr Gln Tyr Gly Arg
        910                 915                 920

Tyr Tyr Pro His Ile Gly Asn Gln Val Val Tyr Pro Val Pro Ala Gly
925                 930                 935                 940

Ile Leu Asp Tyr Arg Gly Glu Asn Thr Ile Gly Leu Ala Val Trp Ala
                945                 950                 955

Gln Ser Glu Asp Gly Ala Ala Val Ser Val Asp Trp Arg Val Asn Tyr
                960                 965                 970

Val Ala Asp Ser Ser Leu Asp Val Ala Gly Ile Gly Glu Glu Arg Leu
        975                 980                 985

Arg Pro Gly Tyr Glu Lys Val Arg Glu Lys Phe Ala
        990                 995                 1000
```

```
<210> SEQ ID NO 73
<211> LENGTH: 1000
<212> TYPE: PRT
<213> ORGANISM: Aspergillus westerdijkiae
<220> FEATURE:
<221> NAME/KEY: mat_peptide
<222> LOCATION: (1)..(1000)

<400> SEQUENCE: 73
```

| | | | | | | | | | | | | | | | |
|---|---|---|---|---|---|---|---|---|---|---|---|---|---|---|---|
| Ala | Gln | Asn | Gln | Ser | Asp | Ser | Asp | Trp | Pro | Leu | His | Asp | Asn | Gly | Leu |
| 1 | | | | 5 | | | | | 10 | | | | | 15 | |
| Asn | Thr | Ala | Val | Gln | Trp | Asp | His | Tyr | Ser | Phe | His | Val | His | Gly | Gln |
| | | | 20 | | | | | 25 | | | | | 30 | | |
| Arg | Ile | Phe | Ile | Phe | Ser | Gly | Glu | Phe | His | Tyr | Trp | Arg | Ile | Pro | Val |
| | | | 35 | | | | 40 | | | | | 45 | | | |
| Pro | Glu | Leu | Trp | Arg | Asp | Ile | Leu | Glu | Lys | Val | Lys | Ala | Thr | Gly | Phe |
| | 50 | | | | | 55 | | | | | 60 | | | | |
| Thr | Ala | Phe | Ala | Phe | Tyr | Ser | Ser | Trp | Ala | Tyr | His | Ala | Pro | Asn | Asn |
| 65 | | | | | 70 | | | | | 75 | | | | | 80 |
| His | Thr | Val | Asp | Phe | His | Thr | Gly | Ala | Arg | Asp | Ile | Thr | Pro | Ile | Phe |
| | | | | 85 | | | | | 90 | | | | | 95 | |
| Glu | Leu | Ala | Lys | Glu | Leu | Gly | Met | Tyr | Met | Ile | Val | Arg | Pro | Gly | Pro |
| | | | 100 | | | | | 105 | | | | | 110 | | |
| Tyr | Val | Asn | Ala | Glu | Ala | Ser | Ala | Gly | Gly | Phe | Pro | Leu | Trp | Ala | Thr |
| | | | 115 | | | | 120 | | | | | 125 | | | |
| Thr | Gly | Ala | Tyr | Gly | Ser | Met | Arg | Asn | Asp | Asp | Pro | Arg | Tyr | Thr | Ala |
| | 130 | | | | | 135 | | | | | 140 | | | | |
| Ala | Trp | Lys | Pro | Tyr | Phe | Glu | Lys | Met | Ser | Gln | Ile | Thr | Ser | Gln | Tyr |
| 145 | | | | | 150 | | | | | 155 | | | | | 160 |
| Gln | Ile | Thr | Asp | Gly | Glu | Asn | Thr | Phe | Cys | Tyr | Gln | Ile | Glu | Asn | Glu |
| | | | | 165 | | | | | 170 | | | | | 175 | |
| Tyr | Gly | Gln | Gln | Trp | Val | Gly | Asp | Pro | Arg | Asp | Arg | Asn | Pro | Asn | Lys |
| | | | 180 | | | | | 185 | | | | | 190 | | |
| Thr | Ala | Val | Ala | Tyr | Met | Glu | Leu | Leu | Glu | Glu | Ser | Ala | Arg | Glu | Asn |
| | | | 195 | | | | | 200 | | | | | 205 | | |
| Gly | Ile | Val | Val | Pro | Leu | Thr | Ala | Asn | Asp | Pro | Asn | Leu | Asn | Thr | Arg |
| | 210 | | | | | 215 | | | | | 220 | | | | |
| Ser | Trp | Gly | Asn | Asp | Trp | Ser | Asn | Ala | Gly | Gly | Asn | Val | Asp | Val | Pro |
| 225 | | | | | 230 | | | | | 235 | | | | | 240 |
| Gly | Val | Asp | Ser | Tyr | Pro | Ser | Cys | Trp | Thr | Cys | Asp | Val | Ser | Gln | Cys |
| | | | | 245 | | | | | 250 | | | | | 255 | |
| Thr | Ser | Thr | Asn | Gly | Glu | Tyr | Val | Pro | Tyr | Lys | Val | Ile | Pro | Tyr | Tyr |
| | | | 260 | | | | | 265 | | | | | 270 | | |
| Asp | Tyr | Phe | Gln | Glu | Val | Gln | Pro | Ser | Met | Pro | Ala | Phe | Met | Pro | Glu |
| | | | 275 | | | | | 280 | | | | | 285 | | |
| Phe | Gln | Gly | Gly | Ser | Tyr | Asn | Pro | Trp | Ala | Gly | Pro | Glu | Gly | Gly | Cys |
| | 290 | | | | | 295 | | | | | 300 | | | | |
| Pro | Glu | Asp | Thr | Gly | Ala | Asp | Phe | Ala | Asn | Leu | Phe | Tyr | Arg | Trp | Asn |
| 305 | | | | | 310 | | | | | 315 | | | | | 320 |
| Ile | Ala | Gln | Arg | Val | Thr | Ala | Met | Ser | Leu | Tyr | Met | Val | Phe | Gly | Gly |
| | | | | 325 | | | | | 330 | | | | | 335 | |
| Thr | Asn | Trp | Gly | Ser | Leu | Ala | Ala | Pro | Val | Thr | Ala | Thr | Ser | Tyr | Asp |
| | | | 340 | | | | | 345 | | | | | 350 | | |
| Tyr | Ser | Ser | Pro | Ile | Ala | Glu | Asp | Arg | Ser | Ile | Gly | Asp | Lys | Tyr | Tyr |
| | | | 355 | | | | | 360 | | | | | 365 | | |

```
Glu Thr Lys Leu Leu Ser Leu Phe Thr Arg Ser Ala Lys Asp Leu Thr
    370                 375                 380

Met Thr Asp Leu Ile Gly Asn Gly Thr Lys Tyr Thr Asp Asn Ala Ala
385                 390                 395                 400

Val Ser Ala Tyr Glu Leu Arg Asn Pro Glu Thr Asn Gly Ala Phe Tyr
                405                 410                 415

Val Thr Ile His Lys Asp Thr Val Gly Ser Asp Glu Ser Phe Lys
                420                 425                 430

Leu His Val Asn Thr Ser Ala Gly Ala Leu Thr Ile Pro Ser Glu Gly
            435                 440                 445

Ala Lys Ile Arg Leu Asn Gly His Gln Ser Lys Ile Ile Val Thr Asp
450                 455                 460

Phe Ala Phe Gly Ser Lys Thr Leu Leu Tyr Ser Thr Ala Glu Val Leu
465                 470                 475                 480

Thr Tyr Ala Val Ile Asp Asp Gln Pro Thr Leu Val Leu Trp Val Pro
                485                 490                 495

Lys Gly Glu Ser Gly Glu Phe Ala Val Lys Gly Thr Lys Ser Gly Lys
                500                 505                 510

Val Ala Ser Cys Asn Gly Cys Ser Ser Val Lys Phe Asn Gly Lys Lys
            515                 520                 525

Asp His Val Val Gly Phe Thr Gln Ala Lys Gly Met Ser Val Tyr
            530                 535                 540

Gln Leu Asp Asp Asp Val Arg Val Val Val Leu Asp Arg Ser Ser Ala
545                 550                 555                 560

Tyr His Phe Trp Ala Pro Thr Leu Thr Asp Asp Pro Ile Ala Pro Glu
                565                 570                 575

Asp Glu Ile Val Leu Val Glu Gly Pro Tyr Leu Val Arg Ser Ala Ser
            580                 585                 590

Val Glu Gly Ser Thr Leu Ala Leu Arg Gly Asp Ser Thr Asp Lys Thr
            595                 600                 605

Asn Leu Glu Val Phe Ala Pro Lys Ser Val Lys Thr Ile Thr Trp Asn
610                 615                 620

Gly Lys Lys Val Lys Ser Ser Glu Thr Ser Tyr Gly Ser Leu Lys Ala
625                 630                 635                 640

Thr Leu Ala Ala Pro Pro Ser Ile Lys Leu Pro Ser Phe Gly Ser Trp
                645                 650                 655

Arg Ser Asn Asp Ser Leu Pro Glu Arg Leu Glu Ser Tyr Asp Asp Ser
                660                 665                 670

Gly Pro Ala Trp Val Asp Ala Asn His Glu Thr Thr Leu Asn Pro His
            675                 680                 685

Pro Pro Val Thr Thr Pro Val Leu Tyr Ala Asn Glu Tyr Gly Phe His
690                 695                 700

Asn Gly Val Arg Leu Trp Arg Gly Tyr Phe Asn Gly Thr Ala Ser Gly
705                 710                 715                 720

Val Phe Leu Asn Ile Gln Gly Gly Ala Ala Phe Gly Trp Ser Ala Tyr
                725                 730                 735

Leu Asn Gly His Phe Leu Gly Ser Tyr Leu Gly Asn Ala Thr Ile Ala
            740                 745                 750

Gln Ala Asn Lys Thr Leu Thr Phe Pro Asn Asn Thr Leu His Thr Arg
            755                 760                 765

Pro Gly Ser Arg Asn Thr Leu Leu Val Ile His Asp Asp Thr Gly His
770                 775                 780
```

Asp Gln Thr Thr Gly Val Leu Asn Pro Arg Gly Ile Ile Glu Ala Arg
785                 790                 795                 800

Leu Leu Gly Ser Asn Ala Pro Asn Phe Thr His Trp Arg Leu Ala Gly
            805                 810                 815

Thr Ala Gly Gly Glu Ser Asn Leu Asp Pro Val Arg Gly Val Tyr Asn
            820                 825                 830

Glu Asp Gly Leu His Ala Glu Arg Val Gly Trp His Leu Pro Gly Phe
            835                 840                 845

Asp Asp Ser Asp Trp Pro Val Thr Asn His Ser Ser Ser Ser Ser Ser
            850                 855                 860

Ser Lys Ser Leu Ser Thr Leu Ser Phe Thr Gly Ala Thr Val Arg Phe
865                 870                 875                 880

Phe Arg Thr Thr Ile Pro Leu Asn Ile Pro Ser Gly Leu Asp Val Ser
            885                 890                 895

Ile Ser Phe Leu Leu Gly Thr Pro Thr Gly Thr Ser Lys Ala Tyr Arg
            900                 905                 910

Ala Gln Leu Phe Val Asn Gly Tyr Gln Tyr Gly Arg Tyr Tyr Pro His
            915                 920                 925

Ile Gly Asn Gln Val Val Tyr Pro Val Pro Ala Gly Ile Leu Asp Tyr
            930                 935                 940

Arg Gly Glu Asn Thr Ile Gly Leu Ala Val Trp Ala Gln Ser Glu Asp
945                 950                 955                 960

Gly Ala Ala Val Ser Val Asp Trp Arg Val Asn Tyr Val Ala Asp Ser
                    965                 970                 975

Ser Leu Asp Val Ala Gly Ile Gly Glu Glu Arg Leu Arg Pro Gly Tyr
            980                 985                 990

Glu Lys Val Arg Glu Lys Phe Ala
            995                 1000

<210> SEQ ID NO 74
<211> LENGTH: 3299
<212> TYPE: DNA
<213> ORGANISM: Aspergillus wentii
<220> FEATURE:
<221> NAME/KEY: CDS
<222> LOCATION: (1)..(789)
<220> FEATURE:
<221> NAME/KEY: sig_peptide
<222> LOCATION: (1)..(60)
<220> FEATURE:
<221> NAME/KEY: mat_peptide
<222> LOCATION: (61)..(3296)
<220> FEATURE:
<221> NAME/KEY: CDS
<222> LOCATION: (836)..(1829)
<220> FEATURE:
<221> NAME/KEY: CDS
<222> LOCATION: (1877)..(2170)
<220> FEATURE:
<221> NAME/KEY: CDS
<222> LOCATION: (2220)..(2291)
<220> FEATURE:
<221> NAME/KEY: CDS
<222> LOCATION: (2339)..(2426)
<220> FEATURE:
<221> NAME/KEY: CDS
<222> LOCATION: (2474)..(3296)

<400> SEQUENCE: 74 atg gcg cgc att ttc cat ttg ttt ctt gcc cta ctt tca agt ata ggg      48
Met Ala Arg Ile Phe His Leu Phe Leu Ala Leu Leu Ser Ser Ile Gly
-20                 -15                 -10                 -5 ctt ttg gca gct gca gag tca caa tgg cct ctc cac gat aac agc tta     96

```
                Leu Leu Ala Ala Ala Glu Ser Gln Trp Pro Leu His Asp Asn Ser Leu
                            -1  1                   5                   10 aac acc gtc gtt caa tgg gat cat tac agc ttc cag atc cac ggg cag              144
Asn Thr Val Val Gln Trp Asp His Tyr Ser Phe Gln Ile His Gly Gln
        15                  20                  25 aga atc ttc gtc ttc tcc ggt gaa ttc cac tac tgg cgc att cca gtt              192
Arg Ile Phe Val Phe Ser Gly Glu Phe His Tyr Trp Arg Ile Pro Val
    30                  35                  40 cca gga cta tgg agg gat att ctt gag aag att aaa gcg gct gga ttt              240
Pro Gly Leu Trp Arg Asp Ile Leu Glu Lys Ile Lys Ala Ala Gly Phe
45                  50                  55                  60 act gca ttc gca ttt tac tcc agt tgg gct tac cat gcg cca aat aac              288
Thr Ala Phe Ala Phe Tyr Ser Ser Trp Ala Tyr His Ala Pro Asn Asn
            65                  70                  75 cat acc gtt gac ttt tcg acc ggt gct cgt gat atc aca cct att ttc              336
His Thr Val Asp Phe Ser Thr Gly Ala Arg Asp Ile Thr Pro Ile Phe
        80                  85                  90 gaa ctt gcc aag gag ttg ggc ttg tat atc atc gtt cgc cca ggg cca              384
Glu Leu Ala Lys Glu Leu Gly Leu Tyr Ile Ile Val Arg Pro Gly Pro
    95                  100                 105 tat gtc aat gcg gaa gcc aat gct ggt ggc ttt ccc ttg tgg ctg acg              432
Tyr Val Asn Ala Glu Ala Asn Ala Gly Gly Phe Pro Leu Trp Leu Thr
110                 115                 120 act ggg gaa tac gga acg cta cgc aat gac gat gaa cgc tat act gcc              480
Thr Gly Glu Tyr Gly Thr Leu Arg Asn Asp Asp Glu Arg Tyr Thr Ala
125                 130                 135                 140 gcg tgg aag ccg tac ttc act aaa atg tcg cag att acg agc aaa tat              528
Ala Trp Lys Pro Tyr Phe Thr Lys Met Ser Gln Ile Thr Ser Lys Tyr
            145                 150                 155 cag atc acg gat ggc gag aac acc ttg ttt tat cag att gaa aac gaa              576
Gln Ile Thr Asp Gly Glu Asn Thr Leu Phe Tyr Gln Ile Glu Asn Glu
        160                 165                 170 tac gga gac cag tgg atc ggc gat cca agt gat cga gtt ccg aat aat              624
Tyr Gly Asp Gln Trp Ile Gly Asp Pro Ser Asp Arg Val Pro Asn Asn
    175                 180                 185 act gca att gct tat atg gag ctt ctc gag gcg agt gca cgg gaa aac              672
Thr Ala Ile Ala Tyr Met Glu Leu Leu Glu Ala Ser Ala Arg Glu Asn
190                 195                 200 ggc atc aat gta cct ctc acc gcg aat gat cct aat atg aac tcg aaa              720
Gly Ile Asn Val Pro Leu Thr Ala Asn Asp Pro Asn Met Asn Ser Lys
205                 210                 215                 220 tct tgg ggg aaa gat tgg tct aat gct ggt gga aac gtt gac gcc cct              768
Ser Trp Gly Lys Asp Trp Ser Asn Ala Gly Gly Asn Val Asp Ala Pro
            225                 230                 235 ggc ttg gac tct tac ccg tcg gtaggttaac cataactcta agactggatt                 819
Gly Leu Asp Ser Tyr Pro Ser
            240 attctgacag tagcag tgt tgg acg tgt gat att agc caa tgc acc tcg acg            871
                  Cys Trp Thr Cys Asp Ile Ser Gln Cys Thr Ser Thr
                              245                 250                 255 aat ggc gag tat gtg ccg tac aaa gta atg cag tat tac gac tac ttc              919
Asn Gly Glu Tyr Val Pro Tyr Lys Val Met Gln Tyr Tyr Asp Tyr Phe
        260                 265                 270 caa gaa gtt caa ccg aca acg ccg tct ttc atg ccc gag ttc cag ggc              967
Gln Glu Val Gln Pro Thr Thr Pro Ser Phe Met Pro Glu Phe Gln Gly
    275                 280                 285 ggt tct tac aat ccc tgg gca gga cct gaa ggt gga tgc tcc gag aat              1015
Gly Ser Tyr Asn Pro Trp Ala Gly Pro Glu Gly Gly Cys Ser Glu Asn
290                 295                 300
```

-continued

| | | | | | | | | | | | | | | | | |
|---|---|---|---|---|---|---|---|---|---|---|---|---|---|---|---|---|
| acc | ggg | gca | gac | ttt | gcg | aat | ctg | ttc | tat | cgg | tgg | aac | att | ggc | cag | 1063 |
| Thr | Gly | Ala | Asp | Phe | Ala | Asn | Leu | Phe | Tyr | Arg | Trp | Asn | Ile | Gly | Gln | |
| | 305 | | | | 310 | | | | | 315 | | | | | | |

| | | | | | | | | | | | | | | | | |
|---|---|---|---|---|---|---|---|---|---|---|---|---|---|---|---|---|
| cat | gtg | acg | gct | atg | agt | ctg | tac | atg | cta | tac | gga | ggt | acg | aat | tgg | 1111 |
| His | Val | Thr | Ala | Met | Ser | Leu | Tyr | Met | Leu | Tyr | Gly | Gly | Thr | Asn | Trp | |
| 320 | | | | | 325 | | | | | 330 | | | | | 335 | |

| | | | | | | | | | | | | | | | | |
|---|---|---|---|---|---|---|---|---|---|---|---|---|---|---|---|---|
| ggg | tcg | ctc | gct | gca | ccg | gtg | acg | gca | agt | agt | tat | gac | tac | tca | gcc | 1159 |
| Gly | Ser | Leu | Ala | Ala | Pro | Val | Thr | Ala | Ser | Ser | Tyr | Asp | Tyr | Ser | Ala | |
| | | | | 340 | | | | | 345 | | | | | 350 | | |

| | | | | | | | | | | | | | | | | |
|---|---|---|---|---|---|---|---|---|---|---|---|---|---|---|---|---|
| ccg | att | tcc | gaa | gat | cgg | tct | att | ggg | gca | aag | tat | tat | gag | act | aaa | 1207 |
| Pro | Ile | Ser | Glu | Asp | Arg | Ser | Ile | Gly | Ala | Lys | Tyr | Tyr | Glu | Thr | Lys | |
| | | | 355 | | | | | 360 | | | | | 365 | | | |

| | | | | | | | | | | | | | | | | |
|---|---|---|---|---|---|---|---|---|---|---|---|---|---|---|---|---|
| cta | ctg | gca | ttg | ttc | acg | cgg | tgt | gca | aga | gat | ttg | acc | atg | act | gaa | 1255 |
| Leu | Leu | Ala | Leu | Phe | Thr | Arg | Cys | Ala | Arg | Asp | Leu | Thr | Met | Thr | Glu | |
| | | 370 | | | | | 375 | | | | | 380 | | | | |

| | | | | | | | | | | | | | | | | |
|---|---|---|---|---|---|---|---|---|---|---|---|---|---|---|---|---|
| ttg | att | gga | aat | gga | act | cag | tat | acc | gat | aat | ata | gca | gtg | gaa | gca | 1303 |
| Leu | Ile | Gly | Asn | Gly | Thr | Gln | Tyr | Thr | Asp | Asn | Ile | Ala | Val | Glu | Ala | |
| 385 | | | | | 390 | | | | | 395 | | | | | | |

| | | | | | | | | | | | | | | | | |
|---|---|---|---|---|---|---|---|---|---|---|---|---|---|---|---|---|
| tac | gaa | ttg | agg | aat | ccg | cag | acc | aat | gcc | ggt | ttc | tac | gtt | acc | atc | 1351 |
| Tyr | Glu | Leu | Arg | Asn | Pro | Gln | Thr | Asn | Ala | Gly | Phe | Tyr | Val | Thr | Ile | |
| 400 | | | | | 405 | | | | | 410 | | | | | 415 | |

| | | | | | | | | | | | | | | | | |
|---|---|---|---|---|---|---|---|---|---|---|---|---|---|---|---|---|
| cac | agc | aac | tct | tcc | tct | ggg | aca | aac | gag | gcc | ttt | caa | ctt | cag | gtc | 1399 |
| His | Ser | Asn | Ser | Ser | Ser | Gly | Thr | Asn | Glu | Ala | Phe | Gln | Leu | Gln | Val | |
| | | | | 420 | | | | | 425 | | | | | 430 | | |

| | | | | | | | | | | | | | | | | |
|---|---|---|---|---|---|---|---|---|---|---|---|---|---|---|---|---|
| aac | act | tct | gtc | gga | ggt | ctg | act | gtt | cct | agc | cat | gga | ggt | act | ata | 1447 |
| Asn | Thr | Ser | Val | Gly | Gly | Leu | Thr | Val | Pro | Ser | His | Gly | Gly | Thr | Ile | |
| | | | 435 | | | | | 440 | | | | | 445 | | | |

| | | | | | | | | | | | | | | | | |
|---|---|---|---|---|---|---|---|---|---|---|---|---|---|---|---|---|
| cgt | ctc | aat | ggt | cac | cag | tcc | aag | att | atc | gtg | acg | gac | ttt | aca | ttt | 1495 |
| Arg | Leu | Asn | Gly | His | Gln | Ser | Lys | Ile | Ile | Val | Thr | Asp | Phe | Thr | Phe | |
| | | 450 | | | | | 455 | | | | | 460 | | | | |

| | | | | | | | | | | | | | | | | |
|---|---|---|---|---|---|---|---|---|---|---|---|---|---|---|---|---|
| ggt | tcc | aag | act | ctt | ctc | tat | tcc | acc | gcg | gag | gtt | ctc | acc | tac | gct | 1543 |
| Gly | Ser | Lys | Thr | Leu | Leu | Tyr | Ser | Thr | Ala | Glu | Val | Leu | Thr | Tyr | Ala | |
| | 465 | | | | | 470 | | | | | 475 | | | | | |

| | | | | | | | | | | | | | | | | |
|---|---|---|---|---|---|---|---|---|---|---|---|---|---|---|---|---|
| gtg | ttg | gat | gac | aaa | cct | aca | ctt | gtc | ctc | tgg | gta | cct | acc | gga | gaa | 1591 |
| Val | Leu | Asp | Asp | Lys | Pro | Thr | Leu | Val | Leu | Trp | Val | Pro | Thr | Gly | Glu | |
| 480 | | | | | 485 | | | | | 490 | | | | | 495 | |

| | | | | | | | | | | | | | | | | |
|---|---|---|---|---|---|---|---|---|---|---|---|---|---|---|---|---|
| tcc | ggc | gag | ttc | tcc | atc | aaa | gga | gtc | aag | tct | gga | tca | gtc | agt | aac | 1639 |
| Ser | Gly | Glu | Phe | Ser | Ile | Lys | Gly | Val | Lys | Ser | Gly | Ser | Val | Ser | Asn | |
| | | | | 500 | | | | | 505 | | | | | 510 | | |

| | | | | | | | | | | | | | | | | |
|---|---|---|---|---|---|---|---|---|---|---|---|---|---|---|---|---|
| tgt | cag | ggc | tgc | tcg | ggt | atg | ggt | ttc | tac | cag | gaa | aat | ggt | ggt | ctc | 1687 |
| Cys | Gln | Gly | Cys | Ser | Gly | Met | Gly | Phe | Tyr | Gln | Glu | Asn | Gly | Gly | Leu | |
| | | | 515 | | | | | 520 | | | | | 525 | | | |

| | | | | | | | | | | | | | | | | |
|---|---|---|---|---|---|---|---|---|---|---|---|---|---|---|---|---|
| acg | gta | aga | ttc | acc | cag | tca | tct | gga | atg | agc | atc | ctc | cag | ctc | gac | 1735 |
| Thr | Val | Arg | Phe | Thr | Gln | Ser | Ser | Gly | Met | Ser | Ile | Leu | Gln | Leu | Asp | |
| | | 530 | | | | | 535 | | | | | 540 | | | | |

| | | | | | | | | | | | | | | | | |
|---|---|---|---|---|---|---|---|---|---|---|---|---|---|---|---|---|
| gat | gta | cgc | gtg | gtt | tta | ctc | gat | aga | aca | agc | gca | tat | aat | ttc | tgg | 1783 |
| Asp | Val | Arg | Val | Val | Leu | Leu | Asp | Arg | Thr | Ser | Ala | Tyr | Asn | Phe | Trp | |
| | 545 | | | | | 550 | | | | | 555 | | | | | |

| | | | | | | | | | | | | | |
|---|---|---|---|---|---|---|---|---|---|---|---|---|---|
| gcg | cct | gca | ttg | aca | aat | gac | cca | ttt | gtt | cca | gag | aca | gaa | agt | g | 1829 |
| Ala | Pro | Ala | Leu | Thr | Asn | Asp | Pro | Phe | Val | Pro | Glu | Thr | Glu | Ser | |
| 560 | | | | | 565 | | | | | 570 | | | | | |

| | | | | | |
|---|---|---|---|---|---|
| gtatgtttcg cctgatttat taattggcat ttactaaccg gtcgaag tt | ctg | att | 1884 |
| | Val | Leu | Ile | |
| | | | 575 | |

| | | | | | | | | | | | | | | | |
|---|---|---|---|---|---|---|---|---|---|---|---|---|---|---|---|
| caa | ggt | cca | tac | ctc | gtt | cgc | ggt | gcc | aaa | att | act | gaa | tca | act | ctt | 1932 |
| Gln | Gly | Pro | Tyr | Leu | Val | Arg | Gly | Ala | Lys | Ile | Thr | Glu | Ser | Thr | Leu |
| | | 580 | | | | | 585 | | | | | 590 | | | |

| | | | | | | | | | | | | | | | |
|---|---|---|---|---|---|---|---|---|---|---|---|---|---|---|---|
| gca | gtg | act | ggt | gat | tct | gtg | gat | gct | acg | agt | atc | gag | gtc | ttc | gca | 1980 |
| Ala | Val | Thr | Gly | Asp | Ser | Val | Asp | Ala | Thr | Ser | Ile | Glu | Val | Phe | Ala |
| | 595 | | | | | 600 | | | | | 605 | | | | |

```
ccc cag acc ttg gat aca atc acc tgg aat ggc aaa gag gtc aaa acc      2028
Pro Gln Thr Leu Asp Thr Ile Thr Trp Asn Gly Lys Glu Val Lys Thr
610                 615                 620                 625 acg agg acg gaa tat gga agt ctg cgg gct tct ctt gct gca cca cca      2076
Thr Arg Thr Glu Tyr Gly Ser Leu Arg Ala Ser Leu Ala Ala Pro Pro
                630                 635                 640 tct att aag tta ccc tcg ttg aca tcg tgg aaa aca aaa gac agt cta      2124
Ser Ile Lys Leu Pro Ser Leu Thr Ser Trp Lys Thr Lys Asp Ser Leu
    645                 650                 655 cca gag cgg ttg cca tca tat gat gac tct ggt gag gcg tgg gct g        2170
Pro Glu Arg Leu Pro Ser Tyr Asp Asp Ser Gly Glu Ala Trp Ala
660                 665                 670 gtaagtgcca cttatctatc tacactcact caatgctaat cgaggatag at  gcc aac    2227
                                                         Asp Ala Asn
                                                                 675 cat atg aca act tcg aat cca cat aaa cca gaa act tat ccc gtt ctt      2275
His Met Thr Thr Ser Asn Pro His Lys Pro Glu Thr Tyr Pro Val Leu
                    680                 685                 690 tat ggg gat gat tat g gtatgtccat tgtatccatg atagttatca ataagctaac    2331
Tyr Gly Asp Asp Tyr
695 aaagaag gc  ttc cac aac ggc atc cgt ctc tgg cga gga tac ttt aac      2379
        Gly Phe His Asn Gly Ile Arg Leu Trp Arg Gly Tyr Phe Asn
            700                 705                 710 aac acc gcg aaa ggc gtc tac ctg aac atc caa gga gga aca gct tt       2426
Asn Thr Ala Lys Gly Val Tyr Leu Asn Ile Gln Gly Gly Thr Ala Phe
                715                 720                 725 gtaagatcca tctcttttcc atttaggtga acaagctaac aaatcag t ggc tgg tct    2483
                                                     Gly Trp Ser gcc tat ctg aac ggc cac ttc ctc tcc tct tac ctg ggc aat gca aca      2531
Ala Tyr Leu Asn Gly His Phe Leu Ser Ser Tyr Leu Gly Asn Ala Thr
730                 735                 740                 745 gaa acc caa gga aat aag acc atc ctc ttc cca tct gat atc ctc tcc      2579
Glu Thr Gln Gly Asn Lys Thr Ile Leu Phe Pro Ser Asp Ile Leu Ser
                750                 755                 760 aca aaa cca gaa acg aat cca aat acc ctc ctc atc atc cac gat gac      2627
Thr Lys Pro Glu Thr Asn Pro Asn Thr Leu Leu Ile Ile His Asp Asp
    765                 770                 775 aca ggc cac gac caa aca acc ggc gtt ctc aac ccg cgc ggc atc ctc      2675
Thr Gly His Asp Gln Thr Thr Gly Val Leu Asn Pro Arg Gly Ile Leu
        780                 785                 790 gaa gca cgt ctc ctc gac gaa gac gag aaa agc agt gaa gac ctc gca      2723
Glu Ala Arg Leu Leu Asp Glu Asp Glu Lys Ser Ser Glu Asp Leu Ala
795                 800                 805 ttt acg cac tgg cgc gtt gca ggt aca gct gga gga gaa tcg aat ctc      2771
Phe Thr His Trp Arg Val Ala Gly Thr Ala Gly Gly Glu Ser Asn Leu
810                 815                 820                 825 gat ccc gtc cgc ggc gta tac aat gaa gac gga cta tac gcc gaa cgg      2819
Asp Pro Val Arg Gly Val Tyr Asn Glu Asp Gly Leu Tyr Ala Glu Arg
                830                 835                 840 atg ggc tgg cat tta ccc ggt ttc gac gat agt gat tgg tct acg att      2867
Met Gly Trp His Leu Pro Gly Phe Asp Asp Ser Asp Trp Ser Thr Ile
                    845                 850                 855 aac aca acc acg tcc agt act acc agc agc ccc cca tta aca ttc acc      2915
Asn Thr Thr Thr Ser Ser Thr Thr Ser Ser Pro Pro Leu Thr Phe Thr
                860                 865                 870 aac gca acc atc caa ttc ttc cga agc gtc atc ccc ctc gac ctc ccc      2963
Asn Ala Thr Ile Gln Phe Phe Arg Ser Val Ile Pro Leu Asp Leu Pro
875                 880                 885
```

```
aac aac acc gac aca tcc atg tcc ttc atc ctc tcc act cca tcc acc    3011
Asn Asn Thr Asp Thr Ser Met Ser Phe Ile Leu Ser Thr Pro Ser Thr
890             895                 900                 905 agc agc aaa gcc tac cgc gcc caa ata ttc ata aac ggg tac caa tac    3059
Ser Ser Lys Ala Tyr Arg Ala Gln Ile Phe Ile Asn Gly Tyr Gln Tyr
            910                 915                 920 ggc cgg tac aac ccc cac atc ggg aac cag gtg gtc ttc ccc gtt ccg    3107
Gly Arg Tyr Asn Pro His Ile Gly Asn Gln Val Val Phe Pro Val Pro
                925                 930                 935 ccg ggg ata ctg gat tac cac ggc gac aac acg att gga gta gcg gtg    3155
Pro Gly Ile Leu Asp Tyr His Gly Asp Asn Thr Ile Gly Val Ala Val
        940                 945                 950 tgg gca cag agc gag gat ggg gcg agt att gaa tta gat tgg agg gtg    3203
Trp Ala Gln Ser Glu Asp Gly Ala Ser Ile Glu Leu Asp Trp Arg Val
    955                 960                 965 aat tac gtt gct gat agt tcg ctg gat gtg ggc cgt ttg gat gag ggg    3251
Asn Tyr Val Ala Asp Ser Ser Leu Asp Val Gly Arg Leu Asp Glu Gly
970                 975                 980                 985 gga tcg ctg agg ccg ggg tgg agt gag gag agg ttg agg ttt gcg tga   3299
Gly Ser Leu Arg Pro Gly Trp Ser Glu Glu Arg Leu Arg Phe Ala
                990                 995                 1000

<210> SEQ ID NO 75
<211> LENGTH: 1020
<212> TYPE: PRT
<213> ORGANISM: Aspergillus wentii

<400> SEQUENCE: 75

Met Ala Arg Ile Phe His Leu Phe Leu Ala Leu Ser Ser Ile Gly
-20                 -15                 -10                 -5

Leu Leu Ala Ala Ala Glu Ser Gln Trp Pro Leu His Asp Asn Ser Leu
        -1  1                 5                  10

Asn Thr Val Val Gln Trp Asp His Tyr Ser Phe Gln Ile His Gly Gln
             15                  20                  25

Arg Ile Phe Val Phe Ser Gly Glu Phe His Tyr Trp Arg Ile Pro Val
         30                  35                  40

Pro Gly Leu Trp Arg Asp Ile Leu Glu Lys Ile Lys Ala Gly Phe
45                  50                  55                  60

Thr Ala Phe Ala Phe Tyr Ser Ser Trp Ala Tyr His Ala Pro Asn Asn
                 65                  70                  75

His Thr Val Asp Phe Ser Thr Gly Ala Arg Asp Ile Thr Pro Ile Phe
             80                  85                  90

Glu Leu Ala Lys Glu Leu Gly Leu Tyr Ile Ile Val Arg Pro Gly Pro
         95                 100                 105

Tyr Val Asn Ala Glu Ala Asn Ala Gly Gly Phe Pro Leu Trp Leu Thr
110                 115                 120

Thr Gly Glu Tyr Gly Thr Leu Arg Asn Asp Asp Glu Arg Tyr Thr Ala
125                 130                 135                 140

Ala Trp Lys Pro Tyr Phe Thr Lys Met Ser Gln Ile Thr Ser Lys Tyr
                145                 150                 155

Gln Ile Thr Asp Gly Glu Asn Thr Leu Phe Tyr Gln Ile Glu Asn Glu
            160                 165                 170

Tyr Gly Asp Gln Trp Ile Gly Asp Pro Ser Asp Arg Val Pro Asn Asn
        175                 180                 185

Thr Ala Ile Ala Tyr Met Glu Leu Leu Glu Ala Ser Ala Arg Glu Asn
    190                 195                 200
```

-continued

```
Gly Ile Asn Val Pro Leu Thr Ala Asn Asp Pro Asn Met Asn Ser Lys
205                 210                 215                 220

Ser Trp Gly Lys Asp Trp Ser Asn Ala Gly Gly Asn Val Asp Ala Pro
            225                 230                 235

Gly Leu Asp Ser Tyr Pro Ser Cys Trp Thr Cys Asp Ile Ser Gln Cys
                240                 245                 250

Thr Ser Thr Asn Gly Glu Tyr Val Pro Tyr Lys Val Met Gln Tyr Tyr
            255                 260                 265

Asp Tyr Phe Gln Glu Val Gln Pro Thr Thr Pro Ser Phe Met Pro Glu
270                 275                 280

Phe Gln Gly Gly Ser Tyr Asn Pro Trp Ala Gly Pro Glu Gly Gly Cys
285                 290                 295                 300

Ser Glu Asn Thr Gly Ala Asp Phe Ala Asn Leu Phe Tyr Arg Trp Asn
                305                 310                 315

Ile Gly Gln His Val Thr Ala Met Ser Leu Tyr Met Leu Tyr Gly Gly
                320                 325                 330

Thr Asn Trp Gly Ser Leu Ala Ala Pro Val Thr Ala Ser Ser Tyr Asp
            335                 340                 345

Tyr Ser Ala Pro Ile Ser Glu Asp Arg Ser Ile Gly Ala Lys Tyr Tyr
350                 355                 360

Glu Thr Lys Leu Leu Ala Leu Phe Thr Arg Cys Ala Arg Asp Leu Thr
365                 370                 375                 380

Met Thr Glu Leu Ile Gly Asn Gly Thr Gln Tyr Thr Asp Asn Ile Ala
                385                 390                 395

Val Glu Ala Tyr Glu Leu Arg Asn Pro Gln Thr Asn Ala Gly Phe Tyr
            400                 405                 410

Val Thr Ile His Ser Asn Ser Ser Gly Thr Asn Glu Ala Phe Gln
            415                 420                 425

Leu Gln Val Asn Thr Ser Val Gly Gly Leu Thr Val Pro Ser His Gly
            430                 435                 440

Gly Thr Ile Arg Leu Asn Gly His Gln Ser Lys Ile Ile Val Thr Asp
445                 450                 455                 460

Phe Thr Phe Gly Ser Lys Thr Leu Leu Tyr Ser Thr Ala Glu Val Leu
                465                 470                 475

Thr Tyr Ala Val Leu Asp Asp Lys Pro Thr Leu Val Leu Trp Val Pro
            480                 485                 490

Thr Gly Glu Ser Gly Glu Phe Ser Ile Lys Gly Val Lys Ser Gly Ser
            495                 500                 505

Val Ser Asn Cys Gln Gly Cys Ser Gly Met Gly Phe Tyr Gln Glu Asn
510                 515                 520

Gly Gly Leu Thr Val Arg Phe Thr Gln Ser Ser Gly Met Ser Ile Leu
525                 530                 535                 540

Gln Leu Asp Asp Val Arg Val Leu Leu Asp Arg Thr Ser Ala Tyr
                545                 550                 555

Asn Phe Trp Ala Pro Ala Leu Thr Asn Asp Pro Phe Val Pro Glu Thr
            560                 565                 570

Glu Ser Val Leu Ile Gln Gly Pro Tyr Leu Val Arg Gly Ala Lys Ile
            575                 580                 585

Thr Glu Ser Thr Leu Ala Val Thr Gly Asp Ser Val Asp Ala Thr Ser
            590                 595                 600

Ile Glu Val Phe Ala Pro Gln Thr Leu Asp Thr Ile Thr Trp Asn Gly
605                 610                 615                 620

Lys Glu Val Lys Thr Thr Arg Thr Glu Tyr Gly Ser Leu Arg Ala Ser
```

```
                    625                 630                 635
Leu Ala Ala Pro Pro Ser Ile Lys Leu Pro Ser Leu Thr Ser Trp Lys
                640                 645                 650

Thr Lys Asp Ser Leu Pro Glu Arg Leu Pro Ser Tyr Asp Asp Ser Gly
                655                 660                 665

Glu Ala Trp Ala Asp Ala Asn His Met Thr Thr Ser Asn Pro His Lys
                670                 675                 680

Pro Glu Thr Tyr Pro Val Leu Tyr Gly Asp Asp Tyr Gly Phe His Asn
685                 690                 695                 700

Gly Ile Arg Leu Trp Arg Gly Tyr Phe Asn Asn Thr Ala Lys Gly Val
                705                 710                 715

Tyr Leu Asn Ile Gln Gly Gly Thr Ala Phe Gly Trp Ser Ala Tyr Leu
                720                 725                 730

Asn Gly His Phe Leu Ser Ser Tyr Leu Gly Asn Ala Thr Glu Thr Gln
                735                 740                 745

Gly Asn Lys Thr Ile Leu Phe Pro Ser Asp Ile Leu Ser Thr Lys Pro
                750                 755                 760

Glu Thr Asn Pro Asn Thr Leu Leu Ile Ile His Asp Asp Thr Gly His
765                 770                 775                 780

Asp Gln Thr Thr Gly Val Leu Asn Pro Arg Gly Ile Leu Glu Ala Arg
                785                 790                 795

Leu Leu Asp Glu Asp Glu Lys Ser Ser Glu Asp Leu Ala Phe Thr His
                800                 805                 810

Trp Arg Val Ala Gly Thr Ala Gly Gly Glu Ser Asn Leu Asp Pro Val
                815                 820                 825

Arg Gly Val Tyr Asn Glu Asp Gly Leu Tyr Ala Glu Arg Met Gly Trp
                830                 835                 840

His Leu Pro Gly Phe Asp Asp Ser Asp Trp Ser Thr Ile Asn Thr Thr
845                 850                 855                 860

Thr Ser Ser Thr Thr Ser Ser Pro Pro Leu Thr Phe Thr Asn Ala Thr
                865                 870                 875

Ile Gln Phe Phe Arg Ser Val Ile Pro Leu Asp Leu Pro Asn Asn Thr
                880                 885                 890

Asp Thr Ser Met Ser Phe Ile Leu Ser Thr Pro Ser Thr Ser Ser Lys
                895                 900                 905

Ala Tyr Arg Ala Gln Ile Phe Ile Asn Gly Tyr Gln Tyr Gly Arg Tyr
                910                 915                 920

Asn Pro His Ile Gly Asn Gln Val Val Phe Pro Val Pro Pro Gly Ile
925                 930                 935                 940

Leu Asp Tyr His Gly Asp Asn Thr Ile Gly Val Ala Val Trp Ala Gln
                945                 950                 955

Ser Glu Asp Gly Ala Ser Ile Glu Leu Asp Trp Arg Val Asn Tyr Val
                960                 965                 970

Ala Asp Ser Ser Leu Asp Val Gly Arg Leu Asp Glu Gly Gly Ser Leu
                975                 980                 985

Arg Pro Gly Trp Ser Glu Glu Arg Leu Arg Phe Ala
                990                 995                 1000

<210> SEQ ID NO 76
<211> LENGTH: 1000
<212> TYPE: PRT
<213> ORGANISM: Aspergillus wentii
<220> FEATURE:
<221> NAME/KEY: mat_peptide
<222> LOCATION: (1)..(1000)
```

<400> SEQUENCE: 76

Ala Glu Ser Gln Trp Pro Leu His Asp Asn Ser Leu Asn Thr Val Val
1               5                   10                  15

Gln Trp Asp His Tyr Ser Phe Gln Ile His Gly Gln Arg Ile Phe Val
            20                  25                  30

Phe Ser Gly Glu Phe His Tyr Trp Arg Ile Pro Val Pro Gly Leu Trp
        35                  40                  45

Arg Asp Ile Leu Glu Lys Ile Lys Ala Ala Gly Phe Thr Ala Phe Ala
50                  55                  60

Phe Tyr Ser Ser Trp Ala Tyr His Ala Pro Asn Asn His Thr Val Asp
65                  70                  75                  80

Phe Ser Thr Gly Ala Arg Asp Ile Thr Pro Ile Phe Glu Leu Ala Lys
            85                  90                  95

Glu Leu Gly Leu Tyr Ile Ile Val Arg Pro Gly Pro Tyr Val Asn Ala
            100                 105                 110

Glu Ala Asn Ala Gly Gly Phe Pro Leu Trp Leu Thr Thr Gly Glu Tyr
            115                 120                 125

Gly Thr Leu Arg Asn Asp Asp Glu Arg Tyr Thr Ala Ala Trp Lys Pro
130                 135                 140

Tyr Phe Thr Lys Met Ser Gln Ile Thr Ser Lys Tyr Gln Ile Thr Asp
145                 150                 155                 160

Gly Glu Asn Thr Leu Phe Tyr Gln Ile Glu Asn Glu Tyr Gly Asp Gln
            165                 170                 175

Trp Ile Gly Asp Pro Ser Asp Arg Val Pro Asn Asn Thr Ala Ile Ala
            180                 185                 190

Tyr Met Glu Leu Leu Glu Ala Ser Ala Arg Glu Asn Gly Ile Asn Val
        195                 200                 205

Pro Leu Thr Ala Asn Asp Pro Asn Met Asn Ser Lys Ser Trp Gly Lys
210                 215                 220

Asp Trp Ser Asn Ala Gly Gly Asn Val Asp Ala Pro Gly Leu Asp Ser
225                 230                 235                 240

Tyr Pro Ser Cys Trp Thr Cys Asp Ile Ser Gln Cys Thr Ser Thr Asn
            245                 250                 255

Gly Glu Tyr Val Pro Tyr Lys Val Met Gln Tyr Tyr Asp Tyr Phe Gln
            260                 265                 270

Glu Val Gln Pro Thr Thr Pro Ser Phe Met Pro Glu Phe Gln Gly Gly
        275                 280                 285

Ser Tyr Asn Pro Trp Ala Gly Pro Glu Gly Gly Cys Ser Glu Asn Thr
        290                 295                 300

Gly Ala Asp Phe Ala Asn Leu Phe Tyr Arg Trp Asn Ile Gly Gln His
305                 310                 315                 320

Val Thr Ala Met Ser Leu Tyr Met Leu Tyr Gly Gly Thr Asn Trp Gly
            325                 330                 335

Ser Leu Ala Ala Pro Val Thr Ala Ser Ser Tyr Asp Tyr Ser Ala Pro
            340                 345                 350

Ile Ser Glu Asp Arg Ser Ile Gly Ala Lys Tyr Tyr Glu Thr Lys Leu
            355                 360                 365

Leu Ala Leu Phe Thr Arg Cys Ala Arg Asp Leu Thr Met Thr Glu Leu
            370                 375                 380

Ile Gly Asn Gly Thr Gln Tyr Thr Asp Asn Ile Ala Val Glu Ala Tyr
385                 390                 395                 400

Glu Leu Arg Asn Pro Gln Thr Asn Ala Gly Phe Tyr Val Thr Ile His

-continued

```
                405                 410                 415
Ser Asn Ser Ser Ser Gly Thr Asn Glu Ala Phe Gln Leu Gln Val Asn
                420                 425                 430

Thr Ser Val Gly Gly Leu Thr Val Pro Ser His Gly Gly Thr Ile Arg
                435                 440                 445

Leu Asn Gly His Gln Ser Lys Ile Ile Val Thr Asp Phe Thr Phe Gly
            450                 455                 460

Ser Lys Thr Leu Leu Tyr Ser Thr Ala Glu Val Leu Thr Tyr Ala Val
465                 470                 475                 480

Leu Asp Asp Lys Pro Thr Leu Val Leu Trp Val Pro Thr Gly Glu Ser
                485                 490                 495

Gly Glu Phe Ser Ile Lys Gly Val Lys Ser Gly Ser Val Ser Asn Cys
                500                 505                 510

Gln Gly Cys Ser Gly Met Gly Phe Tyr Gln Glu Asn Gly Gly Leu Thr
            515                 520                 525

Val Arg Phe Thr Gln Ser Ser Gly Met Ser Ile Leu Gln Leu Asp Asp
            530                 535                 540

Val Arg Val Val Leu Leu Asp Arg Thr Ser Ala Tyr Asn Phe Trp Ala
545                 550                 555                 560

Pro Ala Leu Thr Asn Asp Pro Phe Val Pro Glu Thr Glu Ser Val Leu
                565                 570                 575

Ile Gln Gly Pro Tyr Leu Val Arg Gly Ala Lys Ile Thr Glu Ser Thr
            580                 585                 590

Leu Ala Val Thr Gly Asp Ser Val Asp Ala Thr Ser Ile Glu Val Phe
            595                 600                 605

Ala Pro Gln Thr Leu Asp Thr Ile Thr Trp Asn Gly Lys Glu Val Lys
        610                 615                 620

Thr Thr Arg Thr Glu Tyr Gly Ser Leu Arg Ala Ser Leu Ala Ala Pro
625                 630                 635                 640

Pro Ser Ile Lys Leu Pro Ser Leu Thr Ser Trp Lys Thr Lys Asp Ser
                645                 650                 655

Leu Pro Glu Arg Leu Pro Ser Tyr Asp Asp Ser Gly Glu Ala Trp Ala
            660                 665                 670

Asp Ala Asn His Met Thr Thr Ser Asn Pro His Lys Pro Glu Thr Tyr
            675                 680                 685

Pro Val Leu Tyr Gly Asp Asp Tyr Gly Phe His Asn Gly Ile Arg Leu
        690                 695                 700

Trp Arg Gly Tyr Phe Asn Asn Thr Ala Lys Gly Val Tyr Leu Asn Ile
705                 710                 715                 720

Gln Gly Gly Thr Ala Phe Gly Trp Ser Ala Tyr Leu Asn Gly His Phe
                725                 730                 735

Leu Ser Ser Tyr Leu Gly Asn Ala Thr Glu Thr Gln Gly Asn Lys Thr
            740                 745                 750

Ile Leu Phe Pro Ser Asp Ile Leu Ser Thr Lys Pro Glu Thr Asn Pro
            755                 760                 765

Asn Thr Leu Leu Ile Ile His Asp Asp Thr Gly His Asp Gln Thr Thr
        770                 775                 780

Gly Val Leu Asn Pro Arg Gly Ile Leu Glu Ala Arg Leu Leu Asp Glu
785                 790                 795                 800

Asp Glu Lys Ser Ser Glu Asp Leu Ala Phe Thr His Trp Arg Val Ala
                805                 810                 815

Gly Thr Ala Gly Gly Glu Ser Asn Leu Asp Pro Val Arg Gly Val Tyr
            820                 825                 830
```

Asn Glu Asp Gly Leu Tyr Ala Glu Arg Met Gly Trp His Leu Pro Gly
    835                 840                 845

Phe Asp Ser Asp Trp Ser Thr Ile Asn Thr Thr Thr Ser Ser Thr
850                 855                 860

Thr Ser Ser Pro Pro Leu Thr Phe Thr Asn Ala Thr Ile Gln Phe Phe
865                 870                 875                 880

Arg Ser Val Ile Pro Leu Asp Leu Pro Asn Asn Thr Asp Thr Ser Met
            885                 890                 895

Ser Phe Ile Leu Ser Thr Pro Ser Thr Ser Ser Lys Ala Tyr Arg Ala
        900                 905                 910

Gln Ile Phe Ile Asn Gly Tyr Gln Tyr Gly Arg Tyr Asn Pro His Ile
    915                 920                 925

Gly Asn Gln Val Val Phe Pro Val Pro Pro Gly Ile Leu Asp Tyr His
930                 935                 940

Gly Asp Asn Thr Ile Gly Val Ala Val Trp Ala Gln Ser Glu Asp Gly
945                 950                 955                 960

Ala Ser Ile Glu Leu Asp Trp Arg Val Asn Tyr Val Ala Asp Ser Ser
            965                 970                 975

Leu Asp Val Gly Arg Leu Asp Glu Gly Gly Ser Leu Arg Pro Gly Trp
        980                 985                 990

Ser Glu Glu Arg Leu Arg Phe Ala
        995                 1000

<210> SEQ ID NO 77
<211> LENGTH: 3310
<212> TYPE: DNA
<213> ORGANISM: Aspergillus lentulus
<220> FEATURE:
<221> NAME/KEY: CDS
<222> LOCATION: (1)..(801)
<220> FEATURE:
<221> NAME/KEY: sig_peptide
<222> LOCATION: (1)..(60)
<220> FEATURE:
<221> NAME/KEY: mat_peptide
<222> LOCATION: (61)..(3307)
<220> FEATURE:
<221> NAME/KEY: CDS
<222> LOCATION: (851)..(1847)
<220> FEATURE:
<221> NAME/KEY: CDS
<222> LOCATION: (1899)..(2192)
<220> FEATURE:
<221> NAME/KEY: CDS
<222> LOCATION: (2246)..(2317)
<220> FEATURE:
<221> NAME/KEY: CDS
<222> LOCATION: (2367)..(2454)
<220> FEATURE:
<221> NAME/KEY: CDS
<222> LOCATION: (2518)..(3307)

<400> SEQUENCE: 77 atg gcg cac atc tac caa ctt ctc ctt ctt ctt ctt tca aat ctg tgg    48
Met Ala His Ile Tyr Gln Leu Leu Leu Leu Leu Leu Ser Asn Leu Trp
-20                 -15                 -10                 -5 ttc gcg aca gct gct cag aac cag tca gag act gaa tgg cct ctt cat    96
Phe Ala Thr Ala Ala Gln Asn Gln Ser Glu Thr Glu Trp Pro Leu His
        -1  1               5                   10 gat aat ggc ttg agc aag gta gtg caa tgg gac cac tat agc ttc cac   144
Asp Asn Gly Leu Ser Lys Val Val Gln Trp Asp His Tyr Ser Phe His
            15                  20                  25 gtc aac ggg cag agg atc ttc gtc ttt tcc ggc gaa ttc cat tac tgg   192

|  |  |  |  |  |  |  |  |  |  |  |  |  |  |  |
|---|---|---|---|---|---|---|---|---|---|---|---|---|---|---|
| Val | Asn | Gly | Gln | Arg | Ile | Phe | Val | Phe | Ser | Gly | Glu | Phe | His | Tyr | Trp |
|  | 30 |  |  |  | 35 |  |  |  |  | 40 |  |  |  |  |

```
cgt att cca gtc ccc gag ttg tgg agg gat gtt ctc gag aag gtg aaa       240
Arg Ile Pro Val Pro Glu Leu Trp Arg Asp Val Leu Glu Lys Val Lys
 45          50                  55                  60 gct acc ggt ttc act gcg ttt gcg ttc tac tct agc tgg gcc tat cat       288
Ala Thr Gly Phe Thr Ala Phe Ala Phe Tyr Ser Ser Trp Ala Tyr His
                 65                  70                  75 gcg ccc aac aac cac acg gtc gac ttc tcg acc ggc gct cgc gat atc       336
Ala Pro Asn Asn His Thr Val Asp Phe Ser Thr Gly Ala Arg Asp Ile
             80                  85                  90 acg ccc atc ttt gag ctt gca aag gag ctc ggc atg tat atg att gtg       384
Thr Pro Ile Phe Glu Leu Ala Lys Glu Leu Gly Met Tyr Met Ile Val
         95                 100                 105 cgc ccc ggg ccc tac gtc aat gct gaa gcc agc gcg ggc ggc ttc cct       432
Arg Pro Gly Pro Tyr Val Asn Ala Glu Ala Ser Ala Gly Gly Phe Pro
     110                 115                 120 ctg tgg ctg acg act ggc gag tat ggc tcg ctg cgg aat gat gac ccg       480
Leu Trp Leu Thr Thr Gly Glu Tyr Gly Ser Leu Arg Asn Asp Asp Pro
125                 130                 135                 140 cgg tat acg gcc gca tgg acg ccg tac ttt gcc aac atg tcg caa atc       528
Arg Tyr Thr Ala Ala Trp Thr Pro Tyr Phe Ala Asn Met Ser Gln Ile
                145                 150                 155 act agc aag tat cag gtt acg gat gga cat aac acg ctc gtc tac cag       576
Thr Ser Lys Tyr Gln Val Thr Asp Gly His Asn Thr Leu Val Tyr Gln
            160                 165                 170 att gag aat gag tac ggt cag cag tgg atc gga gat ccc aag gat cgc       624
Ile Glu Asn Glu Tyr Gly Gln Gln Trp Ile Gly Asp Pro Lys Asp Arg
        175                 180                 185 aag ccg aat aag act gcg gtt gct tac atg gag ctc ttg gaa gca tct       672
Lys Pro Asn Lys Thr Ala Val Ala Tyr Met Glu Leu Leu Glu Ala Ser
    190                 195                 200 gct cgt gag aat ggt atc act gtg cca ttg aca agc aac gat ccc aac       720
Ala Arg Glu Asn Gly Ile Thr Val Pro Leu Thr Ser Asn Asp Pro Asn
205                 210                 215                 220 atg aac tcg aaa tct tgg gga tcg gac tgg tcc aat gct gga ggc aat       768
Met Asn Ser Lys Ser Trp Gly Ser Asp Trp Ser Asn Ala Gly Gly Asn
                225                 230                 235 gtc gac gtg gct ggt ttg gat tct tat ccg tcg gtgagttacc attagatcct    821
Val Asp Val Ala Gly Leu Asp Ser Tyr Pro Ser
            240                 245 ttttatttgt ttcgttctga ctgttgaag tgc tgg aca tgc gac gtg agc caa       874
                                Cys Trp Thr Cys Asp Val Ser Gln
                                            250                 255 tgt acc tcc acc aat ggg gag tat gtt ccc tac aaa gtg att gat tat       922
Cys Thr Ser Thr Asn Gly Glu Tyr Val Pro Tyr Lys Val Ile Asp Tyr
                260                 265                 270 tac gac tac ttc caa gaa gtt cag cca act ctt ccc tcg ttc atg ccc       970
Tyr Asp Tyr Phe Gln Glu Val Gln Pro Thr Leu Pro Ser Phe Met Pro
            275                 280                 285 gag ttc cag ggc ggt tcg tac aac ccc tgg gcc ggt cct gaa ggt gga      1018
Glu Phe Gln Gly Gly Ser Tyr Asn Pro Trp Ala Gly Pro Glu Gly Gly
        290                 295                 300 tgt cct cag gac acc ggc gcc gag ttt gct aac ctg ttc tac cga tgg      1066
Cys Pro Gln Asp Thr Gly Ala Glu Phe Ala Asn Leu Phe Tyr Arg Trp
    305                 310                 315 aac att ggc cag cga gtg acc gcc atg agt ctg tat atg ctg tac gga      1114
Asn Ile Gly Gln Arg Val Thr Ala Met Ser Leu Tyr Met Leu Tyr Gly
320                 325                 330                 335
```

```
gga acc aac tgg ggt gca att gct gct cct gtg aca gca acc agc tac       1162
Gly Thr Asn Trp Gly Ala Ile Ala Ala Pro Val Thr Ala Thr Ser Tyr
            340                 345                 350 gac tac tcc gct ccc atc tcc gaa gac cgc tcg att gga gcc aag tat       1210
Asp Tyr Ser Ala Pro Ile Ser Glu Asp Arg Ser Ile Gly Ala Lys Tyr
            355                 360                 365 tcc gag acc aag cta ctg gca ttg ttc acc cgt acc gca aag gac ctc       1258
Ser Glu Thr Lys Leu Leu Ala Leu Phe Thr Arg Thr Ala Lys Asp Leu
            370                 375                 380 aca atg aca gag gcg atc ggg aac gga aca caa tat acc acc aac aca       1306
Thr Met Thr Glu Ala Ile Gly Asn Gly Thr Gln Tyr Thr Thr Asn Thr
        385                 390                 395 gcc gtc cgt gca ttc gag ttg aga aat cct cag acc aac gcc ggg ttc       1354
Ala Val Arg Ala Phe Glu Leu Arg Asn Pro Gln Thr Asn Ala Gly Phe
400                 405                 410                 415 tac gtc aca ttc cac aac gac acc acc gtt ggt gga aat caa gcg ttc       1402
Tyr Val Thr Phe His Asn Asp Thr Thr Val Gly Gly Asn Gln Ala Phe
                420                 425                 430 aaa ctc cat gtc aac act tct gtc ggt gcc ttg act gtc ccc aag aac       1450
Lys Leu His Val Asn Thr Ser Val Gly Ala Leu Thr Val Pro Lys Asn
            435                 440                 445 gag ggt gtg atc cag ctg aat ggt cat caa tcc aag atc atc gtg acc       1498
Glu Gly Val Ile Gln Leu Asn Gly His Gln Ser Lys Ile Ile Val Thr
        450                 455                 460 gac ttc acg ctc ggc aaa cgt act ctt ctc tat tca act gcc gag gtc       1546
Asp Phe Thr Leu Gly Lys Arg Thr Leu Leu Tyr Ser Thr Ala Glu Val
    465                 470                 475 ttg acc tac gcc gtt ttt gaa gac agg ccc acc ctc gtg ctc tgg gtt       1594
Leu Thr Tyr Ala Val Phe Glu Asp Arg Pro Thr Leu Val Leu Trp Val
480                 485                 490                 495 cct act ggg gaa tcc ggc gag ttc gcg atc aag gga gcc aag tca gga       1642
Pro Thr Gly Glu Ser Gly Glu Phe Ala Ile Lys Gly Ala Lys Ser Gly
                500                 505                 510 aag gtt gaa aat ggc gat ggc tgc tcg gga atc aaa ttt gag agt gag       1690
Lys Val Glu Asn Gly Asp Gly Cys Ser Gly Ile Lys Phe Glu Ser Glu
            515                 520                 525 aag aac tat ctc gtc gtg aat ttc tct cag gcc aag gga ttg agc gtc       1738
Lys Asn Tyr Leu Val Val Asn Phe Ser Gln Ala Lys Gly Leu Ser Val
        530                 535                 540 ttg cgg ctc gat aat ggt gtg cgc gtg gtt ctg ctc gac aag gcc gcc       1786
Leu Arg Leu Asp Asn Gly Val Arg Val Val Leu Leu Asp Lys Ala Ala
    545                 550                 555 gcg tac cgc ttc tgg gct cct gca ttg aca aat gat cct gtc gtg caa       1834
Ala Tyr Arg Phe Trp Ala Pro Ala Leu Thr Asn Asp Pro Val Val Gln
560                 565                 570                 575 gag gcc gaa act g gtaagttcac ttcatgcgta gtacattgtc atttcatact         1887
Glu Ala Glu Thr aatggttaca g tg  ctc gtc cac ggc ccg tac ctt gtt cgc tcc gcc agc      1936
             Val Leu Val His Gly Pro Tyr Leu Val Arg Ser Ala Ser
                     580                 585                 590 gtg tcg aag tcc aca ctg gcg ctc cga gga gac tca gtc gag aag acg       1984
Val Ser Lys Ser Thr Leu Ala Leu Arg Gly Asp Ser Val Glu Lys Thr
            595                 600                 605 aca ctg gaa atc ttc gca cct cac agc gtg agg gag att acc tgg aat       2032
Thr Leu Glu Ile Phe Ala Pro His Ser Val Arg Glu Ile Thr Trp Asn
        610                 615                 620 ggg aaa caa gtg aag acc tct cag act tca tat ggc agt ctc aaa gcg       2080
Gly Lys Gln Val Lys Thr Ser Gln Thr Ser Tyr Gly Ser Leu Lys Ala
625                 630                 635                 640
```

```
act ctc gct gca ccg ccg acc ata aag tta ccc gct ctc acc tcc tgg      2128
Thr Leu Ala Ala Pro Pro Thr Ile Lys Leu Pro Ala Leu Thr Ser Trp
                    645                 650                 655 aga tcc aac gac agc ttg ccg gag cgg ctt cca tcg tat gac gat tcc      2176
Arg Ser Asn Asp Ser Leu Pro Glu Arg Leu Pro Ser Tyr Asp Asp Ser
                660                 665                 670 gga ccg gcc tgg att g gtgagttgga ttccaatcga tctggcctgg acgaaatcta   2232
Gly Pro Ala Trp Ile
            675 atgcgtttga cag ag  gca aac cac atg acc aca tct aac ccc agt aaa       2280
                   Glu Ala Asn His Met Thr Thr Ser Asn Pro Ser Lys
                               680                 685 cct gca acc ctt cca gtc cta tac gca gac gaa tac g gtatgtcaac         2327
Pro Ala Thr Leu Pro Val Leu Tyr Ala Asp Glu Tyr
690                 695                 700 ctctataccg acaccatcac aagtctaacc cgcctacag gc  ttc cac aac ggc       2380
                                              Gly Phe His Asn Gly
                                                              705 gtc cgc ctc tgg cgc ggc tac ttc aac ggc tct gct tcc gga gtc tac      2428
Val Arg Leu Trp Arg Gly Tyr Phe Asn Gly Ser Ala Ser Gly Val Tyr
                710                 715                 720 ctc aac atc caa gga gga agc gcc tt  gtacgttacc ctccccatcc             2474
Leu Asn Ile Gln Gly Gly Ser Ala Phe
                725             730 cctctcaact atctcatcga aactaacaac ctcccctccg cag c  ggc tgg tcc gcc   2530
                                                   Gly Trp Ser Ala
                                                                735 tgg cta aac ggc cac ttc ctc gac tcc cac ctc ggc gac gca aca acc      2578
Trp Leu Asn Gly His Phe Leu Asp Ser His Leu Gly Asp Ala Thr Thr
                740                 745                 750 tcc caa gca aac aaa acc ctc ccc ttc cca ccc tcc ctc ctc aac ccc      2626
Ser Gln Ala Asn Lys Thr Leu Pro Phe Pro Pro Ser Leu Leu Asn Pro
                755                 760                 765 acc gaa aac gtc ctc ctc atc gtc cac gac gac aca ggc cac gac cag      2674
Thr Glu Asn Val Leu Leu Ile Val His Asp Asp Thr Gly His Asp Gln
                770                 775                 780 aca acc ggc gcc cta aac cca cgc ggc atc ctc gcg gcc cgc ctc ctc      2722
Thr Thr Gly Ala Leu Asn Pro Arg Gly Ile Leu Ala Ala Arg Leu Leu
                785                 790                 795 tcc aac gac tcc tcg tcc ccc gcg ccg gaa ttc acc cgc tgg cgc ctc      2770
Ser Asn Asp Ser Ser Ser Pro Ala Pro Glu Phe Thr Arg Trp Arg Leu
800                 805                 810                 815 gcc ggc acc gca ggc ggg gaa tcg aac ctc gat ccc atc cgc ggc gtc      2818
Ala Gly Thr Ala Gly Gly Glu Ser Asn Leu Asp Pro Ile Arg Gly Val
                820                 825                 830 ttc aac gag gac ggc ctc ttc gca gaa cgc atg ggc tgg cac ctc ccc      2866
Phe Asn Glu Asp Gly Leu Phe Ala Glu Arg Met Gly Trp His Leu Pro
                835                 840                 845 ggc ttc gac gac agc gcc tgg acg gcc gag aac tca act gca tcc acc      2914
Gly Phe Asp Asp Ser Ala Trp Thr Ala Glu Asn Ser Thr Ala Ser Thr
                850                 855                 860 tcg gca ctg agc ttc acc ggc gca acc gtc cgc ttc ttc cgc acc gtc      2962
Ser Ala Leu Ser Phe Thr Gly Ala Thr Val Arg Phe Phe Arg Thr Val
865                 870                 875 gtc ccc ctc gat atc cct gct ggt ctg gac gtc tcc gtc tcc ttc gtg      3010
Val Pro Leu Asp Ile Pro Ala Gly Leu Asp Val Ser Val Ser Phe Val
880                 885                 890                 895 ctc tcg acc cca tcg aat gcg ccc aag gga tac cgc gca cag ctg ttc      3058
Leu Ser Thr Pro Ser Asn Ala Pro Lys Gly Tyr Arg Ala Gln Leu Phe
                900                 905                 910
```

-continued

```
gtc aat ggg tac cag tat ggt cgg tac aac cca cac atc ggc aat cag    3106
Val Asn Gly Tyr Gln Tyr Gly Arg Tyr Asn Pro His Ile Gly Asn Gln
        915                 920                 925 gtg gtg ttc cct gtt ccg ccg ggt att ctc gat tac cag gga gat aac    3154
Val Val Phe Pro Val Pro Pro Gly Ile Leu Asp Tyr Gln Gly Asp Asn
        930                 935                 940 acg atc ggg ttg gcg gtc tgg gcg cag acg gaa gag ggg gcg agt atc    3202
Thr Ile Gly Leu Ala Val Trp Ala Gln Thr Glu Glu Gly Ala Ser Ile
945                 950                 955 cag gtg gac tgg aag gtg aat tac gtg gcg gat agc tcg ttg agt gtc    3250
Gln Val Asp Trp Lys Val Asn Tyr Val Ala Asp Ser Ser Leu Ser Val
960                 965                 970                 975 gct gga ttt ggg aaa ggc ttg agg ccg ggt tgg acc gag gag cgg ttg    3298
Ala Gly Phe Gly Lys Gly Leu Arg Pro Gly Trp Thr Glu Glu Arg Leu
                980                 985                 990 aag ttt acc tag                                                    3310
Lys Phe Thr
```

<210> SEQ ID NO 78
<211> LENGTH: 1014
<212> TYPE: PRT
<213> ORGANISM: Aspergillus lentulus

<400> SEQUENCE: 78

```
Met Ala His Ile Tyr Gln Leu Leu Leu Leu Leu Ser Asn Leu Trp
-20              -15                 -10                  -5

Phe Ala Thr Ala Ala Gln Asn Gln Ser Glu Thr Glu Trp Pro Leu His
            -1  1               5                  10

Asp Asn Gly Leu Ser Lys Val Val Gln Trp Asp His Tyr Ser Phe His
                15                  20                  25

Val Asn Gly Gln Arg Ile Phe Val Phe Ser Gly Glu Phe His Tyr Trp
            30                  35                  40

Arg Ile Pro Val Pro Glu Leu Trp Arg Asp Val Leu Glu Lys Val Lys
45                  50                  55                  60

Ala Thr Gly Phe Thr Ala Phe Ala Phe Tyr Ser Ser Trp Ala Tyr His
                65                  70                  75

Ala Pro Asn Asn His Thr Val Asp Phe Ser Thr Gly Ala Arg Asp Ile
            80                  85                  90

Thr Pro Ile Phe Glu Leu Ala Lys Glu Leu Gly Met Tyr Met Ile Val
            95                 100                 105

Arg Pro Gly Pro Tyr Val Asn Ala Glu Ala Ser Ala Gly Gly Phe Pro
        110                 115                 120

Leu Trp Leu Thr Thr Gly Glu Tyr Gly Ser Leu Arg Asn Asp Asp Pro
125                 130                 135                 140

Arg Tyr Thr Ala Ala Trp Thr Pro Tyr Phe Ala Asn Met Ser Gln Ile
                145                 150                 155

Thr Ser Lys Tyr Gln Val Thr Asp Gly His Asn Thr Leu Val Tyr Gln
            160                 165                 170

Ile Glu Asn Glu Tyr Gly Gln Gln Trp Ile Gly Asp Pro Lys Asp Arg
            175                 180                 185

Lys Pro Asn Lys Thr Ala Val Ala Tyr Met Glu Leu Leu Glu Ala Ser
        190                 195                 200

Ala Arg Glu Asn Gly Ile Thr Val Pro Leu Thr Ser Asn Asp Pro Asn
205                 210                 215                 220

Met Asn Ser Lys Ser Trp Gly Ser Asp Trp Ser Asn Ala Gly Gly Asn
                225                 230                 235
```

-continued

Val Asp Val Ala Gly Leu Asp Ser Tyr Pro Ser Cys Trp Thr Cys Asp
            240                 245                 250

Val Ser Gln Cys Thr Ser Thr Asn Gly Glu Tyr Val Pro Tyr Lys Val
            255                 260                 265

Ile Asp Tyr Tyr Asp Tyr Phe Gln Glu Val Gln Pro Thr Leu Pro Ser
270                 275                 280

Phe Met Pro Glu Phe Gln Gly Gly Ser Tyr Asn Pro Trp Ala Gly Pro
285                 290                 295                 300

Glu Gly Gly Cys Pro Gln Asp Thr Gly Ala Glu Phe Ala Asn Leu Phe
                305                 310                 315

Tyr Arg Trp Asn Ile Gly Gln Arg Val Thr Ala Met Ser Leu Tyr Met
            320                 325                 330

Leu Tyr Gly Gly Thr Asn Trp Gly Ala Ile Ala Ala Pro Val Thr Ala
            335                 340                 345

Thr Ser Tyr Asp Tyr Ser Ala Pro Ile Ser Glu Asp Arg Ser Ile Gly
350                 355                 360

Ala Lys Tyr Ser Glu Thr Lys Leu Leu Ala Leu Phe Thr Arg Thr Ala
365                 370                 375                 380

Lys Asp Leu Thr Met Thr Glu Ala Ile Gly Asn Gly Thr Gln Tyr Thr
                385                 390                 395

Thr Asn Thr Ala Val Arg Ala Phe Glu Leu Arg Asn Pro Gln Thr Asn
            400                 405                 410

Ala Gly Phe Tyr Val Thr Phe His Asn Asp Thr Thr Val Gly Gly Asn
            415                 420                 425

Gln Ala Phe Lys Leu His Val Asn Thr Ser Val Gly Ala Leu Thr Val
430                 435                 440

Pro Lys Asn Glu Gly Val Ile Gln Leu Asn Gly His Gln Ser Lys Ile
445                 450                 455                 460

Ile Val Thr Asp Phe Thr Leu Gly Lys Arg Thr Leu Leu Tyr Ser Thr
                465                 470                 475

Ala Glu Val Leu Thr Tyr Ala Val Phe Glu Asp Arg Pro Thr Leu Val
            480                 485                 490

Leu Trp Val Pro Thr Gly Glu Ser Gly Glu Phe Ala Ile Lys Gly Ala
            495                 500                 505

Lys Ser Gly Lys Val Glu Asn Gly Asp Gly Cys Ser Gly Ile Lys Phe
510                 515                 520

Glu Ser Glu Lys Asn Tyr Leu Val Val Asn Phe Ser Gln Ala Lys Gly
525                 530                 535                 540

Leu Ser Val Leu Arg Leu Asp Asn Gly Val Arg Val Leu Leu Asp
                545                 550                 555

Lys Ala Ala Ala Tyr Arg Phe Trp Ala Pro Ala Leu Thr Asn Asp Pro
            560                 565                 570

Val Val Gln Glu Ala Glu Thr Val Leu Val His Gly Pro Tyr Leu Val
            575                 580                 585

Arg Ser Ala Ser Val Ser Lys Ser Thr Leu Ala Leu Arg Gly Asp Ser
            590                 595                 600

Val Glu Lys Thr Thr Leu Glu Ile Phe Ala Pro His Ser Val Arg Glu
605                 610                 615                 620

Ile Thr Trp Asn Gly Lys Gln Val Lys Thr Ser Gln Thr Ser Tyr Gly
                625                 630                 635

Ser Leu Lys Ala Thr Leu Ala Ala Pro Thr Ile Lys Leu Pro Ala
            640                 645                 650

-continued

```
Leu Thr Ser Trp Arg Ser Asn Asp Ser Leu Pro Glu Arg Leu Pro Ser
            655                 660                 665

Tyr Asp Asp Ser Gly Pro Ala Trp Ile Glu Ala Asn His Met Thr Thr
    670                 675                 680

Ser Asn Pro Ser Lys Pro Ala Thr Leu Pro Val Leu Tyr Ala Asp Glu
685                 690                 695                 700

Tyr Gly Phe His Asn Gly Val Arg Leu Trp Arg Gly Tyr Phe Asn Gly
                705                 710                 715

Ser Ala Ser Gly Val Tyr Leu Asn Ile Gln Gly Gly Ser Ala Phe Gly
            720                 725                 730

Trp Ser Ala Trp Leu Asn Gly His Phe Leu Asp Ser His Leu Gly Asp
        735                 740                 745

Ala Thr Thr Ser Gln Ala Asn Lys Thr Leu Pro Phe Pro Pro Ser Leu
    750                 755                 760

Leu Asn Pro Thr Glu Asn Val Leu Leu Ile Val His Asp Asp Thr Gly
765                 770                 775                 780

His Asp Gln Thr Thr Gly Ala Leu Asn Pro Arg Gly Ile Leu Ala Ala
                785                 790                 795

Arg Leu Leu Ser Asn Asp Ser Ser Pro Ala Pro Glu Phe Thr Arg
            800                 805                 810

Trp Arg Leu Ala Gly Thr Ala Gly Gly Glu Ser Asn Leu Asp Pro Ile
        815                 820                 825

Arg Gly Val Phe Asn Glu Asp Gly Leu Phe Ala Glu Arg Met Gly Trp
    830                 835                 840

His Leu Pro Gly Phe Asp Asp Ser Ala Trp Thr Ala Glu Asn Ser Thr
845                 850                 855                 860

Ala Ser Thr Ser Ala Leu Ser Phe Thr Gly Ala Thr Val Arg Phe Phe
                865                 870                 875

Arg Thr Val Val Pro Leu Asp Ile Pro Ala Gly Leu Asp Val Ser Val
            880                 885                 890

Ser Phe Val Leu Ser Thr Pro Ser Asn Ala Pro Lys Gly Tyr Arg Ala
        895                 900                 905

Gln Leu Phe Val Asn Gly Tyr Gln Tyr Gly Arg Tyr Asn Pro His Ile
    910                 915                 920

Gly Asn Gln Val Val Phe Pro Val Pro Pro Gly Ile Leu Asp Tyr Gln
925                 930                 935                 940

Gly Asp Asn Thr Ile Gly Leu Ala Val Trp Ala Gln Thr Glu Glu Gly
                945                 950                 955

Ala Ser Ile Gln Val Asp Trp Lys Val Asn Tyr Val Ala Asp Ser Ser
            960                 965                 970

Leu Ser Val Ala Gly Phe Gly Lys Gly Leu Arg Pro Gly Trp Thr Glu
        975                 980                 985

Glu Arg Leu Lys Phe Thr
    990
```

<210> SEQ ID NO 79
<211> LENGTH: 994
<212> TYPE: PRT
<213> ORGANISM: Aspergillus lentulus
<220> FEATURE:
<221> NAME/KEY: mat_peptide
<222> LOCATION: (1)..(994)

<400> SEQUENCE: 79

```
Ala Gln Asn Gln Ser Glu Thr Glu Trp Pro Leu His Asp Asn Gly Leu
1               5                   10                  15
```

-continued

```
Ser Lys Val Val Gln Trp Asp His Tyr Ser Phe His Val Asn Gly Gln
            20                  25                  30

Arg Ile Phe Val Phe Ser Gly Glu Phe His Tyr Trp Arg Ile Pro Val
        35                  40                  45

Pro Glu Leu Trp Arg Asp Val Leu Glu Lys Val Lys Ala Thr Gly Phe
50                  55                  60

Thr Ala Phe Ala Phe Tyr Ser Ser Trp Ala Tyr His Ala Pro Asn Asn
65                  70                  75                  80

His Thr Val Asp Phe Ser Thr Gly Ala Arg Asp Ile Thr Pro Ile Phe
                85                  90                  95

Glu Leu Ala Lys Glu Leu Gly Met Tyr Met Ile Val Arg Pro Gly Pro
            100                 105                 110

Tyr Val Asn Ala Glu Ala Ser Ala Gly Gly Phe Pro Leu Trp Leu Thr
        115                 120                 125

Thr Gly Glu Tyr Gly Ser Leu Arg Asn Asp Asp Pro Arg Tyr Thr Ala
130                 135                 140

Ala Trp Thr Pro Tyr Phe Ala Asn Met Ser Gln Ile Thr Ser Lys Tyr
145                 150                 155                 160

Gln Val Thr Asp Gly His Asn Thr Leu Val Tyr Gln Ile Glu Asn Glu
                165                 170                 175

Tyr Gly Gln Gln Trp Ile Gly Asp Pro Lys Asp Arg Lys Pro Asn Lys
            180                 185                 190

Thr Ala Val Ala Tyr Met Glu Leu Leu Glu Ala Ser Ala Arg Glu Asn
        195                 200                 205

Gly Ile Thr Val Pro Leu Thr Ser Asn Asp Pro Asn Met Asn Ser Lys
210                 215                 220

Ser Trp Gly Ser Asp Trp Ser Asn Ala Gly Gly Asn Val Asp Val Ala
225                 230                 235                 240

Gly Leu Asp Ser Tyr Pro Ser Cys Trp Thr Cys Asp Val Ser Gln Cys
                245                 250                 255

Thr Ser Thr Asn Gly Glu Tyr Val Pro Tyr Lys Val Ile Asp Tyr Tyr
            260                 265                 270

Asp Tyr Phe Gln Glu Val Gln Pro Thr Leu Pro Ser Phe Met Pro Glu
        275                 280                 285

Phe Gln Gly Gly Ser Tyr Asn Pro Trp Ala Gly Pro Glu Gly Gly Cys
290                 295                 300

Pro Gln Asp Thr Gly Ala Glu Phe Ala Asn Leu Phe Tyr Arg Trp Asn
305                 310                 315                 320

Ile Gly Gln Arg Val Thr Ala Met Ser Leu Tyr Met Leu Tyr Gly Gly
                325                 330                 335

Thr Asn Trp Gly Ala Ile Ala Ala Pro Val Thr Ala Thr Ser Tyr Asp
            340                 345                 350

Tyr Ser Ala Pro Ile Ser Glu Asp Arg Ser Ile Gly Ala Lys Tyr Ser
        355                 360                 365

Glu Thr Lys Leu Leu Ala Leu Phe Thr Arg Thr Ala Lys Asp Leu Thr
370                 375                 380

Met Thr Glu Ala Ile Gly Asn Gly Thr Gln Tyr Thr Thr Asn Thr Ala
385                 390                 395                 400

Val Arg Ala Phe Glu Leu Arg Asn Pro Gln Thr Asn Ala Gly Phe Tyr
                405                 410                 415

Val Thr Phe His Asn Asp Thr Thr Val Gly Gly Asn Gln Ala Phe Lys
            420                 425                 430
```

```
Leu His Val Asn Thr Ser Val Gly Ala Leu Thr Val Pro Lys Asn Glu
         435                 440                 445

Gly Val Ile Gln Leu Asn Gly His Gln Ser Lys Ile Ile Val Thr Asp
    450                 455                 460

Phe Thr Leu Gly Lys Arg Thr Leu Leu Tyr Ser Thr Ala Glu Val Leu
465                 470                 475                 480

Thr Tyr Ala Val Phe Glu Asp Arg Pro Thr Leu Val Leu Trp Val Pro
                485                 490                 495

Thr Gly Glu Ser Gly Glu Phe Ala Ile Lys Gly Ala Lys Ser Gly Lys
                500                 505                 510

Val Glu Asn Gly Asp Gly Cys Ser Gly Ile Lys Phe Glu Ser Glu Lys
    515                 520                 525

Asn Tyr Leu Val Val Asn Phe Ser Gln Ala Lys Gly Leu Ser Val Leu
530                 535                 540

Arg Leu Asp Asn Gly Val Arg Val Val Leu Leu Asp Lys Ala Ala Ala
545                 550                 555                 560

Tyr Arg Phe Trp Ala Pro Ala Leu Thr Asn Asp Pro Val Val Gln Glu
                565                 570                 575

Ala Glu Thr Val Leu Val His Gly Pro Tyr Leu Val Arg Ser Ala Ser
            580                 585                 590

Val Ser Lys Ser Thr Leu Ala Leu Arg Gly Asp Ser Val Glu Lys Thr
    595                 600                 605

Thr Leu Glu Ile Phe Ala Pro His Ser Val Arg Glu Ile Thr Trp Asn
    610                 615                 620

Gly Lys Gln Val Lys Thr Ser Gln Thr Ser Tyr Gly Ser Leu Lys Ala
625                 630                 635                 640

Thr Leu Ala Ala Pro Pro Thr Ile Lys Leu Pro Ala Leu Thr Ser Trp
                645                 650                 655

Arg Ser Asn Asp Ser Leu Pro Glu Arg Leu Pro Ser Tyr Asp Asp Ser
                660                 665                 670

Gly Pro Ala Trp Ile Glu Ala Asn His Met Thr Thr Ser Asn Pro Ser
            675                 680                 685

Lys Pro Ala Thr Leu Pro Val Leu Tyr Ala Asp Glu Tyr Gly Phe His
    690                 695                 700

Asn Gly Val Arg Leu Trp Arg Gly Tyr Phe Asn Gly Ser Ala Ser Gly
705                 710                 715                 720

Val Tyr Leu Asn Ile Gln Gly Gly Ser Ala Phe Gly Trp Ser Ala Trp
                725                 730                 735

Leu Asn Gly His Phe Leu Asp Ser His Leu Gly Asp Ala Thr Thr Ser
                740                 745                 750

Gln Ala Asn Lys Thr Leu Pro Phe Pro Pro Ser Leu Leu Asn Pro Thr
            755                 760                 765

Glu Asn Val Leu Leu Ile Val His Asp Asp Thr Gly His Asp Gln Thr
770                 775                 780

Thr Gly Ala Leu Asn Pro Arg Gly Ile Leu Ala Ala Arg Leu Leu Ser
785                 790                 795                 800

Asn Asp Ser Ser Pro Ala Pro Glu Phe Thr Arg Trp Arg Leu Ala
                805                 810                 815

Gly Thr Ala Gly Gly Glu Ser Asn Leu Asp Pro Ile Arg Gly Val Phe
                820                 825                 830

Asn Glu Asp Gly Leu Phe Ala Glu Arg Met Gly Trp His Leu Pro Gly
                835                 840                 845

Phe Asp Asp Ser Ala Trp Thr Ala Glu Asn Ser Thr Ala Ser Thr Ser
```

```
                        850                 855                 860
Ala Leu Ser Phe Thr Gly Ala Thr Val Arg Phe Phe Arg Thr Val Val
865                 870                 875                 880

Pro Leu Asp Ile Pro Ala Gly Leu Asp Val Ser Val Ser Phe Val Leu
                885                 890                 895

Ser Thr Pro Ser Asn Ala Pro Lys Gly Tyr Arg Ala Gln Leu Phe Val
                900                 905                 910

Asn Gly Tyr Gln Tyr Gly Arg Tyr Asn Pro His Ile Gly Asn Gln Val
                915                 920                 925

Val Phe Pro Val Pro Pro Gly Ile Leu Asp Tyr Gln Gly Asp Asn Thr
            930                 935                 940

Ile Gly Leu Ala Val Trp Ala Gln Thr Glu Glu Gly Ala Ser Ile Gln
945                 950                 955                 960

Val Asp Trp Lys Val Asn Tyr Val Ala Asp Ser Ser Leu Ser Val Ala
                965                 970                 975

Gly Phe Gly Lys Gly Leu Arg Pro Gly Trp Thr Glu Glu Arg Leu Lys
                980                 985                 990

Phe Thr

<210> SEQ ID NO 80
<211> LENGTH: 5
<212> TYPE: PRT
<213> ORGANISM: Artificial Sequence
<220> FEATURE:
<223> OTHER INFORMATION: SEQ ID NO: 80 is the conserved motif
      Y[Y/F][D/Q][Y/H/W]F.
<220> FEATURE:
<221> NAME/KEY: MISC_FEATURE
<222> LOCATION: (2)..(2)
<223> OTHER INFORMATION: The amino acid in position 2 of the conserved
      motif is either phenylalanine (F) or tyrosine (Y).
<220> FEATURE:
<221> NAME/KEY: MISC_FEATURE
<222> LOCATION: (3)..(3)
<223> OTHER INFORMATION: The amino acid in position 3 of the conserved
      motif is either aspartic acid (D) or glutamine (Q).
<220> FEATURE:
<221> NAME/KEY: MISC_FEATURE
<222> LOCATION: (4)..(4)
<223> OTHER INFORMATION: The amino acid in position 4 of the conserved
      motif is either phenylalanine (F), tyrosine (Y) or tryptophan (W).

<400> SEQUENCE: 80

Tyr Xaa Xaa Xaa Phe
1               5

<210> SEQ ID NO 81
<211> LENGTH: 6
<212> TYPE: PRT
<213> ORGANISM: Artificial Sequence
<220> FEATURE:
<223> OTHER INFORMATION: SEQ ID NO: 81 is the conserved motif
      K[Y/F][Y/S]ETK.
<220> FEATURE:
<221> NAME/KEY: MISC_FEATURE
<222> LOCATION: (2)..(2)
<223> OTHER INFORMATION: The amino acid in position 2 of the conserved
      motif is either phenylalanine (F) or tyrosine (Y).
<220> FEATURE:
<221> NAME/KEY: MISC_FEATURE
<222> LOCATION: (3)..(3)
<223> OTHER INFORMATION: The amino acid in position 3 of the conserved
      motif is either serine (S) or tyrosine (Y).

<400> SEQUENCE: 81

Lys Xaa Xaa Glu Thr Lys
```

<210> SEQ ID NO 82
<211> LENGTH: 1013
<212> TYPE: PRT
<213> ORGANISM: Penicillium chrysogenum

<400> SEQUENCE: 82

Met Thr Arg Ile Leu Asn Cys Leu Leu Val Leu Leu Ala Cys Leu Gly
1               5                   10                  15

Val Ser Ser Lys Ala Glu Asp Gln Ala Val Thr Gln Trp Pro Leu Gln
            20                  25                  30

Asp Asn Gly Leu Asn Thr Val Val Gln Trp Asp His Tyr Ser Phe Gln
        35                  40                  45

Ile Asn Gly Gln Arg Ile Phe Ile Phe Ser Gly Glu Phe His Tyr Trp
    50                  55                  60

Arg Ile Pro Val Pro Ala Leu Trp Arg Asp Ile Leu Glu Lys Ile Lys
65                  70                  75                  80

Ala Ala Gly Phe Thr Ala Phe Ala Phe Tyr Ser Ser Trp Ala Tyr His
                85                  90                  95

Ala Pro Asn Asn Ala Thr Val Asp Phe Thr Thr Gly Ala Arg Asp Ile
            100                 105                 110

Thr Pro Ile Phe Glu Leu Ala Lys Glu Leu Gly Met Tyr Ile Ile Val
        115                 120                 125

Arg Pro Gly Pro Tyr Val Asn Ala Glu Ala Asn Ala Gly Gly Phe Pro
    130                 135                 140

Leu Trp Val Thr Thr Gly Asp Tyr Gly Thr Leu Arg Asn Asp Asp Thr
145                 150                 155                 160

Arg Tyr Thr Asn Ala Trp Thr Pro Tyr Phe Thr Glu Val Thr Glu Ile
                165                 170                 175

Thr Ser Arg Tyr Gln Val Thr Asp Gly His Tyr Ser Ile Val Tyr Gln
            180                 185                 190

Ile Glu Asn Glu Tyr Gly Asn Gln Trp Leu Gly Asp Pro Thr Leu Arg
        195                 200                 205

Val Pro Asn Glu Thr Ala Ile Ala Tyr Met Glu Leu Leu Lys Ala Asn
    210                 215                 220

Ala Arg Asp Asn Gly Ile Thr Leu Pro Leu Thr Val Asn Asp Pro Asn
225                 230                 235                 240

Met Lys Thr His Ser Trp Gly Lys Asp Trp Ser Asp Ala Gly Gly Asn
                245                 250                 255

Val Asp Ala Ala Gly Leu Asp Ser Tyr Pro Ser Cys Trp Thr Cys Asp
            260                 265                 270

Ile Ser Gln Cys Thr Ser Thr Asn Gly Ala Tyr Val Pro Phe Gln Val
        275                 280                 285

Leu Glu Tyr His Asp Tyr Phe Gln Glu Ser Gln Pro Ser Met Pro Ala
    290                 295                 300

Phe Met Pro Glu Phe Gln Gly Gly Ser Tyr Asn Pro Trp Gly Gly Pro
305                 310                 315                 320

Glu Gly Gly Cys Pro Gly Asp Ile Gly Asp Phe Ala Asn Leu Phe
                325                 330                 335

Tyr Arg Trp Asn Ile Gly Gln Arg Val Thr Ala Met Ser Leu Tyr Met
            340                 345                 350

Met Phe Gly Gly Gln Asn Pro Gly Ala Met Ala Ala Pro Val Thr Ala
        355                 360                 365

-continued

Ser Ser Tyr Asp Tyr Ser Ala Pro Ile Ser Glu Asp Arg Ser Ile Trp
    370                 375                 380

Ser Lys Tyr His Glu Thr Lys Leu Leu Ala Leu Phe Thr Arg Ser Ala
385                 390                 395                 400

Lys Asp Leu Thr Met Thr Glu Leu Met Gly Asn Gly Thr Gln Tyr Thr
                405                 410                 415

Asp Asn Pro Ala Val Arg Ala Tyr Glu Leu Arg Asn Pro Glu Thr Asn
            420                 425                 430

Ser Ala Phe Tyr Ala Thr Phe His Ser Asn Thr Ser Ile Ser Thr Asn
        435                 440                 445

Glu Pro Phe His Leu Lys Val Asn Thr Ser Ala Gly Val Leu Thr Val
    450                 455                 460

Pro Lys Tyr Ala Ser Thr Ile Arg Leu Asn Gly His Gln Ser Lys Ile
465                 470                 475                 480

Ile Val Thr Asp Phe Thr Phe Gly Ser Lys Ser Leu Leu Tyr Ser Thr
                485                 490                 495

Ala Glu Val Leu Thr Tyr Ala Val Phe Asp Lys Lys Pro Thr Leu Val
            500                 505                 510

Leu Trp Val Pro Thr Gly Glu Ser Gly Glu Phe Ser Ile Lys Gly Ala
        515                 520                 525

Lys Lys Gly Ser Ile Lys Lys Cys Gln Gly Cys Ser Arg Val Lys Phe
    530                 535                 540

Ile Lys Glu His Gly Gly Leu Thr Thr Ser Leu Thr Gln Ser Ala Gly
545                 550                 555                 560

Met Thr Val Leu Glu Phe Asp Asp Gly Val Arg Val Ile Leu Leu Asp
                565                 570                 575

Arg Thr Ser Ala Tyr Asp Phe Trp Ala Pro Ala Leu Thr Asn Asp Pro
            580                 585                 590

Phe Val Pro Glu Thr Glu Ser Val Leu Ile Gln Gly Pro Tyr Leu Val
        595                 600                 605

Arg Asp Ala Lys Leu Ser Gly Ser Lys Leu Ala Ile Thr Gly Asp Val
    610                 615                 620

Val Asn Ala Thr Thr Leu Asp Val Phe Ala Pro Lys Gly Val Lys Ser
625                 630                 635                 640

Val Thr Trp Asn Gly Lys Lys Val Asp Thr His Ser Thr Glu Tyr Gly
                645                 650                 655

Ser Leu Lys Gly Ser Leu Asp Ala Pro Gln Ser Ile Lys Leu Pro Ala
            660                 665                 670

Leu Ala Ser Trp Lys Ser Lys Asp Ser Leu Pro Glu Arg Phe Ala Asp
        675                 680                 685

Tyr Asp Asp Ser Gly Ala Ala Trp Val Asp Ala Asn His Met Thr Thr
    690                 695                 700

Leu Asn Pro Arg Thr Pro Thr Ser Leu Pro Val Leu Tyr Ala Asp Gln
705                 710                 715                 720

Tyr Gly Phe His Asn Gly Val Arg Leu Trp Arg Gly Tyr Phe Asn Gly
                725                 730                 735

Thr Ala Thr Gly Ala Phe Ile Asn Val Gln Gly Gly Ser Ala Phe Gly
            740                 745                 750

Trp Ser Ala Trp Leu Asn Gly Glu Phe Leu Ala Ser His Leu Gly Asn
        755                 760                 765

Ala Thr Thr Ser Gln Ala Asn Leu Ser Leu Ser Phe Thr Asp Ala Thr
    770                 775                 780

Leu His Thr Asp Thr Pro Asn Val Leu Leu Ile Val His Asp Asp Thr

```
                785                 790                 795                 800

Gly His Asp Gln Thr Thr Gly Ala Leu Asn Pro Arg Gly Ile Met Asp
                805                 810                 815

Ala Lys Leu Leu Gly Ser Asp Ser Gly Phe Thr His Trp Arg Leu Ala
                820                 825                 830

Gly Thr Ala Gly Gly Glu Ser Asp Leu Asp Pro Val Arg Gly Val Tyr
                835                 840                 845

Asn Glu Asp Gly Leu Phe Ala Glu Arg Val Gly Trp His Leu Pro Gly
                850                 855                 860

Phe Asp Asp Ser Asp Trp Gly Glu Glu Ala Ser Ala Lys Asp Ser Thr
865                 870                 875                 880

Thr Ser Val Leu Ser Phe Glu Gly Ala Thr Val Arg Phe Phe Arg Thr
                885                 890                 895

Thr Cys Pro Leu Asp Ile Pro Ala His Thr Asp Val Ser Ile Ser Phe
                900                 905                 910

Val Leu Ser Thr Pro Ala Gly Ala Thr Thr Glu Tyr Arg Ala Gln Leu
                915                 920                 925

Phe Val Asn Gly Tyr Gln Tyr Gly Arg Tyr Asn Pro Tyr Ile Gly Asn
                930                 935                 940

Gln Val Val Tyr Pro Val Pro Val Gly Ile Leu Asp Tyr Lys Gly Glu
945                 950                 955                 960

Asn Thr Ile Gly Val Ala Val Trp Ala Gln Ser Glu Glu Gly Ala Ser
                965                 970                 975

Ile Gly Ile Asp Trp Arg Val Asn Tyr Leu Ala Asp Ser Ser Leu Asp
                980                 985                 990

Val Ala Ser Trp Asp Thr Lys Asp Leu Arg Pro Gly Trp Thr Glu Glu
                995                 1000                1005

Arg Val Lys Tyr Ala
        1010

<210> SEQ ID NO 83
<211> LENGTH: 352
<212> TYPE: PRT
<213> ORGANISM: Penicillium chrysogenum

<400> SEQUENCE: 83

Met Leu Pro His Leu Leu Ala Ala Gln Leu Phe Ala Ser Ser
1               5                   10                  15

Ser Ala Ala Leu Thr Tyr Asn Gly Ala Asp Ile Ser Ser Leu Leu Val
                20                  25                  30

Glu Glu Gly Lys Gly Val Ser Tyr Lys Asn Leu Ala Gly Thr Pro Glu
            35                  40                  45

Lys Leu Glu Thr Ile Leu Ser Ala Ser Gly Val Asn Ser Val Arg Gln
        50                  55                  60

Arg Ile Trp Val Asn Pro Ser Asp Gly Ser Tyr Asp Leu Asp Tyr Asn
65                  70                  75                  80

Val Lys Leu Ala Lys Arg Val Gln Ala Gln Gly Met Gly Thr Tyr Leu
                85                  90                  95

Asp Leu His Tyr Ser Asp Thr Trp Ala Asp Pro Lys Ser Gln Thr Thr
                100                 105                 110

Pro Ser Gly Trp Ser Thr Thr Asp Ile Gly Ile Leu Ala Gly Gln Val
            115                 120                 125

Tyr Asp Tyr Thr Leu Asp Val Cys Asn Thr Phe Ala Ala Asn Lys Ile
        130                 135                 140
```

```
Asp Val Asp Ile Val Ser Ile Gly Asn Glu Ile Arg Asn Gly Leu Leu
145                 150                 155                 160

Trp Pro Leu Gly Gly Thr Ser Asn Tyr Asn Asn Ile Ala Arg Leu Leu
                165                 170                 175

His Ser Ala Ala Trp Gly Val Lys Asp Ser Lys Leu Ala Thr Thr Pro
            180                 185                 190

Lys Ile Met Ile His Leu Asp Asn Gly Trp Asp Ser Gly Ala Gln Ser
        195                 200                 205

Tyr Phe Tyr Asp Gln Val Leu Ala Pro Gly Ser Gly Leu Val Ser Thr
    210                 215                 220

Asp Phe Asp Tyr Ile Gly Val Ser Tyr Tyr Pro Phe Tyr Asn Ala Asp
225                 230                 235                 240

Ala Thr Leu Ala Ala Leu Lys Thr Ser Leu Thr Asn Leu His Ser Lys
                245                 250                 255

Tyr Lys Lys Glu Thr Leu Val Val Glu Thr Asn Trp Pro Phe Ser Cys
                260                 265                 270

Pro Asn Pro Glu Tyr Ala Phe Pro Thr Asp Leu Lys Asp Ile Pro Phe
            275                 280                 285

Ser Val Glu Gly Gln Gln Thr Phe Leu Gln Arg Leu Ala Lys Ala Val
    290                 295                 300

Glu Val Gly Gly Leu Gly Ile Tyr Tyr Trp Glu Pro Ala Trp Val
305                 310                 315                 320

Asp Asn Ala Gly Leu Gly Ser Ser Cys Asp Asp Asn Leu Phe Phe Ala
                325                 330                 335

Trp Ser Asn Asp Gln Ala Arg Ala Ser Leu Asp Thr Leu Gly Gly Leu
                340                 345                 350
```

<210> SEQ ID NO 84
<211> LENGTH: 1007
<212> TYPE: PRT
<213> ORGANISM: Aspergillus niger

<400> SEQUENCE: 84

```
Met Lys Leu Ser Ser Ala Cys Ala Ile Ala Leu Leu Ala Ala Gln Ala
1               5                   10                  15

Ala Gly Ala Ser Ile Lys His Arg Ile Asn Gly Phe Thr Leu Thr Glu
                20                  25                  30

His Ser Asp Pro Ala Lys Arg Glu Leu Leu Gln Lys Tyr Val Thr Trp
            35                  40                  45

Asp Asp Lys Ser Leu Phe Ile Asn Gly Glu Arg Ile Met Ile Phe Ser
        50                  55                  60

Gly Glu Phe His Pro Phe Arg Leu Pro Val Lys Glu Leu Gln Leu Asp
65                  70                  75                  80

Ile Phe Gln Lys Val Lys Ala Leu Gly Phe Asn Cys Val Ser Phe Tyr
                85                  90                  95

Val Asp Trp Ala Leu Val Glu Gly Lys Pro Gly Glu Tyr Arg Ala Asp
                100                 105                 110

Gly Ile Phe Asp Leu Glu Pro Phe Phe Asp Ala Ala Ser Glu Ala Gly
            115                 120                 125

Ile Tyr Leu Leu Ala Arg Pro Gly Pro Tyr Ile Asn Ala Glu Ser Ser
        130                 135                 140

Gly Gly Gly Phe Pro Gly Trp Leu Gln Arg Val Asn Gly Thr Leu Arg
145                 150                 155                 160

Ser Ser Asp Lys Ala Tyr Leu Asp Ala Thr Asp Asn Tyr Val Ser His
                165                 170                 175
```

```
Val Ala Ala Thr Ile Ala Lys Tyr Gln Ile Thr Asn Gly Gly Pro Ile
                180                 185                 190

Ile Leu Tyr Gln Pro Glu Asn Glu Tyr Thr Ser Gly Cys Cys Gly Val
            195                 200                 205

Glu Phe Pro Asp Pro Val Tyr Met Gln Tyr Val Glu Asp Gln Ala Arg
210                 215                 220

Asn Ala Gly Val Val Ile Pro Leu Ile Asn Asn Asp Ala Ser Ala Ser
225                 230                 235                 240

Gly Asn Asn Ala Pro Gly Thr Gly Lys Gly Ala Val Asp Ile Tyr Gly
                245                 250                 255

His Asp Ser Tyr Pro Leu Gly Phe Asp Cys Ala Asn Pro Thr Val Trp
            260                 265                 270

Pro Ser Gly Asp Leu Pro Thr Asn Phe Arg Thr Leu His Leu Glu Gln
            275                 280                 285

Ser Pro Thr Thr Pro Tyr Ala Ile Val Glu Phe Gln Gly Gly Ser Tyr
            290                 295                 300

Asp Pro Trp Gly Gly Pro Gly Phe Ala Ala Cys Ser Glu Leu Leu Asn
305                 310                 315                 320

Asn Glu Phe Glu Arg Val Phe Tyr Lys Asn Asp Phe Ser Phe Gln Ile
                325                 330                 335

Ala Ile Met Asn Leu Tyr Met Ile Phe Gly Gly Thr Asn Trp Gly Asn
            340                 345                 350

Leu Gly Tyr Pro Asn Gly Tyr Thr Ser Tyr Asp Tyr Gly Ser Ala Val
            355                 360                 365

Thr Glu Ser Arg Asn Ile Thr Arg Glu Lys Tyr Ser Glu Leu Lys Leu
370                 375                 380

Leu Gly Asn Phe Ala Lys Val Ser Pro Gly Tyr Leu Thr Ala Ser Pro
385                 390                 395                 400

Gly Asn Leu Thr Thr Ser Gly Tyr Ala Asp Thr Thr Asp Leu Thr Val
                405                 410                 415

Thr Pro Leu Leu Gly Asn Ser Thr Gly Ser Phe Phe Val Val Arg His
            420                 425                 430

Ser Asp Tyr Ser Ser Glu Glu Ser Thr Ser Tyr Lys Leu Arg Leu Pro
            435                 440                 445

Thr Ser Ala Gly Ser Val Thr Ile Pro Gln Leu Gly Gly Thr Leu Thr
            450                 455                 460

Leu Asn Gly Arg Asp Ser Lys Ile His Val Thr Asp Tyr Asn Val Ser
465                 470                 475                 480

Gly Thr Asn Ile Ile Tyr Ser Thr Ala Glu Val Phe Thr Trp Lys Lys
                485                 490                 495

Phe Ala Asp Gly Lys Val Leu Val Leu Tyr Gly Gly Ala Gly Glu His
            500                 505                 510

His Glu Leu Ala Ile Ser Thr Lys Ser Asn Val Thr Val Ile Glu Gly
            515                 520                 525

Ser Glu Ser Gly Ile Ser Ser Lys Gln Thr Ser Ser Ser Val Val Val
            530                 535                 540

Gly Trp Asp Val Ser Thr Thr Arg Arg Ile Ile Gln Val Gly Asp Leu
545                 550                 555                 560

Lys Ile Leu Leu Leu Asp Arg Asn Ser Ala Tyr Asn Tyr Trp Val Pro
                565                 570                 575

Gln Leu Ala Thr Asp Gly Thr Ser Pro Gly Phe Ser Thr Pro Glu Lys
            580                 585                 590
```

```
Val Ala Ser Ser Ile Ile Val Lys Ala Gly Tyr Leu Val Arg Thr Ala
            595                 600                 605

Tyr Leu Lys Gly Ser Gly Leu Tyr Leu Thr Ala Asp Phe Asn Ala Thr
    610                 615                 620

Thr Ser Val Glu Val Ile Gly Val Pro Ser Thr Ala Lys Asn Leu Phe
625                 630                 635                 640

Ile Asn Gly Asp Lys Thr Ser His Thr Val Asp Lys Asn Gly Ile Trp
                645                 650                 655

Ser Ala Thr Val Asp Tyr Asn Ala Pro Asp Ile Ser Leu Pro Ser Leu
            660                 665                 670

Lys Asp Leu Asp Trp Lys Tyr Val Asp Thr Leu Pro Glu Ile Gln Ser
            675                 680                 685

Ser Tyr Asp Asp Ser Leu Trp Pro Ala Ala Asp Leu Lys Gln Thr Lys
            690                 695                 700

Asn Thr Leu Arg Ser Leu Thr Thr Pro Thr Ser Leu Tyr Ser Ser Asp
705                 710                 715                 720

Tyr Gly Phe His Thr Gly Tyr Leu Leu Tyr Arg Gly His Phe Thr Ala
                725                 730                 735

Thr Gly Asn Glu Ser Thr Phe Ala Ile Asp Thr Gln Gly Gly Ser Ala
            740                 745                 750

Phe Gly Ser Ser Val Trp Leu Asn Gly Thr Tyr Leu Gly Ser Trp Thr
            755                 760                 765

Gly Leu Tyr Ala Asn Ser Asp Tyr Asn Ala Thr Tyr Asn Leu Pro Gln
            770                 775                 780

Leu Gln Ala Gly Lys Thr Tyr Val Ile Thr Val Val Ile Asp Asn Met
785                 790                 795                 800

Gly Leu Glu Glu Asn Trp Thr Val Gly Glu Asp Leu Met Lys Thr Pro
                805                 810                 815

Arg Gly Ile Leu Asn Phe Leu Leu Ala Gly Arg Pro Ser Ser Ala Ile
            820                 825                 830

Ser Trp Lys Leu Thr Gly Asn Leu Gly Gly Glu Asp Tyr Glu Asp Lys
            835                 840                 845

Val Arg Gly Pro Leu Asn Glu Gly Gly Leu Tyr Ala Glu Arg Gln Gly
850                 855                 860

Phe His Gln Pro Glu Pro Ser Gln Asn Trp Lys Ser Ser Ser Pro
865                 870                 875                 880

Leu Glu Gly Leu Ser Glu Ala Gly Ile Gly Phe Tyr Ser Ala Ser Phe
                885                 890                 895

Asp Leu Asp Leu Pro Lys Gly Trp Asp Val Pro Leu Phe Leu Asn Ile
            900                 905                 910

Gly Asn Ser Thr Thr Pro Ser Pro Tyr Arg Val Gln Val Tyr Val Asn
            915                 920                 925

Gly Tyr Gln Tyr Ala Lys Tyr Ile Ser Asn Ile Gly Pro Gln Thr Ser
            930                 935                 940

Phe Pro Val Pro Glu Gly Ile Leu Asn Tyr Arg Gly Thr Asn Trp Leu
945                 950                 955                 960

Ala Val Thr Leu Trp Ala Leu Asp Ser Ala Gly Gly Lys Leu Glu Ser
                965                 970                 975

Leu Glu Leu Ser Tyr Thr Thr Pro Val Leu Thr Ala Leu Gly Glu Val
            980                 985                 990

Glu Ser Val Asp Gln Pro Lys Tyr  Lys Lys Arg Lys Gly  Ala Tyr
            995                 1000                1005
```

```
<210> SEQ ID NO 85
<211> LENGTH: 350
<212> TYPE: PRT
<213> ORGANISM: Aspergillus niger

<400> SEQUENCE: 85

Met Ile Tyr Pro Leu Leu Ser Ala Leu Pro Leu Leu Ser Ala
1               5                   10                  15

Ala Leu Thr Tyr Arg Gly Ala Asp Ile Ser Ser Leu Leu Ile Glu Glu
            20                  25                  30

Asp Ala Gly Ile Ser Tyr Lys Asn Leu Asn Gly Glu Thr Gln Ala Leu
        35                  40                  45

Glu Asp Ile Leu Val Asn Asn Gly Val Asn Ser Ile Arg Gln Arg Val
    50                  55                  60

Trp Val Asp Pro Ser Asp Gly Ser Tyr Asp Leu Asp Tyr Asn Leu Lys
65                  70                  75                  80

Leu Ala Lys Arg Val Gln Ala Ala Gly Met Ser Ile Tyr Leu Asp Leu
                85                  90                  95

His Leu Ser Asp Thr Trp Ala Asp Pro Ser Asp Gln Thr Thr Pro Thr
            100                 105                 110

Gly Trp Ser Thr Thr Asp Ile Asp Thr Leu Thr Trp Gln Leu Tyr Asn
        115                 120                 125

Tyr Thr Leu Asp Val Cys Asn Thr Phe Ala Glu Asn Asp Ile Asp Ile
    130                 135                 140

Glu Ile Val Ser Ile Gly Asn Glu Ile Ser Ser Gly Leu Leu Trp Pro
145                 150                 155                 160

Leu Gly Lys Thr Ser Asn Tyr Asp Asn Ile Ala Lys Leu Leu His Ser
                165                 170                 175

Gly Ala Trp Gly Val Lys Asp Ser Asn Gln Ala Thr Thr Pro Lys Ile
            180                 185                 190

Met Ile His Leu Asp Asn Gly Trp Asp Trp Glu Gln Glu Tyr Phe
        195                 200                 205

Tyr Lys Thr Val Leu Ala Thr Gly Ser Leu Leu Ser Thr Asp Phe Asp
    210                 215                 220

Leu Met Gly Val Ser Tyr Tyr Pro Phe Tyr Asn Ser Glu Ala Thr Leu
225                 230                 235                 240

Ser Ala Leu Gln Thr Ser Leu Thr Asn Met Gln Ser Asn Tyr Asp Lys
                245                 250                 255

Ser Val Val Val Glu Thr Asn Trp Pro Val Ser Cys Pro Asp Pro
            260                 265                 270

Glu Tyr Ser Phe Pro Ser Asp Leu Ser Ser Ile Pro Phe Ser Ala Ala
        275                 280                 285

Gly Gln Glu Glu Phe Leu Glu Lys Leu Ala Glu Val Val Glu Gly Val
    290                 295                 300

Thr Asp Gly Leu Gly Ile Tyr Tyr Trp Glu Pro Ala Trp Val Asp Asn
305                 310                 315                 320

Ala Ala Leu Ala Ser Ser Cys Ala Asp Asn Leu Met Val Asp Ile Asp
                325                 330                 335

Thr Asp Glu Val Leu Glu Ser Val Thr Val Phe Glu Asp Leu
            340                 345                 350
```